United States Patent
Zhang et al.

(10) Patent No.: US 11,001,829 B2
(45) Date of Patent: *May 11, 2021

(54) FUNCTIONAL SCREENING WITH OPTIMIZED FUNCTIONAL CRISPR-CAS SYSTEMS

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Silvana Konermann, Cambridge, MA (US); Mark D. Brigham, Cambridge, MA (US); Alexandra Trevino, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,081

(22) Filed: Mar. 24, 2017

(65) Prior Publication Data

US 2018/0057810 A1    Mar. 1, 2018

Related U.S. Application Data

(63) Continuation-in-part of application No. PCT/US2015/051830, filed on Sep. 24, 2015.

(60) Provisional application No. 62/181,687, filed on Jun. 18, 2015, provisional application No. 62/181,690, filed on Jun. 18, 2015, provisional application No. 62/087,475, filed on Dec. 4, 2014, provisional application No. 62/087,546, filed on Dec. 4, 2014, provisional application No. 62/055,460, filed on Sep. 25, 2014, provisional application No. 62/055,487, filed on Sep. 25, 2014.

(51) Int. Cl.

| | | |
|---|---|---|
| *C12N 15/10* | (2006.01) | |
| *C12N 9/22* | (2006.01) | |
| *C12N 15/11* | (2006.01) | |
| *A61K 48/00* | (2006.01) | |
| *C12N 15/113* | (2010.01) | |
| *C12N 15/63* | (2006.01) | |
| *C12N 15/90* | (2006.01) | |
| *C12Q 1/6876* | (2018.01) | |

(52) U.S. Cl.
CPC ........ *C12N 15/1024* (2013.01); *A61K 48/005* (2013.01); *C12N 9/22* (2013.01); *C12N 15/102* (2013.01); *C12N 15/111* (2013.01); *C12N 15/113* (2013.01); *C12N 15/63* (2013.01); *C12N 15/907* (2013.01); *C12Q 1/6876* (2013.01); *C07K 2319/00* (2013.01); *C12N 2310/10* (2013.01); *C12N 2310/16* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 4,873,316 | A | 10/1989 | Meade et al. |
| 5,543,158 | A | 8/1996 | Gref et al. |
| 5,580,859 | A | 12/1996 | Felgner et al. |
| 5,589,466 | A | 12/1996 | Felgner et al. |
| 5,593,972 | A | 1/1997 | Weiner et al. |
| 5,846,946 | A | 12/1998 | Huebner et al. |
| 5,855,913 | A | 1/1999 | Hanes et al. |
| 5,985,309 | A | 11/1999 | Edwards et al. |
| 6,007,845 | A | 12/1999 | Domb et al. |
| 6,603,061 | B1 | 8/2003 | Armstrong et al. |
| 6,750,059 | B1 | 6/2004 | Blakesley et al. |
| 7,259,015 | B2 | 8/2007 | Kingsman et al. |
| 7,303,910 | B2 | 12/2007 | Bebbington et al. |

(Continued)

FOREIGN PATENT DOCUMENTS

| | | |
|---|---|---|
| EP | 0264166 A1 | 4/1988 |
| EP | 1519714 A1 | 4/2005 |

(Continued)

OTHER PUBLICATIONS

Malina et al., "Repurposing CRISPR/Cas9 for in situ functional assays" 27 Genes & Development 2602-2614 (2013).*

(Continued)

*Primary Examiner* — Nancy J Leith

(74) *Attorney, Agent, or Firm* — Johnson, Marcou, Isaacs & Nix, LLC; F. Brent Nix, Esq.; Rachel Rutledge, Esq.

(57) ABSTRACT

The invention provides for systems, methods, and compositions for altering expression of target gene sequences and related gene products. Provided are structural information on the Cas protein of the CRISPR-Cas system, use of this information in generating modified components of the CRISPR complex, vectors and vector systems which encode one or more components or modified components of a CRISPR complex, as well as methods for the design and use of such vectors and components. Also provided are methods of directing CRISPR complex formation in eukaryotic cells and methods for utilizing the CRISPR-Cas system. In particular the present invention comprehends optimized functional CRISPR-Cas enzyme systems.

7 Claims, 95 Drawing Sheets

Specification includes a Sequence Listing.

(56) References Cited

U.S. PATENT DOCUMENTS

| | | |
|---|---|---|
| 7,351,585 B2 | 4/2008 | Mitrophanous et al. |
| 7,745,651 B2 | 6/2010 | Heyes et al. |
| 7,776,321 B2 | 8/2010 | Cascalho et al. |
| 7,799,565 B2 | 9/2010 | MacLachlan et al. |
| 7,803,397 B2 | 9/2010 | Heyes et al. |
| 7,838,658 B2 | 11/2010 | MacLachlan et al. |
| 7,868,149 B2 | 1/2011 | Boukharov et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 8,058,069 B2 | 11/2011 | Yaworski et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,283,333 B2 | 10/2012 | Yaworski et al. |
| 8,404,658 B2 | 3/2013 | Hajjar et al. |
| 8,454,972 B2 | 6/2013 | Nabel et al. |
| 8,507,272 B2 | 8/2013 | Zhang et al. |
| 8,697,359 B1 | 4/2014 | Zhang |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,267,135 B2 * | 2/2016 | Church ............... C12N 15/102 |
| 2004/0013648 A1 | 1/2004 | Kingsman et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0100536 A1 | 4/2009 | Adams et al. |
| 2009/0111106 A1 | 4/2009 | Mitrophanous et al. |
| 2010/0317109 A1 | 12/2010 | Maden et al. |
| 2011/0059502 A1 | 3/2011 | Chalasani |
| 2011/0117189 A1 | 5/2011 | Mazzone et al. |
| 2011/0195123 A1 | 8/2011 | Shemi |
| 2011/0293571 A1 | 12/2011 | Widdowson et al. |
| 2011/0293703 A1 | 12/2011 | Mahon et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0170753 A1 | 6/2014 | Zhang |
| 2014/0171156 A1 | 6/2014 | Pattikonda et al. |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2016/0024524 A1* | 1/2016 | Joung ............... C12N 9/22 435/462 |
| 2016/0237456 A1* | 8/2016 | Church ............... C12N 15/102 |

FOREIGN PATENT DOCUMENTS

| | | |
|---|---|---|
| EP | 1664316 A1 | 6/2006 |
| EP | 1766035 A1 | 3/2007 |
| EP | 1781593 A2 | 5/2007 |
| EP | 2771468 A1 | 9/2014 |
| EP | 2784162 A1 | 10/2014 |
| EP | 2764103 B1 | 8/2015 |
| WO | 9639154 A1 | 12/1996 |
| WO | 9703211 A1 | 1/1997 |
| WO | 2011028929 A3 | 3/2011 |
| WO | 2012135025 A2 | 10/2012 |
| WO | 2013071440 A1 † | 5/2013 |
| WO | 2014018423 A2 | 1/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 † | 6/2014 |
| WO | 2014093709 A1 | 6/2014 |
| WO | 2014093712 A1 | 6/2014 |
| WO | 2014093718 A1 | 6/2014 |
| WO | 2015089486 | 6/2014 |
| WO | 2014204723 A1 | 12/2014 |
| WO | 2014204724 A1 | 12/2014 |
| WO | 2014204725 A1 | 12/2014 |
| WO | 2014204726 A1 | 12/2014 |
| WO | 2014204727 A1 | 12/2014 |
| WO | 2014204728 A1 | 12/2014 |
| WO | 2014204729 A1 | 12/2014 |
| WO | 2015040075 A1 † | 3/2015 |
| WO | 2015089419 A2 | 6/2015 |
| WO | 2015139139 | 9/2015 |
| WO | 2016049258 A2 | 3/2016 |

OTHER PUBLICATIONS

Nishimasu et al., "Crystal Structure of Cas9 in Complex with Guide RNA and Target DNA" 156 Cell 935-949 (Feb. 13, 2014).*

Brosnan et al., "The long and the short of noncoding RNAs" 21 Current Opinion in Cell Biology 416-425 (2009).*

International Search Report dated Mar. 21, 2016, which issued during prosecution of International Application No. PCT/US2015/051830.

Konermann, et. al., "Genome-scale transcriptional activation by an engineered CRISPR-Cas9 complex", Nature, 2014, 517:583-588.

Mali, et al., "CAS9 transcriptional activators for target specificity screening and paired nickases for cooperative genome engineering", Nature Biotechnology, 2013, 31:833-838, including Supplementary Information.

Zalatan, et. al., "Engineering Complex Synthetic Transcriptional Programs with CRISPR RNA Scaffolds", Cell, 2015, 160:339-350.

Alhasan, et al., "Exosome Encased Spherical Nucleic Acid Gold Nanoparticle Conjugates as Potent MicroRNA Regulation Agents", Small, vol. 10, Issue 1, Jan. 15, 2014, pp. 186-192.

Cabili, et al., "Integrative annotation of human large intergenic noncoding RNAs reveals global properties and specific subclasses", Genes & development 25, 2011, pp. 1915-1927.

Cech, et al., "The Noncoding RNA Revolution—Trashing Old Rules to Forge New Ones", Cell, vol. 157, No. 1, Mar. 27, 2014, p. 77-p. 94.

Chao, et al., "Structural Basis for the Coevolution of a Viral RNA-Protein Complex", Nature Structural & Molecular Biology, vol. 15, No. 15, No. 1, Jan. 2008, pp. 103-105.

Chen, et al., "Dynamic Imaging of Genomic Loci in Living Human Cells by an Optimized CRISPR/Cas System", Cell, vol. 155, Dec. 2013, pp. 1479-1491.

(56) References Cited

OTHER PUBLICATIONS

Choi, et al., "Mechanism for the Endocytosis of Spherical Nucleic Acid Nanoparticle Conjugates", PNAS, vol. 110, No. 19, 2013, pp. 7625-7630.
Cong, et al., "Multiplex Genome Engineering Using CRISPR/Cas Systems", Science, vol. 339, No. 6121, Feb. 14, 2013, pp. 819-823.
Cutler, et al., "Polyvalent Nucleic Acid Nanostructures", Journal of the American Chemical Society, vol. 133, Issue 24, Jun. 22, 2011, pp. 9254-9257.
Cutler, et al., "Spherical Nucleic Acids", Journal of the American Chemical Society, vol. 134, Issue 3, 2012, pp. 1376-1391.
Engreitz, et al., "The Xist lncrna Exploits Three-Dimensional Genome Architecture to Spread Across the X-Chromosome", Science, vol. 341, No. 6147, Aug. 16, 2013, 18 pages.
Fonfara, et al., "Phylogeny of Cas9 determines functional exchangeability of dual-RNA and Cas9 among orthologous type II CRISPR-Cas systems", Nucleic Acids Research, vol. 42, No. 4, 2014, pp. 2577-2590.
Fu, et al., "High frequency off-target mutagenesis induced by CRISPR-Cas nucleases in human cells", Nat Biotechnol., 31(9), pp. 822-826, Sep. 2013.
Gilbert, et al., "CRISPR-Mediated Modular RNA-Guided Regulation of Transcription in Eukaryotes", Cell, vol. 154, No. 2, Jul. 18, 2013, pp. 442-451.
Gorecka, et al., "Crystal structure of RuvC resolvase in complex with Holliday junction substrate.", Nucleic Acids Res, 41(21), Aug. 2013, pp. 9945-9955.
Gratz, et al., "Genome engineering of Drosophila with the CRISPR RNA-guided Cas9 nuclease", Genetics 194, Aug. 2013, pp. 1029-1035.
Hao, et al., "Nucleic Acid-Gold Nanoparticle Conjugates as Mimics of microRNA", Small, vol. 7, Issue 22, Nov. 18, 2011, pp. 3158-3162.
Holm, et al., "Dali Server: Conservation Mapping in 3D", Nucleic acids research, vol. 38, May 10, 2010, pp. W545-W549.
Hsu, et al., "DNA Targeting Specificity of RNA-Guided Cas9 Nucleases", Nat. Biotechnol. vol. 31, No. 9, Sep. 3, 2013, pp. 827-832.
Hwang, et al., "Efficient genome editing in zebrafish using a CRISPR-Cas system", Nature Biotechnology, vol. 31, No. 3, Mar. 2013, pp. 227-229.
Jensen, et al., "Spherical Nucleic Acid Nanoparticle Conjugates as an RNAi-Based Therapy for Glioblastoma", Science Translational Medicine, vol. 5, Issue 209, Oct. 30, 2013, 209ra152, pp. 1-11.
Koike-Yusa, et al., "Genome-Wide Recessive Genetic Screening in Mammalian Cells with a Lentiviral CRISPR-Guide RNA Library", Nature Biotechnology, vol. 32, 2014, pp. 267-273.
Konermann, et al., "Optical Control of Mammalian Endogenous Transcription and Epigenetic States", Nature, vol. 500, No. 7463, Aug. 22, 2013, pp. 472-476.
Konieczkowski, "A Melanoma Cell State Distinction Influences Sensitivity to MAPK Pathway Inhibitors", Cancer Discovery, vol. 4, No. 7, Jul. 2014, pp. 816-827.
Kretz, et al., "Control of Somatic Tissue Differentiation by the Long Non-coding RNA TINCR", Nature, vol. 493, No. 7431, Jan. 10, 2013, pp. 231-235.
Maeder, et al., "CRISPR RNA-Guided Activation of Endogenous Human Genes", Nature Methods, vol. 10, No. 10, Oct. 2013, pp. 977-979.
Maeder, "Targeted DNA Demethylation and Endogenous Gene Activation Using Programmable TALE-TET1 Fusions", Nature Biotechnology, vol. 31, No. 12, Dec. 2013, pp. 1137-1142.
Mali, et al., "RNA-Guided Human Genome Engineering via Cas9", Science, 339, 2013, pp. 823-826.
Mariner, et al., "Human Alu RNA is a Modular Transacting Repressor of mRNA Transcription during Heat Shock", Molecular Cell 29, 2008, pp. 499-509.
Marinho, et al., "Hydrogen peroxide sensing, signaling and regulation of transcription factors", Redox Biology, 2, 2014, pp. 535-562.
Mirkin, "Interview: An Interview with Chad Mirkin: Nanomedicine Expert", Nanomedicine, vol. 7, Issue 5, May 2012, pp. 635-638.
Perez-Pinera, et al., "RNA-Guided Gene Activation by CRISPR-Cas9-Based Transcription Factors", Nature Methods, vol. 10, No. 10, Oct. 2013, pp. 973-976.
Perez-Pinera, et al., "Synergistic and Tunable Human Gene Activation by Combinations of Synthetic Transcription Factors", Nature Methods, vol. 10, No. 3, Mar. 2013, pp. 239-242.
Qi, et al., "Repurposing CRISPR as an RNA-guided platform for sequence-specific control of gene expression", Cell 152, Feb. 28, 2013, pp. 1173-1183.
Sanjana, et al., "Improved vectors and genome-wide libraries for CRISPR screening", Nature Methods, vol. 11, No. 8, Aug. 2014, pp. 783-784.
Shalem, et al., "Genome-Scale CRISPR-Cas9 Knockout Screening in Human Cells", Science, vol. 343, No. 6166, 2014, pp. 84-87.
The Broad Institute, Inc., "International Preliminary Report on Patentability issued in International Application No. PCT/US2015/051830", dated Apr. 6, 2017, 13 pages.
Wang, et al., "Genetic Screens in Human Cells Using the CRISPR/Cas9 System", Science, vol. 343, No. 6166, Jan. 3, 2014, pp. 80-84.
Weintraub, "The new gold standard", Nature, vol. 495, Mar. 14, 2013, pp. S14-S16.
Wiedenheft, et al., "RNA-guided complex from a bacterial immune system enhances target recognition through seed sequence interactions", Proc. Natl. Acad. Sci., vol. 108, No. 25, Jun. 21, 2011, pp. 10092-10097.
Wiedenheft, et al., "Structures of the RNA-guided surveillance complex from a bacterial immune system", Nature, vol. 477, Sep. 22, 2011, pp. 486-489.
Wu, et al., "Fluorescence Fluctuation Spectroscopy Enables Quantitative Imaging of Single Mrnas in Living Cells", Biophysical Journal, vol. 102, No. 12, Jun. 20, 2012, pp. 2936-2944.
Wu, et al., "Genome-Wide Binding of the CRISPR Endonuclease Cas9 in Mammalian Cells", Nature Biotechnology, vol. 32, No. 7, Jul. 2014, pp. 670-676.
Yang, "One-step generation of mice carrying reporter and conditional alleles by CRISPR/Cas-mediated genome engineering", Cell, vol. 154, Sep. 12, 2013, pp. 1370-1379.
Young, et al., "Hollow Spherical Nucleic Acids for Intracellular Gene Regulation Based Upon Biocompatible Silica Shells", Nano Letters, vol. 12, Issue 7, Jul. 11, 2012, pp. 3867-3871.
Zhang, et al., "A Strategy for Increasing Drug Solubility and Efficacy through Covalent Attachment to Polyvalent DNA-Nanoparticle Conjugates", ACS Nano, vol. 5, Issue 9, Sep. 27, 2011, pp. 6962-6970.
Zhang, et al., "Antibody-linked Spherical Nucleic Acids for Cellular Targeting", Journal of the American Chemical Society, vol. 134, Issue 40, Oct. 10, 2012, pp. 16488-16491.
Zhang, et al., "Efficient construction of sequence-specific TAL effectors for modulating mammalian transcription", Nature Biotechnology, vol. 29, No. 2, 2011, pp. 149-153.
Zheng, et al., "Topical Delivery of siRNA-Based Spherical Nucleic Acid Nanoparticle Conjugates for Gene Regulation", PNAS, vol. 109, No. 30, Jul. 24, 2012, pp. 11975-11980.

\* cited by examiner
† cited by third party

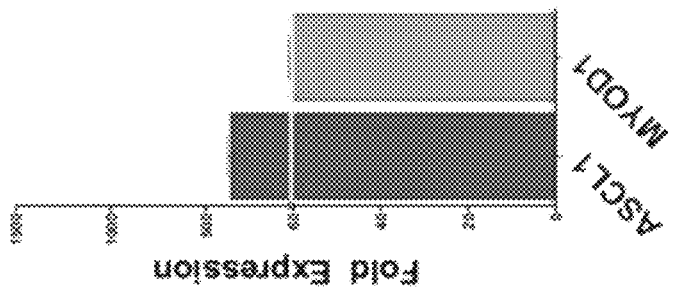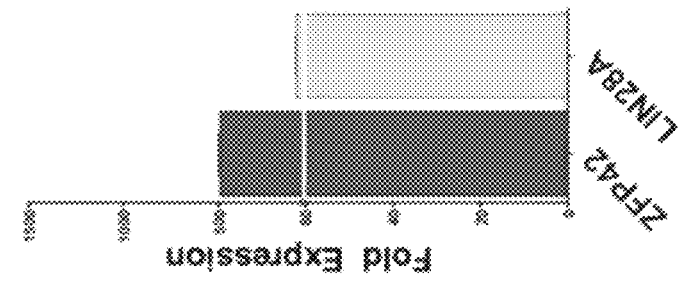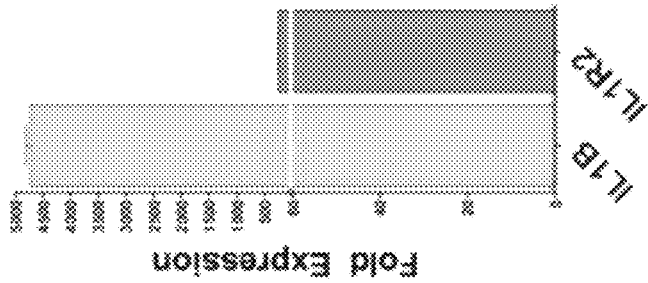
FIG. 20 CONTINUED

FIG. 21A
FIG. 21B
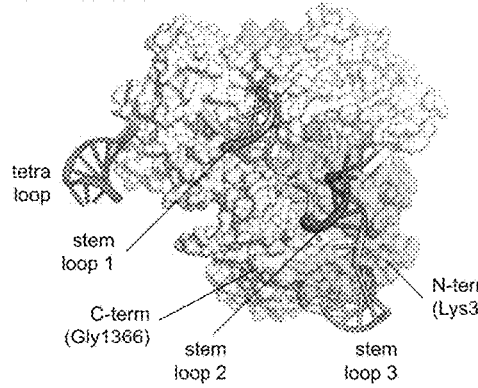
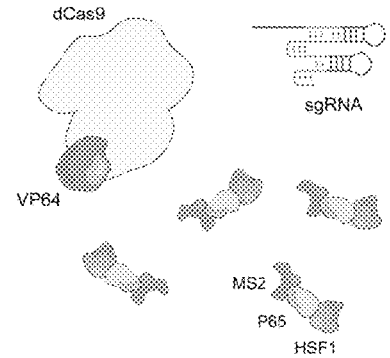
FIG. 21C
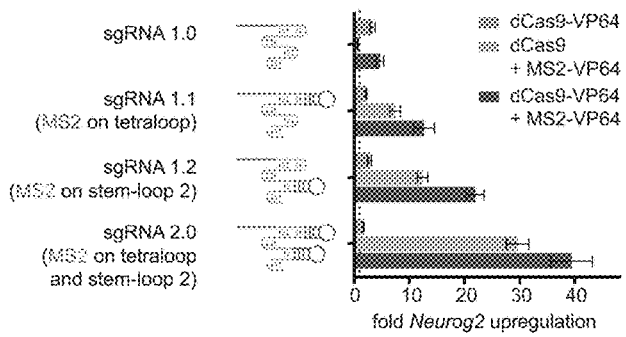
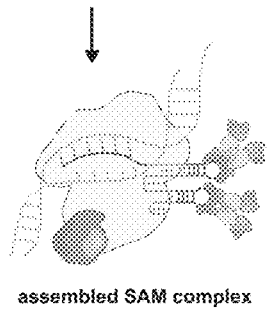
FIG. 21D
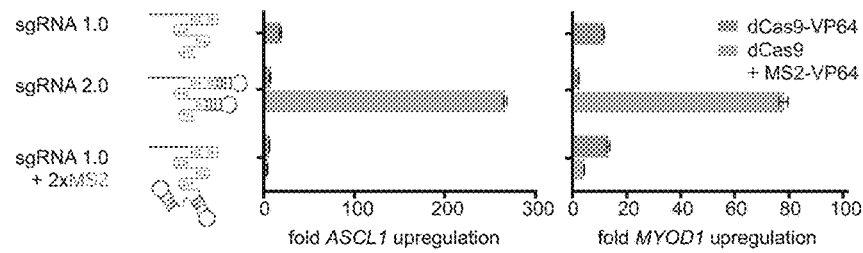
FIG. 21E
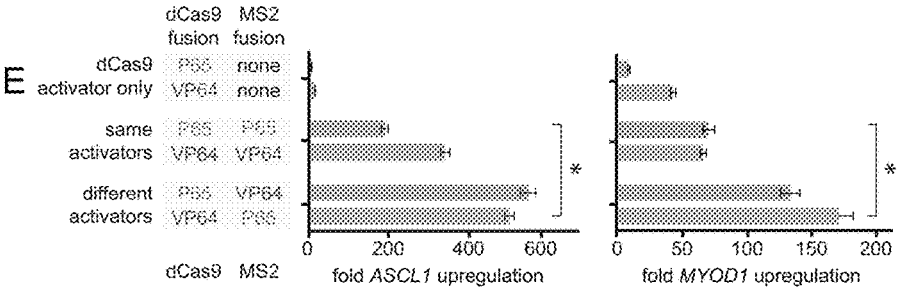
FIG. 21F
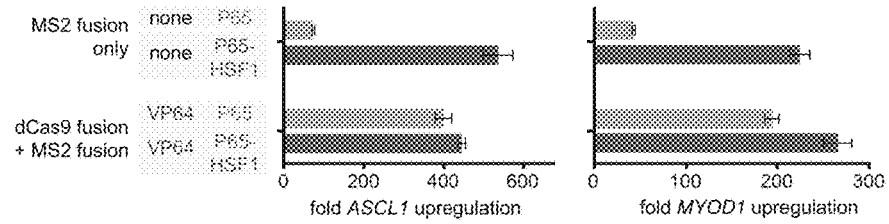

FIG. 25A
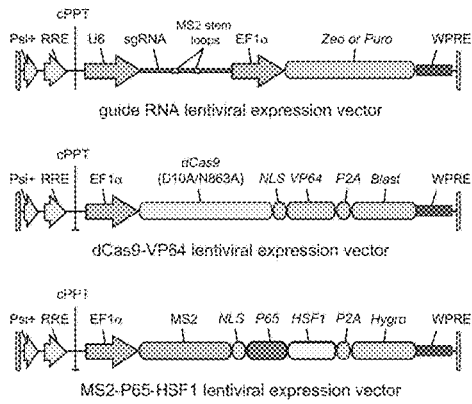
FIG. 25B
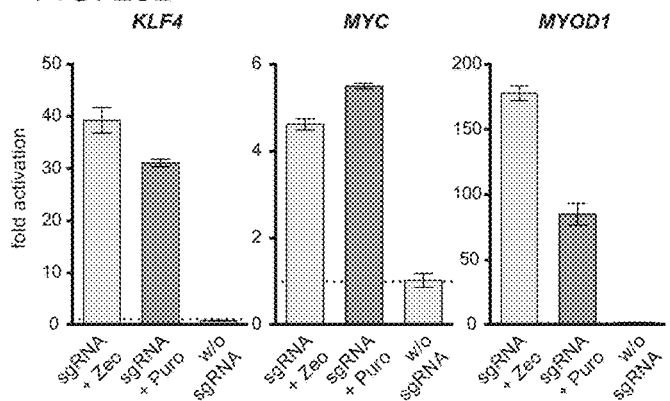
FIG. 25C
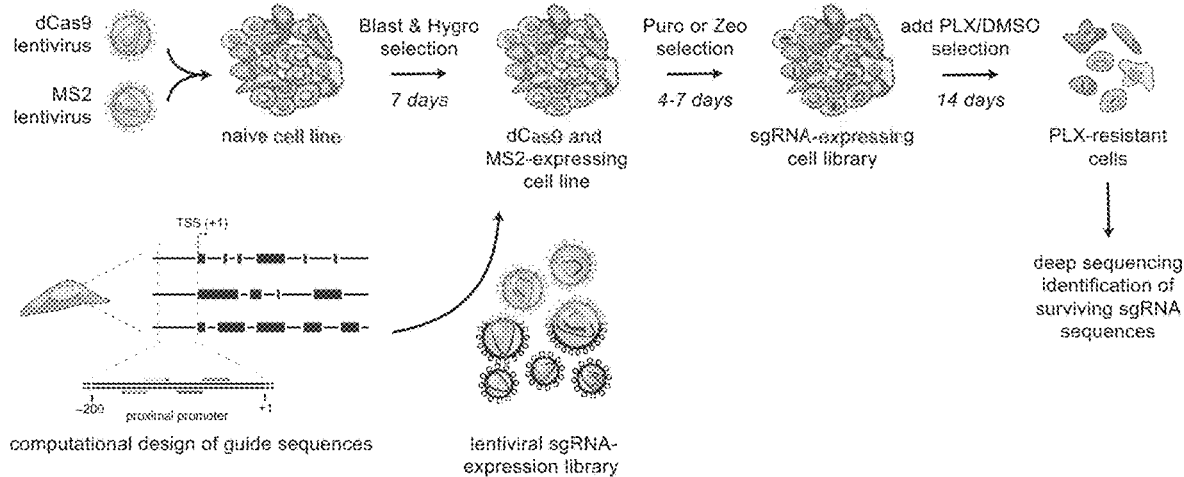
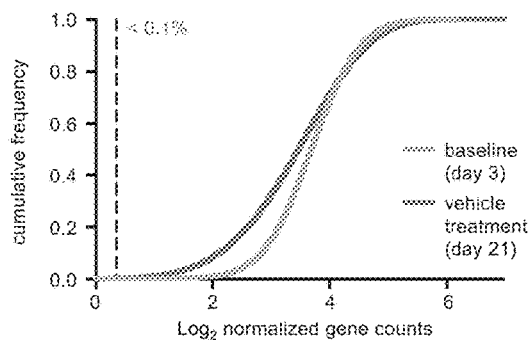
FIG. 25D
FIG. 25E

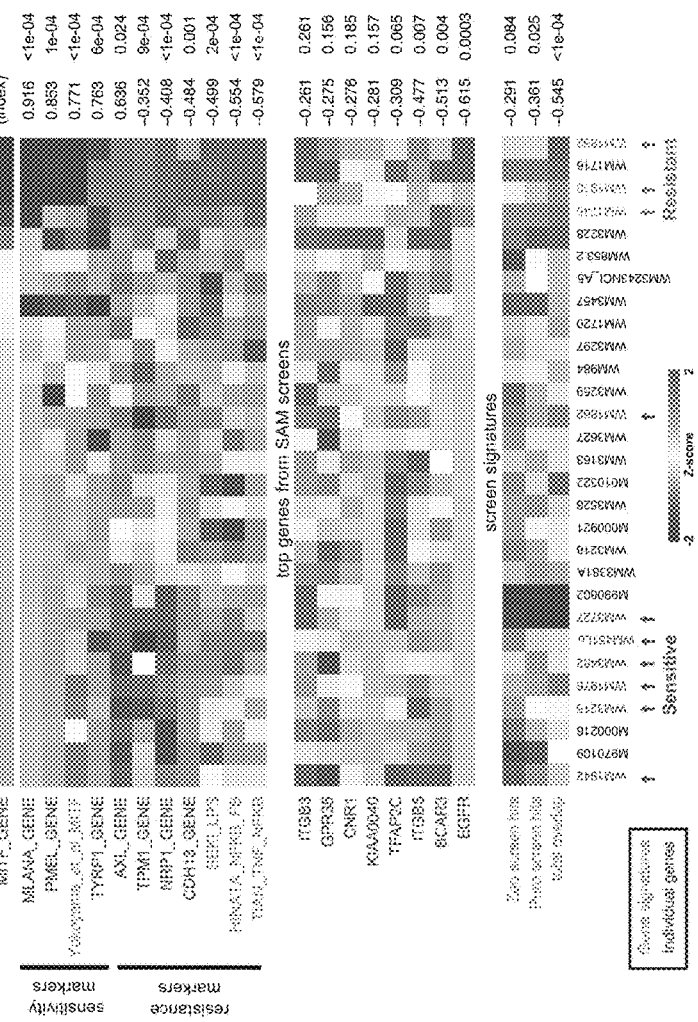# FIG. 26C / FIG. 26F
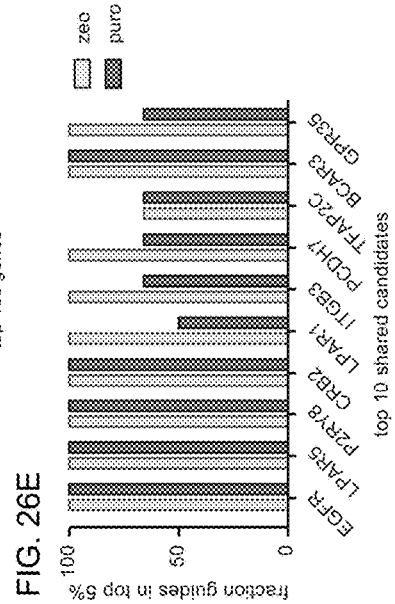

FIG. 27A
FIG. 27B
FIG. 27C
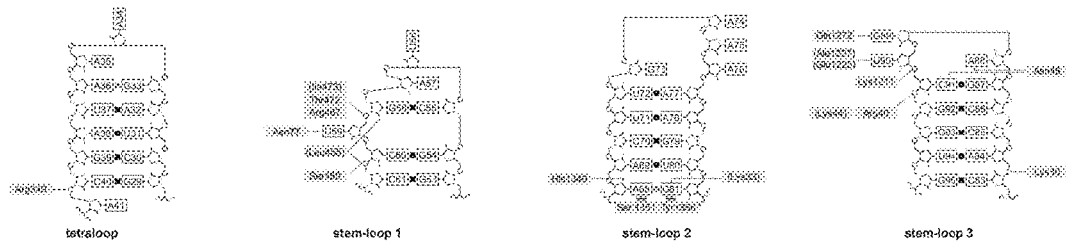
FIG. 27D
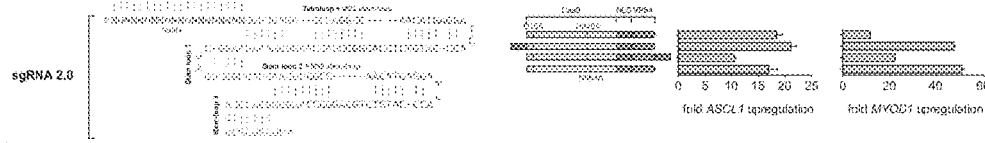
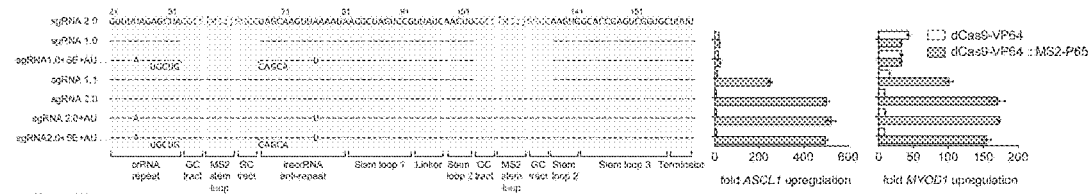
FIG. 27E
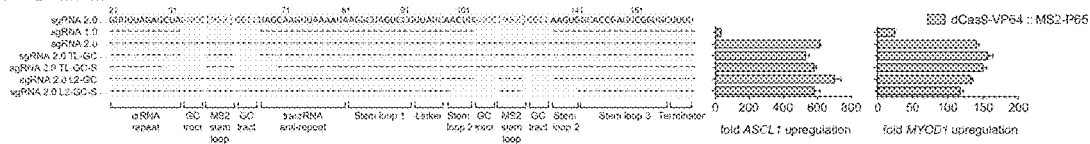

FIG. 36A
FIG. 36B
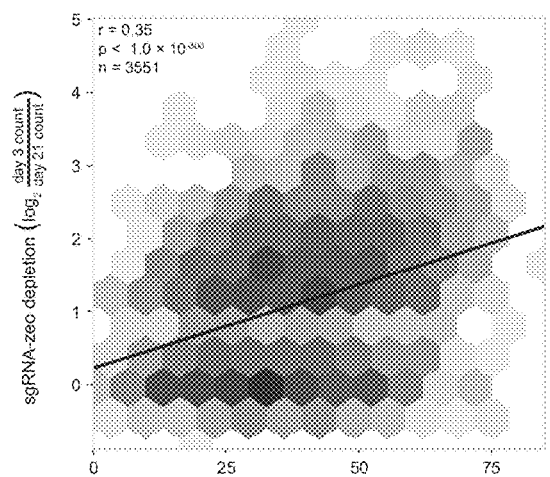
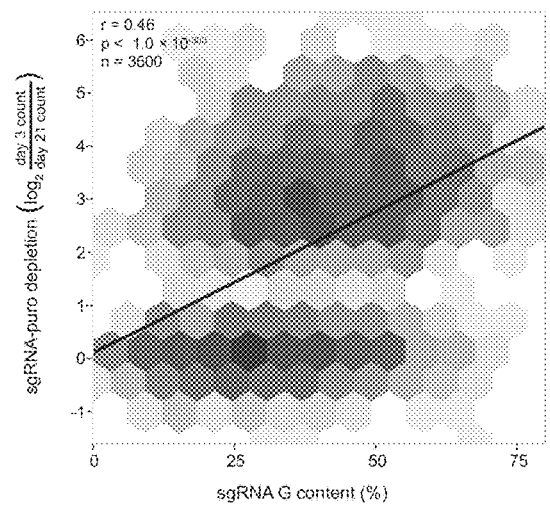
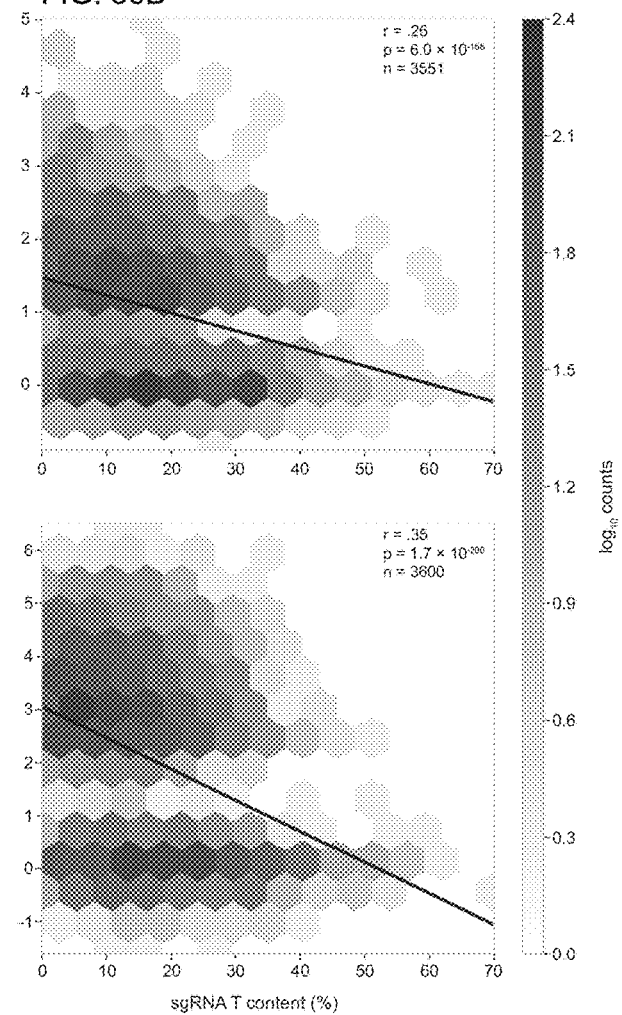
FIG. 36C
FIG. 36D

1  SgRNA Scaffolds 1.1  Standard guide scaffold (sgRNA 1.0)

NNNNNNNNNNNNNNNNNNNNNGTTTTAGAGCTAGAAATAGCAAGTTAAAATAAGGCTAGTCCGTT
ATCAACTTGAAAAAGTGGCACCGAGTCGGTGCTTTTT 1.2  Tetraloop MS2 stem loop insertion sgRNA scaffold (sgRNA 1.1)

NNNNNNNNNNNNNNNNNNNNNGTTTTAGAGCTAGGCCAACATGAGGATCACCCATGTCTGCAGGG
CCTAGCAAGTTAAAATAAGGCTAGTCCGTTATCACGCCGAAAGGCGGGCACCGAGTCGGTGCTT
TTT 1.3  Loop 2 MS2 stem loop insertion sgRNA scaffold (sgRNA 1.2)

NNNNNNNNNNNNNNNNNNNNNGTTTTAGAGCTAGAAATAGCAAGTTAAAATAAGGCTAGTCCGTT
ATCAACTTGGCCAACATGAGGATCACCCATGTCTGCAGGGCCAAGTGGCACCGAGTCGGTGCTT
TTT 1.4  Tetraloop and Loop 2 MS2 stem loop insertion sgRNA scaffold (sgRNA 2.0)

NNNNNNNNNNNNNNNNNNNNNGTTTTAGAGCTAGGCCAACATGAGGATCACCCATGTCTGCAGGG
CCTAGCAAGTTAAAATAAGGCTAGTCCGTTATCAACTTGGCCAACATGAGGATCACCCATGTCT
GCAGGGCCAAGTGGCACCGAGTCGGTGCTTTTT

2  MS2 Constructs

FIG. 37A

2.1 MS2-NLS-VP64

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTACAGCGCTGGAGGAGGTGGAAGCGGAGGAGGAGGAAGCGGAGGAGGAGGTAGCGGACCTA
AGAAAAAGAGGAAGGTGGCGGCCGCTGGATCCGGACGGGCTGACGCATTGGACGATTTTGATCT
GGATATGCTGGGAAGTGACGCCCTCGATGATTTTGACCTTGACATGCTTGGTTCGGATGCCCTT
GATGACTTTGACCTCGACATGCTCGGCAGTGACGCCCTTGATGATTTCGACCTGGACATGCTGA
TTAAC

2.1.1 MS2

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTAC

2.1.2 NLS

GGACCTAAGAAAAAGAGGAAGGTGGCGGCCGCT

2.1.3 VP64

GGACGGGCTGACGCATTGGACGATTTTGATCTGGATATGCTGGGAAGTGACGCCCTCGATGATT
TTGACCTTGACATGCTTGGTTCGGATGCCCTTGATGACTTTGACCTCGACATGCTCGGCAGTGA
CGCCCTTGATGATTTCGACCTGGACATGCTGATTAAC

FIG. 37B

2.2 MS2-NLS-P65

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTACAGCGCTGGAGGAGGTGGAAGCGGAGGAGGAGGAAGCGGAGGAGGAGGTAGCGGACCTA
AGAAAAAGAGGAAGGTGGCGGCCGCTGGATCCCCTTCAGGGCAGATCAGCAACCAGGCCCTGGC
TCTGGCCCCTAGCTCCGCTCCAGTGCTGGCCCAGACTATGGTGCCCTCTAGTGCTATGGTGCCT
CTGGCCCAGCCACCTGCTCCAGCCCCTGTGCTGACCCCAGGACCACCCCAGTCACTGAGCGCTC
CAGTGCCCAAGTCTACACAGGCCGGCGAGGGACTCTGAGTGAAGCTCTGCTGCACCTGCAGTT
CGACGCTGATGAGGACCTGGGAGCTCTGCTGGGGAACAGCACCGATCCCGGAGTGTTCACAGAT
CTGGCCTCCGTGGACAACTCTGAGTTTCAGCAGCTGCTGAATCAGGGCGTGTCCATGTCTCATA
GTACAGCCGAACCAATGCTGATGGAGTACCCCGAAGCCATTACCCGGCTGGTGACCGGCAGCCA
GCGGCCCCCCGACCCCGCTCCAACTCCCCTGGGAACCAGCGGCCTGCCTAATGGGCTGTCCGGA
GATGAAGACTTCTCAAGCATCGCTGATATGGACTTTAGTGCCCTGCTGTCACAGATTTCCTCTA
GTGGGCAG

2.2.1 MS2

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTAC

2.2.2 NLS

GGACCTAAGAAAAAGAGGAAGGTGGCGGCCGCT

CCTTCAGGGCAGATCAGCAACCAGGCCCTGGCTCTGGCCCCTAGCTCCGCTCCAGTGCTGGCCC
AGACTATGGTGCCCTCTAGTGCTATGGTGCCTCTGGCCCAGCCACCTGCTCCAGCCCCTGTGCT
GACCCCAGGACCACCCCAGTCACTGAGCGCTCCAGTGCCCAAGTCTACACAGGCCGGCGAGGGG
ACTCTGAGTGAAGCTCTGCTGCACCTGCAGTTCGACGCTGATGAGGACCTGGGAGCTCTGCTGG
GGAACAGCACCGATCCCGGAGTGTTCACAGATCTGGCCTCCGTGGACAACTCTGAGTTTCAGCA
GCTGCTGAATCAGGGCGTGTCCATGTCTCATAGTACAGCCGAACCAATGCTGATGGAGTACCCC
GAAGCCATTACCCGGCTGGTGACCGGCAGCCAGCGGCCCCCCGACCCCGCTCCAACTCCCCTGG
GAACCAGCGGCCTGCCTAATGGGCTGTCCGGAGATGAAGACTTCTCAAGCATCGCTGATATGGA
CTTTAGTGCCCTGCTGTCACAGATTTCCTCTAGTGGGCAG

2.3 MS2-NLS-P65-HSF1

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTACAGCGCTGGAGGAGGTGGAAGCGGAGGAGGAGGAAGCGGAGGAGGAGGTAGCGGACCTA
AGAAAAAGAGGAAGGTGGCGGCCGCTGGATCCCCTTCAGGGCAGATCAGCAACCAGGCCCTGGC
TCTGGCCCCTAGCTCCGCTCCAGTGCTGGCCCAGACTATGGTGCCCTCTAGTGCTATGGTGCCT
CTGGCCCAGCCACCTGCTCCAGCCCCTGTGCTGACCCCAGGACCACCCCAGTCACTGAGCGCTC
CAGTGCCCAAGTCTACACAGGCCGGCGAGGGGACTCTGAGTGAAGCTCTGCTGCACCTGCAGTT
CGACGCTGATGAGGACCTGGGAGCTCTGCTGGGGAACAGCACCGATCCCGGAGTGTTCACAGAT
CTGGCCTCCGTGGACAACTCTGAGTTTCAGCAGCTGCTGAATCAGGGCGTGTCCATGTCTCATA
GTACAGCCGAACCAATGCTGATGGAGTACCCCGAAGCCATTACCCGGCTGGTGACCGGCAGCCA
GCGGCCCCCCGACCCCGCTCCAACTCCCCTGGGAACCAGCGGCCTGCCTAATGGGCTGTCCGGA
GATGAAGACTTCTCAAGCATCGCTGATATGGACTTTAGTGCCCTGCTGTCACAGATTTCCTCTA
GTGGGCAGGGAGGAGGTGGAAGCGGCTTCAGCGTGGACACCAGTGCCCTGCTGGACCTGTTCAG
CCCCTCGGTGACCGTGCCCGACATGAGCCTGCCTGACCTTGACAGCAGCCTGGCCAGTATCCAA
GAGCTCCTGTCTCCCCAGGAGCCCCCAGGCCTCCCGAGGCAGAGAACAGCAGCCCGGATTCAG
GGAAGCAGCTGGTGCACTACACAGCGCAGCCGCTGTTCCTGCTGGACCCCGGCTCCGTGGACAC
CGGGAGCAACGACCTGCCGGTGCTGTTTGAGCTGGGAGAGGGCTCCTACTTCTCCGAAGGGGAC
GGCTTCGCCGAGGACCCCACCATCTCCCTGCTGACAGGCTCGGAGCCTCCCAAAGCCAAGGACC
CCACTGTCTCC

FIG. 37D 2.3.1 MS2

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTAC 2.3.2 NLS

GGACCTAAGAAAAAGAGGAAGGTGGCGGCCGCT 2.3.3 P65

CCTTCAGGGCAGATCAGCAACCAGGCCCTGGCTCTGGCCCCTAGCTCCGCTCCAGTGCTGGCCC
AGACTATGGTGCCCTCTAGTGCTATGGTGCCTCTGGCCCAGCCACCTGCTCCAGCCCCTGTGCT
GACCCCAGGACCACCCCAGTCACTGAGCGCTCCAGTGCCCAAGTCTACACAGGCCGGCGAGGGG
ACTCTGAGTGAAGCTCTGCTGCACCTGCAGTTCGACGCTGATGAGGACCTGGGAGCTCTGCTGG
GGAACAGCACCGATCCCGGAGTGTTCACAGATCTGGCCTCCGTGGACAACTCTGAGTTTCAGCA
GCTGCTGAATCAGGGCGTGTCCATGTCTCATAGTACAGCCGAACCAATGCTGATGGAGTACCCC
GAAGCCATTACCCGGCTGGTGACCGGCAGCCAGCGGCCCCCCGACCCCGCTCCAACTCCCCTGG
GAACCAGCGGCCTGCCTAATGGGCTGTCCGGAGATGAAGACTTCTAAGCATCGCTGATATGGA
CTTTAGTGCCCTGCTGTCACAGATTTCCTCTAGTGGGCAG 2.3.4 HSF1

GGCTTCAGCGTGGACACCAGTGCCCTGCTGGACCTGTTCAGCCCCTCGGTGACCGTGCCCGACA
TGAGCCTGCCTGACCTTGACAGCAGCCTGGCCAGTATCCAAGAGCTCCTGTCTCCCCAGGAGCC
CCCCAGGCCTCCCGAGGCAGAGAACAGCAGCCCGGATTCAGGGAAGCAGCTGGTGCACTACACA
GCGCAGCCGCTGTTCCTGCTGGACCCCGGCTCCGTGGACACCGGGAGCAACGACCTGCCGGTGC
TGTTTGAGCTGGGAGAGGGCTCCTACTTCTCCGAAGGGGACGGCTTCGCCGAGGACCCCACCAT
CTCCCTGCTGACAGGCTCGGAGCCTCCCAAAGCCAAGGACCCCACTGTCTCC

FIG. 37E

2.4 MS2-NLS-P65-Myod1

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTACAGCGCTGGAGGAGGTGGAAGCGGAGGAGGAGGAAGCGGAGGAGGAGGTAGCGGACCTA
AGAAAAAGAGGAAGGTGGCGGCCGCTGGATCCCCTTCAGGGCAGATCAGCAACCAGGCCCTGGC
TCTGGCCCCTAGCTCCGCTCCAGTGCTGGCCCAGACTATGGTGCCCTCTAGTGCTATGGTGCCT
CTGGCCCAGCCACCTGCTCCAGCCCTGTGCTGACCCCAGGACCACCCCAGTCACTGAGCGCTC
CAGTGCCCAAGTCTACACAGGCCGGCGAGGGGACTCTGAGTGAAGCTCTGCTGCACCTGCAGTT
CGACGCTGATGAGGACCTGGGAGCTCTGCTGGGGAACAGCACCGATCCCGGAGTGTTCACAGAT
CTGGCCTCCGTGGACAACTCTGAGTTTCAGCAGCTGCTGAATCAGGGCGTGTCCATGTCTCATA
GTACAGCCGAACCAATGCTGATGGAGTACCCCGAAGCCATTACCCGGCTGGTGACCGGCAGCCA
GCGGCCCCCCGACCCCGCTCCAACTCCCCTGGGAACCAGCGGCCTGCCTAATGGGCTGTCCGGA
GATGAAGACTTCTCAAGCATCGCTGATATGGACTTTAGTGCCCTGCTGTCACAGATTTCCTCTA
GTGGGCAGGGAGGAGGTGGAAGCATGGAGCTTCTTTCTCCTCCTCTGCGGGATGTTGACCTGAC
TGCGCCCGACGGCTCTCTTTGCTCCTTCGCCACAACCGACGACTTCTACGATGATCCATGTTTT
GACAGCCCCGATCTCAGGTTCTTTGAGGATCTCGATCCTAGACTGATGCACGTGGGCGCACTGC
TCAAACCTGAGGAACATAGC

2.4.1 MS2

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTAC

2.4.2 NLS

GGACCTAAGAAAAAGAGGAAGGTGGCGGCCGCT

CCTTCAGGGCAGATCAGCAACCAGGCCCTGGCTCTGGCCCCTAGCTCCGCTCCAGTGCTGGCCC
AGACTATGGTGCCCTCTAGTGCTATGGTGCCTCTGGCCCAGCCACCTGCTCCAGCCCCTGTGCT
GACCCCAGGACCACCCCAGTCACTGAGCGCTCCAGTGCCCAAGTCTACACAGGCCGGCGAGGGG
ACTCTGAGTGAAGCTCTGCTGCACCTGCAGTTCGACGCTGATGAGGACCTGGGAGCTCTGCTGG
GGAACAGCACCGATCCCGGAGTGTTCACAGATCTGGCCTCCGTGGACAACTCTGAGTTTCAGCA
GCTGCTGAATCAGGGCGTGTCCATGTCTCATAGTACAGCCGAACCAATGCTGATGGAGTACCCC
GAAGCCATTACCCGGCTGGTGACCGGCAGCCAGCGGCCCCCCGACCCCGCTCCAACTCCCCTGG
GAACCAGCGGCCTGCCTAATGGGCTGTCCGGAGATGAAGACTTCTCAAGCATCGCTGATATGGA
CTTTAGTGCCCTGCTGTCACAGATTTCCTCTAGTGGGCAG

2.4.4 Myod1

ATGGAGCTTCTTTCTCCTCCTCTGCGGGATGTTGACCTGACTGCGCCCGACGGCTCTCTTTGCT
CCTTCGCCACAACCGACGACTTCTACGATGATCCATGTTTTGACAGCCCCGATCTCAGGTTCTT
TGAGGATCTCGATCCTAGACTGATGCACGTGGGCGCACTGCTCAAACCTGAGGAACATAGC

3 dCas9 Constructs

3.1 dCas9(D10A, H840A)-NLS-VP64

GACAAGAAGTACAGCATCGGCCTGGCCATCGGCACCAACTCTGTGGGCTGGGCCGTGATCACCG
ACGAGTACAAGGTGCCCAGCAAGAAATTCAAGGTGCTGGGCAACACCGACCGGCACAGCATCAA
GAAGAACCTGATCGGAGCCCTGCTGTTCGACAGCGGCGAAACAGCCGAGGCCACCCGGCTGAAG
AGAACCGCCAGAAGAAGATACACCAGACGGAAGAACCGGATCTGCTATCTGCAAGAGATCTTCA
GCAACGAGATGGCCAAGGTGGACGACAGCTTCTTCCACAGACTGGAAGAGTCCTTCCTGGTGGA
AGAGGATAAGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACAAGGCCGACC
TGCGGCTGATCTATCTGGCCCTGGCCCACATGATCAAGTTCCGGGGCCACTTCCTGATCGAGGG
CGACCTGAACCCCGACAACAGCGACGTGGACAAGCTGTTCATCCAGCTGGTGCAGACCTACAAC
CAGCTGTTCGAGGAAAACCCCATCAACGCCAGCGGCGTGGACGCCAAGGCCATCCTGTCTGCCA
GACTGAGCAAGAGCAGACGGCTGGAAAATCTGATCGCCCAGCTGCCCGGCGAGAAGAAGAATGG
CCTGTTCGGCAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGC

FIG. 37G

```
TGGCCCAGATCGGCGACCAGTACGCCGACCTGTTTCTGGCCGCCAAGAACCTGTCCGACGCCAT
CCTGCTGAGCGACATCCTGAGAGTGAACACCGAGATCACCAAGGCCCCCCTGAGCGCCTCTATG
ATCAAGAGATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGCTACATTGA
CGGCGGAGCCAGCCAGGAAGAGTTCTACAAGTTCATCAAGCCCATCCTGGAAAAGATGGACGGC
ACCGAGGAACTGCTCGTGAAGCTGAACAGAGAGGACCTGCTGCGGAAGCAGCGGACCTTCGACA
ACGGCAGCATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGAAAGAGCGAGG
AAACCATCACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGCACAGCCTG
CTGTACGAGTACTTCACCGTGTATAACGAGCTGACCAAAGTGAAATACGTGACCGAGGGAATGA
GAAAGCCCGCCTTCCTGAGCGGCGAGCAGAAAAAGGCCATCGTGGACCTGCTGTTCAAGACCAA
CCGGAAAGTGACCGTGAAGCAGCTGAAAGAGGACTACTTCAAGAAAATCGAGTGCTTCGACTCC
GTGGAAATCTCCGGCGTGGAAGATCGGTTCAACGCCTCCCTGGGCACATACCACGATCTGCTGA
AAATTATCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGGCAGGCTGA
GCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATC
TGGCCGGCAGCCCCGCCATTAAGAAGGGCATCCTGCAGACAGTGAAGGTGGTGGACGAGCTCGT
GAAAGTGATGGGCCGGCACAAGCCCGAGAACATCGTGATCGAAATGGCCAGAGAGAACCAGACC
ACCCAGAAGGGACAGAAGAACAGCCGCGAGAGAATGAAGCGGATCGAAGAGGGCATCAAAGAGC
TGGGCAGCCAGATCCTGAAAGAACACCCCGTGGAAAACACCCAGCTGCAGAACGAGAAGCTGTA
CCTGTACTACCTGCAGAATGGGCGGGATATGTACGTGGACCAGGAACTGGACATCAACCGGCTG
TCCGACTACGATGTGGACGCTATCGTGCCTCAGAGCTTTCTGAAGGACGACTCCATCGACAACA
AGGTGCTGACCAGAAGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTACCCAGAGAAAGTTC
GACAATCTGACCAAGGCCGAGAGAGGCGGCCTGAGCGAACTGGATAAGGCCGGCTTCATCAAGA
GACAGCTGGTGGAAACCCGGCAGATCACAAAGCACGTGGCACAGATCCTGGACTCCCGGATGAA
CACTAAGTACGACGAGAATGACAAGCTGATCCGGGAAGTGAAAGTGATCACCCTGAAGTCCAAG
CTGGTGTCCGATTTCCGGAAGGATTTCCAGTTTTACAAAGTGCGCGAGATCAACAACTACCACC
ACGCCCACGACGCCTACCTGAACGCCGTCGTGGGAACCGCCCTGATCAAAAAGTACCCTAAGCT
GGAAAGCGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACTTTTCA
```

FIG. 37H

```
AGACCGAGATTACCCTGGCCAACGGCGAGATCCGGAAGCGGCCTCTGATCGAGACAAACGGCGA
AACCGGGGAGATCGTGTGGGATAAGGGCCGGGATTTTGCCACCGTGCGGAAAGTGCTGAGCATG
CCCCAAGTGAATATCGTGAAAAAGACCGAGGTGCAGACAGGCGGCTTCAGCAAAGAGTCTATCC
TGCCCAAGAGGAACAGCGATAAGCTGATCGCCAGAAAGAAGGACTGGGACCCTAAGAAGTACGG
CGGCTTCGACAGCCCCACCGTGGCCTATTCTGTGCTGGTGGTGGCCAAAGTGGAAAAGGGCAAG
TCCAAGAAACTGAAGAGTGTGAAAGAGCTGCTGGGGATCACCATCATGGAAAGAAGCAGCTTCG
AGAAGAATCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGGCCTCTGCC
GGCGAACTGCAGAAGGGAAACGAACTGGCCCTGCCCTCCAAATATGTGAACTTCCTGTACCTGG
CCAGCCACTATGAGAAGCTGAAGGGCTCCCCGAGGATAATGAGCAGAAACAGCTGTTTGTGGA
ACAGCACAAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAAGCCCATCA
GAGAGCAGGCCGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGTGCTGGACGCC
ACCCTGATCCACCAGAGCATCACCGGCCTGTACGAGACACGGATCGACCTGTCTCAGCTGGGAG
GCGACAGCGCTGGAGGAGGTGGAAGCGGAGGAGGAGGAAGCGGAGGAGGAGGTAGCGGACCTAA
GAAAAAGAGGAAGGTGGCGGCCGCTGGATCCGGACGGGCTGACGCATTGGACGATTTTGATCTG
GATATGCTGGGAAGTGACGCCCTCGATGATTTTGACCTTGACATGCTTGGTTCGGATGCCCTTG
ATGACTTTGACCTCGACATGCTCGGCAGTGACGCCCTTGATGATTTCGACCTGGACATGCTGAT
TAAC
```

3.1.1 dCas9(D10A, H840A)

```
GACAAGAAGTACAGCATCGGCCTGGCCATCGGCACCAACTCTGTGGGCTGGGCCGTGATCACCG
ACGAGTACAAGGTGCCCAGCAAGAAATTCAAGGTGCTGGGCAACACCGACCGGCACAGCATCAA
GAAGAACCTGATCGGAGCCCTGCTGTTCGACAGCGGCGAAACAGCCGAGGCCACCCGGCTGAAG
AGAACCGCCAGAAGAAGATACACCAGACGGAAGAACCGGATCTGCTATCTGCAAGAGATCTTCA
GCAACGAGATGGCCAAGGTGGACGACAGCTTCTTCCACAGACTGGAAGAGTCCTTCCTGGTGGA
AGAGGATAAGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACAAGGCCGACC
TGCGGCTGATCTATCTGGCCCTGGCCCACATGATCAAGTTCCGGGGCCACTTCCTGATCGAGGG
CGACCTGAACCCCGACAACAGCGACGTGGACAAGCTGTTCATCCAGCTGGTGCAGACCTACAAC
CAGCTGTTCGAGGAAAACCCCATCAACGCCAGCGGCGTGGACGCCAAGGCCATCCTGTCTGCCA
GACTGAGCAAGAGCAGACGGCTGGAAAATCTGATCGCCCAGCTGCCCGGCGAGAAGAAGAATGG
CCTGTTCGGCAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGC
```

```
TGGCCCAGATCGGCGACCAGTACGCCGACCTGTTTCTGGCCGCCAAGAACCTGTCCGACGCCAT
CCTGCTGAGCGACATCCTGAGAGTGAACACCGAGATCACCAAGGCCCCCCTGAGCGCCTCTATG
ATCAAGAGATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGCTACATTGA
CGGCGGAGCCAGCCAGGAAGAGTTCTACAAGTTCATCAAGCCCATCCTGGAAAAGATGGACGGC
ACCGAGGAACTGCTCGTGAAGCTGAACAGAGAGGACCTGCTGCGGAAGCAGCGGACCTTCGACA
ACGGCAGCATCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGAAAGAGCGAGG
AAACCATCACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGCACAGCCTG
CTGTACGAGTACTTCACCGTGTATAACGAGCTGACCAAAGTGAAATACGTGACCGAGGGAATGA
GAAAGCCCGCCTTCCTGAGCGGCGAGCAGAAAAAGGCCATCGTGGACCTGCTGTTCAAGACCAA
CCGGAAAGTGACCGTGAAGCAGCTGAAAGAGGACTACTTCAAGAAAATCGAGTGCTTCGACTCC
GTGGAAATCTCCGGCGTGGAAGATCGGTTCAACGCCTCCCTGGGCACATACCACGATCTGCTGA
AAATTATCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGGCAGGCTGA
GCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATC
TGGCCGGCAGCCCCGCCATTAAGAAGGGCATCCTGCAGACAGTGAAGGTGGTGGACGAGCTCGT
GAAAGTGATGGGCCGGCACAAGCCCGAGAACATCGTGATCGAAATGGCCAGAGAGAACCAGACC
ACCCAGAAGGGACAGAAGAACAGCCGCGAGAGAATGAAGCGGATCGAAGAGGGCATCAAAGAGC
TGGGCAGCCAGATCCTGAAAGAACACCCCGTGGAAAACACCCAGCTGCAGAACGAGAAGCTGTA
CCTGTACTACCTGCAGAATGGGCGGGATATGTACGTGGACCAGGAACTGGACATCAACCGGCTG
TCCGACTACGATGTGGACGCTATCGTGCCTCAGAGCTTTCTGAAGGACGACTCCATCGACAACA
AGGTGCTGACCAGAAGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTACCCAGAGAAAGTTC
GACAATCTGACCAAGGCCGAGAGAGGCGGCCTGAGCGAACTGGATAAGGCCGGCTTCATCAAGA
GACAGCTGGTGGAAACCCGGCAGATCACAAAGCACGTGGCACAGATCCTGGACTCCCGGATGAA
CACTAAGTACGACGAGAATGACAAGCTGATCCGGGAAGTGAAAGTGATCACCCTGAAGTCCAAG
CTGGTGTCCGATTTCCGGAAGGATTTCCAGTTTTACAAAGTGCGCGAGATCAACAACTACCACC
ACGCCCACGACGCCTACCTGAACGCCGTCGTGGGAACCGCCCTGATCAAAAAGTACCCTAAGCT
GGAAAGCGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACTTTTCA
```

FIG. 37J

AGACCGAGATTACCCTGGCCAACGGCGAGATCCGGAAGCGGCCTCTGATCGAGACAAACGGCGA
AACCGGGGAGATCGTGTGGGATAAGGGCCGGGATTTTGCCACCGTGCGGAAAGTGCTGAGCATG
CCCCAAGTGAATATCGTGAAAAAGACCGAGGTGCAGACAGGCGGCTTCAGCAAAGAGTCTATCC
TGCCCAAGAGGAACAGCGATAAGCTGATCGCCAGAAAGAAGGACTGGGACCCTAAGAAGTACGG
CGGCTTCGACAGCCCCACCGTGGCCTATTCTGTGCTGGTGGTGGCCAAAGTGGAAAAGGGCAAG
TCCAAGAAACTGAAGAGTGTGAAAGAGCTGCTGGGGATCACCATCATGGAAAGAAGCAGCTTCG
AGAAGAATCCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGGCCTCTGCC
GGCGAACTGCAGAAGGGAAACGAACTGGCCCTGCCCTCCAAATATGTGAACTTCCTGTACCTGG
CCAGCCACTATGAGAAGCTGAAGGGCTCCCCCGAGGATAATGAGCAGAAACAGCTGTTTGTGGA
ACAGCACAAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACGGGATAAGCCCATCA
GAGAGCAGGCCGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGTGCTGGACGCC
ACCCTGATCCACCAGAGCATCACCGGCCTGTACGAGACACGGATCGACCTGTCTCAGCTGGGAG
GCGAC 3.1.2 NLS

GGACCTAAGAAAAAGAGGAAGGTGGCGGCCGCT 3.1.3 VP64

GGACGGGCTGACGCATTGGACGATTTTGATCTGGATATGCTGGGAAGTGACGCCCTCGATGATT
TTGACCTTGACATGCTTGGTTCGGATGCCCTTGATGACTTTGACCTCGACATGCTCGGCAGTGA
CGCCCTTGATGATTTCGACCTGGACATGCTGATTAAC 3.2 dCas9(D10A, H840A)-NLS-P65

GACAAGAAGTACAGCATCGGCCTGGCCATCGGCACCAACTCTGTGGGCTGGGCCGTGATCACCG
ACGAGTACAAGGTGCCCAGCAAGAAATTCAAGGTGCTGGGCAACACCGACCGGCACAGCATCAA
GAAGAACCTGATCGGAGCCCTGCTGTTCGACAGCGGCGAAACAGCCGAGGCCACCCGGCTGAAG
AGAACCGCCAGAAGAAGATACACCAGACGGAAGAACCGGATCTGCTATCTGCAAGAGATCTTCA
GCAACGAGATGGCCAAGGTGGACGACAGCTTCTTCCACAGACTGGAAGAGTCCTTCCTGGTGGA
AGAGGATAAGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACAAGGCCGACC

FIG. 37K

```
TGCGGCTGATCTATCTGGCCCTGGCCCACATGATCAAGTTCCGGGGCCACTTCCTGATCGAGGG
CGACCTGAACCCCGACAACAGCGACGTGGACAAGCTGTTCATCCAGCTGGTGCAGACCTACAAC
CAGCTGTTCGAGGAAAACCCCATCAACGCCAGCGGCGTGGACGCCAAGGCCATCCTGTCTGCCA
GACTGAGCAAGAGCAGACGGCTGGAAAATCTGATCGCCCAGCTGCCCGGCGAGAAGAAGAATGG
CCTGTTCGGCAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGC
TGGCCCAGATCGGCGACCAGTACGCCGACCTGTTTCTGGCCGCCAAGAACCTGTCCGACGCCAT
CCTGCTGAGCGACATCCTGAGAGTGAACACCGAGATCACCAAGGCCCCCCTGAGCGCCTCTATG
ATCAAGAGATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGCTACATTGA
CGGCGGAGCCAGCCAGGAAGAGTTCTACAAGTTCATCAAGCCCATCCTGGAAAAGATGGACGGC
ACCGAGGAACTGCTCGTGAAGCTGAACAGAGAGGACCTGCTGCGGAAGCAGCGGACCTTCGACA
ACGGCAGCATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGAAAGAGCGAGG
AAACCATCACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGCACAGCCTG
CTGTACGAGTACTTCACCGTGTATAACGAGCTGACCAAAGTGAAATACGTGACCGAGGGAATGA
GAAAGCCCGCCTTCCTGAGCGGCGAGCAGAAAAAGGCCATCGTGGACCTGCTGTTCAAGACCAA
CCGGAAAGTGACCGTGAAGCAGCTGAAAGAGGACTACTTCAAGAAAATCGAGTGCTTCGACTCC
GTGGAAATCTCCGGCGTGGAAGATCGGTTCAACGCCTCCCTGGGCACATACCACGATCTGCTGA
AAATTATCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGGCAGGCTGA
GCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATC
TGGCCGGCAGCCCCGCCATTAAGAAGGGCATCCTGCAGACAGTGAAGGTGGTGGACGAGCTCGT
GAAAGTGATGGGCCGGCACAAGCCCGAGAACATCGTGATCGAAATGGCCAGAGAGAACCAGACC
ACCCAGAAGGGACAGAAGAACAGCCGCGAGAGAATGAAGCGGATCGAAGAGGGCATCAAAGAGC
TGGGCAGCCAGATCCTGAAAGAACACCCCGTGGAAAACACCCAGCTGCAGAACGAGAAGCTGTA
CCTGTACTACCTGCAGAATGGGCGGGATATGTACGTGGACCAGGAACTGGACATCAACCGGCTG
TCCGACTACGATGTGGACGCTATCGTGCCTCAGAGCTTTCTGAAGGACGACTCCATCGACAACA
AGGTGCTGACCAGAAGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTACCCAGAGAAAGTTC
GACAATCTGACCAAGGCCGAGAGAGGCGGCCTGAGCGAACTGGATAAGGCCGGCTTCATCAAGA
```

FIG. 37L

```
GACAGCTGGTGGAAACCCGGCAGATCACAAAGCACGTGGCACAGATCCTGGACTCCCGGATGAA
CACTAAGTACGACGAGAATGACAAGCTGATCCGGGAAGTGAAAGTGATCACCCTGAAGTCCAAG
CTGGTGTCCGATTTCCGGAAGGATTTCCAGTTTTACAAAGTGCGCGAGATCAACAACTACCACC
ACGCCCACGACGCCTACCTGAACGCCGTCGTGGGAACCGCCCTGATCAAAAGTACCCTAAGCT
GGAAAGCGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACAAACGGCGA
AACCGGGGAGATCGTGTGGGATAAGGGCCGGGATTTTGCCACCGTGCGGAAAGTGCTGAGCATG
CCCCAAGTGAATATCGTGAAAAAGACCGAGGTGCAGACAGGCGGCTTCAGCAAAGAGTCTATCC
TGCCCAAGAGGAACAGCGATAAGCTGATCGCCAGAAAGAAGGACTGGGACCCTAAGAAGTACGG
CGGCTTCGACAGCCCCACCGTGGCCTATTCTGTGCTGGTGGTGGCCAAAGTGGAAAAGGGCAAG
TCCAAGAAACTGAAGAGTGTGAAAGAGCTGCTGGGGATCACCATCATGGAAAGAAGCAGCTTCG
AGAAGAATCCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGGCCTCTGCC
GGCGAACTGCAGAAGGGAAACGAACTGGCCCTGCCCTCCAAATATGTGAACTTCCTGTACCTGG
CCAGCCACTATGAGAAGCTGAAGGGCTCCCCGAGGATAATGAGCAGAAACAGCTGTTTGTGGA
ACAGCACAAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAAGCCCATCA
GAGAGCAGGCCGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGTGCTGGACGCC
ACCCTGATCCACCAGAGCATCACCGGCCTGTACGAGACACGGATCGACCTGTCTCAGCTGGGAG
GCGACAGCGCTGGAGGAGGTGGAAGCGGAGGAGGAGGAAGCGGAGGAGGAGGTAGCGGACCTAA
GAAAAAGAGGAAGGTGGCGGCCGCTGGATCCCCTTCAGGGCAGATCAGCAACCAGGCCCTGGCT
CTGGCCCCTAGCTCCGCTCCAGTGCTGGCCCAGACTATGGTGCCCTCTAGTGCTATGGTGCCTC
TGGCCCAGCCACCTGCTCCAGCCCCTGTGCTGACCCCAGGACCACCCCAGTCACTGAGCGCTCC
AGTGCCCAAGTCTACACAGGCCGGCGAGGGGACTCTGAGTGAAGCTCTGCTGCACCTGCAGTTC
GACGCTGATGAGGACCTGGGAGCTCTGCTGGGGAACAGCACCGATCCCGGAGTGTTCACAGATC
TGGCCTCCGTGGACAACTCTGAGTTTCAGCAGCTGCTGAATCAGGGCGTGTCCATGTCTCATAG
TACAGCCGAACCAATGCTGATGGAGTACCCCGAAGCCATTACCCGGCTGGTGACCGGCAGCCAG
CGGCCCCCGACCCCGCTCCAACTCCCCTGGGAACCAGCGGCCTGCCTAATGGGCTGTCCGGAG
ATGAAGACTTCTCAAGCATCGCTGATATGGACTTTAGTGCCCTGCTGTCACAGATTTCCTCTAG
TGGGCAG
```

FIG. 37M 3.2.1 dCas9(D10A, H840A)

```
GACAAGAAGTACAGCATCGGCCTGGCCATCGGCACCAACTCTGTGGGCTGGGCCGTGATCACCG
ACGAGTACAAGGTGCCCAGCAAGAAATTCAAGGTGCTGGGCAACACCGACCGGCACAGCATCAA
GAAGAACCTGATCGGAGCCCTGCTGTTCGACAGCGGCGAAACAGCCGAGGCCACCCGGCTGAAG
AGAACCGCCAGAAGAAGATACACCAGACGGAAGAACCGGATCTGCTATCTGCAAGAGATCTTCA
GCAACGAGATGGCCAAGGTGGACGACAGCTTCTTCCACAGACTGGAAGAGTCCTTCCTGGTGGA
AGAGGATAAGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACAAGGCCGACC
TGCGGCTGATCTATCTGGCCCTGGCCCACATGATCAAGTTCCGGGGCCACTTCCTGATCGAGGG
CGACCTGAACCCCGACAACAGCGACGTGGACAAGCTGTTCATCCAGCTGGTGCAGACCTACAAC
CAGCTGTTCGAGGAAAACCCCATCAACGCCAGCGGCGTGGACGCCAAGGCCATCCTGTCTGCCA
GACTGAGCAAGAGCAGACGGCTGGAAAATCTGATCGCCCAGCTGCCCGGCGAGAAGAAGAATGG
CCTGTTCGGCAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGC
TGGCCCAGATCGGCGACCAGTACGCCGACCTGTTTCTGGCCGCCAAGAACCTGTCCGACGCCAT
CCTGCTGAGCGACATCCTGAGAGTGAACACCGAGATCACCAAGGCCCCCCTGAGCGCCTCTATG
ATCAAGAGATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGCTACATTGA
CGGCGGAGCCAGCCAGGAAGAGTTCTACAAGTTCATCAAGCCCATCCTGGAAAAGATGGACGGC
ACCGAGGAACTGCTCGTGAAGCTGAACAGAGAGGACCTGCTGCGGAAGCAGCGGACCTTCGACA
ACGGCAGCATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGAAAGAGCGAGG
AAACCATCACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGCACAGCCTG
CTGTACGAGTACTTCACCGTGTATAACGAGCTGACCAAAGTGAAATACGTGACCGAGGGAATGA
GAAAGCCCGCCTTCCTGAGCGGCGAGCAGAAAAAGGCCATCGTGGACCTGCTGTTCAAGACCAA
CCGGAAAGTGACCGTGAAGCAGCTGAAAGAGGACTACTTCAAGAAAATCGAGTGCTTCGACTCC
GTGGAAATCTCCGGCGTGGAAGATCGGTTCAACGCCTCCCTGGGCACATACCACGATCTGCTGA
AAATTATCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGGCAGGCTGA
GCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAA
GAGGACATCCAGAAGCCCAGGTGTCCGGCCAGGGCGATAGCCTGCACGAGCACATTGCCAATC
```

TGGCCGGCAGCCCCGCCATTAAGAAGGGCATCCTGCAGACAGTGAAGGTGGTGGACGAGCTCGT
GAAAGTGATGGGCCGGCACAAGCCCGAGAACATCGTGATCGAAATGGCCAGAGAGAACCAGACC
ACCCAGAAGGGACAGAAGAACAGCCGCGAGAGAATGAAGCGGATCGAAGAGGGCATCAAAGAGC
TGGGCAGCCAGATCCTGAAAGAACACCCCGTGGAAAACACCCAGCTGCAGAACGAGAAGCTGTA
CCTGTACTACCTGCAGAATGGGCGGGATATGTACGTGGACCAGGAACTGGACATCAACCGGCTG
TCCGACTACGATGTGGACGCTATCGTGCCTCAGAGCTTTCTGAAGGACGACTCCATCGACAACA
AGGTGCTGACCAGAAGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTACCCAGAGAAAGTTC
GACAATCTGACCAAGGCCGAGAGAGGCGGCCTGAGCGAACTGGATAAGGCCGGCTTCATCAAGA
GACAGCTGGTGGAAACCCGGCAGATCACAAAGCACGTGGCACAGATCCTGGACTCCCGGATGAA
CACTAAGTACGACGAGAATGACAAGCTGATCCGGGAAGTGAAAGTGATCACCCTGAAGTCCAAG
CTGGTGTCCGATTTCCGGAAGGATTTCCAGTTTTACAAAGTGCGCGAGATCAACAACTACCACC
ACGCCCACGACGCCTACCTGAACGCCGTCGTGGGAACCGCCCTGATCAAAAAGTACCCTAAGCT
GGAAAGCGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACAAACGGCGA
AACCGGGGAGATCGTGTGGGATAAGGGCCGGGATTTTGCCACCGTGCGGAAAGTGCTGAGCATG
CCCCAAGTGAATATCGTGAAAAAGACCGAGGTGCAGACAGGCGGCTTCAGCAAAGAGTCTATCC
TGCCCAAGAGGAACAGCGATAAGCTGATCGCCAGAAAGAAGGACTGGGACCCTAAGAAGTACGG
CGGCTTCGACAGCCCCACCGTGGCCTATTCTGTGCTGGTGGTGGCCAAAGTGGAAAAGGGCAAG
TCCAAGAAACTGAAGAGTGTGAAAGAGCTGCTGGGGATCACCATCATGGAAAGAAGCAGCTTCG
AGAAGAATCCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGGCCTCTGCC
GGCGAACTGCAGAAGGGAAACGAACTGGCCCTGCCCTCCAAATATGTGAACTTCCTGTACCTGG
CCAGCCACTATGAGAAGCTGAAGGGCTCCCCCGAGGATAATGAGCAGAAACAGCTGTTTGTGGA
ACAGCACAAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAAGCCCATCA
GAGAGCAGGCCGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGTGCTGGACGCC
ACCCTGATCCACCAGAGCATCACCGGCCTGTACGAGACACGGATCGACCTGTCTCAGCTGGGAG
GCGAC 3.2.2 NLS

GGACCTAAGAAAAAGAGGAAGGTGGCGGCCGCT

CCTTCAGGGCAGATCAGCAACCAGGCCCTGGCTCTGGCCCCTAGCTCCGCTCCAGTGCTGGCCC
AGACTATGGTGCCCTCTAGTGCTATGGTGCCTCTGGCCCAGCCACCTGCTCCAGCCCCTGTGCT
GACCCCAGGACCACCCCAGTCACTGAGCGCTCCAGTGCCCAAGTCTACACAGGCCGGCGAGGGG
ACTCTGAGTGAAGCTCTGCTGCACCTGCAGTTCGACGCTGATGAGGACCTGGGAGCTCTGCTGG
GGAACAGCACCGATCCCGGAGTGTTCACAGATCTGGCCTCCGTGGACAACTCTGAGTTTCAGCA
GCTGCTGAATCAGGGCGTGTCCATGTCTCATAGTACAGCCGAACCAATGCTGATGGAGTACCCC
GAAGCCATTACCCGGCTGGTGACCGGCAGCCAGCGGCCCCCCGACCCCGCTCCAACTCCCCTGG
GAACCAGCGGCCTGCCTAATGGGCTGTCCGGAGATGAAGACTTCTCAAGCATCGCTGATATGGA
CTTTAGTGCCCTGCTGTCACAGATTTCCTCTAGTGGGCAG

4     Lentiviral Vectors

4.1   pFUGW-EF1α-NLS(SV40)-dCas9(N863)-NLS-VP64-P2A-Blast

TGCAAAGATGGATAAAGTTTTAAACAGAGAGGAATCTTTGCAGCTAATGGACCTTCTAGGTCTT
GAAAGGAGTGGGAATTGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGGGGTAAACT
GGGAAAGTGATGTCGTGTACTGGCTCCGCCTTTTCCCGAGGGTGGGGGAGAACCGTATATAAG
TGCAGTAGTCGCCGTGAACGTTCTTTTTCGCAACGGGTTTGCCGCCAGAACACAGGTAAGTGCC
GTGTGTGGTTCCCGCGGGCCTGGCCTCTTTACGGGTTATGGCCCTTGCGTGCCTTGAATTACTT
CCACTGGCTGCAGTACGTGATTCTTGATCCCGAGCTTCGGGTTGGAAGTGGGTGGGAGAGTTCG
AGGCCTTGCGCTTAAGGAGCCCCTTCGCCTCGTGCTTGAGTTGAGGCCTGGCCTGGGCGCTGGG
GCCGCCGCGTGCGAATCTGGTGGCACCTTCGCGCCTGTCTCGCTGCTTTCGATAAGTCTCTAGC
CATTTAAAATTTTTGATGACCTGCTGCGACGCTTTTTTTCTGGCAAGATAGTCTTGTAAATGCG
GGCCAAGATCTGCACACTGGTATTTCGGTTTTGGGGCCGCGGGCGGCGACGGGGCCCGTGCGT
CCCAGCGCACATGTTCGGCGAGGCGGGGCCTGCGAGCGCGGCCACCGAGAATCGGACGGGGGTA
GTCTCAAGCTGGCCGGCCTGCTCTGGTGCCTGGCCTCGCGCCGCCGTGTATCGCCCCGCCCTGG
GCGGCAAGGCTGGCCCGGTCGGCACCAGTTGCGTGAGCGGAAAGATGGCCGCTTCCCGGCCCTG
CTGCAGGGAGCTCAAAATGGAGGACGCGGCGCTCGGGAGAGCGGGCGGGTGAGTCACCCACACA
AAGGAAAAGGGCCTTTCCGTCCTCAGCCGTCGCTTCATGTGACTCCACGGAGTACCGGGCGCCG
TCCAGGCACCTCGATTAGTTCTCGAGCTTTTGGAGTACGTCGTCTTTAGGTTGGGGGGAGGGGT
TTTATGCGATGGAGTTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATTCTCAAGCCTCAG

FIG. 37P

```
ACAGTGGTTCAAAGTTTTTTTCTTCCATTTCAGGTGTCGTGACGTACGGCCACCCATGAGCCCC
AAGAAGAAGAGAAAGGTGGAGGCCAGCGACAAGAAGTACAGCATCGGCCTGGCCATCGGCACCA
ACTCTGTGGGCTGGGCCGTGATCACCGACGAGTACAAGGTGCCCAGCAAGAAATTCAAGGTGCT
GGGCAACACCGACCGGCACAGCATCAAGAAGAACCTGATCGGAGCCCTGCTGTTCGACAGCGGC
GAAACAGCCGAGGCCACCCGGCTGAAGAGAACCGCCAGAAGAAGATACACCAGACGGAAGAACC
GGATCTGCTATCTGCAAGAGATCTTCAGCAACGAGATGGCCAAGGTGGACGACAGCTTCTTCCA
CAGACTGGAAGAGTCCTTCCTGGTGGAAGAGGATAAGAAGCACGAGCGGCACCCCATCTTCGGC
AACATCGTGGACGAGGTGGCCTACCACGAGAAGTACCCCACCATCTACCACCTGAGAAAGAAAC
TGGTGGACAGCACCGACAAGGCCGACCTGCGGCTGATCTATCTGGCCCTGGCCCACATGATCAA
GTTCCGGGGCCACTTCCTGATCGAGGGCGACCTGAACCCCGACAACAGCGACGTGGACAAGCTG
TTCATCCAGCTGGTGCAGACCTACAACCAGCTGTTCGAGGAAAACCCCATCAACGCCAGCGGCG
TGGACGCCAAGGCCATCCTGTCTGCCAGACTGAGCAAGAGCAGACGGCTGGAAAATCTGATCGC
CCAGCTGCCCGGCGAGAAGAAGAATGGCCTGTTCGGCAACCTGATTGCCCTGAGCCTGGGCCTG
ACCCCCAACTTCAAGAGCAACTTCGACCTGGCCGAGGATGCCAAACTGCAGCTGAGCAAGGACA
CCTACGACGACGACCTGGACAACCTGCTGGCCCAGATCGGCGACCAGTACGCCGACCTGTTTCT
GGCCGCCAAGAACCTGTCCGACGCCATCCTGCTGAGCGACATCCTGAGAGTGAACACCGAGATC
ACCAAGGCCCCCCTGAGCGCCTCTATGATCAAGAGATACGACGAGCACCACCAGGACCTGACCC
TGCTGAAAGCTCTCGTGCGGCAGCAGCTGCCTGAGAAGTACAAAGAGATTTTCTTCGACCAGAG
CAAGAACGGCTACGCCGGCTACATTGACGGCGGAGCCAGCCAGGAAGAGTTCTACAAGTTCATC
AAGCCCATCCTGGAAAAGATGGACGGCACCGAGGAACTGCTCGTGAAGCTGAACAGAGAGGACC
TGCTGCGGAAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGGAAAAGATC
GAGAAGATCCTGACCTTCCGCATCCCCTACTACGTGGGCCCTCTGGCCAGGGGAAACAGCAGAT
TCGCCTGGATGACCAGAAAGAGCGAGGAAACCATCACCCCCTGGAACTTCGAGGAAGTGGTGGA
CAAGGGCGCTTCCGCCCAGAGCTTCATCGAGCGGATGACCAACTTCGATAAGAACCTGCCCAAC
GAGAAGGTGCTGCCCAAGCACAGCCTGCTGTACGAGTACTTCACCGTGTATAACGAGCTGACCA
AAGTGAAATACGTGACCGAGGGAATGAGAAAGCCCGCCTTCCTGAGCGGCGAGCAGAAAAAGGC
CATCGTGGACCTGCTGTTCAAGACCAACCGGAAAGTGACCGTGAAGCAGCTGAAAGAGGACTAC
TTCAAGAAAATCGAGTGCTTCGACTCCGTGGAAATCTCCGGCGTGGAAGATCGGTTCAACGCCT
CCCTGGGCACATACCACGATCTGCTGAAAATTATCAAGGACAAGGACTTCCTGGACAATGAGGA
AAACGAGGACATTCTGGAAGATATCGTGCTGACCCTGACACTGTTTGAGGACAGAGAGATGATC
GAGGAACGGCTGAAAACCTATGCCCACCTGTTCGACGACAAAGTGATGAAGCAGCTGAAGCGGC
GGAGATACACCGGCTGGGGCAGGCTGAGCCGGAAGCTGATCAACGGCATCCGGGACAAGCAGTC
CGGCAAGACAATCCTGGATTTCCTGAAGTCCGACGGCTTCGCCAACAGAAACTTCATGCAGCTG
ATCCACGACGACAGCCTGACCTTTAAAGAGGACATCCAGAAAGCCCAGGTGTCCGGCCAGGGCG
ATAGCCTGCACGAGCACATTGCCAATCTGGCCGGCAGCCCCGCCATTAAGAAGGGCATCCTGCA
```

FIG. 37Q

```
GACAGTGAAGGTGGTGGACGAGCTCGTGAAAGTGATGGGCCGGCACAAGCCCGAGAACATCGTG
ATCGAAATGGCCAGAGAGAACCAGACCACCCAGAAGGGACAGAAGAACAGCCGCGAGAGAATGA
AGCGGATCGAAGAGGGCATCAAAGAGCTGGGCAGCCAGATCCTGAAAGAACACCCCGTGGAAAA
CACCCAGCTGCAGAACGAGAAGCTGTACCTGTACTACCTGCAGAATGGGCGGGATATGTACGTG
GACCAGGAACTGGACATCAACCGGCTGTCCGACTACGATGTGGACCACATCGTGCCTCAGAGCT
TTCTGAAGGACGACTCCATCGACAACAAGGTGCTGACCAGAAGCGACAAGGCCCGGGGCAAGAG
CGACAACGTGCCCTCCGAAGAGGTCGTGAAGAAGATGAAGAACTACTGGCGGCAGCTGCTGAAC
GCCAAGCTGATTACCCAGAGAAAGTTCGACAATCTGACCAAGGCCGAGAGAGGCGGCCTGAGCG
AACTGGATAAGGCCGGCTTCATCAAGAGACAGCTGGTGGAAACCCGGCAGATCACAAAGCACGT
GGCACAGATCCTGGACTCCCGGATGAACACTAAGTACGACGAGAATGACAAGCTGATCCGGGAA
GTGAAAGTGATCACCCTGAAGTCCAAGCTGGTGTCCGATTTCCGGAAGGATTTCCAGTTTTACA
AAGTGCGCGAGATCAACAACTACCACCACGCCCACGACGCCTACCTGAACGCCGTCGTGGGAAC
CGCCCTGATCAAAAAGTACCCTAAGCTGGAAAGCGAGTTCGTGTACGGCGACTACAAGGTGTAC
GACGTGCGGAAGATGATCGCCAAGAGCGAGCAGGAAATCGGCAAGGCTACCGCCAAGTACTTCT
TCTACAGCAACATCATGAACTTTTTCAAGACCGAGATTACCCTGGCCAACGGCGAGATCCGGAA
GCGGCCTCTGATCGAGACAAACGGCGAAACCGGGGAGATCGTGTGGGATAAGGGCCGGGATTTT
GCCACCGTGCGGAAAGTGCTGAGCATGCCCCAAGTGAATATCGTGAAAAAGACCGAGGTGCAGA
CAGGCGGCTTCAGCAAAGAGTCTATCCTGCCCAAGAGGAACAGCGATAAGCTGATCGCCAGAAA
GAAGGACTGGGACCCTAAGAAGTACGGCGGCTTCGACAGCCCCACCGTGGCCTATTCTGTGCTG
GTGGTGGCCAAAGTGGAAAAGGGCAAGTCCAAGAAACTGAAGAGTGTGAAAGAGCTGCTGGGA
TCACCATCATGGAAAGAAGCAGCTTCGAGAAGAATCCCATCGACTTTCTGGAAGCCAAGGGCTA
CAAAGAAGTGAAAAAGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGAACTGGCCCTGCCCT
CCAAATATGTGAACTTCCTGTACCTGGCCAGCCACTATGAGAAGCTGAAGGGCTCCCCCGAGGA
TAATGAGCAGAAACAGCTGTTTGTGGAACAGCACAAGCACTACCTGGACGAGATCATCGAGCAG
ATCAGCGAGTTCTCCAAGAGAGTGATCCTGGCCGACGCTAATCTGGACAAAGTGCTGTCCGCCT
ACAACAAGCACCGGGATAAGCCCATCAGAGAGCAGGCCGAGAATATCATCCACCTGTTTACCCT
GACCAATCTGGGAGCCCCTGCCGCCTTCAAGTACTTTGACACCACCATCGACCGGAAGAGGTAC
ACCAGCACCAAAGAGGTGCTGGACGCCACCCTGATCCACCAGAGCATCACCGGCCTGTACGAGA
CACGGATCGACCTGTCTCAGCTGGGAGGCGACAGCGCTGGAGGAGGTGGAAGCGGAGGAGGAGG
AAGCGGAGGAGGAGGTAGCGGACCTAAGAAAAAGAGGAAGGTGGCGGCCGCTGGATCCGGACGG
GCTGACGCATTGGACGATTTTGATCTGGATATGCTGGGAAGTGACGCCCTCGATGATTTTGACC
TTGACATGCTTGGTTCGGATGCCCTTGATGACTTTGACCTCGACATGCTCGGCAGTGACGCCCT
TGATGATTTCGACCTGGACATGCTGATTAACTGTACAGGCAGTGGAGAGGGCAGAGGAAGTCTG
CTAACATGCGGTGACGTCGAGGAGAATCCTGGCCCAATGGCCAAGCCTTTGTCTCAAGAAGAAT
CCACCCTCATTGAAGAGCAACGGCTACAATCAACAGCATCCCCATCTCTGAAGACTACAGCGT
```

FIG. 37R

CGCCAGCGCAGCTCTCTCTAGCGACGGCCGCATCTTCACTGGTGTCAATGTATATCATTTTACT
GGGGGACCTTGTGCAGAACTCGTGGTGCTGGGCACTGCTGCTGCTGCGGCAGCTGGCAACCTGA
CTTGTATCGTCGCGATCGGAAATGAGAACAGGGGCATCTTGAGCCCCTGCGGACGGTGCCGACA
GGTGCTTCTCGATCTGCATCCTGGGATCAAAGCCATAGTGAAGGACAGTGATGGACAGCCGACG
GCAGTTGGGATTCGTGAATTGCTGCCCTCTGGTTATGTGTGGGAGGGCTAA

4.1.1 EF1α

TGCAAAGATGGATAAAGTTTTAAACAGAGAGGAATCTTTGCAGCTAATGGACCTTCTAGGTCTT
GAAAGGAGTGGGAATTGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGGGGTAAACT
GGGAAAGTGATGTCGTGTACTGGCTCCGCCTTTTTCCCGAGGGTGGGGGAGAACCGTATATAAG
TGCAGTAGTCGCCGTGAACGTTCTTTTTCGCAACGGGTTTGCCGCCAGAACACAGGTAAGTGCC
GTGTGTGGTTCCGCGGGCCTGGCCTCTTTACGGGTTATGGCCCTTGCGTGCCTTGAATTACTT
CCACTGGCTGCAGTACGTGATTCTTGATCCCGAGCTTCGGGTTGGAAGTGGGTGGGAGAGTTCG
AGGCCTTGCGCTTAAGGAGCCCCTTCGCCTCGTGCTTGAGTTGAGGCCTGGCCTGGGCGCTGGG
GCCGCCGCGTGCGAATCTGGTGGCACCTTCGCGCCTGTCTCGCTGCTTTCGATAAGTCTCTAGC
CATTTAAAATTTTTGATGACCTGCTGCGACGCTTTTTTTCTGGCAAGATAGTCTTGTAAATGCG
GGCCAAGATCTGCACACTGGTATTTCGGTTTTTGGGGCCGCGGGCGGCGACGGGGCCCGTGCGT
CCCAGCGCACATGTTCGGCGAGGCGGGGCCTGCGAGCGCGGCCACCGAGAATCGGACGGGGGTA
GTCTCAAGCTGGCCGGCCTGCTCTGGTGCCTGGCCTCGCGCCGCCGTGTATCGCCCCGCCCTGG
GCGGCAAGGCTGGCCCGGTCGGCACCAGTTGCGTGAGCGGAAAGATGGCCGCTTCCCGGCCCTG
CTGCAGGGAGCTCAAAATGGAGGACGCGGCGCTCGGGAGAGCGGGCGGGTGAGTCACCCACACA
AAGGAAAAGGGCCTTTCCGTCCTCAGCCGTCGCTTCATGTGACTCCACGGAGTACCGGGCGCCG
TCCAGGCACCTCGATTAGTTCTCGAGCTTTTGGAGTACGTCGTCTTTAGGTTGGGGGAGGGGT
TTTATGCGATGGAGTTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATTCTCAAGCCTCAG
ACAGTGGTTCAAAGTTTTTTCTTCCATTTCAGGTGTCGTGA

4.1.2 NLS(SV40)

ATGAGCCCCAAGAAGAAGAGAAAGGTGGAGGCCAGC

FIG. 37S

4.1.3 dCas9(N863)

```
GACAAGAAGTACAGCATCGGCCTGGCCATCGGCACCAACTCTGTGGGCTGGGCCGTGATCACCG
ACGAGTACAAGGTGCCCAGCAAGAAATTCAAGGTGCTGGGCAACACCGACCGGCACAGCATCAA
GAAGAACCTGATCGGAGCCCTGCTGTTCGACAGCGGCGAAACAGCCGAGGCCACCCGGCTGAAG
AGAACCGCCAGAAGAAGATACACCAGACGGAAGAACCGGATCTGCTATCTGCAAGAGATCTTCA
GCAACGAGATGGCCAAGGTGGACGACAGCTTCTTCCACAGACTGGAAGAGTCCTTCCTGGTGGA
AGAGGATAAGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACAAGGCCGACC
TGCGGCTGATCTATCTGGCCCTGGCCCACATGATCAAGTTCCGGGGCCACTTCCTGATCGAGGG
CGACCTGAACCCCGACAACAGCGACGTGGACAAGCTGTTCATCCAGCTGGTGCAGACCTACAAC
CAGCTGTTCGAGGAAAACCCCATCAACGCCAGCGGCGTGGACGCCAAGGCCATCCTGTCTGCCA
GACTGAGCAAGAGCAGACGGCTGGAAAATCTGATCGCCCAGCTGCCCGGCGAGAAGAAGAATGG
CCTGTTCGGCAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGC
TGGCCCAGATCGGCGACCAGTACGCCGACCTGTTTCTGGCCGCCAAGAACCTGTCCGACGCCAT
CCTGCTGAGCGACATCCTGAGAGTGAACACCGAGATCACCAAGGCCCCCCTGAGCGCCTCTATG
ATCAAGAGATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGCTACATTGA
CGGCGGAGCCAGCCAGGAAGAGTTCTACAAGTTCATCAAGCCCATCCTGGAAAAGATGGACGGC
ACCGAGGAACTGCTCGTGAAGCTGAACAGAGAGGACCTGCTGCGGAAGCAGCGGACCTTCGACA
ACGGCAGCATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGAAAGAGCGAGG
AAACCATCACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGCACAGCCTG
CTGTACGAGTACTTCACCGTGTATAACGAGCTGACCAAAGTGAAATACGTGACCGAGGGAATGA
GAAAGCCCGCCTTCCTGAGCGGCGAGCAGAAAAAGGCCATCGTGGACCTGCTGTTCAAGACCAA
CCGGAAAGTGACCGTGAAGCAGCTGAAAGAGGACTACTTCAAGAAAATCGAGTGCTTCGACTCC
GTGGAAATCTCCGGCGTGGAAGATCGGTTCAACGCCTCCCTGGGCACATACCACGATCTGCTGA
AAATTATCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGGCAGGCTGA
GCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATC
```

FIG. 37T

```
TGGCCGGCAGCCCCGCCATTAAGAAGGGCATCCTGCAGACAGTGAAGGTGGTGGACGAGCTCGT
GAAAGTGATGGGCCGGCACAAGCCCGAGAACATCGTGATCGAAATGGCCAGAGAGAACCAGACC
ACCCAGAAGGGACAGAAGAACAGCCGCGAGAGAATGAAGCGGATCGAAGAGGGCATCAAAGAGC
TGGGCAGCCAGATCCTGAAAGAACACCCCGTGGAAAACACCCAGCTGCAGAACGAGAAGCTGTA
CCTGTACTACCTGCAGAATGGGCGGGATATGTACGTGGACCAGGAACTGGACATCAACCGGCTG
TCCGACTACGATGTGGACCACATCGTGCCTCAGAGCTTTCTGAAGGACGACTCCATCGACAACA
AGGTGCTGACCAGAAGCGACAAGGCCCGGGGCAAGAGCGACAACGTGCCCTCCGAAGAGGTCGT
GAAGAAGATGAAGAACTACTGGCGGCAGCTGCTGAACGCCAAGCTGATTACCCAGAGAAAGTTC
GACAATCTGACCAAGGCCGAGAGAGGCGGCCTGAGCGAACTGGATAAGGCCGGCTTCATCAAGA
GACAGCTGGTGGAAACCCGGCAGATCACAAAGCACGTGGCACAGATCCTGGACTCCCGGATGAA
CACTAAGTACGACGAGAATGACAAGCTGATCCGGGAAGTGAAAGTGATCACCCTGAAGTCCAAG
CTGGTGTCCGATTTCCGGAAGGATTTCCAGTTTTACAAAGTGCGCGAGATCAACAACTACCACC
ACGCCCACGACGCCTACCTGAACGCCGTCGTGGGAACCGCCCTGATCAAAAAGTACCCTAAGCT
GGAAAGCGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACAAACGGCGA
AACCGGGGAGATCGTGTGGGATAAGGGCCGGGATTTTGCCACCGTGCGGAAAGTGCTGAGCATG
CCCCAAGTGAATATCGTGAAAAAGACCGAGGTGCAGACAGGCGGCTTCAGCAAAGAGTCTATCC
TGCCCAAGAGGAACAGCGATAAGCTGATCGCCAGAAAGAAGGACTGGACCCTAAGAAGTACGG
CGGCTTCGACAGCCCCACCGTGGCCTATTCTGTGCTGGTGGTGGCCAAAGTGGAAAAGGGCAAG
TCCAAGAAACTGAAGAGTGTGAAAGAGCTGCTGGGGATCACCATCATGGAAAGAAGCAGCTTCG
AGAAGAATCCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGGCCTCTGCC
GGCGAACTGCAGAAGGGAAACGAACTGGCCCTGCCCTCCAAATATGTGAACTTCCTGTACCTGG
CCAGCCACTATGAGAAGCTGAAGGGCTCCCCCGAGGATAATGAGCAGAAACAGCTGTTTGTGGA
ACAGCACAAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAAGCCCATCA
GAGAGCAGGCCGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGTGCTGGACGCC
ACCCTGATCCACCAGAGCATCACCGGCCTGTACGAGACACGGATCGACCTGTCTCAGCTGGGAG
GCGAC
```

4.1.4 NLS

```
GGACCTAAGAAAAAGAGGAAGGTGGCGGCCGCT
```

GGACGGGCTGACGCATTGGACGATTTTGATCTGGATATGCTGGGAAGTGACGCCCTCGATGATT
TTGACCTTGACATGCTTGGTTCGGATGCCCTTGATGACTTTGACCTCGACATGCTCGGCAGTGA
CGCCCTTGATGATTTCGACCTGGACATGCTGATTAAC

4.1.6 P2A

GGCAGTGGAGAGGGCAGAGGAAGTCTGCTAACATGCGGTGACGTCGAGGAGAATCCTGGCCCA

4.1.7 Blast

ATGGCCAAGCCTTTGTCTCAAGAAGAATCCACCCTCATTGAAAGAGCAACGGCTACAATCAACA
GCATCCCCATCTCTGAAGACTACAGCGTCGCCAGCGCAGCTCTCTCTAGCGACGGCCGCATCTT
CACTGGTGTCAATGTATATCATTTTACTGGGGGACCTTGTGCAGAACTCGTGGTGCTGGGCACT
GCTGCTGCTGCGGCAGCTGGCAACCTGACTTGTATCGTCGCGATCGGAAATGAGAACAGGGGCA
TCTTGAGCCCCTGCGGACGGTGCCGACAGGTGCTTCTCGATCTGCATCCTGGGATCAAAGCCAT
AGTGAAGGACAGTGATGGACAGCCGACGGCAGTTGGGATTCGTGAATTGCTGCCCTCTGGTTAT
GTGTGGGAGGGCTAA

4.2  pFUGW-EF1α-MS2-NLS-p65-HSF1-P2A-Hygro

TGCAAAGATGGATAAAGTTTTAAACAGAGAGGAATCTTTGCAGCTAATGGACCTTCTAGGTCTT
GAAAGGAGTGGGAATTGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGGGGTAAACT
GGGAAAGTGATGTCGTGTACTGGCTCCGCCTTTTCCCGAGGGTGGGGGAGAACCGTATATAAG
TGCAGTAGTCGCCGTGAACGTTCTTTTTCGCAACGGGTTTGCCGCCAGAACACAGGTAAGTGCC
GTGTGTGGTTCCCGCGGGCCTGGCCTCTTTACGGGTTATGGCCCTTGCGTGCCTTGAATTACTT
CCACCTGGCTGCAGTACGTGATTCTTGATCCCGAGCTTCGGGTTGGAAGTGGGTGGGAGAGTTC
GAGGCCTTGCGCTTAAGGAGCCCCTTCGCCTCGTGCTTGAGTTGAGGCCTGGCCTGGGCGCTGG
GGCCGCCGCGTGCGAATCTGGTGGCACCTTCGCGCCTGTCTCGCTGCTTTCGATAAGTCTCTAG
CCATTTAAAATTTTTGATGACCTGCTGCGACGCTTTTTTTCTGGCAAGATAGTCTTGTAAATGC
GGGCCAAGATCTGCACACTGGTATTTCGGTTTTTGGGGCCGCGGGCGGCGACGGGCCCGTGCG
TCCCAGCGCACATGTTCGGCGAGGCGGGGCCTGCGAGCGCGGCCACCGAGAATCGGACGGGGGT
AGTCTCAAGCTGGCCGGCCTGCTCTGGTGCCTGGCCTCGCGCCGCCGTGTATCGCCCCGCCCTG
GGCGGCAAGGCTGGCCCGGTCGGCACCAGTTGCGTGAGCGGAAAGATGGCCGCTTCCCGGCCCT
GCTGCAGGGAGCTCAAAATGGAGGACGCGGCGCTCGGGAGAGCGGGCGGGTGAGTCACCCACAC

FIG. 37V

```
AAAGGAAAAGGGCCTTTCCGTCCTCAGCCGTCGCTTCATGTGACTCCACGGAGTACCGGGCGCC
GTCCAGGCACCTCGATTAGTTCTCGAGCTTTTGGAGTACGTCGTCTTTAGGTTGGGGGGAGGGG
TTTTATGCGATGGAGTTTCCCCACACTGAGTGGGTGGAGACTGAAGTTAGGCCAGCTTGGCACT
TGATGTAATTCTCCTTGGAATTTGCCCTTTTTGAGTTTGGATCTTGGTTCATTCTCAAGCCTCA
GACAGTGGTTCAAAGTTTTTTTCTTCCATTTCAGGTGTCGTGACGTACGGCCACCATGGCTTCA
AACTTTACTCAGTTCGTGCTCGTGGACAATGGTGGGACAGGGGATGTGACAGTGGCTCCTTCTA
ATTTCGCTAATGGGGTGGCAGAGTGGATCAGCTCCAACTCACGGAGCCAGGCCTACAAGGTGAC
ATGCAGCGTCAGGCAGTCTAGTGCCCAGAAGAGAAAGTATACCATCAAGGTGGAGGTCCCCAAA
GTGGCTACCCAGACAGTGGGCGGAGTCGAACTGCCTGTCGCCGCTTGGAGGTCCTACCTGAACA
TGGAGCTCACTATCCCAATTTTCGCTACCAATTCTGACTGTGAACTCATCGTGAAGGCAATGCA
GGGGCTCCTCAAAGACGGTAATCCTATCCCTTCCGCCATCGCCGCTAACTCAGGTATCTACAGC
GCTGGAGGAGGTGGAAGCGGAGGAGGAGGAAGCGGAGGAGGAGGTAGCGGACCTAAGAAAAGA
GGAAGGTGGCGGCCGCTGGATCCCCTTCAGGGCAGATCAGCAACCAGGCCCTGGCTCTGGCCCC
TAGCTCCGCTCCAGTGCTGGCCCAGACTATGGTGCCCTCTAGTGCTATGGTGCCTCTGGCCCAG
CCACCTGCTCCAGCCCCTGTGCTGACCCCAGGACCACCCCAGTCACTGAGCGCTCCAGTGCCCA
AGTCTACACAGGCCGGCGAGGGGACTCTGAGTGAAGCTCTGCTGCACCTGCAGTTCGACGCTGA
TGAGGACCTGGGAGCTCTGCTGGGGAACAGCACCGATCCCGGAGTGTTCACAGATCTGGCCTCC
GTGGACAACTCTGAGTTTCAGCAGCTGCTGAATCAGGGCGTGTCCATGTCTCATAGTACAGCCG
AACCAATGCTGATGGAGTACCCCGAAGCCATTACCCGGCTGGTGACCGGCAGCCAGCGGCCCCC
CGACCCCGCTCCAACTCCCCTGGGAACCAGCGGCCTGCCTAATGGGCTGTCCGGAGATGAAGAC
TTCTCAAGCATCGCTGATATGGACTTTAGTGCCCTGCTGTCACAGATTTCCTCTAGTGGGCAGG
GAGGAGGTGGAAGCGGCTTCAGCGTGGACACCAGTGCCCTGCTGGACCTGTTCAGCCCCTCGGT
GACCGTGCCCGACATGAGCCTGCCTGACCTTGACAGCAGCCTGGCCAGTATCCAAGAGCTCCTG
TCTCCCCAGGAGCCCCCCAGGCCTCCCGAGGCAGAGAACAGCAGCCCGGATTCAGGGAAGCAGC
TGGTGCACTACACAGCGCAGCCGCTGTTCCTGCTGGACCCCGGCTCCGTGGACACCGGGAGCAA
CGACCTGCCGGTGCTGTTTGAGCTGGGAGAGGGCTCCTACTTCTCCGAAGGGGACGGCTTCGCC
GAGGACCCCACCATCTCCCTGCTGACAGGCTCGGAGCCTCCCAAAGCCAAGGACCCCACTGTCT
CCTGTACAGGCAGTGGAGAGGGCAGAGGAAGTCTGCTAACATGCGGTGACGTCGAGGAGAATCC
TGGCCCAACCATGAAAAGCCTGAACTCACCGCTACCTCTGTCGAGAAGTTTCTGATCGAAAAG
TTCGACAGCGTCTCCGACCTGATGCAGCTCTCCGAGGGCGAAGAATCTCGGGCTTTCAGCTTCG
ATGTGGAGGGCGTGGATATGTCCTGCGGGTGAATAGCTGCGCCGATGGTTTCTACAAAGATCG
CTATGTTTATCGGCACTTTGCATCCGCCGCTCTCCCTATTCCCGAAGTGCTTGACATTGGGGAG
TTCAGCGAGAGCCTGACCTATTGCATCTCCCGCCGTGCACAGGGTGTCACCTTGCAAGACCTGC
CTGAAACCGAACTGCCCGCTGTTCTCCAGCCCGTCGCCGAGGCCATGGATGCCATCGCTGCCGC
CGATCTTAGCCAGACCAGCGGGTTCGGCCCATTCGGACCTCAAGGAATCGGTCAATACACTACA
TGGCGCGATTTCATCTGCGCTATTGCTGATCCCCATGTGTATCACTGGCAAACTGTGATGGACG
```

FIG. 37W

ACACCGTCAGTGCCTCCGTCGCCCAGGCTCTCGATGAGCTGATGCTTTGGGCCGAGGACTGCCC
CGAAGTCCGGCACCTCGTGCACGCCGATTTCGGCTCCAACAATGTCCTGACCGACAATGGCCGC
ATAACAGCCGTCATTGACTGGAGCGAGGCCATGTTCGGGATTCCCAATACGAGGTCGCCAACA
TCTTCTTCTGGAGGCCCTGGTTGGCTTGTATGGAGCAGCAGACCGCTACTTCGAGCGGAGGCA
TCCCGAGCTTGCAGGATCTCCTCGGCTCCGGGCTTATATGCTCCGCATTGGTCTTGACCAACTC
TATCAGAGCTTGGTTGACGGCAATTTCGATGATGCAGCTTGGGCTCAGGGTCGCTGCGACGCAA
TCGTCCGGTCCGGAGCCGGGACTGTCGGGCGTACACAAATCGCCCGCAGAAGCGCTGCCGTCTG
GACCGATGGCTGTGTGGAAGTGCTCGCCGATAGTGGAAACAGACGCCCAGCACTCGTCCTAGG
GCAAAGGATCTGCAGTAATGA

4.2.1 EF1α

TGCAAAGATGGATAAAGTTTTAAACAGAGAGGAATCTTTGCAGCTAATGGACCTTCTAGGTCTT
GAAAGGAGTGGGAATTGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGGGGTAAACT
GGGAAAGTGATGTCGTGTACTGGCTCCGCCTTTTTCCCGAGGGTGGGGGAGAACCGTATATAAG
TGCAGTAGTCGCCGTGAACGTTCTTTTTCGCAACGGGTTTGCCGCCAGAACACAGGTAAGTGCC
GTGTGTGGTTCCCGCGGGCCTGGCCTCTTTACGGGTTATGGCCCTTGCGTGCCTTGAATTACTT
CCACCTGGCTGCAGTACGTGATTCTTGATCCCGAGCTTCGGGTTGGAAGTGGGTGGGAGAGTTC
GAGGCCTTGCGCTTAAGGAGCCCCTTCGCCTCGTGCTTGAGTTGAGGCCTGGCCTGGGCGCTGG
GGCCGCCGCGTGCGAATCTGGTGGCACCTTCGCGCCTGTCTCGCTGCTTTCGATAAGTCTCTAG
CCATTTAAAATTTTTGATGACCTGCTGCGACGCTTTTTTTCTGGCAAGATAGTCTTGTAAATGC
GGGCCAAGATCTGCACACTGGTATTTCGGTTTTTGGGGCCGCGGGCGGCGACGGGGCCCGTGCG
TCCCAGCGCACATGTTCGGCGAGGCGGGGCCTGCGAGCGCGGCCACCGAGAATCGGACGGGGGT
AGTCTCAAGCTGGCCGGCCTGCTCTGGTGCCTGGCCTCGCGCCGCCGTGTATCGCCCCGCCCTG
GGCGGCAAGGCTGGCCCGGTCGGCACCAGTTGCGTGAGCGGAAAGATGGCCGCTTCCCGGCCCT
GCTGCAGGGAGCTCAAAATGGAGGACGCGGCGCTCGGGAGAGCGGGCGGGTGAGTCACCCACAC
AAAGGAAAAGGGCCTTTCCGTCCTCAGCCGTCGCTTCATGTGACTCCACGGAGTACCGGGCGCC
GTCCAGGCACCTCGATTAGTTCTCGAGCTTTTGGAGTACGTCGTCTTTAGGTTGGGGGAGGGG
TTTTATGCGATGGAGTTTCCCCACACTGAGTGGGTGGAGACTGAAGTTAGGCCAGCTTGGCACT
TGATGTAATTCTCCTTGGAATTTGCCCTTTTTGAGTTTGGATCTTGGTTCATTCTCAAGCCTCA
GACAGTGGTTCAAAGTTTTTTTCTTCCATTTCAGGTGTCGTGA

ATGGCTTCAAACTTTACTCAGTTCGTGCTCGTGGACAATGGTGGGACAGGGGATGTGACAGTGG
CTCCTTCTAATTTCGCTAATGGGGTGGCAGAGTGGATCAGCTCCAACTCACGGAGCCAGGCCTA
CAAGGTGACATGCAGCGTCAGGCAGTCTAGTGCCCAGAAGAGAAAGTATACCATCAAGGTGGAG
GTCCCCAAAGTGGCTACCCAGACAGTGGGCGGAGTCGAACTGCCTGTCGCCGCTTGGAGGTCCT
ACCTGAACATGGAGCTCACTATCCCAATTTTCGCTACCAATTCTGACTGTGAACTCATCGTGAA
GGCAATGCAGGGGCTCCTCAAAGACGGTAATCCTATCCCTTCCGCCATCGCCGCTAACTCAGGT
ATCTAC

4.2.3 NLS

GGACCTAAGAAAAAGAGGAAGGTGGCGGCCGCT

4.2.4 p65

CCTTCAGGGCAGATCAGCAACCAGGCCCTGGCTCTGGCCCCTAGCTCCGCTCCAGTGCTGGCCC
AGACTATGGTGCCCTCTAGTGCTATGGTGCCTCTGGCCCAGCCACCTGCTCCAGCCCCTGTGCT
GACCCCAGGACCACCCCAGTCACTGAGCGCTCCAGTGCCCAAGTCTACACAGGCCGGCGAGGGG
ACTCTGAGTGAAGCTCTGCTGCACCTGCAGTTCGACGCTGATGAGGACCTGGGAGCTCTGCTGG
GGAACAGCACCGATCCCGGAGTGTTCACAGATCTGGCCTCCGTGGACAACTCTGAGTTTCAGCA
GCTGCTGAATCAGGGCGTGTCCATGTCTCATAGTACAGCCGAACCAATGCTGATGGAGTACCCC
GAAGCCATTACCCGGCTGGTGACCGGCAGCCAGCGGCCCCCCGACCCCGCTCCAACTCCCCTGG
GAACCAGCGGCCTGCCTAATGGGCTGTCCGGAGATGAAGACTTCTCAAGCATCGCTGATATGGA
CTTTAGTGCCCTGCTGTCACAGATTTCCTCTAGTGGGCAG

4.2.5 HSF1

GGCTTCAGCGTGGACACCAGTGCCCTGCTGGACCTGTTCAGCCCCTCGGTGACCGTGCCCGACA
TGAGCCTGCCTGACCTTGACAGCAGCCTGGCCAGTATCCAAGAGCTCCTGTCTCCCAGGAGCC
CCCCAGGCCTCCCGAGGCAGAGAACAGCAGCCCGGATTCAGGGAAGCAGCTGGTGCACTACACA
GCGCAGCCGCTGTTCCTGCTGGACCCCGGCTCCGTGGACACCGGGAGCAACGACCTGCCGGTGC
TGTTTGAGCTGGGAGAGGGCTCCTACTTCTCCGAAGGGGACGGCTTCGCCGAGGACCCCACCAT
CTCCCTGCTGACAGGCTCGGAGCCTCCCAAAGCCAAGGACCCCACTGTCTCC

GGCAGTGGAGAGGGCAGAGGAAGTCTGCTAACATGCGGTGACGTCGAGGAGAATCCTGGCCCA

4.2.7 Hygro

ACCATGAAAAAGCCTGAACTCACCGCTACCTCTGTCGAGAAGTTTCTGATCGAAAAGTTCGACA
GCGTCTCCGACCTGATGCAGCTCTCCGAGGGCGAAGAATCTCGGGCTTTCAGCTTCGATGTGGG
AGGGCGTGGATATGTCCTGCGGGTGAATAGCTGCGCCGATGGTTTCTACAAAGATCGCTATGTT
TATCGGCACTTTGCATCCGCCGCTCTCCCTATTCCGAAGTGCTTGACATTGGGGAGTTCAGCG
AGAGCCTGACCTATTGCATCTCCCGCCGTGCACAGGGTGTCACCTTGCAAGACCTGCCTGAAAC
CGAACTGCCCGCTGTTCTCCAGCCCGTCGCCGAGGCCATGGATGCCATCGCTGCCGCCGATCTT
AGCCAGACCAGCGGGTTCGGCCCATTCGGACCTCAAGGAATCGGTCAATACACTACATGGCGCG
ATTTCATCTGCGCTATTGCTGATCCCCATGTGTATCACTGGCAAACTGTGATGGACGACACCGT
CAGTGCCTCCGTCGCCCAGGCTCTCGATGAGCTGATGCTTTGGGCCGAGGACTGCCCCGAAGTC
CGGCACCTCGTGCACGCCGATTTCGGCTCCAACAATGTCCTGACCGACAATGGCCGCATAACAG
CCGTCATTGACTGGAGCGAGGCCATGTTCGGGGATTCCCAATACGAGGTCGCCAACATCTTCTT
CTGGAGGCCCTGGTTGGCTTGTATGGAGCAGCAGACCCGCTACTTCGAGCGGAGGCATCCCGAG
CTTGCAGGATCTCCTCGGCTCCGGGCTTATATGCTCCGCATTGGTCTTGACCAACTCTATCAGA
GCTTGGTTGACGGCAATTTCGATGATGCAGCTTGGGCTCAGGGTCGCTGCGACGCAATCGTCCG
GTCCGGAGCCGGGACTGTCGGGCGTACACAAATCGCCCGCAGAAGCGCTGCCGTCTGGACCGAT
GGCTGTGTGGAAGTGCTCGCCGATAGTGGAAACAGACGCCCCAGCACTCGTCCTAGGGCAAAGG
ATCTGCAGTAATGA

4.3 pFUGW-U6-sgRNA-EF1α-Zeo

GAGGGCCTATTTCCCATGATTCCTTCATATTTGCATATACGATACAAGGCTGTTAGAGAGATAA
TTGGAATTAATTTGACTGTAAACACAAAGATATTAGTACAAAATACGTGACGTAGAAAGTAATA
ATTTCTTGGGTAGTTTGCAGTTTTAAAATTATGTTTTAAAATGGACTATCATATGCTTACCGTA
ACTTGAAAGTATTTCGATTTCTTGGCTTTATATATCTTGTGGAAAGGACGAAACACCGGAGACG
GGATACCGTCTCTGTTTTAGAGCTAGGCCAACATGAGGATCACCCATGTCTGCAGGGCCTAGCA
AGTTAAAATAAGGCTAGTCCGTTATCAACTTGGCCAACATGAGGATCACCCATGTCTGCAGGGC
CAAGTGGCACCGAGTCGGTGCTTTTTTGGATCCTGCAAAGATGGATAAAGTTTTAAACAGAGA
GGAATCTTTGCAGCTAATGGACCTTCTAGGTCTTGAAAGGAGTGGGAATTGGCTCCGGTGCCCG
TCAGTGGGCAGAGCGCACATCGCCCACAGTCCCCGAGAAGTTGGGGGGAGGGGTCGGCAATTGA
TCCGGTGCCTAGAGAAGGTGGCGCGGGGTAAACTGGGAAAGTGATGTCGTGTACTGGCTCCGCC
TTTTTCCCGAGGGTGGGGGAGAACCGTATATAAGTGCAGTAGTCGCCGTGAACGTTCTTTTTCG

FIG. 37Z

```
CAACGGGTTTGCCGCCAGAACACAGGTAAGTGCCGTGTGTGGTTCCCGCGGGCCTGGCCTCTTT
ACGGGTTATGGCCCTTGCGTGCCTTGAATTACTTCCACTGGCTGCAGTACGTGATTCTTGATCC
CGAGCTTCGGGTTGGAAGTGGGTGGGAGAGTTCGAGGCCTTGCGCTTAAGGAGCCCCTTCGCCT
CGTGCTTGAGTTGAGGCCTGGCCTGGGCGCTGGGGCCGCCGCGTGCGAATCTGGTGGCACCTTC
GCGCCTGTCTCGCTGCTTTCGATAAGTCTCTAGCCATTTAAAATTTTTGATGACCTGCTGCGAC
GCTTTTTTTCTGGCAAGATAGTCTTGTAAATGCGGGCCAAGATCTGCACACTGGTATTTCGGTT
TTTGGGGCCGCGGGCGGCGACGGGGCCCGTGCGTCCCAGCGCACATGTTCGGCGAGGCGGGGCC
TGCGAGCGCGGCCACCGAGAATCGGACGGGGGTAGTCTCAAGCTGGCCGGCCTGCTCTGGTGCC
TGGCCTCGCGCCGCCGTGTATCGCCCCGCCCTGGGCGGCAAGGCTGGCCCGGTCGGCACCAGTT
GCGTGAGCGGAAAGATGGCCGCTTCCCGGCCCTGCTGCAGGGAGCTCAAAATGGAGGACGCGGC
GCTCGGGAGAGCGGGCGGGTGAGTCACCCACACAAAGGAAAAGGGCCTTTCCGTCCTCAGCCGT
CGCTTCATGTGACTCCACGGAGTACCGGGCGCCGTCCAGGCACCTCGATTAGTTCTCGAGCTTT
TGGAGTACGTCGTCTTTAGGTTGGGGGAGGGGTTTTATGCGATGGAGTTTCCCCACACTGAGT
GGGTGGAGACTGAAGTTAGGCCAGCTTGGCACTTGATGTAATTCTCCTTGGAATTTGCCCTTTT
TGAGTTTGGATCTTGGTTCATTCTCAAGCCTCAGACAGTGGTTCAAAGTTTTTTCTTCCATTT
CAGGTGTCGTGATGTACAATGGCCAAGTTGACCAGTGCCGTTCCGGTGCTCACCGCGCGCGACG
TCGCCGGAGCGGTCGAGTTCTGGACCGACCGGCTCGGGTTCTCCCGGGACTTCGTGGAGGACGA
CTTCGCCGGTGTGGTCCGGGACGACGTGACCCTGTTCATCAGCGCGGTCCAGGACCAGGTGGTG
CCGGACAACACCCTGGCCTGGGTGTGGGTGCGCGGCCTGGACGAGCTGTACGCCGAGTGGTCGG
AGGTCGTGTCCACGAACTTCCGGGACGCCTCCGGGCCGGCCATGACCGAGATCGGCGAGCAGCC
GTGGGGGCGGGAGTTCGCCCTGCGCGACCCGGCCGGCAACTGCGTGCACTTCGTGGCCGAGGAG
CAGGACTGA
```

4.3.1 U6

```
GAGGGCCTATTTCCCATGATTCCTTCATATTTGCATATACGATACAAGGCTGTTAGAGAGATAA
TTGGAATTAATTTGACTGTAAACACAAAGATATTAGTACAAAATACGTGACGTAGAAAGTAATA
ATTTCTTGGGTAGTTTGCAGTTTTAAAATTATGTTTTAAAATGGACTATCATATGCTTACCGTA
ACTTGAAAGTATTTCGATTTCTTGGCTTTATATATCTTGTGGAAAGGACGAAACACC
```

4.3.2 sgRNA

```
GTTTTAGAGCTAGGCCAACATGAGGATCACCCATGTCTGCAGGGCCTAGCAAGTTAAAATAAGG
CTAGTCCGTTATCAACTTGGCCAACATGAGGATCACCCATGTCTGCAGGGCCAAGTGGCACCGA
GTCGGTGC
```

TGCAAAGATGGATAAAGTTTTAAACAGAGAGGAATCTTTGCAGCTAATGGACCTTCTAGGTCTT
GAAAGGAGTGGGAATTGGCTCCGGTGCCCGTCAGTGGGCAGAGCGCACATCGCCCACAGTCCCC
GAGAAGTTGGGGGGAGGGGTCGGCAATTGATCCGGTGCCTAGAGAAGGTGGCGCGGGGTAAACT
GGGAAAGTGATGTCGTGTACTGGCTCCGCCTTTTCCCGAGGGTGGGGGAGAACCGTATATAAG
TGCAGTAGTCGCCGTGAACGTTCTTTTCGCAACGGGTTTGCCGCCAGAACACAGGTAAGTGCC
GTGTGTGGTTCCCGCGGGCCTGGCCTCTTTACGGGTTATGGCCCTTGCGTGCCTTGAATTACTT
CCACTGGCTGCAGTACGTGATTCTTGATCCCGAGCTTCGGGTTGGAAGTGGGTGGGAGAGTTCG
AGGCCTTGCGCTTAAGGAGCCCCTTCGCCTCGTGCTTGAGTTGAGGCCTGGCCTGGGCGCTGGG
GCCGCCGCGTGCGAATCTGGTGGCACCTTCGCGCCTGTCTCGCTGCTTTCGATAAGTCTCTAGC
CATTTAAAATTTTTGATGACCTGCTGCGACGCTTTTTTTCTGGCAAGATAGTCTTGTAAATGCG
GGCCAAGATCTGCACACTGGTATTTCGGTTTTTGGGGCCGCGGGCGGCGACGGGGCCCGTGCGT
CCCAGCGCACATGTTCGGCGAGGCGGGGCCTGCGAGCGCGGCCACCGAGAATCGGACGGGGGTA
GTCTCAAGCTGGCCGGCCTGCTCTGGTGCCTGGCCTCGCGCCGCCGTGTATCGCCCCGCCCTGG
GCGGCAAGGCTGGCCCGGTCGGCACCAGTTGCGTGAGCGGAAAGATGGCCGCTTCCGGCCCTG
CTGCAGGGAGCTCAAAATGGAGGACGCGGCGCTCGGGAGAGCGGGCGGGTGAGTCACCCACACA
AAGGAAAAGGGCCTTTCCGTCCTCAGCCGTCGCTTCATGTGACTCCACGGAGTACCGGGCGCCG
TCCAGGCACCTCGATTAGTTCTCGAGCTTTTGGAGTACGTCGTCTTTAGGTTGGGGGGAGGGGT
TTTATGCGATGGAGTTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATTCTCAAGCCTCAG
ACAGTGGTTCAAAGTTTTTTTCTTCCATTTCAGGTGTCGTGA

4.3.4 Zeo

ATGGCCAAGTTGACCAGTGCCGTTCCGGTGCTCACCGCGCGCGACGTCGCCGGAGCGGTCGAGT
TCTGGACCGACCGGCTCGGGTTCTCCCGGGACTTCGTGGAGGACGACTTCGCCGGTGTGGTCCG
GGACGACGTGACCCTGTTCATCAGCGCGGTCCAGGACCAGGTGGTGCCGGACAACACCCTGGCC
TGGGTGTGGGTGCGCGGCCTGGACGAGCTGTACGCCGAGTGGTCGGAGGTCGTGTCCACGAACT
TCCGGGACGCCTCCGGGCCGGCCATGACCGAGATCGGCGAGCAGCCGTGGGGGCGGGAGTTCGC
CCTGCGCGACCCGGCCGGCAACTGCGTGCACTTCGTGGCCGAGGAGCAGGACTGA

4.4 pFUGW-U6-sgRNA-EF1α-Puro

GAGGGCCTATTTCCCATGATTCCTTCATATTTGCATATACGATACAAGGCTGTTAGAGAGATAA
TTGGAATTAATTTGACTGTAAACACAAAGATATTAGTACAAAATACGTGACGTAGAAAGTAATA
ATTTCTTGGGTAGTTTGCAGTTTTAAAATTATGTTTTAAAATGGACTATCATATGCTTACCGTA

FIG. 37BB

```
ACTTGAAAGTATTTCGATTTCTTGGCTTTATATATCTTGTGGAAAGGACGAAACACCGGAGACG
GGATACCGTCTCTGTTTTAGAGCTAGGCCAACATGAGGATCACCCATGTCTGCAGGGCCTAGCA
AGTTAAAATAAGGCTAGTCCGTTATCAACTTGGCCAACATGAGGATCACCCATGTCTGCAGGGC
CAAGTGGCACCGAGTCGGTGCTTTTTTTGGATCCTGCAAAGATGGATAAAGTTTTAAACAGAGA
GGAATCTTTGCAGCTAATGGACCTTCTAGGTCTTGAAAGGAGTGGGAATTGGCTCCGGTGCCCG
TCAGTGGGCAGAGCGCACATCGCCCACAGTCCCCGAGAAGTTGGGGGAGGGGTCGGCAATTGA
TCCGGTGCCTAGAGAAGGTGGCGCGGGGTAAACTGGGAAAGTGATGTCGTGTACTGGCTCCGCC
TTTTTCCCGAGGGTGGGGGAGAACCGTATATAAGTGCAGTAGTCGCCGTGAACGTTCTTTTTCG
CAACGGGTTTGCCGCCAGAACACAGGTAAGTGCCGTGTGTGGTTCCCGCGGGCCTGGCCTCTTT
ACGGGTTATGGCCCTTGCGTGCCTTGAATTACTTCCACCGGCTGCAGTACGTGATTCTTGATCC
CGAGCTTCGGGTTGGAAGTGGGTGGGAGAGTTCGAGGCCTTGCGCTTAAGGAGCCCCTTCGCCT
CGTGCTTGAGTTGAGGCCTGGCCTGGGCGCTGGGCCGCCGCGTGCGAATCTGGTGGCACCTTC
GCGCCTGTCTCGCTGCTTTCGATAAGTCTCTAGCCATTTAAAATTTTTGATGACCTGCTGCGAC
GCTTTTTTTCTGGCAAGATAGTCTTGTAAATGCGGGCCAAGATCTGCACACTGGTATTTCGGTT
TTTGGGGCCGCGGGCGGCGACGGGGCCCGTGCGTCCCAGCGCACATGTTCGGCGAGGCGGGGCC
TGCGAGCGCGGCCACCGAGAATCGGACGGGGGTAGTCTCAAGCTGGCCGGCCTGCTCTGGTGCC
TGGCCTCGCGCCGCCGTGTATCGCCCCGCCCTGGGCGGCAAGGCTGGCCCGGTCGGCACCAGTT
GCGTGAGCGGAAAGATGGCCGCTTCCCGGCCCTGCTGCAGGGAGCTCAAAATGGAGGACGCGGC
GCTCGGGAGAGCGGGCGGGTGAGTCACCCACACAAAGGAAAAGGGCCTTTCCGTCCTCAGCCGT
CGCTTCATGTGACTCCACGGAGTACCGGGCGCCGTCCAGGCACCTCGATTAGTTCTCGAGCTTT
TGGAGTACGTCGTCTTTAGGTTGGGGGAGGGGTTTTATGCGATGGAGTTTCCCCACACTGAGT
GGGTGGAGACTGAAGTTAGGCCAGCTTGGCACTTGATGTAATTCTCCTTGGAATTTGCCCTTTT
TGAGTTTGGATCTTGGTTCATTCTCAAGCCTCAGACAGTGGTTCAAAGTTTTTTCTTCCATTT
CAGGTGTCGTGATGTACAATGACCGAGTACAAGCCCACGGTGCGCCTCGCCACCCGCGACGACG
TCCCCAGGGCCGTACGCACCCTCGCCGCCGCGTTCGCCGACTACCCCGCCACGCGCCACACCGT
CGATCCGGACCGCCACATCGAGCGGGTCACCGAGCTGCAAGAACTCTTCCTCACGCGCGTCGGG
CTCGACATCGGCAAGGTGTGGGTCGCGGACGACGGCGCCGCCGTGGCGGTCTGGACCACGCCGG
AGAGCGTCGAAGCGGGGGCGGTGTTCGCCGAGATCGGCCCGCGCATGGCCGAGTTGAGCGGTTC
CCGGCTGGCCGCGCAGCAACAGATGGAAGGCCTCCTGGCGCCGCACCGGCCCAAGGAGCCCGCG
TGGTTCCTGGCCACCGTCGGAGTCTCGCCCGACCACCAGGGCAAGGGTCTGGGCAGCGCCGTCG
TGCTCCCCGGAGTGGAGGCGGCCGAGCGCGCCGGGGTGCCCGCCTTCCTGGAGACCTCCGCGCC
CCGCAACCTCCCCTTCTACGAGCGGCTCGGCTTCACCGTCACCGCCGACGTCGAGGTGCCCGAA
GGACCGCGCACCTGGTGCATGACCCGCAAGCCCGGTGCCTGA
```

GAGGGCCTATTTCCCATGATTCCTTCATATTTGCATATACGATACAAGGCTGTTAGAGAGATAA
TTGGAATTAATTTGACTGTAAACACAAAGATATTAGTACAAAATACGTGACGTAGAAAGTAATA
ATTTCTTGGGTAGTTTGCAGTTTTAAAATTATGTTTTAAAATGGACTATCATATGCTTACCGTA
ACTTGAAAGTATTTCGATTTCTTGGCTTTATATATCTTGTGGAAAGGACGAAACACC

4.4.2 sgRNA

GTTTTAGAGCTAGGCCAACATGAGGATCACCCATGTCTGCAGGGCCTAGCAAGTTAAAATAAGG
CTAGTCCGTTATCAACTTGGCCAACATGAGGATCACCCATGTCTGCAGGGCCAAGTGGCACCGA
GTCGGTGC

4.4.3 EF1α

TGCAAAGATGGATAAAGTTTTAAACAGAGAGGAATCTTTGCAGCTAATGGACCTTCTAGGTCTT
GAAAGGAGTGGGAATTGGCTCCGGTGCCCGTCAGTGGGCAGAGCGCACATCGCCCACAGTCCCC
GAGAAGTTGGGGGGAGGGGTCGGCAATTGATCCGGTGCCTAGAGAAGGTGGCGCGGGGTAAACT
GGGAAAGTGATGTCGTGTACTGGCTCCGCCTTTTCCCGAGGGTGGGGGAGAACCGTATATAAG
TGCAGTAGTCGCCGTGAACGTTCTTTTTCGCAACGGGTTTGCCGCCAGAACACAGGTAAGTGCC
GTGTGTGGTTCCCGCGGGCCTGGCCTCTTTACGGGTTATGGCCCTTGCGTGCCTTGAATTACTT
CCACCGGCTGCAGTACGTGATTCTTGATCCCGAGCTTCGGGTTGGAAGTGGGTGGGAGAGTTCG
AGGCCTTGCGCTTAAGGAGCCCCTTCGCCTCGTGCTTGAGTTGAGGCCTGGCCTGGGCGCTGGG
GCCGCCGCGTGCGAATCTGGTGGCACCTTCGCGCCTGTCTCGCTGCTTTCGATAAGTCTCTAGC
CATTTAAAATTTTTGATGACCTGCTGCGACGCTTTTTTCTGGCAAGATAGTCTTGTAAATGCG
GGCCAAGATCTGCACACTGGTATTTCGGTTTTTGGGGCCGCGGGCGGCGACGGGGCCCGTGCGT
CCCAGCGCACATGTTCGGCGAGGCGGGGCCTGCGAGCGCGGCCACCGAGAATCGGACGGGGGTA
GTCTCAAGCTGGCCGGCCTGCTCTGGTGCCTGGCCTCGCGCCGCCGTGTATCGCCCCGCCCTGG
GCGGCAAGGCTGGCCCGGTCGGCACCAGTTGCGTGAGCGGAAAGATGGCCGCTTCCCGGCCCTG
CTGCAGGGAGCTCAAAATGGAGGACGCGGCGCTCGGGAGAGCGGGCGGGTGAGTCACCCACACA
AAGGAAAAGGGCCTTTCCGTCCTCAGCCGTCGCTTCATGTGACTCCACGGAGTACCGGGCGCCG
TCCAGGCACCTCGATTAGTTCTCGAGCTTTTGGAGTACGTCGTCTTTAGGTTGGGGGGAGGGGT
TTTATGCGATGGAGTTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATTCTCAAGCCTCAG
ACAGTGGTTCAAAGTTTTTTTCTTCCATTTCAGGTGTCGTGA

FIG. 37DD

4.4.4 Puro

```
ATGACCGAGTACAAGCCCACGGTGCGCCTCGCCACCCGCGACGACGTCCCCAGGGCCGTACGCA
CCCTCGCCGCCGCGTTCGCCGACTACCCCGCCACGCGCCACACCGTCGATCCGGACCGCCACAT
CGAGCGGGTCACCGAGCTGCAAGAACTCTTCCTCACGCGCGTCGGGCTCGACATCGGCAAGGTG
TGGGTCGCGGACGACGGCGCCGCCGTGGCGGTCTGGACCACGCCGGAGAGCGTCGAAGCGGGGG
CGGTGTTCGCCGAGATCGGCCCGCGCATGGCCGAGTTGAGCGGTTCCCGGCTGGCCGCGCAGCA
ACAGATGGAAGGCCTCCTGGCGCCGCACCGGCCCAAGGAGCCCGCGTGGTTCCTGGCCACCGTC
GGAGTCTCGCCCGACCACCAGGGCAAGGGTCTGGGCAGCGCCGTCGTGCTCCCCGGAGTGGAGG
CGGCCGAGCGCGCCGGGGTGCCCGCCTTCCTGGAGACCTCCGCGCCCCGCAACCTCCCCTTCTA
CGAGCGGCTCGGCTTCACCGTCACCGCCGACGTCGAGGTGCCCGAAGGACCGCGCACCTGGTGC
ATGACCCGCAAGCCCGGTGCCTGA
```

FIG. 37EE

Target guide sequences used in this paper

| Gene | Target Sequence |
|---|---|
| Neurog2 | TGGTTCAGTGGCTGCGTGTC |
| ASCL1 | GCAGCCGCTCGCTGCAGCAG |
| MYOD1 | GGGCCCCTGCGGCCACCCCG |
| SOX2 | GCCGGCCGCGCGGGGGAGGC |
| SOX2 | CCATGTGACGGGGGCTGTCA |
| SOX2 | GGCAGGCGAGGAGGGGGAGG |
| SOX2 | GCTGCCGGGTTTTGCATGAA |
| SOX2 | GTATCCCCTCTCGCAGCAAC |
| SOX2 | AGGAGCCGCCGCGCGCTGAT |
| SOX2 | TTTACCCACTTCCTTCGAAA |
| SOX2 | GCAGGGTACTTAAATGAGGA |
| NANOG | CGCCAGGAGGGGTGGGTCTA |
| NANOG | GATTAACTGAGAATTCACAA |
| NANOG | TCTAGTTCCCCACCTAGTCT |
| NANOG | GCCTTGGTGAGACTGGTAGA |
| NANOG | TGTCTTCAGGTTCTGTTGCT |
| NANOG | TGATTTAAAAGTTGGAAACG |
| NANOG | CATATTCCTGATTTAAAAGT |
| NANOG | TCCCAATTTACTGGGATTAC |
| KLF4 | GCGCGCTCCACACAACTCAC |
| KLF4 | AAGGAACGCGCGCCGGCGGC |
| KLF4 | ATGGGAGAAGGCGGAGGAAA |
| KLF4 | GCAACGATGGAAGGGAGCCT |
| KLF4 | GCGCACGTGGGGGCGGGGGA |
| KLF4 | GCCTGGCTGGCGTCACGGCC |
| KLF4 | GCCGCCGACACCACTGCCGC |
| KLF4 | CGGTTCCTCGCGCCCCGCGC |
| POU5F1 (OCT4) | GACACAACTGGCGCCCCTCC |
| POU5F1 (OCT4) | GGGGGGAGAAACTGAGGCGA |
| POU5F1 (OCT4) | TCTGTGGGGACCTGCACTG |
| POU5F1 (OCT4) | GGCACAGTGCCAGAGGTCTG |

FIG. 38A

| | |
|---|---|
| POU5F1 (OCT4) | GGTGAAATGAGGGCTTGCGA |
| POU5F1 (OCT4) | TCAAGGCTAGTGGGTGGGAC |
| POU5F1 (OCT4) | GGTGGTGGCAATGGTGTCTG |
| POU5F1 (OCT4) | ACAGGAATTCAAGACCAGCC |
| VEGFA | GCAAAGAGGGAACGGCTCTC |
| VEGFA | ACAGAGTTTCCGGGGGCGGA |
| VEGFA | CCCTTCATTGCGGCGGGCTG |
| VEGFA | GGCCCGAGCCGCGTGTGGAA |
| VEGFA | GCGGCCGGGGCGGGGTCC |
| VEGFA | TTTAAAGTCGGCTGGTAGC |
| HBG1 | TCCCTGAACTTTTCAAAAAT |
| HBG1 | CACTGGAGCTAGAGACAAGA |
| HBG1 | GTATCCTCTATGATGGGAGA |
| HBG1 | AAAACTGGAATGACTGAAT |
| HBG1 | AAAATTAGCAGTATCCTCTT |
| HBG1 | ATGCAAATATCTGTCTGAAA |
| HBG1 | CTTGACCAATAGCCTTGACA |
| HBG1 | GGCTAGGGATGAAGAATAAA |
| TERT | GCCGCACGCACCTGTTCCCA |
| TERT | CTGCACCCTGGGAGCGCGAG |
| TERT | GCCGGAGCAGCTGCGCTGT |
| TERT | CCAGGACCGCGCTTCCCACG |
| TERT | GAGCTGGAAGGTGAAGGGGC |
| TERT | CCCGACCCCTCCCGGGTCCC |
| TERT | GGAAGGAAGGGGAGGGGCT |
| TERT | GCGGCCCCGCCCTCCTCG |
| IL1B | TTAGTATATGTGGGACAAAG |
| IL1B | GAAATCCAGTATTTTAATG |
| IL1B | GAAAACAATGCATATTTGCA |
| IL1B | CTCTGGTTCATGGAAGGGCA |
| IL1B | AGTATTGGTGGAAGCTTCTT |
| IL1B | TTTAACTTGATTGTGAAATC |
| IL1B | TGGCTTTCAAAAGCAGAAGT |
| IL1B | AAAACAGCGAGGGAGAAAC |
| IL1R2 | AAACTCCACAATCTAGAATA |
| IL1R2 | TTAACAGTTAAAAATCATAC |

FIG. 38B

| | |
|---|---|
| IL1R2 | TGGAAAACCAACTCTTCCAC |
| IL1R2 | AGCATCTTTTCTCTTTAAT |
| IL1R2 | ATCACTTTAAAACCACCTCT |
| IL1R2 | AAACTTATGCGGCGTTTCCT |
| IL1R2 | GAGTACATGATCACCCAGAT |
| IL1R2 | GACCCAGCACTGCAGCCTGG |
| ZFP42 (REX1) | TAGCAATACAGTCACATTAA |
| ZFP42 (REX1) | GCCGGGCGTCTGGGCTCTGG |
| ZFP42 (REX1) | TGCCCGGCGGCCGGGCTGAG |
| ZFP42 (REX1) | GCCTGGGGCCCCGGGCTGA |
| ZFP42 (REX1) | CCGGGCAGAGAGTGAACGCG |
| ZFP42 (REX1) | GCGGCGCCCAGGGCGGGGC |
| ZFP42 (REX1) | ACCCTGGCGGAGCTGATGGG |
| ZFP42 (REX1) | GGGTCTTGGGAGGGGCGCA |
| MYC | GGCCCCACGGAAGCCTGAGC |
| MYC | CAGTGCGTTCTCGGTGTGGA |
| MYC | TTTGTCAAACAGTACTGCTA |
| MYC | GCGCGCGTAGTTAATTCATG |
| MYC | AGCTAGAGTGCTCGGCTGCC |
| MYC | GGTTCCCAAAGCAGAGGGCG |
| MYC | TCTCGCTAATCTCCGCCCAC |
| MYC | CCCTTTATAATGCGAGGGTC |
| LIN28A | AGAAGCAGGCCGCGCATTCC |
| LIN28A | GCGGGTCAGCTCCAAGCAGC |
| LIN28A | TCTGATTGGCCAGCGCCGCC |
| LIN28A | CCCATCTCCAGTTGTGCGTG |
| LIN28A | TCTGAGAAGGGACACCCCAG |
| LIN28A | CGGAGGGAAAGGGAGGGGAA |
| LIN28A | GGGGCTGCCCGCGGGGGGTT |
| LIN28A | GGGAGCCTTTGAAAAGCCGT |
| TINCR | TGGGCAGGCCCGGCCCGGCG |
| TINCR | GCGCACTCTGGGGCCAGCAG |
| TINCR | GGCTGGGATGACCTCGCTGA |
| TINCR | TGATCTTTTAAGGACAGGC |
| TINCR | TCTCAAGTAGCTGGGACTAC |
| TINCR | CAGGTGCGGTGGCTCATGCC |

FIG. 38C

| | |
|---|---|
| TINCR | CTCACTGCAACCTCTGTCTG |
| HOTTIP | GGTGGGGCAGGGAAGGAAGG |
| HOTTIP | GCACCATTCACCCGGGGGAG |
| HOTTIP | TGCACCCGTCGTCCCCGCCG |
| HOTTIP | GTGGGCGGAGCGGGGGGGCC |
| HOTTIP | GCGCGCTCTTCACTTCTTGG |
| HOTTIP | TCGTAGAGAAACATGACGGT |
| HOTTIP | CGCGGCTGCGGCGGCGGCCG |
| HOTTIP | TTGGCGGCCTCTGCGCCCGC |
| PCAT-1 | TCGGAGCCACTCCCTCCTCT |
| PCAT-1 | AATTTGTCATAGTCTTGAGT |
| PCAT-1 | TCTTTTTACATTGACTGATA |
| PCAT-1 | TGCTTTTGAATGAACACCCA |
| PCAT-1 | TTGGGTCTACTCACAATTT |
| PCAT-1 | GTTCTGTGAAGTCCAGTCCC |
| PCAT-1 | AGCAAGTACTCAATATATTT |
| PCAT-1 | AGTAGAGAGGCCAGGCACAG |
| LINC00925 | TAAAATAGAGCGGAGATATC |
| LINC00925 | CCTTCTTGAAGGTGCACTCA |
| LINC00925 | CAGGCTGTGGTTGTGACCTG |
| LINC00925 | TTTCTCCTGCGTCCTGGG |
| LINC00925 | CACGCTTCCAGCCACCCGCT |
| LINC00925 | CGATGCGCTTGCTGGGTCGC |
| LINC00925 | GGCTCCCAGCCCCAGCCCCC |
| LINC00925 | ACCAGCTGCCTTCTTCCCCC |
| LINC00514 | CAGCCCTCCTTCTACCCTT |
| LINC00514 | GGGCAGGAGGTGGAGTGTCA |
| LINC00514 | GGGGGCCGGAGGGGGAGAGG |
| LINC00514 | GCAGGCTGAGAAGGGTGGGC |
| LINC00514 | TCTCATCAAGTGTCCACTCA |
| LINC00514 | GTCTCCATCTCTCCTGCCC |
| LINC00514 | GGGTGTGGAAAGCCTGGTCT |
| LINC00514 | TGACTCTAGGCAGAGTGGGA |
| LINC00028 | TCGCGGCTGGAGGACGCTGC |
| LINC00028 | CGCCCAGCCCCGGGGACG |
| LINC00028 | CAGGGACACGATGGTCCAAA |

FIG. 38D

| | |
|---|---|
| LINC00028 | GTCAGGAGTTTCCAGCCCGA |
| LINC00028 | CCCAGGAGGAGGCTGGGCCC |
| LINC00028 | GAGTGAGTTGGATTAAACTG |
| LINC00028 | CTGCTATACGCGAAGTTGCC |
| LINC00028 | ACGTTCTAGATTCACATGTC |
| Scrambled guide 1 | CTGAAAAGGAAGGAGTTGA |
| Scrambled guide 2 | AAGATGAAAGGAAAGGCGTT |

FIG. 38E

Top 300 depleted genes for A375. Mean depletion for each gene is given as the log2 ratio of Day 21 vs. Day 3 averaged over all sgRNAs for the gene.

| Gene | Mean_Depletion | Rank |
| --- | --- | --- |
| CDKN1A | -2.992660039 | 1 |
| MXI1 | -2.897744853 | 2 |
| STRBP | -2.829748727 | 3 |
| ZNF619 | -2.804758127 | 4 |
| SPANXF1 | -2.726815579 | 5 |
| FAM129B | -2.719695757 | 6 |
| CDKN1A | -2.656298721 | 7 |
| ARPP21 | -2.653166497 | 8 |
| NFATC1 | -2.629949555 | 9 |
| ADAMTS12 | -2.590207051 | 10 |
| SYNCRIP | -2.543127112 | 11 |
| DUSP9 | -2.525451884 | 12 |
| JUNB | -2.490663237 | 13 |
| YAF2 | -2.448742407 | 14 |
| SLC19A1 | -2.448391667 | 15 |
| MYBL1 | -2.447625101 | 16 |
| MEX3A | -2.409240548 | 17 |
| TRIB1 | -2.398434141 | 18 |
| CHST8 | -2.335622871 | 19 |
| ENOX2 | -2.304989857 | 20 |
| RNPEP | -2.279404126 | 21 |
| GRB10 | -2.278152274 | 22 |
| NKX2-1 | -2.277268968 | 23 |
| RTFDC1 | -2.276773205 | 24 |
| PRKAG2 | -2.257706064 | 25 |
| DUSP5 | -2.257470856 | 26 |
| CPEB4 | -2.257275333 | 27 |
| PRAME | -2.253782388 | 28 |
| ZNF583 | -2.236146291 | 29 |

FIG. 39A

| | | |
|---|---|---|
| NTRK2 | -2.187236566 | 30 |
| MEIS3 | -2.18329438 | 31 |
| CRY1 | -2.181419445 | 32 |
| GPR137B | -2.153058431 | 33 |
| TTLL12 | -2.14262453 | 34 |
| EEF1A1 | -2.136133061 | 35 |
| SPNS2 | -2.130267043 | 36 |
| BAG1 | -2.12875898 | 37 |
| PRDM1 | -2.126237386 | 38 |
| NAT8L | -2.11667318 | 39 |
| HSD17B8 | -2.106531573 | 40 |
| GALNT7 | -2.095244894 | 41 |
| WNT3A | -2.090472623 | 42 |
| TGFBR2 | -2.074145064 | 43 |
| RBM47 | -2.071991956 | 44 |
| LOXL4 | -2.061797982 | 45 |
| JADE3 | -2.038321308 | 46 |
| TMSB4Y | -2.026889341 | 47 |
| CHPF | -2.025890484 | 48 |
| MSRB3 | -2.02586623 | 49 |
| ZNF641 | -2.023295975 | 50 |
| DUX4L2 | -2.015241148 | 51 |
| BLOC1S2 | -2.002638012 | 52 |
| FAM49A | -2.001061567 | 53 |
| AUP1 | -1.997624613 | 54 |
| CDKN1C | -1.995664305 | 55 |
| SLC1A1 | -1.990961882 | 56 |
| ASB10 | -1.989066237 | 57 |
| WNK2 | -1.977746737 | 58 |
| ITGA5 | -1.954342921 | 59 |
| NFIC | -1.953212838 | 60 |
| KLK11 | -1.948539824 | 61 |
| WDR91 | -1.938490545 | 62 |
| S100A13 | -1.935432269 | 63 |
| PXDC1 | -1.927854467 | 64 |
| NDNF | -1.921200613 | 65 |

FIG. 39B

| | | |
|---|---|---|
| BRI3 | -1.911739793 | 66 |
| TMEM220 | -1.903966859 | 67 |
| DUSP14 | -1.898023448 | 68 |
| NAA35 | -1.885506504 | 69 |
| ZNF395 | -1.878461929 | 70 |
| MIA3 | -1.870671759 | 71 |
| KCNK10 | -1.867897168 | 72 |
| IGF2BP3 | -1.859186347 | 73 |
| ATP6V0A1 | -1.848977641 | 74 |
| POU3F3 | -1.848092491 | 75 |
| LMNA | -1.847152595 | 76 |
| LHFPL3 | -1.8465067 | 77 |
| ZNF665 | -1.84640875 | 78 |
| DYM | -1.837513747 | 79 |
| KLHL8 | -1.836730363 | 80 |
| WNT7A | -1.836730124 | 81 |
| SEC61A1 | -1.832537638 | 82 |
| TCF7L2 | -1.827830567 | 83 |
| GPRASP2 | -1.823465993 | 84 |
| CACNA1C | -1.821967953 | 85 |
| INO80 | -1.819581697 | 86 |
| MEX3C | -1.818591589 | 87 |
| ERG | -1.808903306 | 88 |
| ESPL1 | -1.801783358 | 89 |
| KLF2 | -1.798003457 | 90 |
| COL1A1 | -1.795687915 | 91 |
| RCC2 | -1.789402047 | 92 |
| PAK1 | -1.781478474 | 93 |
| GALNT13 | -1.779304272 | 94 |
| TMCC3 | -1.779143425 | 95 |
| WDR45B | -1.769033944 | 96 |
| RNF111 | -1.768775527 | 97 |
| BCL3 | -1.76223965 | 98 |
| FAM110B | -1.760460731 | 99 |
| LATS2 | -1.753053715 | 100 |
| GRTP1 | -1.749316218 | 101 |

FIG. 39C

| | | |
|---|---|---|
| 41891 | -1.740174795 | 102 |
| SPIRE2 | -1.737385676 | 103 |
| BIVM-ERCC5 | -1.73527893 | 104 |
| HOXC13 | -1.727592439 | 105 |
| SKI | -1.727146495 | 106 |
| HEXDC | -1.726799679 | 107 |
| BTG2 | -1.723525381 | 108 |
| EID2B | -1.719706185 | 109 |
| NELL2 | -1.718412006 | 110 |
| CELF1 | -1.710704793 | 111 |
| FXYD1 | -1.709774577 | 112 |
| GATA1 | -1.703530563 | 113 |
| AGPAT6 | -1.703304319 | 114 |
| PDGFRB | -1.702489783 | 115 |
| EFHB | -1.699297265 | 116 |
| OTX1 | -1.69840649 | 117 |
| CLIC1 | -1.698145729 | 118 |
| GNAO1 | -1.69117871 | 119 |
| TSPAN5 | -1.690531306 | 120 |
| GLB1 | -1.688687106 | 121 |
| PHF2 | -1.688502906 | 122 |
| MIIP | -1.687831215 | 123 |
| BFSP1 | -1.685843655 | 124 |
| PKDCC | -1.681959775 | 125 |
| UCN3 | -1.681603774 | 126 |
| AKAP11 | -1.681106799 | 127 |
| STK3 | -1.680125551 | 128 |
| DOT1L | -1.679505143 | 129 |
| CRHR1 | -1.678232195 | 130 |
| PLEKHO1 | -1.674893272 | 131 |
| ANKEF1 | -1.674522971 | 132 |
| EBF2 | -1.671684092 | 133 |
| COPE | -1.667505883 | 134 |
| USP28 | -1.666943424 | 135 |
| KMT2B | -1.664730943 | 136 |
| RIMS4 | -1.664556738 | 137 |

FIG. 39D

| | | |
|---|---|---|
| ADAMTS7 | -1.664444631 | 138 |
| FAM9A | -1.661881924 | 139 |
| EPHA2 | -1.65846104 | 140 |
| REEP6 | -1.657571504 | 141 |
| SIAH1 | -1.656570969 | 142 |
| FPR2 | -1.651081286 | 143 |
| AVL9 | -1.650350499 | 144 |
| SP3 | -1.649187872 | 145 |
| PCNXL3 | -1.646537811 | 146 |
| SHROOM4 | -1.645105253 | 147 |
| HNRNPAB | -1.642348412 | 148 |
| CACNA2D1 | -1.639847135 | 149 |
| FGFRL1 | -1.63856667 | 150 |
| SHB | -1.632097534 | 151 |
| CA2 | -1.631971681 | 152 |
| CAMK2N1 | -1.629137656 | 153 |
| ARHGAP4 | -1.62825701 | 154 |
| CPLX2 | -1.626599879 | 155 |
| HOXC11 | -1.626203388 | 156 |
| ITM2C | -1.625957387 | 157 |
| TRNT1 | -1.624893641 | 158 |
| DNAAF2 | -1.624882836 | 159 |
| GCC2 | -1.624354479 | 160 |
| TTC9 | -1.624140349 | 161 |
| IFT81 | -1.622920533 | 162 |
| PLEKHF1 | -1.62180107 | 163 |
| C10orf82 | -1.620405891 | 164 |
| KIAA0753 | -1.619239696 | 165 |
| WDR89 | -1.617607367 | 166 |
| CRCP | -1.611109935 | 167 |
| ADRA1A | -1.602361316 | 168 |
| TXLNG | -1.601904094 | 169 |
| ANKZF1 | -1.601604975 | 170 |
| EFHD2 | -1.599046924 | 171 |
| SERPINI1 | -1.598621083 | 172 |
| MIB1 | -1.597274936 | 173 |

FIG. 39E

| | | |
|---|---|---|
| MEAF6 | -1.593894564 | 174 |
| HLCS | -1.59025755 | 175 |
| ING2 | -1.589728576 | 176 |
| PYROXD2 | -1.589535269 | 177 |
| PPARGC1A | -1.587408566 | 178 |
| ANKRD30A | -1.586667965 | 179 |
| BTBD2 | -1.586118313 | 180 |
| IGSF8 | -1.580902664 | 181 |
| FAM69C | -1.577696726 | 182 |
| PAXIP1 | -1.576009399 | 183 |
| PAOX | -1.575951644 | 184 |
| ZNF667 | -1.572756871 | 185 |
| TCF3 | -1.56874959 | 186 |
| IMPA2 | -1.567559877 | 187 |
| UBE3D | -1.566869169 | 188 |
| SPATA31A1 | -1.566628243 | 189 |
| SLCO4A1 | -1.562067095 | 190 |
| PAPOLB | -1.561157727 | 191 |
| RHOBTB2 | -1.557854541 | 192 |
| WWC1 | -1.557454101 | 193 |
| MLXIP | -1.556308378 | 194 |
| MSH6 | -1.555493523 | 195 |
| TEX28 | -1.555077182 | 196 |
| TLR7 | -1.554718342 | 197 |
| TBC1D22A | -1.553299902 | 198 |
| COBL | -1.552319793 | 199 |
| ZBTB40 | -1.551377333 | 200 |
| EBAG9 | -1.551195482 | 201 |
| BHLHE23 | -1.549931838 | 202 |
| CCNE1 | -1.549380807 | 203 |
| FOSL2 | -1.548586206 | 204 |
| KANK1 | -1.545495013 | 205 |
| UBE2G1 | -1.545073693 | 206 |
| CTSZ | -1.544508991 | 207 |
| PIK3R1 | -1.541543206 | 208 |
| PLCD1 | -1.540526535 | 209 |

FIG. 39F

| | | |
|---|---|---|
| CFHR1 | -1.540322263 | 210 |
| EAPP | -1.539559841 | 211 |
| FOXN2 | -1.536894335 | 212 |
| NRXN3 | -1.536756987 | 213 |
| PRRG4 | -1.536411123 | 214 |
| AURKA | -1.535632929 | 215 |
| POLR2I | -1.535013569 | 216 |
| TEX38 | -1.534957213 | 217 |
| SNRPF | -1.534928953 | 218 |
| FZD6 | -1.534873785 | 219 |
| CHRDL2 | -1.53363039 | 220 |
| CAMK1D | -1.532738633 | 221 |
| TSPAN4 | -1.532033491 | 222 |
| ZNF514 | -1.53035277 | 223 |
| CTAG1A | -1.528262121 | 224 |
| TSPY1 | -1.518969471 | 225 |
| FAM45A | -1.515966792 | 226 |
| PHF23 | -1.514788961 | 227 |
| NRD1 | -1.514485943 | 228 |
| UBR5 | -1.514476856 | 229 |
| GTPBP10 | -1.51320279 | 230 |
| PLEKHM3 | -1.512593991 | 231 |
| TMEM181 | -1.512024763 | 232 |
| ANKRD44 | -1.510607784 | 233 |
| SULT4A1 | -1.510256216 | 234 |
| PDGFC | -1.509051383 | 235 |
| CDYL | -1.508799208 | 236 |
| CDC42EP2 | -1.508624776 | 237 |
| KCNMB3 | -1.507843102 | 238 |
| FOXI1 | -1.507819638 | 239 |
| FHL1 | -1.507785919 | 240 |
| JRK | -1.507056803 | 241 |
| FAM110C | -1.506457203 | 242 |
| NPEPPS | -1.506442168 | 243 |
| CNKSR3 | -1.505895119 | 244 |
| SYNGR1 | -1.50378579 | 245 |

FIG. 39G

| | | |
|---|---|---|
| LIG1 | -1.50220227 | 246 |
| UCK1 | -1.498574732 | 247 |
| PLEKHG3 | -1.498493459 | 248 |
| SHANK2 | -1.496266754 | 249 |
| SYNGR2 | -1.495929066 | 250 |
| FRMPD2 | -1.495810709 | 251 |
| SCAP | -1.494636312 | 252 |
| RGS22 | -1.493115397 | 253 |
| GALNT18 | -1.49152462 | 254 |
| GPAT2 | -1.491059745 | 255 |
| TRIM6-TRIM34 | -1.490703347 | 256 |
| AJUBA | -1.488388821 | 257 |
| GAS8 | -1.486564139 | 258 |
| PLXNA2 | -1.486492818 | 259 |
| RPN2 | -1.485389319 | 260 |
| RBMX | -1.485222602 | 261 |
| FOXF2 | -1.484610716 | 262 |
| ARHGAP31 | -1.483785576 | 263 |
| PNMA5 | -1.4816382 | 264 |
| SLAMF6 | -1.481389938 | 265 |
| HIST1H3J | -1.479761902 | 266 |
| HHAT | -1.479346095 | 267 |
| KCNC3 | -1.478985068 | 268 |
| PFKM | -1.477414591 | 269 |
| CDHR5 | -1.476532282 | 270 |
| GABRB3 | -1.476436096 | 271 |
| POLR1D | -1.476282564 | 272 |
| TTYH2 | -1.475655292 | 273 |
| TMEM198 | -1.475348451 | 274 |
| NRP2 | -1.474615777 | 275 |
| UBE3B | -1.474189706 | 276 |
| ZNF618 | -1.471872622 | 277 |
| PYGO1 | -1.471843021 | 278 |
| SLFN11 | -1.470539972 | 279 |
| LONRF3 | -1.470166863 | 280 |
| TSPAN17 | -1.468806125 | 281 |

FIG. 39H

| | | |
|---|---|---|
| STARD8 | -1.468402107 | 282 |
| HFE2 | -1.467933276 | 283 |
| LTBP1 | -1.466001082 | 284 |
| ENKD1 | -1.464456854 | 285 |
| PIGP | -1.462758078 | 286 |
| CHTF8 | -1.462614997 | 287 |
| EHD2 | -1.462454773 | 288 |
| ST6GAL1 | -1.460732993 | 289 |
| ZNF527 | -1.45924688 | 290 |
| SLC22A17 | -1.459181743 | 291 |
| C17orf62 | -1.458600852 | 292 |
| POLR2G | -1.457145699 | 293 |
| WDR88 | -1.455886365 | 294 |
| USP32 | -1.455612942 | 295 |
| CTNNA2 | -1.452748274 | 296 |
| LCOR | -1.452523453 | 297 |
| HDAC9 | -1.450768923 | 298 |
| WNT7B | -1.449752179 | 299 |
| LRRC4B | -1.449610591 | 300 |

FIG. 39I

Top 100 genes from the output of the RIGER algorithm for the sgRNA-Zeo PLX screen comparing PLX (mean of the two replicates at Day 21) to DMSO control (mean of the two replicates at Day 21). The Kolmogorov-Smirnov method was used to score genes.

| Gene | NES | Gene rank | p-value | p-value rank |
|---|---|---|---|---|
| EGFR | 1.9319 | 1 | 0.00000001 | 1 |
| LPAR5 | 1.9292 | 2 | 0.00000001 | 2 |
| GPR35 | 1.9277 | 3 | 0.0000001 | 3 |
| LPAR1 | 1.9262 | 4 | 0.00000045 | 4 |
| P2RY8 | 1.9248 | 5 | 0.00000045 | 5 |
| ARHGEF1 | 1.9184 | 6 | 0.0000009 | 6 |
| ITGB3 | 1.9116 | 7 | 0.0000031 | 7 |
| ITGA9 | 1.894 | 8 | 0.0000201 | 8 |
| ITGB5 | 1.89 | 9 | 0.000026 | 9 |
| CRB2 | 1.8895 | 10 | 0.00002695 | 10 |
| TYW1 | 1.8833 | 11 | 0.00003825 | 11 |
| VSX1 | 1.8752 | 12 | 0.00005925 | 12 |
| LOC102724862 | 1.8698 | 13 | 0.0000772 | 13 |
| BCAR3 | 1.8552 | 14 | 0.0001412 | 14 |
| PCDH7 | 1.8521 | 15 | 0.0001584 | 15 |
| KIAA0040 | 1.8506 | 16 | 0.0001687 | 16 |
| TFAP2C | 1.8468 | 17 | 0.0001934 | 17 |
| PHB | 1.6441 | 112 | 0.0002845 | 18 |
| IGF1R | 1.8125 | 18 | 0.0005271 | 19 |
| CGB8 | 1.8105 | 19 | 0.0005533 | 20 |
| RNF223 | 1.8075 | 20 | 0.0005983 | 21 |
| TFEB | 1.7961 | 21 | 0.0007757 | 22 |
| TOR3A | 1.7826 | 22 | 0.00103 | 23 |
| MRFAP1 | 1.7815 | 23 | 0.001049 | 24 |
| WNT7A | 1.7763 | 24 | 0.001158 | 25 |
| MEIS2 | 1.775 | 25 | 0.001189 | 26 |
| KCTD20 | 1.7703 | 26 | 0.001303 | 27 |
| SHB | 1.7691 | 27 | 0.001331 | 28 |

FIG. 40A

| | | | | |
|---|---|---|---|---|
| PLEKHG5 | 1.7665 | 28 | 0.001393 | 29 |
| DAG1 | 1.7612 | 29 | 0.00153 | 30 |
| RAPGEF1 | 1.7575 | 30 | 0.001632 | 31 |
| SSC5D | 1.7571 | 31 | 0.001645 | 32 |
| PSMF1 | 1.7564 | 32 | 0.001665 | 33 |
| ZNF747 | 1.7539 | 33 | 0.001736 | 34 |
| SIGIRR | 1.7537 | 34 | 0.001741 | 35 |
| ISLR2 | 1.7503 | 35 | 0.001843 | 36 |
| AARSD1 | 1.7439 | 36 | 0.002044 | 37 |
| SLC32A1 | 1.7418 | 37 | 0.002115 | 38 |
| PLXDC2 | 1.7393 | 38 | 0.002204 | 39 |
| FGF17 | 1.7376 | 39 | 0.002262 | 40 |
| SLC25A20 | 1.7366 | 40 | 0.002296 | 41 |
| DCAF7 | 1.7365 | 41 | 0.002299 | 42 |
| CA12 | 1.7364 | 42 | 0.002303 | 43 |
| MSRB3 | 1.7356 | 43 | 0.002335 | 44 |
| TRIM7 | 1.7353 | 44 | 0.002345 | 45 |
| RRAS2 | 1.7338 | 45 | 0.002397 | 46 |
| OSBPL1A | 1.7278 | 46 | 0.002622 | 47 |
| CEP63 | 1.7275 | 47 | 0.002638 | 48 |
| PHC2 | 1.7252 | 48 | 0.002725 | 49 |
| SPHK1 | 1.7246 | 49 | 0.00275 | 50 |
| ACP6 | 1.7206 | 50 | 0.002914 | 51 |
| NEIL3 | 1.7182 | 51 | 0.003017 | 52 |
| TNNC1 | 1.7141 | 52 | 0.003201 | 53 |
| KIAA1804 | 1.7133 | 53 | 0.003233 | 54 |
| MAP3K11 | 1.7131 | 54 | 0.003242 | 55 |
| ZNF582 | 1.7128 | 55 | 0.003256 | 56 |
| SNX13 | 1.7111 | 56 | 0.003333 | 57 |
| CPLX2 | 1.7104 | 57 | 0.003366 | 58 |
| FGD1 | 1.7102 | 58 | 0.003377 | 59 |
| DTX3 | 1.7093 | 59 | 0.003416 | 60 |
| IFNGR1 | 1.7078 | 60 | 0.003484 | 61 |
| LRRC10B | 1.7075 | 61 | 0.003499 | 62 |
| UBE2E3 | 1.7048 | 62 | 0.003629 | 63 |
| VKORC1 | 1.7028 | 63 | 0.003727 | 64 |

FIG. 40B

| | | | | |
|---|---|---|---|---|
| PPDPF | 1.6994 | 64 | 0.003893 | 65 |
| CCND2 | 1.697 | 65 | 0.004017 | 66 |
| TEAD4 | 1.6967 | 66 | 0.004032 | 67 |
| TMEM26 | 1.6961 | 67 | 0.004065 | 68 |
| HMGXB3 | 1.6959 | 68 | 0.004074 | 69 |
| PDCD4 | 1.6936 | 69 | 0.004192 | 70 |
| COA3 | 1.6924 | 70 | 0.004258 | 71 |
| LAMP5 | 1.6918 | 71 | 0.004287 | 72 |
| NEK5 | 1.6912 | 72 | 0.004322 | 73 |
| MRPS35 | 1.6901 | 73 | 0.004382 | 74 |
| TAPBP | 1.6892 | 74 | 0.004431 | 75 |
| FGF8 | 1.689 | 75 | 0.00444 | 76 |
| GBE1 | 1.6887 | 76 | 0.004455 | 77 |
| KCND1 | 1.6887 | 77 | 0.004458 | 78 |
| TRIB1 | 1.6883 | 78 | 0.004475 | 79 |
| SEBOX | 1.688 | 79 | 0.004493 | 80 |
| ATP10A | 1.6859 | 80 | 0.004614 | 81 |
| RNF41 | 1.6849 | 81 | 0.004673 | 82 |
| PROM1 | 1.6848 | 82 | 0.004676 | 83 |
| BCAP29 | 1.6819 | 83 | 0.004845 | 84 |
| EFNA1 | 1.6783 | 84 | 0.005063 | 85 |
| ZNF83 | 1.6778 | 85 | 0.005091 | 86 |
| MAGEB6 | 1.6774 | 86 | 0.005119 | 87 |
| TAS2R19 | 1.6766 | 87 | 0.005166 | 88 |
| BCAR1 | 1.6744 | 88 | 0.005307 | 89 |
| STAT4 | 1.6739 | 89 | 0.005336 | 90 |
| RPS16 | 1.6721 | 90 | 0.005454 | 91 |
| FICD | 1.6718 | 91 | 0.005475 | 92 |
| CPEB1 | 1.6713 | 92 | 0.005503 | 93 |
| TMEM133 | 1.6694 | 93 | 0.005625 | 94 |
| SNED1 | 1.6693 | 94 | 0.005635 | 95 |
| TCEA2 | 1.6684 | 95 | 0.005691 | 96 |
| GSR | 1.6667 | 96 | 0.005808 | 97 |
| IQGAP3 | 1.6618 | 97 | 0.006145 | 98 |
| RAB42 | 1.6617 | 98 | 0.006149 | 99 |
| ADORA1 | 1.6603 | 99 | 0.006254 | 100 |

FIG. 40C

Top 100 genes from the output of the RIGER algorithm for the sgRNA-Puro PLX screen comparing PLX (mean of the two replicates at Day 21) to DMSO control (mean of the two replicates at Day 21). The Kolmogorov-Smirnov method was used to score genes.

| Gene | NES | Gene rank | p-value | p-value rank |
|---|---|---|---|---|
| EGFR | 1.8164 | 3 | 0.00000001 | 1 |
| LPAR5 | 1.8175 | 1 | 0.00000001 | 2 |
| P2RY8 | 1.8165 | 2 | 0.00000001 | 3 |
| MECOM | 1.8111 | 4 | 0.0000003 | 4 |
| CRB2 | 1.8109 | 5 | 0.00000035 | 5 |
| GLIS3 | 1.7914 | 6 | 0.000014 | 6 |
| PCDH7 | 1.7879 | 7 | 0.00002015 | 7 |
| TFAP2C | 1.7749 | 8 | 0.00005425 | 8 |
| C9orf50 | 1.7679 | 9 | 0.00008335 | 9 |
| LPAR1 | 1.7678 | 10 | 0.000084 | 10 |
| CNR1 | 1.758 | 11 | 0.0001413 | 11 |
| BCAR3 | 1.7565 | 12 | 0.0001516 | 12 |
| ITGB3 | 1.7542 | 13 | 0.000169 | 13 |
| CGNL1 | 1.7529 | 14 | 0.0001793 | 14 |
| ZASP | 1.747 | 15 | 0.0002318 | 15 |
| P2RY1 | 1.7435 | 16 | 0.0002672 | 16 |
| TNRC18 | 1.7352 | 17 | 0.000363 | 17 |
| GPR35 | 1.7297 | 18 | 0.0004385 | 18 |
| ARHGEF2 | 1.7293 | 19 | 0.0004437 | 19 |
| KRAS | 1.7254 | 20 | 0.000504 | 20 |
| PBX2 | 1.7227 | 21 | 0.0005528 | 21 |
| PYGO1 | 1.719 | 22 | 0.0006131 | 22 |
| RASSF5 | 1.7167 | 23 | 0.0006551 | 23 |
| AKR1B1 | 1.7122 | 24 | 0.000745 | 24 |
| ZFHX4 | 1.7106 | 25 | 0.0007778 | 25 |
| ACVR2A | 1.7104 | 26 | 0.0007828 | 26 |
| ITGB5 | 1.7078 | 27 | 0.0008385 | 27 |
| LOC730183 | 1.7072 | 28 | 0.0008523 | 28 |

FIG. 41A

| | | | | |
|---|---|---|---|---|
| COL25A1 | 1.7057 | 29 | 0.0008865 | 29 |
| EPAS1 | 1.7044 | 30 | 0.0009167 | 30 |
| RPS16 | 1.7022 | 31 | 0.0009716 | 31 |
| CST5 | 1.7015 | 32 | 0.000991 | 32 |
| CHN2 | 1.6984 | 33 | 0.001067 | 33 |
| RAPGEF1 | 1.6968 | 34 | 0.001111 | 34 |
| ABLIM2 | 1.6921 | 35 | 0.001241 | 35 |
| GAB2 | 1.69 | 36 | 0.001305 | 36 |
| INHBA | 1.6861 | 37 | 0.001424 | 37 |
| C11orf21 | 1.6851 | 38 | 0.001456 | 38 |
| NEFM | 1.6843 | 39 | 0.001484 | 39 |
| C19orf18 | 1.6841 | 40 | 0.00149 | 40 |
| SLC19A2 | 1.681 | 41 | 0.001591 | 41 |
| DYRK3 | 1.6775 | 42 | 0.001718 | 42 |
| ARHGAP6 | 1.6742 | 43 | 0.001842 | 43 |
| FOXO4 | 1.6723 | 44 | 0.001913 | 44 |
| EIF4EBP2 | 1.6711 | 45 | 0.001955 | 45 |
| TMEM199 | 1.6694 | 46 | 0.002024 | 46 |
| ZCCHC11 | 1.6692 | 47 | 0.00203 | 47 |
| CHID1 | 1.668 | 48 | 0.002082 | 48 |
| MGAT3 | 1.6669 | 49 | 0.002129 | 49 |
| CHST15 | 1.6667 | 50 | 0.002138 | 50 |
| C14orf39 | 1.6649 | 51 | 0.002214 | 51 |
| FSD1 | 1.6636 | 52 | 0.002271 | 52 |
| STAU2 | 1.6629 | 53 | 0.002296 | 53 |
| TRIM65 | 1.6579 | 54 | 0.002526 | 54 |
| JUN | 1.6571 | 55 | 0.002561 | 55 |
| MMRN2 | 1.6555 | 56 | 0.002639 | 56 |
| TMEM129 | 1.6532 | 57 | 0.002748 | 57 |
| BRINP1 | 1.6507 | 58 | 0.002872 | 58 |
| BCL7C | 1.6494 | 59 | 0.002938 | 59 |
| NFS1 | 1.6492 | 60 | 0.002947 | 60 |
| AP4B1 | 1.6487 | 61 | 0.002971 | 61 |
| 41885 | 1.6474 | 62 | 0.003039 | 62 |
| B4GALNT2 | 1.6472 | 63 | 0.003052 | 63 |
| MDK | 1.6447 | 64 | 0.003186 | 64 |

FIG. 41B

| | | | | |
|---|---|---|---|---|
| PABPC5 | 1.6424 | 65 | 0.003309 | 65 |
| TNFRSF1B | 1.6404 | 66 | 0.003425 | 66 |
| MLLT6 | 1.6398 | 67 | 0.003458 | 67 |
| IER3IP1 | 1.6344 | 68 | 0.003784 | 68 |
| PBX1 | 1.6325 | 69 | 0.003907 | 69 |
| BCAS3 | 1.631 | 70 | 0.003993 | 70 |
| HDX | 1.6291 | 71 | 0.00412 | 71 |
| RNF6 | 1.6271 | 72 | 0.00425 | 72 |
| MAP3K11 | 1.6268 | 73 | 0.00427 | 73 |
| CA3 | 1.62 | 74 | 0.004741 | 74 |
| APBB1 | 1.6196 | 75 | 0.004776 | 75 |
| FOXJ1 | 1.6179 | 76 | 0.004905 | 76 |
| LYPD2 | 1.6162 | 77 | 0.005023 | 77 |
| DNASE1L2 | 1.6151 | 78 | 0.005103 | 78 |
| BRI3 | 1.6132 | 79 | 0.005249 | 79 |
| GCK | 1.6112 | 80 | 0.0054 | 80 |
| PRKCE | 1.6081 | 81 | 0.005637 | 81 |
| GCNT1 | 1.6074 | 82 | 0.005693 | 82 |
| CDR2 | 1.6071 | 83 | 0.005713 | 83 |
| DDX11 | 1.6059 | 84 | 0.005807 | 84 |
| SLC2A3 | 1.6015 | 85 | 0.00618 | 85 |
| PAK7 | 1.5993 | 86 | 0.006366 | 86 |
| TCF7L1 | 1.599 | 87 | 0.006387 | 87 |
| SOCS6 | 1.5969 | 88 | 0.006578 | 88 |
| C19orf68 | 1.594 | 89 | 0.006839 | 89 |
| C3orf27 | 1.5938 | 90 | 0.006853 | 90 |
| NBL1 | 1.592 | 91 | 0.007023 | 91 |
| ARHGEF5 | 1.5909 | 92 | 0.007126 | 92 |
| GABRQ | 1.5879 | 93 | 0.007405 | 93 |
| ANKRD29 | 1.5877 | 94 | 0.007428 | 94 |
| ZNF704 | 1.586 | 95 | 0.007587 | 95 |
| RHOG | 1.5853 | 96 | 0.007657 | 96 |
| HOXB4 | 1.5849 | 97 | 0.007701 | 97 |
| CCER1 | 1.5836 | 98 | 0.007833 | 98 |
| ATL1 | 1.5832 | 99 | 0.007874 | 99 |
| RASGRF1 | 1.5831 | 100 | 0.00788 | 100 |

FIG. 41C

TaqMan qPCR probe ID's used to quantify relative RNA expression levels for each gene (Life Technologies)

| Gene | Probe ID |
|---|---|
| ASCL1 | Hs00269932_m1 |
| HBG1/HBG2 | Hs00361131_g1 |
| HOTTIP | Hs00955374_s1 |
| IL1B | Hs01555410_m1 |
| IL1R2 | Hs01030384_m1 |
| KLF4 | Hs00358836_m1 |
| LIN28A | Hs00702808_s1 |
| LINC00028 | Hs04233790_s1 |
| LINC00514 | Hs04273769_m1 |
| LINC00925 | Hs00288663_m1 |
| MYC | Hs00153408_m1 |
| MYOD1 | Hs02330075_g1 |
| NANOG | Hs04260366_g1 |
| NEUROG2 | Mm00437603_g1 |
| PCAT-1 | Hs04275836_s1 |
| POU5F1 | Hs00999632_g1 |
| SOX2 | Hs01053049_s1 |
| TERT | Hs00972656_m1 |
| TINCR | Hs00542141_m1 |
| VEGFA | Hs00900055_m1 |
| ZFP42 | Hs00399279_m1 |

FIG. 42

FUNCTIONAL SCREENING WITH OPTIMIZED FUNCTIONAL CRISPR-CAS SYSTEMS

RELATED APPLICATIONS AND INCORPORATION BY REFERENCE

This application is a Continuation-In-Part of International Application Number PCT/US15/51830 filed on Sep. 24, 2015, which published as WO2016/049258 on Mar. 31, 2016 and claims benefit of and priority to U.S. provisional patent applications 62/055,460 and 62/055,487, filed Sep. 25, 2014, U.S. provisional patent applications 62/087,475, and 62/087,546, filed Dec. 4, 2014, and U.S. provisional patent applications 62/181,687 and 62/181,690, filed Jun. 18, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant numbers MH100706, OD009552 and NS073124 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created Mar. 24, 2017 is named 47267992084_SL.txt and is 567.654 bytes in size.

FIELD OF THE INVENTION

The present invention generally relates to systems, methods and compositions used for the control of gene expression involving sequence targeting, such as genome perturbation or gene-editing, that may use vector systems related to Clustered Regularly Interspaced Short Palindromic Repeats (CRISPR) and components thereof. In particular the present invention comprehends optimized functional CRISPR-Cas enzyme systems.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

There exists a pressing need for alternative and robust systems and techniques for sequence targeting with a wide array of applications. This invention addresses this need and provides related advantages. The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

In an aspect the invention provides non-naturally occurring or engineered composition comprising a guide RNA (sgRNA) comprising a guide sequence capable of hybridizing to a target sequence in a genomic locus of interest in a cell, wherein one or more loop(s) of the sgRNA is modified by the insertion of distinct RNA sequence(s) that bind to two or more adaptor proteins, and wherein each adaptor protein is associated with one or more functional domains; or, wherein the sgRNA is modified to have at least one non-coding functional loop. And when there is more than one functional domain, the functional domains can be same or different, e.g., two of the same or two different activators or repressors. In an aspect the invention provides non-naturally occurring or engineered CRISPR-Cas complex composition comprising the sgRNA as herein-discussed and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences. In an aspect the invention provides a herein-discussed sgRNA or the CRISPR-Cas complex including a non-naturally occurring or engineered composition comprising two or more adaptor proteins, wherein each protein is associated with one or more functional domains and wherein the adaptor protein binds to the distinct RNA sequence(s) inserted into the at least one loop of the sgRNA. In an aspect the invention provides a non-naturally occurring or engineered composition comprising a guide RNA (sgRNA) comprising a guide sequence capable of hybridizing to a target sequence in a genomic locus of interest in a cell, a CRISPR enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation, wherein at least one loop of the sgRNA is modified by the insertion of distinct RNA sequence(s) that bind to one or more adaptor proteins, and wherein the adaptor protein is associated with one or more functional domains; or, wherein the sgRNA is modified to have at least one non-coding functional loop, and wherein the composition comprises two or more adaptor proteins, wherein the each protein is associated with one or more functional domains. In an aspect the invention provides a herein-discussed composition, wherein the CRISPR enzyme has a diminished nuclease activity of at least 97%, or 100% as compared with the CRISPR enzyme not having the at least one mutation. In an aspect the invention provides a herein-discussed composition, wherein the CRISPR enzyme comprises two or more mutations wherein two or more of D10, E762, H840, N854, N863, or D986 according to SpCas9 protein or any corresponding or N580 according to SaCas9 protein ortholog are mutated, or the CRISPR enzyme comprises at least one mutation wherein at least H840 is mutated. In an aspect the invention provides a herein-discussed composition wherein the CRISPR enzyme comprises two or more mutations comprising D10A, E762A, H840A, N854A, N863A or D986A according to SpCas9 protein or any corresponding ortholog, or N580A according to SaCas9 protein, or at least one mutation comprising H840A, or, optionally wherein the CRISPR enzyme comprises: N580A according to SaCas9 protein or any corresponding ortholog; or D10A according to SpCas9 protein, or any corresponding ortholog, and N580A according to SaCas9 protein. In an aspect the invention provides a herein-discussed composition, wherein the CRISPR enzyme comprises H840A, or D10A and H840A, or D10A and N863A, according to SpCas9 protein or any corresponding ortholog. In an aspect the invention provides a herein-discussed composition, wherein the CRISPR enzyme is associated with one or more functional domains. In an aspect the invention provides a herein-discussed composition, wherein the two or more functional domains associated with the adaptor protein is a heterologous functional domain. In an aspect the invention provides a herein-discussed composition, wherein the one or more functional domains associated with the CRISPR enzyme is a heterologous functional domain. In an aspect the invention provides a herein-discussed composition, wherein the adaptor protein is a fusion protein comprising the functional domain, the fusion protein optionally comprising a linker between the adaptor protein and the functional domain, the linker optionally including a GlySer linker. In an aspect the invention provides a herein-discussed composition, wherein the at least one loop of the sgRNA is not modified by the insertion of distinct RNA sequence(s) that bind to the two or more adaptor proteins. In an aspect the invention provides a herein-discussed composition, wherein the one or more functional domains associated with the adaptor protein is a transcriptional activation domain. In an aspect the invention provides a herein-discussed composition, wherein the one or more functional domains associated with the CRISPR enzyme is a transcriptional activation domain. In an aspect the invention provides a herein-discussed composition, wherein the one or more functional domains associated with the adaptor protein is a transcriptional activation domain comprising VP64, p65, MyoD1, HSF1, RTA or SETT/9. In an aspect the invention provides a herein-discussed composition, wherein the one or more functional domains associated with the CRISPR enzyme is a transcriptional activation domain comprises VP64, p65, MyoD1, HSF1, RTA or SETT/9. In an aspect the invention provides a herein-discussed composition, wherein the one or more functional domains associated with the adaptor protein is a transcriptional repressor domain. In an aspect the invention provides a herein-discussed composition, wherein the one or more functional domains associated with the CRISPR enzyme is a transcriptional repressor domain. In an aspect the invention provides a herein-discussed composition, wherein the transcriptional repressor domain is a KRAB domain. In an aspect the invention provides a herein-discussed composition, wherein the transcriptional repressor domain is a NuE domain, NcoR domain, SID domain or a SID4X domain. In an aspect the invention provides a herein-discussed composition, wherein at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity. In an aspect the invention provides a herein-discussed composition, wherein the one or more functional domains associated with the CRISPR enzyme have one or more activities comprising methylase activity, demethylase activity, transcription activation activity, transcription repression activity, transcription release factor activity, histone modification activity, DNA integration activity RNA cleavage activity, DNA cleavage activity, nucleic acid binding activity, or molecular switch activity or chemical inducibility or light inducibility. In an aspect the invention provides a herein-discussed composition, wherein the DNA cleavage activity is due to a Fok1 nuclease. In an aspect the invention provides a herein-discussed composition, wherein the one or more functional domains is attached to the CRISPR enzyme so that upon binding to the sgRNA and target the functional domain is in a spatial orientation allowing for the functional domain to function in its attributed function; or, optionally, wherein the one or more functional domains is attached to the CRISPR enzyme via a linker, optionally a GlySer linker. In an aspect the invention provides a herein-discussed composition, wherein the sgRNA is modified so that, after sgRNA binds the adaptor protein and further binds to the CRISPR enzyme and target, the functional domain is in a spatial orientation allowing for the functional domain to function in its attributed function. In an aspect the invention provides a herein-discussed composition, wherein the one or more functional domains associated with the CRISPR enzyme is attached to the Rec1 domain, the Rec2 domain, the HNH domain, or the PI domain of the SpCas9 protein or any ortholog corresponding to these domains. In an aspect the invention provides a herein-discussed composition, wherein the one or more functional domains associated with the CRISPR enzyme is attached to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains. In an aspect the invention provides a herein-discussed composition, wherein the one or more functional domains associated with the CRISPR enzyme is attached to the Rec1 domain or the Rec2 domain, of the SpCas9 protein or any ortholog corresponding to these domains. In an aspect the invention provides a herein-discussed composition, wherein the one or more functional domains associated with the CRISPR enzyme is attached to the Rec2 domain of the SpCas9 protein or any ortholog corresponding to this domain. In an aspect the invention provides a herein-discussed composition, wherein the at least one loop of the sgRNA is tetraloop and/or loop2. In an aspect the invention provides a herein-discussed composition, wherein the tetraloop and loop 2 of the sgRNA are modified by the insertion of the distinct RNA sequence(s). In an aspect the invention provides a herein-discussed composition, wherein the insertion of distinct RNA sequence(s) that bind to one or more adaptor proteins is an aptamer sequence. In an aspect the invention provides a herein-discussed composition, wherein the aptamer sequence is two or more aptamer sequences specific to the same adaptor protein. In an aspect the invention provides a herein-discussed composition, wherein the aptamer sequence is two or more aptamer sequences specific to different adaptor protein. In an aspect the invention provides a herein-discussed composition, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In an aspect the invention provides a herein-discussed composition, wherein the cell is a eukaryotic cell. In an aspect the invention provides a herein-discussed composition, wherein the eukaryotic cell is a mammalian cell, optionally a mouse cell. In an aspect the invention provides a herein-discussed composition, wherein the mammalian cell is a human cell. In an aspect the invention provides a herein-discussed composition, wherein a first adaptor protein is associated with a p65 domain and a second adaptor protein is associated with a HSF1 domain. In an aspect the invention provides a herein-discussed composition, wherein the composition comprises a CRISPR-Cas complex having at least three functional domains, at least one of which is associated with the CRISPR enzyme and at least two of which are associated with sgRNA.

In an aspect the invention provides a method for introducing a genomic locus event comprising the administration to a host or expression in a host in vivo of one or more of the compositions as herein-discussed. In an aspect the invention provides a herein-discussed method, wherein the genomic locus event comprises affecting gene activation, gene inhibition, or cleavage in the locus.

In an aspect the invention provides a herein-discussed method, wherein the host is a eukaryotic cell. In an aspect the invention provides a herein-discussed method, wherein the host is a mammalian cell, optionally a mouse cell. In an aspect the invention provides a herein-discussed method, wherein the host is a non-human eukaryote. In an aspect the invention provides a herein-discussed method, wherein the non-human eukaryote is a non-human mammal. In an aspect the invention provides a herein-discussed method, wherein the non-human mammal is a mouse.

In an aspect the invention provides a method of modifying a genomic locus of interest to change gene expression in a cell by introducing or expressing in a cell the composition as herein-discussed. In an aspect the invention provides a herein-discussed method comprising the delivery of the composition or nucleic acid molecule(s) coding therefor, wherein said nucleic acid molecule(s) are operatively linked to regulatory sequence(s) and expressed in vivo. In an aspect the invention provides a herein-discussed method wherein the expression in vivo is via a lentivirus, an adenovirus, or an AAV.

In an aspect the invention provides a mammalian cell line of cells as herein-discussed, e.g., wherein the cell line is, optionally, a human cell line or a mouse cell line. In an aspect the invention provides a transgenic mammalian model, optionally a mouse, wherein the model has been transformed with a herein-discussed composition or is a progeny of said transformant.

In an aspect the invention provides a nucleic acid molecule(s) encoding sgRNA or the CRISPR-Cas complex or the composition as herein-discussed. In an aspect the invention provides a vector comprising: a nucleic acid molecule encoding a guide RNA (sgRNA) comprising a guide sequence capable of hybridizing to a target sequence in a genomic locus of interest in a cell, wherein one or more loop(s) of the sgRNA is modified by the insertion of distinct RNA sequence(s) that bind to two or more adaptor proteins, and wherein each adaptor protein is associated with one or more functional domains; or, wherein the sgRNA is modified to have at least one non-coding functional loop. In an aspect the invention provides vector(s) comprising nucleic acid molecule(s) encoding: non-naturally occurring or engineered CRISPR-Cas complex composition comprising the sgRNA herein-discussed, and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences. In an aspect a vector can further comprise regulatory element(s) operable in a eukaryotic cell operably linked to the nucleic acid molecule encoding the guide sequence (sgRNA) and/or the nucleic acid molecule encoding the CRISPR enzyme and/or the optional nuclear localization sequence(s).

In an aspect the invention provides a method of screening for gain of function (GOF) or loss of function (LOF) or for screen non-coding RNAs or potential regulatory regions (e.g. enhancers, repressors) comprising the cell line of as herein-discussed or cells of the model herein-discussed containing or expressing Cas9 and introducing a composition as herein-discussed into cells of the cell line or model, whereby the sgRNA includes either an activator or a repressor, and monitoring for GOF or LOF respectively as to those cells as to which the introduced sgRNA includes an activator or as to those cells as to which the introduced sgRNA includes a repressor. The screening of the instant invention is referred to as a SAM screen.

In an aspect the invention provides a herein-discussed composition wherein the CRISPR enzyme includes one or more functional domains.

In an aspect the invention provides a herein-discussed composition of wherein there is more than one sgRNA, and the sgRNAs target different sequences whereby when the composition is employed, there is multiplexing. In an aspect the invention provides a composition wherein there is more than one sgRNA modified by the insertion of distinct RNA sequence(s) that bind to one or more adaptor proteins. In an aspect the invention provides a herein-discussed composition wherein one or more adaptor proteins associated with one or more functional domains is present and bound to the distinct RNA sequence(s) inserted into the at least one loop of the sgRNA.

In an aspect the invention provides a CRISPR Cas complex comprising a CRISPR enzyme and a guide RNA (sgRNA), wherein the CRISPR enzyme comprises at least one mutation, such that the CRISPR enzyme has no more than 5% of the nuclease activity of the CRISPR enzyme not having the at least one mutation and, optional, at least one or more nuclear localization sequences; the guide RNA (sgRNA) comprises a guide sequence capable of hybridizing to a target sequence in a genomic locus of interest in a cell; and wherein: at least one loop of the sgRNA is modified by the insertion of distinct RNA sequence(s) that bind to one or more adaptor proteins, and wherein the adaptor protein is associated with two or more functional domains, or, wherein the sgRNA is modified to have at least one non-coding functional loop; or the CRISPR enzyme is associated with one or more functional domains and at least one loop of the sgRNA is modified by the insertion of distinct RNA sequence(s) that bind to one or more adaptor proteins, and wherein the adaptor protein is associated with two or more functional domains, or, wherein the sgRNA is modified to have at least one non-coding functional loop.

In an aspect the invention provides a herein-discussed composition wherein the target sequence(s) are non-coding or regulatory sequences. The regulatory sequences can be promoter, enhancer or silencer sequence(s).

In an aspect the invention provides a herein-discussed composition wherein the sgRNA is modified to have at least one non-coding functional loop; e.g., wherein the at least one non-coding functional non-coding loop is repressive; for instance, wherein at least one non-coding functional non-coding loop comprises Alu.

In an aspect the invention provides a genome wide library comprising a plurality of CRISPR-Cas system guide RNAs (sgRNAs) comprising guide sequences, each of which is capable of hybridizing to a target sequence in a genomic locus of interest in a cell and whereby the library is capable of targeting a plurality of target sequences in a plurality of genomic loci in a population of eukaryotic cells, wherein in each sgRNA at least one loop is modified by the insertion of distinct RNA sequence(s) that binds to one or more or two or more adaptor proteins, and wherein the adaptor protein is associated with one or more functional domains; or, wherein the sgRNA is modified to have at least one non-coding functional loop. And when there is more than one functional domain, the functional domains can be same or different, e.g., two of the same or two different activators or repressors. In an aspect the invention provides a library of non-naturally occurring or engineered CRISPR-Cas complexes composition(s) comprising sgRNAs of this invention and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences. In an aspect the invention provides a sgRNA(s) or CRISPR-Cas complex(es) of the invention including a non-naturally occurring or engineered composition comprising one or two or more adaptor proteins, wherein each protein is associated with one or more functional domains and wherein the adaptor protein binds to the distinct RNA sequence(s) inserted into the at least one loop of the sgRNA.

In an aspect the invention provides a library of non-naturally occurring or engineered compositions, each comprising a guide RNA (sgRNA) comprising a guide sequence capable of hybridizing to a target sequence in a genomic locus of interest in a cell, a CRISPR enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation, wherein at least one loop of the sgRNA is modified by the insertion of distinct RNA sequence(s) that bind to one or more adaptor proteins, and wherein the adaptor protein is associated with one or more functional domains, wherein the composition comprises one or more or two or more adaptor proteins, wherein the each protein is associated with one or more functional domains, and wherein the sgRNAs comprise a genome wide library comprising a plurality of CRISPR-Cas system guide RNAs (sgRNAs). In an aspect the invention provides a library as herein-discussed, wherein the CRISPR enzyme has a diminished nuclease activity of at least 97%, or 100% as compared with the CRISPR enzyme not having the at least one mutation. In an aspect the invention provides a library as herein-discussed, wherein the CRISPR enzyme comprises two or more mutations wherein two or more of D10, E762, H840, N854, N863, or D986 according to SpCas9 protein or any corresponding ortholog are mutated, or the CRISPR enzyme comprises at least one mutation wherein at least H840 is mutated. In an aspect the invention provides a library as herein-discussed wherein the CRISPR enzyme comprises two or more mutations comprising D10A, E762A, H840A, N854A, N863A or D986A according to SpCas9 protein or any corresponding ortholog, or at least one mutation comprising H840A. In an aspect the invention provides a library as herein-discussed, wherein the CRISPR enzyme comprises H840A, or D10A and H840A, or D10A and N863A, according to SpCas9 protein or any corresponding ortholog. In an aspect the invention provides a library as herein-discussed, wherein the CRISPR enzyme is associated with one or more functional domains. In an aspect the invention provides a library as herein-discussed, wherein the one or two or more functional domains associated with the adaptor protein is a heterologous functional domain. In an aspect the invention provides a library as herein-discussed, wherein the one or more functional domains associated with the CRISPR enzyme is a heterologous functional domain. In an aspect the invention provides a library as herein-discussed, wherein the adaptor protein is a fusion protein comprising the functional domain. In an aspect the invention provides a library as herein discussed, wherein the at least one loop of the sgRNA is not modified by the insertion of distinct RNA sequence(s) that bind to the one or two or more adaptor proteins. In an aspect the invention provides a library as herein-discussed, wherein the one or two or more functional domains associated with the adaptor protein is a transcriptional activation domain. In an aspect the invention provides a library as herein discussed, wherein the one or two or more functional domains associated with the CRISPR enzyme is a transcriptional activation domain. In an aspect the invention provides a library as herein-discussed, wherein the one or two or more functional domains associated with the adaptor protein is a transcriptional activation domain comprising VP64, p65, MyoD1 or HSF1. In an aspect the invention provides a library as herein discussed, wherein the one or more functional domains associated with the CRISPR enzyme is a transcriptional activation domain comprises VP64, p65, MyoD1 or HSF1. In an aspect the invention provides a library as herein-discussed, wherein the one or two or more functional domains associated with the adaptor protein is a transcriptional repressor domain. In an aspect the invention provides a library as herein-discussed, wherein the one or more functional domains associated with the CRISPR enzyme is a transcriptional repressor domain. In an aspect the invention provides a library as herein-discussed, wherein the transcriptional repressor domain is a KRAB domain. In an aspect the invention provides a library as herein-discussed, wherein the transcriptional repressor domain is a SID domain or a SID4X domain. In an aspect the invention provides a library as herein-discussed, wherein at least one of the one or two or more functional domains associated with the adaptor protein have one or more activities comprising methylase activity, demethylase activity, transcription activation activity, transcription repression activity, transcription release factor activity, histone modification activity, RNA cleavage activity, DNA cleavage activity or nucleic acid binding activity. In an aspect the invention provides a library as herein-discussed, wherein the one or more functional domains associated with the CRISPR enzyme have one or more activities comprising methylase activity, demethylase activity, transcription activation activity, transcription repression activity, transcription release factor activity, histone modification activity, RNA cleavage activity, DNA cleavage activity, nucleic acid binding activity, or molecular switch activity or chemical inducibility or light inducibility. In an aspect the invention provides a library of as herein-discussed, wherein the DNA cleavage activity is a Fok1 nuclease. In an aspect the invention provides a library as herein-discussed, wherein the one or more functional domains is attached to the CRISPR enzyme so that upon binding to the sgRNA and target the functional domain is in a spatial orientation allowing for the functional domain to function in its attributed function. In an aspect the invention provides a library as herein-discussed, wherein the sgRNA is modified so that, after sgRNA binds the adapter protein and further binds to the CRISPR enzyme and target, the functional domain is in a spatial orientation allowing for the functional domain to function in its attributed function. In an aspect the invention provides a library as herein-discussed, wherein the one or more functional domains associated with the CRISPR enzyme is attached to the N terminus of the CRISPR enzyme. In an aspect the invention provides a library as herein-discussed, wherein the one or more functional domains associated with the CRISPR enzyme is attached to the Rec1 domain, the Rec2 domain, the HNH domain, or the PI domain of the SpCas9 protein or any ortholog corresponding to these domains. In an aspect the invention provides a library as herein-discussed, wherein the one or more functional domains associated with the CRISPR enzyme is attached to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains. In an aspect the invention provides a library as herein discussed, wherein the one or more functional domains associated with the CRISPR enzyme is attached to the Rec1 domain or the Rec2 domain, of the SpCas9 protein or any ortholog corresponding to these domains. In an aspect the invention provides a library as herein discussed, wherein the one or more functional domains associated with the CRISPR enzyme is attached to the Rec2 domain of the SpCas9 protein or any ortholog corresponding to this domain. In an aspect the invention provides a library as herein discussed, wherein the at least one loop of the sgRNA is tetraloop and/or loop2. In an aspect the invention provides a library as herein discussed, wherein the tetraloop and loop 2 of the sgRNA are modified by the insertion of the distinct RNA sequence(s). In an aspect the invention provides a library as herein discussed, wherein the insertion of distinct RNA sequence(s) that bind to one or more adaptor proteins is an aptamer sequence. In an aspect the invention provides a library as herein discussed, wherein the aptamer sequence is two or more aptamer sequences specific to the same adaptor protein. In an aspect the invention provides a library as herein discussed, wherein the aptamer sequence is two or more aptamer sequences specific to different adaptor protein. In an aspect the invention provides a library as herein discussed, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In an aspect the invention provides a library as herein discussed, wherein the cell population of cells is a population of eukaryotic cells. In an aspect the invention provides a library as herein discussed, wherein the eukaryotic cell is a mammalian cell. In an aspect the invention provides a library as herein discussed, wherein the mammalian cell is a human cell. In an aspect the invention provides a library as herein discussed, wherein the population of cells is a population of embryonic stem (ES) cells. In an aspect the invention provides a library as herein discussed, wherein the target sequence in the genomic locus is a non-coding sequence. In an aspect the invention provides a library as herein discussed, wherein gene function of one or more gene products is altered by said targeting; or wherein as to gene function there is gain of function; or wherein as to gene function there is change of function; or wherein as to gene function there is reduced function; or wherein the screen is for non-coding RNAs or potential regulatory regions (e.g. enhancers, repressors). In an aspect the invention provides a library as herein discussed, wherein said targeting results in a knockout of gene function. In an aspect the invention provides a library as herein discussed, wherein the targeting is of about 100 or more sequences. In an aspect the invention provides a library as herein discussed, wherein the targeting is of about 1000 or more sequences. In an aspect the invention provides a library as herein discussed, wherein the targeting is of about 20,000 or more sequences. In an aspect the invention provides a library as herein discussed, wherein the targeting is of the entire genome. In an aspect the invention provides a library as herein discussed, wherein the targeting is of a panel of target sequences focused on a relevant or desirable pathway. In an aspect the invention provides a library as herein discussed, wherein the pathway is an immune pathway. In an aspect the invention provides a library as herein discussed, wherein the pathway is a cell division pathway. In an aspect the invention provides a library as herein discussed, wherein the alteration of gene function comprises: introducing into each cell in the population of cells a vector system of one or more vectors comprising an engineered, non-naturally occurring CRISPR-Cas system comprising I. a Cas protein, and II. one or more guide RNAs, wherein components I and II may be same or on different vectors of the system, integrating components I and II into each cell, wherein the guide sequence targets a unique gene in each cell, wherein the Cas protein is operably linked to a regulatory element, wherein when transcribed, the guide RNA comprising the guide sequence directs sequence-specific binding of a CRISPR-Cas system to a target sequence in the genomic loci of the unique gene, inducing cleavage of the genomic loci by the Cas protein, and confirming different mutations in a plurality of unique genes in each cell of the population of cells thereby generating a mutant cell library. In an aspect the invention provides a library as herein discussed, wherein the one or more vectors are plasmid vectors. In an aspect the invention provides a library as herein discussed, wherein the regulatory element is an inducible promoter. In an aspect the invention provides a library as herein discussed, wherein the inducible promoter is a doxycycline inducible promoter. In an aspect the invention provides a library as herein discussed wherein the confirming of different mutations is by whole exome sequencing. In an aspect the invention provides a library as herein discussed, wherein the mutation is achieved in 100 or more unique genes. In an aspect the invention provides a library as herein discussed, wherein the mutation is achieved in 1000 or more unique genes. In an aspect the invention provides a library as herein discussed, wherein the mutation is achieved in 20,000 or more unique genes. In an aspect the invention provides a library as herein discussed, wherein the mutation is achieved in the entire genome. In an aspect the invention provides a library as herein discussed, wherein the alteration of gene function is achieved in a plurality of unique genes which function in a particular physiological pathway or condition. In an aspect the invention provides a library as herein discussed, wherein the pathway or condition is an immune pathway or condition. In an aspect the invention provides a library as herein discussed, wherein the pathway or condition is a cell division pathway or condition. In an aspect the invention provides a library as herein discussed, wherein a first adaptor protein is associated with a p65 domain and a second adaptor protein is associated with a HSF1 domain. In an aspect the invention provides a library as herein discussed, wherein each a CRISPR-Cas complex has at least three functional domains, at least one of which is associated with the CRISPR enzyme and at least two of which are associated with sgRNA. In an aspect the invention provides a library as herein discussed, wherein the alteration in gene function is a knockout mutation.

In an aspect the invention provides a method for functional screening genes of a genome in a pool of cells ex vivo or in vivo comprising the administration or expression of a library comprising a plurality of CRISPR-Cas system guide RNAs (sgRNAs) and wherein the screening further comprises use of a CRISPR enzyme, wherein the CRISPR complex is modified to comprise a heterologous functional domain. In an aspect the invention provides a method for screening a genome comprising the administration to a host or expression in a host in vivo of a library. In an aspect the invention provides a method as herein discussed further comprising an activator administered to the host or expressed in the host. In an aspect the invention provides a method as herein discussed wherein the activator is attached to a CRISPR enzyme. In an aspect the invention provides a method as herein discussed wherein the activator is attached to the N terminus or the C terminus of the CRISPR enzyme. In an aspect the invention provides a method as herein discussed wherein the activator is attached to a sgRNA loop. In an aspect the invention provides a method as herein discussed further comprising a repressor administered to the host or expressed in the host. In an aspect the invention provides a method as herein discussed, wherein the screening comprises affecting and detecting gene activation, gene inhibition, or cleavage in the locus. In an aspect the invention provides a method as herein discussed, wherein the host is a eukaryotic cell. In an aspect the invention provides a method as herein discussed, wherein the host is a mammalian cell. In an aspect the invention provides a method as herein discussed, wherein the host is a non-human eukaryote. In an aspect the invention provides a method as herein discussed, wherein the non-human eukaryote is a non-human mammal. In an aspect the invention provides a method as herein discussed, wherein the non-human mammal is a mouse. In an aspect the invention provides a method as herein discussed comprising the delivery of the CRISPR-Cas complexes or component(s) thereof or nucleic acid molecule(s) coding therefor, wherein said nucleic acid molecule(s) are operatively linked to regulatory sequence(s) and expressed in vivo. In an aspect the invention provides a method as herein discussed wherein the expressing in vivo is via a lentivirus, an adenovirus, or an AAV. In an aspect the invention provides a method as herein discussed wherein the delivery is via a particle, a nanoparticle, a lipid or a cell penetrating peptide (CPP).

In an aspect the invention provides a pair of CRISPR-Cas complexes, each comprising a guide RNA (sgRNA) comprising a guide sequence capable of hybridizing to a target sequence in a genomic locus of interest in a cell, wherein at least one loop of each sgRNA is modified by the insertion of distinct RNA sequence(s) that bind to one or more adaptor proteins, and wherein the adaptor protein is associated with one or more functional domains, wherein each sgRNA of each CRISPR-Cas comprises a functional domain having a DNA cleavage activity. In an aspect the invention provides a paired CRISPR-Cas complexes as herein-discussed, wherein the DNA cleavage activity is due to a Fok1 nuclease.

In an aspect the invention provides a method for cutting a target sequence in a genomic locus of interest comprising delivery to a cell of the CRISPR-Cas complexes or component(s) thereof or nucleic acid molecule(s) coding therefor, wherein said nucleic acid molecule(s) are operatively linked to regulatory sequence(s) and expressed in vivo. In an aspect the invention provides a method as herein-discussed wherein the delivery is via a lentivirus, an adenovirus, or an AAV. In an aspect the invention provides a method as herein-discussed or paired CRISPR-Cas complexes as herein-discussed wherein the target sequence for a first complex of the pair is on a first strand of double stranded DNA and the target sequence for a second complex of the pair is on a second strand of double stranded DNA. In an aspect the invention provides a method as herein-discussed or paired CRISPR-Cas complexes as herein-discussed wherein the target sequences of the first and second complexes are in proximity to each other such that the DNA is cut in a manner that facilitates homology directed repair. In an aspect a herein method can further include introducing into the cell template DNA. In an aspect, a herein method or herein paired CRISPR-Cas complexes can involve wherein each CRISPR-Cas complex has a CRISPR enzyme that is mutated such that it has no more than about 5% of the nuclease activity of the CRISPR enzyme that is not mutated.

In an aspect the invention provides a library, method or complex as herein-discussed wherein the sgRNA is modified to have at least one non-coding functional loop, e.g., wherein the at least one non-coding functional loop is repressive; for instance, wherein the at least one non-coding functional loop comprises Alu.

In one aspect, the invention provides a method for altering or modifying expression of a gene product. The said method may comprise introducing into a cell containing and expressing a DNA molecule encoding the gene product an engineered, non-naturally occurring CRISPR-Cas system comprising a Cas protein and guide RNA that targets the DNA molecule, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides an engineered, non-naturally occurring CRISPR-Cas system comprising a Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and a second regulatory element operably linked to a Cas protein. Components (a) and (b) may be located on same or different vectors of the system. The guide RNA targets the DNA molecule encoding the gene product in a cell and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and (b) a second regulatory element operably linked to an enzyme-coding sequence encoding said CRISPR enzyme comprising a nuclear localization sequence; wherein components (a) and (b) are located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is *S. pneumoniae*, *S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

With respect to use of the CRISPR-Cas system generally, mention is made of the documents, including patent applications, patents, and patent publications cited throughout this disclosure as embodiments of the invention can be used as in those documents. CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at newphytologist.com); Caliando et al, "Targeted DNA degradation using a CRISPR device stably carried in the host genome, NATURE COMMUNICATIONS 6:6989, DOI: 10.1038/ncomms7989, nature.com/naturecommunications DOI: 10.1038/ncomms7989; U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cell(s) in which one or more mutations have been introduced to be selected. In a preferred embodiment, the CRISPR enzyme is Cas9. In another preferred embodiment of the invention the cell to be selected may be a eukaryotic cell. Aspects of the invention allow for selection of specific cells without requiring a selection marker or a two-step process that may include a counter-selection system.

In a further aspect, the invention involves a computer-assisted method for identifying or designing potential compounds to fit within or bind to CRISPR-Cas9 system or a functional portion thereof or vice versa (a computer-assisted method for identifying or designing potential CRISPR-Cas9 systems or a functional portion thereof for binding to desired compounds) or a computer-assisted method for identifying or designing potential CRISPR-Cas9 systems (e.g., with regard to predicting areas of the CRISPR-Cas9 system to be able to be manipulated—for instance, based on crystal structure data or based on data of Cas9 orthologs, or with respect to where a functional group such as an activator or repressor can be attached to the CRISPR-Cas9 system, or as to Cas9 truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Cas9 crystal structure, e.g., in the CRISPR-Cas9 system binding domain or alternatively or additionally in domains that vary based on variance among Cas9 orthologs or as to Cas9s or as to nickases or as to functional groups, optionally with structural information from CRISPR-Cas9 system complex(es), thereby generating a data set;

(b) comparing, using said processor, said data set to a computer database of structures stored in said computer data storage system, e.g., structures of compounds that bind or putatively bind or that are desired to bind to a CRISPR-Cas9 system or as to Cas9 orthologs (e.g., as Cas9s or as to domains or regions that vary amongst Cas9 orthologs) or as to the CRISPR-Cas9 crystal structure or as to nickases or as to functional groups;

(c) selecting from said database, using computer methods, structure(s)—e.g., CRISPR-Cas9 structures that may bind to desired structures, desired structures that may bind to certain CRISPR-Cas9 structures, portions of the CRISPR-Cas9 system that may be manipulated, e.g., based on data from other portions of the CRISPR-Cas9 crystal structure and/or from Cas9 orthologs, truncated Cas9s, novel nickases or particular functional groups, or positions for attaching functional groups or functional-group-CRISPR-Cas9 systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-Cas9 system;

or, said method comprising: providing the co-ordinates of at least two atoms of the CRISPR-Cas9 crystal structure, e.g., at least two atoms of the herein Crystal Structure Table of the CRISPR-Cas9 crystal structure or co-ordinates of at least a sub-domain of the CRISPR-Cas9 crystal structure ("selected co-ordinates"), providing the structure of a candidate comprising a binding molecule or of portions of the CRISPR-Cas9 system that may be manipulated, e.g., based on data from other portions of the CRISPR-Cas9 crystal structure and/or from Cas9 orthologs, or the structure of functional groups, and fitting the structure of the candidate to the selected co-ordinates, to thereby obtain product data comprising CRISPR-Cas9 structures that may bind to desired structures, desired structures that may bind to certain CRISPR-Cas9 structures, portions of the CRISPR-Cas9 system that may be manipulated, truncated Cas9s, novel nickases, or particular functional groups, or positions for attaching functional groups or functional-group-CRISPR-Cas9 systems, with output thereof; and optionally synthesizing compound(s) from said product data and further optionally comprising testing said synthesized compound(s) as or in a CRISPR-Cas9 system.

The testing can comprise analyzing the CRISPR-Cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (eg POWERPOINT), internet, email, documentary communication such as a computer program (eg WORD) document and the like. Accordingly, the invention also comprehends computer readable media containing: atomic co-ordinate data according to the herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The invention further comprehends a method of doing business comprising providing to a user the computer system or the media or the three dimensional structure of CRISPR-Cas9 or at least one sub-domain thereof, or structure factor data for CRISPR-Cas9, said structure set forth in and said structure factor data being derivable from the atomic co-ordinate data of herein-referenced Crystal Structure, or the herein computer media or a herein data transmission.

A "binding site" or an "active site" comprises or consists essentially of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further.

By "root mean square (or rms) deviation", we mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g. so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

In particular embodiments of the invention, the conformational variations in the crystal structures of the CRISPR-Cas9 system or of components of the CRISPR-Cas9 provide important and critical information about the flexibility or movement of protein structure regions relative to nucleotide (RNA or DNA) structure regions that may be important for CRISPR-Cas system function. The structural information provided for Cas9 (e.g. *S. pyogenes* Cas9) as the CRISPR enzyme in the present application may be used to further engineer and optimize the CRISPR-Cas system and this may be extrapolated to interrogate structure-function relationships in other CRISPR enzyme systems as well, e.g, other Type II CRISPR enzyme systems.

The invention comprehends optimized functional CRISPR-Cas enzyme systems, especially in combination with the present modified guides and also where the CRISPR enzyme is also associated with a functional domain. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain. In some embodiments, a mutation at N580 according to SaCas9 protein is preferred. In particular, it is preferred in place of the mutation, in Sa Cas9, corresponding to H840 in Sp Cas9. In some embodiments, in Sa Cas9, mutation at D10 and N580 are preferred. In some embodiments, the N580 mutation may be N580A according to SaCas9 protein. It is believed, without being bound by theory, that this is a more predictable mutation for protein function than the H840A equivalent, which may change binding behavior.

The structural information provided herein allows for interrogation of sgRNA (or chimeric RNA) interaction with the target DNA and the CRISPR enzyme (e.g. Cas9) permitting engineering or alteration of sgRNA structure to optimize functionality of the entire CRISPR-Cas system. For example, loops of the sgRNA may be extended, without colliding with the Cas9 protein by the insertion of adaptor proteins that can bind to RNA. These adaptor proteins can further recruit effector proteins or fusions which comprise one or more functional domains.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

Aspects of the invention encompass a non-naturally occurring or engineered composition that may comprise a guide RNA (sgRNA) comprising a guide sequence capable of hybridizing to a target sequence in a genomic locus of interest in a cell and a CRISPR enzyme that may comprise at least one or more nuclear localization sequences, wherein the CRISPR enzyme comprises two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the CRISPR enzyme comprises two or more mutations in a residue selected from the group consisting of D10, E762, H840, N854, N863, or D986. In a further embodiment the CRISPR enzyme comprises two or more mutations selected from the group comprising D10A, E762A, H840A, N854A, N863A or D986A. As mentioned above, N580, especially N580A, according to SaCas9 protein is used, especially in Sa Cas9. In another embodiment, the functional domain is a transcriptional activation domain, e.g. VP64. In another embodiment, the functional domain is a transcriptional repressor domain, e.g. KRAB domain, SID domain or a SID4X domain. In embodiments of the invention, the one or more heterologous functional domains have one or more activities selected from the group consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein.

An aspect of the invention is that the above elements are comprised in a single composition or comprised in individual compositions. These compositions may advantageously be applied to a host to elicit a functional effect on the genomic level.

In general, the sgRNA are modified in a manner that provides specific binding sites (e.g. aptamers) for adapter proteins comprising one or more functional domains (e.g. via fusion protein) to bind to. The modified sgRNA are modified such that once the sgRNA forms a CRISPR complex (i.e. CRISPR enzyme binding to sgRNA and target) the adapter proteins bind and, the functional domain on the adapter protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target.

The skilled person will understand that modifications to the sgRNA which allow for binding of the adapter+functional domain but not proper positioning of the adapter+functional domain (e.g. due to steric hindrance within the three dimensional structure of the CRISPR complex) are modifications which are not intended. The one or more modified sgRNA may be modified at the tetra loop, the stem-loop 1, stem-loop 2, or stem-loop 3, as described herein, preferably at either the tetra loop or stem-loop 2, and most preferably at both the tetra loop and stem-loop 2.

As explained herein the functional domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some cases it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g. aptamers) specific to the same or different adapter protein. The sgRNA may be designed to bind to the promoter region −1000−+1 nucleic acids upstream of the transcription start site (i.e. TSS), preferably −200 nucleic acids. This positioning improves functional domains which affect gene activation (e.g. transcription activators) or gene inhibition (e.g. transcription repressors). The modified sgRNA may be one or more modified sgRNAs targeted to one or more target loci (e.g. at least 1 sgRNA, at least 2 sgRNA, at least 5 sgRNA, at least 10 sgRNA, at least 20 sgRNA, at least 30 sgRNA, at least 50 sgRNA) comprised in a composition.

Further, the CRISPR enzyme with diminished nuclease activity is most effective when the nuclease activity is inactivated (e.g. nuclease inactivation of at least 70%, at least 80%, at least 90%, at least 95%, at least 97%, or 100% as compared with the wild type enzyme; or to put in another way, a Cas9 enzyme or CRISPR enzyme having advantageously about 0% of the nuclease activity of the non-mutated or wild type Cas9 enzyme or CRISPR enzyme, or no more than about 3% or about 5% or about 10% of the nuclease activity of the non-mutated or wild type Cas9 enzyme or CRISPR enzyme). This is possible by introducing mutations into the RuvC and HNH nuclease domains of the SpCas9 and orthologs thereof. For example utilizing mutations in a residue selected from the group consisting of D10, E762, H840, N854, N863, or D986 and more preferably introducing one or more of the mutations selected from the group consisting of D10A, E762A, H840A, N854A, N863A or D986A. A preferable pair of mutations is D10A with H840A, more preferable is D10A with N863A of SpCas9 and orthologs thereof. In some embodiments, N580A according to SaCas9 protein, may be used, as discussed herein.

The inactivated CRISPR enzyme may have associated (e.g. via fusion protein) one or more functional domains, like for example as described herein for the modified sgRNA adaptor proteins, including for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) (as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated CRISPR enzyme is one which allows for correct spatial orientation for the functional domain to affect the target with the attributed functional effect. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target, and a nuclease (e.g. Fok1) will be advantageously positioned to cleave or partially cleave the target. This may include positions other than the N-/C-terminus of the CRISPR enzyme.

Due to crystal structure experiments, the Applicant has identified that positioning the functional domain in the Rec1 domain, the Rec2 domain, the HNH domain, or the PI domain of the SpCas9 protein or any ortholog corresponding to these domains is advantageous. Positioning of the functional domains to the Rec1 domain or the Rec2 domain, of the SpCas9 protein or any ortholog corresponding to these domains, in some instances may be preferred. Positioning of the functional domains to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preferred. Fok1 functional domain may be attached at the N terminus. When more than one functional domain is included, the functional domains may be the same or different.

The adaptor protein may be any number of proteins that binds to an aptamer or recognition site introduced into the modified sgRNA and which allows proper positioning of one or more functional domains, once the sgRNA has been incorporated into the CRISPR complex, to affect the target with the attributed function. As explained in detail in this application such may be coat proteins, preferably bacteriophage coat proteins. The functional domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified sgRNA, the inactivated CRISPR enzyme (with or without functional domains), and the binding protein with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g. lentiviral vector, adenoviral vector, AAV vector). As explained herein, use of different selection markers (e.g. for lentiviral sgRNA selection) and concentration of sgRNA (e.g. dependent on whether multiple sgRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g. gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals. (See, e.g., Platt et al., Cell (2014), DOI:10.1016/j.cell.2014.09.014, or PCT patent publications cited herein, such as WO 2014/093622 (PCT/US2013/074667), which are not believed prior to the present invention or application). For example, the target cell comprises CRISPR enzyme (e.g. Cas9) conditionally or inducibly (e.g. in the form of Cre dependent constructs) and/or the adapter protein conditionally or inducibly and, on expression of a vector introduced into the target cell, the vector expresses that which induces or gives rise to the condition of CRISPR enzyme (e.g. Cas9) expression and/or adaptor expression in the target cell. By applying the teaching and compositions of the current invention with the known method of creating a CRISPR complex, inducible genomic events affected by functional domains are also an aspect of the current invention. One more example of this is the creation of a CRISPR knock-in/conditional transgenic animal (e.g. mouse comprising e.g. a Lox-Stop-polyA-Lox(LSL) cassette) and subsequent delivery of one or more compositions providing one or more modified sgRNA (e.g. –200 nucleotides to TSS of a target gene of interest for gene activation purposes) as described herein (e.g. modified sgRNA with one or more aptamers recognized by coat proteins, e.g. MS2), one or more adapter proteins as described herein (MS2 binding protein linked to one or more VP64) and means for inducing the conditional animal (e.g. Cre recombinase for rendering Cas9 expression inducible). Alternatively, the adaptor protein may be provided as a conditional or inducible element with a conditional or inducible CRISPR enzyme to provide an effective model for screening purposes, which advantageously only requires minimal design and administration of specific sgRNAs for a broad number of applications.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 21A-F shows structure-guided design and optimization of an RNA-guided transcription activation complex. a, The crystal structure of the Cas9-sgRNA-target DNA tertiary complex (PDB ID: 4O08) reveals the occlusion of N- and C-terminal fusion sites from the target DNA. The sgRNA tetraloop and stem-loop 2 largely do not contact Cas9 amino acid residues in this conformation and can be modified without altering existing Cas9-sgRNA interactions. b, Diagram of three-component transcriptional activation system (SAM): sgRNA2.0, the MS2-p65-HSF1 transcription transactivator, and the dCas9-VP64 fusion protein. MS2 stem-loop additions on the sgRNA are highlighted in red. c, Design and optimization of sgRNA scaffolds for optimal recruitment of MS2-VP64 transactivators. d, MS2 stem-loop placement within the sgRNA significantly affects transcription activation efficiency. e, Combinations of different activation domains act in synergy to further enhance the level of transcription activation. f, Addition of the HSF1 transactivation domain to MS2-p65 further increases the efficiency of transcription activation. All values are mean+–SEM with n=3. * indicate p<0.05 based on Student's t-test.

FIGS. 25A-E shows genome-scale lentiviral screen in mammalian cells using SAM. a, Design of three lentiviral vectors for expressing sgRNA2.0, dCas9-VP64, and MS2-p65-HSF1. Each vector contains a distinct selection marker to enable co-selection of cells expressing all three vectors. b, Lentiviral delivery of SAM components was tested by first generating 293FT cell lines stably integrated with dCas9-VP64 and MS2-p65-HSF1, and subsequently transducing these cells with single-gene targeting lentiviral sgRNA2.0s at MOI<0.2. Transcription activation efficiency is measured 4 days post sgRNA2.0s lentivirus transduction and selection with Zeocin or Puromycin. All values are mean+–SEM with n=3. c, Flow chart of transcription activation screening using SAM. d, Cumulative frequency of sgRNA2.0s 3 and 21 days after transduction in A375 cells. Shift in the 21-day curve represents the depletion in a subset of sgRNA2.0s. Less than 0.1% of all guides are not detected at day 3 (detected by less than 10 reads). e, Gene categories showing significant depletion based on Ingenuity Pathway Analysis (p<0.01 after B—H FDR correction). Categories on the left are based on the 1000 most depleted guides and categories on the right are based on the 1000 genes with the highest depletion based on the average of all 3 guides/gene.

FIGS. 26A-F shows genome-scale gene activation screening identifies mediators of BRAF inhibitor resistance. a, Box plot showing the distribution of sgRNA2.0 frequencies at different time points post lentiviral transduction, with and without treatment with PLX-4720. Vehicle is DMSO. Two infection replicates are shown. b, Scatterplot showing enrichment of specific sgRNA2.0s after PLX-4720 treatment. c, Identification of top candidate genes using the RIGER P value analysis (KS method) based on the average of both infection replicates. Genes are organized by positions within chromosomes. d, RIGER P values for the top 100 hits from SAM and GeCKO screens, for gene perturbations resulting in BRAF inhibitor resistance. e, The top 10 shared candidates from Puromycin and Zeocin screens, identified using RIGER are shown. For both screens, the percent of unique sgRNA2.0s targeting each gene that are in the top 5% of all enriched sgRNA2.0s is plotted. f, Heat map of z-scores with each column representing a different $BRAF^{V600}$ melanoma short-term culture and rows representing expression of BRAF-inhibitor marker genes and signatures (upper panel), expression of SAM top screen hits (middle panel) and screen signature scores (see methods for signature generation using single-sample Gene Set Enrichment Analysis) (bottom panel). A distinct transcriptional state of genes and signatures represents BRAF-inhibition resistance as previously defined (Konieczkowski, D. J. et al. *Cancer discovery* 4, 816-827, doi:10.1158/2159-8290.CD-13-0424 (2014)). Columns are sorted by MITF expression with high expression indicating BRAF inhibitor sensitivity. Top hits from the SAM screen are significantly associated with the resistant state (MITF low expression and high levels of resistance markers). A subset of samples were previously tested for PLX sensitivity (blue text/arrows) and resistance (red text/arrows). IC: Information Coefficient (see methods for details). P-values are generated using a permutation test (n=10,000).

FIGS. 27A-E shows structure-guided engineering of Cas9 sgRNA. a, Schematic of the sgRNA stem-loops showing contacts between each stem-loop and Cas9. Contacting amino acid residues are highlighted in yellow. Tetraloop and stem-loop 2 do not have any contacts with Cas9 whereas stem-loops 1 and 3 share extensive contacts with Cas9 (SEQ ID NOS 141, 10 and 142, respectively, in order of appearance). b, sgRNA2.0 with MS2 stem-loops inserted into the tetraloop and stem-loop 2 (SEQ ID NO: 143). c, Addition of a second NLS or an alternative HNH domain inactivating point mutation in Cas9 improve efficiency of transcription activation for MYOD1. d, dCas9-VP64 activators exhibit improved performance by recruitment of MS2-P65 to the tetraloop and stem-loop 2. Addition of an AU flip or extension in the tetraloop does not increased effectiveness of dCas9-mediated transcription activation (SEQ ID NOS 144-146, 50, 147-150, 148, 144, 151, 148, 144-146, 152-153, 146, 154-155 and 146, respectively, in order of appearance). e, Tetraloop and stem-loop 2 are amenable to replacement with MS2 stem-loops. Base changes from the sgRNA2.0 scaffold are shown at the respective positions, with dashes indicating unaltered bases and bases below dashes indicating insertions. Deletions are indicated by absence of dashes at respective positions. All figures are n=3 and mean±SEM (SEQ ID NOS 144-146, 50, 147-148, 144-146, 50, 156, 146, 157-158, 146, 144, 151, 148, 144 and 159-160, respectively, in order of appearance).

FIGS. 36A-D shows correlation between sgRNA sequence content and level of depletion in significantly depleted genes. Heat maps of sgRNA nucleotide content versus depletion after 21 days. sgRNA targeting significantly depleted genes (from RIGER analysis) in sgRNA-zeo (a, b) or sgRNA-puro (c, d) screens were analyzed for trends with G content (a, c) or T content (b, d) in the sgRNA sequence. sgRNA depletion is positively correlated with G content and negatively correlated with T content. Other bases analyzed (A and C) had significant (p<0.0007) but weak (r<0.2) negative correlation.

FIGS. 37A-EE shows exemplary supplementary sequences of Example 8 (SEQ ID NOS 56, 53-55, 57, 161-163, 72, 161-162, 164-165, 161-162, 164, 166-167, 161-162, 164, 168-170, 162-163, 171, 170, 162, 164, 172-175, 162-163, 176-179, 161-162, 164, 166, 176, 180-182, 184-187, 182, 184 and 188-189, respectively, in order of appearance).

FIGS. 38A-E shows exemplary target guide sequences used in Example 8 (SEQ ID NOS 190, 58-59, 191-332 and 183, respectively, in order of appearance).

FIGS. 39A-I shows top 300 depleted genes for A375 in Example 8. Mean depletion for each gene is given as the log 2 ratio of Day 21 vs. Day 3 averaged over all sgRNAs for the gene.

FIGS. 40A-C shows top 100 genes from the output of the RIGER algorithm for the sgRNA-Zeo PLX screen comparing PLX (mean of the two replicates at Day 21) to DMSO control (mean of the two replicates at Day 21) in Example 8. The Kolmogorov-Smirnov method was used to score genes.

FIGS. 41A-C shows top 100 genes from the output of the RIGER algorithm for the sgRNA-Puro PLX screen comparing PLX (mean of the two replicates at Day 21) to DMSO control (mean of the two replicates at Day 21) in Example 8. The Kolmogorov-Smirnov method was used to score genes.

FIG. 42 shows TaqMan qPCR probe ID's used to quantify relative RNA expression levels for each gene (Life Technologies).

Figure 1A:
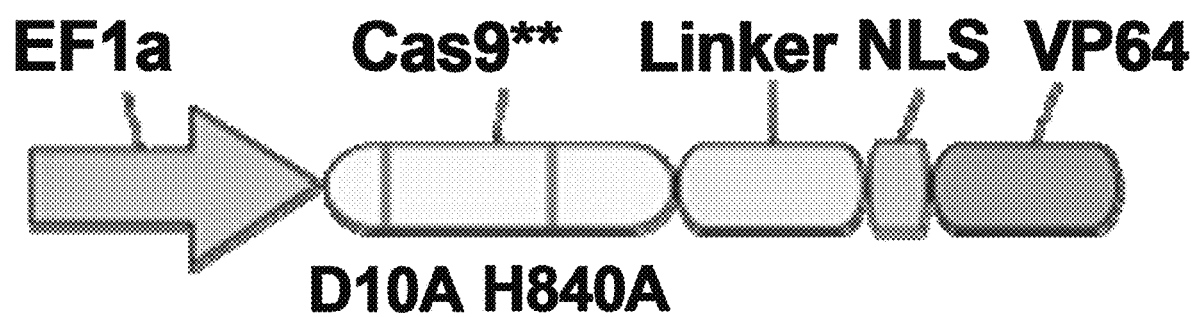
FIG. 1A shows DNA construct design of the previously studied dCas9 activator design. An activation domain is fused to the C-term of a catalytically inactive dCas via a linker. An NLS is incorporated between Cas9 and VP64.

The figures herein are for illustrative purposes only and are not necessarily drawn to scale.

DETAILED DESCRIPTION OF THE INVENTION

In particular, Applicants have found that the MS2-binding loop ggccAACATGAGGATCACCCATGTCTGCAGggcc (SEQ ID NO: 1) may replace nucleotides +13 to +16 and nucleotides +53 to +56 of the standard sgRNA backbone. The resulting structure is an sgRNA scaffold in which the tetraloop and stem-loop 2 sequences have been replaced by an MS2 binding loop. Without being bound by theory, the tetraloop and stemloop 2 were selected for replacement based on information obtained from the Cas9/RNA/DNA crystal structure. Specifically, the tetraloop and stem-loop 2 were found to protrude from the Cas9 protein in such a way which suggested that adding an MS2 binding loop would not interfere with any Cas9 residues. Additionally, the proximity of the tetraloop and stem-loop 2 sites to the DNA suggested that localization to these locations would result in a high degree of interaction between the DNA and any recruited protein, such as a transcriptional activator.

In some embodiments, the guide is modified such that nucleotides corresponding to +13 to +16 and/or nucleotides corresponding to +53 to +56 of the standard sgRNA backbone are replaced by the distinct RNA.

In some embodiments, the adaptor protein is an RNA-binding protein. The RNA-binding protein recognises corresponding distinct RNA sequences, which may be aptamers. For example, the MS2 RNA-binding protein recognises and binds specifically to the MS2 aptamer (or vice versa).

In some embodiments, the repression domain(s) for the guide and/or the CRISPR enzyme may be those show in Example(s) herein to act as follows:
  SID4X domain, which represses transcriptional activity;
  KRAB domain, which represses transcriptional activity;
  the NUE domain, which increases repressive histone methylation; and
  the NcoR domain, which recruits histone deacetylases leading to repressive histone modifications.
Exemplary sequences for repressor domains are to be found in Example(s) herein.

The Examples and Figures also shows an orthogonal approach. One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:

Guide 1—MS2 aptamer-------MS2 RNA-binding protein-------VP64 activator; and

Guide 2—PP7 aptamer-------PP7 RNA-binding protein-------SID4x repressor.

The Figures and Examples provide an illustration of orthogonal PP7/MS2 gene targeting. In Example(s), sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For instance, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

The use of a two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for instance 10 or 20 or 30 and so forth, whilst only one (or at least a minimal number) of Cas9s to be delivered, as a comparatively small number of Cas9s can be used with a large number of modified guides.

The fusion between the adaptor protein and the activator or repressor may include a linker. For instance, GlySer linkers GGGS (SEQ ID NO: 2) can be used. They can be used in repeats of 3 ((GGGGS)$_3$) (SEQ ID NO: 3) or 6 (SEQ ID NO: 4), 9 (SEQ ID NO: 5) or even 12 (SEQ ID NO: 6) or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

In some embodiments, use of an NLS is envisaged. Applicants found that the NLS from SV40 was helpful in this regard, especially when using lentiviral delivery methods.

A PP7 variant may be used in some embodiments. For instance, Applicants found that the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells." *Biophysical journal* 102. 12 (2012): 2936-2944. and Chao, Jeffrey A., et al. "Structural basis for the coevolution of a viral RNA-protein complex." *Nature structural & molecular biology* 15.1 (2007): 103-105), worked well. As such, in some embodiments, where the adaptor protein is an RNA-binding protein and that RNA-binding protein is PP7, the PP7 may be the variant described above, i.e. with amino acids 68-69 mutated to SG and/or amino acids 70-75 deleted from the wild type protein.

Similarly, an MS2 variant may also be used, such as the N55 mutant, especially the N55K mutant. This is the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010), and was shown to work in Example(s) herein.

Applicants have shown in Example(s) that both insertions in the tetraloop and loop 2 are effective. A most efficient combination uses an insertion of aptamers (in this case MS2 loops, but Applicants also show that other aptamers may be used as well) in both in the tetraloop and in loop 2 of the sgRNA. Applicants also show that this may be used in combination with a dCas9-vp64 and MS2-vp64 construct, in other words where the CRISPR enzyme is also modified. This new activator design (See Figures, e.g., as to red bar for the TL+L2: Ms2) was found to mediate much higher target gene upregulation compared to the previous design (See Figures).

It is also envisaged that other activators may be used. For instance, Example(s) showed that an improved Cas9 activator architecture consists of a sgRNA with MS2 loop insertions in the tetraloop and loop 2 in combination with either MS2-VP64 and dCas9-P65 or MS2-P65 and dCas9-VP64. In other words, 2 different activators can be used, one associated with the CRISPR enzyme (Cas9) and one with the guide via the aptamer. Applicants showed increased effectiveness of this design compared to the standard C-terminal fusion of VP64 to Cas9. Applicants further confirmed the hypothesis that a combination of two different activation domains could improve target gene activation (via synergy, e.g. by recruiting different epigenetic modulators, general transcription factors and co-activators). Applicants also determined that the alternative guide architecture optimized for CRISPR/Cas9 imaging in: Chen, Baohui, et al. "Dynamic Imaging of Genomic Loci in Living Human Cells by an Optimized CRISPR/Cas System." Cell 155.7 (2013): 1479-1491 did not exhibit any improvement over the standard architecture.

Of course, it is envisaged that the activators in these instances may be replaced with repressors.

Applicants also looked at the arrangement of the distinct RNA sequences (preferably aptamers) within the stem-loop 2 and tetraloop of the resent modified guides. Example(s) herein further look at the use of GC tracts. These are preferred in some embodiments. The GC tract may be GC or GGGGC or CCCCG or CGCC or compliments thereof or a mixture of C and G from 2 nucleotides up to, for instance 10, 15 or 20 nucleotides. In the particular instance, the MS2-binding loop sequence:

(SEQ ID NO: 1)
ggccAACATGAGGATCACCCATGTCTGCAGggcc replaced nucleotides +13 to +16 of the standard sgRNA backbone, as above. Of interest here, the sequence CGCC replaced nucleotides +49 to +52 of the standard sgRNA backbone. The sequence GGCG also replaced nucleotides +57 to +60 of the standard sgRNA backbone. The tetraloop MS2-binding loop insertion was designed with the same rationale as described herein. Essentially, CGCC and GGCG sequences replace the stem portion of stem-loop 2. The increased base-pairing strength of the CGCC-GGCG stem compared to the original ACTT-AAGT stem was hypothesized to provide additional stability to the stem-loop 2 structure, thereby increasing sgRNA performance or longevity.

Accordingly, in some embodiments, one or more GC tracts may replace stem portion of stem-loop 2. In some embodiments, one or more GC tracts may replace stem portion of the tetraloop.

When reference is made to the stem-loop 2 or tetraloop being modified (including replaced) by distinct RNA sequence(s) then this preferably encompasses modification (or replacement) of the 3 or 4 nucleotides of the guide that were found to protrude beyond the enzyme-sgRNA-DNA complex. Suitable numbering will be apparent based on the secondary structure of the guide on its own, i.e. by looking for the loops corresponding to the stem-loop 2 and the tetraloop (or by engineering them in), but exemplary number is around +13-16 and/or either side of +49-52 (with one or two nucleotides leeway either side possible, such as +48-52, or +49 to 53 for example).

A particularly preferred arrangement is to have the aptamer followed by a GGGS linker (SEQ ID NO: 2), preferably (GGGS)$_3$ (SEQ ID NO: 7), together with an NLS, preferably that from SV40.

Applicants, in Example(s) herein, generated a dCas9-based light-inducible MS2-effector, characterized by an MS2-CIB1 recruitment component bound to dCas9-sgRNA, and a CRY2-VP64 transcriptional activator domain. Upon activation with blue light, CRY2-VP64 associate with MS2-CIB1, enabling the recruitment of the transcriptional machinery to the target locus.

Thus, in some embodiments, the adaptor protein may be fused (or otherwise associated) to a first inducible element, whilst the functional domain may be fused (or otherwise associated) to a second and complimentary inducible element. The complementarity may be provided by heterodimeric binding partners. A preferred example of first and second complementary inducible elements is the CIB1 and CRY2 system. The CIB1 domain is a heterodimeric binding partner of the light-sensitive Cryptochrome 2 (CRY2).

In Example(s) herein Applicants replaced dCas9 Rec2 domain with a transcriptional effector domain; replace dCas9 HNH domain with a transcriptional effector domain; inserted a transcriptional effector domain at sites of flexible linkers within dCas9 (amino acid 553, 575, or 1153); and created catalytically inactive dCas9 by combination of D10A and N863A mutations, rather than D10A and H840A mutations. Any of these are preferred in certain distinct embodiments.

In some embodiments, Rec2 may be modified, preferably where amino acids 175-306 of dCas9 were replaced with one of the following inserts, with subdomains listed from N- to C-terminus:

```
VP64 activation domain
3X GGGGS linker (SEQ ID NO: 3), VP64 activation
domain, 3X GGGGS linker (SEQ ID NO: 3)

p65 activation domain
3X GGGGS linker (SEQ ID NO: 3), p65 activation
domain, 3X GGGGS linker (SEQ ID NO: 3)
```

In some embodiments, HNH may be modified. For instance, in Applicants replaced AA775-901 (of the HNH domain). This may be with either an activator, such as vp64 or P65, or a repressor. The activator or repressor may be flanked by a (GGGGS)3 (SEQ ID NO: 3) or a (GGGGS)6 (SEQ ID NO: 4) linker on both sides of the inserted transcriptional effector domain.

Insertions of transcriptional domains into 3 loops of dCas9 are also envisaged. In addition to replacing an existing domain (e.g. HNH, Rec2) with a transcriptional effector domain, it may be useful, in some embodiments, to insert a transcriptional effector domain at different positions in the Cas9 protein. Applicants identified three favorable positions: G533, F575 and K1153. The locations of G533 and K1153 in the Cas9 protein is indicated in the corresponding Figure(s). Applicants insert either vp64 or P65 flanked by a (GGGGS)1 (SEQ ID NO: 8) or a (GGGGS)3 (SEQ ID NO: 3) linker on both sides of the inserted transcriptional effector domain at these three locations. As such, in some embodiments, the Cas9 may be modified by insertion of one or more functional domains at any one or more of position corresponding to G533, F575 and K1153 according to SpCas9.

In some embodiments, novel dCas9 mutants are provided. Catalytically inactive dCas9 may be generated by combination of D10A and N863A mutations, rather than D10A and H840A mutations, as shown in Example(s) herein. This numbering refers to Sp Cas9, so corresponding positions in orthologs are envisaged. Applicants also provide N580A as a preferred alternative in Sa Cas9, especially in combination with D10.

As shown in Example(s) herein, N863, especially N863A, referring to Sp Cas9, is also useful in a dead Cas9 and is preferred in some embodiments.

The Example(s) also showed that a combination of different activator domains had an improved effect. For instance the construct with a p65-HSF1 fusion was found to be a more potent activator than the construct with p65 alone (See also Figures). Thus, fusions of two or more activators are preferred in some embodiments. Fusions of two or more repressors are also preferred in some embodiments. The activators or repressors may be in any combination of those known in the art and in particular those especially reference herein.

Of particular note was the use in Example(s) of an orthogonal system, a combined approach using one activator and one repressor. Different guides and different RNA/adaptor protein pairs allowed for activation at one locus and repression at another locus.

Applicants observed significant activation for each of a number purportedly difficult gene targets. Additionally, Applicants observed that the success rate of guide sequences typically increased with closer proximity to the transcriptional start site (TSS) of the target gene. In a preferred embodiment of the invention, for particular targets, within 200 bp of the TSS is deemed to be an advantageous window to select guide RNAs. This information may also be useful for selection of sgRNA guide sequences.

Multiplexed activation has also been shown in Example(s) herein. One important possible advantage of the ability of Applicants' system to provide robust activation with a single guide would be the capacity to easily activate a panel of genes simultaneously (by co-delivery to multiple guides for these genes), which would be intractable if a large number of guides would be required for activation of each gene alone. In order to test the ability of Applicants' system (NLS-dCAS(D10,H840A)-NLS-VP64 in combination with MS2-NLS-P65-HSF1) to activate multiple genes simultaneously, Applicants co-transfected guides targeting 2, 4, 6, 8 or 10 genes at once. Activation of multiple genes was highly successful, as even for a combination of 10 genes each gene was activated significantly. (see also Figures). In some embodiments, therefore, an adaptor protein may advantageously be linked or fused to fused or linked activators, as also discussed above, or repressors. This may then be delivered with multiple guides to different targets. This is therefore especially useful in a screening method where the activation or repression of one or more genes is to be interrogated.

Example(s) herein also focus on the identification of two 4ntd stretches in the guides that are exposed "outside" of Cas9-guide-target DNA complex (no contact between these 4 nt stem terminations and Cas9 amino acids were identified in the crystal). One 4ntd stretch falls in the tetraloop, the other 4ntd stretch falls in the stem-loop 2. Either or both of these 4ntd stretches can be replaced by aptamer sequence. Each or both can either be replaced completely or partially, or that either or both may be retained completely and a noncoding loop can be added after the 4 ntds. The aptamers is a polynucleotide and may be DNA or RNA, but RNA is preferred. The aptamer has a corresponding RNA-binding protein that recognises a specific RNA sequence.

Thus, the MS2 system used here comprises an RNA sequence inserted into the guide (at one or both of the above locations) and a corresponding MS2 (RNA-binding) protein. The RNA-binding protein may then be fused to a functional domain such as an activator or a repressor. Instead of being fused directly to a functional domain, the RNA-binding protein could be fused to a further element such as an antibody that can then bind to and recognise a functional domain or a molecule fused to a functional domain, similar to the heteroduplex CIB1-Cry2 system described above. This may allow for greater temporal or spatial control.

In short, a specific RNA sequence may be inserted into the exposed guide loop(s) and a corresponding RNA-binding protein may be used, whether that is fused to a functional domain, or a further element which in turn recognises or binds specifically to a functional domain. The functional domain may be a transacting activator or a repressor.

This can be used in Screening Methods to assess G.O.F (Gain Of Function) and/or Loss of Function and/or to screen for non-coding RNAs or potential regulatory regions (e.g. enhancers, repressors) (SAM).

Identification of the stem-loop 2 and the tetraloop is herein discussed and the skilled person may also want to refer to the Figures for guidance. The Figures show nucleotide numbering corresponding to the stem-loop 2 and the tetraloop. For instance, in some embodiments, the tetraloop is or includes nucleotides G29 to A41 of the guide tested and comprises 5'-GCUAGAAUAGCA-3' (positions 29-41) (SEQ ID NO: 9). Guide nucleotides, such as C40, may preferably interact with Cas9 amino acid Arg340. In some embodiments, stem-loop 2 may be or include nucleotides A68 to G81 of the guide used (5'-AACUUGAAAAAGUG-3' (SEQ ID NO: 10)). Enzyme amino acids His1349 and Ser1351 may, in some embodiments, interact with guide nucleotides, such as A68. In some embodiments, Lys33 and Tyr1356 may interact with nucleotide G81.

In some embodiments, it is preferable to use complimentary GGCC inserts (GC tracts) flanking the MS insert (the 5'-GGCC-3' being complimentary to the same sequence at the 3' end (and in the opposite orientation i.e. 3'CCGG-5', as shown in Figure(s)).

Although single MS2 addition (i.e. to one or other of the tetraloop or stem-loop 2) shows an improvement in terms of Gain of Function (gene upregulation) compared to a standard guide, the double addition (MS2 on both loops) shows even stronger upregulation. The use of two or more functional domains with the guide is therefore preferred.

As mentioned herein, having one activator, such as VP64, bound to Cas9 and a separate similar activator, again VP64, bound to the guide via MS2 shows the greatest improvement in terms of Gain of Function (gene upregulation). Other activators or repressors may be exchanged here for the activator mentioned.

Applicants also show in Example(s) an improvement in terms of Gain of Function (gene upregulation) compared a prior art MS-guide RNA arrangement where the MS2 is attached at the 3' end of the guide. This art approach is as opposed to the present loops which are both internal and certainly not 3' terminal or are at least followed (in the 3' direction) by an additional loop (stem-loop 3).

LincRNAs (a non-coding RNA produced from bi-directional promoters—the other direction being RNA corresponding to the gene of interest) may also be targeted via the guides and/or interrogated (see Example 13).

Example(s) also show that lentivirus based delivery is useful. Overall, the system showed enhanced transcriptional activation. It is thus useful in a genome-wide transcriptional activation or overexpression screening methods. For instance, the invention may be used to identify genes whose upregulation causes a certain phenotypic result—e.g., resistance to BRAF kinase inhibitor in cancer cells.

Applicants, without being bound by theory, believe that guide direction does not significantly affect activation activity, instead the primary factor influencing activation potency is that the sgRNA site is located within the −200 to +1 bp proximal promoter region. This region is therefore a preferred target for the guide(s).

The adaptor protein (and hence its corresponding distinct RNA (preferably an aptamer) is preferably chosen from within bacteriophage coat proteins. Preferred examples include those discussed herein.

Example(s) herein show that an inducible structural design activation mediator transgenic model, in this case a mouse, may be established. A repression model may be similarity generated. Preferably, a mouse engineered with the Lox-Stop-polyA-Lox(LSL) cassette upstream to the coding region of the SpCas9-VP64 fusion protein is established. A second mouse may be engineered with the Lox-Stop-polyA-Lox(LSL) cassette upstream to the coding region of the SpCas9-VP64 fusion protein and upstream to the coding region of the MS2-P65-HSF1 fusion protein.

Example(s) herein investigate targets lincRNAs of unknown function to determine aberrant phenotypes. It includes an investigation of Gain of Function and Loss of unction in human cell lines (using Cre inducibility) and mice through use of guides including an activator or a repressor.

When looking at lincRNAs, guides may be designed to target the promoter region. Ideally, this should be within 1000 nucleotides upstream of the TTS of the target, in this case, lincRNAs of unknown function. Animals, such as mice, may then be screened for aberrant phenotypes. (See Example 13)

Cells for which the sgRNA has an activator may be monitored for Gain of Function, whilst cells for which the sgRNA has a repressor may be monitored for Loss of Function. In this fashion, mammalian, including mouse and human cells, can be screened.

In an aspect, the vector systems used in the methods of the invention comprise one or more lentiviral vector(s). In a preferred embodiment, the one or more lentiviral vectors may comprise a codon optimized nuclear localization signal (NLS), a codon optimized P2A bicistronic linker sequence and an optimally placed U6 driven guide RNA cassette. In another aspect the vector system comprises two lentiviral vectors, wherein one lentiviral vector comprises the Cas9 enzyme and the other lentiviral vector comprises the guide RNA selected from the libraries of the invention. In an embodiment of the invention, each vector has a different selection marker, e.g. a different antibiotic resistance marker. The invention also comprehends kits comprising the libraries of the invention. In certain aspects, the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

Accordingly, Examples herein show that creation of a non-human animal or cell may be realistically provided. It has preferably been altered, or is a progeny of said altered animal or cell, to constitutively or conditionally express a Cas9 with one or more mutations to modify catalytic activity, as discussed herein. The model may be used for screening with appropriate guides and with different adaptors and activators or repressors as discussed herein for multiplexing to show up and/or down-regulation of target gene function. Thus, corresponding cell lines and transgenic mammalian models are provided. Further guidance on models and cell lines is provided herein.

The exposed or extraneous portion of the guide (when the guide-Cas9-DNA complex is formed) is preferably a 4 (four) nucleotide stretch. In some embodiments, the stretch may be in the tetraloop. In some embodiments, the stretch may be in the stem-loop 2. In some embodiments, stretches in both the tetraloop and the stem-loop 2 are envisaged.

This stretch may be modified, altered or entirely replaced. It is not generally preferred to reduce the number of nucleotides in the exposed stretch to less than 4 for stearic reasons as this could affect the secondary structure of the rest of the guide and thus affect formation of the Cas9-guide-DNA complex or the exposure of the stretch.

It may be modified or altered in that all four of the original 4 nucleotides in the stretch are retained and additions (or further nucleotides) are made between 1 and 2, 2 and 3, or 3 and 4. It is also envisaged that additions may be made immediately 5' to 1 or 3' immediately to 4. The stem may be flexible, but it is preferred that it is largely self-complementary throughout.

Unafold is a software tool that can be used to help predict RNA secondary structure in the guide and so assist the skilled person in determine what changes to the guide RNA may be acceptable within the framework discussed herein.

Ideally, the loop feature should be retained but protein binding section of the distinct RNA added to the guide will determine this. The non-loop ends abutting the edge of the enzyme should ideally be retained in the sense that they need to be present, but the primary sequence of the original guide can be changed, for instance by insertion of one or more GC tract(s). Ideally, this should be done at the non-loop (non-protein-binding end) of the distinct RNA added, which may be extended. The secondary structure of the non-protein-binding region of the distinct RNA should preferably form a stem, as mentioned.

It is preferred to avoid bulges or loops in the exposed section (non-protein-binding section of the distinct RNA, i.e. that between the edge of the enzyme complex and the protein binding domain of the distinct RNA/Aptamer). Rather, it is preferred to retain a stem as secondary structure in the exposed section.

A stem may be formed in the RNA through use of complimentary sections of roughly the same length, with mismatches minimized. The maximum length of the stem (or number of nucleotides forming the stem in both the 5' to 3' and 3' to 5' strands) is preferably 100 nucleotides or so in total (i.e. 2 sections of approx. 50 nucleotides) to reduce stearic effects and reduce possible formation of additional secondary or tertiary structure in the nucleotides. However, 50-60 nucleotides may be a more preferable maximum, but given the general need to keep package size down, 10 to 20 or 30 is most preferable, whilst, 8, 10 or 12 is most preferred.

A preferred minimum length is 4 nucleotides either side of the protein-binding loop.

Also provided are methods of upregulation of gene expression in a target locus comprising administration of the present modified guides directed to the target, where the adaptor protein is associated with an activator. The CRISPR enzyme may also be modified with a functional domain.

Also provided are methods of downregulation of gene expression in a target locus comprising administration of the present modified guides directed to the target, where the adaptor protein is associated with a repressor. The CRISPR enzyme may also be modified with a functional domain.

Such methods may be used in a method of treating a subject in need thereof, for example a subject requiring gene upregulation or gene downregulation, as appropriate. A multiplex method may also be used where one gene is upregulated and another is down regulated for instance by following the orthogonal approach discussed herein.

Also provided is the present compositions and systems for use in such methods of treatment. Use of the present compositions and systems in the manufacture of a medicament for such treatment is also provided.

In some embodiments, the functional domains associated with the adaptor protein or the CRISPR enzyme is a transcriptional activation domain comprising VP64, p65, MyoD1, HSF1, RTA or SET7/9. Other references herein to activation (or activator) domains in respect of those associated with the adaptor protein(s) include any known transcriptional activation domain and specifically VP64, p65, MyoD1, HSF1, RTA or SET7/9.

In an aspect the invention provides a composition as herein discussed wherein the one or more functional domains associated with the adaptor protein have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

In an aspect the invention provides a composition as herein discussed wherein the one or more functional domains associated with the CRISPR enzyme have one or more activities comprising methylase activity, demethylase activity, transcription activation activity, transcription repression activity, transcription release factor activity, histone modification activity, RNA cleavage activity, DNA cleavage activity, DNA integration activity, nucleic acid binding activity, or molecular switch activity or chemical inducibility or light inducibility.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains.

In an aspect the invention provides a method as herein discussed, wherein the genomic locus event comprises affecting gene activation, gene inhibition, or cleavage in the locus, or insertion of DNA.

In any aspect where two or more functional domains are used, these functional domains may be the same or different, and are preferably different functional domains.

is between 10 to 30 nucleotides in length and the CRISPR/Cas enzyme is a Type II Cas9 enzyme.

Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains.

TABLE 1

HDAC Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDAC8 | — | — | X. laevis | 325 | 1-325 | 325 | 1-272: HDAC |
| HDAC I | RPD3 | — | — | S. cerevisiae | 433 | 19-340 (Vannier) | 322 | 19-331: HDAC |
| HDAC IV | MesoLo4 | — | — | M. loti | 300 | 1-300 (Gregoretti) | 300 | — |
| HDAC IV | HDAC11 | — | — | H. sapiens | 347 | 1-347 (Gao) | 347 | 14-326: HDAC |
| HD2 | HDT1 | — | — | A. thaliana | 245 | 1-211 (Wu) | 211 | — |
| SIRT I | SIRT3 | H3K9Ac H4K16Ac H3K56Ac | — | H. sapiens | 399 | 143-399 (Scher) | 257 | 126-382: SIRT |
| SIRT I | HST2 | — | — | C. albicans | 331 | 1-331 (Hnisz) | 331 | — |
| SIRT I | CobB | — | — | E. coli (K12) | 242 | 1-242 (Landry) | 242 | — |
| SIRT I | HST2 | — | — | S. cerevisiae | 357 | 8-298 (Wilson) | 291 | — |
| SIRT III | SIRT5 | H4K8Ac H4K16Ac | — | H. sapiens | 310 | 37-310 (Gertz) | 274 | 41-309: SIRT |
| SIRT III | Sir2A | — | — | P. falciparum | 273 | 1-273 (Zhu) | 273 | 19-273: SIRT |
| SIRT IV | SIRT6 | H3K9Ac H3K56Ac | — | H. sapiens | 355 | 1-289 (Tennen) | 289 | 35-274: SIRT |

In an aspect, in herein-discussed compositions, the target sequence(s) can be non-coding or regulatory (including promoter, especially the proximal promoter) or enhancer or silencer sequence(s).

In relation to the guides in general, but specifically in respect of the present modified sgRNA and the complex formed therewith, it is preferable that the guide has one or more of the following features. In some embodiments, the tracr sequence has one or more hairpins and is 30 or more nucleotides in length, more preferably 40 or more nucleotides in length, or more preferably 50 or more nucleotides in length. In some embodiments, the guide sequence is between 10 to 30 nucleotides in length. In some embodiments, the CRISPR/Cas enzyme is a Type II Cas9 enzyme. In some embodiments, the tracr sequence has one or more hairpins and is 30 or more nucleotides in length, more preferably 40 or more nucleotides in length, or more preferably 50 or more nucleotides in length, the guide sequence Accordingly, the repressor domains of the present invention may be selected from histone methyltransferases (HMTs), histone deacetylases (HDACs), histone acetyltransferase (HAT) inhibitors, as well as HDAC and HMT recruiting proteins.

The HDAC domain may be any of those in the table above, namely: HDAC8, RPD3, MesoLo4, HDAC11, HDT1, SIRT3, HST2, CobB, HST2, SIRT5, Sir2A, or SIRT6.

In some embodiment, the functional domain may be a HDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

TABLE 2

HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | R. norvegicus | 492 | 207-492 (Nan) | 286 | — |
| Sin3a | MBD2b | — | — | H. sapiens | 262 | 45-262 (Boeke) | 218 | — |
| Sin3a | Sin3a | — | — | H. sapiens | 1273 | 524-851 (Laherty) | 328 | 627-829: HDAC1 interaction |
| NcoR | NcoR | — | — | H. sapiens | 2440 | 420-488 (Zhang) | 69 | — |
| NuRD | SALL1 | — | — | M. musculus | 1322 | 1-93 (Lauberth) | 93 | — |
| CoREST | RCOR1 | — | — | H. sapiens | 482 | 81-300 (Gu, Ouyang) | 220 | — |

In some embodiment, the functional domain may be a Methyltransferase (HMT) Effector Domain. Preferred examples include those in the Table below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

TABLE 3

Histone Methyltransferase (HMT) Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | C. trachomatis | 219 | 1-219 (Pennini) | 219 | — |
| SET | vSET | — | H3K27me3 | P. bursaria chlorella virus | 119 | 1-119 (Mujtaba) | 119 | 4-112: SET2 |
| SUV39 family | EHMT2/G9A | H1.4K2, H3K9, H3K27 | H3K9me1/2, H1K25me1 | M. musculus | 1263 | 969-1263 (Tachibana) | 295 | 1025-1233: preSET, SET, postSET |
| SUV39 | SUV39H1 | — | H3K9me2/3 | H. sapiens | 412 | 79-412 (Snowden) | 334 | 172-412: preSET, SET, postSET |
| Suvar3-9 | dim-5 | — | H3K9me3 | N. crassa | 331 | 1-331 (Rathert) | 331 | 77-331: preSET, SET, postSET |
| Suvar3-9 (SUVH subfamily) | KYP | — | H3K9me1/2 | A. thaliana | 624 | 335-601 (Jackson) | 267 | — |
| Suvar3-9 (SUVR subfamily) | SUVR4 | H3K9me1 | H3K9me2/3 | A. thaliana | 492 | 180-492 (Thorstensen) | 313 | 192-462: preSET, SET, postSET |
| Suvar4-20 | SET4 | — | H4K20me3 | C. elegans | 288 | 1-288 (Vielle) | 288 | — |
| SET8 | SET1 | — | H4K20me1 | C. elegans | 242 | 1-242 (Vielle) | 242 | — |
| SET8 | SETD8 | — | H4K20me1 | H. sapiens | 393 | 185-393 (Couture) | 209 | 256-382: SET |
| SET8 | TgSET8 | — | H4K20me1/2/3 | T. gondii | 1893 | 1590-1893 (Sautel) | 304 | 1749-1884: SET |

In some embodiment, the functional domain may be a Histone Methyltransferase (HMT) Recruiter Effector Domain. Preferred examples include those in the Table below, namely Hp1a, PHF 19, and NIPP1.

TABLE 4

Histone Methyltransferase (HMT) Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | *M. musculus* | 191 | 73-191 | 119 (Hathaway) | 121-179: chromoshadow |
| — | PHF19 | — | H3K27me3 | *H. sapiens* | 580 | (1-250) + GGSG linker (SEQ ID NO: 11) + (500-580) | 335 (Ballaré) | 163-250: PHD2 |
| — | NIPP1 | — | H3K27me3 | *H. sapiens* | 351 | 1-329 (Jin) | 329 | 310-329: EED |

In some embodiment, the functional domain may be Histone Acetyltransferase Inhibitor Effector Domain. Preferred examples include SET/TAF-1β listed in the Table below.

TABLE 5

Histone Acetyltransferase Inhibitor Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | *M. musculus* | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

The term "associated with" is used here in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognises an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

RNA sequences that bind to protein sequences are known, in particular aptamers, but the way in which they bind to, for example, an adaptor protein is that the RNA sequence recognises and forms a complex with a corresponding RNA-binding domain or portion on the protein. This is an analogous situation to the manner in which an antibody recognises an epitope. Thus, in some embodiments, the distinct RNA sequence recognises and binds to a complementary RNA-binding domain or portion on the adaptor protein. In some embodiments, the distinct RNA sequence is an aptamer. The functioning of an aptamer is well-known in the way that is associates with its corresponding protein.

The distinct RNA sequence is a sequence that is different in origin and/or sequence from the guide into which it is inserted. The insertion may include the replacement (deletion) of one or more of the original guide nucleotides at the insertion site. Alternatively, the original guide nucleotides may be retained with the insertion site between them such that the inserted nucleotides separate the previously neighbouring (in terms of primary structure) original nucleotides. The distinct RNA sequence thus may differs in the sense that it has a different primary structure (nucleotide sequence) from the nucleotides that it is replacing. Either way, if replacing or if merely inserting without deletion, the overall primary sequence of the resulting modified guide will change. Thus, in one embodiment, a distinct RNA sequence is one that results in a different sequence (primary structure) in the resulting modified guide.

In some embodiments, the methods provided herein may occur ex vivo unless otherwise apparent.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814, 263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014; PCT/US2014/041808 filed Jun. 11, 2014; and PCT/US2014/62558 filed Oct. 28, 2014, and U.S. Provisional Patent Applications Ser. Nos. 61/915, 150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836, 101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915, 260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096, 324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec.

2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Also, "Dimeric CRISPR RNA-guided Fok1 nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided Fok1 Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of U.S. provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30° C., e.g., 20-25° C., e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a $C_{1-6}$ alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG (SEQ ID NO: 12) where NNNNNNNNNNNNXGG (SEQ ID NO: 13) (N is A, G, T, or C; and X can be anything) has a single occurrence in the genome. A unique target sequence in a genome may include an S. pyogenes Cas9 target site of the form MMMMMMMMMNNNNNNNNNNNNXGG (SEQ ID NO: 14) where NNNNNNNNNNNXGG (SEQ ID NO: 15) (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNNXXAGAAW (SEQ ID NO: 16) where NNNNNNNNNNNNXXAGAAW (SEQ ID NO: 17) (N is A, G, T, or C; X can be anything; and W is A or T) has a single occurrence in the genome. A unique target sequence in a genome may include an S. thermophilus CRISPR1 Cas9 target site of the form MMMMMMMMMNNNNNNNNNNNNXXAGAAW (SEQ ID NO: 18) where NNNNNNNNNNNXXAGAAW (SEQ ID NO: 19) (N is A, G, T, or C; X can be anything; and W is A or T) has a single occurrence in the genome. For the S.

pyogenes Cas9, a unique target sequence in a genome may include a Cas9 target site of the form MMMMMMMMMNNNNNNNNNNNNNXGGXG (SEQ ID NO: 20) where NNNNNNNNNNNNNXGGXG (SEQ ID NO: 21) (N is A, G, T, or C; and X can be anything) has a single occurrence in the genome. A unique target sequence in a genome may include an *S. pyogenes* Cas9 target site of the form MMMMMMMMMNNNNNNNNNNNNNXGGXG (SEQ ID NO: 22) where NNNNNNNNNNNXGGXG (SEQ ID NO: 23) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataa ggcttcatgccgaaat-caacaccctgtcattttatggcagggtgttttcgttatttaaTTTTTT (SEQ ID NO: 24); (2) NNNNNNNNNNNNNNNNNN-NNNgttttgtactctcaGAAAtgcagaagctacaaagataaggctt-catgccg aaatcaacaccctgtcattttatggcagggtgttttcgttatttaaT-TTTTT (SEQ ID NO: 25); (3) NNNNNNNNNNNNNNNNNNNNgttttgtactctcaG-AAAtgcagaagctacaaagataaggcttcatgccg aaatcaacaccctgtcat-tttatggcagggtgtTTTTTT (SEQ ID NO: 26); (4) NNNNNNNNNNNNNNNNNNNNgttt-tagagctaGAAAtagcaagttaaaataaggctagtccgttatcaactt gaaaaagtggcaccgagtcggtgcTTTTTT (SEQ ID NO: 27); (5) NNNNNNNNNNNNNNNNNNNNgttt-tagagctaGAAATAGcaagttaaaataaggctagtccgttatcaac ttgaaaaagtgTTTTTTT (SEQ ID NO: 28); and (6) NNNNNNNNNNNNNNNNNNNNgttt-tagagctagAAATAGcaagttaaaataaggctagtccgttatcaTT TTTTT (SEQ ID NO: 29). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 30) in the EMX1 gene of the human genome, deep sequencing can be used to assess the level of modification at the following two off-target loci, 1: 5'-GAGTCCTAGCAGGAGAAGAA-3' (SEQ ID NO: 31) and 2: 5'-GAGTCTAAGCAGAAGAAGAA-3' (SEQ ID NO: 32). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9, (*S. pyogenes* Cas9) or saCas9, (*S. aureus* Cas9). StCas9" refers to wild type Cas9 from *S. thermophilus*, the protein sequence of which is given in the SwissProt database under accession number G3ECR1. Similarly, *S. pyogenes* Cas9 or spCas9. is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCas9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 33); the NLS from nucleoplasmin (e.g. the nucleoplasmin bipartite NLS with the sequence KRPAATKKAGQAKKKK (SEQ ID NO: 34)); the c-myc NLS having the amino acid sequence PAAKRVKLD (SEQ ID NO: 35) or RQRRNELKRSP (SEQ ID NO: 36); the hRNPA1 M9 NLS having the sequence NQSSNFGPMKGGNFG-GRSSGPYGGGGQYFAKPRNQGGY (SEQ ID NO: 37); the sequence RMRIZFKNKGKDTAELRRRRVEVS-VELRKAKKDEQILKRRNV (SEQ ID NO: 38) of the IBB domain from importin-alpha; the sequences VSRKRPRP (SEQ ID NO: 39) and PPKKARED (SEQ ID NO: 40) of the myoma T protein; the sequence PQPKKKPL (SEQ ID NO: 41) of human p53; the sequence SALIKKKKKMAP (SEQ ID NO: 42) of mouse c-abl IV; the sequences DRLRR (SEQ ID NO: 43) and PKQKKRK (SEQ ID NO: 44) of the influenza virus NS1; the sequence RKLKKKIKKL (SEQ ID NO: 45) of the Hepatitis virus delta antigen; the sequence REKKKFLKRR (SEQ ID NO: 46) of the mouse Mx1 protein; the sequence KRKGDEVDGVDEVAKKKSKK (SEQ ID NO: 47) of the human poly(ADP-ribose) polymerase; and the sequence RKCLQAGMNLEARKTKK (SEQ ID NO: 48) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). The target can be a control element or a regulatory element or a promoter or an enhancer or a silencer. The promoter may, in some embodiments, be in the region of +200 bp or even +1000 bp from the TTS. In some embodiments, the regulatory region may be an enhancer. The enhancer is typically more than +1000 bp from the TTS. More in particular, expression of eukaryotic protein-coding genes generally is regulated through multiple cis-acting transcription-control regions. Some control elements are located close to the start site (promoter-proximal elements), whereas others lie more distant (enhancers and silencers) Promoters determine the site of transcription initiation and direct binding of RNA polymerase II. Three types of promoter sequences have been identified in eukaryotic DNA. The TATA box, the most common, is prevalent in rapidly transcribed genes. Initiator promoters infrequently are found in some genes, and CpG islands are characteristic of transcribed genes. Promoter-proximal elements occur within ≈200 base pairs of the start site. Several such elements, containing up to ≈20 base pairs, may help regulate a particular gene. Enhancers, which are usually ≈100-200 base pairs in length, contain multiple 8- to 20-bp control elements. They may be located from 200 base pairs to tens of kilobases upstream or downstream from a promoter, within an intron, or downstream from the final exon of a gene. Promoter-proximal elements and enhancers may be cell-type specific, functioning only in specific differentiated cell types. However, any of these regions can be the target sequence and are encompassed by the concept that the target can be a control element or a regulatory element or a promoter or an enhancer or a silencer.

Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9. An advantage of the present methods is that the CRISPR system minimizes or avoids off-target binding and its resulting side effects. This is achieved using systems arranged to have a high degree of sequence specificity for the target DNA.

In relation to a CRISPR-Cas complex or system preferably, the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II Cas9 enzyme.

The Examples show an orthogonal approach. One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:
Guide 1—MS2 aptamer--------MS2 RNA-binding protein--------VP64 activator; and
Guide 2—PP7 aptamer--------PP7 RNA-binding protein--------SID4x repressor.

The Figures also provide an illustration of orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

Further, the Examples provide an alternative option for orthogonal repression; including to incorporate non-coding rna loops with transactive repressive function into the guide (either at similar positions to the MS2/PP7 loops integrated into the guide or at the 3' terminus of the guide). For instance, guides were designed with non-coding (but known to be repressive) RNA loops (e.g. using the Alu repressor (in RNA) that interferes with RNA polymerase II in mammalian cells). The Alu RNA sequence was located: in place of the MS2 RNA sequences as used herein (e.g. at tetraloop and/or stem-loop 2); and/or at 3' terminus of the guide. This gives possible combinations of MS2, PP7 or Alu at the tetraloop and/or stem-loop 2 positions, as well as, optionally, addition of Alu at the 3' end of the guide (with or without a linker).

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number of modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS (SEQ ID NO: 2) can be used. They can be used in repeats of 3 ((GGGGS)$_3$) (SEQ ID NO: 3) or 6 (SEQ ID NO: 4), 9 (SEQ ID NO: 5) or even 12 (SEQ ID NO: 6) or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

The invention comprehends a CRISPR Cas complex comprising a CRISPR enzyme and a guide RNA (sgRNA), wherein the CRISPR enzyme comprises at least one mutation, such that the CRISPR enzyme has no more than 5% of the nuclease activity of the CRISPR enzyme not having the at least one mutation and, optional, at least one or more nuclear localization sequences; the guide RNA (sgRNA) comprises a guide sequence capable of hybridizing to a target sequence in a genomic locus of interest in a cell; and wherein: the CRISPR enzyme is associated with two or more functional domains; or at least one loop of the sgRNA is modified by the insertion of distinct RNA sequence(s) that bind to one or more adaptor proteins, and wherein the adaptor protein is associated with two or more functional domains; or the CRISPR enzyme is associated with one or more functional domains and at least one loop of the sgRNA is modified by the insertion of distinct RNA sequence(s) that bind to one or more adaptor proteins, and wherein the adaptor protein is associated with one or more functional domains.

Delivery Generally

Vector delivery, e.g., plasmid, viral delivery: The CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^9$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 µmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 µl of a recombinant lentivirus having a titer of $1 \times 10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1 \times 10^9$ transducing units (TU)/ml may be contemplated.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package Cas9 coding nucleic acid molecules, e.g., DNA, into vectors, e.g., viral vectors, to mediate genome modification in vivo include:

To achieve NHEJ-mediated gene knockout:
Single virus vector:
  Vector containing two or more expression cassettes:
  Promoter-Cas9 coding nucleic acid molecule-terminator
  Promoter-gRNA1-terminator
  Promoter-gRNA2-terminator
  Promoter-gRNA(N)-terminator (up to size limit of vector)
Double virus vector:
  Vector 1 containing one expression cassette for driving the expression of Cas9
  Promoter-Cas9 coding nucleic acid molecule-terminator
  Vector 2 containing one more expression cassettes for driving the expression of one or more guideRNAs
  Promoter-gRNA1-terminator
  Promoter-gRNA(N)-terminator (up to size limit of vector)
To mediate homology-directed repair.
  In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, CAG, CBh, PGK, SV40, Ferritin heavy or light chains, etc.

For brain or other CNS expression, can use promoters: Synapsin I for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.
The promoter used to drive guide RNA can include:
Pol III promoters such as U6 or H1
Use of Pol II promoter and intronic cassettes to express gRNA
Adeno Associated Virus (AAV)

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:
  Low toxicity (this may be due to the purification method not requiring ultra centrifugation of cell particles that can activate the immune response)
  Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

TABLE 6

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 7

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4° C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used and/or adapted to the CRISPR-Cas system of the present invention. A minimum of $2.5 \times 10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm² tissue culture flasks coated with fibronectin (25 mg/cm²) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GC-CACC)-Cas9-3' UTR from beta globin-polyA tail (a string of 120 or more adenines) (SEQ ID NO: 49). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Nanoparticles

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used and/or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas RNA in or associated with the LNP may be contemplated, especially for a formulation containing DLinKC2-DMA.

Preparation of LNPs and CRISPR Cas encapsulation may be used and/or adapted from Rosin et al, Molecular Therapy, vol. 19, No. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas RNA may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes.

Nanoparticle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof.

Preparation of large LNPs may be used and/or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45 µm syringe filter.

Spherical Nucleic Acid (SNA™) constructs and other nanoparticles (particularly gold nanoparticles) are also contemplated as a means to deliver CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHS-ester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Nanoparticles

In terms of this invention, it is preferred to have one or more components of CRISPR complex, e.g., CRISPR enzyme or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable nanoparticles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can be envisioned that such conjugated lipomers can be used in the context of the CRISPR-Cas system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Qiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidylcholine (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshl-p.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(ω-methoxypoly(ethylene glycol)2000)carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(ω-methoxy poly(ethylene glycol) 2000)carbamoyl]-1,2-dimyristyloxypropylamine, and cationic 1,2-dilinoleyloxy-3-N,N-dimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature-Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid nanoparticles (LNPs). Lipids include, but are not limited to, DLin-KC2-DMA4, C12-200 and colipids distearoylphosphatidylcholine, cholesterol, and PEG-DMG may be formulated with CRISPR Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/distearoylphosphatidylcholine/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine, and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1\times10^5$ cells per well in a 48-well plate.

(2) On the day of treatment, dilute purified +36 GFP protein in serum-free media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1\times10^5$ per well in a 48-well plate.

(2) On the day of treatment, dilute purified +36 GFP protein in serum-free media to a final concentration 2 mM. Add 1 mg of plasmid DNA. Vortex to mix and incubate at room temperature for 10 min.

(3) During incubation, aspirate media from cells and wash once with PBS.

(4) Following incubation of +36 GFP and plasmid DNA, gently add the protein-DNA complexes to cells.

(5) Incubate cells with complexes at 37° C. for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in conjunction with herein teachings can be employed in the delivery of CRISPR Cas system(s) or component(s) thereof or nucleic acid molecule(s) coding therefor.

Implantable Devices

In another embodiment, implantable devices are also contemplated for delivery of the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used and/or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensory nervous sites for analgesic effect; 7. Intra osseous implantation; 8. acute and chronic infection sites; 9. Intra vaginal; 10. Inner ear-auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used and/or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Patient-Specific Screening Methods

A CRISPR-Cas system that targets nucleotide, e.g., trinucleotide repeats can be used to screen patients or patent samples for the presence of such repeats. The repeats can be the target of the RNA of the CRISPR-Cas system, and if there is binding thereto by the CRISPR-Cas system, that binding can be detected, to thereby indicate that such a repeat is present. Thus, a CRISPR-Cas system can be used to screen patients or patient samples for the presence of the repeat. The patient can then be administered suitable compound(s) to address the condition; or, can be administered a CRISPR-Cas system to bind to and cause insertion, deletion or mutation and alleviate the condition.

Nucleic Acids, Amino Acids and Proteins, Regulatory Sequences, Vectors, Etc

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, intrans, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A.; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4$^{th}$ Ed.—Chapter 18), FASTA (Altschul et al., 1990 J Mal. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbial Lett. 1999 174 (2): 247-50; FEMS Microbial Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J Theor. Biol. 119; 205-218). Conservative substitutions may be made, for example according to the table below which describes a generally accepted Venn diagram grouping of amino acids.

TABLE 8

| Set | | Sub-set | |
|---|---|---|---|
| Hydrophobic | FWYHKMIL V AGC | Aromatic Aliphatic | FWYH IL V |
| Polar | WYHKREDCSTNQ | Charged Positively charged Negatively charged | HKRED HKR ED |
| Small | VCAGSPTND | Tiny | AGS |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridyl-alanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 50). This may be followed by the loop sequence GAAA as shown. Both of these are preferred examples.

Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol.

8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Luckow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) VP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736, 465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Modifying a Target

In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence. Similar considerations and conditions apply as above for methods of modifying a target polynucleotide.

Kits

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

Crystallization of CRISPR-Cas9 and Characterization of Crystal Structure

The crystals of the Cas9 can be obtained by techniques of protein crystallography, including batch, liquid bridge, dialysis, vapor diffusion and hanging drop methods. Generally, the crystals of the invention are grown by dissolving substantially pure CRISPR-Cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980,012 filed Apr. 15, 2014; and Nishimasu et al, "Crystal Structure of Cas9 in Complex with Guide RNA and Target DNA," Cell 156(5):935-949, DOI: 10.1016/j.cell.2014.02.001 (2014), each and all of which are incorporated herein by reference.

Uses of the Crystals, Crystal Structure and Atomic Structure Co-Ordinates: The crystals of the Cas9, and particularly the atomic structure co-ordinates obtained therefrom, have a wide variety of uses. The crystals and structure co-ordinates are particularly useful for identifying compounds (nucleic acid molecules) that bind to CRISPR-Cas9, and CRISPR-Cas9s that can bind to particular compounds (nucleic acid molecules). Thus, the structure co-ordinates described herein can be used as phasing models in determining the crystal structures of additional synthetic or mutated CRISPR-Cas9s, Cas9s, nickases, binding domains. The provision of the crystal structure of CRISPR-Cas9 complexed with a nucleic acid molecule as applied in conjunction with the herein teachings provides the skilled artisan with a detailed insight into the mechanisms of action of CRISPR-Cas9. This insight provides a means to design modified CRISPR-Cas9s, such as by attaching thereto a functional group, such as a repressor or activator. While one can attach a functional group such as a repressor or activator to the N or C terminal of CRISPR-Cas9, the crystal structure demonstrates that the N terminal seems obscured or hidden, whereas the C terminal is more available for a functional group such as repressor or activator. Moreover, the crystal structure demonstrates that there is a flexible loop between approximately CRISPR-Cas9 (*S. pyogenes*) residues 534-676 which is suitable for attachment of a functional group such as an activator or repressor. Attachment can be via a linker, e.g., a flexible glycine-serine (GlyGlyGlySer (SEQ ID NO: 2)) or (GGGS)$_3$ (SEQ ID NO: 7) or a rigid alpha-helical linker such as (Ala(GluAlaAlaAlaLys)Ala) (SEQ ID NO: 51). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn.

The provision of the crystal structure of CRISPR-Cas9 complexed with a nucleic acid molecule allows a novel approach for drug or compound discovery, identification, and design for compounds that can bind to CRISPR-Cas9 and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans.

In any event, the determination of the three-dimensional structure of CRISPR-Cas9 (*S. pyogenes* Cas9) complex provides a basis for the design of new and specific nucleic acid molecules that bind to CRISPR-Cas9 (e.g., *S. pyogenes* Cas9), as well as the design of new CRISPR-Cas9 systems, such as by way of modification of the CRISPR-Cas9 system to bind to various nucleic acid molecules, by way of modification of the CRISPR-Cas9 system to have linked thereto to any one or more of various functional groups that may interact with each other, with the CRISPR-Cas9 (e.g., an inducible system that provides for self-activation and/or self-termination of function), with the nucleic acid molecule nucleic acid molecules (e.g., the functional group may be a regulatory or functional domain which may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator; see, e.g., Zhang et al., U.S. Pat. No. 8,507,272, and it is again mentioned that it and all documents cited herein and all appln cited documents are hereby incorporated herein by reference), by way of modification of Cas9, by way of novel nickases). Indeed, the herewith CRISPR-Cas9 (*S. pyogenes* Cas9) crystal structure has a multitude of uses. For example, from knowing the three-dimensional structure of CRISPR-Cas9 (*S. pyogenes* Cas9) crystal structure, computer modelling programs may be used to design or identify different molecules expected to interact with possible or confirmed sites such as binding sites or other structural or functional features of the CRISPR-Cas9 system (e.g., *S. pyogenes* Cas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders to ascertain how well the shape and the chemical structure of the potential binder will bind to a CRISPR-Cas9 system (e.g., *S. pyogenes* Cas9). Computer-assisted, manual examination of the active site or binding site of a CRISPR-Cas9 system (e.g., *S. pyogenes* Cas9) may be performed. Programs such as GRID (P. Goodford, J. Med. Chem, 1985, 28, 849-57)—a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., CRISPR-Cas9 system (e.g., *S. pyogenes* Cas9) and a candidate nucleic acid molecule or a nucleic acid molecule and a candidate CRISPR-Cas9 system (e.g., *S. pyogenes* Cas9); and the CRISPR-Cas9 crystal structure (*S. pyogenes* Cas9) herewith enables such methods. Generally, the tighter the fit, the fewer the steric hindrances, and the greater the attractive forces, the more potent the potential binder, since these properties are consistent with a tighter binding constant. Furthermore, the more specificity in the design of a candidate CRISPR-Cas9 system (e.g., *S. pyogenes* Cas9), the more likely it is that it will not interact with off-target molecules as well. Also, "wet" methods are enabled by the instant invention. For example, in an aspect, the invention provides for a method for determining the structure of a binder (e.g., target nucleic acid molecule) of a candidate CRISPR-Cas9 system (e.g., *S. pyogenes* Cas9) bound to the candidate CRISPR-Cas9 system (e.g., *S. pyogenes* Cas9), said method comprising, (a) providing a first crystal of a candidate CRISPR-Cas9 system (*S. pyogenes* Cas9) according to the invention or a second crystal of a candidate a candidate CRISPR-Cas9 system (e.g., *S. pyogenes* Cas9), (b) contacting the first crystal or second crystal with said binder under conditions whereby a complex may form; and (c) determining the structure of said a candidate (e.g., CRISPR-Cas9 system (e.g., *S. pyogenes* Cas9) or CRISPR-Cas9 system (*S. pyogenes* Cas9) complex. The second crystal may have essentially the same coordinates discussed herein, however due to minor alterations in CRISPR-Cas9 system (e.g., from the Cas9 of such a system being e.g., *S. pyogenes* Cas9 versus being *S. pyogenes* Cas9), wherein "e.g., *S. pyogenes* Cas9" indicates that the Cas9 is a Cas9 and can be of or derived from *S. pyogenes* or an ortholog thereof), the crystal may form in a different space group.

The invention further involves, in place of or in addition to "in silico" methods, other "wet" methods, including high throughput screening of a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)), to select compounds with binding activity. Those pairs of binder and CRISPR-Cas9 system which show binding activity may be selected and further crystallized with the CRISPR-Cas9 crystal having a structure herein, e.g., by co-crystallization or by soaking, for X-ray analysis. The resulting X-ray structure may be compared with that of the Cas9 Crystal Structure for a variety of purposes, e.g., for areas of overlap. Having designed, identified, or selected possible pairs of binder and CRISPR-Cas9 system by determining those which have favorable fitting properties, e.g., predicted strong attraction based on the pairs of binder and CRISPR-Cas9 crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex (es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas9 system or components thereof. These steps may be repeated and re-repeated as necessary. Alternatively or additionally, potential CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of CRISPR-cas systems or complex(es) of unknown structure by using the structural co-ordinates of the Cas9 Crystal Structure. For example, if X-ray crystallographic or NMR spectroscopic data are provided for a CRISPR-cas system or complex of unknown crystal structure, the structure of a CRISPR-Cas9 complex as defined of the Cas9 Crystal Structure Table and the Figures may be used to interpret that data to provide a likely structure for the unknown system or complex by such techniques as by phase modeling in the case of X-ray crystallography. Thus, an inventive method can comprise: aligning a representation of the CRISPR-cas system or complex having an unknown crystal structure with an analogous representation of the CRISPR-cas(9) system and complex of the crystal structure herein to match homologous or analogous regions (e.g., homologous or analogous sequences); modeling the structure of the matched homologous or analogous regions (e.g., sequences) of the CRISPR-cas system or complex of unknown crystal structure based on the structure of the Cas9 Crystal Structure of the corresponding regions (e.g., sequences); and, determining a conformation (e.g. taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as of nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-Cas9 crystal structure and those of a CRISPR-cas system of unknown crystal structure aid in the prediction and determination of the crystal structure of the CRISPR-cas system of unknown crystal structure.

Further still, the aspects of the invention which employ the CRISPR-Cas9 crystal structure in silico may be equally applied to new CRISPR-cas crystal structures divined by using the herein-referenced CRISPR-Cas9 crystal structure. In this fashion, a library of CRISPR-cas crystal structures can be obtained. Rational CRISPR-cas system design is thus provided by the instant invention. For instance, having determined a conformation or crystal structure of a CRISPR-cas system or complex, by the methods described herein, such a conformation may be used in a computer-based methods herein for determining the conformation or crystal structure of other CRISPR-cas systems or complexes whose crystal structures are yet unknown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of a CRISPR-cas system or complex. The system can contain: atomic co-ordinate data according to the herein-referenced Crystal Structure or be derived therefrom e.g., by modeling, said data defining the three-dimensional structure of a CRISPR-cas system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the herein-referenced Crystal Structure or derived therefrom e.g., by homology modeling, said data defining the three-dimensional structure of a CRISPR-cas system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-cas systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein-referenced Crystal Structure gives atomic co-ordinate data for a CRISPR-Cas9 (S. pyogenes), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number.

In particular embodiments of the invention, the conformational variations in the crystal structures of the CRISPR-Cas9 system or of components of the CRISPR-Cas9 provide important and critical information about the flexibility or movement of protein structure regions relative to nucleotide (RNA or DNA) structure regions that may be important for CRISPR-Cas system function. The structural information provided for Cas9 (e.g. S. pyogenes Cas9) as the CRISPR enzyme in the present application may be used to further engineer and optimize the CRISPR-Cas system and this may be extrapolated to interrogate structure-function relationships in other CRISPR enzyme systems as well. An aspect of the invention relates to the crystal structure of S. pyogenes Cas9 in complex with sgRNA and its target DNA at 2.4 Å resolution. The structure revealed a bilobed architecture composed of target recognition and nuclease lobes, accommodating a sgRNA:DNA duplex in a positively-charged groove at their interface. The recognition lobe is essential for sgRNA and DNA binding and the nuclease lobe contains the HNH and RuvC nuclease domains, which are properly positioned for the cleavage of complementary and non-complementary strands of the target DNA, respectively. This high-resolution structure and the functional analyses provided herein elucidate the molecular mechanism of RNA-guided DNA targeting by Cas9, and provides an abundance of information for generating optimized CRISPR-Cas systems and components thereof.

In particular embodiments of the invention, the crystal structure provides a critical step towards understanding the molecular mechanism of RNA-guided DNA targeting by Cas9. The structural and functional analyses herein provide a useful scaffold for rational engineering of Cas9-based genome modulating technologies and may provide guidance as to Cas9-mediated recognition of PAM sequences on the target DNA or mismatch tolerance between the sgRNA: DNA duplex. Aspects of the invention also relate to truncation mutants, e.g. an *S. pyogenes* Cas9 truncation mutant may facilitate packaging of Cas9 into size-constrained viral vectors for in vivo and therapeutic applications. Similarly, future engineering of the PAM Interacting (PI) domain may allow programming of PAM specificity, improve target site recognition fidelity, and increase the versatility of the Cas9 genome engineering platform.

The invention comprehends optimized functional CRISPR-Cas enzyme systems. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The structural information provided herein allows for interrogation of sgRNA (or chimeric RNA) interaction with the target DNA and the CRISPR enzyme (e.g. Cas9) permitting engineering or alteration of sgRNA structure to optimize functionality of the entire CRISPR-Cas system. For example, loops of the sgRNA may be extended, without colliding with the Cas9 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Generation of Optimized Functional
CRISPR-Cas Systems Targeting the Neurog2 Gene
by Modifying sgRNA Architecture with the
Insertion of MS2 Loops into Loops of the sgRNA The crystal structure information (described in U.S. provisional applications 61/915,251 filed Dec. 12, 2013, 61/930,214 filed on Jan. 22, 2014, 61/980,012 filed Apr. 15, 2014; and Nishimasu et al, "Crystal Structure of Cas9 in Complex with Guide RNA and Target DNA," Cell 156(5): 935-949, DOI: dx.doi.org/10.1016/j.cell.2014.02.001 (2014), each and all of which are incorporated herein by reference) provides structural information to modify sgRNA architecture. Applicants determined that there was potentially room for extension of both the tetraloop and loop2 of the sgRNA (without collision with the Cas9 protein). Applicants showed that insertion of MS2 loops at these positions enabled recruitment of MS2 binding proteins to these two locations, and thereby mediated locus specific recruitment of any effector fusions (such as transcriptional activator domains vp64, p65, transcriptional repressor domains SID4X, KRAB, or any epigenetic effector domains). Recruitment of these effector domains to the tetraloop and loop 2 of the sgRNA potentially led to a more favorable positioning relative to the targeted DNA (compared to C-term fusions of effector domains to the Cas9 proteins or addition of Ms2 loops after loop 3 of the sgRNA).

Neuro 2a cells (Sigma-Aldrich) were grown in media containing a 1:1 ratio of OptiMEM (Life Technologies) to high-glucose DMEM with GlutaMax and sodium pyruvate (Life Technologies) supplemented with 5% HyClone heat-inactivated FBS (Thermo Scientific), 1% penicillin/streptomycin (Life Technologies), and passaged at 1:5 every 2 days. 120,000 cells were plated in each well of a 24-well plate 18-20 h before transfection. Cells were transfected with Lipofectamine transfection reagent (Life Technologies) according to the manufacturer's instructions. Plasmid DNA was used for transfection of MS2-vp64 and Cas9 constructs, while PCR product was transfected for the guide RNA expression cassette.

RNA was extracted using the RNeasy kit (Qiagen) according to manufacturer's instructions and 1 mg of RNA per sample was reverse-transcribed using qScript (Quanta Biosystems). Relative mRNA levels were measured by reverse transcription and quantitative PCR (qRT-PCR) using TaqMan probes specific for the targeted gene as well as GAPDH as an endogenous control (Life Technologies). ddCt analysis was used to obtain fold-changes relative to negative controls transfected with GFP only.

Figure 1B:
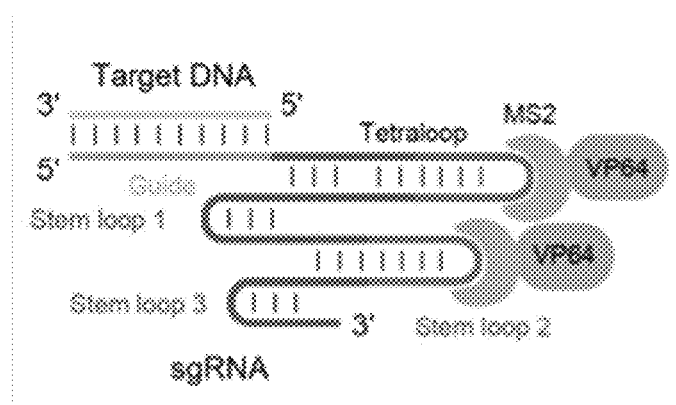
FIG. 1B shows illustration of insertions of MS2 loops in at the end of the Tetraloop and loop 2 of the sgRNA. An MS2-VP64 fusion protein is recruited to these two loops. Together with dCas9 this leads to a recruitment of the VP64 activation domain to the target DNA of the target locus. Inserted MS2 RNA stem-loops are colored dark green.
Figure 2:
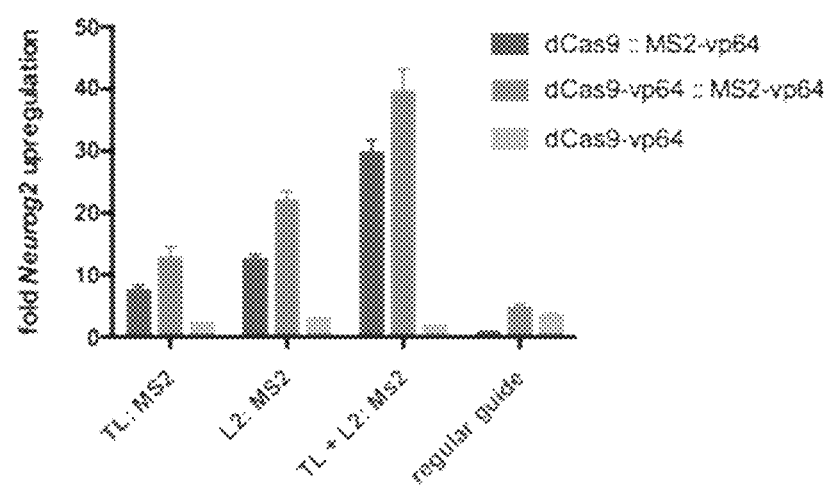
FIG. 2 shows a graphical representation of the upregulation of Neurog2 expression in Neuro2A cells. 4 different guide RNAs including an Ms2 loop inserted in either the tetraloop or loop 2, both loops or none were tested in combination with dCas9 and MS2-vp64, dCas9-vp64 and MS2-vp64 or dCas9-vp64 alone. TL:MS2, MS2 loop insertion into the sgRNA tetraloop; L2: MS2, MS2 loop insertion into loop 2 of the sgRNA. Colors indicate which protein-coding constructs were co-transfected with the corresponding guide.

Results indicated that both insertions in the tetraloop and loop 2 are effective and that the most efficient combination uses an insertion of MS2 loops in both in the tetraloop and in loop 2 of the sgRNA in combination with a dCas9-vp64 and MS2-vp64 construct. This new activator design (illustrated in FIG. 1B and shown as red bar for the TL+L2: Ms2 guide in FIG. 2) was found to mediate much higher target gene upregulation compared to the previous design (illustrated in FIG. 1A and shown as the green bar for the regular guide in FIG. 2).

MS2 Pilot Sequences are indicated below:

```
Neurog2 target sequence
                              (SEQ ID NO: 52)
GATACGATGAAAAGAATAAGC Tetraloop MS2 stem loop insertion sgRNA scaffold
                              (SEQ ID NO: 53)
NNNNNNNNNNNNNNNNNNNNgttttagagctaggccAACATGAGGATCAC CCATGTCTGCAGgcctagcaagttaaaataaggctagtccgttatcaCG CCGAAAGGCGggcaccgAGTcggtgcTTTTT Loop 2 MS2 stem loop insertion sgRNA scaffold
                              (SEQ ID NO: 54)
NNNNNNNNNNNNNNNNNNNNgttttagagctaGAAAtagcaagttaaaat aaggctagtccgttatcaacttggccAACATGAGGATCACCCATGTCTGC AGggccaagtggcaccgAGTcggtgcTTTTT Tetraloop and Loop 2 MS2 stem loop
insertion sgRNA scaffold
                              (SEQ ID NO: 55)
NNNNNNNNNNNNNNNNNNNNgttttagagctaggccAACATGAGGATCAC CCATGTCTGCAGgcctagcaagttaaaataaggctagtccgttatcaac ttggccAACATGAGGATCACCCATGTCTGCAGggccaagtggcaccgAGT cggtgcTTTTT Standard guide scaffold
                              (SEQ ID NO: 56)
NNNNNNNNNNNNNNNNNNNNgttttagagctaGAAAtagcaagttaaaat aaggctagtccgttatcaacttGAAAaagtggcaccgAGTcggtgcTTTT

T

MS2-vp64 sequence
                              (SEQ ID NO: 57)
ATGGCTTCAAACTTTACTCAGTTCGTGCTCGTGGACAATGGTGGGACAGG

GGATGTGACAGTGGCTCCTTCTAATTTCGCTAATGGGGTGGCAGAGTGGA

TCAGCTCCAACTCACGGAGCCAGGCCTACAAGGTGACATGCAGCGTCAGG

CAGTCTAGTGCCCAGAAgAGAAAGTATACCATCAAGGTGGAGGTCCCCAA

AGTGGCTACCCAGACAGTGGGCGGAGTCGAACTGCCTGTCGCCGCTTGGA

GGTCCTACCTGAACATGGAGCTCACTATCCCAATTTTCGCTACCAATTCT

GACTGTGAACTCATCGTGAAGGCAATGCAGGGGCTCCTCAAAGACGGTAA

TCCTATCCCTTCCGCCATCGCCGCTAACTCAGGTATCTACagcgctGGAG

GAGGTGGAAGCGGAGGAGGAGGAAGCGGAGGAGGAGGTAGCggacctaag aaaaagaggaaggtggcggccgctggatccGGACGGGCTGACGCATTGGA

CGATTTTGATCTGGATATGCTGGGAAGTGACGCCCTCGATGATTTTGACC

TTGACATGCTTGGTTCGGATGCCCTTGATGACTTTGACCTCGACATGCTC

GGCAGTGACGCCCTTGATGATTTCGACCTGGACATGCTGATTAAC
```

Figure 3:
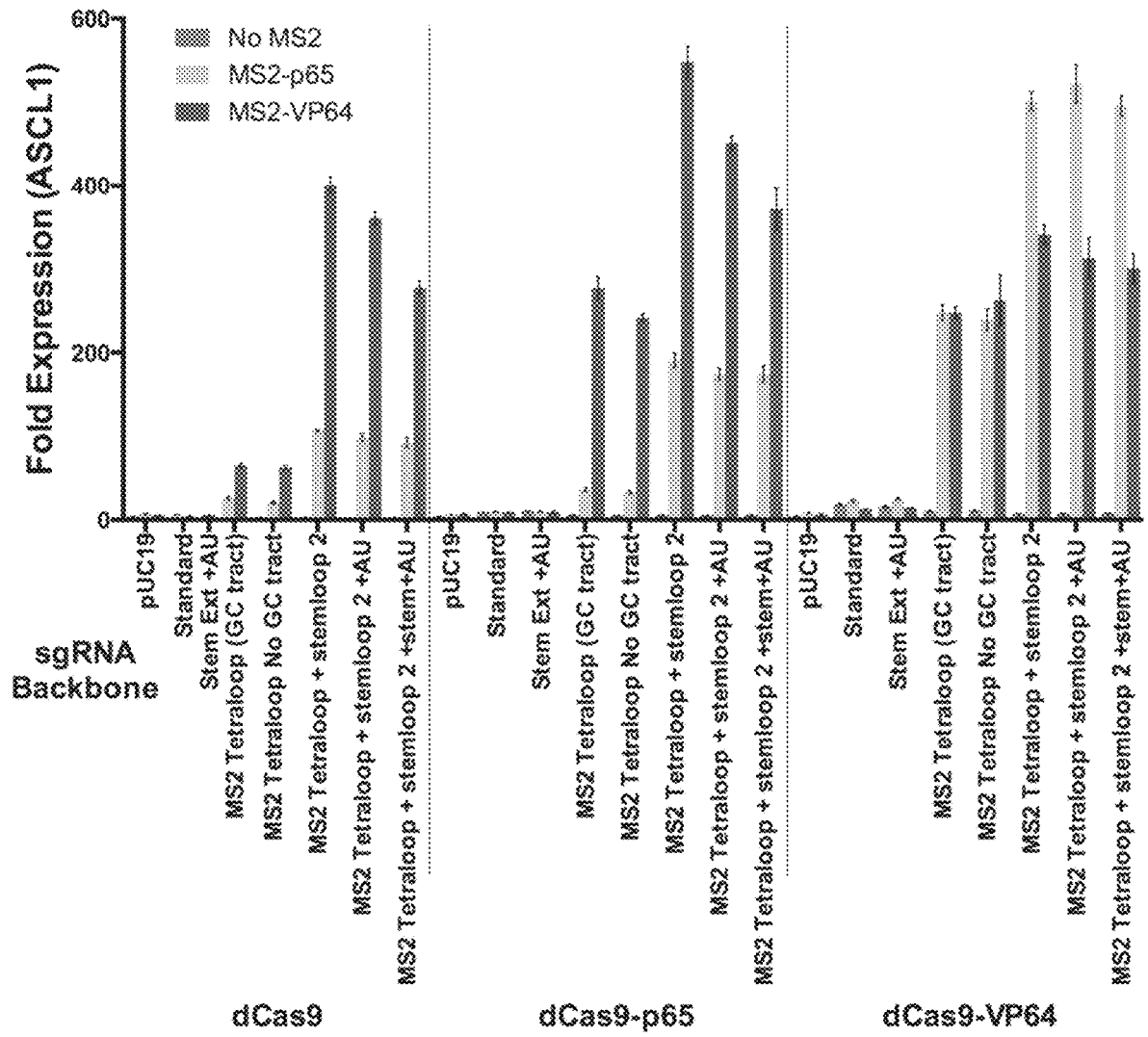
FIG. 3 shows Human ASCL1 upregulation with Cas9-MS2 activators.
Figure 4:
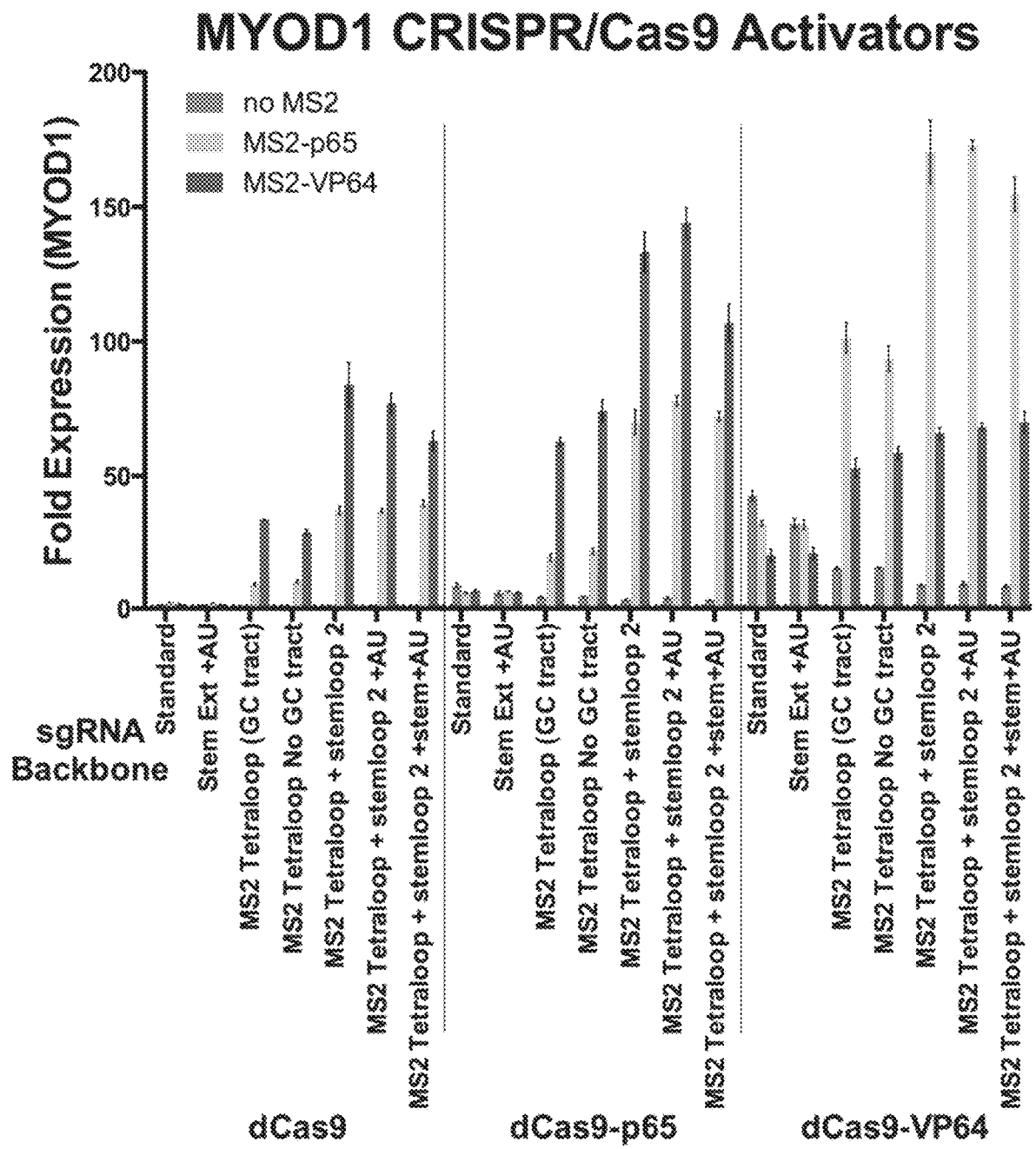
FIG. 4 shows Human MYOD1 upregulation with Cas9-MS2 activators.

Example 2: Further Optimization of Functional CRISPR-Cas Systems by Modifying sgRNA Backbone or Architecture Applicants tested the efficiency of the tetraloop and loop2 MS2 loop insertions on two additional gene targets (human ASCL1 and human MYOD1) and confirmed the increased effectiveness of sgRNA design as described in Example 1 compared to the standard C-terminal fusion of VP64 to Cas9 (See FIGS. 3 and 4). Applicants further tested the hypothesis that a combination of two different activation domains (for e.g. VP64 and P65) could lead to synergy and therefore increased efficiency of target gene upregulation compared to using the same total number of a single type of activation domain. Applicants also tested an alternative guide architecture optimized for CRISPR/Cas9 imaging in: Chen, Baohui, et al. "Dynamic Imaging of Genomic Loci in Living Human Cells by an Optimized CRISPR/Cas System." Cell 155.7 (2013): 1479-1491 in the context of gene activation.

Methods:

```
Target Sequences
ASCL1
                              (SEQ ID NO: 58)
    GCAGCCGCTCGCTGCAGCAG

MYOD1
                              (SEQ ID NO: 59)
    GGGCCCCTGCGGCCACCCCG
```

Cell Culture and Transfection and Gene Expression Analysis

Human HEK293FT cells were maintained in high-glucose DMEM with GlutaMax and sodium pyruvate (Life Technologies) supplemented with 10% heat-inactivated characterized HyClone fetal bovine serum (Thermo Scientific) and 1% penicillin/streptomycin (Life Technologies).

Cells were passaged daily at a ratio 1 to 2 or 1 to 2.5. For MS2/dCas9 activator experiments, 20,000 HEK293FT cells were plated in 100 µL of culture medium in poly-d-lysine coated 96-well plates (BD biosciences). 24 hours after plating, cells were transfected with a 1:1:1 mass ratio of:
- sgRNA backbone plasmid with gene specific targeting sequence or pUC19 control plasmid
- MS2-VP64 plasmid or MS2-p65 plasmid or pUC19 control plasmid
- dCas9 plasmid or dCas9-VP64 plasmid or dCas9-p65 plasmid or pUC19 control plasmid Total plasmid mass per well was 0.3 micrograms. Transfection was performed with 1.5 uL Lipofectamine 2000 (Life Technologies), according to the manufacturer's instructions. Culture medium was changed 5 hours after transfection. 48 hours after transfection, cell lysis and reverse transcription were performed using a Cells-to-Ct kit (Life Technologies). Gene expression levels were quantified by using Taqman qPCR probes (Life technologies) and Fast Advanced Master Mix (Life Technologies). ASCL1 and MYOD1 expression levels were calculated relative to GAPDH expression level. Fold gene expression levels were determined by comparison to samples transfected with GFP plasmid only.

The results indicate that the Applicants validated the efficiency of the tetraloop and loop2 MS2 loop insertions on two additional gene targets and confirmed the increased effectiveness of this design compared to the standard C-terminal fusion of VP64 to Cas9. Applicants further confirmed the hypothesis that a combination of two different activation domains could improve target gene activation (via synergy, e.g. by recruiting different epigenetic modulators, general transcription factors and co-activators). Applicants also determined that the alternative guide architecture optimized for CRISPR/Cas9 imaging in: Chen, Baohui, et al. "Dynamic Imaging of Genomic Loci in Living Human Cells by an Optimized CRISPR/Cas System." Cell 155.7 (2013): 1479-1491 did not exhibit any improvement over the standard architecture.

In conclusion, these experiments showed that an improved Cas9 activator architecture consists of a sgRNA with MS2 loop insertions in the tetraloop and loop 2 in combination with either MS2-VP64 and dCas9-P65 or MS2-P65 and dCas9-VP64.

MS2 sgRNA Scaffold Sequence Information

In all sequences below, NNNNNNNNNNNNNNNNNNNN represents the locus-specific targeting sequence of each sgRNA.

pSAMca006 standard sgRNA backbone
NNNNNNNNNNNNNNNNNNNNgtttagagctaGAAAtagcaagttaaaataaggctagtccgttat caacttgaaaaagtggcaccgagtcggtgcTTTTTTT (SEQ ID NO: 60)

+83 nucleotide chimeric backbone used in Zhang Lab CRISPR/Cas9 publications pSAMca002 Tetraloop stem extension +AU flip sgRNA backbone
NNNNNNNNNNNNNNNNNNNNgtttaagagctatgctgGAAAcagcatagcaagtttaaataaggc tagtccgttatcaacttgaaaaagtggcaccgagtcggtgcTTTTTTT (SEQ ID NO: 61)

Backbone optimized for CRISPR/Cas9 imaging in:
Chen, Baohui, et al. "Dynamic Imaging of Genomic Loci in Living Human Cells by an Optimized CRISPR/Cas System." Cell 155.7 (2013): 1479-1491.

T in location +5 (5th nucleotide after target sequence) exchanged with A in location +36. Authors suggest this change should increase sgRNA concentration by removing putative U6 termination site at location +2 to +5. TGCTG is added after location +12 of standard backbone and CAGCA is added after location +21 of standard backbone. These insertions pair with one another to create an extended stem at the base of the tetraloop. Authors suggest that this stem extension may help stabilize the sgRNA.

pSAMca009 MS2-binding loop on tetraloop and stem-loop 2 sgRNA backbone
NNNNNNNNNNNNNNNNNNNNgttttagagctaggccAACATGAGGATCACCCATG TCTGCAGggcctagcaagttaaaataaggctagtccgttatcaacttggccAACATGAGGATCACC-CATGTCTG CAGggccaagtggcaccgagtcggtgcTTTTTTT (SEQ ID NO: 62)

MS2-binding loop ggccAACATGAGGATCACC-CATGTCTGCAGggcc (SEQ ID NO: 1) replaces nucleotides +13 to +16 and nucleotides +53 to +56 of the standard sgRNA backbone. The resulting structure is an sgRNA scaffold in which the tetraloop and stem-loop 2 sequences have been replaced by an MS2 binding loop. The tetraloop and stem-loop 2 were selected for replacement based on information obtained from the Cas9/RNA/DNA crystal structure. Specifically, the tetraloop and stem-loop 2 were found to protrude from the Cas9 protein in such a way which suggested that adding an MS2 binding loop would not interfere with any Cas9 residues. Additionally, the proximity of the tetraloop and stem-loop 2 sites to the DNA suggested that localization to these locations would result in a high degree of interaction between the DNA and any recruited protein, such as a transcriptional activator.

pSAMca010 MS2-binding loop on tetraloop and stem-loop 2+tetraloop stem extension +AU flip sgRNA backbone
NNNNNNNNNNNNNNNNNNNNgtttaagagc-tatgctgggccAACATGAGGATCACCC ATGTCTGCAGggcccagcatagcaagtttaaataaggctagtccgttat caacttggccAACATGAGGATCACCCA TGTCTGCAGggc-caagtggcaccgagtcggtgcTTTTTTT (SEQ ID NO: 63)

T in location +5 of standard sgRNA backbone exchanged with A in location +36 of standard sgRNA backbone. The stem-loop extension and MS2-binding loop sequence tgctgggccAACATGAGGATCACC-CATGTCTGCAGggcccagca (SEQ ID NO: 64) replaces nucleotides +13 to +16 of the standard sgRNA backbone. The MS2-binding loop sequence ggccAACATGAGGAT-CACCCATGTCTGCAGggcc (SEQ ID NO: 1) replaces nucleotides +53 to +56 of the standard sgRNA backbone. The resulting structure combines the hypotheses described for pSAMca002 and pSAMca009.

pSAMca011 MS2-binding loop on tetraloop and stem-loop 2+AU flip sgRNA backbone
NNNNNNNNNNNNNNNNNNNNgtttaagagctaggccAA-CATGAGGATCACCCATG TCTGCAGggcctagcaagtt taaataaggctagtccgttatcaacttggccAACATGAGGATCACC-CATGTCTG CAGggccaagtggcaccgagtcggtgcTTTTTTT (SEQ ID NO: 65)

T in location +5 of standard sgRNA backbone exchanged with A in location +36 of standard sgRNA backbone. The MS2-binding loop sequence ggccAACATGAGGATCACC-CATGTCTGCAGggcc (SEQ ID NO: 1) replaces nucleotides +13 to +16 and nucleotides +53 to +56 of the standard sgRNA backbone. The resulting structure combines the hypothesis described for pSAMca009 with the AUflip hypothesis of pSAMca002 (removing putative U6 termination). This construct differs from pSAMca010 in that it does not include the additional tgctg tetraloop stem extension from pSAMca002, to determine whether overextending the tetraloop stem would diminish sgRNA functionality in the case of pSAMca010.

pSAMca003 MS2-binding loop on tetraloop+stem-loop 2 GC tract switch sgRNA backbone
NNNNNNNNNNNNNNNNNNNNgttttagagctaggccAA-CATGAGGATCACCCATG TCTGCAGggcctagcaagt-taaaataaggctagtccgttat-caCGCCgaaaGGCGggcaccgagtcggtgcTTTTTTT (SEQ ID NO: 66)

The MS2-binding loop sequence ggccAACATGAGGAT-CACCCATGTCTGCAGggcc (SEQ ID NO: 1) replaces nucleotides +13 to +16 of the standard sgRNA backbone. The sequence CGCC replaces nucleotides +49 to +52 of the standard sgRNA backbone. The sequence GGCG replaces nucleotides +57 to +60 of the standard sgRNA backbone. The tetraloop MS2-binding loop insertion was designed with the same rationale as described for pSAMca009 above. The CGCC and GGCG sequences replace the stem portion of stem-loop 2. The increased base-pairing strength of the CGCC-GGCG stem compared to the original ACTT-AAGT stem was hypothesized to provide additional stability to the stem-loop 2 structure, thereby increasing sgRNA performance or longevity.

pSAMca013 MS2-binding loop on tetraloop No stem-loop 2 GC tract switch sgRNA backbone
NNNNNNNNNNNNNNNNNNNNgttttagagctaggccAA-CATGAGGATCACCCATG TCTGCAGggcctagcaagt-taaaataaggctagtccgttatcaactt-gaaaaagtggcaccgagtcggtgcTTTTTTT (SEQ ID NO: 67)

The MS2-binding loop sequence ggccAACATGAGGAT-CACCCATGTCTGCAGggcc (SEQ ID NO: 1) replaces nucleotides +13 to +16 of the standard sgRNA backbone. The tetraloop MS2-binding loop insertion was designed with the same rationale as described for pSAMca009 above.

pSAMca025 MS2-binding loop on tetraloop and stem-loop 2+2 MS2 binding loops on 3' tail sgRNA backbone
NNNNNNNNNNNNNNNNNNNNgttttagagctaggccAA-CATGAGGATCACCCATG TCTGCAGggcctagcaagt-taaaataaggctagtccgttatcaacttggccAACATGAGGATCACC-CATGTCTG
CAGggccaagtggcaccgagtcggtgcTAACATGAGGATCACC-CATGTCTGCAGTGCAGGTCGAC TCTAGAAACAT-GAGGATCACCCATGTTTTTTTT (SEQ ID NO: 68)

The sequence TAACATGAGGATCACC-CATGTCTGCAGTGCAGGTCGACTCTAGAAACAT-GAGGATC ACCCATGT (SEQ ID NO: 69) comprising two MS2-binding loops separated by a short linker was inserted between nucleotide +76 and +77 of the standard sgRNA backbone. We hypothesize that adding 2 additional MS2-binding loops to the 3' tail of the sgRNA will increase the activity of the MS2/CRISPR/dCas9 activator system by providing a greater number of MS2 domain binding sites and facilitating increased recruitment of activation domains.

pSAMca026 MS2-binding loop on tetraloop and stem-loop 1 and stem-loop 2 sgRNA backbone
NNNNNNNNNNNNNNNNNNNNgttttagagctaggccAA-CATGAGGATCACCCATG TCTGCAGggcctagcaagt-taaaataagggccAACATGAGGATCACC-CATGTCTGCAGggcctccgttat
caacttggccAACATGAGGATCACCCATGTCTGCAGggc-caagtggcaccgagtcggtgcTTTTTTT (SEQ ID NO: 70)

MS2-binding loop ggccAACATGAGGATCACC-CATGTCTGCAGggcc (SEQ ID NO: 1) replaces nucleotides +13 to +16 and nucleotides +35 to +38 and nucleotides +53 to +56 of the standard sgRNA backbone. In addition to the tetraloop and stem-loop 1 MS2-binding loop replacements described for pSAMca009, this structure replaces the loop of stem-loop 1 with an MS2-binding loop. The exposed state of stem-loop 1, as observed in the Cas9/RNA/DNA crystal structure, suggests that adding an MS2-binding loop at this location would not disrupt the Cas9/RNA/DNA interaction. Further, an MS2-binding loop inserted at this location would allow for recruitment of MS2-activator protein in a region local to the target DNA.

MS2-Activator Protein Information

MS2-VP64
DNA sequence
(SEQ ID NO: 57)
ATGGCTTCAAACTTTACTCAGTTCGTGCTCGTGGACAATGGTGGGACAGG

GGATGTGACAGTGGCTCCTTCTAATTTCGCTAATGGGGTGGCAGAGTGGA

TCAGCTCCAACTCACGGAGCCAGGCCTACAAGGTGACATGCAGCGTCAGG

CAGTCTAGTGCCCAGAAgAGAAAGTATACCATCAAGGTGGAGGTCCCCAA

AGTGGCTACCCAGACAGTGGGCGGAGTCGAACTGCCTGTCGCCGCTTGGA

GGTCCTACCTGAACATGGAGCTCACTATCCCAATTTTCGCTACCAATTCT

GACTGTGAACTCATCGTGAAGGCAATGCAGGGGCTCCTCAAAGACGGTAA

TCCTATCCCTTCCGCCATCGCCGCTAACTCAGGTATCTACagcgctGGAG

GAGGTGGAAGCGGAGGAGGAGGAAGCGGAGGAGGAGGTAGCggacctaag aaaaagaggaaggtggcggccgctggatccGGACGGGCTGACGCATTGGA

CGATTTTGATCTGGATATGCTGGGAAGTGACGCCCTCGATGATTTTGACC

TTGACATGCTTGGTTCGGATGCCCTTGATGACTTTGACCTCGACATGCTC

GGCAGTGACGCCCTTGATGATTTCGACCTGGACATGCTGATTAAC

Amino acid sequence
(SEQ ID NO: 71)
MASNFTQFVLVDNGGTGDVTVAPSNFANGVAEWISSNSRSQAYKVTCSVR

QSSAQKRKYTIKVEVPKVATQTVGGVELPVAAWRSYLNMELTIPIFATNS

DCELIVKAMQGLLKDGNPIPSAIAANSGIYSAGGGGSGGGGSGGGGSGPK

KKRKVAAAGSGRADALDDFDLDMLGSDALDDFDLDMLGSDALDDFDLDML

GSDALDDFDLDMLIN

Description

The MS2-VP64 activator protein consists of the following domains from N-term to C-term: the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010), 3×GGGGS linker (SEQ ID NO: 3), SV40 nuclear localization signal, and VP64 activation domain. Functionally, the MS2 domain binds to its specific RNA aptamer, the 3×GGGGS linker (SEQ ID NO: 3) provides mechanical flexibility between the MS2 and VP64 domains, the SV40 nuclear localization signal facilitates transport of the protein into the nucleus, and the VP64 activation domain promotes transcriptional activation.

MS2-p65
DNA sequence
(SEQ ID NO: 72)
ATGGCTTCAAACTTTACTCAGTTCGTGCTCGTGGACAATGGTGGGACAGG

GGATGTGACAGTGGCTCCTTCTAATTTCGCTAATGGGGTGGCAGAGTGGA

TCAGCTCCAACTCACGGAGCCAGGCCTACAAGGTGACATGCAGCGTCAGG

-continued

```
CAGTCTAGTGCCCAGAAgAGAAAGTATACCATCAAGGTGGAGGTCCCCAA

AGTGGCTACCCAGACAGTGGGCGGAGTCGAACTGCCTGTCGCCGCTTGGA

GGTCCTACCTGAACATGGAGCTCACTATCCCAATTTTCGCTACCAATTCT

GACTGTGAACTCATCGTGAAGGCAATGCAGGGGCTCCTCAAAGACGGTAA

TCCTATCCCTTCCGCCATCGCCGCTAACTCAGGTATCTACagcgctGGAG

GAGGTGGAAGCGGAGGAGGAGGAAGCGGAGGAGGAGGTAGCggacctaag aaaaagaggaaggtggcggccgctggatccCCTTCAGGGCAGATCAGCAA

CCAGGCCCTGGCTCTGGCCCCTAGCTCCGCTCCAGTGCTGGCCCAGACTA

TGGTGCCCTCTAGTGCTATGGTGCCTCTGGCCCAGCCACCTGCTCCAGCC

CCTGTGCTGACCCCAGGACCACCCCAGTCACTGAGCGCTCCAGTGCCCAA

GTCTACACAGGCCGGCGAGGGGACTCTGAGTGAAGCTCTGCTGCACCTGC

AGTTCGACGCTGATGAGGACCTGGGAGCTCTGCTGGGGAACAGCACCGAT

CCCGGAGTGTTCACAGATCTGGCCTCCGTGGACAACTCTGAGTTTCAGCA

GCTGCTGAATCAGGGCGTGTCCATGTCTCATAGTACAGCCGAACCAATGC

TGATGGAGTACCCCGAAGCCATTACCCGGCTGGTGACCGGCAGCCAGCGG

CCCCCCGACCCCGCTCCAACTCCCCTGGGAACCAGCGGCCTGCCTAATGG

GCTGTCCGGAGATGAAGACTTCTCAAGCATCGCTGATATGGACTTTAGTG

CCCTGCTGTCACAGATTTCCTCTAGTGGGCAG

Amino acid sequence
                                                (SEQ ID NO: 73)
MASNFTQFVLVDNGGTGDVTVAPSNFANGVAEWISSNSRSQAYKVTCSVR

QSSAQKRKYTIKVEVPKVATQTVGGVELPVAAWRSYLNMELTIPIFATNS

DCELIVKAMQGLLKDGNPIPSAIAANSGIYSAGGGGSGGGGSGGGGSGPK

KKRKVAAAGSPSGQISNQALALAPSSAPVLAQTMVPSSAMVPLAQPPAPA

PVLTPGPPQSLSAPVPKSTQAGEGTLSEALLHLQFDADEDLGALLGNSTD

PGVFTDLASVDNSEFQQLLNQGVSMSHSTAEPMLMEYPEAITRLVTGSQR

PPDPAPTPLGTSGLPNGLSGDEDFSSIADMDFSALLSQISSSGQ
```

Description

The MS2-VP64 activator protein consists of the following domains from N-term to C-term: the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010), 3×GGGGS linker (SEQ ID NO: 3), SV40 nuclear localization signal, and p65 activation domain. Functionally, the MS2 domain binds to its specific RNA aptamer, the 3×GGGGS linker (SEQ ID NO: 3) provides mechanical flexibility between the MS2 and p65 domains, the SV40 nuclear localization signal facilitates transport of the protein into the nucleus, and the p65 activation domain promotes transcriptional activation.

Figure 5:
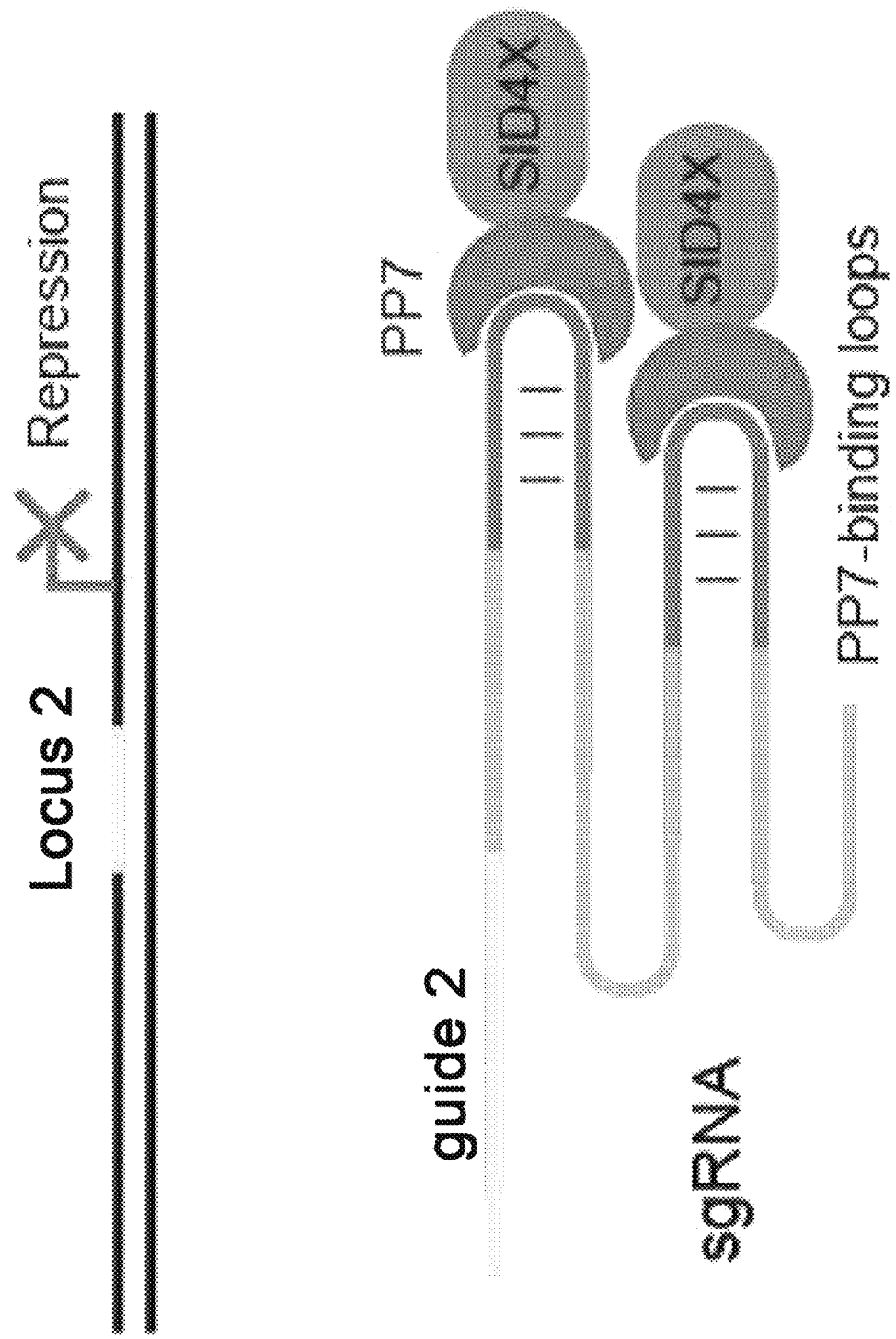
FIG. 5 shows an illustration of orthogonal PP7/MS2 gene targeting. In the schematic, sgRNA targeting different loci are modified with distinct RNA loops in order to recruit MS2-VP64 or PP7-SID4X, which activate and repress their target loci, respectively.
Figure 5:
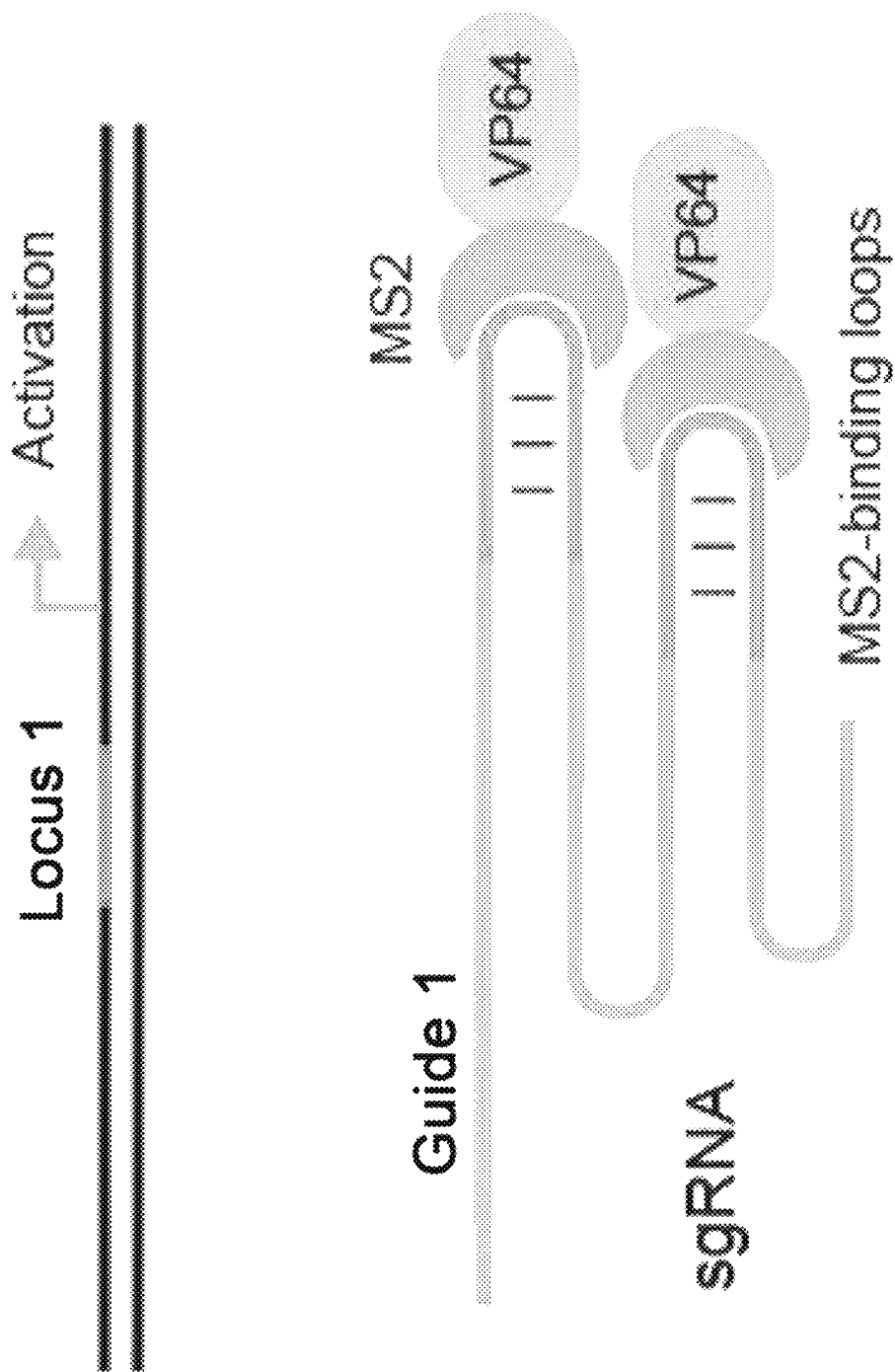

Example 3: Further Optimization of Functional CRISPR-Cas Systems by Multiplexing to Mediate Distinct Effects at Different Genomic Loci Simultaneously PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 may be multiplexed to mediate distinct effects at different genomic loci simultaneously. For example, an sgRNA targeting locus A may be modified with MS2 loops, recruiting MS2-VP64 activators, while another sgRNA targeting locus B may be modified with PP7 loops, recruiting PP7-SID4X repressor domains (FIG. 5). In the same cell, dCas9 may thus mediate orthogonal, locus-specific modifications. This principle may be extended to incorporate other orthogonal RNA-binding proteins such as Q-beta.

PP7-Effector Protein Information

Applicants construct PP7-effector constructs as previously described in Examples 1 and 2. Sequence information on these constructs are provided below:

```
PP7-VP64
DNA sequence
                                                (SEQ ID NO: 74)
ATGTCCAAAACCATCGTTCTTTCGGTCGGCGAGGCTACTCGCACTCTGAC

TGAGATCCAGTCCACCGCAGACCGTCAGATCTTCGAAGAGAAGGTCGGGC

CTCTGGTGGGTCGGCTGCGCCTCACGGCTTCGCTCCGTCAAAACGGAGCC

AAGACCGCGTATCGCGTCAACCTAAAACTGGATCAGGCGGACGTCGTTGA

TTCCGGACTTCCGAAAGTGCGCTACACTCAGGTATGGTCGCACGACGTGA

CAATCGTTGCGAATAGCACCGAGGCCTCGCGCAAATCGTTGTACGATTTG

ACCAAGTCCCTCGTCGCGACCTCGCAGGTCGAAGATCTTGTCGTCAACCT

TGTGCCGCTGGGCCGTagcgctGGAGGAGGTGGAAGCGGAGGAGGAGGAA

GCGGAGGAGGAGGTAGCggacctaagaaaaagaggaaggtggcggccgct ggatccGGACGGGCTGACGCATTGGACGATTTTGATCTGGATATGCTGGG

AAGTGACGCCCTCGATGATTTTGACCTTGACATGCTTGGTTCGGATGCCC

TTGATGACTTTGACCTCGACATGCTCGGCAGTGACGCCCTTGATGATTTC

GACCTGGACATGCTGATTAAC

Amino acid sequence
                                                (SEQ ID NO: 75)
MSKTIVLSVGEATRTLTEIQSTADRQIFEEKVGPLVGRLRLTASLRQNGA

KTAYRVNLKLDQADVVDSGLPKVRYTQVWSHDVTIVANSTEASRKSLYDL

TKSLVATSQVEDLVVNLVPLGRSAGGGGSGGGGSGGGGSGPKKKRKVAAA

GSGRADALDDFDLDMLGSDALDDFDLDMLGSDALDDFDLDMLGSDALDDF

DLDMLIN
```

Description

The PP7-VP64 activator protein consists of the following domains from N-term to C-term: the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells." Biophysical journal 102.12 (2012): 2936-2944. and Chao, Jeffrey A., et al. "Structural basis for the coevolution of a viral RNA-protein complex." Nature structural & molecular biology 15.1 (2007): 103-105), 3×GGGGS linker (SEQ ID NO: 3), SV40 nuclear localization signal, and VP64 activation domain. Functionally, the PP7 domain binds to its specific RNA aptamer, the 3×GGGGS linker (SEQ ID NO:

PP7-SID4X
DNA sequence
(SEQ ID NO: 76)
ATGTCCAAAACCATCGTTCTTTCGGTCGGCGAGGCTACTCGCACTCTGAC

TGAGATCCAGTCCACCGCAGACCGTCAGATCTTCGAAGAGAAGGTCGGGC

CTCTGGTGGGTCGGCTGCGCCTCACGGCTTCGCTCCGTCAAAACGGAGCC

AAGACCGCGTATCGCGTCAACCTAAAACTGGATCAGGCGGACGTCGTTGA

TTCCGGACTTCCGAAAGTGCGCTACACTCAGGTATGGTCGCACGACGTGA

CAATCGTTGCGAATAGCACCGAGGCCTCGCGCAAATCGTTGTACGATTTG

ACCAAGTCCCTCGTCGCGACCTCGCAGGTCGAAGATCTTGTCGTCAACCT

TGTGCCGCTGGGCCGTagcgctGGAGGAGGTGGAAGCGGAGGAGGAGGAA

GCGGAGGAGGAGGTAGCggacctaagaaaaagaggaaggtggcggccgct ggatccATGAACATCCAGATGCTGCTGGAGGCCGCTGACTACCTGGAACG

GAGAGAGCGCGAAGCCGAGCACGGATATGCTTCAATGCTGCCCGGAAGCG

GCATGAATATTCAGATGCTGCTGGAGGCTGCTGATTACCTGGAAAGGCGC

GAACGGGAGGCCGAACATGGCTATGCTTCCATGCTGCCTGGGTCTGGAAT

GAATATCCAAATGCTGCTGGAGGCAGCCGATTACCTGGAACGGAGAGAAA

GAGAAGCCGAGCACGGATACGCCAGCATGCTGCCAGGCAGCGGGATGAAC

ATACAAATGCTGCTGGAGGCTGCCGATTACCTGGAGAGGCGCGAGAGAGA

AGCTGAACATGGCTATGCCTCTATGCTGCCC

Amino acid sequence
(SEQ ID NO: 77)
MSKTIVLSVGEATRTLTEIQSTADRQIFEEKVGPLVGRLRLTASLRQNGA

KTAYRVNLKLDQADVVDSGLPKVRYTQVWSHDVTIVANSTEASRKSLYDL

TKSLVATSQVEDLVVNLVPLGRSAGGGGSGGGGSGGGGSGPKKKRKVAAA

GSMNIQMLLEAADYLERREREAEHGYASMLPGSGMNIQMLLEAADYLERR

EREAEHGYASMLPGSGMNIQMLLEAADYLERREREAEHGYASMLPGSGMN

IQMLLEAADYLERREREAEHGYASMLP

Description

The PP7-SID4X repressor protein consists of the following domains from N-term to C-term: the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells." Biophysical journal 102.12 (2012): 2936-2944. and Chao, Jeffrey A., et al. "Structural basis for the coevolution of a viral RNA-protein complex." Nature structural & molecular biology 15.1 (2007): 103-105), 3×GGGGS linker (SEQ ID NO: 3), SV40 nuclear localization signal, and SID4X repressor domain. Functionally, the PP7 domain binds to its specific RNA aptamer, the 3×GGGGS linker (SEQ ID NO: 3) provides mechanical flexibility between the MS2 and SID4X domains, the SV40 nuclear localization signal facilitates transport of the protein into the nucleus, and the SID4X domain represses transcriptional activity.

PP7-KRAB
DNA sequence
(SEQ ID NO: 78)
ATGTCCAAAACCATCGTTCTTTCGGTCGGCGAGGCTACTCGCACTCTGAC

TGAGATCCAGTCCACCGCAGACCGTCAGATCTTCGAAGAGAAGGTCGGGC

CTCTGGTGGGTCGGCTGCGCCTCACGGCTTCGCTCCGTCAAAACGGAGCC

AAGACCGCGTATCGCGTCAACCTAAAACTGGATCAGGCGGACGTCGTTGA

TTCCGGACTTCCGAAAGTGCGCTACACTCAGGTATGGTCGCACGACGTGA

CAATCGTTGCGAATAGCACCGAGGCCTCGCGCAAATCGTTGTACGATTTG

ACCAAGTCCCTCGTCGCGACCTCGCAGGTCGAAGATCTTGTCGTCAACCT

TGTGCCGCTGGGCCGTagcgctGGAGGAGGTGGAAGCGGAGGAGGAGGAA

GCGGAGGAGGAGGTAGCggacctaagaaaaagaggaaggtggcggccgct ggatccgctttgtctcctcagcactctgctgtcactcaaggaagtatcat caagaacaaggagggcatggatgctaagtcactaactgcctggtcccgga cactggtgaccttcaaggatgtatttgtggacttcaccagggaggagtgg aagctgctggacactgctcagcagatcgtgtacagaaatgtgatgctgga gaactataagaacctggtttccttgggttatcagcttactaagccagatg tgatcctccggttggagaagggagaagagccctggctggtggagagagaa attcaccaagagacccatcctgattcagagactgcatttgaaatcaaatc atcagtt Amino acid sequence
(SEQ ID NO: 79)
MSKTIVLSVGEATRTLTEIQSTADRQIFEEKVGPLVGRLRLTASLRQNGA

KTAYRVNLKLDQADVVDSGLPKVRYTQVWSHDVTIVANSTEASRKSLYDL

TKSLVATSQVEDLVVNLVPLGRSAGGGGSGGGGSGGGGSGPKKKRKVAAA

GSALSPQHSAVTQGSIIKNKEGMDAKSLTAWSRTLVTFKDVFVDFTREEW

KLLDTAQQIVYRNVMLENYKNLVSLGYQLTKPDVILRLEKGEEPWLVERE

IHQETHPDSETAFEIKSSV

Description

The PP7-KRAB repressor protein consists of the following domains from N-term to C-term: the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells." Biophysical journal 102.12 (2012): 2936-2944. and Chao, Jeffrey A., et al. "Structural basis for the coevolution of a viral RNA-protein complex." Nature structural & molecular biology 15.1 (2007): 103-105), 3×GGGGS linker (SEQ ID NO: 3), SV40 nuclear localization signal, and KRAB repressor domain. Functionally, the PP7 domain binds to its specific RNA aptamer, the 3×GGGGS linker (SEQ ID NO: 3) provides mechanical flexibility between the MS2 and KRAB domains, the SV40 nuclear localization signal facilitates transport of the protein into the nucleus, and the KRAB domain represses transcriptional activity.

PP7-NUE
DNA sequence (SEQ ID NO: 80)
ATGTCCAAAACCATCGTTCTTTCGGTCGGCGAGGCTACTCGCACTCTGAC

TGAGATCCAGTCCACCGCAGACCGTCAGATCTTCGAAGAGAAGGTCGGGC

CTCTGGTGGGTCGGCTGCGCCTCACGGCTTCGCTCCGTCAAAACGGAGCC

AAGACCGCGTATCGCGTCAACCTAAAACTGGATCAGGCGGACGTCGTTGA

TTCCGGACTTCCGAAAGTGCGCTACACTCAGGTATGGTCGCACGACGTGA

CAATCGTTGCGAATAGCACCGAGGCCTCGCGCAAATCGTTGTACGATTTG

ACCAAGTCCCTCGTCGCGACCTCGCAGGTCGAAGATCTTGTCGTCAACCT

TGTGCCGCTGGGCCGTagcgctGGAGGAGGTGGAAGCGGAGGAGGAGGAA

GCGGAGGAGGAGGTAGCggacctaagaaaaagaggaaggtggcggccgct ggatccACTACCAACTCCACTCAGGACACACTGTATCTCAGCCTCCACGG

CGGAATCGACTCCGCCATCCCATACCCCGTGAGGAGAGTCGAGCAGCTGC

TCCAGTTCTCTTTTCTGCCCGAACTCCAGTTCCAGAACGCCGCTGTGAAA

CAGAGAATCCAGCGCCTGTGCTATAGAGAGGAAAAGCGGCTGGCTGTCAG

CTCCCTCGCAAAGTGGCTGGGCCAGCTCCACAAACAGAGGCTGAGAGCAC

CAAAGAACCCCCCTGTGGCCATTTGTTGGATCAATAGTTACGTGGGCTAT

GGAGTCTTTGCCCGGGAGTCTATTCCCGCTTGGAGTTACATCGGCGAATA

TACCGGCATCCTGCGGCGCCGACAGGCTCTGTGGCTCGACGAGAACGATT

ACTGCTTCCGCTATCCTGTGCCACGCTACTCATTCCGATATTTTACCATC

GACAGCGGGATGCAGGGTAACGTCACAAGGTTCATCAATCACTCCGATAA

CCCTAATCTGGAGGCAATCGGGGCCTTCGAAAACGGTATCTTCCATATCA

TCATCAGGGCCATCAAGGATATCCTGCCCGGGGAGGAACTCTGTTACCAC

TATGGACCTCTGTACTGGAAGCATCGAAAGAAAAGGGAGGAGTTCGTGCC

ACAGGAGGAA

Amino acid sequence (SEQ ID NO: 81)
MSKTIVLSVGEATRTLTEIQSTADRQIFEEKVGPLVGRLRLTASLRQNGA

KTAYRVNLKLDQADVVDSGLPKVRYTQVWSHDVTIVANSTEASRKSLYDL

TKSLVATSQVEDLVVNLVPLGRSAGGGGSGGGGSGGGGSGPKKKRKVAAA

GSTTNSTQDTLYLSLHGGIDSAIPYPVRRVEQLLQFSFLPELQFQNAAVK

QRIQRLCYREEKRLAVSSLAKWLGQLHKQRLRAPKNPPVAICWINSYVGY

GVFARESIPAWSYIGEYTGILRRRQALWLDENDYCFRYPVPRYSFRYFTI

DSGMQGNVTRFINHSDNPNLEAIGAFENGIFHIIIRAIKDILPGEELCYH

YGPLYWKHRKKREEFVPQEE

Description

The PP7-NUE histone effector protein consists of the following domains from N-term to C-term: the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells." Biophysical journal 102.12 (2012): 2936-2944. and Chao, Jeffrey A., et al. "Structural basis for the coevolution of a viral RNA-protein complex." Nature structural & molecular biology 15.1 (2007): 103-105), 3×GGGGS linker (SEQ ID NO: 3), SV40 nuclear localization signal, and the NUE histone methyltransferase domain from *Chlamydia trachomatis*. Functionally, the PP7 domain binds to its specific RNA aptamer, the 3×GGGGS linker (SEQ ID NO: 3) provides mechanical flexibility between the MS2 and NUE domains, the SV40 nuclear localization signal facilitates transport of the protein into the nucleus, and the NUE domain increases repressive histone methylation.

PP7-NcoR
DNA sequence (SEQ ID NO: 82)
ATGTCCAAAACCATCGTTCTTTCGGTCGGCGAGGCTACTCGCACTCTGAC

TGAGATCCAGTCCACCGCAGACCGTCAGATCTTCGAAGAGAAGGTCGGGC

CTCTGGTGGGTCGGCTGCGCCTCACGGCTTCGCTCCGTCAAAACGGAGCC

AAGACCGCGTATCGCGTCAACCTAAAACTGGATCAGGCGGACGTCGTTGA

TTCCGGACTTCCGAAAGTGCGCTACACTCAGGTATGGTCGCACGACGTGA

CAATCGTTGCGAATAGCACCGAGGCCTCGCGCAAATCGTTGTACGATTTG

ACCAAGTCCCTCGTCGCGACCTCGCAGGTCGAAGATCTTGTCGTCAACCT

TGTGCCGCTGGGCCGTagcgctGGAGGAGGTGGAAGCGGAGGAGGAGGAA

GCGGAGGAGGAGGTAGCggacctaagaaaaagaggaaggtggcggccgct ggatccAACGGGCTGATGGAGGACCCAATGAAAGTCTACAAGGACAGGCA

GTTTATGAACGTGTGGACCGACCACGAGAAGGAAATCTTCAAGGATAAGT

TCATCCAGCATCCCAAAAATTTCGGCCTGATCGCCAGCTACCTGGAGAGG

AAGTCCGTGCCTGACTGCGTCCTGTACTATTACCTCACAAAGAAAAACGA

AAATTACAAA

Amino acid sequence (SEQ ID NO: 83)
MSKTIVLSVGEATRTLTEIQSTADRQIFEEKVGPLVGRLRLTASLRQNGA

KTAYRVNLKLDQADVVDSGLPKVRYTQVWSHDVTIVANSTEASRKSLYDL

TKSLVATSQVEDLVVNLVPLGRSAGGGGSGGGGSGGGGSGPKKKRKVAAA

GSNGLMEDPMKVYKDRQFMNVWTDHEKEIFKDKFIQHPKNFGLIASYLER

KSVPDCVLYYYLTKKNENYK

Description

The PP7-NcoR histone effector protein consists of the following domains from N-term to C-term: the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells." Biophysical journal 102.12 (2012): 2936-2944. and Chao, Jeffrey A., et al. "Structural basis for the coevolution of a viral RNA-protein complex." Nature structural & molecular biology 15.1 (2007): 103-105), 3×GGGGS linker (SEQ ID NO: 3), SV40 nuclear localization signal, and the HDAC recruiter domain of the human NcoR protein (amino acids 420-488 of wild type). Functionally, the PP7 domain binds to its specific RNA aptamer, the 3×GGGGS linker (SEQ ID NO: 3) provides mechanical flexibility between the MS2 and NcoR domains, the SV40 nuclear localization signal facilitates transport of the protein into the nucleus, and the NcoR domain recruits histone deacetylases leading to repressive histone modifications.

Other potential orthogonal RNA-binding proteins: Additional orthogonal RNA-binding protein/aptamer combinations exist within the diversity of bacteriophage coat proteins. These alternative combinations may be used to develop transcriptional modulators or DNA-effectors analogous to those Applicants have described for MS2 and PP7. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

Example 4: MS2 CasLITE

Further embodiments of the invention include modification of sgRNA architecture with MS2 loops as described in Examples 1 and 2 with further application in inducible CRISPR-Cas systems as described in PCT Application PCT/US2013/051418, entitled "INDUCIBLE DNA BINDING PROTEINS AND GENOME PERTURBATION TOOLS AND APPLICATIONS THEREOF" filed on Jul. 21, 2013 and published as PCT Publication WO2014018423A2 on Jan. 30, 2014, the contents of which are incorporated herein by reference in their entirety.

Applicants previously showed that CRY2 and CIB1 proteins may be fused to transcription activation domains and DNA-binding domains, respectively, in order to allow locus-specific light-inducible control of endogenous transcription (Konermann S, Brigham M D, Trevino A E, Hsu P D, Heidenreich M, Cong L, Platt R J, Scott D A, Church G M, Zhang F. "Optical control of endogenous mammalian transcription and epigenetic states." Nature. 2013 Aug. 22; 500(7463):472-6). Applicants further showed that this system may be extended to dCas9 transcriptional effectors. Applicants generate an analogous dCas9-based light-inducible MS2-effector, characterized by an MS2-CIB1 recruitment component bound to dCas9-sgRNA, and a CRY2-VP64 transcriptional activator domain. Upon activation with blue light, CRY2-VP64 associate with MS2-CIB1, enabling the recruitment of the transcriptional machinery to the target locus.

The novel MS2-CIB1 inducible recruitment complex consists of the following domains from N-term to C-term: the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010), 3×GGGGS linker (SEQ ID NO: 3), SV40 nuclear localization signal, and p65 activation domain. Functionally, the MS2 domain binds to its specific RNA aptamer, the 3×GGGGS linker (SEQ ID NO: 3) provides mechanical flexibility between the MS2 and CIB1 domains, the SV40 nuclear localization signal facilitates transport of the protein into the nucleus, and the CIB1 domain is a heterodimeric binding partner of the light-sensitive Cryptochrome 2 (CRY2).

The alternative sgRNA designs, orthogonal RNA-binding proteins, and MS2 fusion architectures discussed in previous Examples are entirely compatible with the MS2-CIB1 fusion, with CIB1 acting as the "effector" domain. dCas9-CIB1, which are previously described, may also be compatible with MS2-CIB1—i.e., using dCas9-CIB1 and MS2-CIB1 fusions in tandem may provide functional advantages for inducible manipulation of target gene expression. Finally, optimized LITE architectures may be employed as described in Konermann et al 2013.

Sequence information for MS2 CasLITE constructs are provided below:

```
MS2-CIB1 DNA Sequence
                                          (SEQ ID NO: 84)
ATGGCTTCAAACTTTACTCAGTTCGTGCTCGTGGACAATGGTGGGACAGG

GGATGTGACAGTGGCTCCTTCTAATTTCGCTAATGGGGTGGCAGAGTGGA

TCAGCTCCAACTCACGGAGCCAGGCCTACAAGGTGACATGCAGCGTCAGG

CAGTCTAGTGCCCAGAAgAGAAAGTATACCATCAAGGTGGAGGTCCCCAA

AGTGGCTACCCAGACAGTGGGCGGAGTCGAACTGCCTGTCGCCGCTTGGA

GGTCCTACCTGAACATGGAGCTCACTATCCCAATTTTCGCTACCAATTCT

GACTGTGAACTCATCGTGAAGGCAATGCAGGGGCTCCTCAAAGACGGTAA

TCCTATCCCTTCCGCCATCGCCGCTAACTCAGGTATCTACagcgctGGAG

GAGGTGGAAGCGGAGGAGGAGGAAGCGGAGGAGGAGGTAGCggacctaag aaaaagaggaaggtggcggccgctggatccAACGGCGCGATTGGTGGGGA

TTTGCTGCTTAACTTTCCCGACATGTCCGTGTTGGAACGTCAGCGCGCAC

ATTTGAAGTATCTTAACCCCACCTTCGACTCCCCGTTGGCCGGGTTCTTT

GCGGACTCATCTATGATTACGGGAGGGGAAATGGACAGCTACCTCTCAAC

GGCCGGATTGAATCTTCCGATGATGTATGGAGAAACCACTGTAGAAGGCG

ACTCGCGACTCTCGATTTCGCCTGAAACGACGCTGGGAACAGGGAACTTC

AAGAAACGGAAATTCGACACGGAGACAAAAGATTGCAACGAAAAGAAGAA

GAAAATGACCATGAATCGCGATGATCTGGTAGAGGAGGGAGAGGAGGAAA

AGTCGAAGATTACTGAACAGAACAATGGGTCTACCAAAAGTATCAAAAAG

ATGAAGCACAAAGCTAAGAAAGAAGAGAACAATTTCAGCAATGACAGCAG

TAAAGTCACAAAAGAACTGGAGAAAACGGATTACATTCACGTGAGGGCGC

GACGAGGGCAGGCTACAGATTCACATTCAATTGCGGAGAGAGTACGGAGA

GAGAAAATCTCAGAAAGGATGAAGTTCCTCCAAGACCTTGTGCCAGGTTG

TGACAAGATCACAGGCAAAGCAGGAATGCTGGATGAGATCATCAACTACG

TCCAATCGTTGCAAAGACAAATTGAGTTTCTCTCGATGAAACTGGCCATC

GTGAATCCTAGACCGGATTTCGACATGGATGACATCTTTGCGAAAGAAGT

GGCATCCACTCCCATGACGGTTGTGCCCTCACCGGAGATGGTCTTGTCTG

GTTACAGCCACGAAATGGTGCATTCGGGTTATTCAAGCGAGATGGTCAAT

TCGGGATACCTTCACGTCAATCCCATGCAGCAGGTGAATACTTCCAGTGA

TCCACTCTCCTGCTTTAACAACGGCGAGGCCCCTTCGATGTGGGACTCCC

ACGTACAGAATCTCTATGGAAATCTCGGAGTC

MS2-CIB1 Amino Acid Sequence:
                                          (SEQ ID NO: 85)
MASNFTQFVLVDNGGTGDVTVAPSNFANGVAEWISSNSRSQAYKVTCSVR

QSSAQKRKYTIKVEVPKVATQTVGGVELPVAAWRSYLNMELTIPIFATNS

DCELIVKAMQGLLKDGNPIPSAIAANSGIYSAGGGGSGGGGSGGGGSGPK

KKRKVAAAGSNGAIGGDLLLNFPDMSVLERQRAHLKYLNPTFDSPLAGFF

ADSSMITGGEMDSYLSTAGLNLPMMYGETTVEGDSRLSISPETTLGTGNF

KKRKFDTETKDCNEKKKKMTMNRDDLVEEGEEEKSKITEQNNGSTKSIKK
```

```
MKHKAKKEENNFSNDSSKVTKELEKTDYIHVRARRGQATDSHSIAERVRR

EKISERMKFLQDLVPGCDKITGKAGMLDEIINYVQSLQRQIEFLSMKLAI

VNPRPDFDMDDIFAKEVASTPMTVVPSPEMVLSGYSHEMVHSGYSSEMVN

SGYLHVNPMQQVNTSSDPLSCFNNGEAPSMWDSHVQNLYGNLGV
```

Example 5: New dCas9 Activator Constructs Informed by Crystal Structure Information An optimized CRISPR/Cas9 activator system requires improvements not only in the sgRNA backbone, but in the dCas9-activator fusion constructs. The Cas9/RNA/DNA crystal structure has led to the generation of several hypotheses for improving dCas9-activator function. The crystal structure showed that the C-terminus of dCas9, where the activation domain of the standard dCas9-activator is fused, is poorly localized to the target DNA. Most, but not all, of these hypotheses seek to improve dCas9-activator function by finding preferable locations for the activation domain within the dCas9 protein, rather than at the C-terminus.

In brief:

Replace dCas9 Rec2 domain with transcriptional effector domain

Replace dCas9 HNH domain with transcriptional effector domain

Insert transcriptional effector domain with at sites of flexible linkers within dCas9: amino acid 553, 575, or 1153

Create catalytically inactive dCas9 by combination of D10A and N863A mutations, rather than D10A and H840A mutations.

Replacing the dCas9 Rec2 domain with transcriptional effector domain:

The Cas9/RNA/DNA crystal structure experiments showed that a Cas9 mutant from which the Rec2 domain had been deleted maintained a significant level of nuclease activity. This finding suggests that the Rec2 domain is not essential for the formation of the Cas9/RNA/DNA complex. We hypothesize that replacing the Rec2 domain in dCas9 with a transcriptional effector domain would not inhibit formation of the dCas9/RNA/DNA complex and could facilitate a more efficient interaction between the transcriptional effector domain and the target DNA. Several constructs have been synthesized to investigate this theory.

In each case amino acids 175-306 of dCas9 were replaced with one of the following inserts, with subdomains listed from N- to C-terminus:

VP64 activation domain

3×GGGGS linker (SEQ ID NO: 3), VP64 activation domain, 3×GGGGS linker (SEQ ID NO: 3)

p65 activation domain

3×GGGGS linker (SEQ ID NO: 3), p65 activation domain, 3×GGGGS linker (SEQ ID NO: 3)

TABLE 9

| | Corresponding constructs |
|---|---|
| pSAMca042 | dCas(hel2-->vp64) |
| pSAMca043 | dCas(hel2-->vp64, GSlinker) |
| pSAMca044 | dCas(hel2-->P65) |
| pSAMca045 | dCas(hel2-->P65 GSlinker) |

Figure 6:
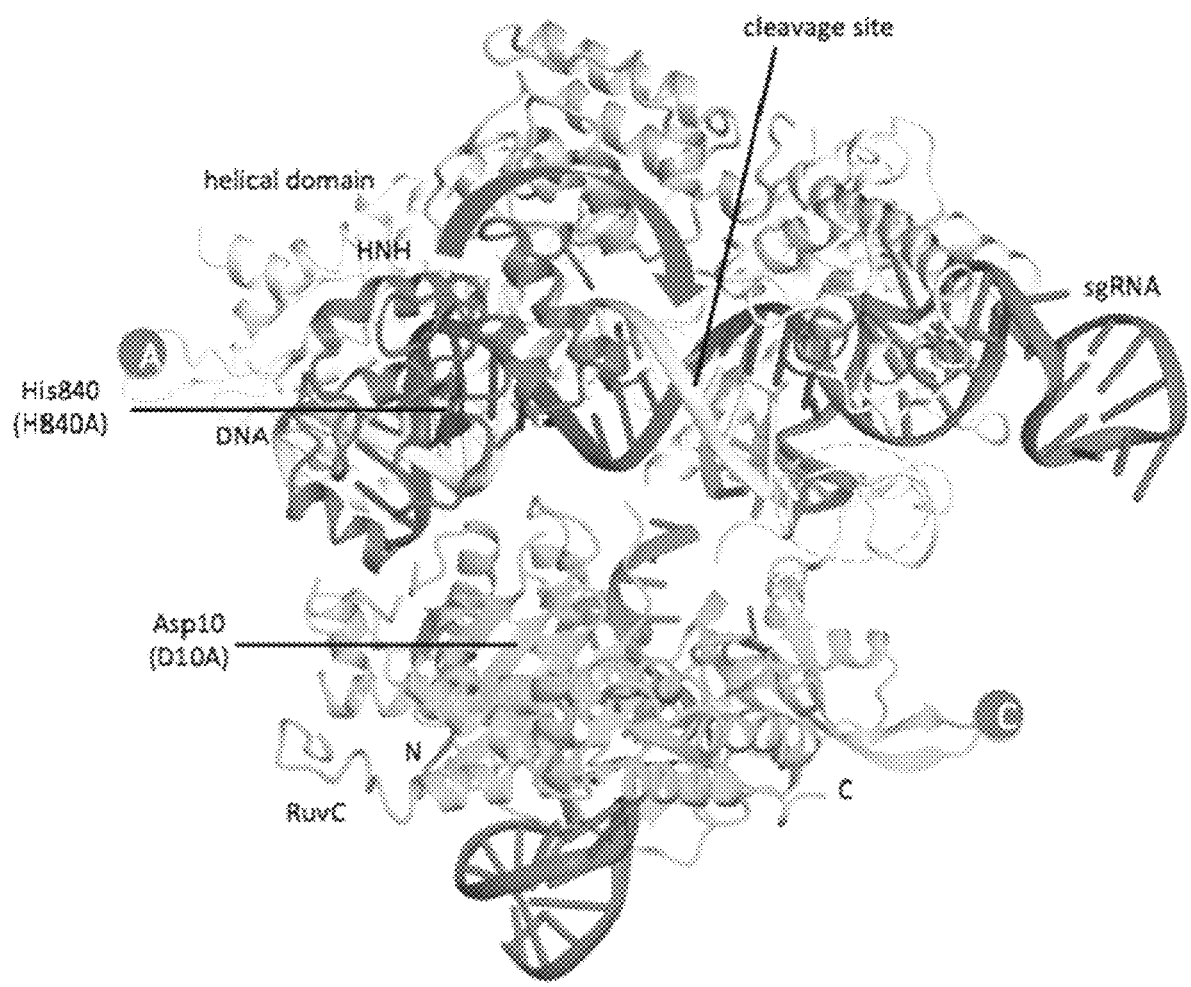
FIG. 6 shows the positions of transcriptional domain replacements and insertions in Cas9. The HNH domain is colored pink. The curved arrow indicates the movement of the HNH domain relative to the DNA (yellow) RNA (blue) duplex due to a conformational change. The A in a red circle indicates the first loop (AA G533) used for insertion of a transcriptional effector domain and its position relative to the target DNA. The third loop (K1153) for insertion of a transcriptional effector domain is indicated by a C on a red circle.

Replacing the HNH domain with a transcriptional effector domain:

Based on the crystal structure, the HNH domain is located close to the DNA/RNA hybrid. In addition, it was found that it is a flexible domain that can move as a consequence of conformational changes while Cas9 is binding target DNA. It is flanked by a disordered linker on the N-term and the a39-a40 linker on the C-term, which can undergo a conformational change to an extended a-helix, moving the HNH domain closer to its target DNA bases. The proximity to target DNA and the flexibility identified in the crystal make a replacement of this nuclease domain with a transcriptional effector domain promising. See FIG. 6 for illustration.

Applicants replace AA775-901 (of the HNH domain) with either vp64 or P65 flanked by a (GGGGS)3 (SEQ ID NO: 3) or a (GGGGS)6 (SEQ ID NO: 4) linker on both sides of the inserted transcriptional effector domain.

TABLE 10

| | Corresponding constructs |
|---|---|
| pSAMca050 | dCas9(HNH-->vp64, 3XGS) |
| pSAMca051 | dCas9(HNH-->vp64, 6XGS) |
| pSAMca052 | dCas9(HNH-->P65, 3XGS) |
| pSAMca053 | dCas9(HNH-->P65, 6XGS) |

Insertions of transcriptional domains into 3 loops of dCas9:

In addition to replacing an existing domain (e.g. HNH, Rec2) with a transcriptional effector domain, it may be possible to insert a transcriptional effector domain at different positions in the Cas9 protein. The crystal structure helps in identifying promising loops for such an insertion (favorable properties for a place for insertion include low secondary structure complexity (loop versus helix or sheet, unobstructed space for the additional domain, proximity to target DNA and no current interactions with either target DNA or sgRNA (as these may be disrupted by the addition of the transcriptional effector domain)).

Applicants identified three favorable positions: G533, F575 and K1153. The locations of G533 and K1153 in the Cas9 protein is indicated in the corresponding FIG. 6. Applicants insert either vp64 or P65 flanked by a (GGGGS)1 (SEQ ID NO: 8) or a (GGGGS)3 (SEQ ID NO: 3) linker on both sides of the inserted transcriptional effector domain at these three locations.

TABLE 11

| | Corresponding constructs |
|---|---|
| pSAMca054 | dCas9(G533-vp64, 1XGS) |
| pSAMca055 | dCas9(G533-vp64, 3XGS) |
| pSAMca056 | dCas9(G533-P65, 1XGS) |
| pSAMca057 | dCas9(G533-P65, 3XGS) |
| pSAMca058 | dCas9(F575-vp64, 1XGS) |
| pSAMca059 | dCas9(F575-vp64, 3XGS) |
| pSAMca060 | dCas9(F575-P65, 1XGS) |
| pSAMca061 | dCas9(F575-P65, 3XGS) |
| pSAMca062 | dCas9(K1 153-vp64, 1XGS) |
| pSAMca063 | dCas9(K1 153-vp64, 3XGS) |
| pSAMca064 | dCas9(K1 153-P65, 1XGS) |
| pSAMca065 | dCas9(K1 153-P65, 3XGS) | dCas activator sequence information is provided below:

```
Replacing the dCas9 Rec2 domain with transcriptional effector domain
pSAMca042 dCas(hel2-->vp64) - DNA
                                                              (SEQ ID NO: 86)
atgGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACA

GCGGCGAAACAGCCGAGGCCACCCGGCTGAAGAGAACCGCCAGAAGAAGATACAC

CAGACGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGAT

AAGAAGCACGAGCGGCACCCCATCTTCGGCAACATCGTGGACGAGGTGGCCTACCA

CGAGAAGTACCCCACCATCTACCACCTGAGAAAGAAACTGGTGGACAGCACCGACA

AGGCCGACCTGCGGCTGATCTATCTGGCCCTGGCCCACATGATCAAGTTCCGGGGCC

ACTTCCTGATCGAGGGCGACCTGAACGGACGGGCTGACGCATTGGACGATTTTGATC

TGGATATGCTGGGAAGTGACGCCCTCGATGATTTTGACCTTGACATGCTTGGTTCGG

ATGCCCTTGATGACTTTGACCTCGACATGCTCGGCAGTGACGCCCTTGATGATTTCG

ACCTGGACATGCTGATTAACAGAGTGAACACCGAGATCACCAAGGCCCCCCTGAGC

GCCTCTATGATCAAGAGATACGACGAGCACCACCAGGACCTGACCCTGCTGAAAGC

TCTCGTGCGGCAGCAGCTGCCTGAGAAGTACAAAGAGATTTTCTTCGACCAGAGCA

AGAACGGCTACGCCGGCTACATTGACGGCGGAGCCAGCCAGGAAGAGTTCTACAAG

TTCATCAAGCCCATCCTGGAAAAGATGGACGGCACCGAGGAACTGCTCGTGAAGCT

GAACAGAGAGGACCTGCTGCGGAAGCAGCGGACCTTCGACAACGGCAGCATCCCCC

ACCAGATCCACCTGGGAGAGCTGCACGCCATTCTGCGGCGGCAGGAAGATTTTTAC

CCATTCCTGAAGGACAACCGGGAAAAGATCGAGAAGATCCTGACCTTCCGCATCCC

CTACTACGTGGGCCCTCTGGCCAGGGGAAACAGCAGATTCGCCTGGATGACCAGAA

AGAGCGAGGAAACCATCACCCCCTGGAACTTCGAGGAAGTGGTGGACAAGGGCGCT

TCCGCCCAGAGCTTCATCGAGCGGATGACCAACTTCGATAAGAACCTGCCCAACGA

GAAGGTGCTGCCCAAGCACAGCCTGCTGTACGAGTACTTCACCGTGTATAACGAGCT

GACCAAAGTGAAATACGTGACCGAGGGAATGAGAAAGCCCGCCTTCCTGAGCGGCG

AGCAGAAAAAGGCCATCGTGGACCTGCTGTTCAAGACCAACCGGAAAGTGACCGTG

AAGCAGCTGAAAGAGGACTACTTCAAGAAAATCGAGTGCTTCGACTCCGTGGAAAT

CTCCGGCGTGGAAGATCGGTTCAACGCCTCCCTGGGCACATACCACGATCTGCTGAA

AATTATCAAGGACAAGGACTTCCTGGACAATGAGGAAAACGAGGACATTCTGGAAG

ATATCGTGCTGACCCTGACACTGTTTGAGGACAGAGAGATGATCGAGGAACGGCTG

AAAACCTATGCCCACCTGTTCGACGACAAAGTGATGAAGCAGCTGAAGCGGCGGAG

ATACACCGGCTGGGGCAGGCTGAGCCGGAAGCTGATCAACGGCATCCGGGACAAGC

AGTCCGGCAAGACAATCCTGGATTTCCTGAAGTCCGACGGCTTCGCCAACAGAAAC

TTCATGCAGCTGATCCACGACGACAGCCTGACCTTTAAAGAGGACATCCAGAAAGC

CCAGGTGTCCGGCCAGGGCGATAGCCTGCACGAGCACATTGCCAATCTGGCCGGCA

GCCCCGCCATTAAGAAGGGCATCCTGCAGACAGTGAAGGTGGTGGACGAGCTCGTG

AAAGTGATGGGCCGGCACAAGCCCGAGAACATCGTGATCGAAATGGCCAGAGAGA

ACCAGACCACCCAGAAGGGACAGAAGAACAGCCGCGAGAGAATGAAGCGGATCGA
```

```
AGAGGGCATCAAAGAGCTGGGCAGCCAGATCCTGAAAGAACACCCCGTGGAAAAC

ACCCAGCTGCAGAACGAGAAGCTGTACCTGTACTACCTGCAGAATGGGCGGATAT

GTACGTGGACCAGGAACTGGACATCAACCGGCTGTCCGACTACGATGTGGACgcTAT

CGTGCCTCAGAGCTTTCTGAAGGACGACTCCATCGACAACAAGGTGCTGACCAGAA

GCGACAAGAACCGGGGCAAGAGCGACAACGTGCCCTCCGAAGAGGTCGTGAAGAA

GATGAAGAACTACTGGCGGCAGCTGCTGAACGCCAAGCTGATTACCCAGAGAAAGT

TCGACAATCTGACCAAGGCCGAGAGAGGCGGCCTGAGCGAACTGGATAAGGCCGGC

TTCATCAAGAGACAGCTGGTGGAAACCCGGCAGATCACAAAGCACGTGGCACAGAT

CCTGGACTCCCGGATGAACACTAAGTACGACGAGAATGACAAGCTGATCCGGGAAG

TGAAAGTGATCACCCTGAAGTCCAAGCTGGTGTCCGATTTCCGGAAGGATTTCCAGT

TTTACAAAGTGCGCGAGATCAACAACTACCACCACGCCCACGACGCCTACCTGAAC

GCCGTCGTGGGAACCGCCCTGATCAAAAAGTACCCTAAGCTGGAAAGCGAGTTCGT

GTACGGCGACTACAAGGTGTACGACGTGCGGAAGATGATCGCCAAGAGCGAGCAGG

AAATCGGCAAGGCTACCGCCAAGTACTTCTTCTACAGCAACATCATGAACTTTTTCA

AGACCGAGATTACCCTGGCCAACGGCGAGATCCGGAAGCGGCCTCTGATCGAGACA

AACGGCGAAACCGGGGAGATCGTGTGGGATAAGGGCCGGGATTTTGCCACCGTGCG

GAAAGTGCTGAGCATGCCCCAAGTGAATATCGTGAAAAAGACCGAGGTGCAGACAG

GCGGCTTCAGCAAAGAGTCTATCCTGCCCAAGAGGAACAGCGATAAGCTGATCGCC

AGAAAGAAGGACTGGGACCCTAAGAAGTACGGCGGCTTCGACAGCCCCACCGTGGC

CTATTCTGTGCTGGTGGTGGCCAAAGTGGAAAAGGGCAAGTCCAAGAAACTGAAGA

GTGTGAAAGAGCTGCTGGGGATCACCATCATGGAAAGAAGCAGCTTCGAGAAGAAT

CCCATCGACTTTCTGGAAGCCAAGGGCTACAAAGAAGTGAAAAAGGACCTGATCAT

CAAGCTGCCTAAGTACTCCCTGTTCGAGCTGGAAAACGGCCGGAAGAGAATGCTGG

CCTCTGCCGGCGAACTGCAGAAGGGAAACGAACTGGCCCTGCCCTCCAAATATGTG

AACTTCCTGTACCTGGCCAGCCACTATGAGAAGCTGAAGGGCTCCCCCGAGGATAA

TGAGCAGAAACAGCTGTTTGTGGAACAGCACAAGCACTACCTGGACGAGATCATCG

AGCAGATCAGCGAGTTCTCCAAGAGAGTGATCCTGGCCGACGCTAATCTGGACAAA

GTGCTGTCCGCCTACAACAAGCACCGGGATAAGCCCATCAGAGAGCAGGCCGAGAA

TATCATCCACCTGTTTACCCTGACCAATCTGGGAGCCCCTGCCGCCTTCAAGTACTTT

GACACCACCATCGACCGGAAGAGGTACACCAGCACCAAAGAGGTGCTGGACGCCAC

CCTGATCCACCAGAGCATCACCGGCCTGTACGAGACACGGATCGACCTGTCTCAGCT

GGGAGGCGACagcgctGGAGGAGGTGGAAGCGGAGGAGGAGGAAGCGGAGGAGGAG

GTAGCggacctaagaaaaagaggaaggtggcggccgct pSAMca042 dCas(hel2-->vp64) - amino acid
                                                      (SEQ ID NO: 87)
MDKKYSIGLAIGTNSVGWAVITDEYKVPSKKFKVLGNTDRHSIKKNLIGALLF

DSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEG

DLNGRADALDDFDLDMLGSDALDDFDLDMLGSDALDDFDLDMLGSDALDDFDLDMLI

NRVNTEITKAPLSASMIKRYDEHHQDLTLLKALVRQQLPEKYKEIFFDQSKNGYAGYID

GGASQEEFYKFIKPILEKMDGTEELLVKLNREDLLRKQRTFDNGSIPHQIHLGELHAILRR

QEDFYPFLKDNREKIEKILTFRIPYYVGPLARGNSRFAWMTRKSEETITPWNFEEVVDKG
```

-continued

ASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVSGQGDSLHEH

IANLAGSPAIKKGILQTVKVVDELVKVMGRHKPENIVIEMARENQTTQKGQKNSRERM

KRIEEGIKELGSQILKEHPVENTQLQNEKLYLYYLQNGRDMYVDQELDINRLSDYDVDA

IVPQSFLKDDSIDNKVLTRSDKNRGKSDNVPSEEVVKKMKNYWRQLLNAKLITQRKFD

NLTKAERGGLSELDKAGFIKRQLVETRQITKHVAQILDSRMNTKYDENDKLIREVKVITL

KSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKG

RDFATVRKVLSMPQVNIVKKTEVQTGGFSKESILPKRNSDKLIARKKDWDPKKYGGFDS

PTVAYSVLVVAKVEKGKSKKLKSVKELLGITIMERSSFEKNPIDFLEAKGYKEVKKDLII

KLPKYSLFELENGRKRMLASAGELQKGNELALPSKYVNFLYLASHYEKLKGSPEDNEQ

KQLFVEQHKHYLDEIIEQISEFSKRVILADANLDKVLSAYNKHRDKPIREQAENIIHLFTL

TNLGAPAAFKYFDTTIDRKRYTSTKEVLDATLIHQSITGLYETRIDLSQLGGDSAGGGGS

GGGGSGGGGSGPKKKRKVAAA pSAMca043 dCas(hel2-->vp64, GSlinker) - DNA (SEQ ID NO: 88)

atgGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACA

GCGGCGAAACAGCCGAGGCCACCCGGCTGAAGAGAACCGCCAGAAGAAGATACAC

CAGACGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGAT

AAGAAGCACGAGCGGCACCCCATCTTCGGCAACATCGTGGACGAGGTGGCCTACCA

CGAGAAGTACCCCACCATCTACCACCTGAGAAAGAAACTGGTGGACAGCACCGACA

AGGCCGACCTGCGGCTGATCTATCTGGCCCTGGCCCACATGATCAAGTTCCGGGGCC

ACTTCCTGATCGAGGGCGACCTGAACGGCGGGGAGGCTCCGGTGGTGGGGGCAGC

GGAGGGGGGGCAGCGGACGGGCTGACGCATTGGACGATTTTGATCTGGATATGCT

GGGAAGTGACGCCCTCGATGATTTTGACCTTGACATGCTTGGTTCGGATGCCCTTGA

TGACTTTGACCTCGACATGCTCGGCAGTGACGCCCTTGATGATTTCGACCTGGACAT

GCTGATTAACGGCGGGGAGGCTCCGGTGGTGGGGGCAGCGGAGGGGGGGCAGC

AGAGTGAACACCGAGATCACCAAGGCCCCCCTGAGCGCCTCTATGATCAAGAGATA

CGACGAGCACCACCAGGACCTGACCCTGCTGAAAGCTCTCGTGCGGCAGCAGCTGC

CTGAGAAGTACAAAGAGATTTTCTTCGACCAGAGCAAGAACGGCTACGCCGGCTAC

ATTGACGGCGGAGCCAGCCAGGAAGAGTTCTACAAGTTCATCAAGCCCATCCTGGA

AAAGATGGACGGCACCGAGGAACTGCTCGTGAAGCTGAACAGAGAGGACCTGCTGC

GGAAGCAGCGGACCTTCGACAACGGCAGCATCCCCCACCAGATCCACCTGGGAGAG

CTGCACGCCATTCTGCGGCGGCAGGAAGATTTTTACCCATTCCTGAAGGACAACCGG

GAAAAGATCGAGAAGATCCTGACCTTCCGCATCCCCTACTACGTGGGCCCTCTGGCC

AGGGGAAACAGCAGATTCGCCTGGATGACCAGAAAGAGCGAGGAAACCATCACCC

-continued

```
CCTGGAACTTCGAGGAAGTGGTGGACAAGGGCGCTTCCGCCCAGAGCTTCATCGAG
CGGATGACCAACTTCGATAAGAACCTGCCCAACGAGAAGGTGCTGCCCAAGCACAG
CCTGCTGTACGAGTACTTCACCGTGTATAACGAGCTGACCAAAGTGAAATACGTGAC
CGAGGGAATGAGAAAGCCCGCCTTCCTGAGCGGCGAGCAGAAAAAGGCCATCGTG
GACCTGCTGTTCAAGACCAACCGGAAAGTGACCGTGAAGCAGCTGAAAGAGGACTA
CTTCAAGAAAATCGAGTGCTTCGACTCCGTGGAAATCTCCGGCGTGGAAGATCGGTT
CAACGCCTCCCTGGGCACATACCACGATCTGCTGAAAATTATCAAGGACAAGGACT
TCCTGGACAATGAGGAAAACGAGGACATTCTGGAAGATATCGTGCTGACCCTGACA
CTGTTTGAGGACAGAGAGATGATCGAGGAACGGCTGAAAACCTATGCCCACCTGTT
CGACGACAAAGTGATGAAGCAGCTGAAGCGGCGGAGATACACCGGCTGGGGCAGG
CTGAGCCGGAAGCTGATCAACGGCATCCGGGACAAGCAGTCCGGCAAGACAATCCT
GGATTTCCTGAAGTCCGACGGCTTCGCCAACAGAAACTTCATGCAGCTGATCCACGA
CGACAGCCTGACCTTTAAAGAGGACATCCAGAAAGCCCAGGTGTCCGGCCAGGGCG
ATAGCCTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGGCACAA
GCCCGAGAACATCGTGATCGAAATGGCCAGAGAGAACCAGACCACCCAGAAGGGA
CAGAAGAACAGCCGCGAGAGAATGAAGCGGATCGAAGAGGGCATCAAAGAGCTGG
GCAGCCAGATCCTGAAAGAACACCCCGTGGAAAACACCCAGCTGCAGAACGAGAA
GCTGTACCTGTACTACCTGCAGAATGGGCGGGATATGTACGTGGACCAGGAACTGG
ACATCAACCGGCTGTCCGACTACGATGTGGACgcTATCGTGCCTCAGAGCTTTCTGAA
GGACGACTCCATCGACAACAAGGTGCTGACCAGAAGCGACAAGAACCGGGGCAAG
AGCGACAACGTGCCCTCCGAAGAGGTCGTGAAGAAGATGAAGAACTACTGGCGGCA
GCTGCTGAACGCCAAGCTGATTACCCAGAGAAAGTTCGACAATCTGACCAAGGCCG
AGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACAC
TAAGTACGACGAGAATGACAAGCTGATCCGGGAAGTGAAAGTGATCACCCTGAAGT
CCAAGCTGGTGTCCGATTTCCGGAAGGATTTCCAGTTTTACAAAGTGCGCGAGATCA
ACAACTACCACCACGCCCACGACGCCTACCTGAACGCCGTCGTGGGAACCGCCCTG
ATCAAAAAGTACCCTAAGCTGGAAAGCGAGTTCGTGTACGGCGACTACAAGGTGTA
CGACGTGCGGAAGATGATCGCCAAGAGCGAGCAGGAAATCGGCAAGGCTACCGCC
AAGTACTTCTTCTACAGCAACATCATGAACTTTTTCAAGACCGAGATTACCCTGGCC
AACGGCGAGATCCGGAAGCGGCCTCTGATCGAGACAAACGGCGAAACCGGGGAGA
TCGTGTGGGATAAGGGCCGGGATTTTGCCACCGTGCGGAAAGTGCTGAGCATGCCC
CAAGTGAATATCGTGAAAAAGACCGAGGTGCAGACAGGCGGCTTCAGCAAAGAGTC
TATCCTGCCCAAGAGGAACAGCGATAAGCTGATCGCCAGAAAGAAGGACTGGGACC
CTAAGAAGTACGGCGGCTTCGACAGCCCCACCGTGGCCTATTCTGTGCTGGTGGTGG
CCAAAGTGGAAAAGGGCAAGTCCAAGAAACTGAAGAGTGTGAAAGAGCTGCTGGG
GATCACCATCATGGAAAGAAGCAGCTTCGAGAAGAATCCCATCGACTTTCTGGAAG
CCAAGGGCTACAAAGAAGTGAAAAAGGACCTGATCATCAAGCTGCCTAAGTACTCC
CTGTTCGAGCTGGAAAACGGCCGGAAGAGAATGCTGGCCTCTGCCGGCGAACTGCA
GAAGGGAAACGAACTGGCCCTGCCCTCCAAATATGTGAACTTCCTGTACCTGGCCA
```

```
GCCACTATGAGAAGCTGAAGGGCTCCCCCGAGGATAATGAGCAGAAACAGCTGTTT

GTGGAACAGCACAAGCACTACCTGGACGAGATCATCGAGCAGATCAGCGAGTTCTC

CAAGAGAGTGATCCTGGCCGACGCTAATCTGGACAAAGTGCTGTCCGCCTACAACA

AGCACCGGGATAAGCCCATCAGAGAGCAGGCCGAGAATATCATCCACCTGTTTACC

CTGACCAATCTGGGAGCCCCTGCCGCCTTCAAGTACTTTGACACCACCATCGACCGG

AAGAGGTACACCAGCACCAAAGAGGTGCTGGACGCCACCCTGATCCACCAGAGCAT

CACCGGCCTGTACGAGACACGGATCGACCTGTCTCAGCTGGGAGGCGACagcgctGGA

GGAGGTGGAAGCGGAGGAGGAGGAAGCGGAGGAGGAGGTAGCggacctaagaaaaagaggaa ggtggcggccgct
``` pSAMca043 dCas(he12-->vp64, GSlinker) - amino acid (SEQ ID NO: 89)

```
MDKKYSIGLAIGTNSVGWAVITDEYKVPSKKFKVLGNTDRHSIKKNLIGALLF

DSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEG

DLNGGGGSGGGGSGGGGSGRADALDDFDLDMLGSDALDDFDLDMLGSDALDDFDLD

MLGSDALDDFDLDMLINGGGGSGGGGSGGGGSRVNTEITKAPLSASMIKRYDEHHQDL

TLLKALVRQQLPEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIEKILTFRIPYYVGP

LARGNSRFAWMTRKSEETITPWNFEEVVDKGASAQSFIERMTNFDKNLPNEKVLPKHSL

LYEYFTVYNELTKVKYVTEGMRKPAFLSGEQKKAIVDLLFKTNRKVTVKQLKEDYFKK

IECFDSVEISGVEDRFNASLGTYHDLLKIIKDKDFLDNEENEDILEDIVLTLTLFEDREMIE

ERLKTYAHLFDDKVMKQLKRRRYTGWGRLSRKLINGIRDKQSGKTILDFLKSDGFANR

NFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNE

KLYLYYLQNGRDMYVDQELDINRLSDYDVDAIVPQSFLKDDSIDNKVLTRSDKNRGKS

DNVPSEEVVKKMKNYWRQLLNAKLITQRKFDNLTKAERGGLSELDKAGFIKRQLVETR

QITKHVAQILDSRMNTKYDENDKLIREVKVITLKSKLVSDFRKDFQFYKVREINNYHHA

HDAYLNAVVGTALIKKYPKLESEFVYGDYKVYDVRKMIAKSEQEIGKATAKYFFYSNI

MNFFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEV

LDATLIHQSITGLYETRIDLSQLGGDSAGGGGSGGGGSGGGGSGPKKKRKVAAA
``` pSAMca044 dCas(he12-->P65) - DNA (SEQ ID NO: 90)

```
atgGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACA

GCGGCGAAACAGCCGAGGCCACCCGGCTGAAGAGAACCGCCAGAAGAAGATACAC

CAGACGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGAT
```

-continued

```
AAGAAGCACGAGCGGCACCCCATCTTCGGCAACATCGTGGACGAGGTGGCCTACCA
CGAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGCC
ACTTCCTGATCGAGGGCGACCTGAACCCTTCAGGGCAGATCAGCAACCAGGCCCTG
GCTCTGGCCCCTAGCTCCGCTCCAGTGCTGGCCCAGACTATGGTGCCCTCTAGTGCT
ATGGTGCCTCTGGCCCAGCCACCTGCTCCAGCCCCTGTGCTGACCCCAGGACCACCC
CAGTCACTGAGCGCTCCAGTGCCCAAGTCTACACAGGCCGGCGAGGGGACTCTGAG
TGAAGCTCTGCTGCACCTGCAGTTCGACGCTGATGAGGACCTGGGAGCTCTGCTGGG
GAACAGCACCGATCCCGGAGTGTTCACAGATCTGGCCTCCGTGGACAACTCTGAGTT
TCAGCAGCTGCTGAATCAGGGCGTGTCCATGTCTCATAGTACAGCCGAACCAATGCT
GATGGAGTACCCCGAAGCCATTACCCGGCTGGTGACCGGCAGCCAGCGGCCCCCCG
ACCCCGCTCCAACTCCCCTGGGAACCAGCGGCCTGCCTAATGGGCTGTCCGGAGATG
AAGACTTCTCAAGCATCGCTGATATGGACTTTAGTGCCCTGCTGTCACAGATTTCCTC
TAGTGGGCAGAGAGTGAACACCGAGATCACCAAGGCCCCCCTGAGCGCCTCTATGA
TCAAGAGATACGACGAGCACCACCAGGACCTGACCCTGCTGAAAGCTCTCGTGCGG
CAGCAGCTGCCTGAGAAGTACAAAGAGATTTTCTTCGACCAGAGCAAGAACGGCTA
CGCCGGCTACATTGACGGCGGAGCCAGCCAGGAAGAGTTCTACAAGTTCATCAAGC
CCATCCTGGAAAAGATGGACGGCACCGAGGAACTGCTCGTGAAGCTGAACAGAGAG
GACCTGCTGCGGAAGCAGCGGACCTTCGACAACGGCAGCATCCCCCACCAGATCCA
CCTGGGAGAGCTGCACGCCATTCTGCGGCGGCAGGAAGATTTTTACCCATTCCTGAA
GGACAACCGGGAAAAGATCGAGAAGATCCTGACCTTCCGCATCCCCTACTACGTGG
GCCCTCTGGCCAGGGGAAACAGCAGATTCGCCTGGATGACCAGAAAGAGCGAGGA
AACCATCACCCCCTGGAACTTCGAGGAAGTGGTGGACAAGGGCGCTTCCGCCCAGA
GCTTCATCGAGCGGATGACCAACTTCGATAAGAACCTGCCCAACGAGAAGGTGCTG
CCCAAGCACAGCCTGCTGTACGAGTACTTCACCGTGTATAACGAGCTGACCAAAGT
GAAATACGTGACCGAGGGAATGAGAAAGCCCGCCTTCCTGAGCGGCGAGCAGAAA
AAGGCCATCGTGGACCTGCTGTTCAAGACCAACCGGAAAGTGACCGTGAAGCAGCT
GAAAGAGGACTACTTCAAGAAAATCGAGTGCTTCGACTCCGTGGAAATCTCCGGCG
TGGAAGATCGGTTCAACGCCTCCCTGGGCACATACCACGATCTGCTGAAAATTATCA
AGGACAAGGACTTCCTGGACAATGAGGAAAACGAGGACATTCTGGAAGATATCGTG
CTGACCCTGACACTGTTTGAGGACAGAGAGATGATCGAGGAACGGCTGAAAACCTA
TGCCCACCTGTTCGACGACAAAGTGATGAAGCAGCTGAAGCGGCGGAGATACACCG
GCTGGGGCAGGCTGAGCCGGAAGCTGATCAACGGCATCCGGGACAAGCAGTCCGGC
AAGACAATCCTGGATTTCCTGAAGTCCGACGGCTTCGCCAACAGAAACTTCATGCAG
CTGATCCACGACGACAGCCTGACCTTTAAAGAGGACATCCAGAAAGCCCAGGTGTC
CGGCCAGGGCGATAGCCTGCACGAGCACATTGCCAATCTGGCCGGCAGCCCCGCCA
TTAAGAAGGGCATCCTGCAGACAGTGAAGGTGGTGGACGAGCTCGTGAAAGTGATG
GGCCGGCACAAGCCCGAGAACATCGTGATCGAAATGGCCAGAGAGAACCAGACCA
CCCAGAAGGGACAGAAGAACAGCCGCGAGAGAATGAAGCGGATCGAAGAGGGCAT
CAAAGAGCTGGGCAGCCAGATCCTGAAAGAACACCCCGTGGAAAACACCCAGCTGC
AGAACGAGAAGCTGTACCTGTACTACCTGCAGAATGGGCGGGATATGTACGTGGAC
```

-continued

```
CAGGAACTGGACATCAACCGGCTGTCCGACTACGATGTGGACgcTATCGTGCCTCAG
AGCTTTCTGAAGGACGACTCCATCGACAACAAGGTGCTGACCAGAAGCGACAAGAA
CCGGGGCAAGAGCGACAACGTGCCCTCCGAAGAGGTCGTGAAGAAGATGAAGAAC
TACTGGCGGCAGCTGCTGAACGCCAAGCTGATTACCCAGAGAAAGTTCGACAATCT
GACCAAGGCCGAGAGAGGCGGCCTGAGCGAACTGGATAAGGCCGGCTTCATCAAG
AGACAGCTGGTGGAAACCCGGCAGATCACAAAGCACGTGGCACAGATCCTGGACTC
CCGGATGAACACTAAGTACGACGAGAATGACAAGCTGATCCGGGAAGTGAAAGTGA
TCACCCTGAAGTCCAAGCTGGTGTCCGATTTCCGGAAGGATTTCCAGTTTTACAAAG
TGCGCGAGATCAACAACTACCACCACGCCCACGACGCCTACCTGAACGCCGTCGTG
GGAACCGCCCTGATCAAAAAGTACCCTAAGCTGGAAAGCGAGTTCGTGTACGGCGA
CTACAAGGTGTACGACGTGCGGAAGATGATCGCCAAGAGCGAGCAGGAAATCGGCA
AGGCTACCGCCAAGTACTTCTTCTACAGCAACATCATGAACTTTTTCAAGACCGAGA
TTACCCTGGCCAACGGCGAGATCCGGAAGCGGCCTCTGATCGAGACAAACGGCGAA
ACCGGGGAGATCGTGTGGGATAAGGGCCGGGATTTTGCCACCGTGCGGAAAGTGCT
GAGCATGCCCCAAGTGAATATCGTGAAAAAGACCGAGGTGCAGACAGGCGGCTTCA
GCAAAGAGTCTATCCTGCCCAAGAGGAACAGCGATAAGCTGATCGCCAGAAAGAAG
GACTGGGACCCTAAGAAGTACGGCGGCTTCGACAGCCCCACCGTGGCCTATTCTGTG
CTGGTGGTGGCCAAAGTGGAAAAGGGCAAGTCCAAGAAACTGAAGAGTGTGAAAG
AGCTGCTGGGGATCACCATCATGGAAAGAAGCAGCTTCGAGAAGAATCCCATCGAC
TTTCTGGAAGCCAAGGGCTACAAAGAAGTGAAAAAGGACCTGATCATCAAGCTGCC
TAAGTACTCCCTGTTCGAGCTGGAAAACGGCCGGAAGAGAATGCTGGCCTCTGCCG
GCGAACTGCAGAAGGGAAACGAACTGGCCCTGCCCTCCAAATATGTGAACTTCCTG
TACCTGGCCAGCCACTATGAGAAGCTGAAGGGCTCCCCCGAGGATAATGAGCAGAA
ACAGCTGTTTGTGGAACAGCACAAGCACTACCTGGACGAGATCATCGAGCAGATCA
GCGAGTTCTCCAAGAGAGTGATCCTGGCCGACGCTAATCTGGACAAAGTGCTGTCCG
CCTACAACAAGCACCGGGATAAGCCCATCAGAGAGCAGGCCGAGAATATCATCCAC
CTGTTTACCCTGACCAATCTGGGAGCCCCTGCCGCCTTCAAGTACTTTGACACCACC
ATCGACCGGAAGAGGTACACCAGCACCAAAGAGGTGCTGGACGCCACCCTGATCCA
CCAGAGCATCACCGGCCTGTACGAGACACGGATCGACCTGTCTCAGCTGGGAGGCG
ACagcgctGGAGGAGGTGGAAGCGGAGGAGGAGGAAGCGGAGGAGGAGGTAGCggacct
aagaaaaagaggaaggtggcggccgct
``` pSAMca044 dCas(hel2-->P65) - amino acid
(SEQ ID NO: 91)

```
MDKKYSIGLAIGTNSVGWAVITDEYKVPSKKFKVLGNTDRHSIKKNLIGALLF
DSGETAEATRLKRTARRRYTRRKNRICYLQEIFSNEMAKVDDSFFHRLEESFLVEEDKK
HERHPIFGNIVDEVAYHEKYPTIYHLRKKLVDSTDKADLRLIYLALAHMIKFRGHFLIEG
DLNPSGQISNQALALAPSSAPVLAQTMVPSSAMVPLAQPPAPAPVLTPGPPQSLSAPVPK
STQAGEGTLSEALLHLQFDADEDLGALLGNSTDPGVFTDLASVDNSEFQQLLNQGVSMS
HSTAEPMLMEYPEAITRLVTGSQRPPDPAPTPLGTSGLPNGLSGDEDFSSIADMDFSALLS
QISSSGQRVNTEITKAPLSASMIKRYDEHHQDLTLLKALVRQQLPEKYKEIFFDQSKNGY
AGYIDGGASQEEFYKFIKPILEKMDGTEELLVKLNREDLLRKQRTFDNGSIPHQIHLGEL
```

-continued

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGDSA

GGGGSGGGGSGGGGSGPKKKRKVAAA pSAMca045 dCas(hel2-->P65 GSlinker) - DNA (SEQ ID NO: 92)

atgGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACA

GCGGCGAAACAGCCGAGGCCACCCGGCTGAAGAGAACCGCCAGAAGAAGATACAC

CAGACGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGAT

AAGAAGCACGAGCGGCACCCCATCTTCGGCAACATCGTGGACGAGGTGGCCTACCA

CGAGAAGTACCCCACCATCTACCACCTGAGAAAGAAACTGGTGGACAGCACCGACA

AGGCCGACCTGCGGCTGATCTATCTGGCCCTGGCCCACATGATCAAGTTCCGGGGCC

ACTTCCTGATCGAGGGCGACCTGAACGGCGGGGGAGGCTCCGGTGGTGGGGGCAGC

GGAGGGGGGGCAGCCCTTCAGGGCAGATCAGCAACCAGGCCCTGGCTCTGGCCCC

TAGCTCCGCTCCAGTGCTGGCCCAGACTATGGTGCCCTCTAGTGCTATGGTGCCTCT

GGCCCAGCCACCTGCTCCAGCCCCTGTGCTGACCCCAGGACCACCCCAGTCACTGAG

CGCTCCAGTGCCCAAGTCTACACAGGCCGGCGAGGGGACTCTGAGTGAAGCTCTGC

TGCACCTGCAGTTCGACGCTGATGAGGACCTGGGAGCTCTGCTGGGGAACAGCACC

GATCCCGGAGTGTTCACAGATCTGGCCTCCGTGGACAACTCTGAGTTTCAGCAGCTG

CTGAATCAGGGCGTGTCCATGTCTCATAGTACAGCCGAACCAATGCTGATGGAGTAC

CCCGAAGCCATTACCCGGCTGGTGACCGGCAGCCAGCGGCCCCCGACCCCGCTCC

AACTCCCCTGGGAACCAGCGGCCTGCCTAATGGGCTGTCCGGAGATGAAGACTTCTC

AAGCATCGCTGATATGGACTTTAGTGCCCTGCTGTCACAGATTTCCTCTAGTGGGCA

GGGCGGGGAGGCTCCGGTGGTGGGGGCAGCGGAGGGGGGGCAGCAGAGTGAAC

ACCGAGATCACCAAGGCCCCCCTGAGCGCCCTCTATGATCAAGAGATACGACGAGCA

CCACCAGGACCTGACCCTGCTGAAAGCTCTCGTGCGGCAGCAGCTGCCTGAGAAGT

```
ACAAAGAGATTTTCTTCGACCAGAGCAAGAACGGCTACGCCGGCTACATTGACGGC
GGAGCCAGCCAGGAAGAGTTCTACAAGTTCATCAAGCCCATCCTGGAAAAGATGGA
CGGCACCGAGGAACTGCTCGTGAAGCTGAACAGAGAGGACCTGCTGCGGAAGCAGC
GGACCTTCGACAACGGCAGCATCCCCCACCAGATCCACCTGGGAGAGCTGCACGCC
ATTCTGCGGCGGCAGGAAGATTTTTACCCATTCCTGAAGGACAACCGGGAAAAGAT
CGAGAAGATCCTGACCTTCCGCATCCCCTACTACGTGGGCCCTCTGGCCAGGGGAAA
CAGCAGATTCGCCTGGATGACCAGAAAGAGCGAGGAAACCATCACCCCCTGGAACT
TCGAGGAAGTGGTGGACAAGGGCGCTTCCGCCCAGAGCTTCATCGAGCGGATGACC
AACTTCGATAAGAACCTGCCCAACGAGAAGGTGCTGCCCAAGCACAGCCTGCTGTA
CGAGTACTTCACCGTGTATAACGAGCTGACCAAAGTGAAATACGTGACCGAGGGAA
TGAGAAAGCCCGCCTTCCTGAGCGGCGAGCAGAAAAAGGCCATCGTGGACCTGCTG
TTCAAGACCAACCGGAAAGTGACCGTGAAGCAGCTGAAAGAGGACTACTTCAAGAA
AATCGAGTGCTTCGACTCCGTGGAAATCTCCGGCGTGGAAGATCGGTTCAACGCCTC
CCTGGGCACATACCACGATCTGCTGAAAATTATCAAGGACAAGGACTTCCTGGACA
ATGAGGAAAACGAGGACATTCTGGAAGATATCGTGCTGACCCTGACACTGTTTGAG
GACAGAGAGATGATCGAGGAACGGCTGAAAACCTATGCCCACCTGTTCGACGACAA
AGTGATGAAGCAGCTGAAGCGGCGGAGATACACCGGCTGGGGCAGGCTGAGCCGG
AAGCTGATCAACGGCATCCGGGACAAGCAGTCCGGCAAGACAATCCTGGATTTCCT
GAAGTCCGACGGCTTCGCCAACAGAAACTTCATGCAGCTGATCCACGACGACAGCC
TGACCTTTAAAGAGGACATCCAGAAAGCCCAGGTGTCCGGCCAGGGCGATAGCCTG
CACGAGCACATTGCCAATCTGGCCGGCAGCCCCGCCATTAAGAAGGGCATCCTGCA
GACAGTGAAGGTGGTGGACGAGCTCGTGAAAGTGATGGGCCGGCACAAGCCCGAG
AACATCGTGATCGAAATGGCCAGAGAGAACCAGACCACCCAGAAGGGACAGAAGA
ACAGCCGCGAGAGAATGAAGCGGATCGAAGAGGGCATCAAAGAGCTGGGCAGCCA
GATCCTGAAAGAACACCCCGTGGAAAACACCCAGCTGCAGAACGAGAAGCTGTACC
TGTACTACCTGCAGAATGGGCGGGATATGTACGTGGACCAGGAACTGGACATCAAC
CGGCTGTCCGACTACGATGTGGACgcTATCGTGCCTCAGAGCTTTCTGAAGGACGACT
CCATCGACAACAAGGTGCTGACCAGAAGCGACAAGAACCGGGGCAAGAGCGACAA
CGTGCCCTCCGAAGAGGTCGTGAAGAAGATGAAGAACTACTGGCGGCAGCTGCTGA
ACGCCAAGCTGATTACCCAGAGAAAGTTCGACAATCTGACCAAGGCCGAGAGAGGC
GGCCTGAGCGAACTGGATAAGGCCGGCTTCATCAAGAGACAGCTGGTGGAAACCCG
GCAGATCACAAAGCACGTGGCACAGATCCTGGACTCCCGGATGAACACTAAGTACG
ACGAGAATGACAAGCTGATCCGGGAAGTGAAAGTGATCACCCTGAAGTCCAAGCTG
GTGTCCGATTTCCGGAAGGATTTCCAGTTTTACAAAGTGCGCGAGATCAACAACTAC
CACCACGCCCACGACGCCTACCTGAACGCCGTCGTGGGAACCGCCCTGATCAAAAA
GTACCCTAAGCTGGAAAGCGAGTTCGTGTACGGCGACTACAAGGTGTACGACGTGC
GGAAGATGATCGCCAAGAGCGAGCAGGAAATCGGCAAGGCTACCGCCAAGTACTTC
TTCTACAGCAACATCATGAACTTTTTCAAGACCGAGATTACCCTGGCCAACGGCGAG
ATCCGGAAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAGTGAATA
```

```
TCGTGAAAAAGACCGAGGTGCAGACAGGCGGCTTCAGCAAAGAGTCTATCCTGCCC

AAGAGGAACAGCGATAAGCTGATCGCCAGAAAGAAGGACTGGGACCCTAAGAAGT

ACGGCGGCTTCGACAGCCCCACCGTGGCCTATTCTGTGCTGGTGGTGGCCAAAGTGG

AAAAGGGCAAGTCCAAGAAACTGAAGAGTGTGAAAGAGCTGCTGGGGATCACCATC

ATGGAAAGAAGCAGCTTCGAGAAGAATCCCATCGACTTTCTGGAAGCCAAGGGCTA

CAAAGAAGTGAAAAAGGACCTGATCATCAAGCTGCCTAAGTACTCCCTGTTCGAGC

TGGAAAACGGCCGGAAGAGAATGCTGGCCTCTGCCGGCGAACTGCAGAAGGGAAA

CGAACTGGCCCTGCCCTCCAAATATGTGAACTTCCTGTACCTGGCCAGCCACTATGA

GAAGCTGAAGGGCTCCCCCGAGGATAATGAGCAGAAACAGCTGTTTGTGGAACAGC

ACAAGCACTACCTGGACGAGATCATCGAGCAGATCAGCGAGTTCTCCAAGAGAGTG

ATCCTGGCCGACGCTAATCTGGACAAAGTGCTGTCCGCCTACAACAAGCACCGGGA

TAAGCCCATCAGAGAGCAGGCCGAGAATATCATCCACCTGTTTACCCTGACCAATCT

GGGAGCCCCTGCCGCCTTCAAGTACTTTGACACCACCATCGACCGGAAGAGGTACA

CCAGCACCAAAGAGGTGCTGGACGCCACCCTGATCCACCAGAGCATCACCGGCCTG

TACGAGACACGGATCGACCTGTCTCAGCTGGGAGGCGACagcgctGGAGGAGGTGGAA

GCGGAGGAGGAGGAAGCGGAGGAGGAGGTAGCggacctaagaaaaagaggaaggtggcggccgct pSAMca045 dCas(hel2-->P65 GSlinker) - amino acid
                                                        (SEQ ID NO: 93)
MDKKYSIGLAIGTNSVGWAVITDEYKVPSKKFKVLGNTDRHSIKKNLIGALLF

DSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEG

DLNGGGGSGGGGSGGGGSPSGQISNQALALAPSSAPVLAQTMVPSSAMVPLAQPPAPAP

VLTPGPPQSLSAPVPKSTQAGEGTLSEALLHLQFDADEDLGALLGNSTDPGVFTDLASV

DNSEFQQLLNQGVSMSHSTAEPMLMEYPEAITRLVTGSQRPPDPAPTPLGTSGLPNGLSG

DEDFSSIADMDFSALLSQISSSGQGGGGSGGGGSGGGGSRVNTEITKAPLSASMIKRYDE

HHQDLTLLKALVRQQLPEKYKEIFFDQSKNGYAGYIDGGASQEEFYKFIKPILEKMDGTE

ELLVKLNREDLLRKQRTFDNGSIPHQIHLGELHAILRRQEDFYPFLKDNREKIEKILTFRIP

YYVGPLARGNSRFAWMTRKSEETITPWNFEEVVDKGASAQSFIERMTNFDKNLPNEKV

LPKHSLLYEYFTVYNELTKVKYVTEGMRKPAFLSGEQKKAIVDLLFKTNRKVTVKQLK

EDYFKKIECFDSVEISGVEDRFNASLGTYHDLLKIIKDKDFLDNEENEDILEDIVLTLTLFE

DREMIEERLKTYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVENT

QLQNEKLYLYYLQNGRDMYVDQELDINRLSDYDVDAIVPQSFLKDDSIDNKVLTRSDK

NRGKSDNVPSEEVVKKMKNYWRQLLNAKLITQRKFDNLTKAERGGLSELDKAGFIKRQ

LVETRQITKHVAQILDSRMNTKYDENDKLIREVKVITLKSKLVSDFRKDFQFYKVREINN

YHHAHDAYLNAVVGTALIKKYPKLESEFVYGDYKVYDVRKMIAKSEQEIGKATAKYFF

YSNIMNFFKTEITLANGEIRKRPLIETNGETGEIVWDKGRDFATVRKVLSMPQVNIVKKT

EVQTGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRMLASA
```

GELQKGNELALPSKYVNFLYLASHYEKLKGSPEDNEQKQLFVEQHKHYLDEIIEQISEFS

KRVILADANLDKVLSAYNKHRDKPIREQAENIIHLFTLTNLGAPAAFKYFDTTIDRKRYT

STKEVLDATLIHQSITGLYETRIDLSQLGGDSAGGGGSGGGGSGGGGSGPKKKRKVAAA

Replacing the HNH domain with a transcriptional effector domain
pSAMca050 dCas9(HNH-->vp64, 3XGS) - DNA (SEQ ID NO: 94)

atgGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACA

GCGGCGAAACAGCCGAGGCCACCCGGCTGAAGAGAACCGCCAGAAGAAGATACAC

CAGACGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGAT

AAGAAGCACGAGCGGCACCCCATCTTCGGCAACATCGTGGACGAGGTGGCCTACCA

CGAGAAGTACCCCACCATCTACCACCTGAGAAAGAAACTGGTGGACAGCACCGACA

AGGCCGACCTGCGGCTGATCTATCTGGCCCTGGCCCACATGATCAAGTTCCGGGGCC

ACTTCCTGATCGAGGGCGACCTGAACCCCGACAACAGCGACGTGGACAAGCTGTTC

ATCCAGCTGGTGCAGACCTACAACCAGCTGTTCGAGGAAAACCCCATCAACGCCAG

CGGCGTGGACGCCAAGGCCATCCTGTCTGCCAGACTGAGCAAGAGCAGACGGCTGG

AAAATCTGATCGCCCAGCTGCCCGGCGAGAAGAAGAATGGCCTGTTCGGCAACCTG

ATTGCCCTGAGCCTGGGCCTGACCCCCAACTTCAAGAGCAACTTCGACCTGGCCGAG

GATGCCAAACTGCAGCTGAGCAAGGACACCTACGACGACGACCTGGACAACCTGCT

GGCCCAGATCGGCGACCAGTACGCCGACCTGTTTCTGGCCGCCAAGAACCTGTCCG

ACGCCATCCTGCTGAGCGACATCCTGAGAGTGAACACCGAGATCACCAAGGCCCCC

CTGAGCGCCTCTATGATCAAGAGATACGACGAGCACCACCAGGACCTGACCCTGCT

GAAAGCTCTCGTGCGGCAGCAGCTGCCTGAGAAGTACAAAGAGATTTTCTTCGACC

AGAGCAAGAACGGCTACGCCGGCTACATTGACGGCGGAGCCAGCCAGGAAGAGTTC

TACAAGTTCATCAAGCCCATCCTGGAAAAGATGGACGGCACCGAGGAACTGCTCGT

GAAGCTGAACAGAGAGGACCTGCTGCGGAAGCAGCGGACCTTCGACAACGGCAGC

ATCCCCCACCAGATCCACCTGGGAGAGCTGCACGCCATTCTGCGGCGGCAGGAAGA

TTTTTACCCATTCCTGAAGGACAACCGGGAAAAGATCGAGAAGATCCTGACCTTCCG

CATCCCCTACTACGTGGGCCCTCTGGCCAGGGGAAACAGCAGATTCGCCTGGATGA

CCAGAAAGAGCGAGGAAACCATCACCCCCTGGAACTTCGAGGAAGTGGTGGACAA

GGGCGCTTCCGCCCAGAGCTTCATCGAGCGGATGACCAACTTCGATAAGAACCTGC

CCAACGAGAAGGTGCTGCCCAAGCACAGCCTGCTGTACGAGTACTTCACCGTGTAT

AACGAGCTGACCAAAGTGAAATACGTGACCGAGGGAATGAGAAAGCCCGCCTTCCT

GAGCGGCGAGCAGAAAAAGGCCATCGTGGACCTGCTGTTCAAGACCAACCGGAAA

GTGACCGTGAAGCAGCTGAAAGAGGACTACTTCAAGAAAATCGAGTGCTTCGACTC

CGTGGAAATCTCCGGCGTGGAAGATCGGTTCAACGCCTCCCTGGGCACATACCACG

ATCTGCTGAAAATTATCAAGGACAAGGACTTCCTGGACAATGAGGAAAACGAGGAC

ATTCTGGAAGATATCGTGCTGACCCTGACACTGTTTGAGGACAGAGAGATGATCGA

GGAACGGCTGAAAACCTATGCCCACCTGTTCGACGACAAAGTGATGAAGCAGCTGA

AGCGGCGGAGATACACCGGCTGGGGCAGGCTGAGCCGGAAGCTGATCAACGGCATC

```
CGGGACAAGCAGTCCGGCAAGACAATCCTGGATTTCCTGAAGTCCGACGGCTTCGC

CAACAGAAACTTCATGCAGCTGATCCACGACGACAGCCTGACCTTTAAAGAGGACA

TCCAGAAAGCCCAGGTGTCCGGCCAGGGCGATAGCCTGCACGAGCACATTGCCAAT

CTGGCCGGCAGCCCCGCCATTAAGAAGGGCATCCTGCAGACAGTGAAGGTGGTGGA

CGAGCTCGTGAAAGTGATGGGCCGGCACAAGCCCGAGAACATCGTGATCGAAATGG

CCAGAGAGAACCAGACCACCCAGAAGGGACAGAAGGGCGGGGGAGGCTCCGGTGG

TGGGGGCAGCGGAGGGGGGGCAGCGGACGGGCTGACGCATTGGACGATTTTGATC

TGGATATGCTGGGAAGTGACGCCCTCGATGATTTTGACCTTGACATGCTTGGTTCGG

ATGCCCTTGATGACTTTGACCTCGACATGCTCGGCAGTGACGCCCTTGATGATTTCG

ACCTGGACATGCTGATTAACGGCGGGGGAGGCTCCGGTGGTGGGGGCAGCGGAGGG

GGGGGCAGCACCAAGGCCGAGAGAGGCGGCCTGAGCGAACTGGATAAGGCCGGCT

TCATCAAGAGACAGCTGGTGGAAACCCGGCAGATCACAAAGCACGTGGCACAGATC

CTGGACTCCCGGATGAACACTAAGTACGACGAGAATGACAAGCTGATCCGGGAAGT

GAAAGTGATCACCCTGAAGTCCAAGCTGGTGTCCGATTTCCGGAAGGATTTCCAGTT

TTACAAAGTGCGCGAGATCAACAACTACCACCACGCCCACGACGCCTACCTGAACG

CCGTCGTGGGAACCGCCCTGATCAAAAAGTACCCTAAGCTGGAAAGCGAGTTCGTG

TACGGCGACTACAAGGTGTACGACGTGCGGAAGATGATCGCCAAGAGCGAGCAGGA

AATCGGCAAGGCTACCGCCAAGTACTTCTTCTACAGCAACATCATGAACTTTTTCAA

GACCGAGATTACCCTGGCCAACGGCGAGATCCGGAAGCGGCCTCTGATCGAGACAA

ACGGCGAAACCGGGGAGATCGTGTGGGATAAGGGCCGGGATTTTGCCACCGTGCGG

AAAGTGCTGAGCATGCCCCAAGTGAATATCGTGAAAAAGACCGAGGTGCAGACAGG

CGGCTTCAGCAAAGAGTCTATCCTGCCCAAGAGGAACAGCGATAAGCTGATCGCCA

GAAAGAAGGACTGGGACCCTAAGAAGTACGGCGGCTTCGACAGCCCCACCGTGGCC

TATTCTGTGCTGGTGGTGGCCAAAGTGGAAAAGGGCAAGTCCAAGAAACTGAAGAG

TGTGAAAGAGCTGCTGGGGATCACCATCATGGAAAGAAGCAGCTTCGAGAAGAATC

CCATCGACTTTCTGGAAGCCAAGGGCTACAAAGAAGTGAAAAAGGACCTGATCATC

AAGCTGCCTAAGTACTCCCTGTTCGAGCTGGAAAACGGCCGGAAGAGAATGCTGGC

CTCTGCCGGCGAACTGCAGAAGGGAAACGAACTGGCCCTGCCCTCCAAATATGTGA

ACTTCCTGTACCTGGCCAGCCACTATGAGAAGCTGAAGGGCTCCCCCGAGGATAAT

GAGCAGAAACAGCTGTTTGTGGAACAGCACAAGCACTACCTGGACGAGATCATCGA

GCAGATCAGCGAGTTCTCCAAGAGAGTGATCCTGGCCGACGCTAATCTGGACAAAG

TGCTGTCCGCCTACAACAAGCACCGGGATAAGCCCATCAGAGAGCAGGCCGAGAAT

ATCATCCACCTGTTTACCCTGACCAATCTGGGAGCCCCTGCCGCCTTCAAGTACTTTG

ACACCACCATCGACCGGAAGAGGTACACCAGCACCAAAGAGGTGCTGGACGCCACC

CTGATCCACCAGAGCATCACCGGCCTGTACGAGACACGGATCGACCTGTCTCAGCTG

GGAGGCGACagcgctGGAGGAGGTGGAAGCGGAGGAGGAGGAAGCGGAGGAGGAGGT

AGCGgaacctaagaaaaagaggaaggtggcggccgct pSAMca050 dCas9(HNH-->vp64, 3XGS) - AA
                                                    (SEQ ID NO: 95)
MDKKYSIGLAIGTNSVGWAVITDEYKVPSKKFKVLGNTDRHSIKKNLIGALLF

DSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEG
```

-continued

DLNPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEIFF

DQSKNGYAGYIDGGASQEEFYKFIKPILEKMDGTEELLVKLNREDLLRKQRTFDNGSIPH

QIHLGELHAILRRQEDFYPFLKDNREKIEKILTFRIPYYVGPLARGNSRFAWMTRKSEETI

TPWNFEEVVDKGASAQSFIERMTNFDKNLPNEKVLPKHSLLYEYFTVYNELTKVKYVTE

GMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDSLTFKEDIQKA

QVSGQGDSLHEHIANLAGSPAIKKGILQTVKVVDELVKVMGRHKPENIVIEMARENQTT

QKGQKGGGGSGGGGSGGGGSGRADALDDFDLDMLGSDALDDFDLDMLGSDALDDFD

LDMLGSDALDDFDLDMLINGGGGSGGGGSGGGGSTKAERGGLSELDKAGFIKRQLVET

RQITKHVAQILDSRMNTKYDENDKLIREVKVITLKSKLVSDFRKDFQFYKVREINNYHH

AHDAYLNAVVGTALIKKYPKLESEFVYGDYKVYDVRKMIAKSEQEIGKATAKYFFYSNI

MNFFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEV

LDATLIHQSITGLYETRIDLSQLGGDSAGGGGSGGGGSGGGGSGPKKKRKVAAA pSAMca051 dCas9(HNH-->vp64, 6XGS) - DNA (SEQ ID NO: 96)

AAGAAGTACAGCATCGGCCTGGCCATCGGCACCAACTCTGTGGGCTGGGC

CGTGATCACCGACGAGTACAAGGTGCCCAGCAAGAAATTCAAGGTGCTGGGCAACA

CCGACCGGCACAGCATCAAGAAGAACCTGATCGGAGCCCTGCTGTTCGACAGCGGC

GAAACAGCCGAGGCCACCCGGCTGAAGAGAACCGCCAGAAGAAGATACACCAGAC

GGAAGAACCGGATCTGCTATCTGCAAGAGATCTTCAGCAACGAGATGGCCAAGGTG

GACGACAGCTTCTTCCACAGACTGGAAGAGTCCTTCCTGGTGGAAGAGGATAAGAA

GCACGAGCGGCACCCCATCTTCGGCAACATCGTGGACGAGGTGGCCTACCACGAGA

AGTACCCCACCATCTACCACCTGAGAAAGAAACTGGTGGACAGCACCGACAAGGCC

GACCTGCGGCTGATCTATCTGGCCCTGGCCCACATGATCAAGTTCCGGGGCCACTTC

CTGATCGAGGGCGACCTGAACCCCGACAACAGCGACGTGGACAAGCTGTTCATCCA

GCTGGTGCAGACCTACAACCAGCTGTTCGAGGAAAACCCCATCAACGCCAGCGGCG

TGGACGCCAAGGCCATCCTGTCTGCCAGACTGAGCAAGAGCAGACGGCTGGAAAAT

CTGATCGCCCAGCTGCCCGGCGAGAAGAAGAATGGCCTGTTCGGCAACCTGATTGC

CCTGAGCCTGGGCCTGACCCCCAACTTCAAGAGCAACTTCGACCTGGCCGAGGATG

CCAAACTGCAGCTGAGCAAGGACACCTACGACGACGACCTGGACAACCTGCTGGCC

CAGATCGGCGACCAGTACGCCGACCTGTTTCTGGCCGCCAAGAACCTGTCCGACGCC

ATCCTGCTGAGCGACATCCTGAGAGTGAACACCGAGATCACCAAGGCCCCCCTGAG

CGCCTCTATGATCAAGAGATACGACGAGCACCACCAGGACCTGACCCTGCTGAAAG

CTCTCGTGCGGCAGCAGCTGCCTGAGAAGTACAAAGAGATTTTCTTCGACCAGAGCA

-continued

```
AGAACGGCTACGCCGGCTACATTGACGGCGGAGCCAGCCAGGAAGAGTTCTACAAG
TTCATCAAGCCCATCCTGGAAAAGATGGACGGCACCGAGGAACTGCTCGTGAAGCT
GAACAGAGAGGACCTGCTGCGGAAGCAGCGGACCTTCGACAACGGCAGCATCCCCC
ACCAGATCCACCTGGGAGAGCTGCACGCCATTCTGCGGCGGCAGGAAGATTTTTAC
CCATTCCTGAAGGACAACCGGGAAAAGATCGAGAAGATCCTGACCTTCCGCATCCC
CTACTACGTGGGCCCTCTGGCCAGGGGAAACAGCAGATTCGCCTGGATGACCAGAA
AGAGCGAGGAAACCATCACCCCCTGGAACTTCGAGGAAGTGGTGGACAAGGGCGCT
TCCGCCCAGAGCTTCATCGAGCGGATGACCAACTTCGATAAGAACCTGCCCAACGA
GAAGGTGCTGCCCAAGCACAGCCTGCTGTACGAGTACTTCACCGTGTATAACGAGCT
GACCAAAGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTGACCGTG
AAGCAGCTGAAAGAGGACTACTTCAAGAAAATCGAGTGCTTCGACTCCGTGGAAAT
CTCCGGCGTGGAAGATCGGTTCAACGCCTCCCTGGGCACATACCACGATCTGCTGAA
AATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGGCGGAG
ATACACCGGCTGGGGCAGGCTGAGCCGGAAGCTGATCAACGGCATCCGGGACAAGC
AGTCCGGCAAGACAATCCTGGATTTCCTGAAGTCCGACGGCTTCGCCAACAGAAAC
TTCATGCAGCTGATCCACGACGACAGCCTGACCTTTAAGGAGGACATCCAGAAAGC
CCAGGTGTCCGGCCAGGGCGATAGCCTGCACGAGCACATTGCCAATCTGGCCGGCA
GCCCCGCCATTAAGAAGGGCATCCTGCAGACAGTGAAGGTGGTGGACGAGCTCGTG
AAAGTGATGGGCCGGCACAAGCCCGAGAACATCGTGATCGAAATGGCCAGAGAGA
ACCAGACCACCCAGAAGGGACAGAAGGGGGGTGGTGGAAGTGGCGGTGGCGGCTC
CGGAGGAGGAGGAAGCGGCGGCGGTGGTAGTGGCGGCGGCGGAAGCGGAGGCGGC
GGCTCCGGACGGGCTGACGCATTGGACGATTTTGATCTGGATATGCTGGGAAGTGAC
GCCCTCGATGATTTTGACCTTGACATGCTTGGTTCGGATGCCCTTGATGACTTTGACC
TCGACATGCTCGGCAGTGACGCCCTTGATGATTTCGACCTGGACATGCTGATTAACG
GGGGTGGTGGAAGTGGCGGTGGCGGCTCCGGAGGAGGAGGAAGCGGCGGCGGTGG
TAGTGGCGGCGGCGAAGCGGAGGCGGCGGCTCCACCAAGGCCGAGAGAGGCGGC
CTGAGCGAACTGGATAAGGCCGGCTTCATCAAGAGACAGCTGGTGGAAACCCGGCA
GATCACAAAGCACGTGGCACAGATCCTGGACTCCCGGATGAACACTAAGTACGACG
AGAATGACAAGCTGATCCGGGAAGTGAAAGTGATCACCCTGAAGTCCAAGCTGGTG
TCCGATTTCCGGAAGGATTTCCAGTTTTACAAAGTGCGCGAGATCAACAACTACCAC
CACGCCCACGACGCCTACCTGAACGCCGTCGTGGGAACCGCCCTGATCAAAAAGTA
CCCTAAGCTGGAAAGCGAGTTCGTGTACGGCGACTACAAGGTGTACGACGTGCGGA
AGATGATCGCCAAGAGCGAGCAGGAAATCGGCAAGGCTACCGCCAAGTACTTCTTC
TACAGCAACATCATGAACTTTTTCAAGACCGAGATTACCCTGGCCAACGGCGAGATC
CGGAAGCGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGAATATCG
TGAAAAAGACCGAGGTGCAGACAGGCGGCTTCAGCAAAGAGTCTATCCTGCCCAAG
AGGAACAGCGATAAGCTGATCGCCAGAAAGAAGGACTGGGACCCTAAGAAGTACG
```

-continued

```
GCGGCTTCGACAGCCCCACCGTGGCCTATTCTGTGCTGGTGGTGGCCAAAGTGGAAA

AGGGCAAGTCCAAGAAACTGAAGAGTGTGAAAGAGCTGCTGGGGATCACCATCATG

GAAAGAAGCAGCTTCGAGAAGAATCCCATCGACTTTCTGGAAGCCAAGGGCTACAA

AGAAGTGAAAAAGGACCTGATCATCAAGCTGCCTAAGTACTCCCTGTTCGAGCTGG

AAAACGGCCGGAAGAGAATGCTGGCCTCTGCCGGCGAACTGCAGAAGGGAAACGA

ACTGGCCCTGCCCTCCAAATATGTGAACTTCCTGTACCTGGCCAGCCACTATGAGAA

GCTGAAGGGCTCCCCCGAGGATAATGAGCAGAAACAGCTGTTTGTGGAACAGCACA

AGCACTACCTGGACGAGATCATCGAGCAGATCAGCGAGTTCTCCAAGAGAGTGATC

CTGGCCGACGCTAATCTGGACAAAGTGCTGTCCGCCTACAACAAGCACGGGATAA

GCCCATCAGAGAGCAGGCCGAGAATATCATCCACCTGTTTACCCTGACCAATCTGGG

AGCCCCTGCCGCCTTCAAGTACTTTGACACCACCATCGACCGGAAGAGGTACACCA

GCACCAAAGAGGTGCTGGACGCCACCCTGATCCACCAGAGCATCACCGGCCTGTAC

GAGACACGGATCGACCTGTCTCAGCTGGGAGGCGACagcgctGGAGGAGGTGGAAGCG

GAGGAGGAGGAAGCGGAGGAGGAGGTAGCggacctaagaaaaagaggaaggtggcggccgctgctagcG

GCAG pSAMca051 dCas9(HNH-->vp64, 6XGS) - AA
                                                          (SEQ ID NO: 97)
KKYSIGLAIGTNSVGWAVITDEYKVPSKKFKVLGNTDRHSIKKNLIGALLFDS

GETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMQLK

RRRYTGWGRLSRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIEMARENQTTQ

KGQKGGGSGGGGSGGGGSGGGGSGGGGSGGGGSGRADALDDFDLDMLGSDALDDF

DLDMLGSDALDDFDLDMLGSDALDDFDLDMLINGGGGSGGGGSGGGGSGGGGSGGG

GSGGGGSTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGDSA

GGGGSGGGGSGGGGSGPKKKRKVAAAASG
```

-continued pSAMca052 dCas9(HNH-->P65, 3XGS) - DNA (SEQ ID NO: 98)

GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGGACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

GCGCTTCCGCCCAGAGCTTCATCGAGCGGATGACCAACTTCGATAAGAACCTGCCCA

ACGAGAAGGTGCTGCCCAAGCACAGCCTGCTGTACGAGTACTTCACCGTGTATAAC

GAGCTGACCAAAGTGAAATACGTGACCGAGGGAATGAGAAAGCCCGCCTTCCTGAG

CGGCGAGCAGAAAAAGGCCATCGTGGACCTGCTGTTCAAGACCAACCGGAAAGTGA

CCGTGAAGCAGCTGAAAGAGGACTACTTCAAGAAAATCGAGTGCTTCGACTCCGTG

GAAATCTCCGGCGTGGAAGATCGGTTCAACGCCTCCCTGGGCACATACCACGATCTG

CTGAAAATTATCAAGGACAAGGACTTCCTGGACAATGAGGAAAACGAGGACATTCT

GGAAGATATCGTGCTGACCCTGACACTGTTTGAGGACAGAGAGATGATCGAGGAAC

GGCTGAAAACCTATGCCCACCTGTTCGACGACAAAGTGATGAAGCAGCTGAAGCGG

CGGAGATACACCGGCTGGGGCAGGCTGAGCCGGAAGCTGATCAACGGCATCCGGGA

CAAGCAGTCCGGCAAGACAATCCTGGATTTCCTGAAGTCCGACGGCTTCGCCAACA

GAAACTTCATGCAGCTGATCCACGACGACAGCCTGACCTTTAAAGAGGACATCCAG

AAAGCCCAGGTGTCCGGCCAGGGCGATAGCCTGCACGAGCACATTGCCAATCTGGC

CGGCAGCCCCGCCATTAAGAAGGGCATCCTGCAGACAGTGAAGGTGGTGGACGAGC

-continued

```
TCGTGAAAGTGATGGGCCGGCACAAGCCCGAGAACATCGTGATCGAAATGGCCAGA

GAGAACCAGACCACCCAGAAGGGACAGAAGGGCGGGGGAGGCTCCGGTGGTGGGG

GCAGCGGAGGGGGGGCAGCCCTTCAGGGCAGATCAGCAACCAGGCCCTGGCTCTG

GCCCCTAGCTCCGCTCCAGTGCTGGCCCAGACTATGGTGCCCTCTAGTGCTATGGTG

CCTCTGGCCCAGCCACCTGCTCCAGCCCCTGTGCTGACCCCAGGACCACCCCAGTCA

CTGAGCGCTCCAGTGCCCAAGTCTACACAGGCCGGCGAGGGGACTCTGAGTGAAGC

TCTGCTGCACCTGCAGTTCGACGCTGATGAGGACCTGGGAGCTCTGCTGGGGAACAG

CACCGATCCCGGAGTGTTCACAGATCTGGCCTCCGTGGACAACTCTGAGTTTCAGCA

GCTGCTGAATCAGGGCGTGTCCATGTCTCATAGTACAGCCGAACCAATGCTGATGGA

GTACCCCGAAGCCATTACCCGGCTGGTGACCGGCAGCCAGCGGCCCCCCGACCCCG

CTCCAACTCCCTGGGAACCAGCGGCCTGCCTAATGGGCTGTCCGGAGATGAAGAC

TTCTCAAGCATCGCTGATATGGACTTTAGTGCCCTGCTGTCACAGATTTCCTCTAGTG

GGCAGGGCGGGGGAGGCTCCGGTGGTGGGGGCAGCGGAGGGGGGGCAGCACCAA

GGCCGAGAGAGGCGGCCTGAGCGAACTGGATAAGGCCGGCTTCATCAAGAGACAG

CTGGTGGAAACCCGGCAGATCACAAAGCACGTGGCACAGATCCTGGACTCCCGGAT

GAACACTAAGTACGACGAGAATGACAAGCTGATCCGGGAAGTGAAAGTGATCACCC

TGAAGTCCAAGCTGGTGTCCGATTTCCGGAAGGATTTCCAGTTTTACAAAGTGCGCG

AGATCAACAACTACCACCACGCCCACGACGCCTACCTGAACGCCGTCGTGGGAACC

GCCCTGATCAAAAAGTACCCTAAGCTGGAAAGCGAGTTCGTGTACGGCGACTACAA

GGTGTACGACGTGCGGAAGATGATCGCCAAGAGCGAGCAGGAAATCGGCAAGGCT

ACCGCCAAGTACTTCTTCTACAGCAACATCATGAACTTTTTCAAGACCGAGATTACC

CTGGCCAACGGCGAGATCCGGAAGCGGCCTCTGATCGAGACAAACGGCGAAACCGG

GGAGATCGTGTGGGATAAGGGCCGGGATTTTGCCACCGTGCGGAAAGTGCTGAGCA

TGCCCCAAGTGAATATCGTGAAAAAGACCGAGGTGCAGACAGGCGGCTTCAGCAAA

GAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGT

GGTGGCCAAAGTGGAAAAGGGCAAGTCCAAGAAACTGAAGAGTGTGAAAGAGCTG

CTGGGGATCACCATCATGGAAAGAAGCAGCTTCGAGAAGAATCCCATCGACTTTCT

GGAAGCCAAGGGCTACAAAGAAGTGAAAAAGGACCTGATCATCAAGCTGCCTAAGT

ACTCCCTGTTCGAGCTGGAAAACGGCCGGAAGAGAATGCTGGCCTCTGCCGGCGAA

CTGCAGAAGGGAAACGAACTGGCCCTGCCCTCCAAATATGTGAACTTCCTGTACCTG

GCCAGCCACTATGAGAAGCTGAAGGGCTCCCCCGAGGATAATGAGCAGAAACAGCT

GTTTGTGGAACAGCACAAGCACTACCTGGACGAGATCATCGAGCAGATCAGCGAGT

TCTCCAAGAGAGTGATCCTGGCCGACGCTAATCTGGACAAAGTGCTGTCCGCCTACA

ACAAGCACCGGGATAAGCCCATCAGAGAGCAGGCCGAGAATATCATCCACCTGTTT

ACCCTGACCAATCTGGGAGCCCCTGCCGCCTTCAAGTACTTTGACACCACCATCGAC

CGGAAGAGGTACACCAGCACCAAAGAGGTGCTGGACGCCACCCTGATCCACCAGAG

CATCACCGGCCTGTACGAGACACGGATCGACCTGTCTCAGCTGGGAGGCGAC
``` pSAMca052 dCas9(HNH-->P65, 3XGS) - AA (SEQ ID NO: 99)

DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIEMARENQTTQ

KGQKGGGGSGGGGSGGGGSPSGQISNQALALAPSSAPVLAQTMVPSSAMVPLAQPPAP

APVLTPGPPQSLSAPVPKSTQAGEGTLSEALLHLQFDADEDLGALLGNSTDPGVFTDLAS

VDNSEFQQLLNQGVSMSHSTAEPMLMEYPEAITRLVTGSQRPPDPAPTPLGTSGLPNGLS

GDEDFSSIADMDFSALLSQISSSGQGGGGSGGGGSGGGGSTKAERGGLSELDKAGFIKR

QLVETRQITKHVAQILDSRMNTKYDENDKLIREVKVITLKSKLVSDFRKDFQFYKVREIN

NYHHAHDAYLNAVVGTALIKKYPKLESEFVYGDYKVYDVRKMIAKSEQEIGKATAKYF

FYSNIMNFFKTEITLANGEIRKRPLIETNGETGEIVWDKGRDFATVRKVLSMPQVNIVKK

TEVQTGGFSKESILPKRNSDKLIARKKDWDPKKYGGFDSPTVAYSVLVVAKVEKGKSK

KLKSVKELLGITIMERSSFEKNPIDFLEAKGYKEVKKDLIIKLPKYSLFELENGRKRMLAS

AGELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRKRY

TSTKEVLDATLIHQSITGLYETRIDLSQLGGD pSAMca053 dCas9(HNH-->P65, 6XGS) - DNA (SEQ ID NO: 100)

gGACAAGAAGTACAGCATCGGCCTGGCCATCGGCACCAACTCTGTGGGCT

GGGCCGTGATCACCGACGAGTACAAGGTGCCCAGCAAGAAATTCAAGGTGCTGGGC

AACACCGACCGGCACAGCATCAAGAAGAACCTGATCGGAGCCCTGCTGTTCGACAG

CGGCGAAACAGCCGAGGCCACCCGGCTGAAGAGAACCGCCAGAAGAAGATACACC

AGACGGAAGAACCGGATCTGCTATCTGCAAGAGATCTTCAGCAACGAGATGGCCAA

GGTGGACGACAGCTTCTTCCACAGACTGGAAGAGTCCTTCCTGGTGGAAGAGGATA

AGAAGCACGAGCGGCACCCCATCTTCGGCAACATCGTGGACGAGGTGGCCTACCAC

GAGAAGTACCCCACCATCTACCACCTGAGAAAGAAACTGGTGGACAGCACCGACAA

GGCCGACCTGCGGCTGATCTATCTGGCCCTGGCCCACATGATCAAGTTCCGGGGCCA

CTTCCTGATCGAGGGCGACCTGAACCCCGACAACAGCGACGTGGACAAGCTGTTCA

TCCAGCTGGTGCAGACCTACAACCAGCTGTTCGAGGAAAACCCCATCAACGCCAGC

GGCGTGGACGCCAAGGCCATCCTGTCTGCCAGACTGAGCAAGAGCAGACGGCTGGA

AAATCTGATCGCCCAGCTGCCCGGCGAGAAGAAGAATGGCCTGTTCGGCAACCTGA

TTGCCCTGAGCCTGGGCCTGACCCCCAACTTCAAGAGCAACTTCGACCTGGCCGAGG

-continued

```
ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGGACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

GCGCTTCCGCCCAGAGCTTCATCGAGCGGATGACCAACTTCGATAAGAACCTGCCCA

ACGAGAAGGTGCTGCCCAAGCACAGCCTGCTGTACGAGTACTTCACCGTGTATAAC

GAGCTGACCAAAGTGAAATACGTGACCGAGGGAATGAGAAAGCCCGCCTTCCTGAG

CGGCGAGCAGAAAAAGGCCATCGTGGACCTGCTGTTCAAGACCAACCGGAAAGTGA

CCGTGAAGCAGCTGAAAGAGGACTACTTCAAGAAAATCGAGTGCTTCGACTCCGTG

GAAATCTCCGGCGTGGAAGATCGGTTCAACGCCTCCCTGGGCACATACCACGATCTG

CTGAAAATTATCAAGGACAAGGACTTCCTGGACAATGAGGAAAACGAGGACATTCT

GGAAGATATCGTGCTGACCCTGACACTGTTTGAGGACAGAGAGATGATCGAGGAAC

GGCTGAAAACCTATGCCCACCTGTTCGACGACAAAGTGATGAAGCAGCTGAAGCGG

CGGAGATACACCGGCTGGGGCAGGCTGAGCCGGAAGCTGATCAACGGCATCCGGGA

CAAGCAGTCCGGCAAGACAATCCTGGATTTCCTGAAGTCCGACGGCTTCGCCAACA

GAAACTTCATGCAGCTGATCCACGACGACAGCCTGACCTTTAAAGAGGACATCCAG

AAAGCCCAGGTGTCCGGCCAGGGCGATAGCCTGCACGAGCACATTGCCAATCTGGC

CGGCAGCCCCGCCATTAAGAAGGGCATCCTGCAGACAGTGAAGGTGGTGGACGAGC

TCGTGAAAGTGATGGGCCGGCACAAGCCCGAGAACATCGTGATCGAAATGGCCAGA

GAGAACCAGACCACCCAGAAGGGACAGAAGGGGGTGGTGGAAGTGGCGGTGGCG

GCTCCGGAGGAGGAGGAAGCGGCGGCGGTGGTAGTGGCGGCGGCGGAAGCGGAGG

CGGCGGCTCCCCTTCAGGGCAGATCAGCAACCAGGCCCTGGCTCTGGCCCCTAGCTC

CGCTCCAGTGCTGGCCCAGACTATGGTGCCCTCTAGTGCTATGGTGCCTCTGGCCCA

GCCACCTGCTCCAGCCCCTGTGCTGACCCCAGGACCACCCCAGTCACTGAGCGCTCC

AGTGCCCAAGTCTACACAGGCCGGCGAGGGGACTCTGAGTGAAGCTCTGCTGCACC

TGCAGTTCGACGCTGATGAGGACCTGGGAGCTCTGCTGGGGAACAGCACCGATCCC

GGAGTGTTCACAGATCTGGCCTCCGTGGACAACTCTGAGTTTCAGCAGCTGCTGAAT

CAGGGCGTGTCCATGTCTCATAGTACAGCCGAACCAATGCTGATGGAGTACCCCGA

AGCCATTACCCGGCTGGTGACCGGCAGCCAGCGGCCCCCCGACCCCGCTCCAACTCC

CCTGGGAACCAGCGGCCTGCCTAATGGGCTGTCCGGAGATGAAGACTTCTCAAGCA

TCGCTGATATGGACTTTAGTGCCCTGCTGTCACAGATTTCCTCTAGTGGGCAGGGG

GTGGTGGAAGTGGCGGTGGCGGCTCCGGAGGAGGAGGAAGCGGCGGCGGTGGTAG
```

```
TGGCGGCGGCGGAAGCGGAGGCGGCGGCTCCACCAAGGCCGAGAGAGGCGGCCTG

AGCGAACTGGATAAGGCCGGCTTCATCAAGAGACAGCTGGTGGAAACCCGGCAGAT

CACAAAGCACGTGGCACAGATCCTGGACTCCCGGATGAACACTAAGTACGACGAGA

ATGACAAGCTGATCCGGGAAGTGAAAGTGATCACCCTGAAGTCCAAGCTGGTGTCC

GATTTCCGGAAGGATTTCCAGTTTTACAAAGTGCGCGAGATCAACAACTACCACCAC

GCCCACGACGCCTACCTGAACGCCGTCGTGGGAACCGCCCTGATCAAAAAGTACCC

TAAGCTGGAAAGCGAGTTCGTGTACGGCGACTACAAGGTGTACGACGTGCGGAAGA

TGATCGCCAAGAGCGAGCAGGAAATCGGCAAGGCTACCGCCAAGTACTTCTTCTAC

AGCAACATCATGAACTTTTTCAAGACCGAGATTACCCTGGCCAACGGCGAGATCCG

GAAGCGGCCTCTGATCGAGACAAACGGCGAAACCGGGGAGATCGTGTGGGATAAG

GGCCGGGATTTTGCCACCGTGCGGAAAGTGCTGAGCATGCCCCAAGTGAATATCGT

GAAAAAGACCGAGGTGCAGACAGGCGGCTTCAGCAAAGAGTCTATCCTGCCCAAGA

GGAACAGCGATAAGCTGATCGCCAGAAAGAAGGACTGGGACCCTAAGAAGTACGG

CGGCTTCGACAGCCCCACCGTGGCCTATTCTGTGCTGGTGGTGGCCAAAGTGGAAAA

GGGCAAGTCCAAGAAACTGAAGAGTGTGAAAGAGCTGCTGGGGATCACCATCATGG

AAAGAAGCAGCTTCGAGAAGAATCCCATCGACTTTCTGGAAGCCAAGGGCTACAAA

GAAGTGAAAAAGGACCTGATCATCAAGCTGCCTAAGTACTCCCTGTTCGAGCTGGA

AAACGGCCGGAAGAGAATGCTGGCCTCTGCCGGCGAACTGCAGAAGGGAAACGAA

CTGGCCCTGCCCTCCAAATATGTGAACTTCCTGTACCTGGCCAGCCACTATGAGAAG

CTGAAGGGCTCCCCCGAGGATAATGAGCAGAAACAGCTGTTTGTGGAACAGCACAA

GCACTACCTGGACGAGATCATCGAGCAGATCAGCGAGTTCTCCAAGAGAGTGATCC

TGGCCGACGCTAATCTGGACAAAGTGCTGTCCGCCTACAACAAGCACCGGGATAAG

CCCATCAGAGAGCAGGCCGAGAATATCATCCACCTGTTTACCCTGACCAATCTGGGA

GCCCCTGCCGCCTTCAAGTACTTTGACACCACCATCGACCGGAAGAGGTACACCAGC

ACCAAAGAGGTGCTGGACGCCACCCTGATCCACCAGAGCATCACCGGCCTGTACGA

GACACGGATCGACCTGTCTCAGCTGGGAGGCGACagcgctGGAGGAGGTGGAAGCGGA

GGAGGAGGAAGCGGAGGAGGAGGTAGCggacctaagaaaaagaggaaggtggc
```
pSAMca053 dCas9(HNH-->P65, 6XGS) - AA
(SEQ ID NO: 101)
```
DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIEMARENQTTQ
```

KGQKGGGGSGGGGSGGGGSGGGGSGGGGSGGGGSGGGGSPSGQISNQALALAPSSAPVLAQT

MVPSSAMVPLAQPPAPAPVLTPGPPQSLSAPVPKSTQAGEGTLSEALLHLQFDADEDLG

ALLGNSTDPGVFTDLASVDNSEFQQLLNQGVSMSHSTAEPMLMEYPEAITRLVTGSQRP

PDPAPTPLGTSGLPNGLSGDEDFSSIADMDFSALLSQISSSGQGGGGSGGGGSGGGGSGG

GGSGGGGSGGGGSTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKL

ESEFVYGDYKVYDVRKMIAKSEQEIGKATAKYFFYSNIMNFFKTEITLANGEIRKRPLIET

NGETGEIVWDKGRDFATVRKVLSMPQVNIVKKTEVQTGGFSKESILPKRNSDKLIARKK

DWDPKKYGGFDSPTVAYSVLVVAKVEKGKSKKLKSVKELLGITIMERSSFEKNPIDFLE

AKGYKEVKKDLIIKLPKYSLFELENGRKRMLASAGELQKGNELALPSKYVNFLYLASHY

EKLKGSPEDNEQKQLFVEQHKHYLDEIIEQISEFSKRVILADANLDKVLSAYNKHRDKPI

REQAENIIHLFTLTNLGAPAAFKYFDTTIDRKRYTSTKEVLDATLIHQSITGLYETRIDLSQ

LGGD

Insertions of transcriptional domains into 3 loops of dCas9
pSAMca054 dCas9(G533-vp64, 1XGS) - DNA
(SEQ ID NO: 102)

GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGCACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

-continued

```
GCGCTTCCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTATAAC
GAGCTGACCAAAGTGAAATACGTGACCGAGGGAGGAGGGGGGGCAGCGGACGGG
CTGACGCATTGGACGATTTTGATCTGGATATGCTGGGAAGTGACGCCCTCGATGATT
TTGACCTTGACATGCTTGGTTCGGATGCCCTTGATGACTTTGACCTCGACATGCTCGG
CAGTGACGCCCTTGATGATTTCGACCTGGACATGCTGATTAACGGCGGGGGAGGCTC
CATGAGAAAGCCCGCCTTCCTGAGCGGCGAGCAGAAAAAGGCCATCGTGGACCTGC
TGTTCAAGACCAACCGGAAAGTGACCGTGAAGCAGCTGAAAGAGGACTACTTCAAG
AAAATCGAGTGCTTCGACTCCGTGGAAATCTCCGGCGTGGAAGATCGGTTCAACGCC
TCCCTGGGCACATACCACGATCTGCTGAAAATTATCAAGGACAAGGACTTCCTGGAC
AATGAGGAAAACGAGGACATTCTGGAAGATATCGTGCTGACCCTGACACTGTTTGA
GGACAGAGAGATGATCGAGGAACGGCTGAAAACCTATGCCCACCTGTTCGACGACA
AAGTGATGAAGCAGCTGAAGCGGCGGAGATACACCGGCTGGGGCAGGCTGAGCCG
GAAGCTGATCAACGGCATCCGGGACAAGCAGTCCGGCAAGACAATCCTGGATTTCC
TGAAGTCCGACGGCTTCGCCAACAGAAACTTCATGCAGCTGATCCACGACGACAGC
CTGACCTTTAAAGAGGACATCCAGAAAGCCCAGGTGTCCGGCCAGGGCGATAGCCT
GCACGAGCACATTGCCAATCTGGCCGGCAGCCCCGCCATTAAGAAGGGCATCCTGC
AGACAGTGAAGGTGGTGGACGAGCTCGTGAAAGTGATGGGCCGGCACAAGCCCGA
GAACATCGTGATCGAAATGGCCAGAGAGAACCAGACCACCCAGAAGGGACAGAAG
AACAGCCGCGAGAGAATGAAGCGGATCGAAGAGGGCATCAAAGAGCTGGGCAGCC
AGATCCTGAAAGAACACCCCGTGGAAAACACCCAGCTGCAGAACGAGAAGCTGTAC
CTGTACTACCTGCAGAATGGGCGGGATATGTACGTGGACCAGGAACTGGACATCAA
CCGGCTGTCCGACTACGATGTGGACgcTATCGTGCCTCAGAGCTTTCTGAAGGACGA
CTCCATCGACAACAAGGTGCTGACCAGAAGCGACAAGAACCGGGGCAAGAGCGAC
AACGTGCCCTCCGAAGAGGTCGTGAAGAAGATGAAGAACTACTGGCGGCAGCTGCT
GAACGCCAAGCTGATTACCCAGAGAAAGTTCGACAATCTGACCAAGGCCGAGAGAG
GCGGCCTGAGCGAACTGGATAAGGCCGGCTTCATCAAGAGACAGCTGGTGGAAACC
CGGCAGATCACAAAGCACGTGGCACAGATCCTGGACTCCCGGATGAACACTAAGTA
CGACGAGAATGACAAGCTGATCCGGGAAGTGAAAGTGATCACCCTGAAGTCCAAGC
TGGTGTCCGATTTCCGGAAGGATTTCCAGTTTTACAAAGTGCGCGAGATCAACAACT
ACCACCACGCCCACGACGCCTACCTGAACGCCGTCGTGGGAACCGCCCTGATCAAA
AAGTACCCTAAGCTGGAAAGCGAGTTCGTGTACGGCGACTACAAGGTGTACGACGT
GCGGAAGATGATCGCCAAGAGCGAGCAGGAAATCGGCAAGGCTACCGCCAAGTAC
TTCTTCTACAGCAACATCATGAACTTTTTCAAGACCGAGATTACCCTGGCCAACGGC
GAGATCCGGAAGCGGCCTCTGATCGAGACAAACGGCGAAACCGGGGAGATCGTGTG
GGATAAGGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCTATCCTG
CCCAAGAGGAACAGCGATAAGCTGATCGCCAGAAAGAAGGACTGGGACCCTAAGA
AGTACGGCGGCTTCGACAGCCCCACCGTGGCCTATTCTGTGCTGGTGGTGGCCAAAG
TGGAAAAGGGCAAGTCCAAGAAACTGAAGAGTGTGAAAGAGCTGCTGGGGATCAC
```

```
CATCATGGAAAGAAGCAGCTTCGAGAAGAATCCCATCGACTTTCTGGAAGCCAAGG

GCTACAAAGAAGTGAAAAAGGACCTGATCATCAAGCTGCCTAAGTACTCCCTGTTC

GAGCTGGAAAACGGCCGGAAGAGAATGCTGGCCTCTGCCGGCGAACTGCAGAAGG

GAAACGAACTGGCCCTGCCCTCCAAATATGTGAACTTCCTGTACCTGGCCAGCCACT

ATGAGAAGCTGAAGGGCTCCCCCGAGGATAATGAGCAGAAACAGCTGTTTGTGGAA

CAGCACAAGCACTACCTGGACGAGATCATCGAGCAGATCAGCGAGTTCTCCAAGAG

AGTGATCCTGGCCGACGCTAATCTGGACAAAGTGCTGTCCGCCTACAACAAGCACC

GGGATAAGCCCATCAGAGAGCAGGCCGAGAATATCATCCACCTGTTTACCCTGACC

AATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACagcgctGGAGGAGG

TGGAAGCGGAGGAGGAGGAAGCGGAGGAGGAGGTAGCggacctaagaaaaagaggaaggtggcg gccgct
``` pSAMca054 dCas9(G533-vp64, 1XGS) - AA (SEQ ID NO: 103)

DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

GGGGSGRADALDDFDLDMLGSDALDDFDLDMLGSDALDDFDLDMLGSDALDDFDLD

MLINGGGGSMRKPAFLSGEQKKAIVDLLFKTNRKVTVKQLKEDYFKKIECFDSVEISGV

EDRFNASLGTYHDLLKIIKDKDFLDNEENEDILEDIVLTLTLFEDREMIEERLKTYAHLFD

DKVMKQLKRRRYTGWGRLSRKLINGIRDKQSGKTILDFLKSDGFANRNFMQLIHDDSLT

FKEDIQKAQVSGQGDSLHEHIANLAGSPAIKKGILQTVKVVDELVKVMGRHKPENIVIE

MARENQTTQKGQKNSRERMKRIEEGIKELGSQILKEHPVENTQLQNEKLYLYYLQNGR

DMYVDQELDINRLSDYDVDAIVPQSFLKDDSIDNKVLTRSDKNRGKSDNVPSEEVVKK

MKNYWRQLLNAKLITQRKFDNLTKAERGGLSELDKAGFIKRQLVETRQITKHVAQILDS

RMNTKYDENDKLIREVKVITLKSKLVSDFRKDFQFYKVREINNYHHAHDAYLNAVVGT

ALIKKYPKLESEFVYGDYKVYDVRKMIAKSEQEIGKATAKYFFYSNIMNFFKTEITLANG

EIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNELALPSKYV

NFLYLASHYEKLKGSPEDNEQKQLFVEQHKHYLDEIIEQISEFSKRVILADANLDKVLSA

YNKHRDKPIREQAENIIHLFTLTNLGAPAAFKYFDTTIDRKRYTSTKEVLDATLIHQSITG

LYETRIDLSQLGGDSAGGGGSGGGGSGGGGSGPKKKRKVAAA

-continued pSAMca055 dCas9(G533-vp64, 3XGS) - DNA (SEQ ID NO: 104)

```
GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGGACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

GCGCTTCCGCCCAGAGCTTCATCGAGCGGATGACCAACTTCGATAAGAACCTGCCCA

ACGAGAAGGTGCTGCCCAAGCACAGCCTGCTGTACGAGTACTTCACCGTGTATAAC

GAGCTGACCAAAGTGAAATACGTGACCGAGGGAGGAGGGGGGGGCAGCGGACGGG

CTGACGCATTGGACGATTTTGATCTGGATATGCTGGGAAGTGACGCCCTCGATGATT

TTGACCTTGACATGCTTGGTTCGGATGCCCTTGATGACTTTGACCTCGACATGCTCGG

CAGTGACGCCCTTGATGATTTCGACCTGGACATGCTGATTAACGGCGGGGGAGGCTC

CATGGAGAAGCCCGCCTTCCTGAGCGGCGAGCAGAAAAAGGCCATCGTGGACCTGC

TGTTCAAGACCAACCGGAAAGTGACCGTGAAGCAGCTGAAAGAGGACTACTTCAAG

AAAATCGAGTGCTTCGACTCCGTGGAAATCTCCGGCGTGGAAGATCGGTTCAACGCC

TCCCTGGGCACATACCACGATCTGCTGAAAATTATCAAGGACAAGGACTTCCTGGAC

AATGAGGAAAACGAGGACATTCTGGAAGATATCGTGCTGACCCTGACACTGTTTGA

GGACAGAGAGATGATCGAGGAACGGCTGAAAACCTATGCCCACCTGTTCGACGACA

AAGTGATGAAGCAGCTGAAGCGGCGGAGATACACCGGCTGGGGCAGGCTGAGCCG

GAAGCTGATCAACGGCATCCGGGACAAGCAGTCCGGCAAGACAATCCTGGATTTCC
```

-continued

```
TGAAGTCCGACGGCTTCGCCAACAGAAACTTCATGCAGCTGATCCACGACGACAGC

CTGACCTTTAAAGAGGACATCCAGAAAGCCCAGGTGTCCGGCCAGGGCGATAGCCT

GCACGAGCACATTGCCAATCTGGCCGGCAGCCCCGCCATTAAGAAGGGCATCCTGC

AGACAGTGAAGGTGGTGGACGAGCTCGTGAAAGTGATGGGCCGGCACAAGCCCGA

GAACATCGTGATCGAAATGGCCAGAGAGAACCAGACCACCCAGAAGGGACAGAAG

AACAGCCGCGAGAGAATGAAGCGGATCGAAGAGGGCATCAAAGAGCTGGGCAGCC

AGATCCTGAAAGAACACCCCGTGGAAAACACCCAGCTGCAGAACGAGAAGCTGTAC

CTGTACTACCTGCAGAATGGGCGGGATATGTACGTGGACCAGGAACTGGACATCAA

CCGGCTGTCCGACTACGATGTGGACgcTATCGTGCCTCAGAGCTTTCTGAAGGACGA

CTCCATCGACAACAAGGTGCTGACCAGAAGCGACAAGAACCGGGGCAAGAGCGAC

AACGTGCCCTCCGAAGAGGTCGTGAAGAAGATGAAGAACTACTGGCGGCAGCTGCT

GAACGCCAAGCTGATTACCCAGAGAAAGTTCGACAATCTGACCAAGGCCGAGAGAG

GCGGCCTGAGCGAACTGGATAAGGCCGGCTTCATCAAGAGACAGCTGGTGGAAACC

CGGCAGATCACAAAGCACGTGGCACAGATCCTGGACTCCCGGATGAACACTAAGTA

CGACGAGAATGACAAGCTGATCCGGGAAGTGAAAGTGATCACCCTGAAGTCCAAGC

TGGTGTCCGATTTCCGGAAGGATTTCCAGTTTTACAAAGTGCGCGAGATCAACAACT

ACCACCACGCCCACGACGCCTACCTGAACGCCGTCGTGGGAACCGCCCTGATCAAA

AAGTACCCTAAGCTGGAAAGCGAGTTCGTGTACGGCGACTACAAGGTGTACGACGT

GCGGAAGATGATCGCCAAGAGCGAGCAGGAAATCGGCAAGGCTACCGCCAAGTAC

TTCTTCTACAGCAACATCATGAACTTTTTCAAGACCGAGATTACCCTGGCCAACGGC

GAGATCCGGAAGCGGCCTCTGATCGAGACAAACGGCGAAACCGGGGAGATCGTGTG

GGATAAGGGCCGGGATTTTGCCACCGTGCGGAAAGTGCTGAGCATGCCCCAAGTGA

ATATCGTGAAAAAGACCGAGGTGCAGACAGGCGGCTTCAGCAAAGAGTCTATCCTG

CCCAAGAGGAACAGCGATAAGCTGATCGCCAGAAAGAAGGACTGGGACCCTAAGA

AGTACGGCGGCTTCGACAGCCCCACCGTGGCCTATTCTGTGCTGGTGGTGGCCAAAG

TGGAAAAGGGCAAGTCCAAGAAACTGAAGAGTGTGAAAGAGCTGCTGGGGATCAC

CATCATGGAAAGAAGCAGCTTCGAGAAGAATCCCATCGACTTTCTGGAAGCCAAGG

GCTACAAAGAAGTGAAAAAGGACCTGATCATCAAGCTGCCTAAGTACTCCCTGTTC

GAGCTGGAAAACGGCCGGAAGAGAATGCTGGCCTCTGCCGGCGAACTGCAGAAGG

GAAACGAACTGGCCCTGCCCTCCAAATATGTGAACTTCCTGTACCTGGCCAGCCACT

ATGAGAAGCTGAAGGGCTCCCCCGAGGATAATGAGCAGAAACAGCTGTTTGTGGAA

CAGCACAAGCACTACCTGGACGAGATCATCGAGCAGATCAGCGAGTTCTCCAAGAG

AGTGATCCTGGCCGACGCTAATCTGGACAAAGTGCTGTCCGCCTACAACAAGCACC

GGGATAAGCCCATCAGAGAGCAGGCCGAGAATATCATCCACCTGTTTACCCTGACC

AATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACAgcgctGGAGGAGG

TGGAAGCGGAGGAGGAGGAAGCGGAGGAGGAGGTAGCGgacctaagaaaaagaggaaggtggcg gccgctgctag
```

-continued pSAMca055 dCas9(G533-vp64, 3XGS) - AA (SEQ ID NO: 105)

DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

GGGGSGRADALDDFDLDMLGSDALDDFDLDMLGSDALDDFDLDMLGSDALDDFDLD

MLINGGGGSMRKPAFLSGEQKKAIVDLLFKTNRKVTVKQLKEDYFKKIECFDSVEISGV

EDRFNASLGTYHDLLKIIKDKDFLDNEENEDILEDIVLTLTLFEDREMIEERLKTYAHLFD

DKVMKQLKRRRYTGWGRLSRKLINGIRDKQSGKTILDFLKSDGFANRNFMQLIHDDSLT

FKEDIQKAQVSGQGDSLHEHIANLAGSPAIKKGILQTVKVVDELVKVMGRHKPENIVIE

MARENQTTQKGQKNSRERMKRIEEGIKELGSQILKEHPVENTQLQNEKLYLYYLQNGR

DMYVDQELDINRLSDYDVDAIVPQSFLKDDSIDNKVLTRSDKNRGKSDNVPSEEVVKK

MKNYWRQLLNAKLITQRKFDNLTKAERGGLSELDKAGFIKRQLVETRQITKHVAQILDS

RMNTKYDENDKLIREVKVITLKSKLVSDFRKDFQFYKVREINNYHHAHDAYLNAVVGT

ALIKKYPKLESEFVYGDYKVYDVRKMIAKSEQEIGKATAKYFFYSNIMNFFKTEITLANG

EIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNELALPSKYV

NFLYLASHYEKLKGSPEDNEQKQLFVEQHKHYLDEIIEQISEFSKRVILADANLDKVLSA

YNKHRDKPIREQAENIIHLFTLTNLGAPAAFKYFDTTIDRKRYTSTKEVLDATLIHQSITG

LYETRIDLSQLGGDSAGGGGSGGGGSGGGGSGPKKKRKVAAAA pSAMca056 dCas9(G533-P65, 1XGS) - DNA (SEQ ID NO: 106)

GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

-continued

```
ATGCCAAACTGCAGCTGAGCAAGGACACCTACGACGACGACCTGGACAACCTGCTG
GCCCAGATCGGCGACCAGTACGCCGACCTGTTTCTGGCCGCCAAGAACCTGTCCGAC
GCCATCCTGCTGAGCGACATCCTGAGAGTGAACACCGAGATCACCAAGGCCCCCCT
GAGCGCCTCTATGATCAAGAGATACGACGAGCACCACCAGGACCTGACCCTGCTGA
AAGCTCTCGTGCGGCAGCAGCTGCCTGAGAAGTACAAAGAGATTTTCTTCGACCAG
AGCAAGAACGGCTACGCCGGCTACATTGACGGCGGAGCCAGCCAGGAAGAGTTCTA
CAAGTTCATCAAGCCCATCCTGGAAAAGATGGACGGCACCGAGGAACTGCTCGTGA
AGCTGAACAGAGAGGACCTGCTGCGGAAGCAGCGGACCTTCGACAACGGCAGCATC
CCCCACCAGATCCACCTGGGAGAGCTGCACGCCATTCTGCGGCGGCAGGAAGATTT
TTACCCATTCCTGAAGGACAACCGGGAAAAGATCGAGAAGATCCTGACCTTCCGCA
TCCCCTACTACGTGGGCCCTCTGGCCAGGGGAAACAGCAGATTCGCCTGGATGACC
AGAAAGAGCGAGGAAACCATCACCCCCTGGAACTTCGAGGAAGTGGTGGACAAGG
GCGCTTCCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTATAAC
GAGCTGACCAAAGTGAAATACGTGACCGAGGGAGGAGGGGGAGGCAGCCCTTCAG
GGCAGATCAGCAACCAGGCCCTGGCTCTGGCCCCTAGCTCCGCTCCAGTGCTGGCCC
AGACTATGGTGCCCTCTAGTGCTATGGTGCCTCTGGCCCAGCCACCTGCTCCAGCCC
CTGTGCTGACCCCAGGACCACCCCAGTCACTGAGCGCTCCAGTGCCCAAGTCTACAC
AGGCCGGCGAGGGGACTCTGAGTGAAGCTCTGCTGCACCTGCAGTTCGACGCTGAT
GAGGACCTGGGAGCTCTGCTGGGGAACAGCACCGATCCCGGAGTGTTCACAGATCT
GGCCTCCGTGGACAACTCTGAGTTTCAGCAGCTGCTGAATCAGGGCGTGTCCATGTC
TCATAGTACAGCCGAACCAATGCTGATGGAGTACCCCGAAGCCATTACCCGGCTGG
TGACCGGCAGCCAGCGGCCCCCCGACCCCGCTCCAACTCCCCTGGGAACCAGCGGC
CTGCCTAATGGGCTGTCCGGAGATGAAGACTTCTCAAGCATCGCTGATATGGACTTT
AGTGCCCTGCTGTCACAGATTTCCTCTAGTGGGCAGGGAGGGGGGGGCAGCATGAG
AAAGCCCGCCTTCCTGAGCGGCGAGCAGAAAAAGGCCATCGTGGACCTGCTGTTCA
AGACCAACCGGAAAGTGACCGTGAAGCAGCTGAAAGAGGACTACTTCAAGAAAATC
GAGTGCTTCGACTCCGTGGAAATCTCCGGCGTGGAAGATCGGTTCAACGCCTCCCTG
GGCACATACCACGATCTGCTGAAAATTATCAAGGACAAGGACTTCCTGGACAATGA
GGAAAACGAGGACATTCTGGAAGATATCGTGCTGACCCTGACACTGTTTGAGGACA
GAGAGATGATCGAGGAACGGCTGAAAACCTATGCCCACCTGTTCGACGACAAAGTG
ATGAAGCAGCTGAAGCGGCGGAGATACACCGGCTGGGGCAGGCTGAGCCGGAAGC
TGATCAACGGCATCCGGGACAAGCAGTCCGGCAAGACAATCCTGGATTTCCTGAAG
TCCGACGGCTTCGCCAACAGAAACTTCATGCAGCTGATCCACGACGACAGCCTGAC
CTTTAAAGAGGACATCCAGAAAGCCCAGGTGTCCGGCCAGGGCGATAGCCTGCACG
AGCACATTGCCAATCTGGCCGGCAGCCCCGCCATTAAGAAGGGCATCCTGCAGACA
GTGAAGGTGGTGGACGAGCTCGTGAAAGTGATGGGCCGGCACAAGCCCGAGAACAT
CGTGATCGAAATGGCCAGAGAGAACCAGACCACCCAGAAGGGACAGAAGAACAGC
CGCGAGAGAATGAAGCGGATCGAAGAGGGCATCAAAGAGCTGGGCAGCCAGATCC
TGAAAGAACACCCCGTGGAAAACACCCAGCTGCAGAACGAGAAGCTGTACCTGTAC
```

```
TACCTGCAGAATGGGCGGGATATGTACGTGGACCAGGAACTGGACATCAACCGGCT
GTCCGACTACGATGTGGACgcTATCGTGCCTCAGAGCTTTCTGAAGGACGACTCCATC
GACAACAAGGTGCTGACCAGAAGCGACAAGAACCGGGGCAAGAGCGACAACGTGC
CCTCCGAAGAGGTCGTGAAGAAGATGAAGAACTACTGGCGGCAGCTGCTGAACGCC
AAGCTGATTACCCAGAGAAAGTTCGACAATCTGACCAAGGCCGAGAGAGGCGGCCT
GAGCGAACTGGATAAGGCCGGCTTCATCAAGAGACAGCTGGTGGAAACCCGGCAGA
TCACAAAGCACGTGGCACAGATCCTGGACTCCCGGATGAACACTAAGTACGACGAG
AATGACAAGCTGATCCGGGAAGTGAAAGTGATCACCCTGAAGTCCAAGCTGGTGTC
CGATTTCCGGAAGGATTTCCAGTTTTACAAAGTGCGCGAGATCAACAACTACCACCA
CGCCCACGACGCCTACCTGAACGCCGTCGTGGGAACCGCCCTGATCAAAAAGTACC
CTAAGCTGGAAAGCGAGTTCGTGTACGGCGACTACAAGGTGTACGACGTGCGGAAG
ATGATCGCCAAGAGCGAGCAGGAAATCGGCAAGGCTACCGCCAAGTACTTCTTCTA
CAGCAACATCATGAACTTTTTCAAGACCGAGATTACCCTGGCCAACGGCGAGATCC
GGAAGCGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGAATATCG
TGAAAAAGACCGAGGTGCAGACAGGCGGCTTCAGCAAAGAGTCTATCCTGCCCAAG
AGGAACAGCGATAAGCTGATCGCCAGAAAGAAGGACTGGGACCCTAAGAAGTACG
GCGGCTTCGACAGCCCCACCGTGGCCTATTCTGTGCTGGTGGTGGCCAAAGTGGAAA
AGGGCAAGTCCAAGAAACTGAAGAGTGTGAAAGAGCTGCTGGGGATCACCATCATG
GAAAGAAGCAGCTTCGAGAAGAATCCCATCGACTTTCTGGAAGCCAAGGGCTACAA
AGAAGTGAAAAAGGACCTGATCATCAAGCTGCCTAAGTACTCCCTGTTCGAGCTGG
AAAACGGCCGGAAGAGAATGCTGGCCTCTGCCGGCGAACTGCAGAAGGGAAACGA
ACTGGCCCTGCCCTCCAAATATGTGAACTTCCTGTACCTGGCCAGCCACTATGAGAA
GCTGAAGGGCTCCCCCGAGGATAATGAGCAGAAACAGCTGTTTGTGGAACAGCACA
AGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAA
GCCCATCAGAGAGCAGGCCGAGAATATCATCCACCTGTTTACCCTGACCAATCTGGG
AGCCCCTGCCGCCTTCAAGTACTTTGACACCACCATCGACCGGAAGAGGTACACCA
GCACCAAAGAGGTGCTGGACGCCACCCTGATCCACCAGAGCATCACCGGCCTGTAC
GAGACACGGATCGACCTGTCTCAGCTGGGAGGCGACagcgctGGAGGAGGTGGAAGCG
GAGGAGGAGGAAGCGGAGGAGGAGGTAGCggacctaagaaaaagaggaaggtggcggccgctg pSAMca056 dCas9(G533-P65, 1XGS) - AA
                                                          (SEQ ID NO: 107)
DKKYSIGLAIGTNSVGWAVITDEYKVPSKKFKVLGNTDRHSIKKNLIGALLFD
SGETAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGDQYADLFLAA
KNLSDAILLSDILRVNTEITKAPLSASMIKRYDEHHQDLTLLKALVRQQLPEKYKEIFFDQ
SKNGYAGYIDGGASQEEFYKFIKPILEKMDGTEELLVKLNREDLLRKQRTFDNGSIPHQI
HLGELHAILRRQEDFYPFLKDNREKIEKILTFRIPYYVGPLARGNSRFAWMTRKSEETITP
WNFEEVVDKGASAQSFIERMTNFDKNLPNEKVLPKHSLLYEYFTVYNELTKVKYVTEG
```

-continued

GGGGSPSGQISNQALALAPSSAPVLAQTMVPSSAMVPLAQPPAPAPVLTPGPPQSLSAPV

PKSTQAGEGTLSEALLHLQFDADEDLGALLGNSTDPGVFTDLASVDNSEFQQLLNQGVS

MSHSTAEPMLMEYPEAITRLVTGSQRPPDPAPTPLGTSGLPNGLSGDEDFSSIADMDFSA

LLSQISSSGQGGGGSMRKPAFLSGEQKKAIVDLLFKTNRKVTVKQLKEDYFKKIECFDSV

EISGVEDRFNASLGTYHDLLKIIKDKDFLDNEENEDILEDIVLTLTLFEDREMIEERLKTY

AHLFDDKVMKQLKRRRYTGWGRLSRKLINGIRDKQSGKTILDFLKSDGFANRNFMQLI

HDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYL

QNGRDMYVDQELDINRLSDYDVDAIVPQSFLKDDSIDNKVLTRSDKNRGKSDNVPSEE

VVKKMKNYWRQLLNAKLITQRKFDNLTKAERGGLSELDKAGFIKRQLVETRQITKHVA

QILDSRMNTKYDENDKLIREVKVITLKSKLVSDFRKDFQFYKVREINNYHHAHDAYLNA

VVGTALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSKESIL

PKRNSDKLIARKKDWDPKKYGGFDSPTVAYSVLVVAKVEKGKSKKLKSVKELLGITIM

ERSSFEKNPIDFLEAKGYKEVKKDLIIKLPKYSLFELENGRKRMLASAGELQKGNELALP

SKYVNFLYLASHYEKLKGSPEDNEQKQLFVEQHKHYLDEIIEQISEFSKRVILADANLDK

VLSAYNKHRDKPIREQAENIIHLFTLTNLGAPAAFKYFDTTIDRKRYTSTKEVLDATLIHQ

SITGLYETRIDLSQLGGDSAGGGGSGGGGSGGGGSGPKKKRKVAAA pSAMca057 dCas9(G533-P65, 3XGS) - DNA (SEQ ID NO: 108)

GgccaccatgGACAAGAAGTACAGCATCGGCCTGGCCATCGGCACCAACTCTG

TGGGCTGGGCCGTGATCACCGACGAGTACAAGGTGCCCAGCAAGAAATTCAAGGTG

CTGGGCAACACCGACCGGCACAGCATCAAGAAGAACCTGATCGGAGCCCTGCTGTT

CGACAGCGGCGAAACAGCCGAGGCCACCCGGCTGAAGAGAACCGCCAGAAGAAGA

TACACCAGACGGAAGAACCGGATCTGCTATCTGCAAGAGATCTTCAGCAACGAGAT

GGCCAAGGTGGACGACAGCTTCTTCCACAGACTGGAAGAGTCCTTCCTGGTGGAAG

AGGATAAGAAGCACGAGCGGCACCCCATCTTCGGCAACATCGTGGACGAGGTGGCC

TACCACGAAGTACCCCACCATCTACCACCTGAGAAAGAAACTGGTGGACAGCAC

CGACAAGGCCGACCTGCGGCTGATCTATCTGGCCCTGGCCCACATGATCAAGTTCCG

GGGCCACTTCCTGATCGAGGGCGACCTGAACCCCGACAACAGCGACGTGGACAAGC

TGTTCATCCAGCTGGTGCAGACCTACAACCAGCTGTTCGAGGAAAACCCCATCAACG

CCAGCGGCGTGGACGCCAAGGCCATCCTGTCTGCCAGACTGAGCAAGAGCAGACGG

CTGGAAAATCTGATCGCCCAGCTGCCCGGCGAGAAGAAGAATGGCCTGTTCGGCAA

CCTGATTGCCCTGAGCCTGGGCCTGACCCCCAACTTCAAGAGCAACTTCGACCTGGC

CGAGGATGCCAAACTGCAGCTGAGCAAGGACACCTACGACGACGACCTGGACAACC

TGCTGGCCCAGATCGGCGACCAGTACGCCGACCTGTTTCTGGCCGCCAAGAACCTGT

CCGACGCCATCCTGCTGAGCGACATCCTGAGAGTGAACACCGAGATCACCAAGGCC

CCCCTGAGCGCCTCTATGATCAAGAGATACGACGAGCACCACCAGGACCTGACCCT

GCTGAAAGCTCTCGTGCGGCAGCAGCTGCCTGAGAAGTACAAAGAGATTTTCTTCGA

CCAGAGCAAGAACGGCTACGCCGGCTACATTGACGGCGGAGCCAGCCAGGAAGAG

TTCTACAAGTTCATCAAGCCCATCCTGGAAAAGATGGACGGCACCGAGGAACTGCT

-continued

```
CGTGAAGCTGAACAGAGAGGACCTGCTGCGGAAGCAGCGGACCTTCGACAACGGCA
GCATCCCCCACCAGATCCACCTGGGAGAGCTGCACGCCATTCTGCGGCGGCAGGAA
GATTTTTACCCATTCCTGAAGGACAACCGGGAAAAGATCGAGAAGATCCTGACCTTC
CGCATCCCCTACTACGTGGGCCCTCTGGCCAGGGGAAACAGCAGATTCGCCTGGAT
GACCAGAAAGAGCGAGGAAACCATCACCCCCTGGAACTTCGAGGAAGTGGTGGAC
AAGGGCGCTTCCGCCCAGAGCTTCATCGAGCGGATGACCAACTTCGATAAGAACCT
GCCCAACGAGAAGGTGCTGCCCAAGCACAGCCTGCTGTACGAGTACTTCACCGTGT
ATAACGAGCTGACCAAAGTGAAATACGTGACCGAGGGAGGCGGGGGAGGCTCCGG
TGGTGGGGGCAGCGGAGGGGGGGCAGCCCTTCAGGGCAGATCAGCAACCAGGCC
CTGGCTCTGGCCCCTAGCTCCGCTCCAGTGCTGGCCCAGACTATGGTGCCCTCTAGT
GCTATGGTGCCTCTGGCCCAGCCACCTGCTCCAGCCCCTGTGCTGACCCCAGGACCA
CCCCAGTCACTGAGCGCTCCAGTGCCCAAGTCTACACAGGCCGGCGAGGGGACTCT
GAGTGAAGCTCTGCTGCACCTGCAGTTCGACGCTGATGAGGACCTGGGAGCTCTGCT
GGGGAACAGCACCGATCCCGGAGTGTTCACAGATCTGGCCTCCGTGGACAACTCTG
AGTTTCAGCAGCTGCTGAATCAGGGCGTGTCCATGTCTCATAGTACAGCCGAACCAA
TGCTGATGGAGTACCCCGAAGCCATTACCCGGCTGGTGACCGGCAGCCAGCGGCCC
CCCGACCCCGCTCCAACTCCCCTGGGAACCAGCGGCCTGCCTAATGGGCTGTCCGGA
GATGAAGACTTCTCAAGCATCGCTGATATGGACTTTAGTGCCCTGCTGTCACAGATT
TCCTCTAGTGGGCAGGGCGGGGAGGCTCCGGTGGTGGGGGCAGCGGAGGGGGGG
GCAGCATGAGAAAGCCCGCCTTCCTGAGCGGCGAGCAGAAAAAGGCCATCGTGGAC
CTGCTGTTCAAGACCAACCGGAAAGTGACCGTGAAGCAGCTGAAAGAGGACTACTT
CAAGAAAATCGAGTGCTTCGACTCCGTGGAAATCTCCGGCGTGGAAGATCGGTTCA
ACGCCTCCCTGGGCACATACCACGATCTGCTGAAAATTATCAAGGACAAGGACTTCC
TGGACAATGAGGAAAACGAGGACATTCTGGAAGATATCGTGCTGACCCTGACACTG
TTTGAGGACAGAGAGATGATCGAGGAACGGCTGAAAACCTATGCCCACCTGTTCGA
CGACAAAGTGATGAAGCAGCTGAAGCGGCGGAGATACACCGGCTGGGGCAGGCTG
AGCCGGAAGCTGATCAACGGCATCCGGGACAAGCAGTCCGGCAAGACAATCCTGGA
TTTCCTGAAGTCCGACGGCTTCGCCAACAGAAACTTCATGCAGCTGATCCACGACGA
CAGCCTGACCTTTAAAGAGGACATCCAGAAAGCCCAGGTGTCCGGCCAGGGCGATA
GCCTGCACGAGCACATTGCCAATCTGGCCGGCAGCCCCGCCATTAAGAAGGGCATC
CTGCAGACAGTGAAGGTGGTGGACGAGCTCGTGAAAGTGATGGGCCGGCACAAGCC
CGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAGAAGCTG
TACCTGTACTACCTGCAGAATGGCCGGGATATGTACGTGGACCAGGAACTGGACAT
CAACCGGCTGTCCGACTACGATGTGGACgcTATCGTGCCTCAGAGCTTTCTGAAGGA
CGACTCCATCGACAACAAGGTGCTGACCAGAAGCGACAAGAACCGGGGCAAGAGC
GACAACGTGCCCTCCGAAGAGGTCGTGAAGAAGATGAAGAACTACTGGCGGCAGCT
GCTGAACGCCAAGCTGATTACCCAGAGAAAGTTCGACAATCTGACCAAGGCCGAGA
GAGGCGGCCTGAGCGAACTGGATAAGGCCGGCTTCATCAAGAGACAGCTGGTGGAA
ACCCGGCAGATCACAAAGCACGTGGCACAGATCCTGGACTCCCGGATGAACACTAA
```

-continued

```
GTACGACGAGAATGACAAGCTGATCCGGGAAGTGAAAGTGATCACCCTGAAGTCCA
AGCTGGTGTCCGATTTCCGGAAGGATTTCCAGTTTTACAAAGTGCGCGAGATCAACA
ACTACCACCACGCCCACGACGCCTACCTGAACGCCGTCGTGGGAACCGCCCTGATC
AAAAAGTACCCTAAGCTGGAAAGCGAGTTCGTGTACGGCGACTACAAGGTGTACGA
CGTGCGGAAGATGATCGCCAAGAGCGAGCAGGAAATCGGCAAGGCTACCGCCAAG
TACTTCTTCTACAGCAACATCATGAACTTTTTCAAGACCGAGATTACCCTGGCCAAC
GGCGAGATCCGGAAGCGGCCTCTGATCGAGACAAACGGCGAAACCGGGGAGATCG
TGTGGGATAAGGGCCGGGATTTTGCCACCGTGCGGAAAGTGCTGAGCATGCCCCAA
GTGAATATCGTGAAAAAGACCGAGGTGCAGACAGGCGGCTTCAGCAAAGAGTCTAT
CCTGCCCAAGAGGAACAGCGATAAGCTGATCGCCAGAAAGAAGGACTGGGACCCTA
AGAAGTACGGCGGCTTCGACAGCCCCACCGTGGCCTATTCTGTGCTGGTGGTGGCCA
AAGTGGAAAAGGGCAAGTCCAAGAAACTGAAGAGTGTGAAAGAGCTGCTGGGGAT
CACCATCATGGAAAGAAGCAGCTTCGAGAAGAATCCCATCGACTTTCTGGAAGCCA
AGGGCTACAAAGAAGTGAAAAAGGACCTGATCATCAAGCTGCCTAAGTACTCCCTG
TTCGAGCTGGAAAACGGCCGGAAGAGAATGCTGGCCTCTGCCGGCGAACTGCAGAA
GGGAAACGAACTGGCCCTGCCCTCCAAATATGTGAACTTCCTGTACCTGGCCAGCCA
CTATGAGAAGCTGAAGGGCTCCCCCGAGGATAATGAGCAGAAACAGCTGTTTGTGG
AACAGCACAAGCACTACCTGGACGAGATCATCGAGCAGATCAGCGAGTTCTCCAAG
AGAGTGATCCTGGCCGACGCTAATCTGGACAAAGTGCTGTCCGCCTACAACAAGCA
CCGGGATAAGCCCATCAGAGAGCAGGCCGAGAATATCATCCACCTGTTTACCCTGA
CCAATCTGGGAGCCCCTGCCGCCTTCAAGTACTTTGACACCACCATCGACCGGAAGA
GGTACACCAGCACCAAAGAGGTGCTGGACGCCACCCTGATCCACCAGAGCATCACC
GGCCTGTACGAGACACGGATCGACCTGTCTCAGCTGGGAGGCGACagcgctGGAGGAG
GTGGAAGCGGAGGAGGAGGAAGCGGAGGAGGAGGTAGCggacctaagaaaaagaggaaggtggc
ggccgctgctagcGGCAGTGGA
``` pSAMca057 dCas9(G533-P65, 3XGS) - AA (SEQ ID NO: 109)

```
DKKYSIGLAIGTNSVGWAVITDEYKVPSKKFKVLGNTDRHSIKKNLIGALLFD
SGETAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGDQYADLFLAA
KNLSDAILLSDILRVNTEITKAPLSASMIKRYDEHHQDLTLLKALVRQQLPEKYKEIFFDQ
SKNGYAGYIDGGASQEEFYKFIKPILEKMDGTEELLVKLNREDLLRKQRTFDNGSIPHQI
HLGELHAILRRQEDFYPFLKDNREKIEKILTFRIPYYVGPLARGNSRFAWMTRKSEETITP
WNFEEVVDKGASAQSFIERMTNFDKNLPNEKVLPKHSLLYEYFTVYNELTKVKYVTEG
GGGGSGGGGSGGGGSPSGQISNQALALAPSSAPVLAQTMVPSSAMVPLAQPPAPAPVLT
PGPPQSLSAPVPKSTQAGEGTLSEALLHLQFDADEDLGALLGNSTDPGVFTDLASVDNSE
FQQLLNQGVSMSHSTAEPMLMEYPEAITRLVTGSQRPPDPAPTPLGTSGLPNGLSGDEDF
SSIADMDFSALLSQISSSGQGGGGSGGGGSGGGGSMRKPAFLSGEQKKAIVDLLFKTNR
KVTVKQLKEDYFKKIECFDSVEISGVEDRFNASLGTYHDLLKIIKDKDFLDNEENEDILE
```

-continued

DIVLTLTLFEDREMIEERLKTYAHLFDDKVMKQLKRRRYTGWGRLSRKLINGIRDKQSG

KTILDFLKSDGFANRNFMQLIHDDSLTFKEDIQKAQVSGQGDSLHEHIANLAGSPAIKKG

ILQTVKVVDELVKVMGRHKPENIVIEMARENQTTQKGQKNSRERMKRIEEGIKELGSQI

LKEHPVENTQLQNEKLYLYYLQNGRDMYVDQELDINRLSDYDVDAIVPQSFLKDDSID

NKVLTRSDKNRGKSDNVPSEEVVKKMKNYWRQLLNAKLITQRKFDNLTKAERGGLSE

LDKAGFIKRQLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKMIAKSEQE

IGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHKH

YLDEIIEQISEFSKRVILADANLDKVLSAYNKHRDKPIREQAENIIHLFTLTNLGAPAAFKY

FDTTIDRKRYTSTKEVLDATLIHQSITGLYETRIDLSQLGGDSAGGGGSGGGGSGGGGSG

PKKKRKVAAAASGS pSAMca058 dCas9(F575-vp64, 1XGS) - DNA
(SEQ ID NO: 110)
GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGGACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

-continued

```
GCGCTTCCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTATAAC
GAGCTGACCAAAGTGAAATACGTGACCGAGGGAATGAGAAAGCCCGCCTTCCTGAG
CGGCGAGCAGAAAAAGGCCATCGTGGACCTGCTGTTCAAGACCAACCGGAAAGTGA
CCGTGAAGCAGCTGAAAGAGGACTACTTCAAGAAAATCGAGTGCTTCGGAGGGGGA
GGCAGCGGACGGGCTGACGCATTGGACGATTTTGATCTGGATATGCTGGGAAGTGA
CGCCCTCGATGATTTTGACCTTGACATGCTTGGTTCGGATGCCCTTGATGACTTTGAC
CTCGACATGCTCGGCAGTGACGCCCTTGATGATTTCGACCTGGACATGCTGATTAAC
GGCGGGGGAGGCTCCGACTCCGTGGAAATCTCCGGCGTGGAAGATCGGTTCAACGC
CTCCCTGGGCACATACCACGATCTGCTGAAAATTATCAAGGACAAGGACTTCCTGGA
CAATGAGGAAAACGAGGACATTCTGGAAGATATCGTGCTGACCCTGACACTGTTTG
AGGACAGAGAGATGATCGAGGAACGGCTGAAAACCTATGCCCACCTGTTCGACGAC
AAAGTGATGAAGCAGCTGAAGCGGCGGAGATACACCGGCTGGGGCAGGCTGAGCC
GGAAGCTGATCAACGGCATCCGGGACAAGCAGTCCGGCAAGACAATCCTGGATTTC
CTGAAGTCCGACGGCTTCGCCAACAGAAACTTCATGCAGCTGATCCACGACGACAG
CCTGACCTTTAAAGAGGACATCCAGAAAGCCCAGGTGTCCGGCCAGGGCGATAGCC
TGCACGAGCACATTGCCAATCTGGCCGGCAGCCCCGCCATTAAGAAGGGCATCCTG
CAGACAGTGAAGGTGGTGGACGAGCTCGTGAAAGTGATGGGCCGGCACAAGCCCGA
GAACATCGTGATCGAAATGGCCAGAGAGAACCAGACCACCCAGAAGGGACAGAAG
AACAGCCGCGAGAGAATGAAGCGGATCGAAGAGGGCATCAAAGAGCTGGGCAGCC
AGATCCTGAAAGAACACCCCGTGGAAAACACCCAGCTGCAGAACGAGAAGCTGTAC
CTGTACTACCTGCAGAATGGGCGGGATATGTACGTGGACCAGGAACTGGACATCAA
CCGGCTGTCCGACTACGATGTGGACgcTATCGTGCCTCAGAGCTTTCTGAAGGACGA
CTCCATCGACAACAAGGTGCTGACCAGAAGCGACAAGAACCGGGGCAAGAGCGAC
AACGTGCCCTCCGAAGAGGTCGTGAAGAAGATGAAGAACTACTGGCGGCAGCTGCT
GAACGCCAAGCTGATTACCCAGAGAAAGTTCGACAATCTGACCAAGGCCGAGAGAG
GCGGCCTGAGCGAACTGGATAAGGCCGGCTTCATCAAGAGACAGCTGGTGGAAACC
CGGCAGATCACAAAGCACGTGGCACAGATCCTGGACTCCCGGATGAACACTAAGTA
CGACGAGAATGACAAGCTGATCCGGGAAGTGAAAGTGATCACCCTGAAGTCCAAGC
TGGTGTCCGATTTCCGGAAGGATTTCCAGTTTTACAAAGTGCGCGAGATCAACAACT
ACCACCACGCCCACGACGCCTACCTGAACGCCGTCGTGGGAACCGCCCTGATCAAA
AAGTACCCTAAGCTGGAAAGCGAGTTCGTGTACGGCGACTACAAGGTGTACGACGT
GCGGAAGATGATCGCCAAGAGCGAGCAGGAAATCGGCAAGGCTACCGCCAAGTAC
TTCTTCTACAGCAACATCATGAACTTTTTCAAGACCGAGATTACCCTGGCCAACGGC
GAGATCCGGAAGCGGCCTCTGATCGAGACAAACGGCGAAACCGGGGAGATCGTGTG
GGATAAGGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCTATCCTG
CCCAAGAGGAACAGCGATAAGCTGATCGCCAGAAAGAAGGACTGGGACCCTAAGA
AGTACGGCGGCTTCGACAGCCCCACCGTGGCCTATTCTGTGCTGGTGGTGGCCAAAG
TGGAAAAGGGCAAGTCCAAGAAACTGAAGAGTGTGAAAGAGCTGCTGGGGATCAC
```

```
CATCATGGAAAGAAGCAGCTTCGAGAAGAATCCCATCGACTTTCTGGAAGCCAAGG

GCTACAAAGAAGTGAAAAAGGACCTGATCATCAAGCTGCCTAAGTACTCCCTGTTC

GAGCTGGAAAACGGCCGGAAGAGAATGCTGGCCTCTGCCGGCGAACTGCAGAAGG

GAAACGAACTGGCCCTGCCCTCCAAATATGTGAACTTCCTGTACCTGGCCAGCCACT

ATGAGAAGCTGAAGGGCTCCCCCGAGGATAATGAGCAGAAACAGCTGTTTGTGGAA

CAGCACAAGCACTACCTGGACGAGATCATCGAGCAGATCAGCGAGTTCTCCAAGAG

AGTGATCCTGGCCGACGCTAATCTGGACAAAGTGCTGTCCGCCTACAACAAGCACC

GGGATAAGCCCATCAGAGAGCAGGCCGAGAATATCATCCACCTGTTTACCCTGACC

AATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACagcgctGGAGGAGG

TGGAAGCGGAGGAGGAGGAAGCGGAGGAGGAGGTAGCggacctaagaaaaagaggaaggtggcg
``` pSAMca058 dCas9(F575-vp64, 1XGS) - AA
(SEQ ID NO: 111)

```
DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFGGGGSGRADALDDFDL

DMLGSDALDDFDLDMLGSDALDDFDLDMLGSDALDDFDLDMLINGGGGSDSVEISGVE

DRFNASLGTYHDLLKIIKDKDFLDNEENEDILEDIVLTLTLFEDREMIEERLKTYAHLFDD

KVMKQLKRRRYTGWGRLSRKLINGIRDKQSGKTILDFLKSDGFANRNFMQLIHDDSLTF

KEDIQKAQVSGQGDSLHEHIANLAGSPAIKKGILQTVKVVDELVKVMGRHKPENIVIEM

ARENQTTQKGQKNSRERMKRIEEGIKELGSQILKEHPVENTQLQNEKLYLYYLQNGRD

MYVDQELDINRLSDYDVDAIVPQSFLKDDSIDNKVLTRSDKNRGKSDNVPSEEVVKKM

KNYWRQLLNAKLITQRKFDNLTKAERGGLSELDKAGFIKRQLVETRQITKHVAQILDSR

MNTKYDENDKLIREVKVITLKSKLVSDFRKDFQFYKVREINNYHHAHDAYLNAVVGTA

LIKKYPKLESEFVYGDYKVYDVRKMIAKSEQEIGKATAKYFFYSNIMNFFKTEITLANGE

IRKRPLIETNGETGEIVWDKGRDFATVRKVLSMPQVNIVKKTEVQTGGFSKESILPKRNS

DKLIARKKDWDPKKYGGFDSPTVAYSVLVVAKVEKGKSKKLKSVKELLGITIMERSSFE

KNPIDFLEAKGYKEVKKDLIIKLPKYSLFELENGRKRMLASAGELQKGNELALPSKYVN

FLYLASHYEKLKGSPEDNEQKQLFVEQHKHYLDEIIEQISEFSKRVILADANLDKVLSAY

NKHRDKPIREQAENIIHLFTLTNLGAPAAFKYFDTTIDRKRYTSTKEVLDATLIHQSITGL

YETRIDLSQLGGDSAGGGGSGGGGSGGGGSGPKKKRKVA
``` pSAMca059 dCas9(F575-vp64, 3XGS) - DNA
(SEQ ID NO: 112)

```
CAGCATCGGCCTGGCCATCGGCACCAACTCTGTGGGCTGGGCCGTGATCA

CCGACGAGTACAAGGTGCCCAGCAAGAAATTCAAGGTGCTGGGCAACACCGACCGG
```

-continued

```
CACAGCATCAAGAAGAACCTGATCGGAGCCCTGCTGTTCGACAGCGGCGAAACAGC

CGAGGCCACCCGGCTGAAGAGAACCGCCAGAAGAAGATACACCAGACGGAAGAAC

CGGATCTGCTATCTGCAAGAGATCTTCAGCAACGAGATGGCCAAGGTGGACGACAG

CTTCTTCCACAGACTGGAAGAGTCCTTCCTGGTGGAAGAGGATAAGAAGCACGAGC

GGCACCCCATCTTCGGCAACATCGTGGACGAGGTGGCCTACCACGAGAAGTACCCC

ACCATCTACCACCTGAGAAAGAAACTGGTGGACAGCACCGACAAGGCCGACCTGCG

GCTGATCTATCTGGCCCTGGCCCACATGATCAAGTTCCGGGGCCACTTCCTGATCGA

GGGCGACCTGAACCCCGACAACAGCGACGTGGACAAGCTGTTCATCCAGCTGGTGC

AGACCTACAACCAGCTGTTCGAGGAAAACCCCATCAACGCCAGCGGCGTGGACGCC

AAGGCCATCCTGTCTGCCAGACTGAGCAAGAGCAGACGGCTGGAAAATCTGATCGC

CCAGCTGCCCGGCGAGAAGAAGAATGGCCTGTTCGGCAACCTGATTGCCCTGAGCC

TGGGCCTGACCCCCAACTTCAAGAGCAACTTCGACCTGGCCGAGGATGCCAAACTG

CAGCTGAGCAAGGACACCTACGACGACGACCTGGACAACCTGCTGGCCCAGATCGG

CGACCAGTACGCCGACCTGTTTCTGGCCGCCAAGAACCTGTCCGACGCCATCCTGCT

GAGCGACATCCTGAGAGTGAACACCGAGATCACCAAGGCCCCCCTGAGCGCCTCTA

TGATCAAGAGATACGACGAGCACCACCAGGACCTGACCCTGCTGAAAGCTCTCGTG

CGGCAGCAGCTGCCTGAGAAGTACAAAGAGATTTTCTTCGACCAGAGCAAGAACGG

CTACGCCGGCTACATTGACGGCGGAGCCAGCCAGGAAGAGTTCTACAAGTTCATCA

AGCCCATCCTGGAAAAGATGGACGGCACCGAGGAACTGCTCGTGAAGCTGAACAGA

GAGGACCTGCTGCGGAAGCAGCGGACCTTCGACAACGGCAGCATCCCCCACCAGAT

CCACCTGGGAGAGCTGCACGCCATTCTGCGGCGGCAGGAAGATTTTTACCCATTCCT

GAAGGACAACCGGGAAAAGATCGAGAAGATCCTGACCTTCCGCATCCCCTACTACG

TGGGCCCTCTGGCCAGGGGAAACAGCAGATTCGCCTGGATGACCAGAAAGAGCGAG

GAAACCATCACCCCCTGGAACTTCGAGGAAGTGGTGGACAAGGGCGCTTCCGCCCA

GAGCTTCATCGAGCGGATGACCAACTTCGATAAGAACCTGCCCAACGAGAAGGTGC

TGCCCAAGCACAGCCTGCTGTACGAGTACTTCACCGTGTATAACGAGCTGACCAAA

GTGAAATACGTGACCGAGGGAATGAGAAAGCCCGCCTTCCTGAGCGGCGAGCAGAA

AAAGGCCATCGTGGACCTGCTGTTCAAGACCAACCGGAAAGTGACCGTGAAGCAGC

TGAAAGAGGACTACTTCAAGAAAATCGAGTGCTTCGGCGGGGAGGCTCCGGTGGT

GGGGGCAGCGGAGGGGGGGCAGCGGACGGGCTGACGCATTGGACGATTTTGATCT

GGATATGCTGGGAAGTGACGCCCTCGATGATTTTGACCTTGACATGCTTGGTTCGGA

TGCCCTTGATGACTTTGACCTCGACATGCTCGGCAGTGACGCCCTTGATGATTTCGA

CCTGGACATGCTGATTAACGGCGGGGGAGGCTCCGGTGGTGGGGCAGCGGAGGGG

GGGGCAGCGACTCCGTGGAAATCTCCGGCGTGGAAGATCGGTTCAACGCCTCCCTG

GGCACATACCACGATCTGCTGAAAATTATCAAGGACAAGGACTTCCTGGACAATGA

GGAAAACGAGGACATTCTGGAAGATATCGTGCTGACCCTGACACTGTTTGAGGACA

GAGAGATGATCGAGGAACGGCTGAAAACCTATGCCCACCTGTTCGACGACAAAGTG

ATGAAGCAGCTGAAGCGGCGGAGATACACCGGCTGGGGCAGGCTGAGCCGGAAGC

TGATCAACGGCATCCGGGACAAGCAGTCCGGCAAGACAATCCTGGATTTCCTGAAG

TCCGACGGCTTCGCCAACAGAAACTTCATGCAGCTGATCCACGACGACAGCCTGAC
```

-continued

```
CTTTAAAGAGGACATCCAGAAAGCCCAGGTGTCCGGCCAGGGCGATAGCCTGCACG

AGCACATTGCCAATCTGGCCGGCAGCCCCGCCATTAAGAAGGGCATCCTGCAGACA

GTGAAGGTGGTGGACGAGCTCGTGAAAGTGATGGGCCGGCACAAGCCCGAGAACAT

CGTGATCGAAATGGCCAGAGAGAACCAGACCACCCAGAAGGGACAGAAGAACAGC

CGCGAGAGAATGAAGCGGATCGAAGAGGGCATCAAAGAGCTGGGCAGCCAGATCC

TGAAAGAACACCCCGTGGAAAACACCCAGCTGCAGAACGAGAAGCTGTACCTGTAC

TACCTGCAGAATGGGCGGGATATGTACGTGGACCAGGAACTGGACATCAACCGGCT

GTCCGACTACGATGTGGACgcTATCGTGCCTCAGAGCTTTCTGAAGGACGACTCCATC

GACAACAAGGTGCTGACCAGAAGCGACAAGAACCGGGGCAAGAGCGACAACGTGC

CCTCCGAAGAGGTCGTGAAGAAGATGAAGAACTACTGGCGGCAGCTGCTGAACGCC

AAGCTGATTACCCAGAGAAAGTTCGACAATCTGACCAAGGCCGAGAGAGGCGGCCT

GAGCGAACTGGATAAGGCCGGCTTCATCAAGAGACAGCTGGTGGAAACCCGGCAGA

TCACAAAGCACGTGGCACAGATCCTGGACTCCCGGATGAACACTAAGTACGACGAG

AATGACAAGCTGATCCGGGAAGTGAAAGTGATCACCCTGAAGTCCAAGCTGGTGTC

CGATTTCCGGAAGGATTTCCAGTTTTACAAAGTGCGCGAGATCAACAACTACCACCA

CGCCCACGACGCCTACCTGAACGCCGTCGTGGGAACCGCCCTGATCAAAAAGTACC

CTAAGCTGGAAAGCGAGTTCGTGTACGGCGACTACAAGGTGTACGACGTGCGGAAG

ATGATCGCCAAGAGCGAGCAGGAAATCGGCAAGGCTACCGCCAAGTACTTCTTCTA

CAGCAACATCATGAACTTTTTCAAGACCGAGATTACCCTGGCCAACGGCGAGATCC

GGAAGCGGCCTCTGATCGAGACAAACGGCGAAACCGGGGAGATCGTGTGGGATAA

GGGCCGGGATTTTGCCACCGTGCGGAAAGTGCTGAGCATGCCCCAAGTGAATATCG

TGAAAAAGACCGAGGTGCAGACAGGCGGCTTCAGCAAAGAGTCTATCCTGCCCAAG

AGGAACAGCGATAAGCTGATCGCCAGAAAGAAGGACTGGGACCCTAAGAAGTACG

GCGGCTTCGACAGCCCCACCGTGGCCTATTCTGTGCTGGTGGTGGCCAAAGTGGAAA

AGGGCAAGTCCAAGAAACTGAAGAGTGTGAAAGAGCTGCTGGGGATCACCATCATG

GAAAGAAGCAGCTTCGAGAAGAATCCCATCGACTTTCTGGAAGCCAAGGGCTACAA

AGAAGTGAAAAAGGACCTGATCATCAAGCTGCCTAAGTACTCCCTGTTCGAGCTGG

AAAACGGCCGGAAGAGAATGCTGGCCTCTGCCGGCGAACTGCAGAAGGGAAACGA

ACTGGCCCTGCCCTCCAAATATGTGAACTTCCTGTACCTGGCCAGCCACTATGAGAA

GCTGAAGGGCTCCCCCGAGGATAATGAGCAGAAACAGCTGTTTGTGGAACAGCACA

AGCACTACCTGGACGAGATCATCGAGCAGATCAGCGAGTTCTCCAAGAGAGTGATC

CTGGCCGACGCTAATCTGGACAAAGTGCTGTCCGCCTACAACAAGCACCGGGATAA

GCCCATCAGAGAGCAGGCCGAGAATATCATCCACCTGTTTACCCTGACCAATCTGGG

AGCCCCTGCCGCCTTCAAGTACTTTGACACCACCATCGACCGGAAGAGGTACACCA

GCACCAAAGAGGTGCTGGACGCCACCCTGATCCACCAGAGCATCACCGGCCTGTAC

GAGACACGGATCGACCTGTCTCAGCTGGGAGGCGACagcgctGGAGGAGGTGGAAGCG

GAGGAGGAGGAAGCGGAGGAGGAGGTAGCggacctaagaaaaagaggaaggtggcggccgctgctagc pSAMca059 dCas9(F575-vp64, 3XGS) - AA
                                                    (SEQ ID NO: 113)
DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL
```

-continued

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFGGGGSGGGGSGGGGSG

RADALDDFDLDMLGSDALDDFDLDMLGSDALDDFDLDMLGSDALDDFDLDMLINGGG

GSGGGGSGGGGSDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFL

KSDGFANRNFMQLIHDDSLTFKEDIQKAQVSGQGDSLHEHIANLAGSPAIKKGILQTVKV

VDELVKVMGRHKPENIVIEMARENQTTQKGQKNSRERMKRIEEGIKELGSQILKEHPVE

NTQLQNEKLYLYYLQNGRDMYVDQELDINRLSDYDVDAIVPQSFLKDDSIDNKVLTRS

DKNRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKVREI

NNYHHAHDAYLNAVVGTALIKKYPKLESEFVYGDYKVYDVRKMIAKSEQEIGKATAK

YFFYSNIMNFFKTEITLANGEIRKRPLIETNGETGEIVWDKGRDFATVRKVLSMPQVNIV

KKTEVQTGGFSKESILPKRNSDKLIARKKDWDPKKYGGFDSPTVAYSVLVVAKVEKGK

SKKLKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEIIEQIS

EFSKRVILADANLDKVLSAYNKHRDKPIREQAENIIHLFTLTNLGAPAAFKYFDTTIDRK

RYTSTKEVLDATLIHQSITGLYETRIDLSQLGGD pSAMca060 dCas9(F575-P65, 1XGS) - DNA
(SEQ ID NO: 114)

GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

-continued

```
GAGCGCCTCTATGATCAAGAGATACGACGAGCACCACCAGGACCTGACCCTGCTGA
AAGCTCTCGTGCGGCAGCAGCTGCCTGAGAAGTACAAAGAGATTTTCTTCGACCAG
AGCAAGAACGGCTACGCCGGCTACATTGACGGCGGAGCCAGCCAGGAAGAGTTCTA
CAAGTTCATCAAGCCCATCCTGGAAAAGATGGACGGCACCGAGGAACTGCTCGTGA
AGCTGAACAGAGAGGACCTGCTGCGGAAGCAGCGGACCTTCGACAACGGCAGCATC
CCCCACCAGATCCACCTGGGAGAGCTGCACGCCATTCTGCGGCGGCAGGAAGATTT
TTACCCATTCCTGAAGGACAACCGGGAAAAGATCGAGAAGATCCTGACCTTCCGCA
TCCCCTACTACGTGGGCCCTCTGGCCAGGGGAAACAGCAGATTCGCCTGGATGACC
AGAAAGAGCGAGGAAACCATCACCCCCTGGAACTTCGAGGAAGTGGTGGACAAGG
GCGCTTCCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTATAAC
GAGCTGACCAAAGTGAAATACGTGACCGAGGGAATGAGAAAGCCCGCCTTCCTGAG
CGGCGAGCAGAAAAAGGCCATCGTGGACCTGCTGTTCAAGACCAACCGGAAAGTGA
CCGTGAAGCAGCTGAAAGAGGACTACTTCAAGAAAATCGAGTGCTTCGGAGGGGGA
GGCAGCCCTTCAGGGCAGATCAGCAACCAGGCCCTGGCTCTGGCCCCTAGCTCCGCT
CCAGTGCTGGCCCAGACTATGGTGCCCTCTAGTGCTATGGTGCCTCTGGCCCAGCCA
CCTGCTCCAGCCCCTGTGCTGACCCCAGGACCACCCCAGTCACTGAGCGCTCCAGTG
CCCAAGTCTACACAGGCCGGCGAGGGGACTCTGAGTGAAGCTCTGCTGCACCTGCA
GTTCGACGCTGATGAGGACCTGGGAGCTCTGCTGGGGAACAGCACCGATCCCGGAG
TGTTCACAGATCTGGCCTCCGTGGACAACTCTGAGTTTCAGCAGCTGCTGAATCAGG
GCGTGTCCATGTCTCATAGTACAGCCGAACCAATGCTGATGGAGTACCCCGAAGCC
ATTACCCGGCTGGTGACCGGCAGCCAGCGGCCCCCCGACCCCGCTCCAACTCCCCTG
GGAACCAGCGGCCTGCCTAATGGGCTGTCCGGAGATGAAGACTTCTCAAGCATCGC
TGATATGGACTTTAGTGCCCTGCTGTCACAGATTTCCTCTAGTGGGCAGGGAGGGGG
GGGCAGCGACTCCGTGGAAATCTCCGGCGTGGAAGATCGGTTCAACGCCTCCCTGG
GCACATACCACGATCTGCTGAAAATTATCAAGGACAAGGACTTCCTGGACAATGAG
GAAAACGAGGACATTCTGGAAGATATCGTGCTGACCCTGACACTGTTTGAGGACAG
AGAGATGATCGAGGAACGGCTGAAAACCTATGCCCACCTGTTCGACGACAAAGTGA
TGAAGCAGCTGAAGCGGCGGAGATACACCGGCTGGGGCAGGCTGAGCCGGAAGCT
GATCAACGGCATCCGGGACAAGCAGTCCGGCAAGACAATCCTGGATTTCCTGAAGT
CCGACGGCTTCGCCAACAGAAACTTCATGCAGCTGATCCACGACGACAGCCTGACC
TTTAAAGAGGACATCCAGAAAGCCCAGGTGTCCGGCCAGGGCGATAGCCTGCACGA
GCACATTGCCAATCTGGCCGGCAGCCCCGCCATTAAGAAGGGCATCCTGCAGACAG
TGAAGGTGGTGGACGAGCTCGTGAAAGTGATGGGCCGGCACAAGCCCGAGAACATC
GTGATCGAAATGGCCAGAGAGAACCAGACCACCCAGAAGGGACAGAAGAACAGCC
GCGAGAGAATGAAGCGGATCGAAGAGGGCATCAAAGAGCTGGGCAGCCAGATCCT
GAAAGAACACCCCGTGGAAAAACACCCAGCTGCAGAACGAGAAGCTGTACCTGTACT
ACCTGCAGAATGGGCGGGATATGTACGTGGACCAGGAACTGGACATCAACCGGCTG
TCCGACTACGATGTGGACgcTATCGTGCCTCAGAGCTTTCTGAAGGACGACTCCATCG
ACAACAAGGTGCTGACCAGAAGCGACAAGAACCGGGGCAAGAGCGACAACGTGCC
CTCCGAAGAGGTCGTGAAGAAGATGAAGAACTACTGGCGGCAGCTGCTGAACGCCA
```

-continued

```
AGCTGATTACCCAGAGAAAGTTCGACAATCTGACCAAGGCCGAGAGAGGCGGCCTG

AGCGAACTGGATAAGGCCGGCTTCATCAAGAGACAGCTGGTGGAAACCCGGCAGAT

CACAAAGCACGTGGCACAGATCCTGGACTCCCGGATGAACACTAAGTACGACGAGA

ATGACAAGCTGATCCGGGAAGTGAAAGTGATCACCCTGAAGTCCAAGCTGGTGTCC

GATTTCCGGAAGGATTTCCAGTTTTACAAAGTGCGCGAGATCAACAACTACCACCAC

GCCCACGACGCCTACCTGAACGCCGTCGTGGGAACCGCCCTGATCAAAAAGTACCC

TAAGCTGGAAAGCGAGTTCGTGTACGGCGACTACAAGGTGTACGACGTGCGGAAGA

TGATCGCCAAGAGCGAGCAGGAAATCGGCAAGGCTACCGCCAAGTACTTCTTCTAC

AGCAACATCATGAACTTTTTCAAGACCGAGATTACCCTGGCCAACGGCGAGATCCG

GAAGCGGCCTCTGATCGAGACAAACGGCGAAACCGGGGAGATCGTGTGGGATAAG

GGCCGGGATTTTGCCACCGTGCGGAAAGTGCTGAGCATGCCCCAAGTGAATATCGT

GAAAAAGACCGAGGTGCAGACAGGCGGCTTCAGCAAAGAGTCTATCCTGCCCAAGA

GGAACAGCGATAAGCTGATCGCCAGAAAGAAGGACTGGGACCCTAAGAAGTACGG

CGGCTTCGACAGCCCCACCGTGGCCTATTCTGTGCTGGTGGTGGCCAAAGTGGAAAA

GGGCAAGTCCAAGAAACTGAAGAGTGTGAAAGAGCTGCTGGGGATCACCATCATGG

AAAGAAGCAGCTTCGAGAAGAATCCCATCGACTTTCTGGAAGCCAAGGGCTACAAA

GAAGTGAAAAAGGACCTGATCATCAAGCTGCCTAAGTACTCCCTGTTCGAGCTGGA

AAACGGCCGGAAGAGAATGCTGGCCTCTGCCGGCGAACTGCAGAAGGGAAACGAA

CTGGCCCTGCCCTCCAAATATGTGAACTTCCTGTACCTGGCCAGCCACTATGAGAAG

CTGAAGGGCTCCCCCGAGGATAATGAGCAGAAACAGCTGTTTGTGGAACAGCACAA

GCACTACCTGGACGAGATCATCGAGCAGATCAGCGAGTTCTCCAAGAGAGTGATCC

TGGCCGACGCTAATCTGGACAAAGTGCTGTCCGCCTACAACAAGCACCGGGATAAG

CCCATCAGAGAGCAGGCCGAGAATATCATCCACCTGTTTACCCTGACCAATCTGGGA

GCCCCTGCCGCCTTCAAGTACTTTGACACCACCATCGACCGGAAGAGGTACACCAGC

ACCAAAGAGGTGCTGGACGCCACCCTGATCCACCAGAGCATCACCGGCCTGTACGA

GACACGGATCGACCTGTCTCAGCTGGGAGGCGACagcgctGGAGGAGGTGGAAGCGGA

GGAGGAGGAAGCGGAGGAGGAGGTAGCggacctaagaaaaagaggaaggtggcggcc
``` pSAMca060 dCas9(F575-P65, 1XGS) - AA (SEQ ID NO: 115)

DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFGGGGSPSGQISNQALAL

APSSAPVLAQTMVPSSAMVPLAQPPAPAPVLTGPPQSLSAPVPKSTQAGEGTLSEALLH

LQFDADEDLGALLGNSTDPGVFTDLASVDNSEFQQLLNQGVSMSHSTAEPMLMEYPEAI

-continued

TRLVTGSQRPPDPAPTPLGTSGLPNGLSGDEDFSSIADMDFSALLSQISSSGQGGGGSDSV

EISGVEDRFNASLGTYHDLLKIIKDKDFLDNEENEDILEDIVLTLTLFEDREMIEERLKTY

AHLFDDKVMKQLKRRRYTGWGRLSRKLINGIRDKQSGKTILDFLKSDGFANRNFMQLI

HDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYL

QNGRDMYVDQELDINRLSDYDVDAIVPQSFLKDDSIDNKVLTRSDKNRGKSDNVPSEE

VVKKMKNYWRQLLNAKLITQRKFDNLTKAERGGLSELDKAGFIKRQLVETRQITKHVA

QILDSRMNTKYDENDKLIREVKVITLKSKLVSDFRKDFQFYKVREINNYHHAHDAYLNA

VVGTALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSKESIL

PKRNSDKLIARKKDWDPKKYGGFDSPTVAYSVLVVAKVEKGKSKKLKSVKELLGITIM

ERSSFEKNPIDFLEAKGYKEVKKDLIIKLPKYSLFELENGRKRMLASAGELQKGNELALP

SKYVNFLYLASHYEKLKGSPEDNEQKQLFVEQHKHYLDEIIEQISEFSKRVILADANLDK

VLSAYNKHRDKPIREQAENIIHLFTLTNLGAPAAFKYFDTTIDRKRYTSTKEVLDATLIHQ

SITGLYETRIDLSQLGGDSAGGGGSGGGGSGGGGSGPKKKRKVAA pSAMca061 dCas9(F575-P65, 3XGS) - DNA (SEQ ID NO: 116)

accatgGACAAGAAGTACAGCATCGGCCTGGCCATCGGCACCAACTCTGTGG

GCTGGGCCGTGATCACCGACGAGTACAAGGTGCCCAGCAAGAAATTCAAGGTGCTG

GGCAACACCGACCGGCACAGCATCAAGAAGAACCTGATCGGAGCCCTGCTGTTCGA

CAGCGGCGAAACAGCCGAGGCCACCCGGCTGAAGAGAACCGCCAGAAGAAGATAC

ACCAGACGGAAGAACCGGATCTGCTATCTGCAAGAGATCTTCAGCAACGAGATGGC

CAAGGTGGACGACAGCTTCTTCCACAGACTGGAAGAGTCCTTCCTGGTGGAAGAGG

ATAAGAAGCACGAGCGGCACCCCATCTTCGGCAACATCGTGGACGAGGTGGCCTAC

CACGAGAAGTACCCCACCATCTACCACCTGAGAAAGAAACTGGTGGACAGCACCGA

CAAGGCCGACCTGCGGCTGATCTATCTGGCCCTGGCCCACATGATCAAGTTCCGGGG

CCACTTCCTGATCGAGGGCGACCTGAACCCCGACAACAGCGACGTGGACAAGCTGT

TCATCCAGCTGGTGCAGACCTACAACCAGCTGTTCGAGGAAAACCCCATCAACGCC

AGCGGCGTGGACGCCAAGGCCATCCTGTCTGCCAGACTGAGCAAGAGCAGACGGCT

GGAAAATCTGATCGCCCAGCTGCCCGGCGAGAAGAAGAATGGCCTGTTCGGCAACC

TGATTGCCCTGAGCCTGGGCCTGACCCCCAACTTCAAGAGCAACTTCGACCTGGCCG

AGGATGCCAAACTGCAGCTGAGCAAGGACACCTACGACGACGACCTGGACAACCTG

CTGGCCCAGATCGGCGACCAGTACGCCGACCTGTTTCTGGCCGCCAAGAACCTGTCC

GACGCCATCCTGCTGAGCGACATCCTGAGAGTGAACACCGAGATCACCAAGGCCCC

CCTGAGCGCCTCTATGATCAAGAGATACGACGAGCACCACCAGGACCTGACCCTGC

TGAAAGCTCTCGTGCGGCAGCAGCTGCCTGAGAAGTACAAAGAGATTTTCTTCGACC

AGAGCAAGAACGGCTACGCCGGCTACATTGACGGCGGAGCCAGCCAGGAAGAGTTC

TACAAGTTCATCAAGCCCATCCTGGAAAAGATGGACGGCACCGAGGAACTGCTCGT

GAAGCTGAACAGAGAGGACCTGCTGCGGAAGCAGCGGACCTTCGACAACGGCAGC

ATCCCCCACCAGATCCACCTGGGAGAGCTGCACGCCATTCTGCGGCGGCAGGAAGA

TTTTTACCCATTCCTGAAGGACAACCGGGAAAAGATCGAGAAGATCCTGACCTTCCG

CATCCCCTACTACGTGGGCCCTCTGGCCAGGGGAAACAGCAGATTCGCCTGGATGA

```
CCAGAAAGAGCGAGGAAACCATCACCCCCTGGAACTTCGAGGAAGTGGTGGACAA
GGGCGCTTCCGCCCAGAGCTTCATCGAGCGGATGACCAACTTCGATAAGAACCTGC
CCAACGAGAAGGTGCTGCCCAAGCACAGCCTGCTGTACGAGTACTTCACCGTGTAT
AACGAGCTGACCAAAGTGAAATACGTGACCGAGGGAATGAGAAAGCCCGCCTTCCT
GAGCGGCGAGCAGAAAAAGGCCATCGTGGACCTGCTGTTCAAGACCAACCGGAAA
GTGACCGTGAAGCAGCTGAAAGAGGACTACTTCAAGAAAATCGAGTGCTTCGGCGG
GGGAGGCTCCGGTGGTGGGGGCAGCGGAGGGGGGGCAGCCCTTCAGGGCAGATC
AGCAACCAGGCCCTGGCTCTGGCCCCTAGCTCCGCTCCAGTGCTGGCCCAGACTATG
GTGCCCTCTAGTGCTATGGTGCCTCTGGCCCAGCCACCTGCTCCAGCCCCTGTGCTG
ACCCCAGGACCACCCCAGTCACTGAGCGCTCCAGTGCCCAAGTCTACACAGGCCGG
CGAGGGGACTCTGAGTGAAGCTCTGCTGCACCTGCAGTTCGACGCTGATGAGGACCT
GGGAGCTCTGCTGGGGAACAGCACCGATCCCGGAGTGTTCACAGATCTGGCCTCCG
TGGACAACTCTGAGTTTCAGCAGCTGCTGAATCAGGGCGTGTCCATGTCTCATAGTA
CAGCCGAACCAATGCTGATGGAGTACCCCGAAGCCATTACCCGGCTGGTGACCGGC
AGCCAGCGGCCCCCCGACCCCGCTCCAACTCCCCTGGGAACCAGCGGCCTGCCTAAT
GGGCTGTCCGGAGATGAAGACTTCTCAAGCATCGCTGATATGGACTTTAGTGCCCTG
CTGTCACAGATTTCCTCTAGTGGGCAGGGCGGGGAGGCTCCGGTGGTGGGGGCAG
CGGAGGGGGGGCAGCGACTCCGTGGAAATCTCCGGCGTGGAAGATCGGTTCAACG
CCTCCCTGGGCACATACCACGATCTGCTGAAAATTATCAAGGACAAGGACTTCCTGG
ACAATGAGGAAAACGAGGACATTCTGGAAGATATCGTGCTGACCCTGACACTGTTT
GAGGACAGAGAGATGATCGAGGAACGGCTGAAAACCTATGCCCACCTGTTCGACGA
CAAAGTGATGAAGCAGCTGAAGCGGCGGAGATACACCGGCTGGGGCAGGCTGAGC
CGGAAGCTGATCAACGGCATCCGGGACAAGCAGTCCGGCAAGACAATCCTGGATTT
CCTGAAGTCCGACGGCTTCGCCAACAGAAACTTCATGCAGCTGATCCACGACGACA
GCCTGACCTTTAAAGAGGACATCCAGAAAGCCCAGGTGTCCGGCCAGGGCGATAGC
CTGCACGAGCACATTGCCAATCTGGCCGGCAGCCCCGCCATTAAGAAGGGCATCCT
GCAGACAGTGAAGGTGGTGGACGAGCTCGTGAAAGTGATGGGCCGGCACAAGCCCG
AGAACATCGTGATCGAAATGGCCAGAGAGAACCAGACCACCCAGAAGGGACAGAA
GAACAGCCGCGAGAGAATGAAGCGGATCGAAGAGGGCATCAAAGAGCTGGGCAGC
CAGATCCTGAAAGAACACCCCGTGGAAAACACCCAGCTGCAGAACGAGAAGCTGTA
CCTGTACTACCTGCAGAATGGGCGGGATATGTACGTGGACCAGGAACTGGACATCA
ACCGGCTGTCCGACTACGATGTGGACgcTATCGTGCCTCAGAGCTTTCTGAAGGACG
ACTCCATCGACAACAAGGTGCTGACCAGAAGCGACAAGAACCGGGGCAAGAGCGA
CAACGTGCCCTCCGAAGAGGTCGTGAAGAAGATGAAGAACTACTGGCGGCAGCTGC
TGAACGCCAAGCTGATTACCCAGAGAAAGTTCGACAATCTGACCAAGGCCGAGAGA
GGCGGCCTGAGCGAACTGGATAAGGCCGGCTTCATCAAGAGACAGCTGGTGGAAAC
CCGGCAGATCACAAAGCACGTGGCACAGATCCTGGACTCCCGGATGAACACTAAGT
ACGACGAGAATGACAAGCTGATCCGGGAAGTGAAAGTGATCACCCTGAAGTCCAAG
CTGGTGTCCGATTTCCGGAAGGATTTCCAGTTTTACAAAGTGCGCGAGATCAACAAC
TACCACCACGCCCACGACGCCTACCTGAACGCCGTCGTGGGAACCGCCCTGATCAA
```

-continued

```
AAAGTACCCTAAGCTGGAAAGCGAGTTCGTGTACGGCGACTACAAGGTGTACGACG

TGCGGAAGATGATCGCCAAGAGCGAGCAGGAAATCGGCAAGGCTACCGCCAAGTA

CTTCTTCTACAGCAACATCATGAACTTTTTCAAGACCGAGATTACCCTGGCCAACGG

CGAGATCCGGAAGCGGCCTCTGATCGAGACAAACGGCGAAACCGGGGAGATCGTGT

GGGATAAGGGCCGGGATTTTGCCACCGTGCGGAAAGTGCTGAGCATGCCCCAAGTG

AATATCGTGAAAAAGACCGAGGTGCAGACAGGCGGCTTCAGCAAAGAGTCTATCCT

GCCCAAGAGGAACAGCGATAAGCTGATCGCCAGAAAGAAGGACTGGGACCCTAAG

AAGTACGGCGGCTTCGACAGCCCCACCGTGGCCTATTCTGTGCTGGTGGTGGCCAAA

GTGGAAAAGGGCAAGTCCAAGAAACTGAAGAGTGTGAAAGAGCTGCTGGGGATCA

CCATCATGGAAAGAAGCAGCTTCGAGAAGAATCCCATCGACTTTCTGGAAGCCAAG

GGCTACAAGAAGTGAAAAAGGACCTGATCATCAAGCTGCCTAAGTACTCCCTGTT

CGAGCTGGAAAACGGCCGGAAGAGAATGCTGGCCTCTGCCGGCGAACTGCAGAAG

GGAAACGAACTGGCCCTGCCCTCCAAATATGTGAACTTCCTGTACCTGGCCAGCCAC

TATGAGAAGCTGAAGGGCTCCCCCGAGGATAATGAGCAGAAACAGCTGTTTGTGGA

ACAGCACAAGCACTACCTGGACGAGATCATCGAGCAGATCAGCGAGTTCTCCAAGA

GAGTGATCCTGGCCGACGCTAATCTGGACAAAGTGCTGTCCGCCTACAACAAGCAC

CGGGATAAGCCCATCAGAGAGCAGGCCGAGAATATCATCCACCTGTTTACCCTGAC

CAATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACagcgctGGAGGAGG

TGGAAGCGGAGGAGGAGGAAGCGGAGGAGGAGGTAGCggacctaagaaaaagaggaaggtggcg gccgct pSAMca061 dCas9(F575-P65, 3XGS) - AA                       (SEQ ID NO: 117)

TMDKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRLEESFLVEEDK

KHERHPIFGNIVDEVAYHEKYPTIYHLRKKLVDSTDKADLRLIYLALAHMIKFRGHFLIE

GDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLF

LAAKNLSDAILLSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRKQRTFDNGSIP

HQIHLGELHAILRRQEDFYPFLKDNREKIEKILTFRIPYYVGPLARGNSRFAWMTRKSEET

ITPWNFEEVVDKGASAQSFIERMTNFDKNLPNEKVLPKHSLLYEYFTVYNELTKVKYVT

EGMRKPAFLSGEQKKAIVDLLFKTNRKVTVKQLKEDYFKKIECFGGGGSGGGGSGGGG

SPSGQISNQALALAPSSAPVLAQTMVPSSAMVPLAQPPAPAPVLTPGPPQSLSAPVPKST

QAGEGTLSEALLHLQFDADEDLGALLGNSTDPGVFTDLASVDNSEFQQLLNQGVSMSH

STAEPMLMEYPEAITRLVTGSQRPPDPAPTPLGTSGLPNGLSGDEDFSSIADMDFSALLSQ

ISSSGQGGGSGGGGSGGGGSDSVEISGVEDRFNASLGTYHDLLKIIKDKDFLDNEENED

ILEDIVLTLTLFEDREMIEERLKTYAHLFDDKVMKQLKRRRYTGWGRLSRKLINGIRDKQ

SGKTILDFLKSDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRIEEGIKELGS

QILKEHPVENTQLQNEKLYLYYLQNGRDMYVDQELDINRLSDYDVDAIVPQSFLKDDSI
```

```
DNKVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHKH

YLDEIIEQISEFSKRVILADANLDKVLSAYNKHRDKPIREQAENIIHLFTLTNLGAPAAFKY

FDTTIDRKRYTSTKEVLDATLIHQSITGLYETRIDLSQLGGDSAGGGGSGGGGSGGGGSG

PKKKRKVAAA
``` pSAMca062 dCas9(K1153-vp64, 1XGS) - DNA
(SEQ ID NO: 118)

```
GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGGACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

GCGCTTCCGCCCAGAGCTTCATCGAGCGGATGACCAACTTCGATAAGAACCTGCCCA

ACGAGAAGGTGCTGCCCAAGCACAGCCTGCTGTACGAGTACTTCACCGTGTATAAC

GAGCTGACCAAAGTGAAATACGTGACCGAGGGAATGAGAAAGCCCGCCTTCCTGAG
```

```
CGGCGAGCAGAAAAAGGCCATCGTGGACCTGCTGTTCAAGACCAACCGGAAAGTGA

CCGTGAAGCAGCTGAAAGAGGACTACTTCAAGAAAATCGAGTGCTTCGACTCCGTG

GAAATCTCCGGCGTGGAAGATCGGTTCAACGCCTCCCTGGGCACATACCACGATCTG

CTGAAAATTATCAAGGACAAGGACTTCCTGGACAATGAGGAAAACGAGGACATTCT

GGAAGATATCGTGCTGACCCTGACACTGTTTGAGGACAGAGAGATGATCGAGGAAC

GGCTGAAAACCTATGCCCACCTGTTCGACGACAAAGTGATGAAGCAGCTGAAGCGG

CGGAGATACACCGGCTGGGGCAGGCTGAGCCGGAAGCTGATCAACGGCATCCGGGA

CAAGCAGTCCGGCAAGACAATCCTGGATTTCCTGAAGTCCGACGGCTTCGCCAACA

GAAACTTCATGCAGCTGATCCACGACGACAGCCTGACCTTTAAAGAGGACATCCAG

AAAGCCCAGGTGTCCGGCCAGGGCGATAGCCTGCACGAGCACATTGCCAATCTGGC

CGGCAGCCCCGCCATTAAGAAGGGCATCCTGCAGACAGTGAAGGTGGTGGACGAGC

TCGTGAAAGTGATGGGCCGGCACAAGCCCGAGAACATCGTGATCGAAATGGCCAGA

GAGAACCAGACCACCCAGAAGGGACAGAAGAACAGCCGCGAGAGAATGAAGCGGA

TCGAAGAGGGCATCAAAGAGCTGGGCAGCCAGATCCTGAAAGAACACCCCGTGGA

AAACACCCAGCTGCAGAACGAGAAGCTGTACCTGTACTACCTGCAGAATGGGCGGG

ATATGTACGTGGACCAGGAACTGGACATCAACCGGCTGTCCGACTACGATGTGGACg cTATCGTGCCTCAGAGCTTTCTGAAGGACGACTCCATCGACAACAAGGTGCTGACCA

GAAGCGACAAGAACCGGGGCAAGAGCGACAACGTGCCCTCCGAAGAGGTCGTGAA

GAAGATGAAGAACTACTGGCGGCAGCTGCTGAACGCCAAGCTGATTACCCAGAGAA

AGTTCGACAATCTGACCAAGGCCGAGAGAGGCGGCCTGAGCGAACTGGATAAGGCC

GGCTTCATCAAGAGACAGCTGGTGGAAACCCGGCAGATCACAAAGCACGTGGCACA

GATCCTGGACTCCCGGATGAACACTAAGTACGACGAGAATGACAAGCTGATCCGGG

AAGTGAAAGTGATCACCCTGAAGTCCAAGCTGGTGTCCGATTTCCGGAAGGATTTCC

AGTTTTACAAAGTGCGCGAGATCAACAACTACCACCACGCCCACGACGCCTACCTG

AACGCCGTCGTGGGAACCGCCCTGATCAAAAAGTACCCTAAGCTGGAAAGCGAGTT

CGTGTACGGCGACTACAAGGTGTACGACGTGCGGAAGATGATCGCCAAGAGCGAGC

AGGAAATCGGCAAGGCTACCGCCAAGTACTTCTTCTACAGCAACATCATGAACTTTT

TCAAGACCGAGATTACCCTGGCCAACGGCGAGATCCGGAAGCGGCCTCTGATCGAG

ACAAACGGCGAAACCGGGGAGATCGTGTGGGATAAGGGCCGGGATTTTGCCACCGT

GCGGAAAGTGCTGAGCATGCCCCAAGTGAATATCGTGAAAAAGACCGAGGTGCAGA

CAGGCGGCTTCAGCAAAGAGTCTATCCTGCCCAAGAGGAACAGCGATAAGCTGATC

GCCAGAAAGAAGGACTGGGACCCTAAGAAGTACGGCGGCTTCGACAGCCCCACCGT

GGCCTATTCTGTGCTGGTGGTGGCCAAAGTGGAAAAGGGCAAGGGAGGGGGAGGCA

GCGGACGGGCTGACGCATTGGACGATTTTGATCTGGATATGCTGGGAAGTGACGCC

CTCGATGATTTTGACCTTGACATGCTTGGTTCGGATGCCCTTGATGACTTTGACCTCG

ACATGCTCGGCAGTGACGCCCTTGATGATTTCGACCTGGACATGCTGATTAACGGCG

GGGGAGGCTCCTCCAAGAAACTGAAGAGTGTGAAAGAGCTGCTGGGGATCACCATC

ATGGAAAGAAGCAGCTTCGAGAAGAATCCCATCGACTTTCTGGAAGCCAAGGGCTA

CAAAGAAGTGAAAAAGGACCTGATCATCAAGCTGCCTAAGTACTCCCTGTTCGAGC

TGGAAAACGGCCGGAAGAGAATGCTGGCCTCTGCCGGCGAACTGCAGAAGGGAAA

CGAACTGGCCCTGCCCTCCAAATATGTGAACTTCCTGTACCTGGCCAGCCACTATGA
```

-continued

```
GAAGCTGAAGGGCTCCCCCGAGGATAATGAGCAGAAACAGCTGTTTGTGGAACAGC

ACAAGCACTACCTGGACGAGATCATCGAGCAGATCAGCGAGTTCTCCAAGAGAGTG

ATCCTGGCCGACGCTAATCTGGACAAAGTGCTGTCCGCCTACAACAAGCACCGGGA

TAAGCCCATCAGAGAGCAGGCCGAGAATATCATCCACCTGTTTACCCTGACCAATCT

GGGAGCCCTGCCGCCTTCAAGTACTTTGACACCACCATCGACCGGAAGAGGTACA

CCAGCACCAAAGAGGTGCTGGACGCCACCCTGATCCACCAGAGCATCACCGGCCTG

TACGAGACACGGATCGACCTGTCTCAGCTGGGAGGCGACagcgctGGAGGAGGTGGAA

GCGGAGGAGGAGGAAGCGGAGGAGGAGGTAGCGgacctaagaaaaagaggaaggtggcggccgct
``` pSAMca062 dCas9(K1153-vp64, 1XGS) - AA
                                                            (SEQ ID NO: 119)
```
DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYDEND

KLIREVKVITLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYSVLVVAKVEKGKGGGGSGRADALDDFDLDMLGSDALDDFD

LDMLGSDALDDFDLDMLGSDALDDFDLDMLINGGGGSSKKLKSVKELLGITIMERSSFE

KNPIDFLEAKGYKEVKKDLIIKLPKYSLFELENGRKRMLASAGELQKGNELALPSKYVN

FLYLASHYEKLKGSPEDNEQKQLFVEQHKHYLDEIIEQISEFSKRVILADANLDKVLSAY

NKHRDKPIREQAENIIHLFTLTNLGAPAAFKYFDTTIDRKRYTSTKEVLDATLIHQSITGL

YETRIDLSQLGGDSAGGGGSGGGGSGGGGSGPKKKRKVAAA
``` pSAMca063 dCas9(K1153-vp64, 3XGS) - DNA
                                                            (SEQ ID NO: 120)
```
GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG
```

-continued

```
GTGGACGACAGCTTCTTCCACAGACTGGAAGAGTCCTTCCTGGTGGAAGAGGATAA
GAAGCACGAGCGGCACCCCATCTTCGGCAACATCGTGGACGAGGTGGCCTACCACG
AGAAGTACCCCACCATCTACCACCTGAGAAAGAAACTGGTGGACAGCACCGACAAG
GCCGACCTGCGGCTGATCTATCTGGCCCTGGCCCACATGATCAAGTTCCGGGGCCAC
TTCCTGATCGAGGGCGACCTGAACCCCGACAACAGCGACGTGGACAAGCTGTTCAT
CCAGCTGGTGCAGACCTACAACCAGCTGTTCGAGGAAAACCCCATCAACGCCAGCG
GCGTGGACGCCAAGGCCATCCTGTCTGCCAGACTGAGCAAGAGCAGACGGCTGGAA
AATCTGATCGCCCAGCTGCCCGGCGAGAAGAAGAATGGCCTGTTCGGCAACCTGAT
TGCCCTGAGCCTGGGCCTGACCCCCAACTTCAAGAGCAACTTCGACCTGGCCGAGG
ATGCCAAACTGCAGCTGAGCAAGGACACCTACGACGACGACCTGGACAACCTGCTG
GCCCAGATCGGCGACCAGTACGCCGACCTGTTTCTGGCCGCCAAGAACCTGTCCGAC
GCCATCCTGCTGAGCGACATCCTGAGAGTGAACACCGAGATCACCAAGGCCCCCCT
GAGCGCCTCTATGATCAAGAGATACGACGAGCACCACCAGGACCTGACCCTGCTGA
AAGCTCTCGTGCGGCAGCAGCTGCCTGAGAAGTACAAAGAGATTTTCTTCGACCAG
AGCAAGAACGGCTACGCCGGCTACATTGACGGCGGAGCCAGCCAGGAAGAGTTCTA
CAAGTTCATCAAGCCCATCCTGGAAAAGATGGACGGCACCGAGGAACTGCTCGTGA
AGCTGAACAGAGAGGACCTGCTGCGGAAGCAGCGGACCTTCGACAACGGCAGCATC
CCCCACCAGATCCACCTGGGAGAGCTGCACGCCATTCTGCGGCGGCAGGAAGATTT
TTACCCATTCCTGAAGGACAACCGGGAAAAGATCGAGAAGATCCTGACCTTCCGCA
TCCCCTACTACGTGGGCCCTCTGGCCAGGGGAAACAGCAGATTCGCCTGGATGACC
AGAAAGAGCGAGGAAACCATCACCCCCTGGAACTTCGAGGAAGTGGTGGACAAGG
GCGCTTCCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTATAAC
GAGCTGACCAAAGTGAAATACGTGACCGAGGGAATGAGAAAGCCCGCCTTCCTGAG
CGGCGAGCAGAAAAAGGCCATCGTGGACCTGCTGTTCAAGACCAACCGGAAAGTGA
CCGTGAAGCAGCTGAAAGAGGACTACTTCAAGAAAATCGAGTGCTTCGACTCCGTG
GAAATCTCCGGCGTGGAAGATCGGTTCAACGCCTCCCTGGGCACATACCACGATCTG
CTGAAAATTATCAAGGACAAGGACTTCCTGGACAATGAGGAAAACGAGGACATTCT
GGAAGATATCGTGCTGACCCTGACACTGTTTGAGGACAGAGAGATGATCGAGGAAC
GGCTGAAAACCTATGCCCACCTGTTCGACGACAAAGTGATGAAGCAGCTGAAGCGG
CGGAGATACACCGGCTGGGGCAGGCTGAGCCGGAAGCTGATCAACGGCATCCGGGA
CAAGCAGTCCGGCAAGACAATCCTGGATTTCCTGAAGTCCGACGGCTTCGCCAACA
GAAACTTCATGCAGCTGATCCACGACGACAGCCTGACCTTTAAAGAGGACATCCAG
AAAGCCCAGGTGTCCGGCCAGGGCGATAGCCTGCACGAGCACATTGCCAATCTGGC
CGGCAGCCCCGCCATTAAGAAGGGCATCCTGCAGACAGTGAAGGTGGTGGACGAGC
TCGTGAAAGTGATGGGCCGGCACAAGCCCGAGAACATCGTGATCGAAATGGCCAGA
GAGAACCAGACCACCCAGAAGGGACAGAAGAACAGCCGCGAGAGAATGAAGCGGA
TCGAAGAGGGCATCAAAGAGCTGGGCAGCCAGATCCTGAAAGAACACCCCGTGGA
AAACACCCAGCTGCAGAACGAGAAGCTGTACCTGTACTACCTGCAGAATGGGCGGG
ATATGTACGTGGACCAGGAACTGGACATCAACCGGCTGTCCGACTACGATGTGGACg
cTATCGTGCCTCAGAGCTTTCTGAAGGACGACTCCATCGACAACAAGGTGCTGACCA
```

-continued

```
GAAGCGACAAGAACCGGGGCAAGAGCGACAACGTGCCCTCCGAAGAGGTCGTGAA

GAAGATGAAGAACTACTGGCGGCAGCTGCTGAACGCCAAGCTGATTACCCAGAGAA

AGTTCGACAATCTGACCAAGGCCGAGAGAGGCGGCCTGAGCGAACTGGATAAGGCC

GGCTTCATCAAGAGACAGCTGGTGGAAACCCGGCAGATCACAAAGCACGTGGCACA

GATCCTGGACTCCCGGATGAACACTAAGTACGACGAGAATGACAAGCTGATCCGGG

AAGTGAAAGTGATCACCCTGAAGTCCAAGCTGGTGTCCGATTTCCGGAAGGATTTCC

AGTTTTACAAAGTGCGCGAGATCAACAACTACCACCACGCCCACGACGCCTACCTG

AACGCCGTCGTGGGAACCGCCCTGATCAAAAAGTACCCTAAGCTGGAAAGCGAGTT

CGTGTACGGCGACTACAAGGTGTACGACGTGCGGAAGATGATCGCCAAGAGCGAGC

AGGAAATCGGCAAGGCTACCGCCAAGTACTTCTTCTACAGCAACATCATGAACTTTT

TCAAGACCGAGATTACCCTGGCCAACGGCGAGATCCGGAAGCGGCCTCTGATCGAG

ACAAACGGCGAAACCGGGGAGATCGTGTGGGATAAGGGCCGGGATTTTGCCACCGT

GCGGAAAGTGCTGAGCATGCCCCAAGTGAATATCGTGAAAAAGACCGAGGTGCAGA

CAGGCGGCTTCAGCAAAGAGTCTATCCTGCCCAAGAGGAACAGCGATAAGCTGATC

GCCAGAAAGAAGGACTGGGACCCTAAGAAGTACGGCGGCTTCGACAGCCCCACCGT

GGCCTATTCTGTGCTGGTGGTGGCCAAAGTGGAAAAGGGCAAGGGCGGGGGAGGCT

CCGGTGGTGGGGGCAGCGGAGGGGGGGGCAGCGGACGGGCTGACGCATTGGACGA

TTTTGATCTGGATATGCTGGGAAGTGACGCCCTCGATGATTTTGACCTTGACATGCTT

GGTTCGGATGCCCTTGATGACTTTGACCTCGACATGCTCGGCAGTGACGCCCTTGAT

GATTTCGACCTGGACATGCTGATTAACGGCGGGGGAGGCTCCGGTGGTGGGGGCAG

CGGAGGGGGGGGCAGCTCCAAGAAACTGAAGAGTGTGAAAGAGCTGCTGGGGATC

ACCATCATGGAAAGAAGCAGCTTCGAAGAATCCCATCGACTTTCTGGAAGCCAA

GGGCTACAAAGAAGTGAAAAAGGACCTGATCATCAAGCTGCCTAAGTACTCCCTGT

TCGAGCTGGAAAACGGCCGGAAGAGAATGCTGGCCTCTGCCGGCGAACTGCAGAAG

GGAAACGAACTGGCCCTGCCCTCCAAATATGTGAACTTCCTGTACCTGGCCAGCCAC

TATGAGAAGCTGAAGGGCTCCCCCGAGGATAATGAGCAGAAACAGCTGTTTGTGGA

ACAGCACAAGCACTACCTGGACGAGATCATCGAGCAGATCAGCGAGTTCTCCAAGA

GAGTGATCCTGGCCGACGCTAATCTGGACAAAGTGCTGTCCGCCTACAACAAGCAC

CGGGATAAGCCCATCAGAGAGCAGGCCGAGAATATCATCCACCTGTTTACCCTGAC

CAATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACagcgctGGAGGAGG

TGGAAGCGGAGGAGGAGGAAGCGGAGGAGGAGGTAGCggacctaagaaaaagaggaaggtggcg gccgctgctag
``` pSAMca063 dCas9(K1153-vp64, 3XGS) - AA (SEQ ID NO: 121)

```
DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA
```

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYDEND

KLIREVKVITLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYSVLVVAKVEKGKGGGGSGGGGSGGGGSGRADALDDFDLDM

LGSDALDDFDLDMLGSDALDDFDLDMLGSDALDDFDLDMLINGGGGSGGGGSGGGGS

SKKLKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEIIEQIS

EFSKRVILADANLDKVLSAYNKHRDKPIREQAENIIHLFTLTNLGAPAAFKYFDTTIDRK

RYTSTKEVLDATLIHQSITGLYETRIDLSQLGGDSAGGGGSGGGGSGGGGSGPKKKRKV

AAAA pSAMca064 dCas9(K1153-P65, 1XGS) - DNA (SEQ ID NO: 122)
GACAAGAAGTACAGCATCGGCCTGGCCATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAA

GAAGCACGAGCGGCACCCCATCTTCGGCAACATCGTGGACGAGGTGGCCTACCACG

AGAAGTACCCCACCATCTACCACCTGAGAAAGAAACTGGTGGACAGCACCGACAAG

GCCGACCTGCGGCTGATCTATCTGGCCCTGGCCCACATGATCAAGTTCCGGGGCCAC

TTCCTGATCGAGGGCGACCTGAACCCCGACAACAGCGACGTGGACAAGCTGTTCAT

CCAGCTGGTGCAGACCTACAACCAGCTGTTCGAGGAAAACCCCATCAACGCCAGCG

GCGTGGACGCCAAGGCCATCCTGTCTGCCAGACTGAGCAAGAGCAGACGGCTGGAA

AATCTGATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGGCCGAGG

ATGCCAAACTGCAGCTGAGCAAGGACACCTACGACGACGACCTGGACAACCTGCTG

GCCCAGATCGGCGACCAGTACGCCGACCTGTTTCTGGCCGCCAAGAACCTGTCCGAC

GCCATCCTGCTGAGCGACATCCTGAGAGTGAACACCGAGATCACCAAGGCCCCCCT

GAGCGCCTCTATGATCAAGAGATACGACGAGCACCACCAGGACCTGACCCTGCTGA

AAGCTCTCGTGCGGCAGCAGCTGCCTGAGAAGTACAAAGAGATTTTCTTCGACCAG

```
AGCAAGAACGGCTACGCCGGCTACATTGACGGCGGAGCCAGCCAGGAAGAGTTCTA

CAAGTTCATCAAGCCCATCCTGGAAAAGATGGACGGCACCGAGGAACTGCTCGTGA

AGCTGAACAGAGAGGACCTGCTGCGGAAGCAGCGGACCTTCGACAACGGCAGCATC

CCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCA

TCCCCTACTACGTGGGCCCTCTGGCCAGGGGAAACAGCAGATTCGCCTGGATGACC

AGAAAGAGCGAGGAAACCATCACCCCCTGGAACTTCGAGGAAGTGGTGGACAAGG

GCGCTTCCGCCCAGAGCTTCATCGAGCGGATGACCAACTTCGATAAGAACCTGCCCA

ACGAGAAGGTGCTGCCCAAGCACAGCCTGCTGTACGAGTACTTCACCGTGTATAAC

GAGCTGACCAAAGTGAAATACGTGACCGAGGGAATGAGAAAGCCCGCCTTCCTGAG

CGGCGAGCAGAAAAAGGCCATCGTGGACCTGCTGTTCAAGACCAACCGGAAAGTGA

CCGTGAAGCAGCTGAAAGAGGACTACTTCAAGAAAATCGAGTGCTTCGACTCCGTG

GAAATCTCCGGCGTGGAAGATCGGTTCAACGCCTCCCTGGGCACATACCACGATCTG

CTGAAAATTATCAAGGACAAGGACTTCCTGGACAATGAGGAAAACGAGGACATTCT

GGAAGATATCGTGCTGACCCTGACACTGTTTGAGGACAGAGAGATGATCGAGGAAC

GGCTGAAAACCTATGCCCACCTGTTCGACGACAAAGTGATGAAGCAGCTGAAGCGG

CGGAGATACACCGGCTGGGGCAGGCTGAGCCGGAAGCTGATCAACGGCATCCGGGA

CAAGCAGTCCGGCAAGACAATCCTGGATTTCCTGAAGTCCGACGGCTTCGCCAACA

GAAACTTCATGCAGCTGATCCACGACGACAGCCTGACCTTTAAAGAGGACATCCAG

AAAGCCCAGGTGTCCGGCCAGGGCGATAGCCTGCACGAGCACATTGCCAATCTGGC

CGGCAGCCCCGCCATTAAGAAGGGCATCCTGCAGACAGTGAAGGTGGTGGACGAGC

TCGTGAAAGTGATGGGCCGGCACAAGCCCGAGAACATCGTGATCGAAATGGCCAGA

GAGAACCAGACCACCCAGAAGGGACAGAAGAACAGCCGCGAGAGAATGAAGCGGA

TCGAAGAGGGCATCAAAGAGCTGGGCAGCCAGATCCTGAAAGAACACCCCGTGGA

AAACACCCAGCTGCAGAACGAGAAGCTGTACCTGTACTACCTGCAGAATGGGCGGG

ATATGTACGTGGACCAGGAACTGGACATCAACCGGCTGTCCGACTACGATGTGGACg cTATCGTGCCTCAGAGCTTTCTGAAGGACGACTCCATCGACAACAAGGTGCTGACCA

GAAGCGACAAGAACCGGGGCAAGAGCGACAACGTGCCCTCCGAAGAGGTCGTGAA

GAAGATGAAGAACTACTGGCGGCAGCTGCTGAACGCCAAGCTGATTACCCAGAGAA

AGTTCGACAATCTGACCAAGGCCGAGAGAGGCGGCCTGAGCGAACTGGATAAGGCC

GGCTTCATCAAGAGACAGCTGGTGGAAACCCGGCAGATCACAAAGCACGTGGCACA

GATCCTGGACTCCCGGATGAACACTAAGTACGACGAGAATGACAAGCTGATCCGGG

AAGTGAAAGTGATCACCCTGAAGTCCAAGCTGGTGTCCGATTTCCGGAAGGATTTCC

AGTTTTACAAAGTGCGCGAGATCAACAACTACCACCACGCCCACGACGCCTACCTG

AACGCCGTCGTGGGAACCGCCCTGATCAAAAAGTACCCTAAGCTGGAAAGCGAGTT

CGTGTACGGCGACTACAAGGTGTACGACGTGCGGAAGATGATCGCCAAGAGCGAGC

AGGAAATCGGCAAGGCTACCGCCAAGTACTTCTTCTACAGCAACATCATGAACTTTT

TCAAGACCGAGATTACCCTGGCCAACGGCGAGATCCGGAAGCGGCCTCTGATCGAG

ACAAACGGCGAAACCGGGGAGATCGTGTGGGATAAGGGCCGGGATTTTGCCACCGT

GCGGAAAGTGCTGAGCATGCCCCAAGTGAATATCGTGAAAAAGACCGAGGTGCAGA
```

```
CAGGCGGCTTCAGCAAAGAGTCTATCCTGCCCAAGAGGAACAGCGATAAGCTGATC

GCCAGAAAGAAGGACTGGGACCCTAAGAAGTACGGCGGCTTCGACAGCCCCACCGT

GGCCTATTCTGTGCTGGTGGTGGCCAAAGTGGAAAAGGGCAAGGGAGGGGGAGGCA

GCCCTTCAGGGCAGATCAGCAACCAGGCCCTGGCTCTGGCCCCTAGCTCCGCTCCAG

TGCTGGCCCAGACTATGGTGCCCTCTAGTGCTATGGTGCCTCTGGCCCAGCCACCTG

CTCCAGCCCCTGTGCTGACCCCAGGACCACCCCAGTCACTGAGCGCTCCAGTGCCCA

AGTCTACACAGGCCGGCGAGGGGACTCTGAGTGAAGCTCTGCTGCACCTGCAGTTC

GACGCTGATGAGGACCTGGGAGCTCTGCTGGGGAACAGCACCGATCCCGGAGTGTT

CACAGATCTGGCCTCCGTGGACAACTCTGAGTTTCAGCAGCTGCTGAATCAGGGCGT

GTCCATGTCTCATAGTACAGCCGAACCAATGCTGATGGAGTACCCCGAAGCCATTAC

CCGGCTGGTGACCGGCAGCCAGCGGCCCCCCGACCCCGCTCCAACTCCCCTGGGAA

CCAGCGGCCTGCCTAATGGGCTGTCCGGAGATGAAGACTTCTCAAGCATCGCTGATA

TGGACTTTAGTGCCCTGCTGTCACAGATTTCCTCTAGTGGGCAGGGAGGGGGGGCA

GCTCCAAGAAACTGAAGAGTGTGAAAGAGCTGCTGGGGATCACCATCATGGAAAGA

AGCAGCTTCGAGAAGAATCCCATCGACTTTCTGGAAGCCAAGGGCTACAAAGAAGT

GAAAAAGGACCTGATCATCAAGCTGCCTAAGTACTCCCTGTTCGAGCTGGAAAACG

GCCGGAAGAGAATGCTGGCCTCTGCCGGCGAACTGCAGAAGGGAAACGAACTGGCC

CTGCCCTCCAAATATGTGAACTTCCTGTACCTGGCCAGCCACTATGAGAAGCTGAAG

GGCTCCCCCGAGGATAATGAGCAGAAACAGCTGTTTGTGGAACAGCACAAGCACTA

CCTGGACGAGATCATCGAGCAGATCAGCGAGTTCTCCAAGAGAGTGATCCTGGCCG

ACGCTAATCTGGACAAAGTGCTGTCCGCCTACAACAAGCACCGGGATAAGCCCATC

AGAGAGCAGGCCGAGAATATCATCCACCTGTTTACCCTGACCAATCTGGGAGCCCCT

GCCGCCTTCAAGTACTTTGACACCACCATCGACCGGAAGAGGTACACCAGCACCAA

AGAGGTGCTGGACGCCACCCTGATCCACCAGAGCATCACCGGCCTGTACGAGACAC

GGATCGACCTGTCTCAGCTGGGAGGCGACAgcgctGGAGGAGGTGGAAGCGGAGGAGG

AGGAAGCGGAGGAGGAGGTAGCggacctaagaaaaagaggaaggtggcggccgct pSAMca064 dCas9(K1153-P65, 1XGS) - AA
                                                  (SEQ ID NO: 123)
DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIEMARENQTTQ

KGQKNSRERMKRIEEGIKELGSQILKEHPVENTQLQNEKLYYYLQNGRDMYVDQELDI
```

NRLSDYDVDAIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYDEND

KLIREVKVITLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYSVLVVAKVEKGKGGGGSPSGQISNQALALAPSSAPVLAQTMV

PSSAMVPLAQPPAPAPVLTPGPPQSLSAPVPKSTQAGEGTLSEALLHLQFDADEDLGALL

GNSTDPGVFTDLASVDNSEFQQLLNQGVSMSHSTAEPMLMEYPEAITRLVTGSQRPPDP

APTPLGTSGLPNGLSGDEDFSSIADMDFSALLSQISSSGQGGGGSSKKLKSVKELLGITIM

ERSSFEKNPIDFLEAKGYKEVKKDLIIKLPKYSLFELENGRKRMLASAGELQKGNELALP

SKYVNFLYLASHYEKLKGSPEDNEQKQLFVEQHKHYLDEIIEQISEFSKRVILADANLDK

VLSAYNKHRDKPIREQAENIIHLFTLTNLGAPAAFKYFDTTIDRKRYTSTKEVLDATLIHQ

SITGLYETRIDLSQLGGDSAGGGGSGGGGSGGGGSGPKKKRKVAAA pSAMca065 dCas9(K1153-P65, 3XGS) - DNA (SEQ ID NO: 124)

atgGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACA

GCGGCGAAACAGCCGAGGCCACCCGGCTGAAGAGAACCGCCAGAAGAAGATACAC

CAGACGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGAT

AAGAAGCACGAGCGGCACCCCATCTTCGGCAACATCGTGGACGAGGTGGCCTACCA

CGAGAAGTACCCCACCATCTACCACCTGAGAAAGAAACTGGTGGACAGCACCGACA

AGGCCGACCTGCGGCTGATCTATCTGGCCCTGGCCCACATGATCAAGTTCCGGGGCC

ACTTCCTGATCGAGGGCGACCTGAACCCCGACAACAGCGACGTGGACAAGCTGTTC

ATCCAGCTGGTGCAGACCTACAACCAGCTGTTCGAGGAAAACCCCATCAACGCCAG

CGGCGTGGACGCCAAGGCCATCCTGTCTGCCAGACTGAGCAAGAGCAGACGGCTGG

AAAATCTGATCGCCCAGCTGCCCGGCGAGAAGAAGAATGGCCTGTTCGGCAACCTG

ATTGCCCTGAGCCTGGGCCTGACCCCCAACTTCAAGAGCAACTTCGACCTGGCCGAG

GATGCCAAACTGCAGCTGAGCAAGGACACCTACGACGACGACCTGGACAACCTGCT

GGCCCAGATCGGCGACCAGTACGCCGACCTGTTTCTGGCCGCCAAGAACCTGTCCG

ACGCCATCCTGCTGAGCGACATCCTGAGAGTGAACACCGAGATCACCAAGGCCCCC

CTGAGCGCCTCTATGATCAAGAGATACGACGAGCACCACCAGGACCTGACCCTGCT

GAAAGCTCTCGTGCGGCAGCAGCTGCCTGAGAAGTACAAAGAGATTTTCTTCGACC

AGAGCAAGAACGGCTACGCCGGCTACATTGACGGCGGAGCCAGCCAGGAAGAGTTC

TACAAGTTCATCAAGCCCATCCTGGAAAAGATGGACGGCACCGAGGAACTGCTCGT

GAAGCTGAACAGAGAGGACCTGCTGCGGAAGCAGCGGACCTTCGACAACGGCAGC

ATCCCCCACCAGATCCACCTGGGAGAGCTGCACGCCATTCTGCGGCGGCAGGAAGA

TTTTTACCCATTCCTGAAGGACAACCGGGAAAAGATCGAGAAGATCCTGACCTTCCG

CATCCCCTACTACGTGGGCCCTCTGGCCAGGGGAAACAGCAGATTCGCCTGGATGA

CCAGAAAGAGCGAGGAAACCATCACCCCCTGGAACTTCGAGGAAGTGGTGGACAA

-continued

```
GGGCGCTTCCGCCCAGAGCTTCATCGAGCGGATGACCAACTTCGATAAGAACCTGC
CCAACGAGAAGGTGCTGCCCAAGCACAGCCTGCTGTACGAGTACTTCACCGTGTAT
AACGAGCTGACCAAAGTGAAATACGTGACCGAGGGAATGAGAAAGCCCGCCTTCCT
GAGCGGCGAGCAGAAAAAGGCCATCGTGGACCTGCTGTTCAAGACCAACCGGAAA
GTGACCGTGAAGCAGCTGAAAGAGGACTACTTCAAGAAAATCGAGTGCTTCGACTC
CGTGGAAATCTCCGGCGTGGAAGATCGGTTCAACGCCTCCCTGGGCACATACCACG
ATCTGCTGAAAATTATCAAGGACAAGGACTTCCTGGACAATGAGGAAAACGAGGAC
ATTCTGGAAGATATCGTGCTGACCCTGACACTGTTTGAGGACAGAGAGATGATCGA
GGAACGGCTGAAAACCTATGCCCACCTGTTCGACGACAAAGTGATGAAGCAGCTGA
AGCGGCGGAGATACACCGGCTGGGGCAGGCTGAGCCGGAAGCTGATCAACGGCATC
CGGGACAAGCAGTCCGGCAAGACAATCCTGGATTTCCTGAAGTCCGACGGCTTCGC
CAACAGAAACTTCATGCAGCTGATCCACGACGACAGCCTGACCTTTAAAGAGGACA
TCCAGAAAGCCCAGGTGTCCGGCCAGGGCGATAGCCTGCACGAGCACATTGCCAAT
CTGGCCGGCAGCCCCGCCATTAAGAAGGGCATCCTGCAGACAGTGAAGGTGGTGGA
CGAGCTCGTGAAAGTGATGGGCCGGCACAAGCCCGAGAACATCGTGATCGAAATGG
CCAGAGAGAACCAGACCACCCAGAAGGGACAGAAGAACAGCCGCGAGAGAATGAA
GCGGATCGAAGAGGGCATCAAAGAGCTGGGCAGCCAGATCCTGAAAGAACACCCC
GTGGAAAACACCCAGCTGCAGAACGAGAAGCTGTACCTGTACTACCTGCAGAATGG
GCGGGATATGTACGTGGACCAGGAACTGGACATCAACCGGCTGTCCGACTACGATG
TGGACgcTATCGTGCCTCAGAGCTTTCTGAAGGACGACTCCATCGACAACAAGGTGC
TGACCAGAAGCGACAAGAACCGGGGCAAGAGCGACAACGTGCCCTCCGAAGAGGT
CGTGAAGAAGATGAAGAACTACTGGCGGCAGCTGCTGAACGCCAAGCTGATTACCC
AGAGAAAGTTCGACAATCTGACCAAGGCCGAGAGAGGCGGCCTGAGCGAACTGGAT
AAGGCCGGCTTCATCAAGAGACAGCTGGTGGAAACCCGGCAGATCACAAAGCACGT
GGCACAGATCCTGGACTCCCGGATGAACACTAAGTACGACGAGAATGACAAGCTGA
TCCGGGAAGTGAAAGTGATCACCCTGAAGTCCAAGCTGGTGTCCGATTTCCGGAAG
GATTTCCAGTTTTACAAAGTGCGCGAGATCAACAACTACCACCACGCCCACGACGCC
TACCTGAACGCCGTCGTGGGAACCGCCCTGATCAAAAAGTACCCTAAGCTGGAAAG
CGAGTTCGTGTACGGCGACTACAAGGTGTACGACGTGCGGAAGATGATCGCCAAGA
GCGAGCAGGAAATCGGCAAGGCTACCGCCAAGTACTTCTTCTACAGCAACATCATG
AACTTTTTCAAGACCGAGATTACCCTGGCCAACGGCGAGATCCGGAAGCGGCCTCT
GATCGAGACAAACGGCGAAACCGGGGAGATCGTGTGGGATAAGGGCCGGGATTTTG
CCACCGTGCGGAAAGTGCTGAGCATGCCCCAAGTGAATATCGTGAAAAAGACCGAG
GTGCAGACAGGCGGCTTCAGCAAAGAGTCTATCCTGCCCAAGAGGAACAGCGATAA
GCTGATCGCCAGAAAGAAGGACTGGGACCCTAAGAAGTACGGCGGCTTCGACAGCC
CCACCGTGGCCTATTCTGTGCTGGTGGTGGCCAAAGTGGAAAAGGGCAAGGGCGGG
GGAGGCTCCGGTGGTGGGGGCAGCGGAGGGGGGGCAGCCCTTCAGGGCAGATCA
GCAACCAGGCCCTGGCTCTGGCCCCTAGCTCCGCTCCAGTGCTGGCCCAGACTATGG
TGCCCTCTAGTGCTATGGTGCCTCTGGCCCAGCCACCTGCTCCAGCCCCTGTGCTGA
CCCCAGGACCACCCCAGTCACTGAGCGCTCCAGTGCCCAAGTCTACACAGGCCGGC
GAGGGGACTCTGAGTGAAGCTCTGCTGCACCTGCAGTTCGACGCTGATGAGGACCT
```

```
-continued
GGGAGCTCTGCTGGGGAACAGCACCGATCCCGGAGTGTTCACAGATCTGGCCTCCG

TGGACAACTCTGAGTTTCAGCAGCTGCTGAATCAGGGCGTGTCCATGTCTCATAGTA

CAGCCGAACCAATGCTGATGGAGTACCCCGAAGCCATTACCCGGCTGGTGACCGGC

AGCCAGCGGCCCCCCGACCCCGCTCCAACTCCCCTGGGAACCAGCGGCCTGCCTAAT

GGGCTGTCCGGAGATGAAGACTTCTCAAGCATCGCTGATATGGACTTTAGTGCCCTG

CTGTCACAGATTTCCTCTAGTGGGCAGGGCGGGGAGGCTCCGGTGGTGGGGCAG

CGGAGGGGGGGCAGCTCCAAGAAACTGAAGAGTGTGAAAGAGCTGCTGGGGATC

ACCATCATGGAAAGAAGCAGCTTCGAGAAGAATCCCATCGACTTTCTGGAAGCCAA

GGGCTACAAAGAAGTGAAAAAGGACCTGATCATCAAGCTGCCTAAGTACTCCCTGT

TCGAGCTGGAAAACGGCCGGAAGAGAATGCTGGCCTCTGCCGGCGAACTGCAGAAG

GGAAACGAACTGGCCCTGCCCTCCAAATATGTGAACTTCCTGTACCTGGCCAGCCAC

TATGAGAAGCTGAAGGGCTCCCCCGAGGATAATGAGCAGAAACAGCTGTTTGTGGA

ACAGCACAAGCACTACCTGGACGAGATCATCGAGCAGATCAGCGAGTTCTCCAAGA

GAGTGATCCTGGCCGACGCTAATCTGGACAAAGTGCTGTCCGCCTACAACAAGCAC

CGGGATAAGCCCATCAGAGAGCAGGCCGAGAATATCATCCACCTGTTTACCCTGAC

CAATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACAgcgctGGAGGAGG

TGGAAGCGGAGGAGGAGGAAGCGGAGGAGGAGGTAGCggacctaagaaaaagaggaaggtggcg gccgct pSAMca065 dCas9(K1153-P65, 3XGS) - AA
                                                          (SEQ ID NO: 125)
MDKKYSIGLAIGTNSVGWAVITDEYKVPSKKFKVLGNTDRHSIKKNLIGALLF

DSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEG

DLNPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEIFF

DQSKNGYAGYIDGGASQEEFYKFIKPILEKMDGTEELLVKLNREDLLRKQRTFDNGSIPH

QIHLGELHAILRRQEDFYPFLKDNREKIEKILTFRIPYYVGPLARGNSRFAWMTRKSEETI

TPWNFEEVVDKGASAQSFIERMTNFDKNLPNEKVLPKHSLLYEYFTVYNELTKVKYVTE

GMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDSLTFKEDIQKA

QVSGQGDSLHEHIANLAGSPAIKKGILQTVKVVDELVKVMGRHKPENIVIEMARENQTT

QKGQKNSRERMKRIEEGIKELGSQILKEHPVENTQLQNEKLYLYYLQNGRDMYVDQEL

DINRLSDYDVDAIVPQSFLKDDSIDNKVLTRSDKNRGKSDNVPSEEVVKKMKNYWRQL

LNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKL

ESEFVYGDYKVYDVRKMIAKSEQEIGKATAKYFFYSNIMNFFKTEITLANGEIRKRPLIET

NGETGEIVWDKGRDFATVRKVLSMPQVNIVKKTEVQTGGFSKESILPKRNSDKLIARKK
```

DWDPKKYGGFDSPTVAYSVLVVAKVEKGKGGGGSGGGGSGGGGSPSGQISNQALALA

PSSAPVLAQTMVPSSAMVPLAQPPAPAPVLTPGPPQSLSAPVPKSTQAGEGTLSEALLHL

QFDADEDLGALLGNSTDPGVFTDLASVDNSEFQQLLNQGVSMSHSTAEPMLMEYPEAIT

RLVTGSQRPPDPAPTPLGTSGLPNGLSGDEDFSSIADMDFSALLSQISSSGQGGGGSGGG

GSGGGGSSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHKH

YLDEIIEQISEFSKRVILADANLDKVLSAYNKHRDKPIREQAENIIHLFTLTNLGAPAAFKY

FDTTIDRKRYTSTKEVLDATLIHQSITGLYETRIDLSQLGGDSAGGGGSGGGGSGGGGSG

PKKKRKVAAA

Example 6: New Catalytically Inactive dCas9 Proteins

In another aspect of the invention, novel dCas9 mutants are created. Catalytically inactive dCas9 are generated by combination of D10A and N863A mutations, rather than D10A and H840A mutations.

The catalytically inactive dCas9 mutant used in the literature and Applicants' previous experiments was generated by mutations D10A and H840A within the wildtype Cas9 protein. From the crystal structure, Applicants made the observation that H840A fails to form a functional DNA-nickase. This result suggests that the H840A mutation has a greater dysfunctional effect on the Cas9 protein that originally hypothesized; the original theory being that H840A would result in loss of a single nucleophilic site, with no other effects. If the H840A mutation is disrupting other functions or conformational properties of the dCas9 protein, it stands to reason that a dCas9-activator fusion might be partially compromised by H840A. Thus, Applicants are interested in finding other mutations within the HNH domain which could knock out HNH nuclease activity, without disrupting other Cas9 functions. The Cas9/RNA/DNA crystal structure manuscript identifies mutation N863A as precisely such a mutation: N863A knocks out Cas9 double stranded nuclease activity, but permits nickase activity, suggesting that the global function of N863A Cas9 is not fully disrupted. In light of this observation, Applicants have synthesized a double knockout D10A N863A Cas9 mutant for use as a dCas9-activator.

Corresponding Constructs
pSAMca041 dCas(N863A)-vp64

Sequence information for creating catalytically inactive dCas9 by combination of D10A and N863A mutations, rather than D10A and H840A mutations is provided below:

pSAMca041 dCas(N863A)-vp64 - DNA
(SEQ ID NO: 126)
atgGACAAGAAGTACAGCATCGGCCTGGCCATCGGCACCAACTCTGTGGG

CTGGGCCGTGATCACCGACGAGTACAAGGTGCCCAGCAAGAAATTCAAGG

TGCTGGGCAACACCGACCGGCACAGCATCAAGAAGAACCTGATCGGAGCC

CTGCTGTTCGACAGCGGCGAAACAGCCGAGGCCACCCGGCTGAAGAGAAC

CGCCAGAAGAAGATACACCAGACGGAAGAACCGGATCTGCTATCTGCAAG

AGATCTTCAGCAACGAGATGGCCAAGGTGGACGACAGCTTCTTCCACAGA

CTGGAAGAGTCCTTCCTGGTGGAAGAGGATAAGAAGCACGAGCGGCACCC

CATCTTCGGCAACATCGTGGACGAGGTGGCCTACCACGAGAAGTACCCCA

CCATCTACCACCTGAGAAAGAAACTGGTGGACAGCACCGACAAGGCCGAC

CTGCGGCTGATCTATCTGGCCCTGGCCCACATGATCAAGTTCCGGGGCCA

CTTCCTGATCGAGGGCGACCTGAACCCCGACAACAGCGACGTGGACAAGC

TGTTCATCCAGCTGGTGCAGACCTACAACCAGCTGTTCGAGGAAAACCCC

ATCAACGCCAGCGGCGTGGACGCCAAGGCCATCCTGTCTGCCAGACTGAG

CAAGAGCAGACGGCTGGAAAATCTGATCGCCCAGCTGCCCGGCGAGAAGA

AGAATGGCCTGTTCGGCAACCTGATTGCCCTGAGCCTGGGCCTGACCCCC

AACTTCAAGAGCAACTTCGACCTGGCCGAGGATGCCAAACTGCAGCTGAG

CAAGGACACCTACGACGACGACCTGGACAACCTGCTGGCCCAGATCGGCG

ACCAGTACGCCGACCTGTTTCTGGCCGCCAAGAACCTGTCCGACGCCATC

CTGCTGAGCGACATCCTGAGAGTGAACACCGAGATCACCAAGGCCCCCCT

GAGCGCCTCTATGATCAAGAGATACGACGAGCACCACCAGGACCTGACCC

TGCTGAAAGCTCTCGTGCGGCAGCAGCTGCCTGAGAAGTACAAAGAGATT

TTCTTCGACCAGAGCAAGAACGGCTACGCCGGCTACATTGACGGCGGAGC

CAGCCAGGAAGAGTTCTACAAGTTCATCAAGCCCATCCTGGAAAAGATGG

ACGGCACCGAGGAACTGCTCGTGAAGCTGAACAGAGAGGACCTGCTGCGG

AAGCAGCGGACCTTCGACAACGGCAGCATCCCCCACCAGATCCACCTGGG

AGAGCTGCACGCCATTCTGCGGCGGCAGGAAGATTTTTACCCATTCCTGA

AGGACAACCGGGAAAAGATCGAGAAGATCCTGACCTTCCGCATCCCCTAC

TACGTGGGCCCTCTGGCCAGGGGAAACAGCAGATTCGCCTGGATGACCAG

AAAGAGCGAGGAAACCATCACCCCCTGGAACTTCGAGGAAGTGGTGGACA

AGGGCGCTTCCGCCCAGAGCTTCATCGAGCGGATGACCAACTTCGATAAG

AACCTGCCCAACGAGAAGGTGCTGCCCAAGCACAGCCTGCTGTACGAGTA

CTTCACCGTGTATAACGAGCTGACCAAAGTGAAATACGTGACCGAGGGAA

TGAGAAAGCCCGCCTTCCTGAGCGGCGAGCAGAAAAAGGCCATCGTGGAC

CTGCTGTTCAAGACCAACCGGAAAGTGACCGTGAAGCAGCTGAAAGAGGA

CTACTTCAAGAAAATCGAGTGCTTCGACTCCGTGGAAATCTCCGGCGTGG

AAGATCGGTTCAACGCCTCCCTGGGCACATACCACGATCTGCTGAAAATT

ATCAAGGACAAGGACTTCCTGGACAATGAGGAAAACGAGGACATTCTGGA

-continued

```
AGATATCGTGCTGACCCTGACACTGTTTGAGGACAGAGAGATGATCGAGG
AACGGCTGAAAACCTATGCCCACCTGTTCGACGACAAAGTGATGAAGCAG
CTGAAGCGGCGGAGATACACCGGCTGGGGCAGGCTGAGCCGGAAGCTGAT
CAACGGCATCCGGGACAAGCAGTCCGGCAAGACAATCCTGGATTTCCTGA
AGTCCGACGGCTTCGCCAACAGAAACTTCATGCAGCTGATCCACGACGAC
AGCCTGACCTTTAAAGAGGACATCCAGAAAGCCCAGGTGTCCGGCCAGGG
CGATAGCCTGCACGAGCACATTGCCAATCTGGCCGGCAGCCCCGCCATTA
AGAAGGGCATCCTGCAGACAGTGAAGGTGGTGGACGAGCTCGTGAAAGTG
ATGGGCCGGCACAAGCCCGAGAACATCGTGATCGAAATGGCCAGAGAGAA
CCAGACCACCCAGAAGGGACAGAAGAACAGCCGCGAGAGAATGAAGCGGA
TCGAAGAGGGCATCAAAGAGCTGGGCAGCCAGATCCTGAAAGAACACCCC
GTGGAAAACACCCAGCTGCAGAACGAGAAGCTGTACCTGTACTACCTGCA
GAATGGGCGGGATATGTACGTGGACCAGGAACTGGACATCAACCGGCTGT
CCGACTACGATGTGGACCACATCGTGCCTCAGAGCTTTCTGAAGGACGAC
TCCATCGACAACAAGGTGCTGACCAGAAGCGACAAGGCCCGGGGCAAGAG
CGACAACGTGCCCTCCGAAGAGGTCGTGAAGAAGATGAAGAACTACTGGC
GGCAGCTGCTGAACGCCAAGCTGATTACCCAGAGAAAGTTCGACAATCTG
ACCAAGGCCGAGAGAGGCGGCCTGAGCGAACTGGATAAGGCCGGCTTCAT
CAAGAGACAGCTGGTGGAAACCCGGCAGATCACAAAGCACGTGGCACAGA
TCCTGGACTCCCGGATGAACACTAAGTACGACGAGAATGACAAGCTGATC
CGGGAAGTGAAAGTGATCACCCTGAAGTCCAAGCTGGTGTCCGATTTCCG
GAAGGATTTCCAGTTTTACAAAGTGCGCGAGATCAACAACTACCACCACG
CCCACGACGCCTACCTGAACGCCGTCGTGGGAACCGCCCTGATCAAAAAG
TACCCTAAGCTGGAAAGCGAGTTCGTGTACGGCGACTACAAGGTGTACGA
CGTGCGGAAGATGATCGCCAAGAGCGAGCAGGAAATCGGCAAGGCTACCG
CCAAGTACTTCTTCTACAGCAACATCATGAACTTTTTCAAGACCGAGATT
ACCCTGGCCAACGGCGAGATCCGGAAGCGGCCTCTGATCGAGACAAACGG
CGAAACCGGGGAGATCGTGTGGGATAAGGGCCGGGATTTTGCCACCGTGC
GGAAAGTGCTGAGCATGCCCCAAGTGAATATCGTGAAAAAGACCGAGGTG
CAGACAGGCGGCTTCAGCAAAGAGTCTATCCTGCCCAAGAGGAACAGCGA
TAAGCTGATCGCCAGAAAGAAGGACTGGGACCCTAAGAAGTACGGCGGCT
TCGACAGCCCCACCGTGGCCTATTCTGTGCTGGTGGTGGCCAAAGTGGAA
AAGGGCAAGTCCAAGAAACTGAAGAGTGTGAAAGAGCTGCTGGGGATCAC
CATCATGGAAAGAAGCAGCTTCGAGAAGAATCCCATCGACTTTCTGGAAG
CCAAGGGCTACAAAGAAGTGAAAAAGGACCTGATCATCAAGCTGCCTAAG
TACTCCCTGTTCGAGCTGGAAAACGGCCGGAAGAGAATGCTGGCCTCTGC
CGGCGAACTGCAGAAGGGAAACGAACTGGCCCTGCCCTCCAAATATGTGA
ACTTCCTGTACCTGGCCAGCCACTATGAGAAGCTGAAGGGCTCCCCCGAG
GATAATGAGCAGAAACAGCTGTTTGTGGAACAGCACAAGCACTACCTGGA
CGAGATCATCGAGCAGATCAGCGAGTTCTCCAAGAGAGTGATCCTGGCCG
ACGCTAATCTGGACAAAGTGCTGTCCGCCTACAACAAGCACCGGGATAAG
```

-continued

```
CCCATCAGAGAGCAGGCCGAGAATATCATCCACCTGTTTACCCTGACCAA
TCTGGGAGCCCCTGCCGCCTTCAAGTACTTTGACACCACCATCGACCGGA
AGAGGTACACCAGCACCAAAGAGGTGCTGGACGCCACCCTGATCCACCAG
AGCATCACCGGCCTGTACGAGACACGGATCGACCTGTCTCAGCTGGGAGG
CGACagcgctGGAGGAGGTGGAAGCGGAGGAGGAGGAAGCGGAGGAGGAG
GTAGCggacctaagaaaaagaggaaggtggcggccgctggatccGGACGG
GCTGACGCATTGGACGATTTTGATCTGGATATGCTGGGAAGTGACGCCCT
CGATGATTTTGACCTTGACATGCTTGGTTCGGATGCCCTTGATGACTTTG
ACCTCGACATGCTCGGCAGTGACGCCCTTGATGATTTCGACCTGGACATG
CTGATTAAC
``` pSAMca041 dCas(N863A)-vp64 - amino acid
(SEQ ID NO: 127)

```
MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKARGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
```

-continued
SITGLYETRIDLSQLGGDSAGGGGSGGGGSGGGGSGPKKKRKVAAAGSGR

ADALDDFDLDMLGSDALDDFDLDMLGSDALDDFDLDMLGSDALDDFDLDM

LIN

Example 7: MS2 sgRNA Sequence Architecture-New MS2/dCas9/sgRNA Versions

Applicants generated additional 3' MS2 constructs and other MS2 sgRNA modifications to understand the effects of MS2 sgRNA sequence architecture. The experiments performed focused on two further ideas regarding the MS2 sgRNA sequence architecture.

Figure 7:
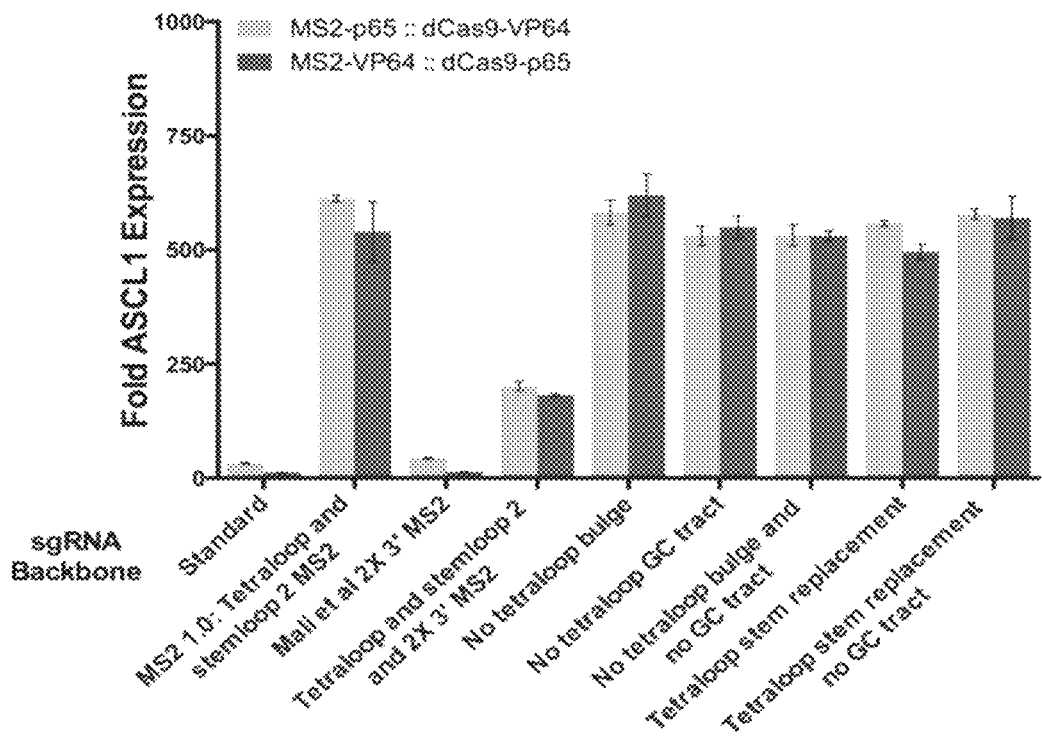
FIG. 7 shows effects of sgRNA modifications on ASCL1 activation. 3' MS2 and modified MS2 1.0 sgRNA architectures were tested for their ability to activate ASCL1.

First, the idea of placing the MS2 binding stems at the 3' end of the sgRNA, rather than inserting these binding sites into the native stem-loops of the sgRNA. The use of a pair of 3' MS2 binding sites had previously been described in Mali, Prashant, et al. "CAS9 transcriptional activators for target specificity screening and paired nickases for cooperative genome engineering." *Nature biotechnology* (2013)), though the system was found to perform more poorly than the standard dCas9-VP64/sgRNA activation system. Applicants found that an sgRNA, of their own design, with 2 MS2 binding sites at the 3' end of the sgRNA, as well as MS2 sites at both the tetraloop and stem-loop 2, activated both ASCL1 and MYOD1 at a higher level than the 3' MS2 sgRNA from Mali et al. (see FIG. 7) However, Applicants' MS2 1.0, with MS2 sites only at the tetraloop and stem-loop 2, was more potent than either of the 3' MS2 sgRNA architectures. (see FIG. 7)

Figure 8:
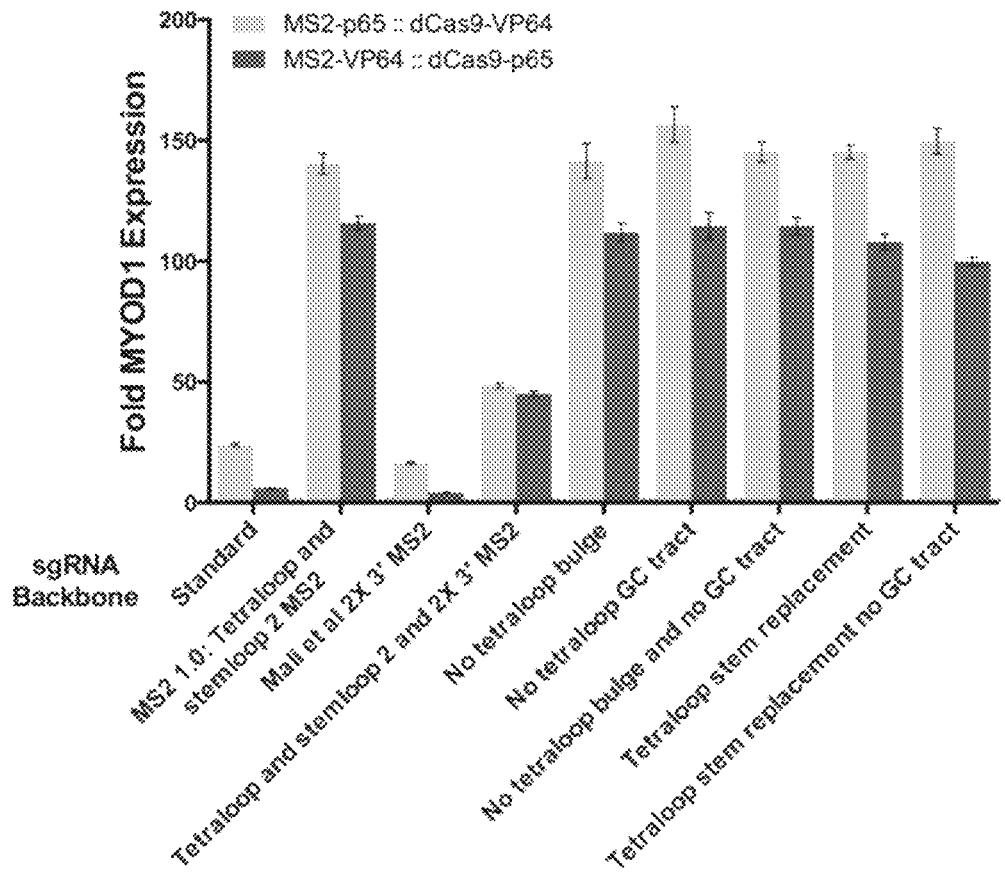
FIG. 8 shows effects of sgRNA modifications MYOD1 activation. 3' MS2 and modified MS2 1.0 sgRNA architectures were tested for their ability to activate ASCL1.
Figure 11:
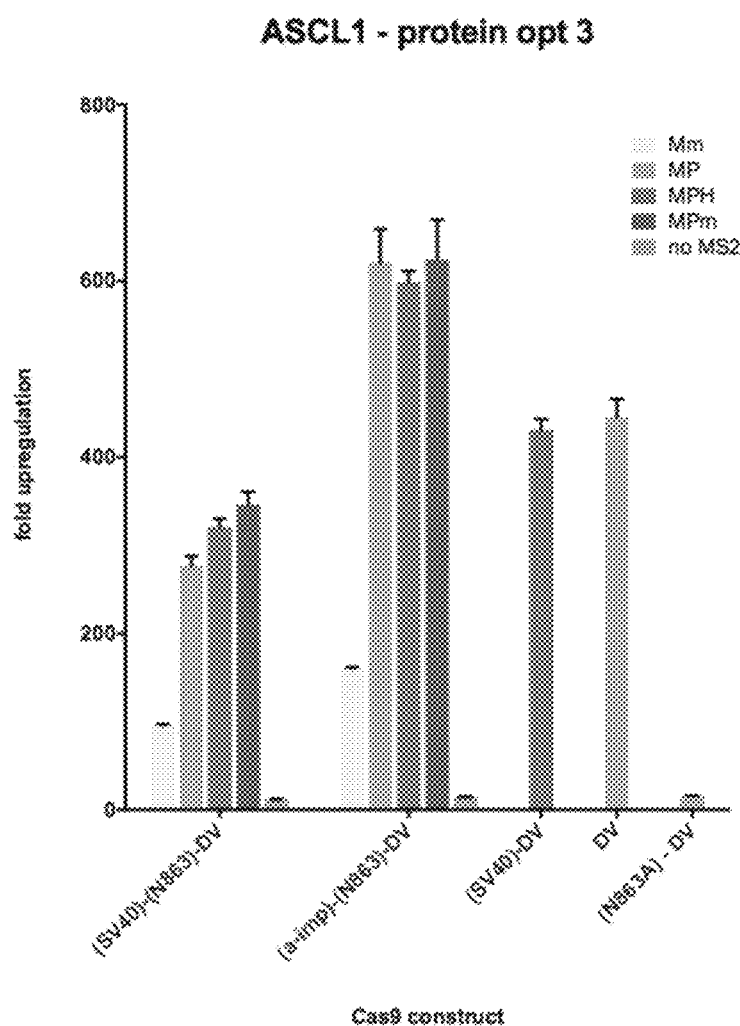
FIG. 11 shows a comparison of different NLS and point mutation dCas-VP64 architectures in combination with MS2 fused to individual or combined activation domains. SV40: SV40 NLS; a-imp: a-importin NLS; DV: dCas-SV40 NLS-VP64; Mm: MS2-ASCL1TAD; MP: MS2-p65; MPH: MS2-p65-HSF1; MPm: MS2-p65-ASCL1TAD. All dCas9 proteins contain D10A mutation and H840A (unless indicated otherwise).

Second, Applicants tested variations within the MS2 1.0 architectures. These modifications included but were not limited to removing the bulge from the MS2 1.0 binding site stem, removing the stabilizing GC tract that had been added to MS2 1.0, shortening the engineered stem by replacing the natural sgRNA stem with the stem of the MS2 binding site, as well as combinations of these approaches. These modifications had little effect on activation level for either ASCL1 or MYOD1, suggesting that the MS2 stem-loops are somewhat robust to structural alterations within the MS2/dCas9/sgRNA activation context. In addition to the tetraloop modifications shown in FIG. 8, equivalent modifications were also tested for the MS2 binding site at stem-loop 2, with similar results.

dCas9 Protein Modifications (NLS, N863A):

Applicants tested two hypotheses for improvement of the dCas9-activator protein. First, the addition of a second SV40 nuclear localization signal, in addition to the NLS contained in the dCas9 to VP64 linker, was examined as a method of improving dCas9 nuclear localization and transcriptional modulation activity. Placement of the second NLS at the N-terminus of the dCas9 was observed to increase activation in several contexts. The effect was diminished when the second NLS was placed at the C-terminus of the VP64 activation domain. Later experiments (FIGS. 11 and 12) would confirm these effects and suggest a possible improvement by use of an N-terminal alpha-importin NLS, rather than a second SV40 signal.

Figure 9:
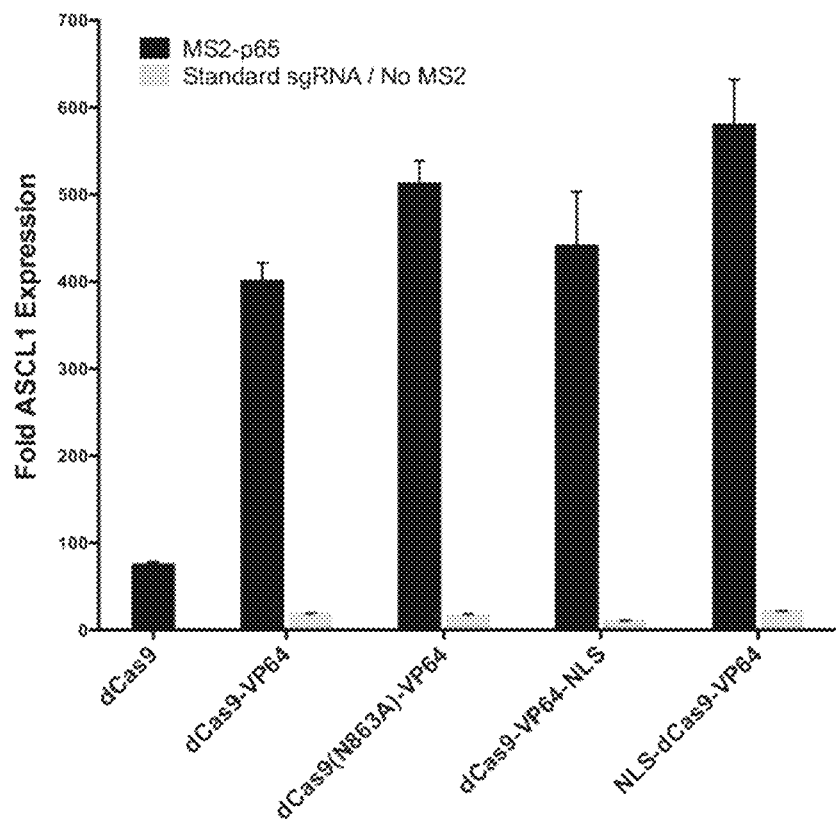
FIG. 9 shows effects of dCas9 NLS and N863A modifications on ASCL1 activation.
Figure 10:
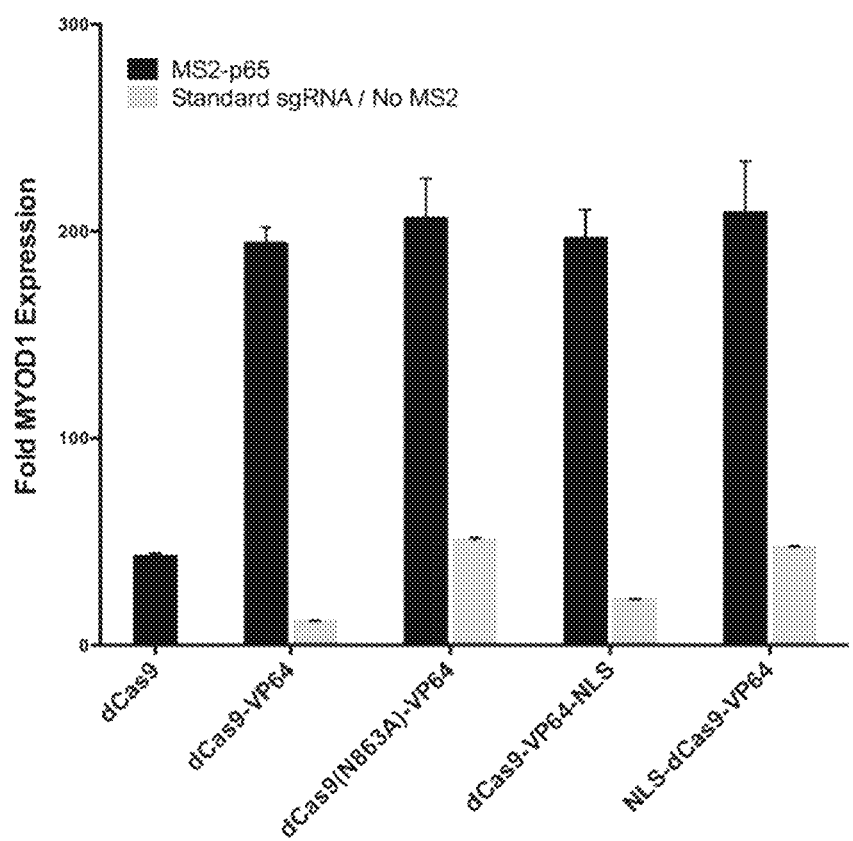
FIG. 10 shows effects of dCas9 NLS and N863A modifications on MYOD1 activation.

Second, Applicants created a version of dCas9 using the N863A mutation, demonstrated in Nishimasu et al., "Crystal structure of Cas9 in complex with guide RNA and target DNA." Cell. 2014 Feb. 27; 156(5):935-49, to be a functional nickase-creating mutation site. This mutation replaces the H840A mutation which was observed to be a suboptimal nickase-creating mutation, suggesting that the H840A mutation, though it can be used with the D10A mutation to abolish nuclease activity, is detrimental in some way to the conformation or functionality of the nickase or dCas9 protein. Applicants observed that the N863A dCas9 acted as a more potent activator protein in certain contexts as shown in FIGS. 9 and 10 for ASCL1 and MYOD1, respectively.

Figure 12:
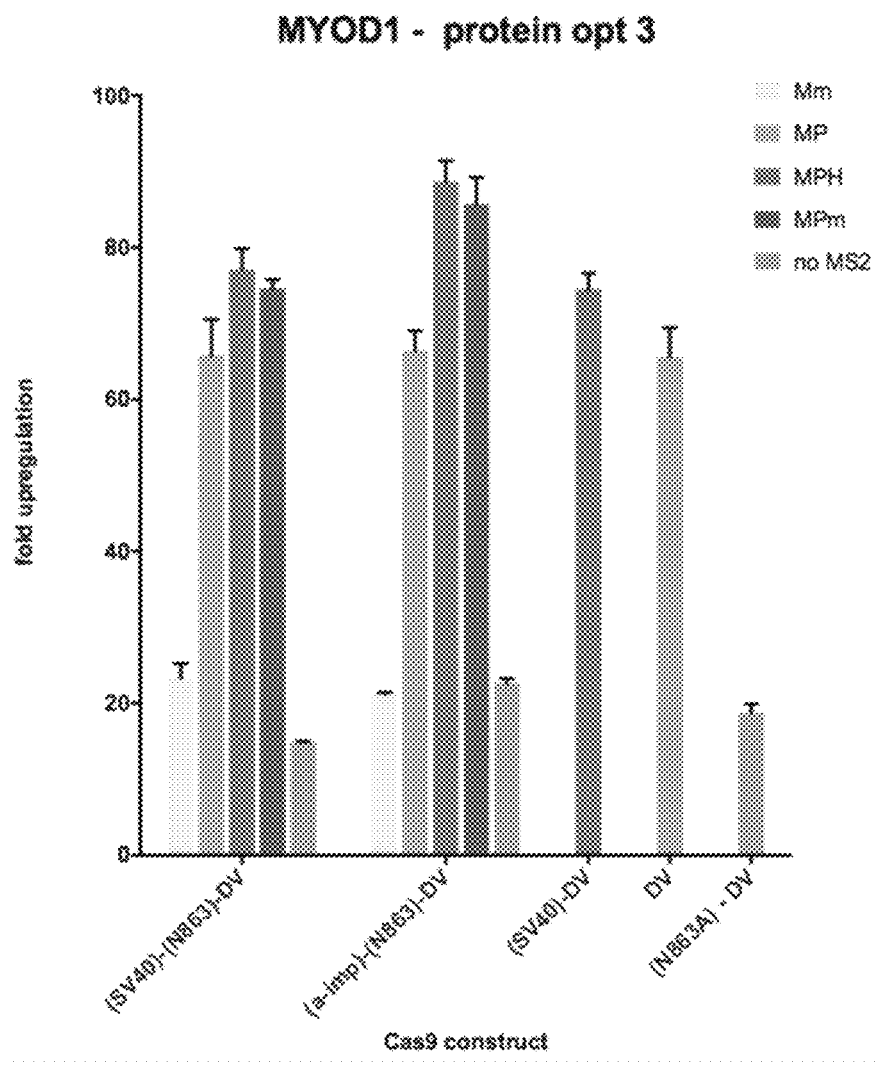
FIG. 12 shows a comparison of different NLS and point mutation dCas-VP64 architectures in combination with MS2 fused to individual or combined activation domains. SV40: SV40 NLS; a-imp: a-importin NLS; DV: dCas-SV40 NLS-VP64; Mm: MS2-MyodTAD; MP: MS2-p65; MPH: MS2-p65-HSF1; MPm: MS2-p65-MyodTAD. All dCas9 proteins contain D10A mutation and H840A (unless indicated otherwise).
Figure 13:
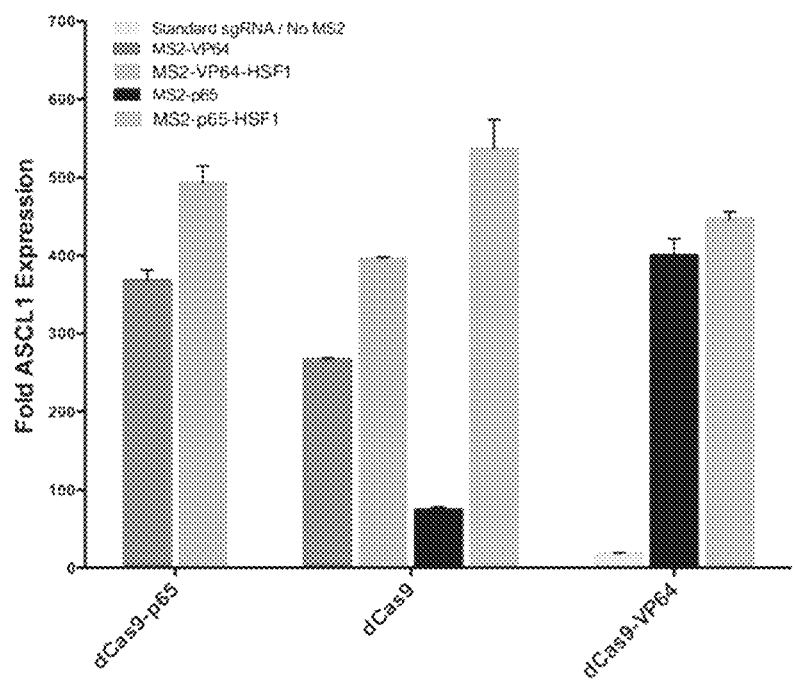
FIG. 13 shows MS2 double activator fusion proteins for ASCL1 activation. Comparisons of MS2-VP64 and MS2-p65 with and without an additional HSF1 activation domain fusion. The greatest relative improvement occurred for dCas9 without its own activation domain. This improvement is particularly important for the future use of the system in multimodal transcriptional modulation, wherein transcriptional modulation occurs only by way of the sgRNA and its aptamerized proteins, not the dCas9, allowing distinct guide sequences to target distinct functionalities.
Figure 14:
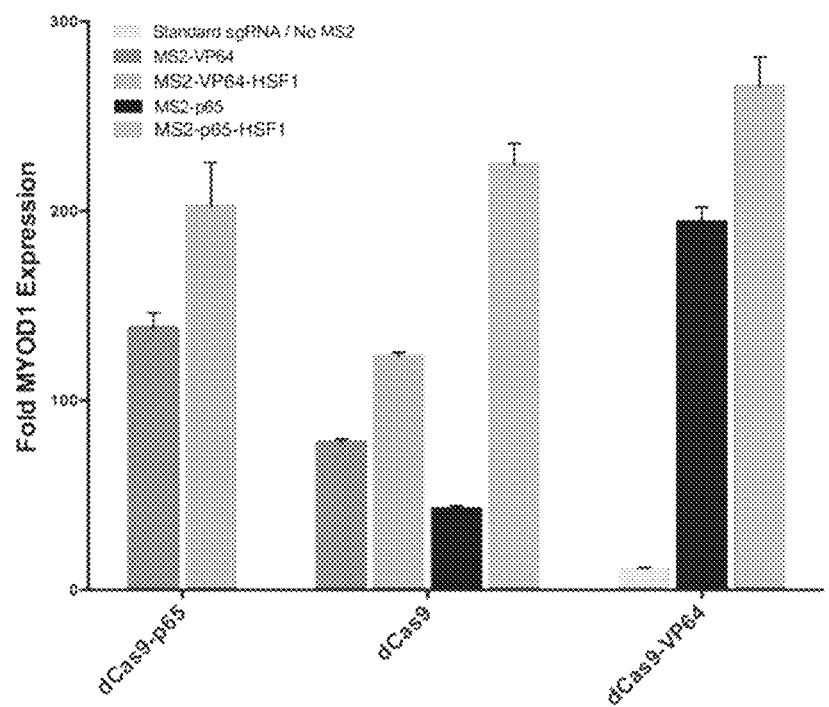
FIG. 14 shows MS2 double activator fusion proteins for MYOD1 activation.

New MS2 Activator Fusions Proteins (HSF1, MyoTAD):

Based on Applicants' previous finding that a combination of two different activation domains (P65 and VP64) in the same activator complex (dCas and MS2) yielded greater activation than either domain simply used twice, Applicants wanted to test the potential for synergy between different activation domains further. Applicants constructed fusion proteins of MS2 with two distinct activation domains—either P65 in combination with HSF1 activation domain or P65 in combination with MyoD transactivation domain. Applicants observed the fold upregulation in both ASCL1 and MYOD1 using constructs with different NLS and point mutation dCas-VP64 architectures in combination with MS2 fused to individual or combined activation domains. It was noticed that the addition of an a-importin NLS had a favorable effect on localizing the Cas9 to the nucleus and that the N863A mutation was an advantageous mutation to generate a potent activator (FIGS. 10 and 12). Applicants also determined that a combination of different activator domains had an increased effect. E.g., The construct with a p65-HSF1 fusion was found to be a more potent activator than the construct with p65 alone (FIGS. 13 and 14).

PP7-VP64 Activation:

In addition to the MS2 phage coat protein, which Applicants have employed, a number of phage coat proteins exhibit RNA sequence specific binding. Applicants designed and tested an orthogonal activation system using the RNA binding domain from the PP7 phage. This new system includes the usual (previously described) dCas9-activator protein, a PP7-activator fusion protein, and an sgRNA with PP7 binding sites integrated at the tetraloop and stem-loop 2. Applicants observed that the PP7 system functions equally as well as the MS2/dCas9/sgRNA activation system. These results suggest that the sgRNA RNA aptamer approach is generalizable and points to the future possibility of orthogonal modulation modalities using dCas9 and mutually exclusive RNA-binding proteins (such as MS2, PP7, qBeta, GA, and others).

Figure 15:
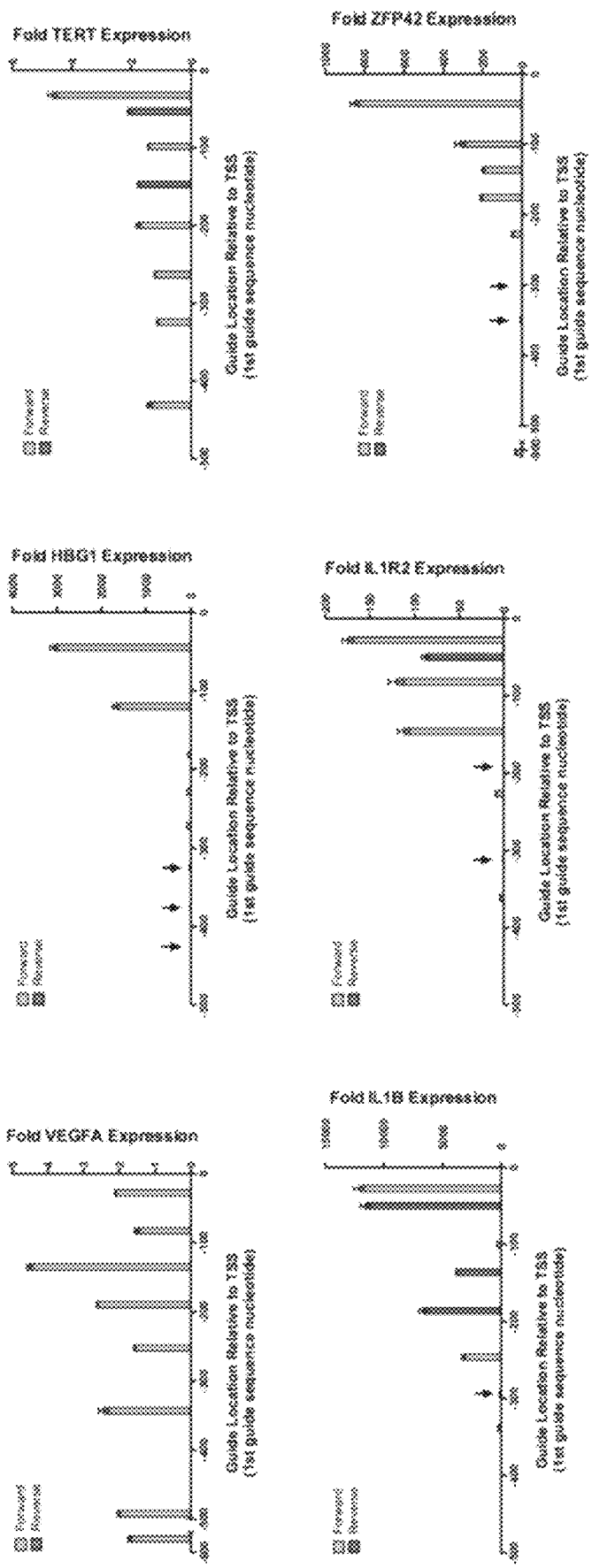
FIG. 15 shows fold expression levels activated by single sgRNA guide sequences for 12 difficult to modulate genes. All activation shown with MS2-p65-HSF1/SV40-dCas9-VP64 system. Guide locations are plotted relative to the TSS of each target.
Figure 15:
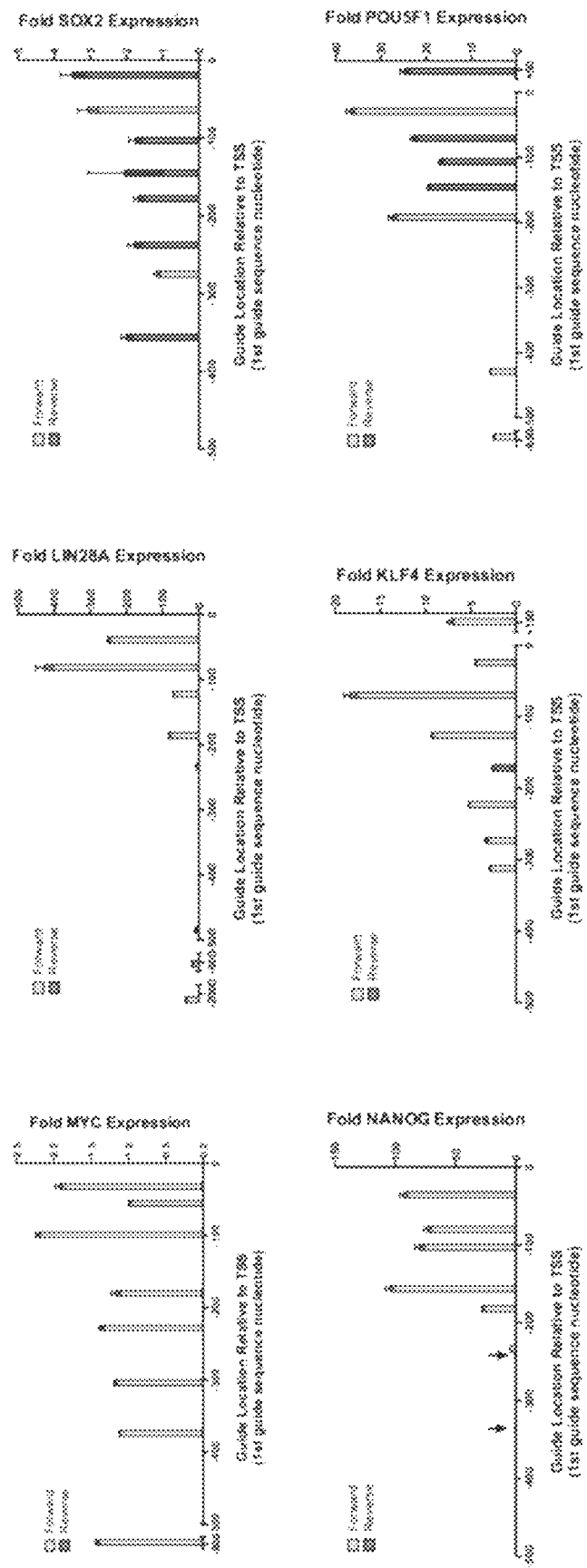

Target Diversity:

Difficult activation targets and sgRNA TSS proximity: Applicants' early work on CRISPR/Cas9 transcriptional modulation, as well as the published literature has found the majority of targets to be unamenable to activation by single sgRNA guides. Applicants selected 12 gene targets from the literature and Applicants own work which had previously proven difficult or intractable to dCas9 mediated activation. (see FIG. 15) Applicants attempted to activate each of these genes with the MS2-p65-HSF1/SV40-dCas9-VP64/sgRNA system using 1 of 8 guide sequences. Applicants observed significant activation for each of these difficult gene targets, with activation levels for the best guide ranging from 2 fold for MYC to >10,000 for IL1B. 8 of the 12 genes exhibited at least 15 fold expression. (see FIG. 15) For each guide sequence tested, the MS2/dCas9 system performed better than the standard dCas9-VP64 architecture, and no standard system fold expression was greater than 2 for any gene. (see FIG. 15) Additionally, Applicants observed that the success rate of guide sequences typically increased with closer proximity to the transcriptional start site (TSS) of the target gene. In a preferred embodiment of the invention, for particular targets, within 200 bp of the TSS is deemEd to be an advantageous window to select guide RNAs. This information could be useful for selection of sgRNA guide sequences for future experiments.

Figure 16:
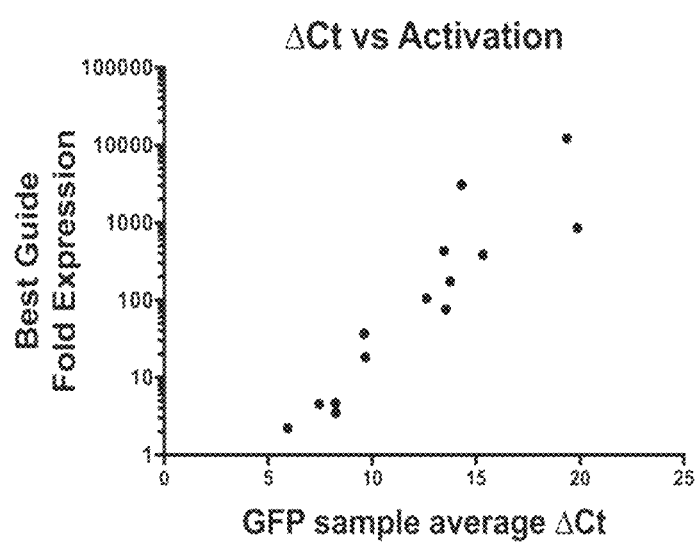
FIG. 16 shows a plot of the fold expression of the best guide sequence against the deltaCt value from qPCR for that gene in control samples for the difficult targets listed above.

Activation Vs. Basal Expression:

An open question in the field of artificial endogenous transcriptional modulation is why are some genes more amenable to activation than others? For the difficult targets listed above, Applicants plotted the fold expression of the best guide sequence against the deltaCt value from qPCR for that gene in control samples. These results suggest a strong inverse correlation between basal gene expression (higher deltaCt corresponds to lower basal expression) and maximal transcriptional activation by the MS2/dCas9/sgRNA system. (see FIG. 16)

Multiplexed Activation:

One important possible advantage of the ability of Applicants' system to provide robust activation with a single guide would be the capacity to easily activate a panel of genes simultaneously (by co-delivery to multiple guides for these genes), which would be intractable if a large number of guides would be required for activation of each gene alone.

Figure 17:
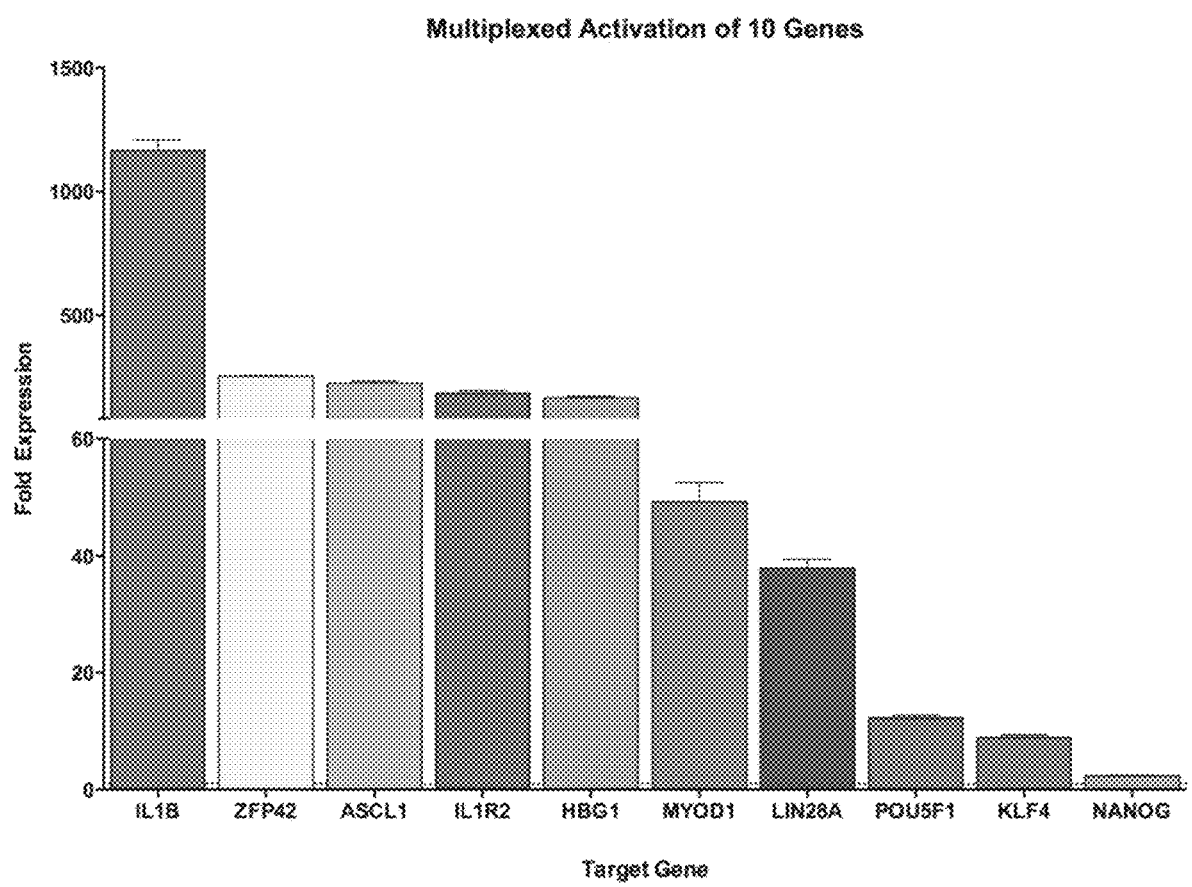
FIG. 17 shows multiplexed activation of ten genes.
Figure 18:
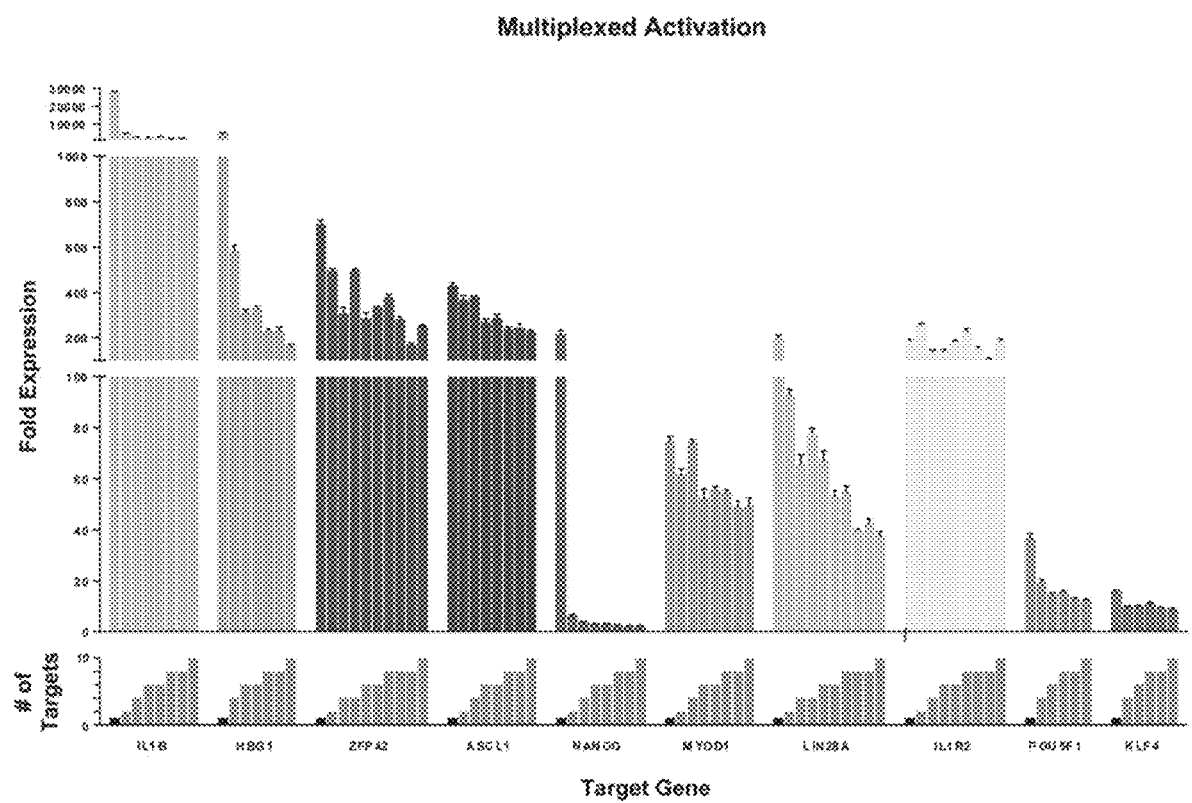
FIG. 18 shows multiplexed activation of target genes.
Figure 19:
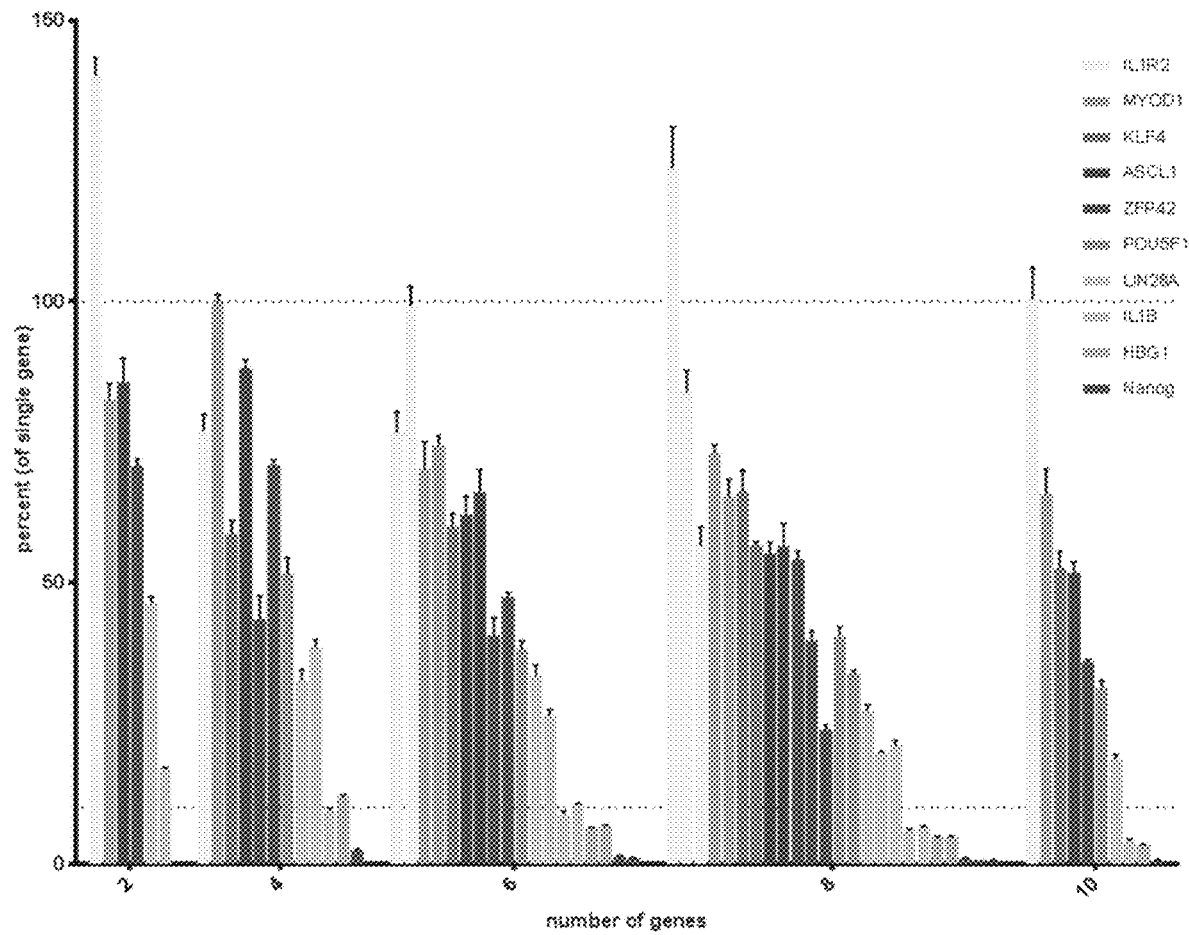
FIG. 19 shows targeting of combinations of 2, 4, 6, 8 or 10 genes simultaneously using the optimal single guide as previously determined. All experiments use NLS-dCAS (D10,H840A)-NLS-VP64 in combination with MS2-NLS-P65-HSF1.
Figure 20:
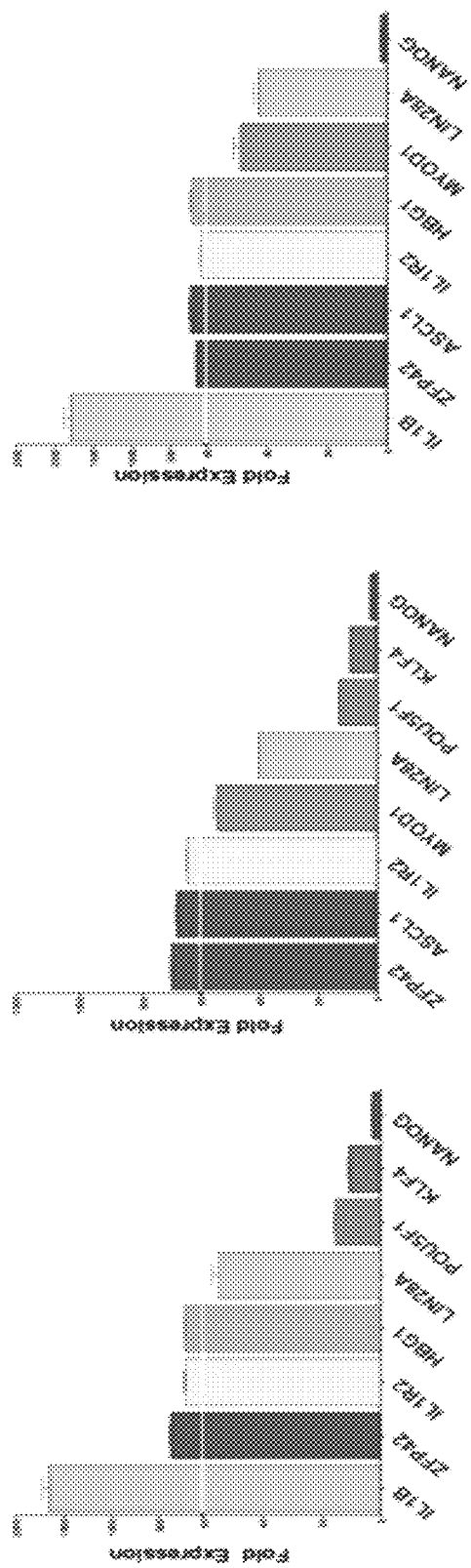
FIG. 20 shows multiplexed activation groups of target genes.
Figure 20:
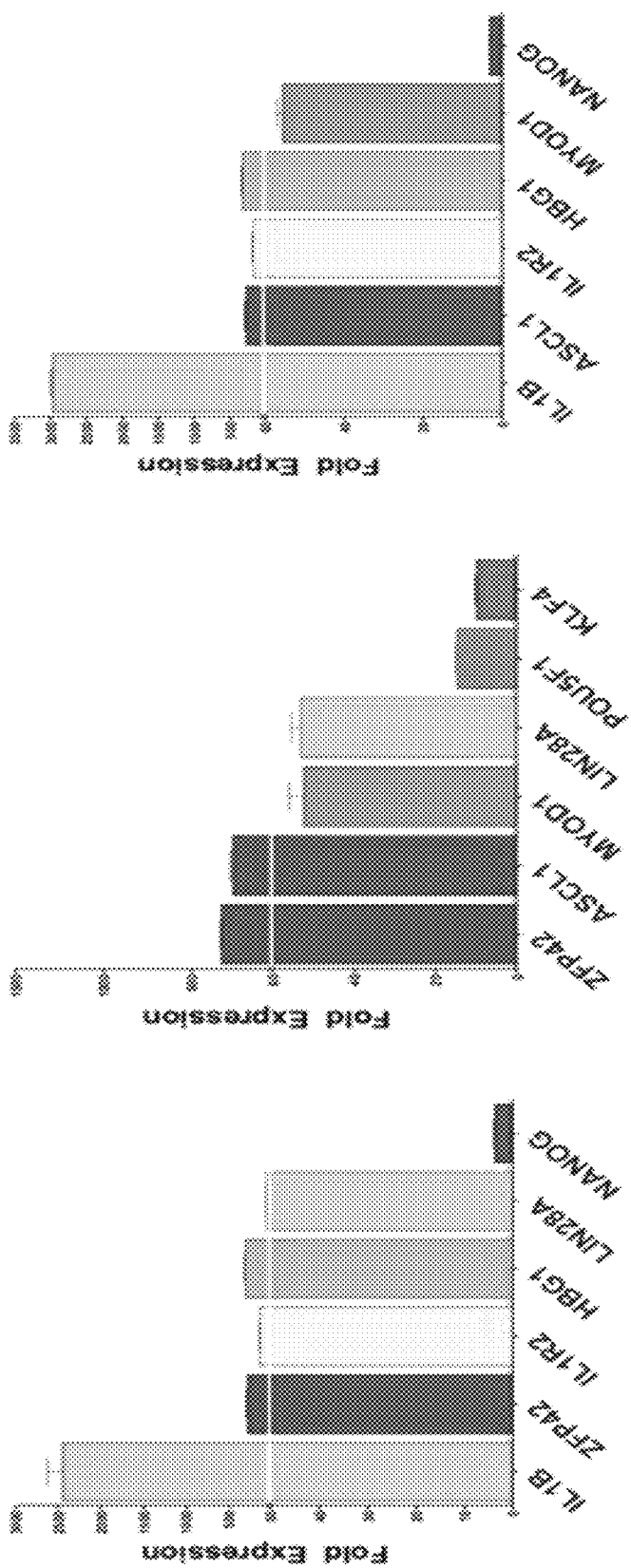
Figure 20:
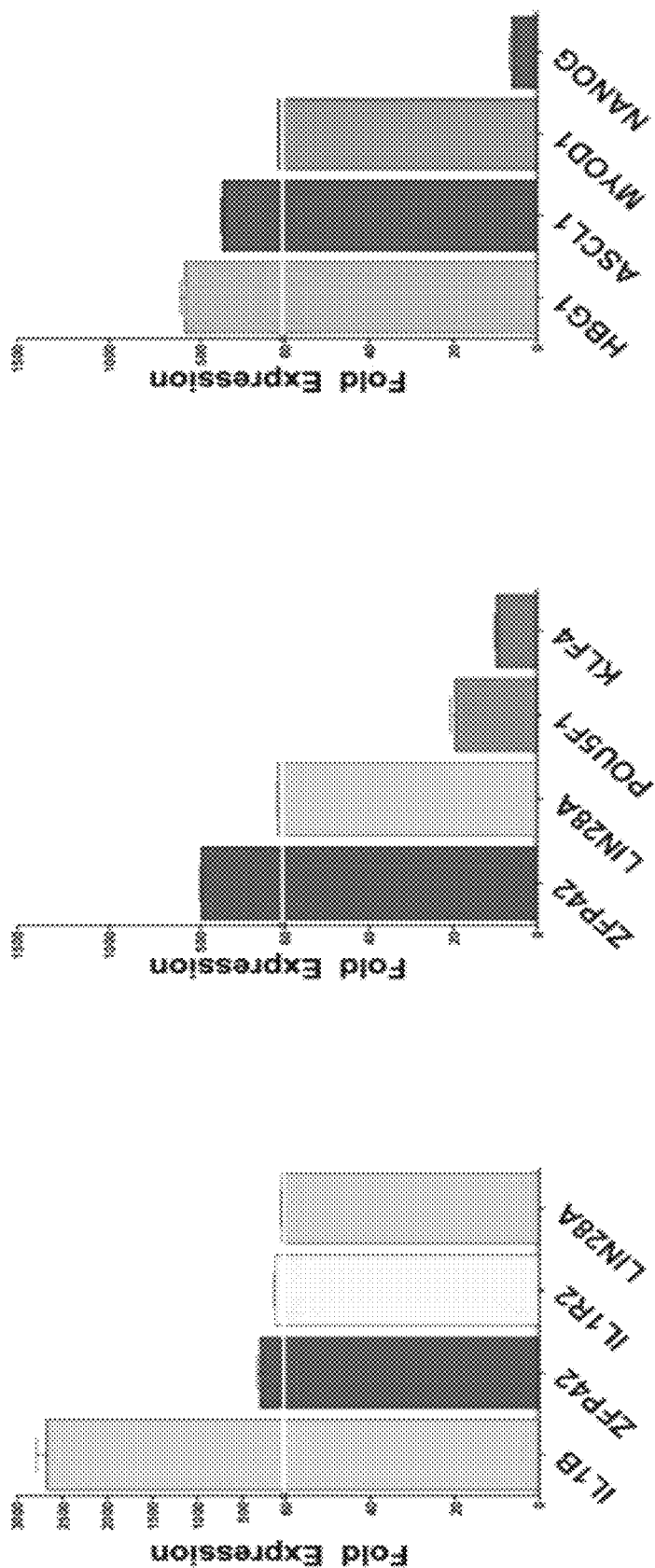

In order to test the ability of Applicants' system (NLS-dCAS(D10,H840A)-NLS-VP64 in combination with MS2-NLS-P65-HSF1) to activate multiple genes simultaneously, Applicants co-transfected guides targeting 2, 4, 6, 8 or 10 genes at once. Activation of multiple genes was highly successful, as even for a combination of 10 genes each gene was activated significantly. (see FIGS. 17-10)

Example 8: Structure-Guided Engineering of a CRISPR-Cas9 Complex for Genome-Scale Gene Activation Systematic interrogation of the functional organization of genomes requires the ability to perturb gene expression in a robust and generalizable manner. Structure-guided engineering of the CRISPR-Cas9 complex to mediate efficient transcriptional activation at endogenous genomic loci is described. Engineered Cas9 activators are used to investigate sgRNA-targeting rules for effective transcriptional activation, to demonstrate efficient multiplexed activation of 10 genes simultaneously, and to upregulate long intergenic non-coding RNA (lincRNA) transcripts. A library consisting of 70,290 guides targeting all human RefSeq coding isoforms was synthesized and SAM applied in a melanoma model to screen for genes whose activation confers resistance to the RAF inhibitor PLX-4720, an analog of the therapeutic compound vemurafenib. Expected resistance genes, such as EGFR and G protein-coupled receptor proteins, were enriched in the top hits, as were potentially novel resistance genes, such as members of the integrin family. The signature of the top screening hits was significantly predictive of BRAF inhibitor-resistant states in 29 short-term patient tumor cultures as well as 27 different melanoma cell lines and 113 primary and metastatic patient melanomas, demonstrating the potential of Cas9 activators as a powerful genetics tool.

Achieving genome-scale systematic perturbations within intact biological systems is important for elucidating the function of genes and epigenetic regulation. Genetic perturbations can be broadly classified as either loss-of-function or gain-of-function (GOF) based on their mode of action. Various genome-scale loss-of-function screening methods have been developed, including RNA interference[1,2] and the RNA-guided endonuclease Cas9 from the microbial adaptive immune system CRISPR[3]. Genome-scale GOF screening approaches have largely remained limited to the use of cDNA library overexpression systems. However, it is difficult to capture the complexity of transcript isoform variance using these libraries, and large cDNA sequences are often difficult to clone into viral expression vectors. Moreover, cDNA constructs tend to overdrive gene expression and may not be reflective of physiological protein levels. More generally, the endogenous regulatory contexts of the overexpressed genes cannot be recapitulated. Therefore, methods to enable genome-scale GOF perturbations at endogenous loci remain sought-after.

Programmable DNA binding proteins have emerged as an exciting platform for modulating transcription at endogenous genomic loci[4-13]. Among the established synthetic transcription factor platforms, the CRISPR-associated endonuclease Cas9 is most easily scaled to facilitate genome-scale perturbations[14-16] due to the simplicity of programming and producing the system relative to zinc finger proteins and transcription activator-like effectors (TALEs). Cas9 nuclease can be easily converted into a RNA-guided DNA binding protein (dCas9) by inactivating both of its catalytic domains[17,18]. dCas9 can be fused with transcription activation domains and retargeted to the promoter region of endogenous genes to achieve targeted modulation of gene expression[7,8,10-12]. Although the current generation of dCas9-based transcription effectors are able to achieve activation of some endogenous loci, the magnitude of transcriptional up-regulation achieved by individual single-guide RNAs (sgRNAs) typically ranges from low to ineffective[8,10,12]. Targeting a combination of sgRNAs tiling to a given promoter region can result in more robust transcriptional activation[10-12], but this requirement presents enormous challenges for scalability, and in particular for establishing pooled, genome-wide GOF screens using dCas9.

In order to improve and expand applications of Cas9, crystallographic studies, elucidating the atomic structure of the Cas9-sgRNA-target DNA tertiary complex[17], were undertaken, enabling rational engineering of Cas9 and sgRNA. This example provides a series of structure-guided engineering steps resulting in a potent transcription activation complex capable of mediating robust up-regulation with a single sgRNA. Using this new activation system, activation of endogenous genes as well as non-coding RNAs is demonstrated, the design rules for effective sgRNA target sites are elucidated, and a genome-wide dCas9-based transcription activation screening system to study targeted therapy resistance in a cellular model of melanoma is established and applied. These results collectively demonstrate the potentially broad applicability of RNA-guided gain-of-function (GOF) screening for functional genomics research.

Structure-Guided Design of a dCas9-Based Transcription Activation Complex

A key step in transforming the Cas9-sgRNA complex into an effective transcriptional activator is finding optimal anchoring positions for the activation domains. An ideal position would be proximally located relative to the target DNA to allow efficient interaction between the transcription machinery and target DNA, as well as permit unobstructed presentation of the transactivating effector to recruit transcription machinery. The crystal structure of the *Streptococcus pyogenes* dCas9 (D10A/H840A) in complex with a single guide RNA (sgRNA) and complementary target DNA[17] revealed a ribonucleoprotein complex in which the sgRNA-target DNA heteroduplex serves as a scaffold for the three-dimensional organization of the Cas9 protein domains. The N- and C-termini of Cas9 are located at the opposite side to the sgRNA-target DNA heteroduplex-binding groove (FIG. 21a), indicating that fusing transactivating peptides at these locations, as reported in previous dCas9-activator designs, may be suboptimal. It was observed that the tetraloop and stem-loop 2 of the sgRNA protrude outside of the Cas9-sgRNA ribonucleoprotein complex, with the distal 4 bp of each stem completely free of interactions with Cas9 amino acid sidechains (FIG. 27a). Both tetraloop and stem-loop 2 are also more proximal to the target DNA than either the N- or C-terminus and could provide better anchoring positions for effectors. Based on these observations and functional data showing that substitutions and deletions in the tetraloop and stem-loop 2 regions of the sgRNA sequence do not affect Cas9 catalytic function[17] (FIG. 21a), it was reasoned that the tetraloop and stem-loop 2 can be extended to incorporate protein-interacting aptamers, facilitating the recruitment of effectors to the Cas9 complex (FIG. 21b).

A minimal hairpin aptamer capable of binding to the bacteriophage coat protein MS2, which is known to be capable of binding MS2 through strong sequence- and structure-specific interactions in mammalian cells[18,19], to incorporate into tetraloop and stem-loop 2 (FIG. 27b) was chosen. Tests were performed to evaluate whether MS2-mediated recruitment of VP64 to the tetraloop and stem-loop 2 could mediate transcriptional up-regulation more efficiently than a dCas9-VP64 fusion alone. Aptamer-mediated recruitment of MS2-VP64 to either tetraloop (sgRNA 1.1) or stem-loop 2 (sgRNA 1.2) mediated 3- and 5-fold higher levels of Neurog2 up-regulation than a dCas9-VP64 fusion (sgRNA 1.0), respectively. Recruitment of VP64 to both positions (sgRNA 2.0) resulted in an additive effect, leading to 12-fold increase over dCas9-VP64 (sgRNA 1.0). Combining sgRNA 2.0 with dCas9-VP64 instead of dCas9 provided an additional 1.3-fold increase in Neurog2 up-regulation.

To confirm that spatial positioning, and not simply the number of activation domains, is the critical factor for effective transcription activation, sgRNA2.0 was compared to a previously described sgRNA bearing two MS2-binding stem-loops at the 3' end (sgRNA+2×MS2)[11]. sgRNA2.0 drove 14- and 8.5-fold higher levels of transcription activation than sgRNA+2×MS2 for ASCL1 and MYOD1, respectively (FIG. 21d).

Effector Domains Act in Synergy to Enhance Transcription Activation

To further improve the potency of Cas9-mediated transcription activation, how transcription activation is achieved in natural contexts was considered. Endogenous transcription factors generally act in synergy with co-factors to stimulate transcription. It was hypothesized that combining VP64 with additional, distinct activation domains could improve activation efficiency through synergy. NF-κB transactivating subunit p65 was chosen, which, while sharing some common co-factors with VP64, recruits a distinct subset of transcription factors and chromatin remodeling complexes. For example, p65 has been shown to recruit Ap-1, ATF/CREB, and Sp1[21], whereas VP64 recruits PC4[22], CBP/p300[23], and the SWI/SNF complex[24].

The effector domain fused to dCas9 and MS2 was varied. Hetero-effector pairing of dCas9 and MS2 fusion proteins (e.g. dCas9-VP64 paired with MS2-p65 or dCas9-p65 with MS2-VP64) provided over 2.5-fold higher transcription activation for both ASCL1 and MYOD1 than same-effector pairing (e.g. dCas9-VP64 paired with MS2-VP64 or dCas9-p65 with MS2-p65) (FIG. 21e). This concept of domain synergy was further explored by introducing the activation domain from human heat-shock factor 1 (HSF1) (Marinho et al., Redox Biol 2014) as a third activation domain, and it was demonstrated that an MS2-p65-HSF1 fusion protein further improved transcriptional activation of ASCL1 (12%) and MYOD1 (37%). Additional modifications to the sgRNA as well as Cas9 protein provided only minor improvements (FIGS. 27c-e). Based on these results it was concluded that the combination of sgRNA2.0, NLS-dCas9-VP64, and MS2-p65-HSF1 comprises the most effective transcription activation system, and designated it SAM. For simplicity, sgRNA2.0 is referred to as sgRNA in subsequent discussions of this example, unless noted otherwise.

Characterization of SAM Efficacy and Determination of sgRNA Efficiency Rules

Figures 22B, 22C, 22D:
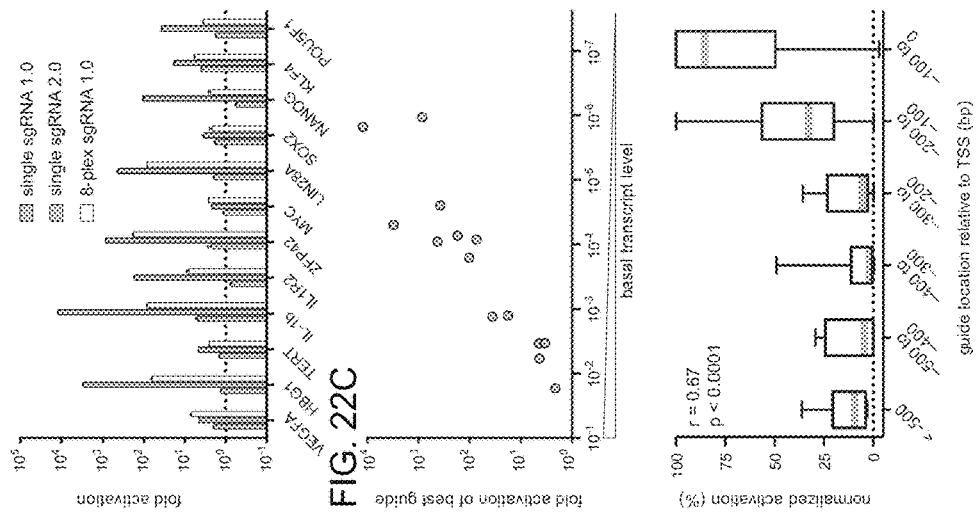
FIGS. 22A-D shows characterization of SAM-mediated gene activation and selection rules for efficient sgRNAs. a, Fold activation of 12 different genes plotted against the location of the sgRNA. Distances are measured in bp relative to the TSS at +1. sgRNA1.0 with dCas9-VP64 (grey), sgRNA2.0 with dCas9-VP64 and MS2-p65-HSF1 (blue). Arrows indicate sgRNA target sites with poor transcription activation. All values are mean±SEM with n=3. b, Comparison of activation efficiency achieved using dCas9-VP64 and a single sgRNA1.0 for the target gene; dCas9-VP64, a single sgRNA2.0 for the same target site as the single sgRNA1.0, and MS2-p65-HSF1; and dCas9-VP64 and a mixture of 8 sgRNAs targeting the same gene. c, Efficiency of target gene transcription activation as a function of their baseline expression levels. Genes with a higher basal level of transcription exhibit a lower fold up-regulation. For each target gene, the baseline expression level is measured using qPCR in the GFP-transfected control cells and expressed as level relative to GAPDH (fold lower expression compared to GAPDH on x-axis). d, Correlation of gene activation efficiency with sgRNA targeting position in the proximal promoter region expressed as distance to the TSS. Activation efficiencies of each sgRNA for the same target gene is normalized against the highest-activating sgRNA. Proximity to the TSS is positively correlated with target up-regulation. Blue lines indicate median values, boxes indicate 25th and 75th percentiles.
Figure 22A:
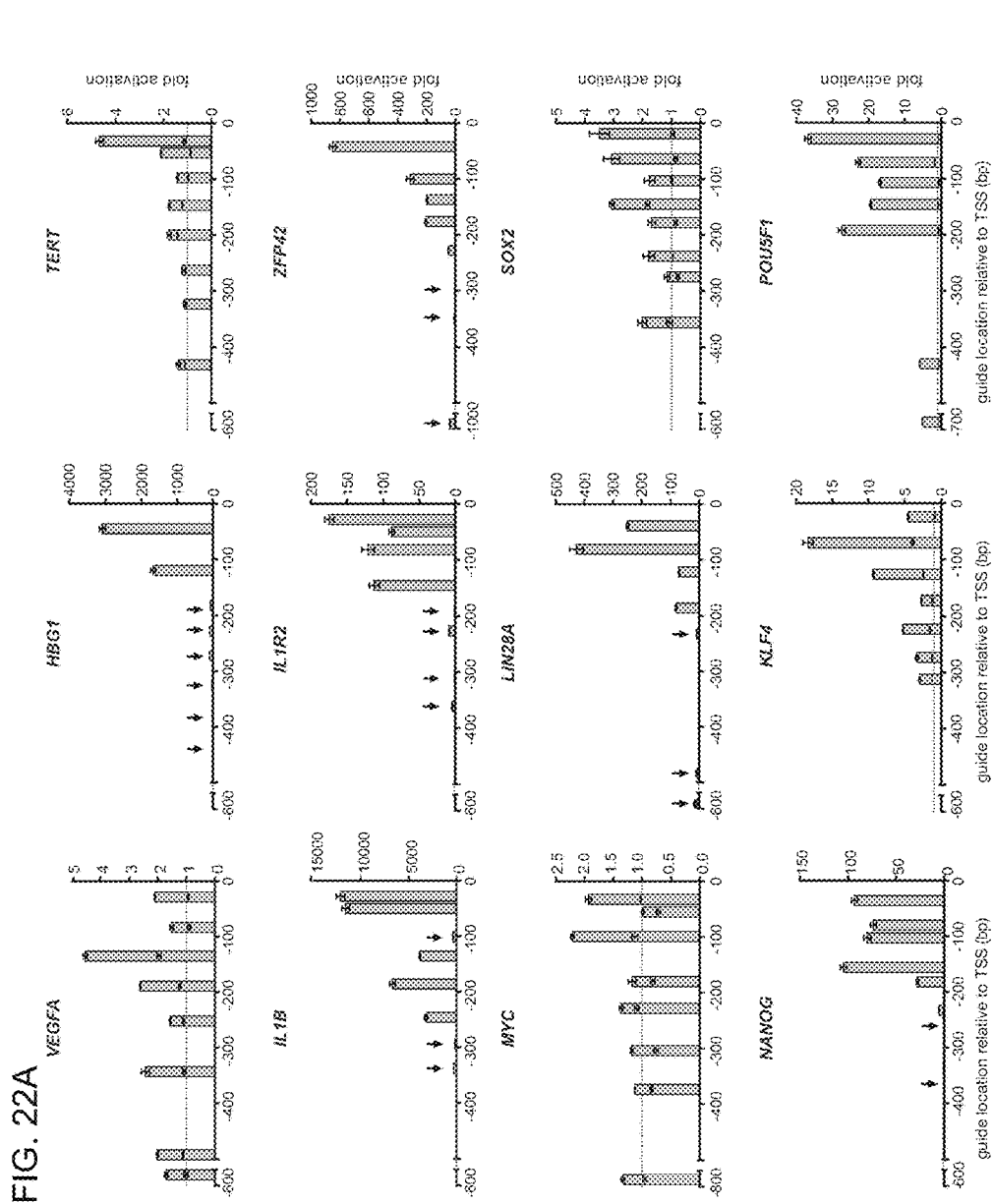

To thoroughly evaluate the effectiveness of SAM for activating endogenous gene transcription, 12 genes were chosen that have been found previously to be difficult to activate using dCas9-VP64 and individual sgRNA1.0 guides[8,11,12]. For each gene, 8 sgRNA target sites spread across the proximal promoter between −1000 bp and the +1 transcription start site (TSS) were selected. For 9 out of 12 genes, the maximum level of activation achieved using dCas9-VP64 with any of the 8 sgRNA1.0 guides was less than 2-fold, while the remaining three genes (ZFP42, KLF4 and IL1b) were maximally activated between 2- and 5-fold (FIG. 22a). In contrast, SAM stimulated transcription at least 2-fold for all genes and more than 15-fold for 8 out of 12 genes. Consistently, SAM performed better than sgRNA1.0+dCas9-VP64 for all 96 guides, with a median gain of 105-fold higher expression up-regulation across all 12 genes.

Figure 28A:
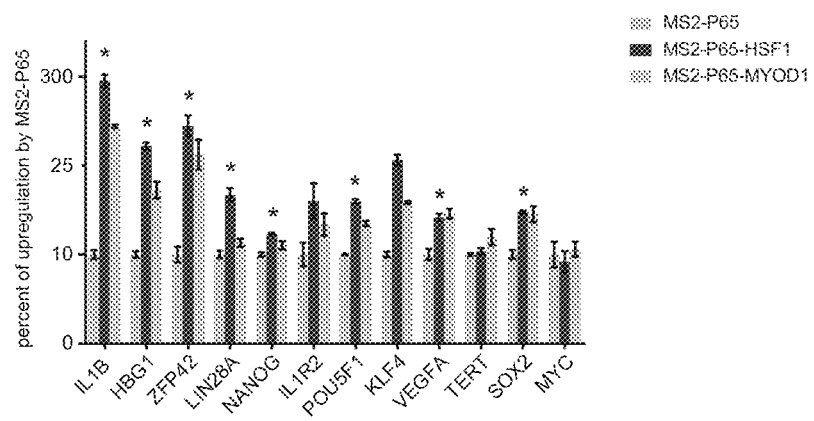
FIGS. 28A-C shows SAM mediates efficient activation of a panel of 12 genes with low levels of non-specific activation. a, Comparison of the activation levels of 12 genes with dCas9-VP64 in combination with MS2-P65, MS2-P65-HSF1, or MS2-P65-MYOD1. MS2-P65-HSF1 mediated significantly higher activation than MS2-P65 alone for 9 out of 12 genes. The best guide out of 8 tested for each gene was used is used in this experiment. Activation levels for each type of MS2-fusion is presented as a percentage relative to the activation achieved using MS2-P65. b, Non-specific background activation by dCas9-VP64 and MS2-p65-HSF1 activator components was determined for all 12 genes. dCas9-VP64 and MS2-p65-HSF1 were co-transfected with non-targeting (scrambled) guides. Cells transfected with GFP were used to measure the baseline expression level for each gene. Only activation of IL1R2 by scrambled guides is significantly different from GFP samples. p<0.05 by Student's t-test. c, The average activation for both scrambled guides shown as % of the on-target activation as shown in a. Activation by scrambled guides measures below 1% of on-target activation for all 12 genes. Error bars indicate S.E.M. and n=3.
Figure 28B:
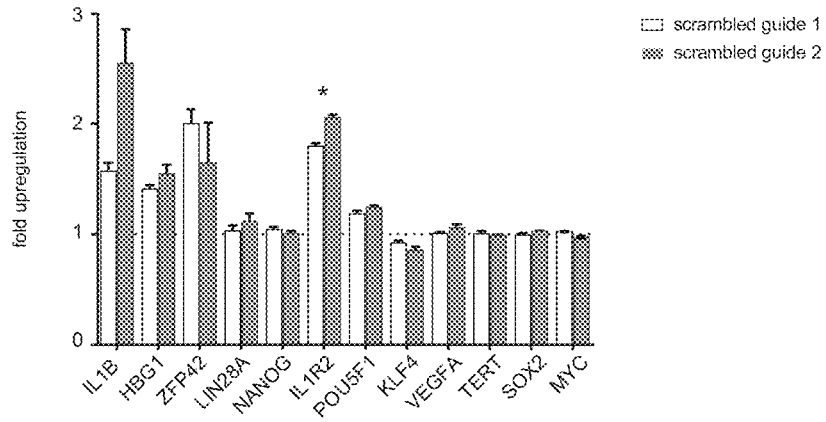
Figure 28C:
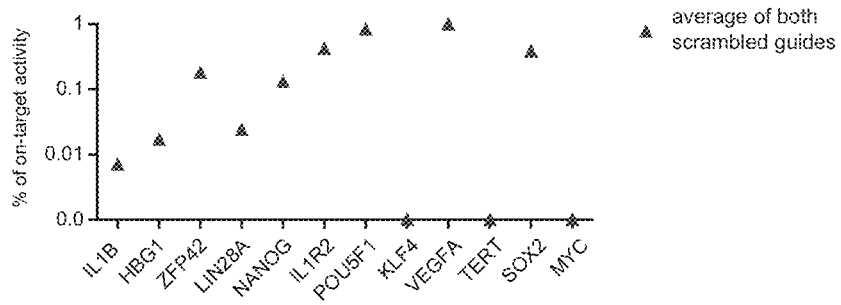

Previous studies have demonstrated that poor activation efficiency of single sgRNA can be overcome by combining dCas9-VP64 with a pool of sgRNAs tiling the proximal promoter region of the target gene[10-12]. Therefore the single sgRNA activation efficiency of SAM was compared with dCas9-VP64 combined with a pool of 8 same-gene targeting sgRNA 1.0 guides. For most genes, SAM with a single sgRNA performed more robustly than dCas9-VP64 with pools of 8 sgRNA1.0 guides (FIG. 22b). On average, SAM with single sgRNAs achieved 15 times more activation than dCas9-VP64 combined with pools of 8 sgRNA 1.0 guides. For all 12 genes, SAM incorporating three distinct activation domains (dCas9-VP64 with either MS2-p65-HSF1 or MS2-p65-MyoD1, whereas MyoD1 is a transactivating peptide derived from the human MYOD1 gene[25]) performed better than SAM incorporating only two distinct activation domains (dCas9-VP64 with MS2-p65) (FIG. 28a). For 9 out of 12 genes, triple-domain SAM achieved between 42% to 196% greater activation than double-domain SAM (p<0.01, Student's t-test with FDR correction). Also, triple-domain SAM with a non-targeting sgRNA generated less than 1% non-specific activation compared to activation by a targeting sgRNA (FIGS. 28b and c).

Next, studies were performed to determine factors that contribute inter- and intragenic variability of activation efficiency by different sgRNAs. For intergene variability, the variation in the activation levels between sgRNAs and target genes was analyzed. Differences in activation levels could stem from how tightly a given locus is regulated and/or from variation in its basal level of transcription. Thus, correlation between basal transcription and the level of transcription activation achieved using SAM was of particular interest. Using the relative transcript level of target genes in control samples, a highly significant correlation between the inverse of basal transcript level and the fold up-regulation achieved using SAM was observed (FIG. 22c; r=0.94, p<0.0001).

Whereas highly expressed genes (e.g. MYC, VEGFA, TERT, SOX2) were moderately upregulated, lowly expressed genes (e.g. HBG1, IL1B, ZFP42) were more significantly upregulated by SAM.

For intragenic variability, the activation data was aggregated for all 96 guides and the distance between the guide RNA target site and the TSS was found to be the most significant predictor of activation efficiency (FIG. 22d; r=0.67, p<0.0001). The strongest guides for each gene were always located within −200 bp and +1. A high fraction of guides were efficient in this window—85% of guides within 200 bp upstream of the TSS achieved at least 25% of the maximal activation of a given gene. This simple finding can be used to inform the selection of efficient sgRNAs for gene activation.

Transcriptional Activation of lincRNAs

Figure 23A:
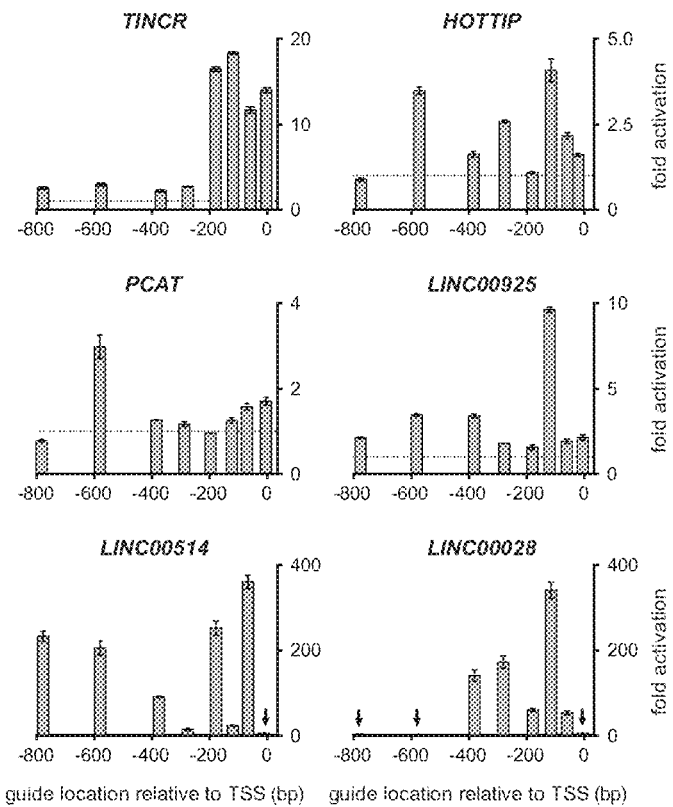
FIGS. 23A-B shows SAM activates characterized and uncharacterized lincRNA transcripts. a, Fold activation of 6 lincRNAs plotted against the location of the sgRNA2.0 relative to the TSS. All values are mean+–SEM with n=3. b, Correlation of sgRNA lincRNA-activation efficiency with sgRNA target distance to the TSS. Activation efficiencies of each sgRNA for the same target lincRNA is normalized against the highest-activating sgRNA. In contrast to coding genes, no significant correlation is observed. Blue lines indicate median values, boxes indicate 25th and 75th percentiles.
Figure 23B:
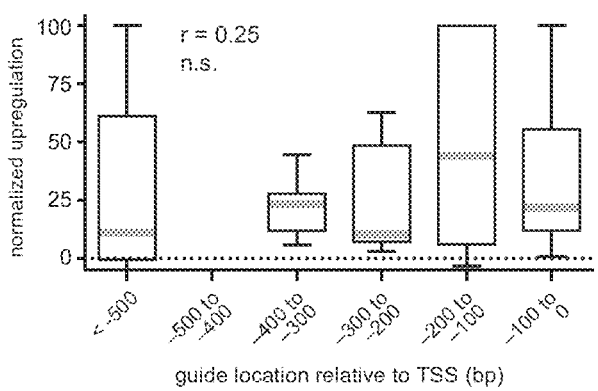

Long intergenic noncoding RNAs (lincRNAs) are a class of non-protein-coding transcripts longer than 200 bp[26]. While numerous lincRNAs have been identified by transcriptome sequencing, most of these molecules lack functional characterization. Nonetheless, some have so far been shown to play crucial roles in epigenetic regulation, cancer, and development[27]. Targeted activation of these transcripts would be a valuable tool for revealing their biological significance. To test whether SAM is able to activate lincRNAs, 3 targets with known functions (TINCR[28], HOTTIP[29], and PCAT[30]) and 3 with unknown functions (LINC00925, LINC00514 and LINC00028) were chosen. Similar to previous mRNA up-regulation experiments, RefSeq annotations were used to select 8 sgRNA target sites from the proximal promoter (−800 bp to +1) of each lincRNA. SAM indeed mediated significant up-regulation of lincRNA transcripts from 3-fold up-regulation of PCAT to 360-fold up-regulation of LINC00514 (FIG. 23a). Interestingly, and in contrast to mRNA data, no significant correlation between the distance of lincRNA-targeted guides to the TSS and fold activation was found (FIG. 23b). Possibly, this discrepancy could arise from the complex isoform structure of non-coding transcripts—the targets all have at least 2 isoforms with a different TSS reported[31].

Figure 29:
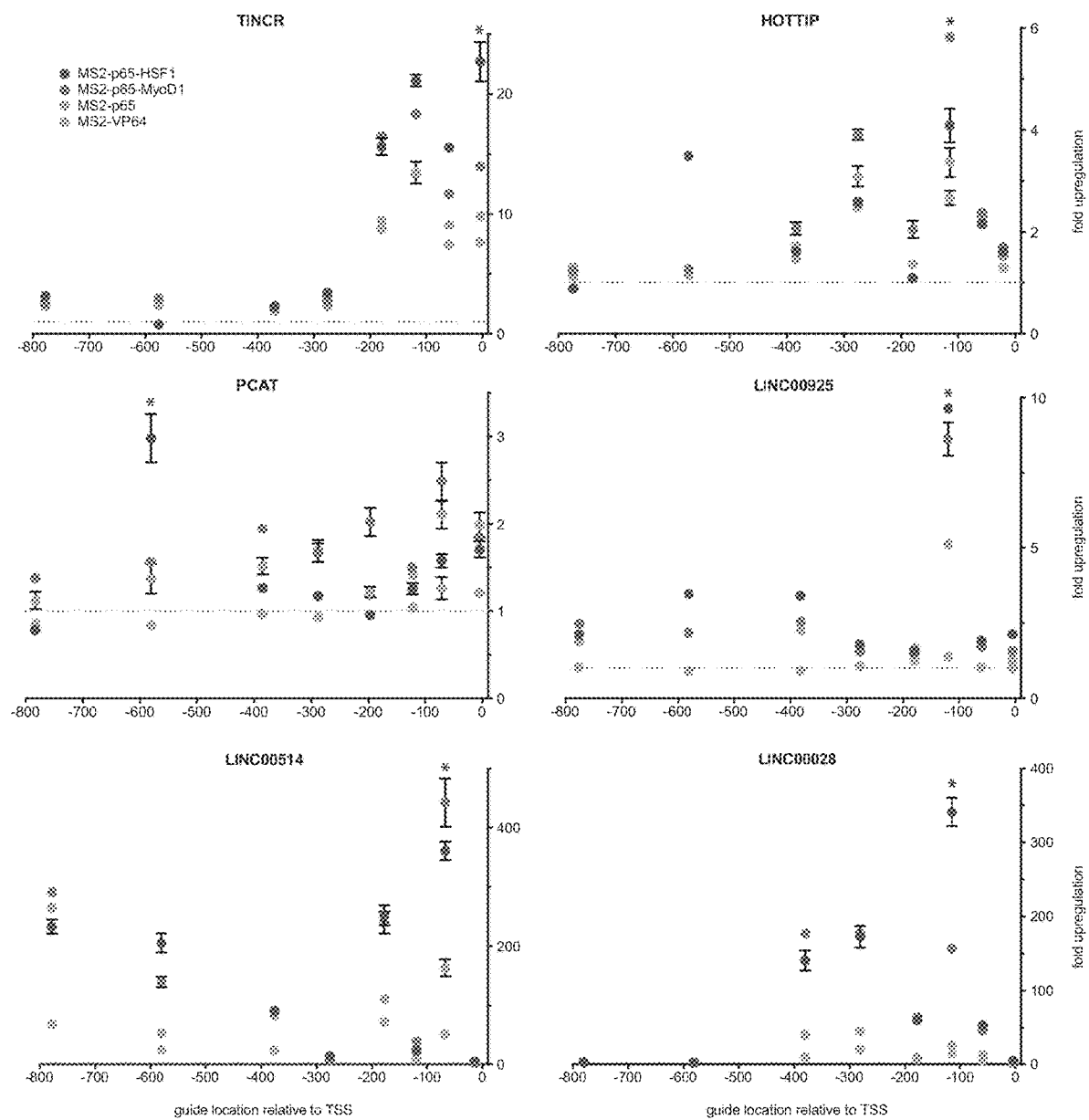
FIG. 29 shows activation of characterized and uncharacterized lincRNAs by SAM. Six lincRNAs were targeted using SAM. For each lincRNA, 8 sgRNAs were designed to target the proximal promoter region (+1 to –800 bp from the TSS) with 4 different MS2 activators (MS2-P65-HSF1, MS2-P65-MyoD1, MS2-P65, and MS2-VP64) in combination with dCas9-VP64. MS2 activators with a combination of 2 different domains (MS2-p65-HSF1 or MS2-p65-MyoD1) consistently provided the highest activation for each lincRNA, p<0.01 for MS2-p65-HSF1 or MS2-p65-MyoD1 vs. MS2-p65.

In order to find an effective activation domain for lincRNAs, the efficacy of different transactivator components was compared. A comparison of MS2 fusions to VP64 alone, p65 alone, p65-HSF1, and p65-MyoD1 for each of the 48 lincRNA-targeting guides was conducted (FIG. 29). Triple domain SAMs, dCas9-VP64 coupled with MS2-p65-HSF1 or MS2-p65-MyoD1, led to significantly higher activation than the dual domain SAM (dCas9-VP64 with MS2-P65) for the best guides for all 6 lincRNAs (p<0.01). Single domain SAM, dCas9-VP64 with MS2-VP64, performed worst for all 6 lincRNAs, suggesting that activation with a complex of synergistic domains may be important for efficient artificial up-regulation of non-coding RNAs based on the domains tested.

SAM Mediates Simultaneous Activation of Multiple Genes

Figure 24A:
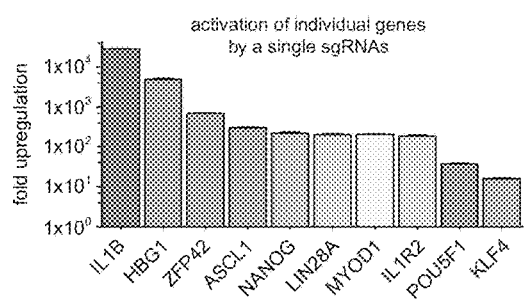
FIGS. 24A-E shows simultaneous activation of endogenous genes using multiplexed sgRNA2.0 expression. a, Activation of individual genes by single sgRNA2.0s with dCas9-VP64 and MS2-p65-HSF1. b, Simultaneous activation of ten genes using a mixture of ten sgRNA2.0s each targeting a different gene. c, The relative efficiency of activation of individual sgRNA2.0 varies depending on the target gene and the number of different-gene targeting sgRNA2.0s. d, Effect of sgRNA dilution on gene activation efficiency. Results are plotted as percentage of activation relative to the fold activation of a single undiluted sgRNA2.0 against the target gene. e, Correlation plot between the activation efficiency of a single 10-fold diluted sgRNA2.0 and the activation efficiency of the same sgRNA2.0 delivered within a mixture of ten different-gene targeting sgRNA2.0s. Performance during sgRNA dilution is significantly predictive of performance in multiplexing, suggesting a guide-autonomous component of multiplexing behaviour. All values are mean+–SEM with n=3.
Figure 24B:
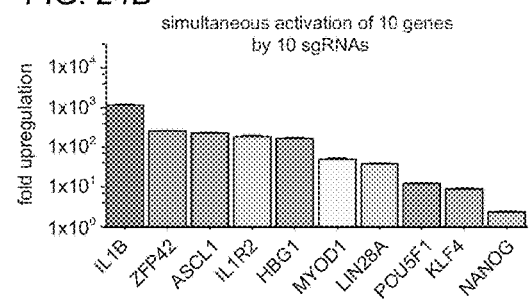
Figure 24C:
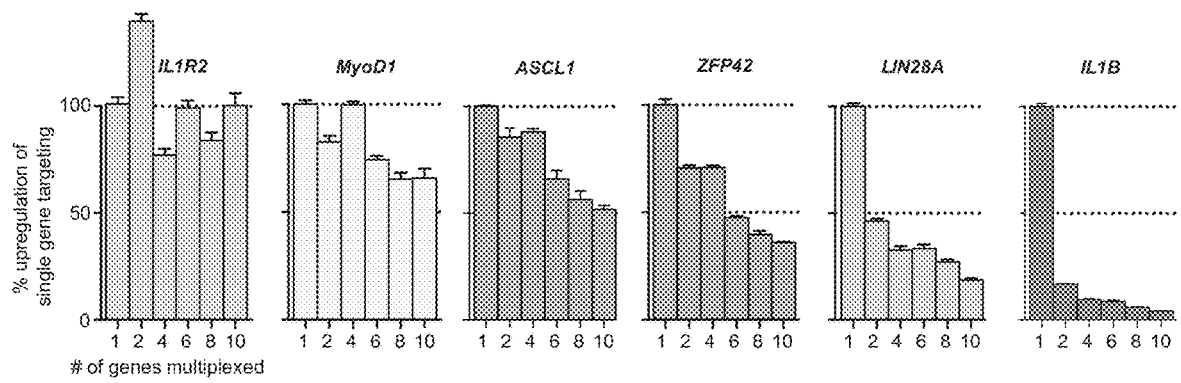
Figure 30:
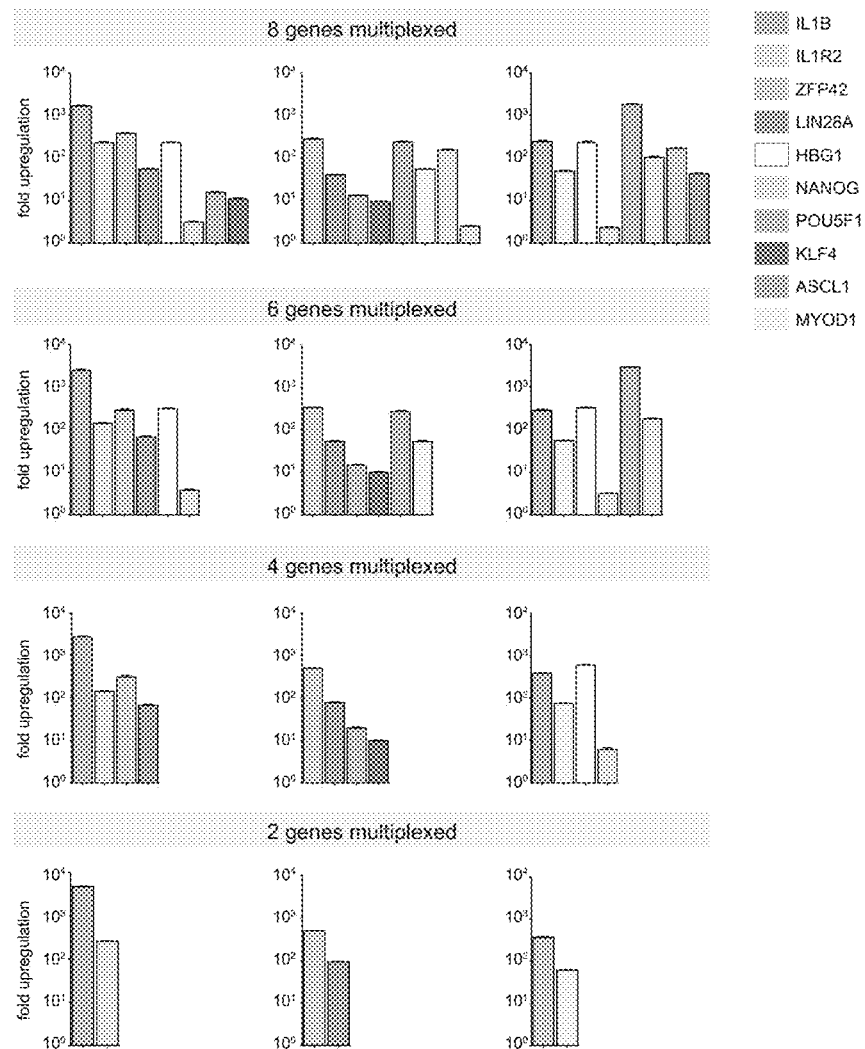
FIG. 30 shows multiplexed activation using SAM. Activation of a panel of 10 genes by combinations of 2, 4, 6, or 8 sgRNAs simultaneously. The mean fold up-regulation is shown on a $\log_{10}$ scale. Error bars indicate S.E.M. and n=3.

In order to study the complexity of gene network and transcription regulation, tools for simultaneous modulation of gene expression at multiple loci are needed. This would enable targeting of multiple elements of a signaling pathway or sets of genes that coordinate signaling in disease states. To that end, it was sought to test whether SAM can activate multiple genes simultaneously, and characterize factors impacting multiplexing performance. Simultaneous activation of three sets of 2, 4, 6 or 8 genes and one set of 10 genes was tested (FIG. 30) by co-expressing combinations of sgRNAs. Successful activation of all genes (>2-fold) for all gene combinations tested, including simultaneous activation of 10 genes was observed (FIGS. 24a and 24b). Most genes (excluding IL1R2) exhibited a drop in the amount of up-regulation achieved when concurrently targeted with 9 other genes (FIGS. 24a and 24b). Interestingly, the relative activation levels of each gene changed between multiplex activation and single-gene activation experiments. For example, whereas NANOG ranked 5th among the 10 targeted genes during single-gene activation, it ranked 10th in the 10-plex activation experiment. Some genes showed no change or only a modest and gradual drop in activation when concurrently targeted alongside an increasing number of genes (e.g. IL1R2, MYOD1, ASCL1). Others, however, displayed a steep decrease in up-regulation when combined with even a single gene partner (e.g. LIN28A, IL1B, NANOG). These distinct behaviours between genes were observed generally, across different gene pairings (FIG. 30).

Figure 24D:
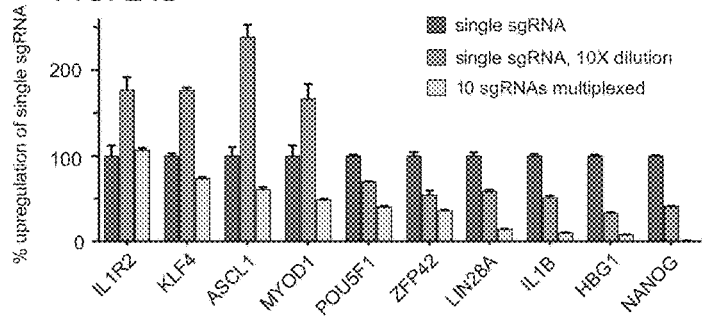
Figure 24E:
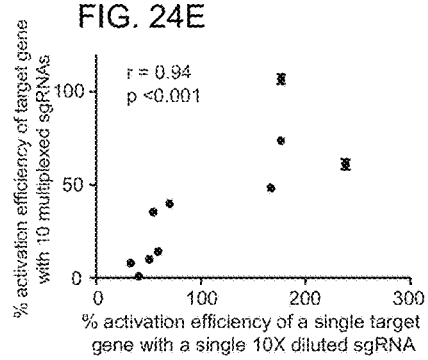

It was evaluated whether reduced activation of targets during multiplexing of 10 genes was due to the reduced amounts of sgRNA or SAM protein components available per gene. Surprisingly, diluting the sgRNA expression plasmid by 10-fold in single-gene activation experiments did not reduce activation for all genes (FIG. 24d). For example, activation for 4 out of 10 genes (IL1R2, KLF4, ASCL1, and MYOD1) increased by an average of 90% with 10× dilution of sgRNA expression plasmid. The remaining 6 genes were decreased by an average of 51%. Genes whose activation was reduced as a result of sgRNA dilution were also dampened by multiplexing (FIG. 24e; r=0.94, p<0.001).

Figure 31A:
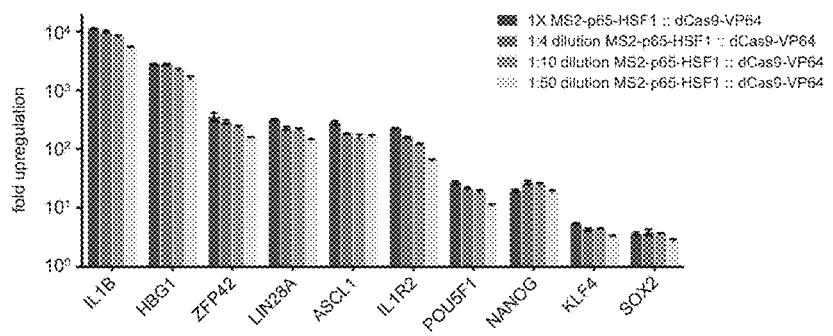
FIGS. 31A-B shows activation of a panel of 12 genes as a function of the dosage of SAM components. a, Effect of MS2-P65-HSF1 and dCas9-VP64 dilution, at 1:1, 1:4, 1:10, and 1:50 of the original dosage for each component, on the effectiveness of transcription up-regulation. The amount of sgRNA expression plasmid is kept constant. b, Effect of diluting all three SAM components (dCas9-VP64, MS2-p65-HSF1, and sgRNA2.0) at 1:4, 1:10, and 1:50 of the original dosage for each component. Fold up-regulation is calculated using GFP-transfected cells as the baseline. Error bars indicate S.E.M. and n=3.
Figure 31B:
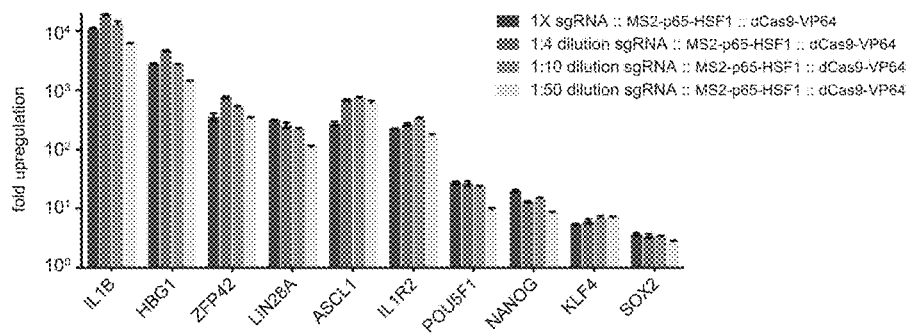

The activation efficiency of SAM was generally stable to dilution of its protein components (dCas9-VP64 and MS2-p65-HSF1). Reducing the amount of expression plasmids for both components by 10-fold led to an average drop of 26% in activation efficiency (FIG. 31a). Activation efficiency was particularly stable when all three components (including sgRNA) were diluted, retaining on average 100% activation efficiency across a 50-fold dilution range (FIG. 31b). The finding that SAM is highly efficient even at low transfection concentrations was particularly promising for application in genome-scale pooled screens, which rely on single copy lentiviral integration.

Development of a Genome-Scale Pooled Transcription Activation Screen

The ability to activate target genes using a single sgRNA opens the possibility of conducting pooled genome-scale pooled transcription activation screening. As a first step towards developing a SAM-based screen, all three components were cloned into lentiviral vectors (FIG. 25a). Each vector encodes a unique selection marker (Blast, Hygro, and Zeocin or Puromycin) to enable selection of cells co-expressing all three SAM components. To assess the efficiency of SAM when delivered via lentivirus at low multiplicity of infection (MOI), three validated genes were targeted: MYC, which is weakly activated; and KLF4 and MYOD1, which are only moderately activated. HEK293FT cells were co-transduced with lenti-dCas9-VP64 and lenti-MS2-p65-HSF1 at MOI<1 and concurrently selected with Blast and Hygro for 7 days. dCas9-VP65- and MS2-p65-HSF1-expressing cells were then transduced with lentiviral sgRNA vectors (lenti-sgRNA) at low MOI (<0.2) and selected for successfully transduced cells using either Puromycin or Zeocin. Target gene expression levels were measured four days post-transduction. All three genes were efficiently upregulated to levels comparable (MYOD1) or greater than those observed after transient SAM transfection (MYC and KLF4). Notably, expression levels achieved with Puromycin or Zeocin resistance markers on the sgRNA construct were not equal (FIG. 25b).

Having validated lentiSAM constructs (lenti-dCas9-VP64, lenti-MS2-p65-HSF1, and lenti-sgRNA), a genome-scale sgRNA library targeting every coding isoform from the RefSeq database (23430 isoforms) was designed. 3 sgRNA per isoform were designed and target sites within 200 bp upstream of the TSS, which was previously determined to provide more efficient activation (FIG. 22d), were chosen. The final library contained 70,290 guides, and two separate libraries with Zeocin (lenti-sgRNA-Zeo) or Puromycin (lenti-sgRNA-Puro) resistance were generated. As gene activation can have both a negative and positive effect on proliferation and cell survival a genome-wide screen for effectors of cellular growth was conducted. A polyclonal A375 melanoma cell line constitutively expressing both dCas9-VP64 and MS2-p65-HSF1 components was generated and these cells were transduced with a genome-scale lenti-sgRNA-Zeo library at a MOI of 0.2 (FIG. 25c). Genomic DNA was extracted 3 and 21 days after transduction by the sgRNA lentivirus, and guide counts were determined by NGS. $Log_2$ normalized guide counts for these two timepoints were compared. As expected for a population under selection, the distribution of guide counts displayed increased variance after 21 days in culture, with a large fraction of guides exhibiting depletion (FIG. 25d) (Wilcoxon rank sum test, p<0.0001). Enrichment of functional gene categories for the top 1000 depleted sgRNAs was analyzed, as well as the top 1000 depleted genes (determined based on the average depletion of all three guides targeted to a given gene), using Ingenuity pathway analysis. Categories with p<0.01 after Benjamini-Hochberg FDR correction are shown in FIG. 25e. Enrichment for cancer and pluripotency related gene categories (including PTEN[32] and STAT[33] signaling pathways, which have been implicated in cancer regulation) was observed. These results suggest that dysregulation of members of these gene categories may negatively impact melanoma proliferation and that SAM can be used for depletion screening.

Figure 26A:
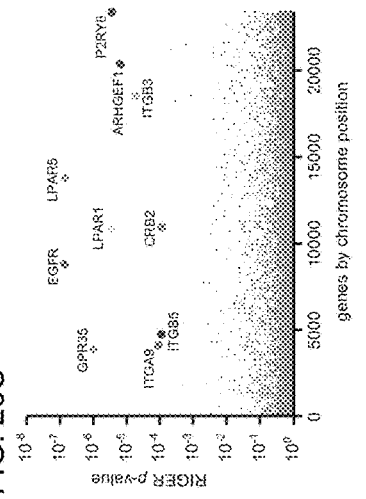

Using Genome-Scale Transcription Activation Screen to Identify Genes Involved in BRAF Inhibitor Resistance Previously it has been demonstrated that genome-scale screening using Cas9-mediated gene knockout can facilitate the identification of loss-of-function mutations that confer BRAF inhibitor resistance in a cell line model of melanoma[14]. The complementary genome-scale transcription activation screen using SAM would enable the identification of gain-of-function perturbations involved in melanoma drug resistance. To test the efficiency of SAM for genome-wide positive selection screening one aim was to identify genes implicated in the development of BRAF inhibitor resistance in $BRAF^{V600E}$ mutant melanoma. The A375 melanoma cell line harbors the $BRAF^{V600E}$ mutation and is naturally sensitive to BRAF inhibitors such as PLX4720 (PLX) and the closely related commercial therapeutic Vemurafenib. Cells harboring sgRNAs that activate genes leading to PLX resistance should therefore be enriched after continued culture in the presence of the drug, whereas no such effect should be observed in cells treated with vehicle only. Normalized guide counts for the input sgRNA-zeo library at the baseline time point (3 days post infection) as well as 14 days post treatment with either PLX or vehicle were analyzed. The sgRNA distribution was significantly different between cells treated with PLX and vehicle for two independent infection replicate screens, with the majority of sgRNAs exhibiting a reduced representation and a small set of guides showing high enrichment for PLX treated cells (Wilcoxon rank sum test, P<0.0001, median −1.3 for PLX vs. DMSO) (FIGS. 26a).

Figure 26B:
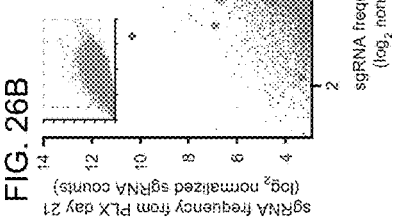
Figure 26D:
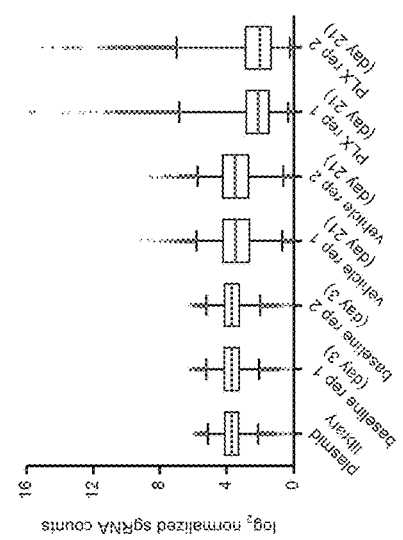
Figure 26E:
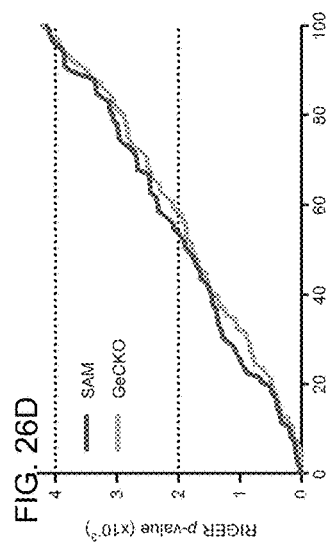
Figure 32A:
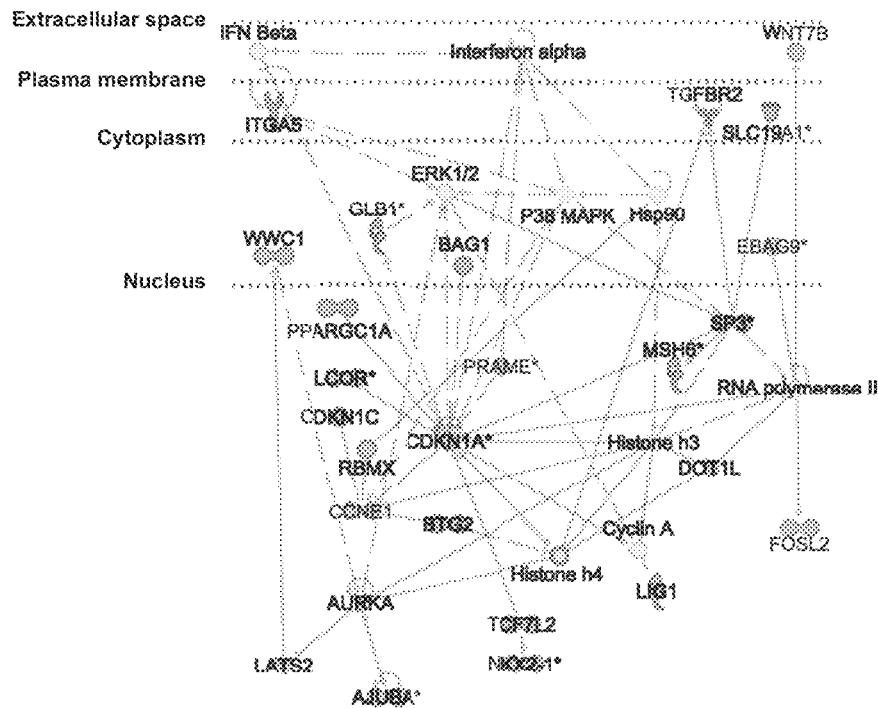
FIGS. 32A-B shows components of Cancer survival and proliferation pathways are depleted in a genome-wide SAM screen. IPA analysis on the top 300 depleted genes based on average depletion of all 3 guides/gene resulted in 2 networks with scores >30. Depleted genes are indicated in red. a, network score=39 with 26 depleted genes in the network. b, network score=37 with 25 depleted genes in the network. Components on all layers of both networks exhibit depletion.
Figure 32B:
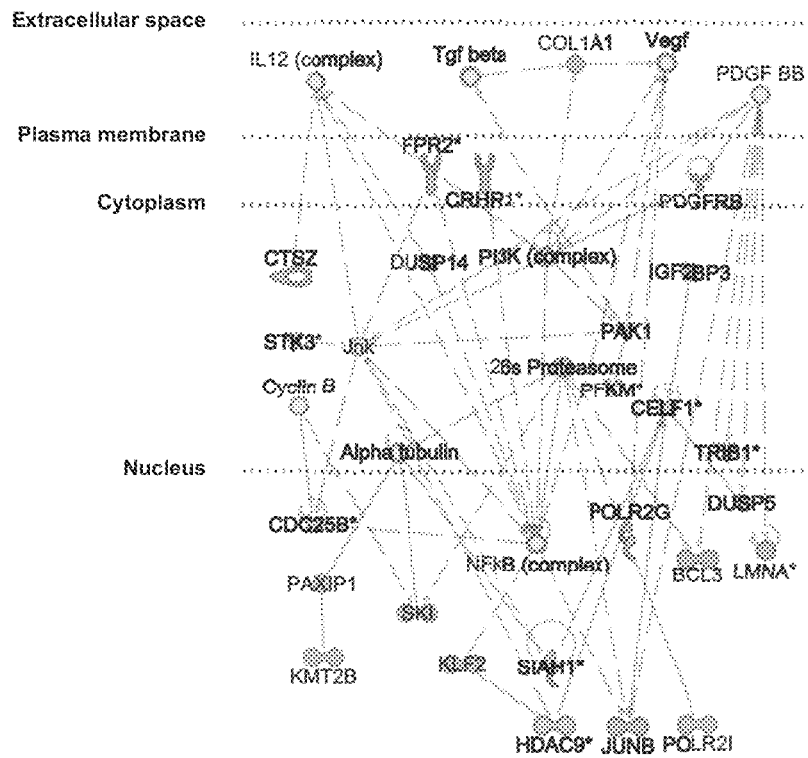
Figure 33A:
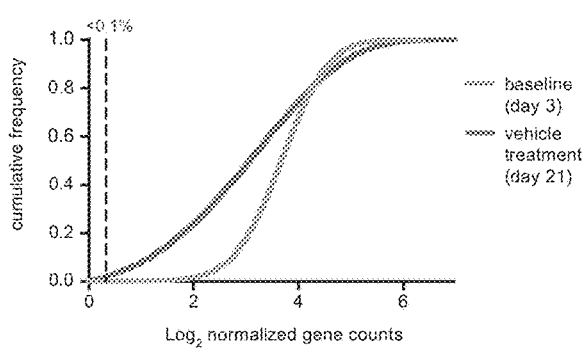
FIGS. 33A-D shows genome-scale lentiviral screen using Puromycin-resistant SAM sgRNA2.0 library. a, Cumulative frequency of sgRNA2.0s 3 and 21 days after transduction of A375 cells with Puromycin-resistant sgRNA2.0 lentivirus. Shift in the 21-day curve represents the depletion of a subset of sgRNA2.0s. b, Box plot showing the distribution of sgRNA2.0 frequencies at different time points post lentiviral transduction with the Puromycin library, after treatment with DMSO vehicle or PLX-4720. Two infection replicates are shown. c, Identification of top candidate genes using the RIGER P value analysis (KS method) based on the average of both infection replicates. Genes are organized by positions within chromosomes. d, Overlap between the top 20 hits from the Zeo and Puro screens. Genes belonging to the same family are indicated by the same color. There is a 50% overlap between the top hits of each screen as shown at the intersection of the Venn diagram.
Figure 33B:
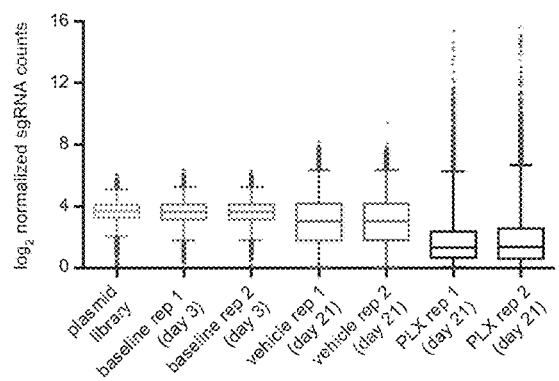
Figure 33C:
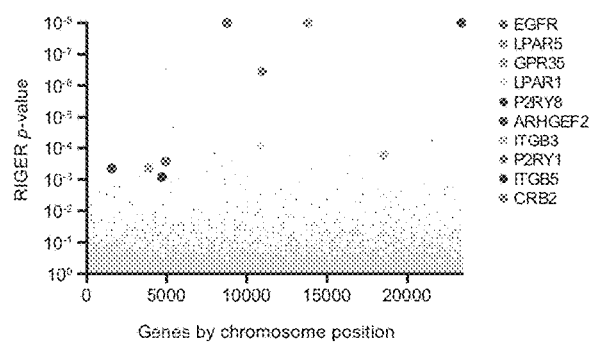
Figure 33D:
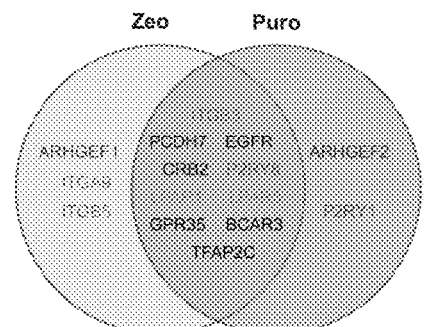

For a number of gene targets, several sgRNAs for the same gene were enriched in PLX-treated cells (FIG. 26b), suggesting the importance of these genes for the formation of PLX resistance. To determine genes exhibiting consistently high enrichment across multiple sgRNAs, the RNAi Gene Enrichment Ranking (RIGER) algorithm (FIG. 26c) was employed. The 10 most significant hits were distributed throughout the genome (FIG. 26c). 50% of the top 20 RIGER hits were replicated in a validation screen using puro selection, rather than zeo, on the sgRNA library (FIG. 32). The significance of the p-values of the top 100 RIGER hits was comparable to those observed for GeCKO screening[14], indicating that the results obtained from the SAM gain-of-function activation screen have similar statistical power compared to Cas9 nuclease-based knockout screening (FIG. 26d). In addition, for the top 10 shared hits between zeo and puro screens, the fraction of effectively enriched guides per gene (present in the top 5% of all guides) was very high with 97% for zeo and 81% for puro (89%±10.7% overall, compared to 78%±27% for the top 10 GECKO hits, FIG. 26e).

Ectopic expression of the top hit from both screens—EGFR—was previously shown to cause PLX resistance in tumor types harboring $BRAF^{V600E}$ mutations by activating AKT in a pathway parallel to BRAF[34]. In addition, patient-derived BRAF mutant melanomas were sensitized to PLX when treated with EGFR and AKT inhibitors[35]. Furthermore, four out of the top 10 hits from the first screen belong to the family of G protein-coupled receptors (GPR35, LPAR1, LPAR5, and P2RY8). GPCR also emerged as the top-ranked protein class conferring resistance to multiple MAP kinase inhibitors in melanoma cells in a recent screen using cDNA overexpression by Johannessen et al.[36] GPR35 and LPAR1 have previously been found to mediate PLX resistance in A375 cells when overexpressed via cDNA[36]. GPR35, LPAR1 and LPAR5 share Gα13 as a downstream target[37,38] and induce cell proliferation through the ERK/GSK3β/β-catenin pathway, leading to a growth advantage in multiple cancer types[39,40]. Although the exact molecular mechanism for P2RY8 action has not been identified, P2RY8 is abundantly expressed in leukemia cells[41]. Overexpression of P2RY8 in NIH3T3 cells with cDNA led to increased CREB, Elk-1, c-Fos, and c-Myc activity, suggesting that P2RY8, may evoke cell proliferation through the ERK pathway[41]. RAF-independent activation of ERK has previously been shown as a resistance mechanism to BRAF inhibitors[42]. A second family of proteins present in the top 20 hits of both screens are Rho guanine nucleotide exchange factors (ARHGEF1 and ARHGEF2) which also act on Gα13, downstream of GPCR. The activation of the GPCR pathway was shown to act as an independent mechanism for resistance to BRAF inhibition therapy through cAMP/PKA-mediated activation of transcription through CREB and ATF1[36]. While only two of the top hits (GPR35 and LPAR1) overlap with the top hits from the Johannessen screen[36], many novel members of the GPCR pathway enriched in the top hits were in agreement with a model where GPCR pathway activation can mediate resistance to MAPK pathway inhibitors. Additionally, top hits include multiple integrin genes (ITGA9, ITGB3, and ITGB5) that have roles in tumorigenesis and malignancy. Particularly, all three integrin hits are capable of driving MAPK signaling and promoting malignancy, anchorage independence, and migration in melanoma and various carcinomas[43-46]. Additionally, ITGB3 is capable of driving cancerous cells towards a stem-like state through NF-κB pathway activation, which has been shown to mediate resistance to BRAF-inhibition therapy[47] (FIG. 26f). Therefore, these integrin top hits may play a role in circumventing BRAF inhibition by activating accessory pathways known to promote resistance and re-activate the MAPK downstream of RAF to promote malignancy.

To verify the biological relevance of the top hits from the genome-wide screen, a collection of gene expression data from BRAF$^{v600}$-mutant melanoma cell lines in the Cancer Cell Line Encyclopedia (CCLE)[48], short-term cultures of patient tumors[49], and a collection of primary and metastatic patient melanoma samples from The Cancer Genome Atlas (TCGA) (tcga-data.nci.nih.gov/tcga/) was examined. As shown previously[47], a distinct transcriptional state defines BRAF-inhibition sensitivity/resistance where sensitive and resistant states are described by activation of endogenous MITF/associated markers (e.g. PMEL) and NF-.kappa.B-pathway activity/associated markers (e.g. AXL), respectively (FIG. 26f). Using gene expression profiles from 29 melanoma short-term cultures, it was found that top genes from the SAM screen were significantly co-expressed within the resistant state and that a gene expression signature representing the top hits was predictive of this BRAF-inhibitor resistant transcriptional state (FIG. 26f; p<0.0001 for overlapping hits from zeo and puro screens).

Figure 34:
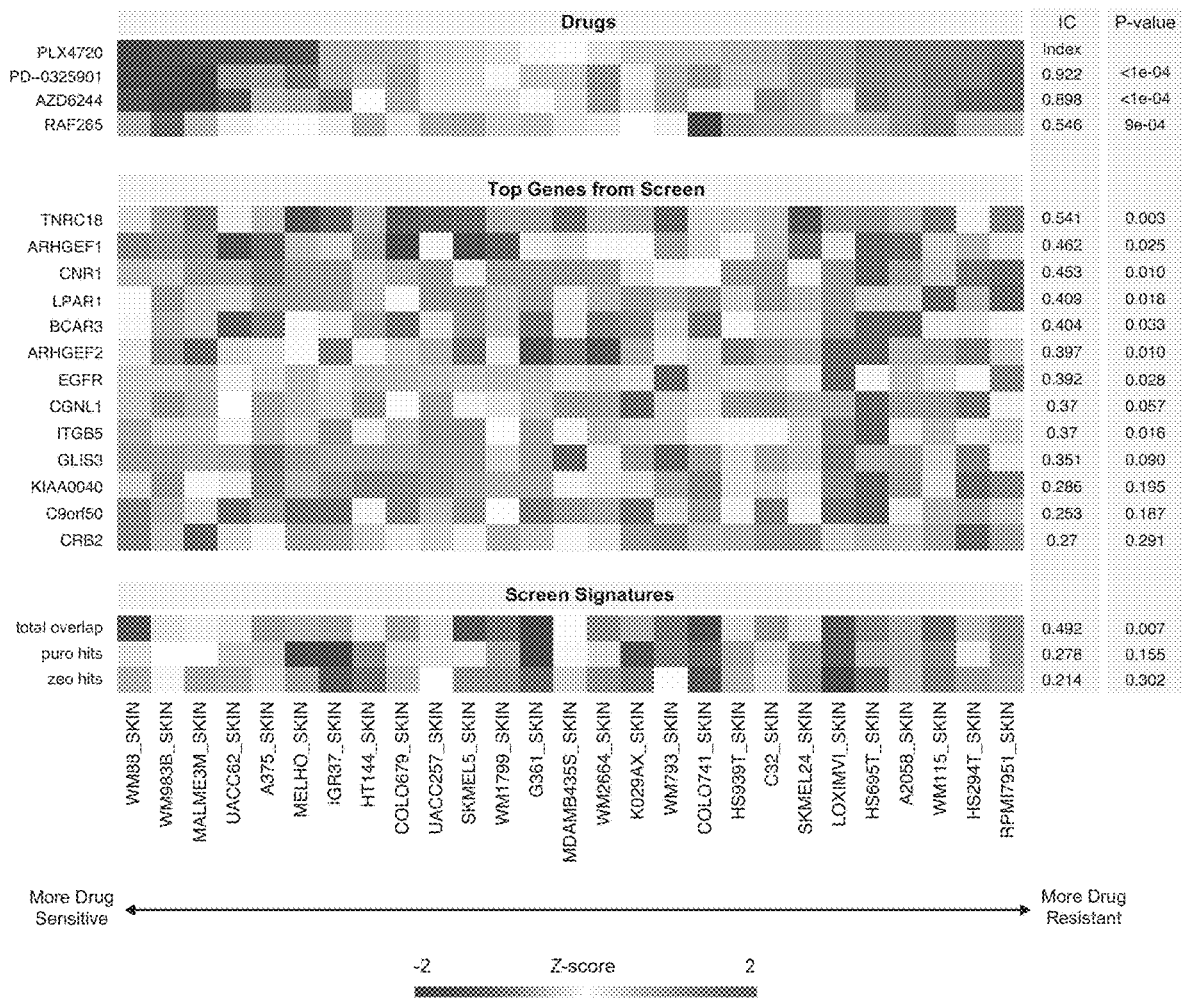
FIG. 34 shows validation of top screen hits using Cancer Cell Line Encyclopedia expression and pharmacological data from additional melanoma cell lines. Heat map of z-scores, with each column representing a different $BRAF^{V600}$ melanoma cell lines and rows representing sensitivity to different drugs (upper panel), expression of SAM top screen hits (middle panel), and SAM screen signature scores (bottom panel, see methods for signature generation). Drug sensitivity is measured as 8-Activity Area (AA) (Barretina, J. et al. *Nature* 483, 603-607, doi:10.1038/nature11003 (2012)). The melanoma cell lines are sorted by PLX drug sensitivity where a lower value (blue) corresponds to increased sensitivity. Also displayed are the sensitivities to related MAPK inhibitors. There is a fraction of cell lines that demonstrate resistance to MAPK inhibitors and in these cell lines, many of the SAM top hits are highly expressed. The signatures comprised of these top hits also are highly scored within the resistant cell lines. Associations are measured using the information coefficient (IC) between PLX-4720 sensitivity (index) and each of the features and p-values are determined using a permutation test. RAF inhibitors: PLX4720 and RAF265; MEK inhibitors: AZD6244 and PD-0325901.
Figure 35:
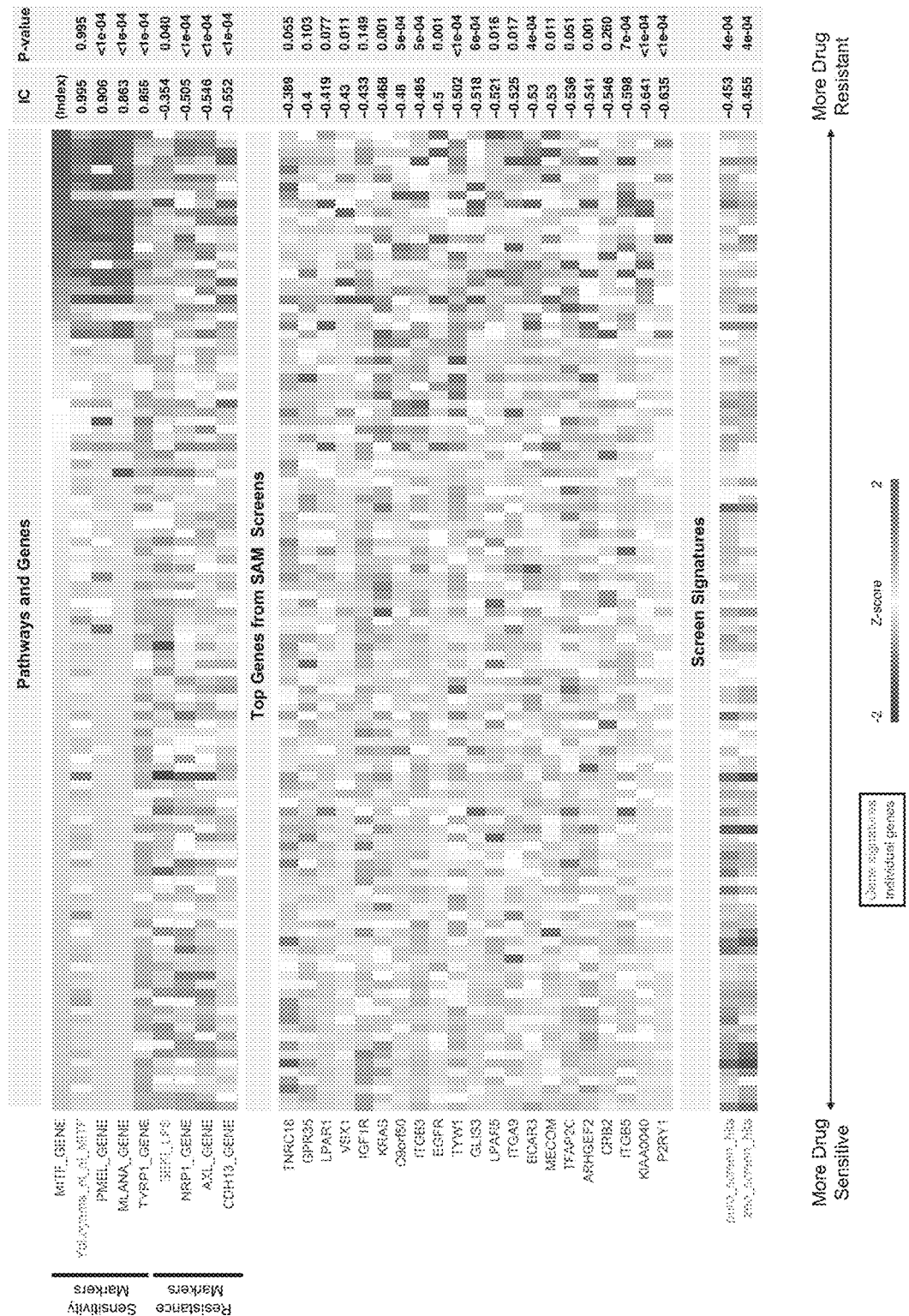
FIG. 35 shows validation of top screen hits in primary and metastatic melanoma patient samples from The Cancer Genome Atlas. Heat map of z-scores with each column representing a different BRAF$^{V600}$ patient melanoma (primary or metastatic) and rows representing expression of gene/signature markers for BRAF-inhibitor sensitivity (top panel), expression of SAM top screen hits (middle panel) and screen signature scores (see methods for signature generation) (bottom panel). Because no pharmacological data is available for these TCGA melanoma samples, TCGA gene expression data is first mapped onto a previously defined transcriptional state for BRAF-inhibitor sensitivity/resistance based on a panel of gene markers and signatures (Konieczkowski, D. J. et al. *Cancer discovery* 4, 816-827, doi:10.1158/2159-8290.CD-13-0424 (2014)). The expression of top SAM screen individual hits is increased and significantly associated with tumors displaying a resistant state (defined as low MITF expression and high expression of resistant markers/signatures). Signatures comprised of the top genes from the SAM screens also are significantly associated with the resistant tumors. The panel of melanoma samples is sorted by decreasing MITF expression where a higher value (red) corresponds to samples that are more sensitive to BRAF inhibition. Associations are measured using the information coefficient (IC) between MITF expression (index) and each of the features and p-values are determined using a permutation test.

The expression of the top hits in 27 BRAF$^{V600}$-mutant melanoma cell lines from CCLE for which gene expression and pharmacological data were available was additionally investigated. The gene expression of the top hits from the activation screen are enriched and significantly associated with resistance to BRAF-inhibition (PLX4720) as is the top-hit signature from the SAM screens (FIG. 34; p=0.007 for overlapping hits from zeo and puro screens). To confirm that the top hits were representative of a resistant state in vivo, gene expression data from 113 primary and metastatic melanoma samples from TCGA (FIG. 35) was analyzed. The same gene and signature markers as described above was used to define sensitive and resistant transcriptional states and found that top hits and signatures from the SAM screens were significantly associated with a BRAF-inhibitor resistant phenotype (FIG. 35, p<0.0001 for both zeo and puro screens). Thus, both in vitro (short-term cultures of patient melanoma samples and a panel of established melanoma cell lines) and in vivo (TCGA), the hits expand the understanding of the transcriptional state associated with BRAF-inhibition resistance with potentially novel therapeutic targets.

In summary, a structure-guided approach has been taken to design a dCas9-based transcription activation system for achieving robust, single sgRNA-mediated gene up-regulation. By engineering the sgRNA to incorporate protein-interacting aptamers, a synthetic transcription activation complex consisting of multiple distinct effector domains that more closely mimic natural transcription activation processes was assembled. Additional developments may be able to take advantage of the modularity and customizability of the sgRNA scaffold to establish a series of sgRNA scaffolds with different aptamers for recruiting distinct types of effectors. For instance, replacement of the MS2 stem-loops with PP7-interacting stem-loops may be used to recruit transcription repression elements.

The exemplary steps toward defining selection rules for potent sgRNAs provided in this example allows one skilled in the art to reveal additional selection criteria, such as sequence-intrinsic properties (FIG. 36), that are useful for guide efficacy.

Further characterization and improved understanding of the targeting specificity will also be useful for continued utility of Cas9 or SAM. Recent analysis of genome-wide dCas9-binding revealed significant concentration-dependent off-target binding[50].

Application of the Cas9 transcription activation complex, either in the context of individual gene perturbation or as genome-scale gene activation libraries, further allows for the dissection of many types of genetic elements, ranging from protein-coding genes to non-coding lincRNA elements. Furthermore, combining SAM with Cas9 mediated genome editing or dCas9-mediated gene repression allows for powerful approaches for studying gene interactions in diverse biological processes in contexts spanning from development and regeneration to many diseases.

Transient Transfection Experiments:

Neuro-2a cells (Sigma-Aldrich) were grown in media containing 1:1 ratio of OptiMEM (Life Technologies) to high-glucose DMEM with GlutaMax and sodium pyruvate (Life Technologies) supplemented with 5% HyClone heat-inactivated FBS (Thermo Scientific), 1% penicillin/streptomycin (Life Technologies), and passaged at 1:5 every 2 days.

HEK293FT cells (Life Technologies) were maintained in high-glucose DMEM with GlutaMax and sodium pyruvate (Life Technologies) supplemented with 10% heat-inactivated characterized HyClone fetal bovine serum (Thermo Scientific) and 1% penicillin/streptomycin (Life Technologies). Cells were passaged daily at a ratio 1:2 or 1:2.5. For gene activation experiments, 20,000 HEK293FT cells/well were plated in 100 μL media in poly-D-lysine coated 96-well plates (BD BioSciences). 24 hours after plating, cells were transfected with a 1:1:1 mass ratio of:

sgRNA plasmid with gene-specific targeting sequence or pUC19 control plasmid

MS2-effector plasmid or pUC19.

dCas9 plasmid, dCas9-effector plasmid, or pUC19.

A total plasmid mass of 0.3 ug/well was transfected using 1.5 uL/well Lipofectamine 2000 (Life Technologies) according to the manufacturer's instructions. Culture medium was changed 5 hours after transfection. 48 hours after transfection, cell lysis and reverse transcription were performed using a Cells-to-Ct kit (Life Technologies). Relative RNA expression levels were quantified by reverse transcription and quantitative PCR (qPCR) using Taqman qPCR probes (Life technologies) and Fast Advanced Master Mix (Life Technologies). qPCR was carried out in 5 uL multiplexed reactions and 384-well format using the Light-Cycler 480 Instrument II. Data was analyzed by the $\Delta\Delta C_t$ method: target Ct values (FAM dye) were normalized to GAPDH Ct values (VIC dye), and fold changes in target gene expression were determined by comparing to GFP-transfected experimental controls.

Lentivirus Production:

HEK293T cells (Life Technologies) were cultured as described above for HEK293FT cells. 1 day prior to transfection, cells were seeded at ~40% confluency (12 T225 flasks for library scale production, 1 T75 flask for individual guide production). Cells were transfected the next day at ~80-90% confluency. For each flask, 20 ug of plasmid containing the vector of interest, 10 ug of pVSVG, and 15 ug of psPAX2 (Addgene) were transfected using 100 uL of Lipofectamine 2000 and 200 uL Plus Reagent (Life Technologies). 5 h after transfection the media was changed. Virus supernatant was harvested 48 h post-transfection, filtered with a 0.45 μm PVDF filter (Millipore), aliquoted, and stored at −80° C.

Lentiviral Transduction:

A375 cells (ATCC) were cultured in RPMI 1640 (Life Technologies) supplemented with 10% FBS (Seradigm) and 1% penicillin/streptomycin (Life Technologies) and passaged every other day at a 1:4 ratio. Cells were transduced with lentivirus via spinfection in 12-well plates. $3 \times 10^6$ cells in 2 mL of media supplemented with 8 ug/mL polybrene (Sigma) were added to each well, supplemented with lentiviral supernatant and centrifuged for 2 h at 1000 g. 24 h after spinfection, cells were detached with TrypLE (Life Technologies) and counted. Cells were replated at low density ($7.5 \times 10^6$ cells per T225 Flask) and a selection agent was added either immediately (zeocin, blasticidin and hygromycin, all Life technologies) or 3 h after plating (puromycin). Concentrations for selection agents were determined using a kill curve: 0.5 ug/ml puromycin, 200 ug/mL zeocin, 2 ug/mL blasticidin, and 300 ug/mL hygromycin. Media was refreshed on day 2 and cells were passaged every other day starting on day 4 after replating. The duration of selection was 4 days for puromycin and 7 days for zeocin, hygromycin and blasticidin. Lentiviral titers were determined by spinfecting cells with 6 different volumes of lentivirus ranging from 0 to 600 uL and counting the number of surviving cells after a complete selection (3-6 days).

Design and Cloning of SAM Library:

RefSeq coding gene isoforms with a unique TSS (total of 23430 isoforms) were targeted with three guides each for a total library of 70300 guides. Guides were designed to target the first 200 bp upstream of each TSS and subsequently filtered for GC content>25% and minimal overlap of the target sequence. After filtering, the remaining guides were scored according to predicted off-target matches based on Hsu et al. and three guides with the best off-target scores were selected. Cloning of the SAM sgRNA libraries was performed as previously described[14] with a minimal representation of 100 transformed colonies/guide.

Depletion and PLX Screen:

A375 cells stably integrated with SAM Cas9 and effector components were transduced with SAM sgRNA libraries as described above at an MOI of 0.2, with a minimal representation of 500 transduced cells/guide. Cells were maintained at >1000 cells/guide during subsequent passaging. At 7 DPI (complete selection, see above), cells were split into vehicle (DMSO) and PLX4720 conditions (2 uM PLX dissolved in DMSO, Selleckchem). Cells were passaged every 2 days for a total of 14 days of drug treatment. >1000 cells/guide were harvested as a baseline at 3 DPI (4 days before treatment) and at 21 DPI (after 14 days of treatment) for gDNA extraction. Genomic DNA was extracted using the Zymo Quick-gDNA midi kit (Zymo Research). PCR of the virally integrated guides was performed on gDNA at the equivalent of >500 cells/guide in 96 parallel reactions using NEBnext High Fidelity 2× Master Mix (New England Biolabs) in a single-step reaction of 22 cycles. Primers are listed below:

```
forward primer:
                                     (SEQ ID NO: 128)
AATGATACGGCGACCACCGAGATCTACACTCTTTCCCTACACGACGCTCT TCCGATCTNNNNNNNN(1-10bp stagger)GCTTTATATATCTTGTGG

AAAGGACGAAACACC 8 bp barcode indicated in red
```

```
reverse primer:
                                     (SEQ ID NO: 129)
CAAGCAGAAGACGGCATACGAGATNNNNNNNNGTGACTGGAGTTCAGACG

TGTGCTC TTCCGATCTGCCAAGTTGATAACGGACTAGCCTT 8 bp index read barcode indicated in red
```

PCR products from all 96 reactions were pooled, purified using Zymo-Spin™ V with Reservoir (Zymo research) and gel extracted using the Zymoclean™ Gel DNA Recovery Kit (Zymo research). Resulting libraries were deep-sequenced on Illumina Miseq and Hiseq platforms with a total coverage of >35 million reads passing filter per library.

NGS and Screen Hits Analysis:

NGS data were demultiplexed using unique index reads. Guide counts were determined based on perfectly-matched sequencing reads only. For each condition, guide counts were normalized to the total number of counts per condition, and $\log_2$ counts were calculated based on these values. Ratios of counts between conditions were calculated as $\log_2((\text{count } 1+1)/(\text{count } 2+1))$ based on normalized counts.

RIGER analysis was performed using GENE-E based on the normalized day 14 log 2 ratios (PLX/DMSO) averaged over two independent infection replicates. All RIGER analysis used the Kolmogorov-Smirnov method as described previously[51], except for FIG. 26c, where the weighted average method was used in order to enable comparison to GeCKO values determined by that method.

Gene Expression and Pharmacological Validation Analysis:

Gene expression data (CCLE, TCGA, short-term cultures) and pharmacological data (CCLE, short-term cultures) were analyzed to better understand the biological relevance of the top gene hits from the SAM screens. In the CCLE dataset[48], gene expression data (RNA-sequencing) and pharmacological data (activity area for MAPK pathway inhibitors) from $BRAF^{V600}$ mutant melanoma cell lines were used to compute the association between PLX-4720 resistance and the gene expression of each of the top hits. Additionally, gene expression signatures comprised of the top hits were generated using single-sample Gene Set Enrichment Analysis (ssGSEA)[52,53], and the associations between PLX-4720 resistance and these signatures were computed.

Gene expression data (Affymetrix GeneChip HT-HGU133) and PLX-4720 pharmacological data ($GI_{50}$; only for a subset of the samples) from short term melanoma cultures (STC)[49] was also used for plotting the gene expression of top hits and their ssGSEA signature scores. Expression data for the STC samples were collapsed to maximum probe value per gene and preprocessed using robust spline normalization.

Gene expression (RNA-sequencing) and genotyping data were collected from 113 $BRAF^{V600}$-mutant primary and metastatic patient tumors from The Cancer Genome Atlas (tcga-data.nci.nih.gov/tcga/) and this data was similarly used for determining the association between resistance and the expression of top hits/ssGSEA signature scores. Because pharmacological data was not available for the STCs (only a subset had PLX-4720 data) and the TCGA melanoma samples, a transcriptional state was plotted using marker genes and signatures[47] in order to identify which samples were resistant to BRAF-inhibition.

Single Sample Gene Set Enrichment Analysis:

While there was a significant association between the overexpression of some of the top individual SAM screen hits and resistance in three external cancer datasets, a more robust scoring system independent of any single gene was sought. Gene expression signatures were generated based on the set of top hits from each of the two SAM screens and for the overlap between them. Using single-sample Gene Set Enrichment analysis (ssGSEA), a score was generated for each sample that represents the enrichment of the SAM screen gene expression signature in that sample and the extent to which those genes are coordinately up- or down-regulated. Additionally, signature gene sets from the Molecular Signature Database (MSigDB)[54] were used in order to fully map the transcriptional BRAF-inhibitor resistant/sensitive states in the short-term culture and TCGA datasets as previously described[47].

Information Coefficient for Measuring Associations in External Datasets:

To measure correlations between different features (signature scores, gene expression, or drug-resistance data) in the external cancer datasets, an information-theoretic approach (Information Coefficient; IC) was used and significance was measured using a permutation test (n=10,000), as previously described[47]. The IC was calculated between the feature used to sort the samples (columns) in each dataset and each of the features plotted in the heatmap (pharmacological data, gene expression, and signature scores).

sgRNA Sequence Analysis:

Depletion for each sgRNA was calculated as the ratio of counts (see "NGS and screen hits analysis") between day 3 and day 21. sgRNAs corresponding to genes with significant depletion (p<=0.05 by RIGER analysis) in sgRNA-puro and sgRNA-zeo libraries were selected for analyses. Selected sgRNA were counted for nucleotide occurrence in the sgRNA sequence, and for each nucleotide type, the correlation and significance with the sgRNA ratio of counts was calculated by Ordinary Least Squares linear regression.

REFERENCES (SPECIFIC TO EXAMPLE 8)

1 Berns, K. et al. A large-scale RNAi screen in human cells identifies new components of the p53 pathway. Nature 428, 431-437, doi:10.1038/nature02371 (2004).
2 Boutros, M. et al. Genome-wide RNAi analysis of growth and viability in Drosophila cells. Science 303, 832-835, doi:10.1126/science.1091266 (2004).
3 Horvath, P. & Barrangou, R. CRISPR/Cas, the immune system of bacteria and archaea. Science 327, 167-170, doi:10.1126/science.1179555 (2010).
4 Beerli, R. R. & Barbas, C. F., 3rd. Engineering polydactyl zinc-finger transcription factors. Nature biotechnology 20, 135-141, doi:10.1038/nbt0202-135 (2002).
5 Beerli, R. R., Segal, D. J., Dreier, B. & Barbas, C. F., 3rd. Toward controlling gene expression at will: specific regulation of the erbB-2/HER-2 promoter by using polydactyl zinc finger proteins constructed from modular building blocks. Proceedings of the National Academy of Sciences of the United States of America 95, 14628-14633 (1998).
6 Zhang, F. et al. Efficient construction of sequence-specific TAL effectors for modulating mammalian transcription. Nature biotechnology 29, 149-153, doi:10.1038/nbt.1775 (2011).
7 Gilbert, L. A. et al. CRISPR-mediated modular RNA-guided regulation of transcription in eukaryotes. Cell 154, 442-451, doi:10.1016/j.cell.2013.06.044 (2013).
8 Konermann, S. et al. Optical control of mammalian endogenous transcription and epigenetic states. Nature 500, 472-476, doi:10.1038/nature12466 (2013).
9 Maeder, M. L. et al. Targeted DNA demethylation and activation of endogenous genes using programmable TALE-TET1 fusion proteins. Nature biotechnology 31, 1137-1142, doi:10.1038/nbt.2726 (2013).
10 Maeder, M. L. et al. CRISPR RNA-guided activation of endogenous human genes. Nature methods 10, 977-979, doi:10.1038/nmeth.2598 (2013).
11 Mali, P. et al. CAS9 transcriptional activators for target specificity screening and paired nickases for cooperative genome engineering. Nature biotechnology 31, 833-838, doi:10.1038/nbt.2675 (2013).
12 Perez-Pinera, P. et al. RNA-guided gene activation by CRISPR-Cas9-based transcription factors. Nature methods 10, 973-976, doi:10.1038/nmeth.2600 (2013).
13 Perez-Pinera, P. et al. Synergistic and tunable human gene activation by combinations of synthetic transcription factors. Nature methods 10, 239-242, doi:10.1038/nmeth.2361 (2013).
14 Shalem, O. et al. Genome-scale CRISPR-Cas9 knockout screening in human cells. Science 343, 84-87, doi:10.1126/science.1247005 (2014).
15 Wang, T., Wei, J. J., Sabatini, D. M. & Lander, E. S. Genetic screens in human cells using the CRISPR-Cas9 system. Science 343, 80-84, doi:10.1126/science.1246981 (2014).
16 Koike-Yusa, H., Li, Y., Tan, E. P., Velasco-Herrera Mdel, C. & Yusa, K. Genome-wide recessive genetic screening in mammalian cells with a lentiviral CRISPR-guide RNA library. Nature biotechnology 32, 267-273, doi:10.1038/nbt.2800 (2014).
17 Nishimasu, H. et al. Crystal structure of Cas9 in complex with guide RNA and target DNA. Cell 156, 935-949, doi:10.1016/j.cell.2014.02.001 (2014).
18 Peabody, D. S. The RNA binding site of bacteriophage MS2 coat protein. The EMBO journal 12, 595-600 (1993).
19 Auslander, S., Auslander, D., Muller, M., Wieland, M. & Fussenegger, M. Programmable single-cell mammalian biocomputers. Nature 487, 123-127, doi:10.1038/nature11149 (2012).
20 Lemon, B. & Tjian, R. Orchestrated response: a symphony of transcription factors for gene control. Genes & development 14, 2551-2569 (2000).
21 van Essen, D., Engist, B., Natoli, G. & Saccani, S. Two modes of transcriptional activation at native promoters by NF-kappaB p65. PLoS biology 7, e73, doi:10.1371/journal.pbio.1000073 (2009).
22 Kretzschmar, M., Kaiser, K., Lottspeich, F. & Meisterernst, M. A novel mediator of class II gene transcription with homology to viral immediate-early transcriptional regulators. Cell 78, 525-534 (1994).
23 Ikeda, K., Stuehler, T. & Meisterernst, M. The H1 and H2 regions of the activation domain of herpes simplex virion protein 16 stimulate transcription through distinct molecular mechanisms. Genes to cells: devoted to molecular & cellular mechanisms 7, 49-58 (2002).
24 Neely, K. E. et al. Activation domain-mediated targeting of the SWI/SNF complex to promoters stimulates transcription from nucleosome arrays. Molecular cell 4, 649-655 (1999).
25 Weintraub, H. et al. Muscle-specific transcriptional activation by MyoD. Genes & development 5, 1377-1386 (1991).
26 Cech, T. R. & Steitz, J. A. The noncoding RNA revolution-trashing old rules to forge new ones. Cell 157, 77-94, doi:10.1016/j.cell.2014.03.008 (2014).

27 Engreitz, J. M. et al. The Xist lncRNA exploits three-dimensional genome architecture to spread across the X chromosome. Science 341, 1237973, doi:10.1126/science.1237973 (2013).
28 Kretz, M. et al. Control of somatic tissue differentiation by the long non-coding RNA TINCR. Nature 493, 231-235, doi:10.1038/nature11661 (2013).
29 Wang, K. C. et al. A long noncoding RNA maintains active chromatin to coordinate homeotic gene expression. Nature 472, 120-124, doi:10.1038/nature09819 (2011).
30 Prensner, J. R. et al. Transcriptome sequencing across a prostate cancer cohort identifies PCAT-1, an unannotated lincRNA implicated in disease progression. Nature biotechnology 29, 742-749, doi:10.1038/nbt.1914 (2011).
31 Cabili, M. N. et al. Integrative annotation of human large intergenic noncoding RNAs reveals global properties and specific subclasses. Genes & development 25, 1915-1927, doi:10.1101/gad.17446611 (2011).
32 Li, J. et al. PTEN, a putative protein tyrosine phosphatase gene mutated in human brain, breast, and prostate cancer. Science 275, 1943-1947 (1997).
33 Bowman, T. et al. Stat3-mediated Myc expression is required for Src transformation and PDGF-induced mitogenesis. Proceedings of the National Academy of Sciences of the United States of America 98, 7319-7324, doi:10.1073/pnas.131568898 (2001).
34 Prahallad, A. et al. Unresponsiveness of colon cancer to BRAF(V600E) inhibition through feedback activation of EGFR. Nature 483, 100-103, doi:10.1038/nature10868 (2012).
35 Held, M. A. et al. Genotype-selective combination therapies for melanoma identified by high-throughput drug screening. Cancer discovery 3, 52-67, doi:10.1158/2159-8290.CD-12-0408 (2013).
36 Johannessen, C. M. et al. A melanocyte lineage program confers resistance to MAP kinase pathway inhibition. Nature 504, 138-142, doi:10.1038/nature12688 (2013).
37 Jenkins, L. et al. Agonist activation of the G protein-coupled receptor GPR35 involves transmembrane domain III and is transduced via Galpha(1)(3) and beta-arrestin-2. British journal of pharmacology 162, 733-748, doi:10.1111/j.1476-5381.2010.01082.x (2011).
38 Choi, J. W. et al. LPA receptors: subtypes and biological actions. Annual review of pharmacology and toxicology 50, 157-186, doi:10.1146/annurev.pharmtox.010909.105753 (2010).
39 Kumar, S. A. et al. Lysophosphatidic acid receptor expression in chronic lymphocytic leukemia leads to cell survival mediated though vascular endothelial growth factor expression. Leukemia & lymphoma 50, 2038-2048, doi:10.3109/10428190903275586 (2009).
40 Okabe, K. et al. Possible involvement of lysophosphatidic acid receptor-5 gene in the acquisition of growth advantage of rat tumor cells. Molecular carcinogenesis 50, 635-642, doi:10.1002/mc.20750 (2011).
41 Fujiwara, S. et al. Transforming activity of purinergic receptor P2Y, G protein coupled, 8 revealed by retroviral expression screening. Leukemia & lymphoma 48, 978-986, doi:10.1080/10428190701225882 (2007).
42 Johannessen, C. M. et al. COT drives resistance to RAF inhibition through MAP kinase pathway reactivation. Nature 468, 968-972, doi:10.1038/nature09627 (2010).
43 Gupta, S. K., Oommen, S., Aubry, M. C., Williams, B. P. & Vlahakis, N. E. Integrin alpha9beta1 promotes malignant tumor growth and metastasis by potentiating epithelial-mesenchymal transition. Oncogene 32, 141-150, doi:10.1038/onc.2012.41 (2013).
44 Bao, W. & Stromblad, S. Integrin alphav-mediated inactivation of p53 controls a MEK1-dependent melanoma cell survival pathway in three-dimensional collagen. The Journal of cell biology 167, 745-756, doi:10.1083/jcb.200404018 (2004).
45 Desgrosellier, J. S. & Cheresh, D. A. Integrins in cancer: biological implications and therapeutic opportunities. Nature reviews. Cancer 10, 9-22, doi:10.1038/nrc2748 (2010).
46 Seguin, L. et al. An integrin beta(3)-KRAS-RalB complex drives tumour stemness and resistance to EGFR inhibition. Nature cell biology 16, 457-468, doi:10.1038/ncb2953 (2014).
47 Konieczkowski, D. J. et al. A melanoma cell state distinction influences sensitivity to MAPK pathway inhibitors. Cancer discovery 4, 816-827, doi:10.1158/2159-8290.CD-13-0424 (2014).
48 Barretina, J. et al. The Cancer Cell Line Encyclopedia enables predictive modelling of anticancer drug sensitivity. Nature 483, 603-607, doi:10.1038/nature11003 (2012).
49 Lin, W. M. et al. Modeling genomic diversity and tumor dependency in malignant melanoma. Cancer research 68, 664-673, doi:10.1158/0008-5472.CAN-07-2615 (2008).
50 Wu, X. et al. Genome-wide binding of the CRISPR endonuclease Cas9 in mammalian cells. Nature biotechnology 32, 670-676, doi:10.1038/nbt.2889 (2014).
51 Luo, B. et al. Highly parallel identification of essential genes in cancer cells. Proceedings of the National Academy of Sciences of the United States of America 105, 20380-20385, doi:10.1073/pnas.0810485105 (2008).
52 Subramanian, A. et al. Gene set enrichment analysis: a knowledge-based approach for interpreting genome-wide expression profiles. Proceedings of the National Academy of Sciences of the United States of America 102, 15545-15550, doi:10.1073/pnas.0506580102 (2005).
53 Barbie, D. A. et al. Systematic RNA interference reveals that oncogenic KRAS-driven cancers require TBK1. Nature 462, 108-112, doi:10.1038/nature08460 (2009).
54 Liberzon, A. et al. Molecular signatures database (MSigDB) 3.0. Bioinformatics 27, 1739-1740, doi:10.1093/bioinformatics/btr260 (2011).

Example 9: Inducible Structural Design Activation Mediators Transgenic Mice

On the basis of Platt et al., Cell (2014), DOI: 10.1016/j.cell.2014.09.014, or PCT patent publications as herein cited, such as WO 2014/093622 (PCT/US2013/074667), an inducible structural design activation mediator transgenic mouse is established. A mouse engineered with the Lox-Stop-polyA-Lox(LSL) cassette upstream to the coding region of the SpCas9-VP64 fusion protein is established. A second mouse engineered with the Lox-Stop-polyA-Lox(LSL) cassette upstream to the coding region of the SpCas9-VP64 fusion protein and upstream to the coding region of the MS2-P65-HSF1 fusion protein is established.

Example 10: Screening for Gain of Function Phenotypes Using Inducible Structural Design Activation Mediators in Cells and Transgenic Mice The mice established in Example 9 are transfected with a AAV-Cre construct coding for and expressing Cre (such as under the control of a U6 promoter) and also coding for and expressing modified sgRNA (such as U6-modified sgRNA), according to the present invention via AAV. sgRNAs are designed to target the promoter region within 1000 nucleotides upstream of the TTS of lincRNAs of unknown function. Animals are screened for aberrant phenotypes.

Human guides and mouse guides of PCT application designating, inter alia, the United States, application No. PCT/US14/41806, filed Jun. 10, 2014, and the applications in the lineage of this PCT application (i.e., guides in the applications as to which PCT/US14/41806 claims priority), all incorporated herein by reference, are modified to contain an activator as herein discussed, or a repressor as herein discussed.

Human cells containing or modified to constitutively express or inducibly express Cas9 are transfected with an AAV construct coding for human sgRNA of PCT application designating, inter alia, the United States, application No. PCT/US14/41806, filed Jun. 10, 2014, and the applications in the lineage of this PCT application (i.e., guides in the applications as to which PCT/US14/41806 claims priority), wherein the guides include either at least one repressor or at least one activator, in accordance with the herein discussion, under the control of and operably linked to a promoter, such as U6-modified sgRNA, according to the present invention; and in the case of such cells wherein the Cas9 is inducibly expressed, Cre induces expression and the construct also via AAV codes for and expresses Cre, such as by way of coding therefor operably linked to a U6 promoter. The cells as to which the sgRNA has a activator are monitored for Gain of Function and the cells as to which the sgRNA has a repressor are monitored for Loss of Function. The cells as to which the modified sgRNA has an activator show gain of function, and the cells as to which the modified sgRNA has a repressor show loss of function. In this fashion, human cells can be screened.

The Cas9 mouse of Example 9, Platt et al., Cell (2014), DOI: 10.1016/j.cdl.2014.09.014 or PCT publications as herein cited, such as WO 2014/093622 (PCT/US2013/074667), and are transfected with a AAV-Cre construct coding for and expressing Cre (such as under the control of a U6 promoter) and also coding for and expressing modified mouse sgRNA (such as U6-modified sgRNA) of PCT application designating, inter alia, the United States, application No. PCT/US14/41806, filed Jun. 10, 2014, and the applications in the lineage of this PCT application (i.e., guides in the applications as to which PCT/US14/41806 claims priority), wherein the guides include either at least one repressor or at least one activator, in accordance with the herein disclosure. The mice as to which the sgRNA has a activator are monitored for Gain of Function and the mice as to which the sgRNA has a repressor are monitored for Loss of Function. The mice as to which the modified sgRNA has an activator show gain of function, and the mice as to which the modified sgRNA has a repressor show loss of function. In this fashion, mice can be screened.

The libraries that are able to be used in accordance with the invention include the GeCKO v1 and GeCKO v2 libraries. These libraries are alternatively referred to herein as GeCKO1 and GeCKO2. Those libraries are also disclosed in each of PCT/US14/41806 and U.S. provisional patent applications 61/960,777, 61/961,980, 61/963,643 and 61/995,636, and especially the CDs filed therewith, and the Budapest Treaty Biological Deposit(s) namely ATCC-Deposit Nos: PTA-121339, PTA-121340, PTA-121341, PTA-121342, PTA-121343, deposited on Jun. 10, 2014, with the American Type Culture Collection on American Type Culture Collection (ATCC), 10801 University Boulevard, Manassas, Va. 20110 USA, under and pursuant to the terms of the Budapest Treaty, made in connection with PCT/US14/41806. The plasmid library (preferably as further cloned into a delivery vector, such as lentivector) may be selected from the group consisting of:

(A) GeCKO1—library of sgRNA plasmids each encoding selected guide sequences and cloned into vector (lentiCRISPRv2)—ATCC Deposit No. PTA121339;
(B) GeCKO2—half library A (human) sgRNA plasmids each encoding selected guide sequences and cloned into vector—ATCC Deposit No. PTA121340;
(C) GeCKO2—half library B (human) of sgRNA plasmids each encoding selected guide sequences and cloned into vector—ATCC Deposit No. PTA121341;
(D) GeCKO2—half library A (mouse) sgRNA plasmids each encoding selected guide sequences and cloned into vector—ATCC Deposit No. PTA121342; and
(E) GeCKO2—half library A (mouse) sgRNA plasmids each encoding selected guide sequences and cloned into vector—ATCC Deposit No. PTA121343;

wherein "GeCKO" stands for Genome-scale CRISPR-Cas9 Knock Out". The various GeCKO libraries have been generated for targeting either human or mouse genomes and consist of a one vector system or a two vector system for delivery of short 20 bp sequences of the sgRNA with or without Cas9. The GeCKO1 library consists of specific sgRNA sequences for gene knock-out in either the human or mouse genome. The GeCKO2 libraries consist of specific sgRNA sequences for gene knock-out in either the human or mouse genome, wherein each species-specific library is delivered as two half-libraries (A and B). When used together, the A and B libraries contain 6 sgRNAs per gene (3 sgRNAs in each library) and may contain 4 sgRNAs per microRNA ("miRNA") for over 1000 miRNA per genome (1864 in human, 1175 in mouse). Any one or more GeCKO library may be used in any one of the methods or in any one of the kits of the present invention. The GeCKO libraries, and specifically each of (A) to (E), above, were deposited with the American Type Culture Collection (ATCC) on Jun. 10, 2014, and are further exemplified in ATCC Deposit Nos: PTA-121339, PTA-121340, PTA-121341, PTA-121342, PTA-121343, deposited on Jun. 10, 2014, as provided herein and in the compact discs created Apr. 11, 2014, as filed in connection with U.S. applications 61/960,777 and 61/995,636, including as the information set forth in those US applications and the compact discs filed therewith is presented herein via the ATCC Deposits. Reference is also made to Shalem et al., Science 3 Jan. 2014: Vol. 343 no. 6166 pp. 84-87 entitled "Genome-Scale CRISPR-Cas9 Knockout Screening In Human Cells" and Sanjana et al., Nature Methods 11, 783-784 (2014) entitled "Improved vectors and genome-wide libraries for CRISPR screening".

In an aspect, the vector systems in the methods of the invention comprise one or more lentiviral vector(s). In a preferred embodiment, the one or more lentiviral vectors may comprise a codon optimized nuclear localization signal (NLS), a codon optimized P2A bicistronic linker sequence and an optimally placed U6 driven guide RNA cassette. In another aspect the vector system comprises two lentiviral vectors, wherein one lentiviral vector comprises the Cas9 enzyme and the other lentiviral vector comprises the guide RNA selected from the libraries of the invention. In an embodiment of the invention, each vector has a different selection marker, e.g. a different antibiotic resistance marker. The invention also comprehends kits comprising the libraries of the invention. In certain aspects, the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

Example 11: Paired Nickase Fok1

Paired CRISPR-Cas complexes having a mutated CRISPR enzyme whereby the CRISPR enzyme is "dead" (has at most 5% nuclease activity of non-mutated Cas9 or CRISPR enzyme), and a Fok1 nuclease is operably linked to sgRNA are delivered to cells, whereby in the pair, a first CRISPR-Cas complex makes a cut at a first loci in the cells and a second CRISPR-Cas complex makes cut at a second loci in the cells; the two Fok1 enzymes provide a double stranded break such as when the first and second loci are at or near each other but on different strands of double stranded DNA, whereby such that the CRISPR-Cas complex(es) provide(s) a particular specific cut or double stranded cut, and the CRISPR-Cas complexes have a greater reduction in off-target cutting, than unmodified CRISPR-Cas complexes. The paired CRISPR-Cas9 complexes can cut the two strands of double stranded DNA such that HDR can occur. In embodiments template DNA is introduced into the cells whereby there is homologous recombination inserting the template DNA where the double stranded cut has been made.

Example 12: Orthogonal Repression with Non-Coding Ma Loops; Non-Coding Loops for Bimodal Cas9 Repression An alternative option for orthogonal repression is to incorporate non-coding rna loops with transactive repressive function into the guide (either at similar positions to the MS2/PP7 loops integrated into the guide or at the 3' terminus of the guide).

The non-coding Alu RNA has previously been described as a transacting repressor interfering with RNA polymerase II in mammalian cells. In addition, a minimal loop required for repression has been identified (sciencedirect.com/science/article/pii/S1097276508000026). Applicants designed guides with different sites of incorporation of the truncated Alu loop (and in combination with PP7 loops). Sequences for these sgRNA backbones are listed below:

Sequences (Guide Backbones)

tetraloop(Alu)-loop2(PP7)
(SEQ ID NO: 130)
gttttagagctagaggcaggagaatggcgtgaacccgggaggtggccgag atcgctccagcctgggtgacagagcgagactctgtctctagcaagttaaa ataaggctagtccgttatcaacttGGAGCAGACGATATGGCGTCGCTCCa agtggcaccgagtcggtgcTTTTTTT tetraloop(PP7)-loop2(Alu)
(SEQ ID NO: 131)
gttttagagctaGGAGCAGACGATATGGCGTCGCTCCtagcaagttaaaa taaggctagtccgttatcaacttgaggcaggagaatggcgtgaacccggg aggtggccgagatcgctccagcctgggtgacagagcgagactctgtctca agtggcaccgagtcggtgcTTTTTTT tetraloop(Alu)-loop2(Alu)
(SEQ ID NO: 132)
gttttagagctagaggcaggagaatggcgtgaacccgggaggtggccgag atcgctccagcctgggtgacagagcgagactctgtctctagcaagttaaa ataaggctagtccgttatcaacttgaggcaggagaatggcgtgaacccgg gaggtggccgagatcgctccagcctgggtgacagagcgagactctgtctc aagtggcaccgagtcggtgcTTTTTTT Sequences (spacer target sequences)

CXCR4 guide 1
(SEQ ID NO: 133)
TACTGGAGCACTCAGGCCCT

CXCR4 guide 2
(SEQ ID NO: 134)
AGGTAGCAAAGTGACGCCGA

CACNAC1A guide 1
(SEQ ID NO: 135)
tgccagagcggcgctcggcg

CACNAC1A guide 2
(SEQ ID NO: 136)
gcggcgcggcgggcccggag

Methods: HEK293FT cells (Life Technologies) were maintained in high-glucose DMEM with GlutaMax and sodium pyruvate (Life Technologies) supplemented with 10% heat-inactivated characterized HyClone fetal bovine serum (Thermo Scientific) and 1% penicillin/streptomycin (Life Technologies). Cells were passaged daily at a ratio 1:2 or 1:2.5. For gene activation experiments, 20,000 HEK293FT cells/well were plated in 100 μL media in poly-D-lysine coated 96-well plates (BD BioSciences). 24 hours after plating, cells were transfected with a 1:1 mass ratio of:

sgRNA plasmid with gene-specific targeting sequence
dCas9 plasmid

A total plasmid mass of 0.3 μg/well was transfected using 0.6 μL/well Lipofectamine 2000 (Life Technologies) according to the manufacturer's instructions. Culture medium was changed 5 hours after transfection. 48 hours after transfection, cell lysis and reverse transcription were performed using a Cells-to-Ct kit (Life Technologies). Relative RNA expression levels were quantified by reverse transcription and quantitative PCR (qPCR) using TaqMan qPCR probes (Life Technologies) and Fast Advanced Master Mix (Life Technologies). qPCR was carried out in 5 μL multiplexed reactions and 384-well format using the LightCycler 480 Instrument II. Data was analyzed by the ΔΔCt method: target Ct values (FAM dye) were normalized to GAPDH Ct values (VIC dye), and fold changes in target gene expression were determined by comparing to GFP-transfected experimental controls.

Figure 43:
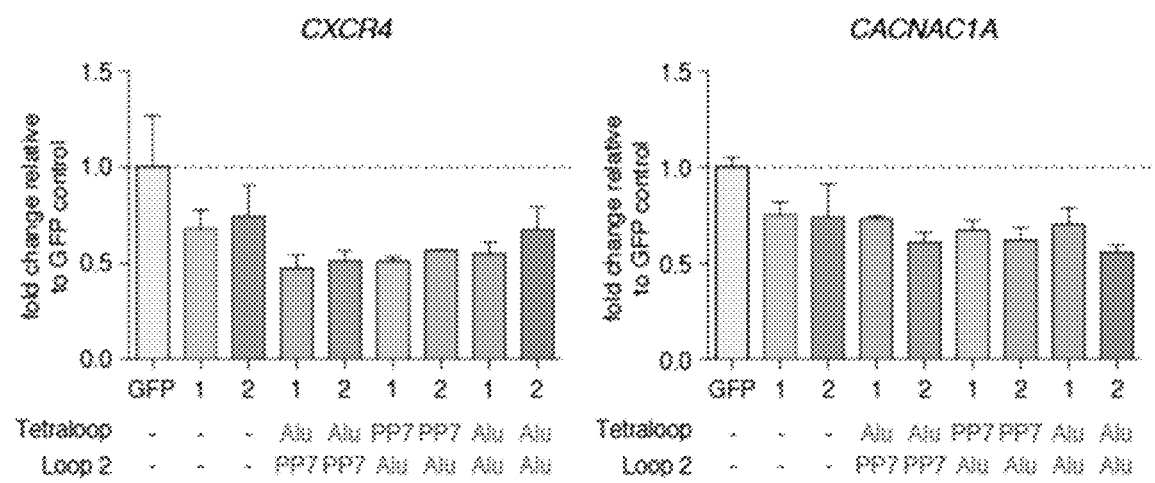
FIG. 43 shows addition of minimal non-coding Alu-loops at the tetraloop and stem-loop 2 is able to repress target gene expression in complex with Sp. dCas9. Two different spacers (labeled 1 and 2 in the figure) were tested for each gene and guide backbone design.

Results: FIG. 43 shows the addition of minimal non-coding Alu-loops at the tetraloop and stem-loop 2 is able to repress target gene expression in complex with Sp. dCas9. Two different spacers (labeled 1 and 2 in the figure) were tested for each gene and guide backbone design. Applicants found that addition of minimal non-coding Alu-loops at the tetraloop and stem-loop 2 is able to repress target gene expression in complex with dCas9. These results demonstrate that insertion of non-coding RNA loops with transacting functionality into the guide (e.g. at the tetraloop and stem-loop 2) is a feasible strategy for creating effective functional Cas9 complexes.

Thus, in accordance with the invention, guides were designed with non-coding (but known to be functional, e.g., repressive) RNA loops (e.g. using the Alu repressor (in RNA) that interferes with RNA polymerase II in mammalian cells). The Alu RNA sequence was located: in place of the MS2 RNA sequences as used herein (e.g. at tetraloop and/or stem-loop 2); and/or at 3' terminus of the guide. This gives possible combinations of MS2, PP7 or Alu at the tetraloop and/or stem-loop 2 positions, as well as, optionally, addition of Alu at the 3' end of the guide (with or without a linker). Sequences of 6 such examples, include:

| Stem Loop 2 | Tetraloop | 3' addition | 3' linker |
| --- | --- | --- | --- |
| PP7 | PP7 | Alu | No |
| PP7 | MS2 | Alu | No |
| MS2 | PP7 | Alu | No |
| MS2 | MS2 | Alu | No |
| PP7 | Alu | None | No |
| Alu | Alu | None | No |

In addition to the foregoing, Applicants designed guides with different sites of incorporation of the truncated Alu loop (and in combination with PP7 loops). Sequences for these sgRNA backbones are listed below:

sgRNA(PP7, PP7, 3'AluRA)
(SEQ ID NO: 137)
gttttagagctaggccGGAGCAGACGATATGGCGTCGCTCCggcctagca agttaaaataaggctagtccgttatcaacttggccGGAGCAGACGATATG GCGTCGCTCCggccaagtggcaccgagtcggtgcgaggcaggagaatggc gtgaacccggGaggtggagcttgcagcgagccgagatcgcgccactgcac tccagcctgggtgacagagcgagactctgtctcTTTTTTT sgRNA(PP7, PP7, 3'linker_sAlu)
(SEQ ID NO: 138)
gttttagagctaggccGGAGCAGACGATATGGCGTCGCTCCggcctagca agttaaaataaggctagtccgttatcaacttggccGGAGCAGACGATATG GCGTCGCTCCggccaagtggcaccgagtcggtgctactaaaaatacaaaa aattgaggcaggagaatggcgtgaacccgggaggtggccgagatcgctcc agcctgggtgacagagcgagactctgtctcTTTTTTT sgRNA(PP7, PP7, 3'linker_AluRA)
(SEQ ID NO: 139)
gttttagagctaggccGGAGCAGACGATATGGCGTCGCTCCggcctagca agttaaaataaggctagtccgttatcaacttggccGGAGCAGACGATATG GCGTCGCTCCggccaagtggcaccgagtcggtgctactaaaaatacaaaa aattgaggcaggagaatggcgtgaacccgggaggtggagcttgcagcgag ccgagatcgcgccactgcactccagcctgggtgacagagcgagactctgt ctcTTTTTTT sgRNA(PP7, PP7, 3'sAlu)
(SEQ ID NO: 140)
gttttagagctaggccGGAGCAGACGATATGGCGTCGCTCCggcctagca agttaaaataaggctagtccgttatcaacttggccGGAGCAGACGATATG GCGTCGCTCCggccaagtggcaccgagtcggtgcgaggcaggagaatggc gtgaacccgggaggtggccgagatcgctccagcctgggtgacagagcgag actctgtctcTTTTTTT sgRNA(Alu-RA, Alu-RA)
(SEQ ID NO: 132)
gttttagagctagaggcaggagaatggcgtgaacccgggaggtggccgag atcgctccagcctgggtgacagagcgagactctgtctctagcaagttaaa ataaggctagtccgttatcaacttgaggcaggagaatggcgtgaacccgg gaggtggccgagatcgctccagcctgggtgacagagcgagactctgtctc aagtggcaccgagtcggtgcTTTTTTT sgRNA(sAlu, sAlu)
(SEQ ID NO: 132)
gttttagagctagaggcaggagaatggcgtgaacccgggaggtggccgag atcgctccagcctgggtgacagagcgagactctgtctctagcaagttaaa ataaggctagtccgttatcaacttgaggcaggagaatggcgtgaacccgg gaggtggccgagatcgctccagcctgggtgacagagcgagactctgtctc aagtggcaccgagtcggtgcTTTTTTT Using methods as discussed above, these guides also provide orthogonal repression.

Example 13: LincRNA Screening (Screening for Non-Coding RNAs; Library Preparation)

In addition to gain of function screening for protein coding genes, SAM was used to screen non-coding RNAs or potential regulatory regions (e.g. enhancers, repressors).

To demonstrate the utility of SAM for screening non-coding elements in the genome Applicants constructed a SAM lincRNA library. The library was designed according to the following principles: The set of lincRNAs targeted was a combined set of lincRNAs described in the BROAD lincRNA catalog (stringent set) (see, e.g., broadinstitute.org/genome_bio/human_liccrnas/ and broadinstitute.org/genome_bio/human_liccrnas/?q=lincRNA_catalo-g) and lincRNAs from Refseq (ncbi.nlm.nih.gov/refseq/). Similar public database resources are available to use to construct libraries targeting other types of noncoding elements. All transcripts from these two sources were compacted into isoforms with unique transcriptional start sites (TSSs). Transcripts with TSSs within 50 bp were compacted into a single isoform. This resulted in a list of 10519 lincRNAs with unique TSSs.

Based on experiments of activation of 6 lincRNAs with SAM Applicants determined to design a library with 10 guides per lincRNA in a window of 0-800 bp upstream of the annotated TSS. Based on observations it was estimated that this should result in multiple active guides per lincRNA in most cases, which is essential for efficient pooled screening. Briefly, sgRNA were picked according to the following criteria:

GC content>25%;
non-overlapping sgRNA target sequences;
avoidance of homopolymer stretches of 4 bases or more (e.g. AAAA); and
preference for sgRNAs with low off-target scores (determined according to Hsu et. al, Nature Biotechnology, 2013).

For spacing of the sgRNAs Applicants selected up to 6 sgRNAs in the first 200 bp upstream of TSS, 2 sgRNA in 200-400 and 2 sgRNAs in 400-800. In cases where these criteria yielded less than 10 sgRNAs per lincRNA, they were gradually relaxed (e.g. by allowing up to 10 bp overlap of target sites, by picking more sgRNAs>200 bp from TSS). When picking sgRNAs for a new transcript, sgRNAs already existing in the library were taken into consideration (e.g. if 2 sgRNAs for a nearby transcript were in the targeting window for the new lincRNA, only 8 new sgRNAs would be added to the library).

In addition Applicants added 500 non-targeting sgRNAs (selected to have a particularly low off-target score in promoter regions) to the library as an internal control.

The final library consists of 96040 sgRNAs. It was produced as an oligo pool containing flanking priming sites on each side. This library can be used for pooled screening of lincRNAs via low-MOI lentiviral transduction of target cells expressing dCas9-VP64 and MS2-P65-HSF1 or other Cas9-based transcriptional regulators.

REFERENCES

1. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
2. Bogdanove, A. J. & Voytas, D. F. TAL effectors: customizable proteins for DNA targeting. *Science* 333, 1843-1846 (2011).
3. Stoddard, B. L. Homing endonuclease structure and function. *Q. Rev. Biophys.* 38, 49-95 (2005).
4. Bae, T. & Schneewind, O. Allelic replacement in *Staphylococcus aureus* with inducible counter-selection. *Plasmid* 55, 58-63 (2006).
5. Sung, C. K., Li, H., Claverys, J. P. & Morrison, D. A. An rpsL cassette, j anus, for gene replacement through negative selection in *Streptococcus pneumoniae*. *Appl. Environ. Microbiol.* 67, 5190-5196 (2001).
6. Sharan, S. K., Thomason, L. C., Kuznetsov, S. G. & Court, D. L. Recombineering: a homologous recombination-based method of genetic engineering. *Nat. Protoc.* 4, 206-223 (2009).
7. Jinek, M. et al. A programmable dual-RNA-guided DNA endonuclease in adaptive bacterial immunity. *Science* 337, 816-821 (2012).
8. Deveau, H., Garneau, J. E. & Moineau, S. CRISPR/Cas system and its role in phage-bacteria interactions. *Annu. Rev. Microbiol.* 64, 475-493 (2010).
9. Horvath, P. & Barrangou, R. CRISPR/Cas, the immune system of bacteria and archaea. *Science* 327, 167-170 (2010).
10. Terns, M. P. & Terns, R. M. CRISPR-based adaptive immune systems. *Curr. Opin. Microbiol.* 14, 321-327 (2011).
11. van der Oost, J., Jore, M. M., Westra, E. R., Lundgren, M. & Brouns, S. J. CRISPR-based adaptive and heritable immunity in prokaryotes. *Trends. Biochem. Sci.* 34, 401-407 (2009).
12. Brouns, S. J. et al. Small CRISPR RNAs guide antiviral defense in prokaryotes. *Science* 321, 960-964 (2008).
13. Carte, J., Wang, R., Li, H., Terns, R. M. & Terns, M. P. Cas6 is an endoribonuclease that generates guide RNAs for invader defense in prokaryotes. *Genes Dev.* 22, 3489-3496 (2008).
14. Deltcheva, E. et al. CRISPR RNA maturation by trans-encoded small RNA and host factor RNase III. *Nature* 471, 602-607 (2011).
15. Hatoum-Aslan, A., Maniv, I. & Marraffini, L. A. Mature clustered, regularly interspaced, short palindromic repeats RNA (crRNA) length is measured by a ruler mechanism anchored at the precursor processing site. *Proc. Natl. Acad. Sci. U.S.A.* 108, 21218-21222 (2011).
16. Haurwitz, R. E., Jinek, M., Wiedenheft, B., Zhou, K. & Doudna, J. A. Sequence- and structure-specific RNA processing by a CRISPR endonuclease. *Science* 329, 1355-1358 (2010).
17. Deveau, H. et al. Phage response to CRISPR-encoded resistance in *Streptococcus thermophilus*. *J. Bacteriol.* 190, 1390-1400 (2008).
18. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* (2012).
19. Makarova, K. S., Aravind, L., Wolf, Y. I. & Koonin, E. V. Unification of Cas protein families and a simple scenario for the origin and evolution of CRISPR-Cas systems. *Biol. Direct.* 6, 38 (2011).
20. Barrangou, R. RNA-mediated programmable DNA cleavage. *Nat. Biotechnol.* 30, 836-838 (2012).
21. Brouns, S. J. Molecular biology. A Swiss army knife of immunity. *Science* 337, 808-809 (2012).
22. Carroll, D. A CRISPR Approach to Gene Targeting. *Mol. Ther.* 20, 1658-1660 (2012).
23. Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
24. Sapranauskas, R. et al. The *Streptococcus thermophilus* CRISPR/Cas system provides immunity in *Escherichia coli*. *Nucleic Acids Res.* (2011).
25. Semenova, E. et al. Interference by clustered regularly interspaced short palindromic repeat (CRISPR) RNA is governed by a seed sequence. *Proc. Natl. Acad. Sci. U.S.A.* (2011).
26. Wiedenheft, B. et al. RNA-guided complex from a bacterial immune system enhances target recognition through seed sequence interactions. *Proc. Natl. Acad. Sci. U.S.A.* (2011).
27. Zahner, D. & Hakenbeck, R. The *Streptococcus pneumoniae* beta-galactosidase is a surface protein. *J. Bacteriol.* 182, 5919-5921 (2000).
28. Marraffini, L. A., Dedent, A. C. & Schneewind, O. Sortases and the art of anchoring proteins to the envelopes of gram-positive bacteria. *Microbiol. Mol. Biol. Rev.* 70, 192-221 (2006).
29. Motamedi, M. R., Szigety, S. K. & Rosenberg, S. M. Double-strand-break repair recombination in *Escherichia coli*: physical evidence for a DNA replication mechanism in vivo. *Genes Dev.* 13, 2889-2903 (1999).
30. Hosaka, T. et al. The novel mutation K87E in ribosomal protein S12 enhances protein synthesis activity during the late growth phase in *Escherichia coli*. *Mol. Genet. Genomics* 271, 317-324 (2004).
31. Costantino, N. & Court, D. L. Enhanced levels of lambda Red-mediated recombinants in mismatch repair mutants. *Proc. Natl. Acad. Sci. U.S.A.* 100, 15748-15753 (2003).
32. Edgar, R. & Qimron, U. The *Escherichia coli* CRISPR system protects from lambda lysogenization, lysogens, and prophage induction. *J. Bacteriol.* 192, 6291-6294 (2010).
33. Marraffini, L. A. & Sontheimer, E. J. Self versus non-self discrimination during CRISPR RNA-directed immunity. *Nature* 463, 568-571 (2010).
34. Fischer, S. et al. An archaeal immune system can detect multiple Protospacer Adjacent Motifs (PAMs) to target invader DNA. *J. Biol. Chem.* 287, 33351-33363 (2012).

35. Gudbergsdottir, S. et al. Dynamic properties of the *Sulfolobus* CRISPR/Cas and CRISPR/Cmr systems when challenged with vector-borne viral and plasmid genes and protospacers. *Mol. Microbiol.* 79, 35-49 (2011).

36. Wang, H. H. et al. Genome-scale promoter engineering by coselection MAGE. *Nat Methods* 9, 591-593 (2012).

37. Cong L, Ran F A, Cox D, Lin S, Barretto R, Habib N, Hsu P D, Wu X, Jiang W, Marraffini L A, Zhang F. Multiplex Genome Engineering Using CRISPR/Cas Systems. *Science.* 2013 Feb. 15; 339(6121):819-23.

38. Mali, P., Yang, L., Esvelt, K. M., Aach, J., Guell, M., DiCarlo, J. E., Norville, J. E., and Church, G. M. (2013b). RNA-guided human genome engineering via Cas9. Science 339, 823-826.

39. Hoskins, J. et al. Genome of the bacterium *Streptococcus pneumoniae* strain R6. *J. Bacteriol.* 183, 5709-5717 (2001).

40. Havarstein, L. S., Coomaraswamy, G. & Morrison, D. A. An unmodified heptadecapeptide pheromone induces competence for genetic transformation in *Streptococcus pneumoniae. Proc. Natl. Acad. Sci. U.S.A.* 92, 11140-11144 (1995).

41. Horinouchi, S. & Weisblum, B. Nucleotide sequence and functional map of pC194, a plasmid that specifies inducible chloramphenicol resistance. *J. Bacteriol.* 150, 815-825 (1982).

42. Horton, R. M. In Vitro Recombination and Mutagenesis of DNA: SOEing Together Tailor-Made Genes. *Methods Mol. Biol.* 15, 251-261 (1993).

43. Podbielski, A., Spellerberg, B., Woischnik, M., Pohl, B. & Lutticken, R. Novel series of plasmid vectors for gene inactivation and expression analysis in group A streptococci (GAS). *Gene* 177, 137-147 (1996).

44. Husmann, L. K., Scott, J. R., Lindahl, G. & Stenberg, L. Expression of the Arp protein, a member of the M protein family, is not sufficient to inhibit phagocytosis of *Streptococcus pyogenes. Infection and immunity* 63, 345-348 (1995).

45. Gibson, D. G. et al. Enzymatic assembly of DNA molecules up to several hundred kilobases. *Nat Methods* 6, 343-345 (2009).

46. Garneau J. E. et al. The CRISPR/Cas bacterial immune system cleaves bacteriophage and plasmid DNA. Nature 468, 67-71 (4 Nov. 2010).

47. Barrangou R. et al. CRISPR provides acquired resistance against viruses in prokaryotes. Science. 2007 Mar. 23; 315(5819):1709-12.

48. Ishino Y. et al. Nucleotide sequence of the iap gene, responsible for alkaline phosphatase isozyme conversion in *Escherichia coli*, and identification of the gene product. J Bacteriol. 1987 December; 169(12):5429-33.

49. Mojica F. J. M et al. Biological significance of a family of regularly spaced repeats in the genomes of Archaea, Bacteria and mitochondria. Molecular Microbiology (2000) 36(1), 244-246.

50. Jansen R. et al. Identification of genes that are associated with DNA repeats in prokaryotes. Molecular Microbiology (2002) 43(6), 1565-1575.

51. Gouet, P., Courcelle, E., Stuart, D. I., and Metoz, F. (1999). ESPript: analysis of multiple sequence alignments in PostScript. Bioinformatics 15, 305-308.

52. Notredame, C., Higgins, D. G., and Heringa, J. (2000). T-Coffee: A novel method for fast and accurate multiple sequence alignment. J Mol Biol 302, 205-217.

53. Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002). PHENIX: building new software for automated crystallographic structure determination. Acta Crystallogr D Biol Crystallogr 58, 1948-1954.

54. Ariyoshi, M., Vassylyev, D. G., Iwasaki, H., Nakamura, H., Shinagawa, H., and Morikawa, K. (1994). Atomic structure of the RuvC resolvase: a holliday junction-specific endonuclease from *E. coli*. Cell 78, 1063-1072.

55. Biertumpfel, C., Yang, W., and Suck, D. (2007). Crystal structure of T4 endonuclease VII resolving a Holliday junction. Nature 449, 616-620.

56. Chen, L., Shi, K., Yin, Z., and Aihara, H. (2013). Structural asymmetry in the *Thermus thermophilus* RuvC dimer suggests a basis for sequential strand cleavages during Holliday junction resolution. Nucleic acids research 41, 648-656.

57. delaFortelle, E., and Bricogne, G. (1997). Maximum-likelihood heavy-atom parameter refinement for multiple isomorphous replacement and multiwavelength anomalous diffraction methods. Methods Enzymol 276, 472-494.

58. Emsley, P., and Cowtan, K. (2004). Coot: model-building tools for molecular graphics. Acta Crystallogr D Biol Crystallogr 60, 2126-2132.

59. Fonfara, I., Le Rhun, A., Chylinski, K., Makarova, K. S., Lecrivain, A. L., Bzdrenga, J., Koonin, E. V., and Charpentier, E. (2013). Phylogeny of Cas9 determines functional exchangeability of dual-RNA and Cas9 among orthologous type II CRISPR-Cas systems. Nucleic acids research.

60. Fu, Y., Foden, J. A., Khayter, C., Maeder, M. L., Reyon, D., Joung, J. K., and Sander, J. D. (2013). High-frequency off-target mutagenesis induced by CRISPR-Cas nucleases in human cells. Nature biotechnology 31, 822-826.

61. Gilbert, L. A., Larson, M. H., Morsut, L., Liu, Z., Brar, G. A., Tones, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.

62. Gorecka, K. M., Komorowska, W., and Nowotny, M. (2013). Crystal structure of RuvC resolvase in complex with Holliday junction substrate. Nucleic Acids Res 41, 9945-9955.

63. Gratz, S. J., Cummings, A. M., Nguyen, J. N., Hamm, D. C., Donohue, L. K., Harrison, M. M., Wildonger, J., and O'Connor-Giles, K. M. (2013). Genome engineering of *Drosophila* with the CRISPR RNA-guided Cas9 nuclease. Genetics 194, 1029-1035.

64. Holm, L., and Rosenstrom, P. (2010). Dali server: conservation mapping in 3D. Nucleic acids research 38, W545-549.

65. Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832.

66. Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using a CRISPR-Cas system. Nature biotechnology 31, 227-229.

67. Kabsch, W. (2010). Xds. Acta crystallographica Section D, Biological crystallography 66, 125-132.

68. Konermann, S., Brigham, M. D., Trevino, A. E., Hsu, P. D., Heidenreich, M., Cong, L., Platt, R. J., Scott, D. A., Church, G. M., and Zhang, F. (2013). Optical control of mammalian endogenous transcription and epigenetic states. Nature 500, 472-476.

69. Li, C. L., Hor, L. I., Chang, Z. F., Tsai, L. C., Yang, W. Z., and Yuan, H. S. (2003). DNA binding and cleavage by the periplasmic nuclease Vvn: a novel structure with a known active site. The EMBO journal 22, 4014-4025.
70. Maeder, M. L., Linder, S. J., Cascio, V. M., Fu, Y., Ho, Q. H., and Joung, J. K. (2013). CRISPR RNA-guided activation of endogenous human genes. Nature methods 10, 977-979.
71. Mali, P., Aach, J., Stranges, P. B., Esvelt, K. M., Moosburner, M., Kosuri, S., Yang, L., and Church, G. M. (2013a). CAS9 transcriptional activators for target specificity screening and paired nickases for cooperative genome engineering. Nature biotechnology 31, 833-838.
72. Marraffini, L. A., and Sontheimer, E. J. (2008). CRISPR interference limits horizontal gene transfer in staphylococci by targeting DNA. Science 322, 1843-1845.
73. Marraffini, L. A., and Sontheimer, E. J. (2010). CRISPR interference: RNA-directed adaptive immunity in bacteria and archaea. Nat Rev Genet 11, 181-190.
74. Mojica, F. J., Diez-Villasenor, C., Garcia-Martinez, J., and Almendros, C. (2009). Short motif sequences determine the targets of the prokaryotic CRISPR defense system. Microbiology 155, 733-740.
75. Pattanayak, V., Lin, S., Guilinger, J. P., Ma, E., Doudna, J. A., and Liu, D. R. (2013). High-throughput profiling of off-target DNA cleavage reveals RNA-programmed Cas9 nuclease specificity. Nature biotechnology 31, 839-843.
76. Perez-Pinera, P., Kocak, D. D., Vockley, C. M., Adler, A. F., Kabadi, A. M., Polstein, L. R., Thakore, P. I., Glass, K. A., Ousterout, D. G., Leong, K. W., et al. (2013). RNA-guided gene activation by CRISPR-Cas9-based transcription factors. Nature methods 10, 973-976.
77. Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell 152, 1173-1183.
78. Ran, F. A., Hsu, P. D., Lin, C. Y., Gootenberg, J. S., Konermann, S., Trevino, A. E., Scott, D. A., Inoue, A., Matoba, S., Zhang, Y., et al. (2013). Double nicking by RNA-guided CRISPR Cas9 for enhanced genome editing specificity. Cell 154, 1380-1389.
79. Sampson, T. R., Saroj, S. D., Llewellyn, A. C., Tzeng, Y. L., and Weiss, D. S. (2013). A CRISPR/Cas system mediates bacterial innate immune evasion and virulence. Nature 497, 254-257.
80. Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.
81. Sheldrick, G. M. (2008). A short history of SHELX Acta crystallographica Section A, Foundations of crystallography 64, 112-122.
82. Spilman, M., Cocozaki, A., Hale, C., Shao, Y., Ramia, N., Terns, R., Terns, M., Li, H., and Stagg, S. (2013). Structure of an RNA silencing complex of the CRISPR-Cas immune system. Molecular cell 52, 146-152.
83. Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.
84. Wang, T., Wei, J. J., Sabatini, D. M., and Lander, E. S. (2014). Genetic screens in human cells using the CRISPR-Cas9 system. Science 343, 80-84.
85. Wiedenheft, B., Lander, G. C., Zhou, K., Jore, M. M., Brouns, S. J., van der Oost, J., Doudna, J. A., and Nogales, E. (2011). Structures of the RNA-guided surveillance complex from a bacterial immune system. Nature 477, 486-489.
86. Winn, M. D., Ballard, C. C., Cowtan, K. D., Dodson, E. J., Emsley, P., Evans, P. R., Keegan, R. M., Krissinel, E. B., Leslie, A. G., McCoy, A., et al. (2011). Overview of the CCP4 suite and current developments. Acta crystallographica Section D, Biological crystallography 67, 235-242.
87. Yang, H., Wang, H., Shivalila, C. S., Cheng, A. W., Shi, L., and Jaenisch, R. (2013). One-step generation of mice carrying reporter and conditional alleles by CRISPR/Cas-mediated genome engineering. Cell 154, 1370-1379.

The invention is further described by the following numbered paragraphs:

1. A non-naturally occurring or engineered composition comprising a guide RNA (sgRNA) comprising a guide sequence capable of hybridizing to a target sequence in a genomic locus of interest in a cell, wherein one or more loop(s) of the sgRNA is modified by the insertion of distinct RNA sequence(s) that bind to two or more adaptor proteins, and wherein each adaptor protein is associated with one or more functional domains; or, wherein the sgRNA is modified to have at least one non-coding functional loop.

2. A non-naturally occurring or engineered CRISPR-Cas complex composition comprising the sgRNA of paragraph 1 and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences.

3. The sgRNA of paragraph 1 or the CRISPR-Cas complex of claim 2 including a non-naturally occurring or engineered composition comprising two or more adaptor proteins, wherein each protein is associated with one or more functional domains and wherein the adaptor protein binds to the distinct RNA sequence(s) inserted into the at least one loop of the sgRNA.

4. A non-naturally occurring or engineered composition comprising
a guide RNA (sgRNA) comprising a guide sequence capable of hybridizing to a target sequence in a genomic locus of interest in a cell,
a CRISPR enzyme comprising at least one or more nuclear localization sequences,
wherein the CRISPR enzyme comprises at least one mutation, such that the CRISPR enzyme has no more than 5% of the nuclease activity of the CRISPR enzyme not having the at least one mutation,
wherein at least one loop of the sgRNA is modified by the insertion of distinct RNA sequence(s) that bind to one or more adaptor proteins, and wherein the adaptor protein is associated with one or more functional domains; or, wherein the sgRNA is modified to have at least one non-coding functional loop,
and wherein the composition comprises two or more adaptor proteins, wherein the each protein is associated with one or more functional domains.

5. The composition of any one of paragraphs 2, 3 or 4, wherein the CRISPR enzyme has a diminished nuclease activity of at least 97%, or 100% as compared with the CRISPR enzyme not having the at least one mutation.

6. The composition of any one of paragraphs 2, 3, 4 or 5, wherein the CRISPR enzyme comprises two or more mutations wherein two or more of D10, E762, H840, N854, N863, or D986 according to SpCas9 protein or any corresponding or N580 according to SaCas9 protein ortholog are mutated, or the CRISPR enzyme comprises at least one mutation wherein at least H840 is mutated.

7. The composition of paragraph 6 wherein the CRISPR enzyme comprises two or more mutations comprising D10A, E762A, H840A, N854A, N863A or D986A according to SpCas9 protein or any corresponding ortholog, or N580A according to SaCas9 protein, or at least one mutation comprising H840A, or, optionally
wherein the CRISPR enzyme comprises:
N580A according to SaCas9 protein or any corresponding ortholog; or
D10A according to SpCas9 protein, or any corresponding ortholog, and N580A according to SaCas9 protein.

8. The composition of any one of paragraphs 2, 3, 4 or 5, wherein the CRISPR enzyme comprises H840A, or D10A and H840A, or D10A and N863A, according to SpCas9 protein or any corresponding ortholog.

9. The composition of any one of paragraphs 2-8, wherein the CRISPR enzyme is associated with one or more functional domains.

10. The composition of paragraph 9, wherein the two or more functional domains associated with the adaptor protein is a heterologous functional domain.

11. The composition of paragraph 9, wherein the one or more functional domains associated with the CRISPR enzyme is a heterologous functional domain.

12. The composition of any one of paragraphs 1-11, wherein the adaptor protein is a fusion protein comprising the functional domain, the fusion protein optionally comprising a linker between the adaptor protein and the functional domain, the linker optionally including a GlySer linker.

13. The composition of any one of paragraphs 1-12, wherein the at least one loop of the sgRNA is not modified by the insertion of distinct RNA sequence(s) that bind to the two or more adaptor proteins.

14. The composition of any one of paragraphs 1-13, wherein the one or more functional domains associated with the adaptor protein is a transcriptional activation domain.

15. The composition of any one of paragraphs 9-14, wherein the one or more functional domains associated with the CRISPR enzyme is a transcriptional activation domain.

16. The composition of any one of paragraphs 1-15, wherein the one or more functional domains associated with the adaptor protein is a transcriptional activation domain comprising VP64, p65, MyoD1, HSF1, RTA or SET7/9.

17. The composition of any one of paragraphs 9-16, wherein the one or more functional domains associated with the CRISPR enzyme is a transcriptional activation domain comprises VP64, p65, MyoD1, HSF1, RTA or SET7/9.

18. The composition of any one of paragraphs 1-13, wherein the one or more functional domains associated with the adaptor protein is a transcriptional repressor domain.

19. The composition of any one of paragraphs 9-14, wherein the one or more functional domains associated with the CRISPR enzyme is a transcriptional repressor domain.

20. The composition of paragraph 18 or 19, wherein the transcriptional repressor domain is a KRAB domain.

21. The composition of paragraph 18 or 19, wherein the transcriptional repressor domain is a NuE domain, NcoR domain, SID domain or a SID4X domain.

22. The composition of any one of paragraphs 1-13, wherein at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity.

23. The composition of any one of paragraphs 9-13, wherein the one or more functional domains associated with the CRISPR enzyme have one or more activities comprising methylase activity, demethylase activity, transcription activation activity, transcription repression activity, transcription release factor activity, histone modification activity, DNA integration activity RNA cleavage activity, DNA cleavage activity, nucleic acid binding activity, or molecular switch activity or chemical inducibility or light inducibility.

24. The composition of any one of paragraphs 22-23, wherein the DNA cleavage activity is due to a Fok1 nuclease.

25. The composition of any one of paragraphs 2-24, wherein the one or more functional domains is attached to the CRISPR enzyme so that upon binding to the sgRNA and target the functional domain is in a spatial orientation allowing for the functional domain to function in its attributed function; or, optionally,
wherein the one or more functional domains is attached to the CRISPR enzyme via a linker, optionally a GlySer linker.

26. The composition of any one of paragraphs 2-25, wherein the sgRNA is modified so that, after sgRNA binds the adaptor protein and further binds to the CRISPR enzyme and target, the functional domain is in a spatial orientation allowing for the functional domain to function in its attributed function.

27. The composition of any one of paragraphs 9-25, wherein the one or more functional domains associated with the CRISPR enzyme is attached to the Rec1 domain, the Rec2 domain, the HNH domain, or the PI domain of the SpCas9 protein or any ortholog corresponding to these domains.

28. The composition of any one of paragraphs 9-27, wherein the one or more functional domains associated with the CRISPR enzyme is attached to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains.

29. The composition of any one of paragraphs 9-27, wherein the one or more functional domains associated with the CRISPR enzyme is attached to the Red 1 domain or the Rec2 domain, of the SpCas9 protein or any ortholog corresponding to these domains.

30. The composition of any one of paragraphs 9-29, wherein the one or more functional domains associated with the CRISPR enzyme is attached to the Rec2 domain of the SpCas9 protein or any ortholog corresponding to this domain.

31. The composition of any one of paragraphs 1-30, wherein the at least one loop of the sgRNA is tetraloop and/or loop2.

32. The composition of any one of paragraphs 1-31, wherein the tetraloop and loop 2 of the sgRNA are modified by the insertion of the distinct RNA sequence(s).

33. The composition of any one of paragraphs 31 or 32, wherein the insertion of distinct RNA sequence(s) that bind to one or more adaptor proteins is an aptamer sequence.

34. The composition of paragraph 33, wherein the aptamer sequence is two or more aptamer sequences specific to the same adaptor protein.

35. The composition of paragraph 33, wherein the aptamer sequence is two or more aptamer sequences specific to different adaptor protein.

36. The composition of any one of the claims above, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

37. The composition of any one of the claims above, wherein the cell is a eukaryotic cell.

38. The composition of paragraph 37, wherein the eukaryotic cell is a mammalian cell, optionally a mouse cell.

39. The composition of paragraph 38, wherein the mammalian cell is a human cell.

40. The composition of any one of the claims above, wherein a first adaptor protein is associated with a p65 domain and a second adaptor protein is associated with a HSF1 domain.

41. The composition of any one of the claims above, wherein the composition comprises a CRISPR-Cas complex having at least three functional domains, at least one of which is associated with the CRISPR enzyme and at least two of which are associated with sgRNA.

42. A method for introducing a genomic locus event comprising the administration to a host or expression in a host in vivo of one or more of the compositions from paragraphs 1-41.

43. The method according to paragraph 42, wherein the genomic locus event comprises affecting gene activation, gene inhibition, or cleavage in the locus.

44. The method according to paragraphs 42 or 43, wherein the host is a eukaryotic cell.

45. The method according to paragraph 44, wherein the host is a mammalian cell, optionally a mouse cell.

46. The method according to paragraphs 42 or 43, wherein the host is a non-human eukaryote.

47. The method according to paragraph 46, wherein the non-human eukaryote is a non-human mammal.

48. The method according to paragraph 47, wherein the non-human mammal is a mouse.

49. A method of modifying a genomic locus of interest to change gene expression in a cell by introducing or expressing in a cell the composition of any of the preceding claims.

50. The method according to any one of paragraphs 42-49 comprising the delivery of the composition or nucleic acid molecule(s) coding therefor, wherein said nucleic acid molecule(s) are operatively linked to regulatory sequence(s) and expressed in vivo.

51. The method according to paragraph 50 wherein the expression in vivo is via a lentivirus, an adenovirus, or an AAV.

52. A mammalian cell line as defined in paragraph 38, 44 or 45, wherein the cell line is, optionally, a human cell line or a mouse cell line.

53. A transgenic mammalian model, optionally a mouse, wherein the model has been transformed with the composition according to paragraph 38 or is a progeny of said transformant.

54. A nucleic acid molecule(s) encoding sgRNA or the CRISPR-Cas complex or the composition of any of the preceding paragraphs.

55. A vector comprising: a nucleic acid molecule encoding a guide RNA (sgRNA) comprising a guide sequence capable of hybridizing to a target sequence in a genomic locus of interest in a cell, wherein one or more loop(s) of the sgRNA is modified by the insertion of distinct RNA sequence(s) that bind to two or more adaptor proteins, and wherein each adaptor protein is associated with one or more functional domains; or, wherein the sgRNA is modified to have at least one non-coding functional loop.

56. Vector(s) comprising nucleic acid molecule(s) encoding: non-naturally occurring or engineered CRISPR-Cas complex composition comprising the sgRNA of paragraph 1, and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences.

57. The nucleic acid molecule of paragraph 54 or the vector of paragraph 55 and 56 further comprising regulatory element(s) operable in a eukaryotic cell operably linked to the nucleic acid molecule encoding the guide sequence (sgRNA) and/or the nucleic acid molecule encoding the CRISPR enzyme and/or the optional nuclear localization sequence(s).

58. A method of screening for gain of function (GOF) or loss of function (LOF) or for non-coding RNAs or potential regulatory regions comprising the cell line of paragraph 52 or cells of the model of paragraph 53 containing or expressing Cas9 and introducing a composition of claim 1 into cells of the cell line or model, whereby the sgRNA includes either an activator or a repressor, and monitoring for GOF or LOF or change due to non-coding RNA or potential regulatory region respectively as to those cells as to which the introduced sgRNA includes an activator or as to those cells as to which the introduced sgRNA includes a repressor.

59. The composition of any preceding claim wherein the CRISPR enzyme includes one or more functional domains.

60. The composition of any preceding claim wherein there is more than one sgRNA, and the sgRNAs target different sequences whereby when the composition is employed, there is multiplexing.

61. The composition of paragraph 60 wherein there is more than one sgRNA modified by the insertion of distinct RNA sequence(s) that bind to one or more adaptor proteins.

62. The composition of paragraph 60 or 61 wherein one or more adaptor proteins associated with one or more functional domains is present and bound to the distinct RNA sequence(s) inserted into the at least one loop of the sgRNA.

63. A CRISPR Cas complex comprising a CRISPR enzyme and a guide RNA (sgRNA), wherein the CRISPR enzyme comprises at least one mutation, such that the CRISPR enzyme has no more than 5% of the nuclease activity of the CRISPR enzyme not having the at least one mutation and, optional, at least one or more nuclear localization sequences; the guide RNA (sgRNA) comprises a guide sequence capable of hybridizing to a target sequence in a genomic locus of interest in a cell; and wherein: at least one loop of the sgRNA is modified by the insertion of distinct RNA sequence(s) that bind to one or more adaptor proteins, and wherein the adaptor protein is associated with two or more functional domains, or, wherein the sgRNA is modified to have at least one non-coding functional loop; or the CRISPR enzyme is associated with one or more functional domains and at least one loop of the sgRNA is modified by the insertion of distinct RNA sequence(s) that bind to one or more adaptor proteins, and wherein the adaptor protein is associated with two or more functional domains, or, wherein the sgRNA is modified to have at least one non-coding functional loop.

64. The composition of any preceding paragraph, wherein the target sequence(s) are non-coding or regulatory sequences.

65. The composition of paragraph 64, wherein the regulatory sequences are promoter, enhancer or silencer sequence(s).

66. The composition of any preceding paragraph wherein the sgRNA is modified to have at least one non-coding functional loop.

67. The composition of paragraph 66 wherein the at least one non-coding functional non-coding loop is repressive.

68. The composition of paragraph 67 wherein at least one non-coding functional non-coding loop comprises Alu.

69. A genome wide library comprising a plurality of CRISPR-Cas system guide RNAs (sgRNAs) comprising guide sequences, each of which is capable of hybridizing to a target sequence in a genomic locus of interest in a cell and whereby the library is capable of targeting a plurality of target sequences in a plurality of genomic loci in a population of eukaryotic cells, wherein in each sgRNA at least one loop is modified by the insertion of distinct RNA sequence(s) that binds to one or more or two or more adaptor proteins, and wherein the adaptor protein is associated with one or more functional domains; or, wherein the sgRNA is modified to have at least one non-coding functional loop.

70. A library of non-naturally occurring or engineered CRISPR-Cas complexes composition(s) comprising the sgRNAs of paragraph 69 and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences.

71. The sgRNAs of paragraph 69 or the CRISPR-Cas complexes of claim 70 including a non-naturally occurring or engineered composition comprising one or two or more adaptor proteins, wherein each protein is associated with one or more functional domains and wherein the adaptor protein binds to the distinct RNA sequence(s) inserted into the at least one loop of the sgRNA.

72. A library of non-naturally occurring or engineered compositions, each comprising
a guide RNA (sgRNA) comprising a guide sequence capable of hybridizing to a target sequence in a genomic locus of interest in a cell,
a CRISPR enzyme comprising at least one or more nuclear localization sequences,
wherein the CRISPR enzyme comprises at least one mutation, such that the CRISPR enzyme has no more than 5% of the nuclease activity of the CRISPR enzyme not having the at least one mutation,
wherein at least one loop of the sgRNA is modified by the insertion of distinct RNA sequence(s) that bind to one or more adaptor proteins, and wherein the adaptor protein is associated with one or more functional domains, wherein the composition comprises one or more or two or more adaptor proteins, wherein the each protein is associated with one or more functional domains; or, wherein the sgRNA is modified to have at least one non-coding functional loop, and
wherein the sgRNAs comprise a genome wide library comprising a plurality of CRISPR-Cas system guide RNAs (sgRNAs), as recited in paragraph 69.

73. The library of any one of paragraphs 70, 71, or 72, wherein the CRISPR enzyme has a diminished nuclease activity of at least 97%, or 100% as compared with the CRISPR enzyme not having the at least one mutation.

74. The library of any one of paragraphs 70, 71, 72 or 73, wherein the CRISPR enzyme comprises two or more mutations wherein two or more of D10, E762, H840, N854, N863, or D986 according to SpCas9 protein or any corresponding ortholog are mutated, or the CRISPR enzyme comprises at least one mutation wherein at least H840 is mutated.

75. The library of paragraph 74 wherein the CRISPR enzyme comprises two or more mutations comprising D10A, E762A, H840A, N854A, N863A or D986A according to SpCas9 protein or any corresponding ortholog, or at least one mutation comprising H840A.

76. The library of any one of paragraphs 70, 71, 72 or 73, wherein the CRISPR enzyme comprises H840A, or D10A and H840A, or D10A and N863A, according to SpCas9 protein or any corresponding ortholog.

77. The library of any one of paragraphs 70-76, wherein the CRISPR enzyme is associated with one or more functional domains.

78. The library of any one of paragraphs 69-77, wherein the one or two or more functional domains associated with the adaptor protein is a heterologous functional domain.

79. The library of paragraph 77, wherein the one or more functional domains associated with the CRISPR enzyme is a heterologous functional domain.

80. The library of any one of paragraphs 69-79, wherein the adaptor protein is a fusion protein comprising the functional domain.

81. The library of any one of paragraphs 69-80, wherein the at least one loop of the sgRNA is not modified by the insertion of distinct RNA sequence(s) that bind to the one or two or more adaptor proteins.

82. The library of any one of paragraphs 69-81, wherein the one or two or more functional domains associated with the adaptor protein is a transcriptional activation domain.

83. The library of any one of paragraphs 77-82, wherein the one or two or more functional domains associated with the CRISPR enzyme is a transcriptional activation domain.

84. The library of any one of paragraphs 69-83, wherein the one or two or more functional domains associated with the adaptor protein is a transcriptional activation domain comprising VP64, p65, MyoD1 or HSF1.

85. The library of any one of paragraphs 77-84, wherein the one or more functional domains associated with the CRISPR enzyme is a transcriptional activation domain comprises VP64, p65, MyoD1 or HSF1.

86. The library of any one of paragraphs 69-81, wherein the one or two or more functional domains associated with the adaptor protein is a transcriptional repressor domain.

87. The library of any one of paragraphs 77-82, wherein the one or more functional domains associated with the CRISPR enzyme is a transcriptional repressor domain.

88. The library of paragraph 86 or 87, wherein the transcriptional repressor domain is a KRAB domain.

89. The library of paragraph 86 or 87, wherein the transcriptional repressor domain is a SID domain or a SID4X domain.

90. The library of any one of paragraphs 69-81, wherein at least one of the one or two or more functional domains associated with the adaptor protein have one or more activities comprising methylase activity, demethylase activity, transcription activation activity, transcription repression activity, transcription release factor activity, histone modification activity, RNA cleavage activity, DNA cleavage activity or nucleic acid binding activity.

91. The library of any one of paragraphs 77-81, wherein the one or more functional domains associated with the CRISPR enzyme have one or more activities comprising methylase activity, demethylase activity, transcription activation activity, transcription repression activity, transcription release factor activity, histone modification activity, RNA cleavage activity, DNA cleavage activity, nucleic acid binding activity, or molecular switch activity or chemical inducibility or light inducibility.

92. The library of any one of paragraphs 90-91, wherein the DNA cleavage activity is a Fok1 nuclease.

93. The library of any one of paragraphs 70-92, wherein the one or more functional domains is attached to the CRISPR enzyme so that upon binding to the sgRNA and target the functional domain is in a spatial orientation allowing for the functional domain to function in its attributed function.

94. The library any one of paragraphs 70-93, wherein the sgRNA is modified so that, after sgRNA binds the adapter protein and further binds to the CRISPR enzyme and target, the functional domain is in a spatial orientation allowing for the functional domain to function in its attributed function.

95. The library any one of paragraphs 77-93, wherein the one or more functional domains associated with the CRISPR enzyme is attached to the N terminus of the CRISPR enzyme.

96. The library any one of paragraphs 77-93, wherein the one or more functional domains associated with the CRISPR enzyme is attached to the Rec1 domain, the Rec2 domain, the HNH domain, or the PI domain of the SpCas9 protein or any ortholog corresponding to these domains.

97. The library any one of paragraphs 77-96, wherein the one or more functional domains associated with the CRISPR enzyme is attached to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains.

98. The library any one of paragraphs 77-96, wherein the one or more functional domains associated with the CRISPR enzyme is attached to the Rec1 domain or the Rec2 domain, of the SpCas9 protein or any ortholog corresponding to these domains.

99. The library of any one of paragraphs 77-98, wherein the one or more functional domains associated with the CRISPR enzyme is attached to the Rec2 domain of the SpCas9 protein or any ortholog corresponding to this domain.

100. The library of any one of paragraphs 69-99, wherein the at least one loop of the sgRNA is tetraloop and/or loop2.

101. The library any one of paragraphs 69-100, wherein the tetraloop and loop 2 of the sgRNA are modified by the insertion of the distinct RNA sequence(s).

102. The library any one of paragraphs 100 or 101, wherein the insertion of distinct RNA sequence(s) that bind to one or more adaptor proteins is an aptamer sequence.

103. The library of paragraph 102, wherein the aptamer sequence is two or more aptamer sequences specific to the same adaptor protein.

104. The library of paragraph 103, wherein the aptamer sequence is two or more aptamer sequences specific to different adaptor protein.

105. The library of any one of the paragraphs above, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

106. The library of any one of the paragraphs above, wherein the cell population of cells is a population of eukaryotic cells.

107. The library of paragraph 106, wherein the eukaryotic cell is a mammalian cell.

108. The library of paragraph 107, wherein the mammalian cell is a human cell.

109. The library of any one of paragraphs 69-105, wherein the population of cells is a population of embryonic stem (ES) cells.

110. The library of any one of paragraphs 69-109, wherein the target sequence in the genomic locus is a non-coding sequence.

111. The library of any one of paragraphs 69-109, wherein gene function of one or more gene products is altered by said targeting; or wherein as to gene function there is gain of function; or wherein as to gene function there is change of function; or wherein as to gene function there is reduced function; or wherein the screen is for non-coding RNAs or potential regulatory regions.

112. The library of any one of paragraphs 69-109, wherein said targeting results in a knockout of gene function.

113. The library of any one of paragraphs 69-109, wherein the targeting is of about 100 or more sequences.

114. The library of any one of paragraphs 69-109, wherein the targeting is of about 1000 or more sequences.

115. The library of any one of paragraphs 69-109, wherein the targeting is of about 20,000 or more sequences.

116. The library of any one of paragraphs 69-109, wherein the targeting is of the entire genome.

117. The library of any one of paragraphs 69-109, wherein the targeting is of a panel of target sequences focused on a relevant or desirable pathway.

118. The library of paragraph 117, wherein the pathway is an immune pathway.

119. The library of paragraph 117, wherein the pathway is a cell division pathway.

120. The library of paragraph 112, wherein the alteration of gene function comprises:
    introducing into each cell in the population of cells a vector system of one or more vectors comprising an engineered, non-naturally occurring CRISPR-Cas system comprising
    I. a Cas protein, and
    II. one or more guide RNAs,
    wherein components I and II may be same or on different vectors of the system,
    integrating components I and II into each cell,
    wherein the guide sequence targets a unique gene in each cell,
    wherein the Cas protein is operably linked to a regulatory element,
    wherein when transcribed, the guide RNA comprising the guide sequence directs sequence-specific binding of a CRISPR-Cas system to a target sequence in the genomic loci of the unique gene,
    inducing cleavage of the genomic loci by the Cas protein, and
    confirming different mutations in a plurality of unique genes in each cell of the population of cells thereby generating a mutant cell library.

121. The library of paragraph 120, wherein the one or more vectors are plasmid vectors.

122. The library of paragraph 120, wherein the regulatory element is an inducible promoter.

123. The library of paragraph 120, wherein the inducible promoter is a doxycycline inducible promoter.

124. The library of paragraph 120, wherein the confirming of different mutations is by whole exome sequencing.

125. The library of paragraph 120, wherein the mutation is achieved in 100 or more unique genes.

126. The library of paragraph 120, wherein the t mutation is achieved in 1000 or more unique genes.

127. The library of paragraph 120, wherein the mutation is achieved in 20,000 or more unique genes.

128. The library of paragraph 120, wherein the mutation is achieved in the entire genome.

129. The library of paragraph 120, wherein the alteration of gene function is achieved in a plurality of unique genes which function in a particular physiological pathway or condition.

130. The library of paragraph 129, wherein the pathway or condition is an immune pathway or condition.

131. The library of paragraph 129, wherein the pathway or condition is a cell division pathway or condition.

132. The library of any one of the paragraphs above, wherein a first adaptor protein is associated with a p65 domain and a second adaptor protein is associated with a HSF1 domain.

133. The library of any one of the paragraphs above, wherein each a CRISPR-Cas complex has at least three functional domains, at least one of which is associated with the CRISPR enzyme and at least two of which are associated with sgRNA.

134. The library of any one of the paragraphs above, wherein the alteration in gene function is a knockout mutation.

135. A method for functional screening genes of a genome in a pool of cells ex vivo or in vivo comprising the administration or expression of a library comprising a plurality of CRISPR-Cas system guide RNAs (sgRNAs) and wherein the screening further comprises use of a CRISPR enzyme, wherein the CRISPR complex is modified to comprise a heterologous functional domain.

136. A method for screening a genome comprising the administration to a host or expression in a host in vivo of a library of any of the preceding claims.

137. The method according to paragraph 135 or 136 further comprising an activator administered to the host or expressed in the host.

138. The method of paragraph 137 wherein the activator is attached to a CRISPR enzyme.

139. The method of paragraph 136 wherein the activator is attached to the N terminus or the C terminus of the CRISPR enzyme.

140. The method of paragraph 137, 138 or 139 wherein the activator is attached to a sgRNA loop.

141. The method according to paragraph 135 or 136 further comprising a repressor administered to the host or expressed in the host.

142. The method according to any one of paragraphs 135-141, wherein the screening comprises affecting and detecting gene activation, gene inhibition, or cleavage in the locus.

143. The method according to any one of paragraphs 135-142, wherein the host is a eukaryotic cell.

144. The method according to paragraph 143, wherein the host is a mammalian cell.

145. The method according to any one of paragraphs 134-141, wherein the host is a non-human eukaryote.

146. The method according to paragraph 145, wherein the non-human eukaryote is a non-human mammal.

147. The method according to paragraph 146, wherein the non-human mammal is a mouse.

148. The method according to any one of paragraphs 135-147 comprising the delivery of the CRISPR-Cas complexes or component(s) thereof or nucleic acid molecule(s) coding therefor, wherein said nucleic acid molecule(s) are operatively linked to regulatory sequence(s) and expressed in vivo.

149. The method according to paragraph 148 wherein the expressing in vivo is via a lentivirus, an adenovirus, or an AAV.

150. The method of paragraph 148 or 149 wherein the delivery is via a particle, a nanoparticle, a lipid or a cell penetrating peptide (CPP).

151. A pair of CRISPR-Cas complexes, each comprising a guide RNA (sgRNA) comprising a guide sequence capable of hybridizing to a target sequence in a genomic locus of interest in a cell, wherein at least one loop of each sgRNA is modified by the insertion of distinct RNA sequence(s) that bind to one or more adaptor proteins, and wherein the adaptor protein is associated with one or more functional domains, wherein each sgRNA of each CRISPR-Cas complex comprises a functional domain having a DNA cleavage activity.

152. The paired CRISPR-Cas complexes of paragraph 151, wherein the DNA cleavage activity is due to a Fok1 nuclease.

153. A method for cutting a target sequence in a genomic locus of interest comprising delivery to a cell of the CRISPR-Cas complexes of paragraphs 151 or 153 or component(s) thereof or nucleic acid molecule(s) coding therefor, wherein said nucleic acid molecule(s) are operatively linked to regulatory sequence(s) and expressed in vivo.

154. The method of paragraph 153 wherein the delivery is via a lentivirus, an adenovirus, or an AAV.

155. The method of any one of paragraphs 153 or 86 or the paired CRISPR-Cas complexes of paragraphs 74 or 75 wherein the target sequence for a first complex of the pair is on a first strand of double stranded DNA and the target sequence for a second complex of the pair is on a second strand of double stranded DNA.

156. The method or the CRISPR-Cas complexes of paragraph 155 wherein the target sequences of the first and second complexes are in proximity to each other such that the DNA is cut in a manner that facilitates homology directed repair.

157. The method of paragraph 156 further including introducing into the cell template DNA.

158. The method of any one of paragraphs 153-157 or the paired CRISPR-Cas complexes of paragraphs 83 to 84 or 87 to 88 wherein each CRISPR-Cas complex has a CRISPR enzyme that is mutated such that it has no more than about 5% of the nuclease activity of the CRISPR enzyme that is not mutated.

159. A library, method or complex of any preceding claim wherein the sgRNA is modified to have at least one non-coding functional loop.

160. The library, method or complex of paragraph 159 wherein the at least one non-coding functional loop is repressive.

161. The library, method or complex of paragraph 160 wherein the at least one non-coding functional loop comprises Alu.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed:

1. A method of screening for gain of function (GOF) or for non-coding RNAs or regulatory regions comprising
introducing a guide RNA into cells of a cell line or animal containing or expressing a Cas 9 enzyme, whereby the guide RNA includes either an activator or a repressor, wherein the guide RNA comprises a guide sequence capable of hybridizing to a target sequence in a genomic locus of interest in a cell, wherein one or more of tetraloop or stem-loop 2 loop(s) of the guide RNA is modified by insertion of distinct RNA sequence(s) that bind to two or more adaptor proteins, the distinct RNA sequence(s) different from each other, and wherein each adaptor protein is linked or fused to one or more activator functional domains; and
monitoring for GOF or change due to non-coding RNA enhancer region or repressor region respectively as to those cells as to which the introduced guide RNA includes an activator or as to those cells as to which the introduced guide RNA includes a repressor.

2. The method of claim 1, wherein the Cas 9 enzyme comprises at least one mutation, such that the Cas9 enzyme has no more than 5% of the nuclease activity of the Cas 9 enzyme not having the at least one mutation.

3. A method for functional screening genes of a genome in a pool of cells ex vivo or in vivo comprising administering or expressing a library comprising a plurality of CRISPR-Cas system guide RNAs, each guide RNA comprising at least one loop selected from tetraloop or stem-loop 2 modified by insertion of distinct RNA sequence(s), the distinct RNA sequence(s) different from each other, and wherein the screening is performed using a CRISPR Cas 9 enzyme modified to comprise a heterologous functional domain, and detecting changes in gene activation, gene inhibition or cleavage in the locus resulting from the targeting.

4. A method for screening a genome comprising administering to or expressing in a host in vivo a library, the library comprising a plurality of CRISPR-Cas 9 system guide RNAs comprising guide sequences, each of which is capable of hybridizing to a target sequence in a genomic locus of interest in a cell and whereby the library is capable of targeting a plurality of target sequences in a plurality of genomic loci in a population of eukaryotic cells,
wherein:
in each guide RNA at least one loop selected from tetraloop or stem-loop 2 is modified by insertion of distinct RNA sequence(s), the distinct RNA sequence (s) different from each other, that binds to one or two or more adaptor proteins, and the adaptor protein is linked or fused to one or more activator functional domains;
wherein optionally the host is a eukaryotic cell, or a mammalian cell, or a non-human eukaryote, or a non-human mammal or a mouse; and
detecting changes in the genomic locus of interest in the cell.

5. The method of claim 4, further comprising administering to or expressing in the host an activator or a repressor, optionally the activator is attached to a CRISPR Cas 9 enzyme, or the activator is attached to an N terminus or C terminus of the CRISPR Cas 9 enzyme, or the activator is attached to a guide RNA loop.

6. The method of claim 4, wherein the screening comprises affecting and detecting gene activation, gene inhibition, or cleavage in the locus.

7. The method of claim 4, further comprising delivering CRISPR-Cas 9 complexes or component(s) thereof or nucleic acid molecule(s) coding therefor, wherein said nucleic acid molecule(s) are operatively linked to regulatory sequence(s) and expressed in vivo, optionally the expressing in vivo is via a lentivirus, an adenovirus, or an AAV; or optionally wherein the delivery is via a particle, a nanoparticle, a lipid or a cell penetrating peptide (CPP).

* * * * *

SEQUENCE LISTING

<160> NUMBER OF SEQ ID NOS: 332

<210> SEQ ID NO 1
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ggccaacatg aggatcaccc atgtctgcag ggcc                              34

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Gly Ser
1

<210> SEQ ID NO 3
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gly Gly Gly Gly Ser Gly Gly Gly Gly Ser Gly Gly Gly Gly Gly
1               5                   10                  15

Gly Gly Gly Ser Gly Gly Gly Gly Ser Gly Gly Gly Gly Ser
            20                  25                  30

<210> SEQ ID NO 5
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gly Gly Gly Gly Ser Gly Gly Gly Gly Ser Gly Gly Gly Gly Gly
1               5                   10                  15

Gly Gly Gly Ser Gly Gly Gly Ser Gly Gly Gly Ser Gly Gly
        20                  25                  30

Gly Gly Ser Gly Gly Gly Gly Ser Gly Gly Gly Ser
        35                  40                  45

<210> SEQ ID NO 6
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly
        20                  25                  30

Gly Gly Ser Gly Gly Gly Gly Ser Gly Gly Gly Ser Gly Gly
        35                  40                  45

Gly Ser Gly Gly Gly Ser Gly Gly Gly Ser
        50                  55                  60

<210> SEQ ID NO 7
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Gly Ser Gly Gly Gly Ser Gly Gly Gly Ser
1               5                   10

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Gly Gly Gly Ser
1               5

<210> SEQ ID NO 9
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gcuagaauag ca                                                          12

<210> SEQ ID NO 10
<211> LENGTH: 14
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 10
aacuugaaaa agug                                                           14

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Ser Gly
1

<210> SEQ ID NO 12
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 12
nnnnnnnnnn nnnnnnnnnn ngg                                                 23

<210> SEQ ID NO 13
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 13
nnnnnnnnnn nnngg                                                          15

<210> SEQ ID NO 14
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: modified_base
```

```
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 14
nnnnnnnnnn nnnnnnnnnn ngg                                           23

<210> SEQ ID NO 15
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 15
nnnnnnnnnn nngg                                                     14

<210> SEQ ID NO 16
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 16
nnnnnnnnnn nnnnnnnnnn nnagaaw                                       27

<210> SEQ ID NO 17
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 17
nnnnnnnnnn nnnnagaaw                                                19

<210> SEQ ID NO 18
```

```
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 18
nnnnnnnnnn nnnnnnnnnn nnagaaw                                27

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 19
nnnnnnnnnn nnnagaaw                                          18

<210> SEQ ID NO 20
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 20
nnnnnnnnnn nnnnnnnnnn nggng                                  25

<210> SEQ ID NO 21
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 21
nnnnnnnnnn nnggng                                                    17

<210> SEQ ID NO 22
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 22
nnnnnnnnnn nnnnnnnnnn nggng                                          25

<210> SEQ ID NO 23
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 23
nnnnnnnnnn nnggng                                                    16

<210> SEQ ID NO 24
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
```

<223> OTHER INFORMATION: a, c, t, g, unknown or other

<400> SEQUENCE: 24

```
nnnnnnnnnn nnnnnnnnnn gttttgtac tctcaagatt tagaaataaa tcttgcagaa    60
gctacaaaga taaggcttca tgccgaaatc aacaccctgt catttatgg cagggtgttt   120 tcgttattta atttttt                                                 137
```

<210> SEQ ID NO 25
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 25

```
nnnnnnnnnn nnnnnnnnnn gttttgtac tctcagaaat gcagaagcta caaagataag    60
gcttcatgcc gaaatcaaca ccctgtcatt ttatggcagg gtgttttcgt tatttaattt   120
ttt                                                                123
```

<210> SEQ ID NO 26
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 26

```
nnnnnnnnnn nnnnnnnnnn gttttgtac tctcagaaat gcagaagcta caaagataag    60
gcttcatgcc gaaatcaaca ccctgtcatt ttatggcagg gtgttttttt             110
```

<210> SEQ ID NO 27
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 27

```
nnnnnnnnnn nnnnnnnnnn gtttagagc tagaaatagc aagttaaaat aaggctagtc    60
cgttatcaac ttgaaaaagt ggcaccgagt cggtgctttt tt                     102
```

<210> SEQ ID NO 28
<211> LENGTH: 88
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 28
nnnnnnnnnn nnnnnnnnnn gttttagagc tagaaatagc aagttaaaat aaggctagtc    60
cgttatcaac ttgaaaaagt gttttttt                                       88

<210> SEQ ID NO 29
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 29
nnnnnnnnnn nnnnnnnnnn gttttagagc tagaaatagc aagttaaaat aaggctagtc    60
cgttatcatt tttttt                                                    76

<210> SEQ ID NO 30
<211> LENGTH: 20
<212> TYPE: DNA
<213> ORGANISM: Homo sapiens

<400> SEQUENCE: 30
gagtccgagc agaagaagaa                                                20

<210> SEQ ID NO 31
<211> LENGTH: 20
<212> TYPE: DNA
<213> ORGANISM: Homo sapiens

<400> SEQUENCE: 31
gagtcctagc aggagaagaa                                                20

<210> SEQ ID NO 32
<211> LENGTH: 20
<212> TYPE: DNA
<213> ORGANISM: Homo sapiens

<400> SEQUENCE: 32
gagtctaagc agaagaagaa                                                20

<210> SEQ ID NO 33
<211> LENGTH: 7
<212> TYPE: PRT
<213> ORGANISM: Simian virus 40

<400> SEQUENCE: 33

Pro Lys Lys Lys Arg Lys Val
1               5

<210> SEQ ID NO 34
<211> LENGTH: 16
<212> TYPE: PRT
<213> ORGANISM: Unknown
```

-continued

```
<220> FEATURE:
<221> NAME/KEY: source
<223> OTHER INFORMATION: /note="Description of Unknown:
      Nucleoplasmin bipartite NLS sequence"

<400> SEQUENCE: 34

Lys Arg Pro Ala Ala Thr Lys Lys Ala Gly Gln Ala Lys Lys Lys Lys
1               5                   10                  15

<210> SEQ ID NO 35
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 35

Pro Ala Ala Lys Arg Val Lys Leu Asp
1               5

<210> SEQ ID NO 36
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 36

Arg Gln Arg Arg Asn Glu Leu Lys Arg Ser Pro
1               5                   10

<210> SEQ ID NO 37
<211> LENGTH: 38
<212> TYPE: PRT
<213> ORGANISM: Homo sapiens

<400> SEQUENCE: 37

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 38
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 38

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40
```

```
<210> SEQ ID NO 39
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 39

Val Ser Arg Lys Arg Pro Arg Pro
1               5

<210> SEQ ID NO 40
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 40

Pro Pro Lys Lys Ala Arg Glu Asp
1               5

<210> SEQ ID NO 41
<211> LENGTH: 8
<212> TYPE: PRT
<213> ORGANISM: Homo sapiens

<400> SEQUENCE: 41

Pro Gln Pro Lys Lys Lys Pro Leu
1               5

<210> SEQ ID NO 42
<211> LENGTH: 12
<212> TYPE: PRT
<213> ORGANISM: Mus musculus

<400> SEQUENCE: 42

Ser Ala Leu Ile Lys Lys Lys Lys Lys Met Ala Pro
1               5                   10

<210> SEQ ID NO 43
<211> LENGTH: 5
<212> TYPE: PRT
<213> ORGANISM: Influenza virus

<400> SEQUENCE: 43

Asp Arg Leu Arg Arg
1               5

<210> SEQ ID NO 44
<211> LENGTH: 7
<212> TYPE: PRT
<213> ORGANISM: Influenza virus

<400> SEQUENCE: 44

Pro Lys Gln Lys Lys Arg Lys
1               5

<210> SEQ ID NO 45
<211> LENGTH: 10
<212> TYPE: PRT
<213> ORGANISM: Hepatitis delta virus
```

```
<400> SEQUENCE: 45

Arg Lys Leu Lys Lys Lys Ile Lys Lys Leu
1               5                   10

<210> SEQ ID NO 46
<211> LENGTH: 10
<212> TYPE: PRT
<213> ORGANISM: Mus musculus

<400> SEQUENCE: 46

Arg Glu Lys Lys Lys Phe Leu Lys Arg Arg
1               5                   10

<210> SEQ ID NO 47
<211> LENGTH: 20
<212> TYPE: PRT
<213> ORGANISM: Homo sapiens

<400> SEQUENCE: 47

Lys Arg Lys Gly Asp Glu Val Asp Gly Val Asp Glu Val Ala Lys Lys
1               5                   10                  15

Lys Ser Lys Lys
            20

<210> SEQ ID NO 48
<211> LENGTH: 17
<212> TYPE: PRT
<213> ORGANISM: Homo sapiens

<400> SEQUENCE: 48

Arg Lys Cys Leu Gln Ala Gly Met Asn Leu Glu Ala Arg Lys Thr Lys
1               5                   10                  15

Lys

<210> SEQ ID NO 49
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120

<210> SEQ ID NO 50
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
guuuuagagc ua                                                          12

<210> SEQ ID NO 51
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 51

Ala Glu Ala Ala Ala Lys Ala
1               5

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
gatacgatga aagaataag c                                                    21

<210> SEQ ID NO 53
<211> LENGTH: 131
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 53
nnnnnnnnnn nnnnnnnnnn gttttagagc taggccaaca tgaggatcac ccatgtctgc         60
agggcctagc aagttaaaat aaggctagtc cgttatcacg ccgaaaggcg ggcaccgagt        120
cggtgctttt t                                                            131

<210> SEQ ID NO 54
<211> LENGTH: 131
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 54
nnnnnnnnnn nnnnnnnnnn gttttagagc tagaaatagc aagttaaaat aaggctagtc         60
cgttatcaac ttggccaaca tgaggatcac ccatgtctgc agggccaagt ggcaccgagt        120
cggtgctttt t                                                            131

<210> SEQ ID NO 55
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
```

<223> OTHER INFORMATION: a, c, t, g, unknown or other

<400> SEQUENCE: 55

```
nnnnnnnnnn nnnnnnnnnn gttttagagc taggccaaca tgaggatcac ccatgtctgc      60
agggcctagc aagttaaaat aaggctagtc cgttatcaac ttggccaaca tgaggatcac     120
ccatgtctgc agggccaagt ggcaccgagt cggtgctttt t                         161
```

<210> SEQ ID NO 56
<211> LENGTH: 101
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 56

```
nnnnnnnnnn nnnnnnnnnn gttttagagc tagaaatagc aagttaaaat aaggctagtc      60
cgttatcaac ttgaaaaagt ggcaccgagt cggtgctttt t                         101
```

<210> SEQ ID NO 57
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"

<400> SEQUENCE: 57

```
atggcttcaa actttactca gttcgtgctc gtggacaatg gtgggacagg ggatgtgaca      60
gtggctcctt ctaatttcgc taatggggtg cagagtgga tcagctccaa ctcacggagc     120
caggcctaca aggtgacatg cagcgtcagg cagtctagtg cccagaagag aaagtatacc    180
atcaaggtgg aggtccccaa agtggctacc cagacagtgg cggagtcga actgcctgtc    240
gccgcttgga ggtcctacct gaacatggag ctcactatcc caattttcgc taccaattct    300
gactgtgaac tcatcgtgaa ggcaatgcag gggctcctca agacggtaa tcctatccct    360
tccgccatcg ccgctaactc aggtatctac agcgctggag gaggtggaag cggaggagga    420
ggaagcggag gaggaggtag cggacctaag aaaaagagga aggtggcggc cgctggatcc    480
ggacgggctg acgcattgga cgattttgat ctggatatgc tgggaagtga cgccctcgat    540
gattttgacc ttgacatgct tggttcggat gcccttgatg actttgacct cgacatgctc    600
ggcagtgacg cccttgatga tttcgacctg gacatgctga ttaac                   645
```

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic oligonucleotide"

<400> SEQUENCE: 58

```
gcagccgctc gctgcagcag                                                 20
```

```
<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
gggcccctgc ggccaccccg                                                  20

<210> SEQ ID NO 60
<211> LENGTH: 103
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 60
nnnnnnnnnn nnnnnnnnnn gttttagagc tagaaatagc aagttaaaat aaggctagtc     60
cgttatcaac ttgaaaaagt ggcaccgagt cggtgctttt ttt                      103

<210> SEQ ID NO 61
<211> LENGTH: 113
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 61
nnnnnnnnnn nnnnnnnnnn gtttaagagc tatgctggaa acagcatagc aagtttaaat     60
aaggctagtc cgttatcaac ttgaaaaagt ggcaccgagt cggtgctttt ttt           113

<210> SEQ ID NO 62
<211> LENGTH: 163
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 62
nnnnnnnnnn nnnnnnnnnn gttttagagc taggccaaca tgaggatcac ccatgtctgc     60
agggcctagc aagttaaaat aaggctagtc cgttatcaac ttggccaaca tgaggatcac    120
ccatgtctgc agggccaagt ggcaccgagt cggtgctttt ttt                      163

<210> SEQ ID NO 63
<211> LENGTH: 173
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 63
nnnnnnnnnn nnnnnnnnnn gtttaagagc tatgctgggc caacatgagg atcacccatg      60
tctgcagggc ccagcatagc aagtttaaat aaggctagtc cgttatcaac ttggccaaca     120
tgaggatcac ccatgtctgc agggccaagt ggcaccgagt cggtgctttt ttt           173

<210> SEQ ID NO 64
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
tgctgggcca acatgaggat cacccatgtc tgcagggccc agca                      44

<210> SEQ ID NO 65
<211> LENGTH: 163
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 65
nnnnnnnnnn nnnnnnnnnn gtttaagagc taggccaaca tgaggatcac ccatgtctgc      60
agggcctagc aagtttaaat aaggctagtc cgttatcaac ttggccaaca tgaggatcac     120
ccatgtctgc agggccaagt ggcaccgagt cggtgctttt ttt                       163

<210> SEQ ID NO 66
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 66
nnnnnnnnnn nnnnnnnnnn gtttagagc taggccaaca tgaggatcac ccatgtctgc       60
agggcctagc aagttaaaat aaggctagtc cgttatcacg ccgaaaggcg ggcaccgagt     120
cggtgctttt ttt                                                       133

<210> SEQ ID NO 67
<211> LENGTH: 133
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 67
nnnnnnnnnn nnnnnnnnnn gttttagagc taggccaaca tgaggatcac ccatgtctgc      60
agggcctagc aagttaaaat aaggctagtc cgttatcaac ttgaaaaagt ggcaccgagt     120
cggtgctttt ttt                                                        133

<210> SEQ ID NO 68
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 68
nnnnnnnnnn nnnnnnnnnn gttttagagc taggccaaca tgaggatcac ccatgtctgc      60
agggcctagc aagttaaaat aaggctagtc cgttatcaac ttggccaaca tgaggatcac     120
ccatgtctgc agggccaagt ggcaccgagt cggtgctaac atgaggatca cccatgtctg     180
cagtgcaggt cgactctaga acatgagga tcacccatgt ttttttt                    227

<210> SEQ ID NO 69
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
taacatgagg atcacccatg tctgcagtgc aggtcgactc tagaaacatg aggatcaccc      60
atgt                                                                  64

<210> SEQ ID NO 70
<211> LENGTH: 193
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 70
nnnnnnnnnn nnnnnnnnnn gttttagagc taggccaaca tgaggatcac ccatgtctgc      60
agggcctagc aagttaaaat aaggggccaa catgaggatc acccatgtct gcagggcctc     120
```

```
cgttatcaac ttggccaaca tgaggatcac ccatgtctgc agggccaagt ggcaccgagt    180
cggtgctttt ttt                                                      193
```

<210> SEQ ID NO 71
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Ser Ala Gly Gly Gly Ser Gly Gly Gly Ser Gly Gly
    130                 135                 140

Gly Gly Ser Gly Pro Lys Lys Lys Arg Lys Val Ala Ala Ala Gly Ser
145                 150                 155                 160

Gly Arg Ala Asp Ala Leu Asp Asp Phe Asp Leu Asp Met Leu Gly Ser
                165                 170                 175

Asp Ala Leu Asp Asp Phe Asp Leu Asp Met Leu Gly Ser Asp Ala Leu
            180                 185                 190

Asp Asp Phe Asp Leu Asp Met Leu Gly Ser Asp Ala Leu Asp Asp Phe
        195                 200                 205

Asp Leu Asp Met Leu Ile Asn
    210                 215
```

<210> SEQ ID NO 72
<211> LENGTH: 1032
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72

```
atggcttcaa actttactca gttcgtgctc gtggacaatg gtgggacagg ggatgtgaca    60
gtggctcctt ctaatttcgc taatggggtg gcagagtgga tcagctccaa ctcacggagc   120
caggcctaca aggtgacatg cagcgtcagg cagtctagtg cccagaagag aaagtatacc   180
atcaaggtgg aggtccccaa agtggctacc cagacagtgg gcggagtcga actgcctgtc   240
gccgcttgga ggtcctacct gaacatggag ctcactatcc caatttttgc taccaattct   300
```

```
gactgtgaac tcatcgtgaa ggcaatgcag gggctcctca aagacggtaa tcctatccct    360
tccgccatcg ccgctaactc aggtatctac agcgctggag gaggtggaag cggaggagga    420
ggaagcggag gaggaggtag cggacctaag aaaaagagga aggtggcggc cgctggatcc    480
ccttcagggc agatcagcaa ccaggccctg gctctggccc ctagctccgc tccagtgctg    540
gcccagacta tggtgccctc tagtgctatg gtgcctctgg cccagccacc tgctccagcc    600
cctgtgctga ccccaggacc accccagtca ctgagcgctc cagtgcccaa gtctacacag    660
gccggcgagg ggactctgag tgaagctctg ctgcacctgc agttcgacgc tgatgaggac    720
ctgggagctc tgctggggaa cagcaccgat cccggagtgt tcacagatct ggcctccgtg    780
gacaactctg agtttcagca gctgctgaat cagggcgtgt ccatgtctca tagtacagcc    840
gaaccaatgc tgatggagta ccccgaagcc attacccggc tggtgaccgg cagccagcgg    900
cccccgacc  ccgctccaac tcccctggga accagcggcc tgcctaatgg gctgtccgga    960
gatgaagact ctcaagcat  cgctgatatg gactttagtg ccctgctgtc acagatttcc   1020
tctagtgggc ag                                                       1032
```

<210> SEQ ID NO 73
<211> LENGTH: 344
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Ser Ala Gly Gly Gly Ser Gly Gly Gly Ser Gly Gly
    130                 135                 140

Gly Gly Ser Gly Pro Lys Lys Lys Arg Lys Val Ala Ala Ala Gly Ser
145                 150                 155                 160

Pro Ser Gly Gln Ile Ser Asn Gln Ala Leu Ala Leu Ala Pro Ser Ser
                165                 170                 175

Ala Pro Val Leu Ala Gln Thr Met Val Pro Ser Ser Ala Met Val Pro
            180                 185                 190

Leu Ala Gln Pro Pro Ala Pro Ala Pro Val Leu Thr Pro Gly Pro Pro
        195                 200                 205

Gln Ser Leu Ser Ala Pro Val Pro Lys Ser Thr Gln Ala Gly Glu Gly
```

-continued

```
              210                 215                 220

Thr Leu Ser Glu Ala Leu Leu His Leu Gln Phe Asp Ala Asp Glu Asp
225                 230                 235                 240

Leu Gly Ala Leu Leu Gly Asn Ser Thr Asp Pro Gly Val Phe Thr Asp
            245                 250                 255

Leu Ala Ser Val Asp Asn Ser Glu Phe Gln Gln Leu Leu Asn Gln Gly
        260                 265                 270

Val Ser Met Ser His Ser Thr Ala Glu Pro Met Leu Met Glu Tyr Pro
    275                 280                 285

Glu Ala Ile Thr Arg Leu Val Thr Gly Ser Gln Arg Pro Pro Asp Pro
290                 295                 300

Ala Pro Thr Pro Leu Gly Thr Ser Gly Leu Pro Asn Gly Leu Ser Gly
305                 310                 315                 320

Asp Glu Asp Phe Ser Ser Ile Ala Asp Met Asp Phe Ser Ala Leu Leu
                325                 330                 335

Ser Gln Ile Ser Ser Ser Gly Gln
            340
```

<210> SEQ ID NO 74
<211> LENGTH: 621
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 74

```
atgtccaaaa ccatcgttct ttcggtcggc gaggctactc gcactctgac tgagatccag    60
tccaccgcag accgtcagat cttcgaagag aaggtcgggc tctctggtgg gtcggctgcgc   120
ctcacggctt cgctccgtca aaacggagcc aagaccgcgt atcgcgtcaa cctaaaactg   180
gatcaggcgg acgtcgttga ttccggactt ccgaaagtgc gctacactca ggtatggtcg   240
cacgacgtga caatcgttgc gaatagcacc gaggcctcgc gcaaatcgtt gtacgatttg   300
accaagtccc tcgtcgcgac ctcgcaggtc gaagatcttg tcgtcaacct tgtgccgctg   360
ggccgtagcg ctggaggagg tggaagcgga ggaggaggaa gcggaggagg aggtagcgga   420
cctaagaaaa agaggaaggt ggcggccgct ggatccggac gggctgacgc attggacgat   480
tttgatctgg atatgctggg aagtgacgcc ctcgatgatt ttgaccttga catgcttggt   540
tcggatgccc ttgatgactt tgacctcgac atgctcggca gtgacgccct tgatgatttc   600
gacctggaca tgctgattaa c                                             621
```

<210> SEQ ID NO 75
<211> LENGTH: 207
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 75

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
```

```
                35                  40                  45
Gly Ala Lys Thr Ala Tyr Arg Val Asn Leu Lys Leu Asp Gln Ala Asp
 50                  55                  60

Val Val Asp Ser Gly Leu Pro Lys Val Arg Tyr Thr Gln Val Trp Ser
 65                  70                  75                  80

His Asp Val Thr Ile Val Ala Asn Ser Thr Glu Ala Ser Arg Lys Ser
                 85                  90                  95

Leu Tyr Asp Leu Thr Lys Ser Leu Val Ala Thr Ser Gln Val Glu Asp
                100                 105                 110

Leu Val Val Asn Leu Val Pro Leu Gly Arg Ser Ala Gly Gly Gly Gly
            115                 120                 125

Ser Gly Gly Gly Ser Gly Gly Gly Ser Gly Pro Lys Lys Lys
        130                 135                 140

Arg Lys Val Ala Ala Ala Gly Ser Gly Arg Ala Asp Ala Leu Asp Asp
145                 150                 155                 160

Phe Asp Leu Asp Met Leu Gly Ser Asp Ala Leu Asp Asp Phe Asp Leu
                165                 170                 175

Asp Met Leu Gly Ser Asp Ala Leu Asp Asp Phe Asp Leu Asp Met Leu
            180                 185                 190

Gly Ser Asp Ala Leu Asp Asp Phe Asp Leu Asp Met Leu Ile Asn
        195                 200                 205

<210> SEQ ID NO 76
<211> LENGTH: 831
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
atgtccaaaa ccatcgttct ttcggtcggc gaggctactc gcactctgac tgagatccag      60
tccaccgcag accgtcagat cttcgaagag aaggtcgggc ctctggtggg tcggctgcgc     120
ctcacggctt cgctccgtca aaacggagcc aagaccgcgt atcgcgtcaa cctaaaactg     180
gatcaggcgg acgtcgttga ttccggactt ccgaaagtgc gctacactca ggtatggtcg     240
cacgacgtga caatcgttgc gaatagcacc gaggcctcgc gcaaatcgtt gtacgatttg     300
accaagtccc tcgtcgcgac ctcgcaggtc gaagatcttg tcgtcaacct tgtgccgctg     360
ggccgtagcg ctggaggagg tggaagcgga ggaggaggaa gcggaggagg aggtagcgga     420
cctaagaaaa gaggaaggt ggcggccgct ggatccatga acatccagat gctgctggag     480
gccgctgact acctggaacg gagagagcgc gaagccgagc acggatatgc ttcaatgctg     540
cccggaagcg gcatgaatat tcagatgctg ctggaggctg ctgattacct ggaaaggcgc     600
gaacgggagg ccgaacatgg ctatgcttcc atgctgcctg gtctggaat gaatatccaa     660 atgctgctgg aggcagccga ttacctggaa cggagagaaa gagaagccga gcacggatac     720
gccagcatgc tgccaggcag cgggatgaac atacaaatgc tgctggaggc tgccgattac     780
ctggagaggc gcgagagaga agctgaacat ggctatgcct ctatgctgcc c              831

<210> SEQ ID NO 77
<211> LENGTH: 277
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 77

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Ser Gly Leu Pro Lys Val Arg Tyr Thr Gln Val Trp Ser
65                  70                  75                  80

His Asp Val Thr Ile Val Ala Asn Ser Thr Glu Ala Ser Arg Lys Ser
                85                  90                  95

Leu Tyr Asp Leu Thr Lys Ser Leu Val Ala Thr Ser Gln Val Glu Asp
            100                 105                 110

Leu Val Val Asn Leu Val Pro Leu Gly Arg Ser Ala Gly Gly Gly Gly
        115                 120                 125

Ser Gly Gly Gly Gly Ser Gly Gly Gly Ser Gly Pro Lys Lys Lys
    130                 135                 140

Arg Lys Val Ala Ala Gly Ser Met Asn Ile Gln Met Leu Leu Glu
145                 150                 155                 160

Ala Ala Asp Tyr Leu Glu Arg Arg Glu Arg Glu Ala Glu His Gly Tyr
                165                 170                 175

Ala Ser Met Leu Pro Gly Ser Gly Met Asn Ile Gln Met Leu Leu Glu
            180                 185                 190

Ala Ala Asp Tyr Leu Glu Arg Arg Glu Arg Glu Ala Glu His Gly Tyr
        195                 200                 205

Ala Ser Met Leu Pro Gly Ser Gly Met Asn Ile Gln Met Leu Leu Glu
    210                 215                 220

Ala Ala Asp Tyr Leu Glu Arg Arg Glu Arg Glu Ala Glu His Gly Tyr
225                 230                 235                 240

Ala Ser Met Leu Pro Gly Ser Gly Met Asn Ile Gln Met Leu Leu Glu
                245                 250                 255

Ala Ala Asp Tyr Leu Glu Arg Arg Glu Arg Glu Ala Glu His Gly Tyr
            260                 265                 270

Ala Ser Met Leu Pro
        275

<210> SEQ ID NO 78
<211> LENGTH: 807
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
atgtccaaaa ccatcgttct ttcggtcggc gaggctactc gcactctgac tgagatccag      60
tccaccgcag accgtcagat cttcgaagag aaggtcgggc tctggtgggt cggctgcgc     120 ctcacggctt cgctccgtca aaacggagcc aagaccgcgt atcgcgtcaa cctaaaactg     180
gatcaggcgg acgtcgttga ttccggactt ccgaaagtgc gctacactca ggtatggtcg     240

```
cacgacgtga caatcgttgc gaatagcacc gaggcctcgc gcaaatcgtt gtacgatttg      300
accaagtccc tcgtcgcgac ctcgcaggtc gaagatcttg tcgtcaacct tgtgccgctg      360
ggccgtagcg ctggaggagg tggaagcgga ggaggaggaa gcggaggagg aggtagcgga      420
cctaagaaaa agaggaaggt ggcggccgct ggatccgctt tgtctcctca gcactctgct      480
gtcactcaag gaagtatcat caagaacaag gagggcatgg atgctaagtc actaactgcc      540
tggtcccgga cactggtgac cttcaaggat gtatttgtgg acttcaccag ggaggagtgg      600
aagctgctgg acactgctca gcagatcgtg tacagaaatg tgatgctgga gaactataag      660
aacctggttt ccttgggtta tcagcttact aagccagatg tgatcctccg gttggagaag      720
ggagaagagc cctggctggt ggagagagaa attcaccaag agacccatcc tgattcagag      780
actgcatttg aaatcaaatc atcagtt                                         807
```

<210> SEQ ID NO 79
<211> LENGTH: 269
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Ser Gly Leu Pro Lys Val Arg Tyr Thr Gln Val Trp Ser
65                  70                  75                  80

His Asp Val Thr Ile Val Ala Asn Ser Thr Glu Ala Ser Arg Lys Ser
                85                  90                  95

Leu Tyr Asp Leu Thr Lys Ser Leu Val Ala Thr Ser Gln Val Glu Asp
            100                 105                 110

Leu Val Val Asn Leu Val Pro Leu Gly Arg Ser Ala Gly Gly Gly Gly
        115                 120                 125

Ser Gly Gly Gly Gly Ser Gly Gly Gly Ser Gly Pro Lys Lys Lys
    130                 135                 140

Arg Lys Val Ala Ala Ala Gly Ser Ala Leu Ser Pro Gln His Ser Ala
145                 150                 155                 160

Val Thr Gln Gly Ser Ile Ile Lys Asn Lys Glu Gly Met Asp Ala Lys
                165                 170                 175

Ser Leu Thr Ala Trp Ser Arg Thr Leu Val Thr Phe Lys Asp Val Phe
            180                 185                 190

Val Asp Phe Thr Arg Glu Glu Trp Lys Leu Leu Asp Thr Ala Gln Gln
        195                 200                 205

Ile Val Tyr Arg Asn Val Met Leu Glu Asn Tyr Lys Asn Leu Val Ser
    210                 215                 220

Leu Gly Tyr Gln Leu Thr Lys Pro Asp Val Ile Leu Arg Leu Glu Lys
225                 230                 235                 240

Gly Glu Glu Pro Trp Leu Val Glu Arg Glu Ile His Gln Glu Thr His
                245                 250                 255
```

Pro Asp Ser Glu Thr Ala Phe Glu Ile Lys Ser Ser Val
            260                 265

<210> SEQ ID NO 80
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
atgtccaaaa ccatcgttct ttcggtcggc gaggctactc gcactctgac tgagatccag      60
tccaccgcag accgtcagat cttcgaagag aaggtcgggc tctggtggg tcggctgcgc     120 ctcacggctt cgctccgtca aacggagcc aagaccgcgt atcgcgtcaa cctaaaactg     180
gatcaggcgg acgtcgttga ttccggactt ccgaaagtgc gctacactca ggtatggtcg     240
cacgacgtga caatcgttgc gaatagcacc gaggcctcgc gcaaatcgtt gtacgatttg     300
accaagtccc tcgtcgcgac ctcgcaggtc gaagatcttg tcgtcaacct tgtgccgctg     360
ggccgtagcg ctggaggagg tggaagcgga ggaggaggaa gcggaggagg aggtagcgga     420
cctaagaaaa agaggaaggt ggcggccgct ggatccacta ccaactccac tcaggacaca     480
ctgtatctca gcctccacgg cggaatcgac tccgccatcc cataccccgt gaggagagtc     540
gagcagctgc tccagttctc ttttctgccc gaactccagt tccagaacgc cgctgtgaaa     600
cagagaatcc agcgcctgtg ctatagagag aaaagcggc tggctgtcag ctccctcgca     660
aagtggctgg ccagctcca aaacagagg ctgagagcac aaagaaccc ccctgtggcc      720 atttgttgga tcaatagtta cgtgggctat ggagtctttg cccgggagtc tattcccgct     780
tggagttaca tcggcgaata taccggcatc ctgcggcgcc gacaggctct gtggctcgac     840
gagaacgatt actgcttccg ctatcctgtg ccacgctact cattccgata ttttaccatc     900
gacagcggga tgcagggtaa cgtcacaagg ttcatcaatc actccgataa ccctaatctg     960
gaggcaatcg gggccttcga aaacggtatc ttccatatca tcatcagggc catcaaggat    1020
atcctgcccg gggaggaact ctgttaccac tatggacctc tgtactggaa gcatcgaaag    1080
aaaagggagg agttcgtgcc acaggaggaa                                     1110

<210> SEQ ID NO 81
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Ser Gly Leu Pro Lys Val Arg Tyr Thr Gln Val Trp Ser

His Asp Val Thr Ile Val Ala Asn Ser Thr Glu Ala Ser Arg Lys Ser
65                  70                  75                  80

Leu Tyr Asp Leu Thr Lys Ser Leu Val Ala Thr Ser Gln Val Glu Asp
            85                  90                  95

Leu Val Asn Leu Val Pro Leu Gly Arg Ser Ala Gly Gly Gly
        115                 120                 125

Ser Gly Gly Gly Ser Gly Gly Gly Ser Gly Pro Lys Lys
    130                 135                 140

Arg Lys Val Ala Ala Gly Ser Thr Thr Asn Ser Thr Gln Asp Thr
145                 150                 155                 160

Leu Tyr Leu Ser Leu His Gly Gly Ile Asp Ser Ala Ile Pro Tyr Pro
                165                 170                 175

Val Arg Arg Val Glu Gln Leu Leu Gln Phe Ser Phe Leu Pro Glu Leu
            180                 185                 190

Gln Phe Gln Asn Ala Ala Val Lys Gln Arg Ile Gln Arg Leu Cys Tyr
                195                 200                 205

Arg Glu Glu Lys Arg Leu Ala Val Ser Ser Leu Ala Lys Trp Leu Gly
210                 215                 220

Gln Leu His Lys Gln Arg Leu Arg Ala Pro Lys Asn Pro Val Ala
225                 230                 235                 240

Ile Cys Trp Ile Asn Ser Tyr Val Gly Tyr Gly Val Phe Ala Arg Glu
                245                 250                 255

Ser Ile Pro Ala Trp Ser Tyr Ile Gly Glu Tyr Thr Gly Ile Leu Arg
            260                 265                 270

Arg Arg Gln Ala Leu Trp Leu Asp Glu Asn Asp Tyr Cys Phe Arg Tyr
            275                 280                 285

Pro Val Pro Arg Tyr Ser Phe Arg Tyr Phe Thr Ile Asp Ser Gly Met
        290                 295                 300

Gln Gly Asn Val Thr Arg Phe Ile Asn His Ser Asp Asn Pro Asn Leu
305                 310                 315                 320

Glu Ala Ile Gly Ala Phe Glu Asn Gly Ile Phe His Ile Ile Arg
            325                 330                 335

Ala Ile Lys Asp Ile Leu Pro Gly Glu Glu Leu Cys Tyr His Tyr Gly
                340                 345                 350

Pro Leu Tyr Trp Lys His Arg Lys Lys Arg Gly Glu Phe Val Pro Gln
            355                 360                 365

Glu Glu
370

<210> SEQ ID NO 82
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
atgtccaaaa ccatcgttct ttcggtcggc gaggctactc gcactctgac tgagatccag      60
tccaccgcag accgtcagat cttcgaagag aaggtcgggc tctggtgggt cggctgcgc     120 ctcacggctt cgctccgtca aaacggagcc aagaccgcgt atcgcgtcaa cctaaaactg     180
gatcaggcgg acgtcgttga ttccggactt ccgaaagtgc gctacactca ggtatggtcg     240

-continued

```
cacgacgtga caatcgttgc gaatagcacc gaggcctcgc gcaaatcgtt gtacgatttg      300
accaagtccc tcgtcgcgac ctcgcaggtc gaagatcttg tcgtcaacct tgtgccgctg      360
ggccgtagcg ctggaggagg tggaagcgga ggaggaggaa gcggaggagg aggtagcgga      420
cctaagaaaa agaggaaggt ggcggccgct ggatccaacg ggctgatgga ggacccaatg      480
aaagtctaca aggacaggca gtttatgaac gtgtggaccg accacgagaa ggaaatcttc      540
aaggataagt tcatccagca tcccaaaaat ttcggcctga tcgccagcta cctggagagg      600
aagtccgtgc ctgactgcgt cctgtactat tacctcacaa agaaaaacga aaattacaaa      660
```

<210> SEQ ID NO 83
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 83

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Ser Gly Leu Pro Lys Val Arg Tyr Thr Gln Val Trp Ser
65                  70                  75                  80

His Asp Val Thr Ile Val Ala Asn Ser Thr Glu Ala Ser Arg Lys Ser
                85                  90                  95

Leu Tyr Asp Leu Thr Lys Ser Leu Val Ala Thr Ser Gln Val Glu Asp
            100                 105                 110

Leu Val Val Asn Leu Val Pro Leu Gly Arg Ser Ala Gly Gly Gly Gly
        115                 120                 125

Ser Gly Gly Gly Gly Ser Gly Gly Gly Ser Gly Pro Lys Lys Lys
    130                 135                 140

Arg Lys Val Ala Ala Ala Gly Ser Asn Gly Leu Met Glu Asp Pro Met
145                 150                 155                 160

Lys Val Tyr Lys Asp Arg Gln Phe Met Asn Val Trp Thr Asp His Glu
                165                 170                 175

Lys Glu Ile Phe Lys Asp Lys Phe Ile Gln His Pro Lys Asn Phe Gly
            180                 185                 190

Leu Ile Ala Ser Tyr Leu Glu Arg Lys Ser Val Pro Asp Cys Val Leu
        195                 200                 205

Tyr Tyr Tyr Leu Thr Lys Lys Asn Glu Asn Tyr Lys
    210                 215                 220
```

<210> SEQ ID NO 84
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 84

```
atggcttcaa actttactca gttcgtgctc gtggacaatg gtgggacagg ggatgtgaca    60
gtggctcctt ctaatttcgc taatggggtg gcagagtgga tcagctccaa ctcacggagc   120
caggcctaca aggtgacatg cagcgtcagg cagtctagtg cccagaagag aaagtatacc   180
atcaaggtgg aggtccccaa agtggctacc agacagtgg gcggagtcga actgcctgtc    240
gccgcttgga ggtcctacct gaacatggag ctcactatcc caattttcgc taccaattct   300
gactgtgaac tcatcgtgaa ggcaatgcag gggctcctca agacggtaa tcctatccct    360
tccgccatcg ccgctaactc aggtatctac agcgctggag gaggtggaag cggaggagga   420
ggaagcggag gaggaggtag cggacctaag aaaaagagga aggtggcggc cgctggatcc   480
aacggcgcga ttggtgggga tttgctgctt aactttcccg acatgtccgt gttggaacgt   540
cagcgcgcac atttgaagta tcttaacccc accttcgact ccccgttggc cgggttcttt   600
gcggactcat ctatgattac gggaggggaa atggacagct acctctcaac ggccggattg   660
aatcttccga tgatgtatgg agaaaccact gtagaaggcg actcgcgact ctcgatttcg   720
cctgaaacga cgctgggaac agggaacttc aagaaacgga aattcgacac ggagacaaaa   780
gattgcaacg aaaagaagaa gaaaatgacc atgaatcgcg atgatctggt agaggaggga   840
gaggaggaaa agtcgaagat tactgaacag aacaatgggt ctaccaaaag tatcaaaaag   900
atgaagcaca aagctaagaa agaagagaac aatttcagca atgacagcag taaagtcaca   960
aaagaactgg agaaaacgga ttacattcac gtgagggcgc gacgagggca ggctacagat  1020
tcacattcaa ttgcggagag agtacggaga gagaaaatct cagaaaggat gaagttcctc  1080
caagaccttg tgccaggttg tgacaagatc acaggcaaag caggaatgct ggatgagatc  1140
atcaactacg tccaatcgtt gcaaagacaa attgagtttc tctcgatgaa actggccatc  1200
gtgaatccta daccggattt cgacatggat gacatctttg cgaaagaagt ggcatccact  1260
cccatgacgg ttgtgccctc accggagatg gtcttgtctg gttacagcca cgaaatggtg  1320
cattcgggtt attcaagcga gatggtcaat tcgggatacc ttcacgtcaa tcccatgcag  1380
caggtgaata cttccagtga tccactctcc tgctttaaca acggcgaggc cccttcgatg  1440
tgggactccc acgtacagaa tctctatgga aatctcggag tc                      1482
```

<210> SEQ ID NO 85
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
```

85                  90                  95
Ala Thr Asn Ser Asp Cys Glu Leu Ile Val Lys Ala Met Gln Gly Leu
                100                 105                 110

Leu Lys Asp Gly Asn Pro Ile Pro Ser Ala Ile Ala Ala Asn Ser Gly
            115                 120                 125

Ile Tyr Ser Ala Gly Gly Gly Ser Gly Gly Gly Ser Gly Gly
130                 135                 140

Gly Gly Ser Gly Pro Lys Lys Arg Lys Val Ala Ala Gly Ser
145                 150                 155                 160

Asn Gly Ala Ile Gly Gly Asp Leu Leu Leu Asn Phe Pro Asp Met Ser
                165                 170                 175

Val Leu Glu Arg Gln Arg Ala His Leu Lys Tyr Leu Asn Pro Thr Phe
                180                 185                 190

Asp Ser Pro Leu Ala Gly Phe Phe Ala Asp Ser Ser Met Ile Thr Gly
            195                 200                 205

Gly Glu Met Asp Ser Tyr Leu Ser Thr Ala Gly Leu Asn Leu Pro Met
        210                 215                 220

Met Tyr Gly Glu Thr Thr Val Glu Gly Asp Ser Arg Leu Ser Ile Ser
225                 230                 235                 240

Pro Glu Thr Thr Leu Gly Thr Gly Asn Phe Lys Lys Arg Lys Phe Asp
                245                 250                 255

Thr Glu Thr Lys Asp Cys Asn Glu Lys Lys Lys Met Thr Met Asn
            260                 265                 270

Arg Asp Asp Leu Val Glu Glu Gly Glu Glu Lys Ser Lys Ile Thr
        275                 280                 285

Glu Gln Asn Asn Gly Ser Thr Lys Ser Ile Lys Lys Met Lys His Lys
                290                 295                 300

Ala Lys Lys Glu Glu Asn Asn Phe Ser Asn Asp Ser Ser Lys Val Thr
305                 310                 315                 320

Lys Glu Leu Glu Lys Thr Asp Tyr Ile His Val Arg Ala Arg Arg Gly
                325                 330                 335

Gln Ala Thr Asp Ser His Ser Ile Ala Glu Arg Val Arg Arg Glu Lys
            340                 345                 350

Ile Ser Glu Arg Met Lys Phe Leu Gln Asp Leu Val Pro Gly Cys Asp
        355                 360                 365

Lys Ile Thr Gly Lys Ala Gly Met Leu Asp Glu Ile Ile Asn Tyr Val
        370                 375                 380

Gln Ser Leu Gln Arg Gln Ile Glu Phe Leu Ser Met Lys Leu Ala Ile
385                 390                 395                 400

Val Asn Pro Arg Pro Asp Phe Asp Met Asp Asp Ile Phe Ala Lys Glu
                405                 410                 415

Val Ala Ser Thr Pro Met Thr Val Val Pro Ser Pro Glu Met Val Leu
            420                 425                 430

Ser Gly Tyr Ser His Glu Met Val His Ser Gly Tyr Ser Ser Glu Met
            435                 440                 445

Val Asn Ser Gly Tyr Leu His Val Asn Pro Met Gln Gln Val Asn Thr
450                 455                 460

Ser Ser Asp Pro Leu Ser Cys Phe Asn Asn Gly Glu Ala Pro Ser Met
465                 470                 475                 480

Trp Asp Ser His Val Gln Asn Leu Tyr Gly Asn Leu Gly Val
            485                 490

<210> SEQ ID NO 86

<211> LENGTH: 3960
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

| | |
|---|---:|
| atggacaaga agtacagcat cggcctggcc atcggcacca actctgtggg ctgggccgtg | 60 |
| atcaccgacg agtacaaggt gcccagcaag aaattcaagg tgctgggcaa caccgaccgg | 120 |
| cacagcatca agaagaacct gatcggagcc ctgctgttcg acagcggcga aacagccgag | 180 |
| gccacccggc tgaagagaac cgccagaaga agatacacca gacggaagaa ccggatctgc | 240 |
| tatctgcaag agatcttcag caacgagatg gccaaggtgg acgacagctt cttccacaga | 300 |
| ctggaagagt ccttcctggt ggaagaggat aagaagcacg agcggcaccc catcttcggc | 360 |
| aacatcgtgg acgaggtggc ctaccacgag aagtacccca ccatctacca cctgagaaag | 420 |
| aaactggtgg acagcaccga caaggccgac ctgcggctga tctatctggc cctggcccac | 480 |
| atgatcaagt tccggggcca cttcctgatc gagggcgacc tgaacggacg ggctgacgca | 540 |
| ttggacgatt ttgatctgga tatgctggga agtgacgccc tcgatgattt tgaccttgac | 600 |
| atgcttggtt cggatgccct tgatgacttt gacctcgaca tgctcggcag tgacgccctt | 660 |
| gatgatttcg acctggacat gctgattaac agagtgaaca ccgagatcac caaggccccc | 720 |
| ctgagcgcct ctatgatcaa gagatacgac gagcaccacc aggacctgac cctgctgaaa | 780 |
| gctctcgtgc ggcagcagct gcctgagaag tacaaagaga ttttcttcga ccagagcaag | 840 |
| aacggctacg ccggctacat tgacggcgga gccagccagg aagagttcta caagttcatc | 900 |
| aagcccatcc tggaaaagat ggacggcacc gaggaactgc tcgtgaagct gaacagagag | 960 |
| gacctgctgc ggaagcagcg gaccttcgac aacggcagca tcccccacca gatccacctg | 1020 |
| ggagagctgc acgccattct gcggcggcag gaagattttt acccattcct gaaggacaac | 1080 |
| cgggaaaaga tcgagaagat cctgaccttc cgcatcccct actacgtggg ccctctggcc | 1140 |
| agggaaaca gcagattcgc ctggatgacc agaaagagcg aggaaaccat cacccccctgg | 1200 |
| aacttcgagg aagtggtgga caagggcgct tccgcccaga gcttcatcga gcggatgacc | 1260 |
| aacttcgata gaaccctgcc caacgagaag gtgctgccca gcacagcct gctgtacgag | 1320 |
| tacttcaccg tgtataacga gctgaccaaa gtgaaatacg tgaccgaggg aatgagaaag | 1380 |
| cccgccttcc tgagcggcga gcagaaaaag gccatcgtgg acctgctgtt caagaccaac | 1440 |
| cggaaagtga ccgtgaagca gctgaaagag gactacttca gaaaaatcga gtgcttcgac | 1500 |
| tccgtggaaa tctccggcgt ggaagatcgg ttcaacgcct ccctgggcac ataccacgat | 1560 |
| ctgctgaaaa ttatcaagga caaggacttc ctggacaatg aggaaaacga ggacattctg | 1620 |
| gaagatatcg tgctgaccct gacactgttt gaggacagag agatgatcga ggaacggctg | 1680 |
| aaaacctatg cccacctgtt cgacgacaaa gtgatgaagc agctgaagcg gcggagatac | 1740 |
| accggctggg gcaggctgag ccggaagctg atcaacggca tccgggacaa gcagtccggc | 1800 |
| aagacaatcc tggatttcct gaagtccgac ggcttcgcca acagaaactt catgcagctg | 1860 |
| atccacgacg acagcctgac ctttaaagag gacatccaga aagcccaggt gtccggccag | 1920 |
| ggcgatagcc tgcacgagca cattgccaat ctggccggca gccccgccat taagaagggc | 1980 |
| atcctgcaga cagtgaaggt ggtggacgag ctcgtgaaag tgatgggccg gcacaagccc | 2040 |
| gagaacatcg tgatcgaaat ggccagagag aaccagacca cccagaaggg acagaagaac | 2100 |

-continued

```
agccgcgaga gaatgaagcg gatcgaagag ggcatcaaag agctgggcag ccagatcctg    2160
aaagaacacc ccgtggaaaa cacccagctg cagaacgaga agctgtacct gtactacctg    2220
cagaatgggc gggatatgta cgtggaccag gaactggaca tcaaccggct gtccgactac    2280
gatgtggacc tatcgtgcc tcagagcttt ctgaaggacg actccatcga caacaaggtg    2340
ctgaccagaa gcgacaagaa ccggggcaag agcgacaacg tgccctccga gaggtcgtg    2400 aagaagatga agaactactg gcggcagctg ctgaacgcca agctgattac ccagagaaag    2460
ttcgacaatc tgaccaaggc cgagagaggc ggcctgagcg aactggataa ggccggcttc    2520
atcaagagac agctggtgga aacccggcag atcacaaagc acgtggcaca gatcctggac    2580
tcccggatga acactaagta cgacgagaat gacaagctga tccgggaagt gaaagtgatc    2640
accctgaagt ccaagctggt gtccgatttc cggaaggatt ccagttttta caagtgcgc    2700 gagatcaaca actaccacca cgcccacgac gcctacctga acgccgtcgt gggaaccgcc    2760
ctgatcaaaa agtaccctaa gctggaaagc gagttcgtgt acggcgacta caaggtgtac    2820
gacgtgcgga agatgatcgc caagagcgag caggaaatcg gcaaggctac cgccaagtac    2880
ttcttctaca gcaacatcat gaacttttc aagaccgaga ttaccctggc caacggcgag    2940
atccggaagc ggcctctgat cgagacaaac ggcgaaaccg gggagatcgt gtgggataag    3000
ggccgggatt ttgccaccgt gcggaaagtg ctgagcatgc cccaagtgaa tatcgtgaaa    3060
aagaccgagg tgcagacagg cggcttcagc aaagagtcta tcctgcccaa gaggaacagc    3120
gataagctga tcgccagaaa gaaggactgg gaccctaaga agtacggcgg cttcgacagc    3180
cccaccgtgg cctattctgt gctggtggtg gccaaagtgg aaaagggcaa gtccaagaaa    3240
ctgaagagtg tgaaagagct gctggggatc accatcatgg aaagaagcag cttcgagaag    3300
aatcccatcg actttctgga agccaagggc tacaaagaag tgaaaaagga cctgatcatc    3360
aagctgccta agtactccct gttcgagctg gaaaacggcc ggaagagaat gctggcctct    3420
gccggcgaac tgcagaaggg aaacgaactg gccctgccct ccaaatatgt gaacttcctg    3480
tacctggcca gccactatga aagctgaag ggctcccccg aggataatga gcagaaacag    3540
ctgtttgtgg aacagcacaa gcactacctg gacgagatca tcgagcagat cagcgagttc    3600
tccaagagag tgatcctggc cgacgctaat ctggacaaag tgctgtccgc ctacaacaag    3660
caccgggata agcccatcag agagcaggcc gagaatatca tccacctgtt taccctgacc    3720
aatctgggag cccctgccgc cttcaagtac tttgacacca ccatcgaccg gaagaggtac    3780
accagcacca aagaggtgct ggacgccacc ctgatccacc agagcatcac cggcctgtac    3840
gagacacgga tcgacctgtc tcagctggga ggcgacagcg ctggaggagg tggaagcgga    3900
ggaggaggaa gcgaggagg aggtagcgga cctaagaaaa agaggaaggt ggcggccgct    3960
```

<210> SEQ ID NO 87
<211> LENGTH: 1320
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe

```
            20                  25                  30
Lys Val Leu Gly Asn Thr Asp Arg His Ser Ile Lys Lys Asn Leu Ile
        35                  40                  45
Gly Ala Leu Leu Phe Asp Ser Gly Glu Thr Ala Glu Ala Thr Arg Leu
        50                  55                  60
Lys Arg Thr Ala Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
            130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Gly
                165                 170                 175
Arg Ala Asp Ala Leu Asp Asp Phe Asp Leu Asp Met Leu Gly Ser Asp
                180                 185                 190
Ala Leu Asp Asp Phe Asp Leu Asp Met Leu Gly Ser Asp Ala Leu Asp
                195                 200                 205
Asp Phe Asp Leu Asp Met Leu Gly Ser Asp Ala Leu Asp Asp Phe Asp
            210                 215                 220
Leu Asp Met Leu Ile Asn Arg Val Asn Thr Glu Ile Thr Lys Ala Pro
225                 230                 235                 240
Leu Ser Ala Ser Met Ile Lys Arg Tyr Asp Glu His His Gln Asp Leu
                245                 250                 255
Thr Leu Leu Lys Ala Leu Val Arg Gln Gln Leu Pro Glu Lys Tyr Lys
            260                 265                 270
Glu Ile Phe Phe Asp Gln Ser Lys Asn Gly Tyr Ala Gly Tyr Ile Asp
            275                 280                 285
Gly Gly Ala Ser Gln Glu Glu Phe Tyr Lys Phe Ile Lys Pro Ile Leu
        290                 295                 300
Glu Lys Met Asp Gly Thr Glu Glu Leu Leu Val Lys Leu Asn Arg Glu
305                 310                 315                 320
Asp Leu Leu Arg Lys Gln Arg Thr Phe Asp Asn Gly Ser Ile Pro His
                325                 330                 335
Gln Ile His Leu Gly Glu Leu His Ala Ile Leu Arg Arg Gln Glu Asp
            340                 345                 350
Phe Tyr Pro Phe Leu Lys Asp Asn Arg Glu Lys Ile Glu Lys Ile Leu
            355                 360                 365
Thr Phe Arg Ile Pro Tyr Tyr Val Gly Pro Leu Ala Arg Gly Asn Ser
        370                 375                 380
Arg Phe Ala Trp Met Thr Arg Lys Ser Glu Glu Thr Ile Thr Pro Trp
385                 390                 395                 400
Asn Phe Glu Glu Val Val Asp Lys Gly Ala Ser Ala Gln Ser Phe Ile
                405                 410                 415
Glu Arg Met Thr Asn Phe Asp Lys Asn Leu Pro Asn Glu Lys Val Leu
            420                 425                 430
Pro Lys His Ser Leu Leu Tyr Glu Tyr Phe Thr Val Tyr Asn Glu Leu
            435                 440                 445
```

```
Thr Lys Val Lys Tyr Val Thr Glu Gly Met Arg Lys Pro Ala Phe Leu
    450                 455                 460
Ser Gly Glu Gln Lys Lys Ala Ile Val Asp Leu Leu Phe Lys Thr Asn
465                 470                 475                 480
Arg Lys Val Thr Val Lys Gln Leu Lys Glu Asp Tyr Phe Lys Lys Ile
                485                 490                 495
Glu Cys Phe Asp Ser Val Glu Ile Ser Gly Val Glu Asp Arg Phe Asn
                500                 505                 510
Ala Ser Leu Gly Thr Tyr His Asp Leu Leu Lys Ile Ile Lys Asp Lys
            515                 520                 525
Asp Phe Leu Asp Asn Glu Glu Asn Glu Asp Ile Leu Glu Asp Ile Val
530                 535                 540
Leu Thr Leu Thr Leu Phe Glu Asp Arg Glu Met Ile Glu Glu Arg Leu
545                 550                 555                 560
Lys Thr Tyr Ala His Leu Phe Asp Asp Lys Val Met Lys Gln Leu Lys
                565                 570                 575
Arg Arg Arg Tyr Thr Gly Trp Gly Arg Leu Ser Arg Lys Leu Ile Asn
            580                 585                 590
Gly Ile Arg Asp Lys Gln Ser Gly Lys Thr Ile Leu Asp Phe Leu Lys
        595                 600                 605
Ser Asp Gly Phe Ala Asn Arg Asn Phe Met Gln Leu Ile His Asp Asp
    610                 615                 620
Ser Leu Thr Phe Lys Glu Asp Ile Gln Lys Ala Gln Val Ser Gly Gln
625                 630                 635                 640
Gly Asp Ser Leu His Glu His Ile Ala Asn Leu Ala Gly Ser Pro Ala
                645                 650                 655
Ile Lys Lys Gly Ile Leu Gln Thr Val Lys Val Val Asp Glu Leu Val
            660                 665                 670
Lys Val Met Gly Arg His Lys Pro Glu Asn Ile Val Ile Glu Met Ala
        675                 680                 685
Arg Glu Asn Gln Thr Thr Gln Lys Gly Gln Lys Asn Ser Arg Glu Arg
    690                 695                 700
Met Lys Arg Ile Glu Glu Gly Ile Lys Glu Leu Gly Ser Gln Ile Leu
705                 710                 715                 720
Lys Glu His Pro Val Glu Asn Thr Gln Leu Gln Asn Glu Lys Leu Tyr
                725                 730                 735
Leu Tyr Tyr Leu Gln Asn Gly Arg Asp Met Tyr Val Asp Gln Glu Leu
            740                 745                 750
Asp Ile Asn Arg Leu Ser Asp Tyr Asp Val Asp Ala Ile Val Pro Gln
        755                 760                 765
Ser Phe Leu Lys Asp Asp Ser Ile Asp Asn Lys Val Leu Thr Arg Ser
    770                 775                 780
Asp Lys Asn Arg Gly Lys Ser Asp Asn Val Pro Ser Glu Glu Val Val
785                 790                 795                 800
Lys Lys Met Lys Asn Tyr Trp Arg Gln Leu Leu Asn Ala Lys Leu Ile
                805                 810                 815
Thr Gln Arg Lys Phe Asp Asn Leu Thr Lys Ala Glu Arg Gly Gly Leu
            820                 825                 830
Ser Glu Leu Asp Lys Ala Gly Phe Ile Lys Arg Gln Leu Val Glu Thr
        835                 840                 845
Arg Gln Ile Thr Lys His Val Ala Gln Ile Leu Asp Ser Arg Met Asn
    850                 855                 860
```

```
Thr Lys Tyr Asp Glu Asn Asp Lys Leu Ile Arg Glu Val Lys Val Ile
865                 870                 875                 880

Thr Leu Lys Ser Lys Leu Val Ser Asp Phe Arg Lys Asp Phe Gln Phe
                885                 890                 895

Tyr Lys Val Arg Glu Ile Asn Asn Tyr His His Ala His Asp Ala Tyr
            900                 905                 910

Leu Asn Ala Val Val Gly Thr Ala Leu Ile Lys Lys Tyr Pro Lys Leu
        915                 920                 925

Glu Ser Glu Phe Val Tyr Gly Asp Tyr Lys Val Tyr Asp Val Arg Lys
    930                 935                 940

Met Ile Ala Lys Ser Glu Gln Glu Ile Gly Lys Ala Thr Ala Lys Tyr
945                 950                 955                 960

Phe Phe Tyr Ser Asn Ile Met Asn Phe Phe Lys Thr Glu Ile Thr Leu
                965                 970                 975

Ala Asn Gly Glu Ile Arg Lys Arg Pro Leu Ile Glu Thr Asn Gly Glu
            980                 985                 990

Thr Gly Glu Ile Val Trp Asp Lys Gly Arg Asp Phe Ala Thr Val Arg
        995                 1000                1005

Lys Val Leu Ser Met Pro Gln Val Asn Ile Val Lys Lys Thr Glu
    1010                1015                1020

Val Gln Thr Gly Gly Phe Ser Lys Glu Ser Ile Leu Pro Lys Arg
    1025                1030                1035

Asn Ser Asp Lys Leu Ile Ala Arg Lys Lys Asp Trp Asp Pro Lys
    1040                1045                1050

Lys Tyr Gly Gly Phe Asp Ser Pro Thr Val Ala Tyr Ser Val Leu
    1055                1060                1065

Val Val Ala Lys Val Glu Lys Gly Lys Ser Lys Lys Leu Lys Ser
    1070                1075                1080

Val Lys Glu Leu Leu Gly Ile Thr Ile Met Glu Arg Ser Ser Phe
    1085                1090                1095

Glu Lys Asn Pro Ile Asp Phe Leu Glu Ala Lys Gly Tyr Lys Glu
    1100                1105                1110

Val Lys Lys Asp Leu Ile Ile Lys Leu Pro Lys Tyr Ser Leu Phe
    1115                1120                1125

Glu Leu Glu Asn Gly Arg Lys Arg Met Leu Ala Ser Ala Gly Glu
    1130                1135                1140

Leu Gln Lys Gly Asn Glu Leu Ala Leu Pro Ser Lys Tyr Val Asn
    1145                1150                1155

Phe Leu Tyr Leu Ala Ser His Tyr Glu Lys Leu Lys Gly Ser Pro
    1160                1165                1170

Glu Asp Asn Glu Gln Lys Gln Leu Phe Val Glu Gln His Lys His
    1175                1180                1185

Tyr Leu Asp Glu Ile Ile Glu Gln Ile Ser Glu Phe Ser Lys Arg
    1190                1195                1200

Val Ile Leu Ala Asp Ala Asn Leu Asp Lys Val Leu Ser Ala Tyr
    1205                1210                1215

Asn Lys His Arg Asp Lys Pro Ile Arg Glu Gln Ala Glu Asn Ile
    1220                1225                1230

Ile His Leu Phe Thr Leu Thr Asn Leu Gly Ala Pro Ala Ala Phe
    1235                1240                1245

Lys Tyr Phe Asp Thr Thr Ile Asp Arg Lys Arg Tyr Thr Ser Thr
    1250                1255                1260

Lys Glu Val Leu Asp Ala Thr Leu Ile His Gln Ser Ile Thr Gly
```

|  | 1265 |  | 1270 |  | 1275 |  |  |  |  |
|---|---|---|---|---|---|---|---|---|---|
| Leu | Tyr | Glu | Thr | Arg | Ile | Asp | Leu | Ser | Gln | Leu | Gly | Gly | Asp | Ser |
|  |  | 1280 |  |  | 1285 |  |  |  | 1290 |

Ala Gly Gly Gly Gly Ser Gly Gly Gly Gly Ser Gly Gly Gly Gly
    1295                1300               1305

Ser Gly Pro Lys Lys Lys Arg Lys Val Ala Ala Ala
    1310               1315               1320

```
<210> SEQ ID NO 88
<211> LENGTH: 4050
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
atggacaaga agtacagcat cggcctggcc atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180 gccaccccggc tgaagagaac cgccagaaga agatacacca gacggaagaa ccggatctgc     240
tatctgcaag atcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg acagcaccga caaggccgac ctgcggctga tctatctggc cctggcccac     480
atgatcaagt tccggggcca cttcctgatc gagggcgacc tgaacggcgg gggaggctcc     540
ggtggtgggg gcagcggagg gggggcagc ggacgggctg acgcattgga cgattttgat     600
ctggatatgc tgggaagtga cgccctcgat gattttgacc ttgacatgct tggttcggat     660
gcccttgatg actttgacct cgacatgctc ggcagtgacg cccttgatga tttcgacctg     720
gacatgctga ttaacggcgg gggaggctcc ggtggtgggg gcagcggagg gggggcagc     780 agagtgaaca ccgagatcac caaggccccc ctgagcgcct ctatgatcaa gagatacgac     840
gagcaccacc aggacctgac cctgctgaaa gctctcgtgc ggcagcagct gcctgagaag     900
tacaaagaga ttttcttcga ccagagcaag aacggctacg ccggctacat tgacggcgga     960
gccagccagg aagagttcta caagttcatc aagcccatcc tggaaaagat ggacggcacc    1020
gaggaactgc tcgtgaagct gaacagagag gacctgctgc ggaagcagcg gaccttcgac    1080
aacggcagca tcccccacca gatccacctg ggagagctgc acgccattct gcggcggcag    1140 gaagatttt acccattcct gaaggacaac cgggaaaaga tcgagaagat cctgaccttc    1200
cgcatcccct actacgtggg ccctctggcc aggggaaaca gcagattcgc ctggatgacc    1260
agaaagagcg aggaaaccat cacccccctgg aacttcgagg aagtggtgga caagggcgct    1320
tccgcccaga gcttcatcga gcggatgacc aacttcgata agaacctgcc caacgagaag    1380
gtgctgccca gcacagcct gctgtacgag tacttcaccg tgtataacga gctgaccaaa    1440
gtgaaatacg tgaccgaggg aatgagaaag cccgccttcc tgagcggcga gcagaaaaag    1500
gccatcgtgg acctgctgtt caagaccaac cggaaagtga ccgtgaagca gctgaaagag    1560
gactacttca gaaaaatcga gtgcttcgac tccgtggaaa tctccggcgt ggaagatcgg    1620
ttcaacgcct ccctgggcac ataccacgat ctgctgaaaa ttatcaagga caaggacttc    1680
```

```
ctggacaatg aggaaaacga ggacattctg gaagatatcg tgctgacccct gacactgttt    1740 gaggacagag agatgatcga ggaacggctg aaaacctatg cccacctgtt cgacgacaaa    1800
gtgatgaagc agctgaagcg gcggagatac accggctggg gcaggctgag ccggaagctg    1860
atcaacggca tccgggacaa gcagtccggc aagacaatcc tggatttcct gaagtccgac    1920
ggcttcgcca acagaaactt catgcagctg atccacgacg acagcctgac ctttaaagag    1980
gacatccaga aagcccaggt gtccggccag ggcgatagcc tgcacgagca cattgccaat    2040
ctggccggca gccccgccat taagaagggc atcctgcaga cagtgaaggt ggtggacgag    2100
ctcgtgaaag tgatgggccg gcacaagccc gagaacatcg tgatcgaaat ggccagagag    2160
aaccagacca cccagaaggg acagaagaac agccgcgaga aatgaagcg gatcgaagag    2220 ggcatcaaag agctgggcag ccagatcctg aaagaacacc ccgtggaaaa cacccagctg    2280
cagaacgaga agctgtacct gtactacctg cagaatgggc gggatatgta cgtggaccag    2340
gaactggaca tcaaccggct gtccgactac gatgtggacg ctatcgtgcc tcagagcttt    2400
ctgaaggacg actccatcga caacaaggtg ctgaccagaa gcgacaagaa ccggggcaag    2460
agcgacaacg tgccctccga agaggtcgtg aagaagatga gaactactg gcggcagctg    2520 ctgaacgcca agctgattac ccagagaaag ttcgacaatc tgaccaaggc cgagagaggc    2580
ggcctgagcg aactggataa ggccggcttc atcaagagac agctggtgga aacccggcag    2640
atcacaaagc acgtggcaca gatcctggac tcccggatga cactaagta cgacgagaat    2700 gacaagctga tccgggaagt gaaagtgatc accctgaagt ccaagctggt gtccgatttc    2760
cggaaggatt tccagtttta caaagtgcgc gagatcaaca actaccacca cgcccacgac    2820
gcctacctga acgccgtcgt gggaaccgcc ctgatcaaaa agtaccctaa gctggaaagc    2880
gagttcgtgt acgcgactaa caaggtgtac gacgtgcgga agatgatcgc caagagcgag    2940
caggaaatcg gcaaggctac cgccaagtac ttcttctaca gcaacatcat gaactttttc    3000
aagaccgaga ttaccctggc caacggcgag atccggaagc ggcctctgat cgagacaaac    3060
ggcgaaaccg gggagatcgt gtgggataag gccgggattt tgccaccgt gcggaaagtg    3120 ctgagcatgc cccaagtgaa tatcgtgaaa aagaccgagg tgcagacagg cggcttcagc    3180
aaagagtcta tcctgcccaa gaggaacagc gataagctga tcgccagaaa gaaggactgg    3240 gacccctaaga agtacggcgg cttcgacagc cccaccgtgg cctattctgt gctggtggtg    3300
gccaaagtgg aaaagggcaa gtccaagaaa ctgaagagtg tgaaagagct gctggggatc    3360
accatcatgg aaagaagcag cttcgagaag aatcccatcg actttctgga agccaagggc    3420
tacaaagaag tgaaaaagga cctgatcatc aagctgccta agtactccct gttcgagctg    3480
gaaaacggcc ggaagagaat gctggcctct gccggcgaac tgcagaaggg aaacgaactg    3540 gccctgcccct ccaaatatgt gaacttcctg tacctggcca gccactatga aagctgaag    3600 ggctcccccg aggataatga gcagaaacag ctgtttgtgg aacagcacaa gcactacctg    3660
gacgagatca tcgagcagat cagcgagttc tccaagagag tgatcctggc cgacgctaat    3720
ctggacaaag tgctgtccgc ctacaacaag caccgggata gcccatcag agagcaggcc    3780 gagaatatca tccaccctgtt taccctgacc aatctgggag ccctgccgc cttcaagtac    3840 tttgacacca ccatcgaccg gaagaggtac accagcacca aagaggtgct ggacgccacc    3900
ctgatccacc agagcatcac cggcctgtac gagacacgga tcgacctgtc tcagctggga    3960
ggcgacagcg ctggaggagg tggaagcgga ggaggaggaa gcggaggagg aggtagcgga    4020
cctaagaaaa agaggaaggt ggcggccgct                                    4050
```

<210> SEQ ID NO 89
<211> LENGTH: 1350
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Gly
                165                 170                 175

Gly Gly Gly Ser Gly Gly Gly Ser Gly Gly Gly Ser Gly Arg
            180                 185                 190

Ala Asp Ala Leu Asp Asp Phe Asp Leu Asp Met Leu Gly Ser Asp Ala
        195                 200                 205

Leu Asp Asp Phe Asp Leu Asp Met Leu Gly Ser Asp Ala Leu Asp Asp
    210                 215                 220

Phe Asp Leu Asp Met Leu Gly Ser Asp Ala Leu Asp Asp Phe Asp Leu
225                 230                 235                 240

Asp Met Leu Ile Asn Gly Gly Gly Ser Gly Gly Gly Ser Gly
                245                 250                 255

Gly Gly Gly Ser Arg Val Asn Thr Glu Ile Thr Lys Ala Pro Leu Ser
            260                 265                 270

Ala Ser Met Ile Lys Arg Tyr Asp Glu His His Gln Asp Leu Thr Leu
        275                 280                 285

Leu Lys Ala Leu Val Arg Gln Gln Leu Pro Glu Lys Tyr Lys Glu Ile
    290                 295                 300

Phe Phe Asp Gln Ser Lys Asn Gly Tyr Ala Gly Tyr Ile Asp Gly Gly
305                 310                 315                 320

Ala Ser Gln Glu Glu Phe Tyr Lys Phe Ile Lys Pro Ile Leu Glu Lys
                325                 330                 335

Met Asp Gly Thr Glu Glu Leu Leu Val Lys Leu Asn Arg Glu Asp Leu
            340                 345                 350
```

-continued

Leu Arg Lys Gln Arg Thr Phe Asp Asn Gly Ser Ile Pro His Gln Ile
        355                 360                 365

His Leu Gly Glu Leu His Ala Ile Leu Arg Arg Gln Glu Asp Phe Tyr
    370                 375                 380

Pro Phe Leu Lys Asp Asn Arg Glu Lys Ile Glu Lys Ile Leu Thr Phe
385                 390                 395                 400

Arg Ile Pro Tyr Tyr Val Gly Pro Leu Ala Arg Gly Asn Ser Arg Phe
                405                 410                 415

Ala Trp Met Thr Arg Lys Ser Glu Glu Thr Ile Thr Pro Trp Asn Phe
            420                 425                 430

Glu Glu Val Val Asp Lys Gly Ala Ser Ala Gln Ser Phe Ile Glu Arg
            435                 440                 445

Met Thr Asn Phe Asp Lys Asn Leu Pro Asn Glu Lys Val Leu Pro Lys
        450                 455                 460

His Ser Leu Leu Tyr Glu Tyr Phe Thr Val Tyr Asn Glu Leu Thr Lys
465                 470                 475                 480

Val Lys Tyr Val Thr Glu Gly Met Arg Lys Pro Ala Phe Leu Ser Gly
                485                 490                 495

Glu Gln Lys Lys Ala Ile Val Asp Leu Leu Phe Lys Thr Asn Arg Lys
            500                 505                 510

Val Thr Val Lys Gln Leu Lys Glu Asp Tyr Phe Lys Lys Ile Glu Cys
        515                 520                 525

Phe Asp Ser Val Glu Ile Ser Gly Val Glu Asp Arg Phe Asn Ala Ser
    530                 535                 540

Leu Gly Thr Tyr His Asp Leu Leu Lys Ile Ile Lys Asp Lys Asp Phe
545                 550                 555                 560

Leu Asp Asn Glu Glu Asn Glu Asp Ile Leu Glu Asp Ile Val Leu Thr
                565                 570                 575

Leu Thr Leu Phe Glu Asp Arg Glu Met Ile Glu Glu Arg Leu Lys Thr
            580                 585                 590

Tyr Ala His Leu Phe Asp Asp Lys Val Met Lys Gln Leu Lys Arg Arg
        595                 600                 605

Arg Tyr Thr Gly Trp Gly Arg Leu Ser Arg Lys Leu Ile Asn Gly Ile
    610                 615                 620

Arg Asp Lys Gln Ser Gly Lys Thr Ile Leu Asp Phe Leu Lys Ser Asp
625                 630                 635                 640

Gly Phe Ala Asn Arg Asn Phe Met Gln Leu Ile His Asp Asp Ser Leu
                645                 650                 655

Thr Phe Lys Glu Asp Ile Gln Lys Ala Gln Val Ser Gly Gln Gly Asp
            660                 665                 670

Ser Leu His Glu His Ile Ala Asn Leu Ala Gly Ser Pro Ala Ile Lys
        675                 680                 685

Lys Gly Ile Leu Gln Thr Val Lys Val Val Asp Glu Leu Val Lys Val
    690                 695                 700

Met Gly Arg His Lys Pro Glu Asn Ile Val Ile Glu Met Ala Arg Glu
705                 710                 715                 720

Asn Gln Thr Thr Gln Lys Gly Gln Lys Asn Ser Arg Glu Arg Met Lys
                725                 730                 735

Arg Ile Glu Glu Gly Ile Lys Glu Leu Gly Ser Gln Ile Leu Lys Glu
            740                 745                 750

His Pro Val Glu Asn Thr Gln Leu Gln Asn Glu Lys Leu Tyr Leu Tyr
        755                 760                 765

Tyr Leu Gln Asn Gly Arg Asp Met Tyr Val Asp Gln Glu Leu Asp Ile

```
             770           775            780
Asn Arg Leu Ser Asp Tyr Asp Val Asp Ala Ile Val Pro Gln Ser Phe
785              790              795                 800

Leu Lys Asp Asp Ser Ile Asp Asn Lys Val Leu Thr Arg Ser Asp Lys
                 805              810                 815

Asn Arg Gly Lys Ser Asp Asn Val Pro Ser Glu Glu Val Val Lys Lys
                 820              825                 830

Met Lys Asn Tyr Trp Arg Gln Leu Leu Asn Ala Lys Leu Ile Thr Gln
                 835              840              845

Arg Lys Phe Asp Asn Leu Thr Lys Ala Glu Arg Gly Gly Leu Ser Glu
850                  855              860

Leu Asp Lys Ala Gly Phe Ile Lys Arg Gln Leu Val Glu Thr Arg Gln
865              870              875                 880

Ile Thr Lys His Val Ala Gln Ile Leu Asp Ser Arg Met Asn Thr Lys
                 885              890                 895

Tyr Asp Glu Asn Asp Lys Leu Ile Arg Glu Val Lys Val Ile Thr Leu
                 900              905              910

Lys Ser Lys Leu Val Ser Asp Phe Arg Lys Asp Phe Gln Phe Tyr Lys
                 915              920              925

Val Arg Glu Ile Asn Asn Tyr His His Ala His Asp Ala Tyr Leu Asn
930              935              940

Ala Val Val Gly Thr Ala Leu Ile Lys Lys Tyr Pro Lys Leu Glu Ser
945              950              955                 960

Glu Phe Val Tyr Gly Asp Tyr Lys Val Tyr Asp Val Arg Lys Met Ile
                 965              970              975

Ala Lys Ser Glu Gln Glu Ile Gly Lys Ala Thr Ala Lys Tyr Phe Phe
                 980              985              990

Tyr Ser Asn Ile Met Asn Phe Phe Lys Thr Glu Ile Thr Leu Ala Asn
                 995              1000             1005

Gly Glu Ile Arg Lys Arg Pro Leu Ile Glu Thr Asn Gly Glu Thr
    1010             1015             1020

Gly Glu Ile Val Trp Asp Lys Gly Arg Asp Phe Ala Thr Val Arg
    1025             1030             1035

Lys Val Leu Ser Met Pro Gln Val Asn Ile Val Lys Lys Thr Glu
    1040             1045             1050

Val Gln Thr Gly Gly Phe Ser Lys Glu Ser Ile Leu Pro Lys Arg
    1055             1060             1065

Asn Ser Asp Lys Leu Ile Ala Arg Lys Lys Asp Trp Asp Pro Lys
    1070             1075             1080

Lys Tyr Gly Gly Phe Asp Ser Pro Thr Val Ala Tyr Ser Val Leu
    1085             1090             1095

Val Val Ala Lys Val Glu Lys Gly Lys Ser Lys Lys Leu Lys Ser
    1100             1105             1110

Val Lys Glu Leu Leu Gly Ile Thr Ile Met Glu Arg Ser Ser Phe
    1115             1120             1125

Glu Lys Asn Pro Ile Asp Phe Leu Glu Ala Lys Gly Tyr Lys Glu
    1130             1135             1140

Val Lys Lys Asp Leu Ile Ile Lys Leu Pro Lys Tyr Ser Leu Phe
    1145             1150             1155

Glu Leu Glu Asn Gly Arg Lys Arg Met Leu Ala Ser Ala Gly Glu
    1160             1165             1170

Leu Gln Lys Gly Asn Glu Leu Ala Leu Pro Ser Lys Tyr Val Asn
    1175             1180             1185
```

```
Phe Leu Tyr Leu Ala Ser His Tyr Glu Lys Leu Lys Gly Ser Pro
        1190                1195                1200
Glu Asp Asn Glu Gln Lys Gln Leu Phe Val Glu Gln His Lys His
    1205                1210                1215
Tyr Leu Asp Glu Ile Ile Glu Gln Ile Ser Glu Phe Ser Lys Arg
    1220                1225                1230
Val Ile Leu Ala Asp Ala Asn Leu Asp Lys Val Leu Ser Ala Tyr
    1235                1240                1245
Asn Lys His Arg Asp Lys Pro Ile Arg Glu Gln Ala Glu Asn Ile
    1250                1255                1260
Ile His Leu Phe Thr Leu Thr Asn Leu Gly Ala Pro Ala Ala Phe
    1265                1270                1275
Lys Tyr Phe Asp Thr Thr Ile Asp Arg Lys Arg Tyr Thr Ser Thr
    1280                1285                1290
Lys Glu Val Leu Asp Ala Thr Leu Ile His Gln Ser Ile Thr Gly
    1295                1300                1305
Leu Tyr Glu Thr Arg Ile Asp Leu Ser Gln Leu Gly Gly Asp Ser
    1310                1315                1320
Ala Gly Gly Gly Gly Ser Gly Gly Gly Ser Gly Gly Gly Gly
    1325                1330                1335
Ser Gly Pro Lys Lys Lys Arg Lys Val Ala Ala Ala
    1340                1345                1350

<210> SEQ ID NO 90
<211> LENGTH: 4347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
atggacaaga agtacagcat cggcctggcc atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca cggaagaa ccggatctgc      240 tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg acagcaccga caaggccgac ctgcggctga tctatctggc cctggcccac     480
atgatcaagt tccggggcca cttcctgatc gagggcgacc tgaacccttc agggcagatc     540
agcaaccagg ccctggctct ggcccctagc tccgctccag tgctggccca gactatggtg     600
ccctctagtg ctatggtgcc tctggcccag ccacctgctc cagcccctgt gctgacccca     660
ggaccacccc agtcactgag cgctccagtg cccaagtcta caggccgg cgagggact      720 ctgagtgaag ctctgctgca cctgcagttc gacgctgatg aggacctggg agctctgctg     780
gggaacagca ccgatcccgg agtgttcaca gatctggcct ccgtggacaa ctctgagttt     840
cagcagctgc tgaatcaggg cgtgtccatg tctcatagta cagccgaacc aatgctgatg     900
gagtaccccg aagccattac ccggctggtg accggcagcc agcggccccc cgaccccgct     960
ccaactcccc tgggaaccag cggcctgcct aatgggctgt ccggagatga agacttctca    1020
```

| | |
|---|---|
| agcatcgctg atatggactt tagtgccctg ctgtcacaga tttcctctag tgggcagaga | 1080 |
| gtgaacaccg atcaccaa ggccccctg acgcctcta tgatcaagag atacgacgag | 1140 |
| caccaccagg acctgaccct gctgaaagct ctcgtgcggc agcagctgcc tgagaagtac | 1200 |
| aaagagattt tcttcgacca gagcaagaac ggctacgccg gctacattga cggcggagcc | 1260 |
| agccaggaag agttctacaa gttcatcaag cccatcctgg aaaagatgga cggcaccgag | 1320 |
| gaactgctcg tgaagctgaa cagagaggac ctgctgcgga agcagcggac cttcgacaac | 1380 |
| ggcagcatcc cccaccagat ccacctggga gagctgcacg ccattctgcg gcggcaggaa | 1440 |
| gattttacc cattcctgaa ggacaaccgg aaaagatcg agaagatcct gaccttccgc | 1500 |
| atcccctact acgtgggccc tctggccagg ggaaacagca gattcgcctg gatgaccaga | 1560 |
| aagagcgagg aaaccatcac ccctggaac ttcgaggaag tggtggacaa gggcgcttcc | 1620 |
| gcccagagct tcatcgagcg atgaccaac ttcgataaga acctgcccaa cgagaaggtg | 1680 |
| ctgcccaagc acagcctgct gtacgagtac ttcaccgtgt ataacgagct gaccaaagtg | 1740 |
| aaatacgtga ccgagggaat gagaaagccc gccttcctga gcggcgagca gaaaaaggcc | 1800 |
| atcgtggacc tgctgttcaa gaccaaccgg aaagtgaccg tgaagcagct gaaagaggac | 1860 |
| tacttcaaga aaatcgagtg cttcgactcc gtggaaatct ccggcgtgga agatcggttc | 1920 |
| aacgcctccc tgggcacata ccacgatctg ctgaaaatta tcaaggacaa ggacttcctg | 1980 |
| gacaatgagg aaaacgagga cattctggaa gatatcgtgc tgaccctgac actgtttgag | 2040 |
| gacagagaga tgatcgagga acggctgaaa acctatgccc acctgttcga cgacaaagtg | 2100 |
| atgaagcagc tgaagcggcg gagatacacc ggctggggca ggctgagccg aaagctgatc | 2160 |
| aacggcatcc gggacaagca gtccggcaag acaatcctgg atttcctgaa gtccgacggc | 2220 |
| ttcgccaaca gaaacttcat gcagctgatc cacgacgaca gcctgacctt taaagaggac | 2280 |
| atccagaaag cccaggtgtc cggccagggc gatagcctgc acgagcacat tgccaatctg | 2340 |
| gccggcagcc ccgccattaa gaagggcatc ctgcagacag tgaaggtggt ggacgagctc | 2400 |
| gtgaaagtga tgggccggca aagcccgag aacatcgtga tcgaaatggc cagagagaac | 2460 |
| cagaccaccc agaagggaca gaagaacagc cgcgagagaa tgaagcggat cgaagagggc | 2520 |
| atcaaagagc tgggcagcca gatcctgaaa gaacaccccg tggaaaacac ccagctgcag | 2580 |
| aacgagaagc tgtacctgta ctacctgcag aatgggcggg atatgtacgt ggaccaggaa | 2640 |
| ctggacatca accggctgtc cgactacgat gtggacgcta tcgtgcctca gagctttctg | 2700 |
| aaggacgact ccatcgacaa caaggtgctg accagaagcg acaagaaccg gggcaagagc | 2760 |
| gacaacgtgc cctccgaaga ggtcgtgaag aagatgaaga actactggcg gcagctgctg | 2820 |
| aacgccaagc tgattcccca gagaaagttc gacaatctga ccaaggccga gagaggcggc | 2880 |
| ctgagcgaac tggataaggc cggcttcatc aagagacagc tggtggaaac cggcagatc | 2940 |
| acaaagcacg tggcacagat cctggactcc cggatgaaca ctaagtacga cgagaatgac | 3000 |
| aagctgatcc gggaagtgaa agtgatcacc ctgaagtcca gctggtgtc cgatttccgg | 3060 |
| aaggatttcc agtttacaa agtgcgcgag atcaacaact accaccacgc ccacgacgcc | 3120 |
| tacctgaacg ccgtcgtggg aaccgccctg atcaaaaagt accctaagct ggaaagcgag | 3180 |
| ttcgtgtacg gcgactacaa ggtgtacgac gtgcggaaga tgatcgccaa gagcgagcag | 3240 |
| gaaatcggca aggctaccgc caagtacttc ttctacagca acatcatgaa cttttttcaag | 3300 |
| accgagatta ccctggccaa cggcgagatc cggaagcggc ctctgatcga gacaaacggc | 3360 |

```
gaaaccgggg agatcgtgtg ggataagggc cgggattttg ccaccgtgcg gaaagtgctg    3420
agcatgcccc aagtgaatat cgtgaaaaag accgaggtgc agacaggcgg cttcagcaaa    3480
gagtctatcc tgcccaagag gaacagcgat aagctgatcg ccagaaagaa ggactgggac    3540
cctaagaagt acggcggctt cgacagcccc accgtggcct attctgtgct ggtggtggcc    3600
aaagtggaaa agggcaagtc caagaaactg aagagtgtga agagctgct ggggatcacc    3660 atcatggaaa gaagcagctt cgagaagaat cccatcgact ttctggaagc caagggctac    3720
aaagaagtga aaaggaccct gatcatcaag ctgcctaagt actccctgtt cgagctggaa    3780
aacggccgga agagaatgct ggcctctgcc ggcgaactgc agaagggaaa cgaactggcc    3840
ctgccctcca aatatgtgaa cttcctgtac ctggccagcc actatgagaa gctgaagggc    3900
tcccccgagg ataatgagca gaaacagctg tttgtggaac agcacaagca ctacctggac    3960
gagatcatcg agcagatcag cgagttctcc aagagagtga tcctggccga cgctaatctg    4020
gacaaagtgc tgtccgccta caacaagcac cgggataagc ccatcagaga gcaggccgag    4080
aatatcatcc acctgtttac cctgaccaat ctgggagccc ctgccgcctt caagtacttt    4140
gacaccacca tcgaccggaa gaggtacacc agcaccaaag aggtgctgga cgccaccctg    4200
atccaccaga gcatcaccgg cctgtacgag acacggatcg acctgtctca gctggggagc    4260
gacagcgctg aggaggtgg aagcggagga ggaggaagcg gaggaggagg tagcggacct    4320
aagaaaaaga ggaaggtggc ggccgct                                         4347
```

<210> SEQ ID NO 91
<211> LENGTH: 1449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

```
Ser Gly Gln Ile Ser Asn Gln Ala Leu Ala Leu Ala Pro Ser Ser Ala
            180                 185                 190

Pro Val Leu Ala Gln Thr Met Val Pro Ser Ser Ala Met Val Pro Leu
        195                 200                 205

Ala Gln Pro Pro Ala Pro Ala Pro Val Leu Thr Pro Gly Pro Pro Gln
    210                 215                 220

Ser Leu Ser Ala Pro Val Pro Lys Ser Thr Gln Ala Gly Glu Gly Thr
225                 230                 235                 240

Leu Ser Glu Ala Leu Leu His Leu Gln Phe Asp Ala Asp Glu Asp Leu
                245                 250                 255

Gly Ala Leu Leu Gly Asn Ser Thr Asp Pro Gly Val Phe Thr Asp Leu
            260                 265                 270

Ala Ser Val Asp Asn Ser Glu Phe Gln Gln Leu Leu Asn Gln Gly Val
        275                 280                 285

Ser Met Ser His Ser Thr Ala Glu Pro Met Leu Met Glu Tyr Pro Glu
    290                 295                 300

Ala Ile Thr Arg Leu Val Thr Gly Ser Gln Arg Pro Pro Asp Pro Ala
305                 310                 315                 320

Pro Thr Pro Leu Gly Thr Ser Gly Leu Pro Asn Gly Leu Ser Gly Asp
                325                 330                 335

Glu Asp Phe Ser Ser Ile Ala Asp Met Asp Phe Ser Ala Leu Leu Ser
            340                 345                 350

Gln Ile Ser Ser Ser Gly Gln Arg Val Asn Thr Glu Ile Thr Lys Ala
        355                 360                 365

Pro Leu Ser Ala Ser Met Ile Lys Arg Tyr Asp Glu His His Gln Asp
    370                 375                 380

Leu Thr Leu Leu Lys Ala Leu Val Arg Gln Gln Leu Pro Glu Lys Tyr
385                 390                 395                 400

Lys Glu Ile Phe Phe Asp Gln Ser Lys Asn Gly Tyr Ala Gly Tyr Ile
                405                 410                 415

Asp Gly Gly Ala Ser Gln Glu Glu Phe Tyr Lys Phe Ile Lys Pro Ile
            420                 425                 430

Leu Glu Lys Met Asp Gly Thr Glu Glu Leu Leu Val Lys Leu Asn Arg
        435                 440                 445

Glu Asp Leu Leu Arg Lys Gln Arg Thr Phe Asp Asn Gly Ser Ile Pro
    450                 455                 460

His Gln Ile His Leu Gly Glu Leu His Ala Ile Leu Arg Arg Gln Glu
465                 470                 475                 480

Asp Phe Tyr Pro Phe Leu Lys Asp Asn Arg Glu Lys Ile Glu Lys Ile
                485                 490                 495

Leu Thr Phe Arg Ile Pro Tyr Tyr Val Gly Pro Leu Ala Arg Gly Asn
            500                 505                 510

Ser Arg Phe Ala Trp Met Thr Arg Lys Ser Glu Glu Thr Ile Thr Pro
        515                 520                 525

Trp Asn Phe Glu Glu Val Val Asp Lys Gly Ala Ser Ala Gln Ser Phe
    530                 535                 540

Ile Glu Arg Met Thr Asn Phe Asp Lys Asn Leu Pro Asn Glu Lys Val
545                 550                 555                 560

Leu Pro Lys His Ser Leu Leu Tyr Glu Tyr Phe Thr Val Tyr Asn Glu
                565                 570                 575

Leu Thr Lys Val Lys Tyr Val Thr Glu Gly Met Arg Lys Pro Ala Phe
            580                 585                 590

Leu Ser Gly Glu Gln Lys Lys Ala Ile Val Asp Leu Leu Phe Lys Thr
```

```
                595                 600                 605
Asn Arg Lys Val Thr Val Lys Gln Leu Lys Glu Asp Tyr Phe Lys Lys
        610                 615                 620
Ile Glu Cys Phe Asp Ser Val Glu Ile Ser Gly Val Glu Asp Arg Phe
625                 630                 635                 640
Asn Ala Ser Leu Gly Thr Tyr His Asp Leu Leu Lys Ile Ile Lys Asp
            645                 650                 655
Lys Asp Phe Leu Asp Asn Glu Glu Asn Glu Asp Ile Leu Glu Asp Ile
            660                 665                 670
Val Leu Thr Leu Thr Leu Phe Glu Asp Arg Glu Met Ile Glu Glu Arg
        675                 680                 685
Leu Lys Thr Tyr Ala His Leu Phe Asp Asp Lys Val Met Lys Gln Leu
        690                 695                 700
Lys Arg Arg Arg Tyr Thr Gly Trp Gly Arg Leu Ser Arg Lys Leu Ile
705                 710                 715                 720
Asn Gly Ile Arg Asp Lys Gln Ser Gly Lys Thr Ile Leu Asp Phe Leu
            725                 730                 735
Lys Ser Asp Gly Phe Ala Asn Arg Asn Phe Met Gln Leu Ile His Asp
            740                 745                 750
Asp Ser Leu Thr Phe Lys Glu Asp Ile Gln Lys Ala Gln Val Ser Gly
        755                 760                 765
Gln Gly Asp Ser Leu His Glu His Ile Ala Asn Leu Ala Gly Ser Pro
    770                 775                 780
Ala Ile Lys Lys Gly Ile Leu Gln Thr Val Lys Val Val Asp Glu Leu
785                 790                 795                 800
Val Lys Val Met Gly Arg His Lys Pro Glu Asn Ile Val Ile Glu Met
                805                 810                 815
Ala Arg Glu Asn Gln Thr Thr Gln Lys Gly Gln Lys Asn Ser Arg Glu
            820                 825                 830
Arg Met Lys Arg Ile Glu Glu Gly Ile Lys Glu Leu Gly Ser Gln Ile
        835                 840                 845
Leu Lys Glu His Pro Val Glu Asn Thr Gln Leu Gln Asn Glu Lys Leu
        850                 855                 860
Tyr Leu Tyr Tyr Leu Gln Asn Gly Arg Asp Met Tyr Val Asp Gln Glu
865                 870                 875                 880
Leu Asp Ile Asn Arg Leu Ser Asp Tyr Asp Val Asp Ala Ile Val Pro
            885                 890                 895
Gln Ser Phe Leu Lys Asp Asp Ser Ile Asp Asn Lys Val Leu Thr Arg
            900                 905                 910
Ser Asp Lys Asn Arg Gly Lys Ser Asp Asn Val Pro Ser Glu Glu Val
        915                 920                 925
Val Lys Lys Met Lys Asn Tyr Trp Arg Gln Leu Leu Asn Ala Lys Leu
    930                 935                 940
Ile Thr Gln Arg Lys Phe Asp Asn Leu Thr Lys Ala Glu Arg Gly Gly
945                 950                 955                 960
Leu Ser Glu Leu Asp Lys Ala Gly Phe Ile Lys Arg Gln Leu Val Glu
            965                 970                 975
Thr Arg Gln Ile Thr Lys His Val Ala Gln Ile Leu Asp Ser Arg Met
            980                 985                 990
Asn Thr Lys Tyr Asp Glu Asn Asp  Lys Leu Ile Arg Glu  Val Lys Val
        995                 1000                1005
Ile Thr  Leu Lys Ser Lys Leu  Val Ser Asp Phe Arg  Lys Asp Phe
    1010                1015                1020
```

-continued

```
Gln Phe Tyr Lys Val Arg Glu Ile Asn Asn Tyr His His Ala His
1025                1030                1035

Asp Ala Tyr Leu Asn Ala Val Val Gly Thr Ala Leu Ile Lys Lys
1040                1045                1050

Tyr Pro Lys Leu Glu Ser Glu Phe Val Tyr Gly Asp Tyr Lys Val
1055                1060                1065

Tyr Asp Val Arg Lys Met Ile Ala Lys Ser Glu Gln Glu Ile Gly
1070                1075                1080

Lys Ala Thr Ala Lys Tyr Phe Phe Tyr Ser Asn Ile Met Asn Phe
1085                1090                1095

Phe Lys Thr Glu Ile Thr Leu Ala Asn Gly Glu Ile Arg Lys Arg
1100                1105                1110

Pro Leu Ile Glu Thr Asn Gly Glu Thr Gly Glu Ile Val Trp Asp
1115                1120                1125

Lys Gly Arg Asp Phe Ala Thr Val Arg Lys Val Leu Ser Met Pro
1130                1135                1140

Gln Val Asn Ile Val Lys Lys Thr Glu Val Gln Thr Gly Gly Phe
1145                1150                1155

Ser Lys Glu Ser Ile Leu Pro Lys Arg Asn Ser Asp Lys Leu Ile
1160                1165                1170

Ala Arg Lys Lys Asp Trp Asp Pro Lys Lys Tyr Gly Gly Phe Asp
1175                1180                1185

Ser Pro Thr Val Ala Tyr Ser Val Leu Val Val Ala Lys Val Glu
1190                1195                1200

Lys Gly Lys Ser Lys Lys Leu Lys Ser Val Lys Glu Leu Leu Gly
1205                1210                1215

Ile Thr Ile Met Glu Arg Ser Ser Phe Glu Lys Asn Pro Ile Asp
1220                1225                1230

Phe Leu Glu Ala Lys Gly Tyr Lys Glu Val Lys Lys Asp Leu Ile
1235                1240                1245

Ile Lys Leu Pro Lys Tyr Ser Leu Phe Glu Leu Glu Asn Gly Arg
1250                1255                1260

Lys Arg Met Leu Ala Ser Ala Gly Glu Leu Gln Lys Gly Asn Glu
1265                1270                1275

Leu Ala Leu Pro Ser Lys Tyr Val Asn Phe Leu Tyr Leu Ala Ser
1280                1285                1290

His Tyr Glu Lys Leu Lys Gly Ser Pro Glu Asp Asn Glu Gln Lys
1295                1300                1305

Gln Leu Phe Val Glu Gln His Lys His Tyr Leu Asp Glu Ile Ile
1310                1315                1320

Glu Gln Ile Ser Glu Phe Ser Lys Arg Val Ile Leu Ala Asp Ala
1325                1330                1335

Asn Leu Asp Lys Val Leu Ser Ala Tyr Asn Lys His Arg Asp Lys
1340                1345                1350

Pro Ile Arg Glu Gln Ala Glu Asn Ile Ile His Leu Phe Thr Leu
1355                1360                1365

Thr Asn Leu Gly Ala Pro Ala Ala Phe Lys Tyr Phe Asp Thr Thr
1370                1375                1380

Ile Asp Arg Lys Arg Tyr Thr Ser Thr Lys Glu Val Leu Asp Ala
1385                1390                1395

Thr Leu Ile His Gln Ser Ile Thr Gly Leu Tyr Glu Thr Arg Ile
1400                1405                1410
```

```
Asp Leu Ser Gln Leu Gly Gly Asp Ser Ala Gly Gly Gly Ser
    1415                1420                1425

Gly Gly Gly Gly Ser Gly Gly Gly Gly Ser Gly Pro Lys Lys Lys
    1430                1435                1440

Arg Lys Val Ala Ala Ala
    1445

<210> SEQ ID NO 92
<211> LENGTH: 4437
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92
atggacaaga agtacagcat cggcctggcc atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca cacggaagaa ccggatctgc     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg acagcaccga caaggccgac ctgcggctga tctatctggc cctggcccac     480
atgatcaagt tccggggcca cttcctgatc gagggcgacc tgaacggcgg gggaggctcc     540
ggtggtgggg gcagcggagg gggggcagc ccttcaggc agatcagcaa ccaggccctg     600
gctctggccc ctagctccgc tccagtgctg gcccagacta tggtgccctc tagtgctatg     660
gtgcctctgg cccagccacc tgctccagcc ctgtgctga ccccaggacc acccagtca     720 ctgagcgctc cagtgcccaa gtctacacag gccggcgagg ggactctgag tgaagctctg     780
ctgcacctgc agttcgacgc tgatgaggac ctgggagctc tgctggggaa cagcaccgat     840
cccggagtgt tcacagatct ggcctccgtg gacaactctg agtttcagca gctgctgaat     900
cagggcgtgt ccatgtctca gtacagcgga accaatgc tgatggagta ccccgaagcc     960
attacccggc tggtgaccgg cagccagcgg cccccgacc ccgctccaac tcccctggga    1020
accagcggcc tgcctaatgg gctgtccgga gatgaagact ctcaagcat cgctgatatg    1080 gactttagtg ccctgctgtc acagatttcc tctagtgggc agggcggggg aggctccggt    1140
ggtgggggca gcggaggggg gggcagcaga gtgaacaccg agatcaccaa ggccccctg    1200 agcgcctcta tgatcaagag atacgacgag caccaccagg acctgaccct gctgaaagct    1260
ctcgtgcggc agcagctgcc tgagaagtac aaagagattt tcttcgacca gagcaagaac    1320
ggctacgccg gctacattga cggcggagcc agcaggaag agttctacaa gttcatcaag    1380
cccatcctgg aaaagatgga cggcaccgag gaactgctcg tgaagctgaa cagagaggac    1440
ctgctgcgga agcagcggac cttcgacaac ggcagcatcc cccaccagat ccacctggga    1500
gagctgcacg ccattctgcg gcggcaggaa gatttttacc cattcctgaa ggacaaccgg    1560
gaaaagatcg agaagatcct gaccttccgc atccctact acgtgggccc tctggccagg    1620
ggaaacagca gattcgcctg gatgaccaga aagagcgagg aaaccatcac cccctggaac    1680
ttcgaggaag tggtggacaa gggcgcttcc gcccagagct tcatcgagcg gatgaccaac    1740
```

-continued

| | |
|---|---|
| ttcgataaga acctgcccaa cgagaaggtg ctgcccaagc acagcctgct gtacgagtac | 1800 |
| ttcaccgtgt ataacgagct gaccaaagtg aaatacgtga ccgagggaat gagaaagccc | 1860 |
| gccttcctga gcggcgagca gaaaaaggcc atcgtggacc tgctgttcaa gaccaaccgg | 1920 |
| aaagtgaccg tgaagcagct gaaagaggac tacttcaaga aaatcgagtg cttcgactcc | 1980 |
| gtggaaatct ccggcgtgga agatcggttc aacgcctccc tgggcacata ccacgatctg | 2040 |
| ctgaaaatta tcaaggacaa ggacttcctg gacaatgagg aaaacgagga cattctggaa | 2100 |
| gatatcgtgc tgaccctgac actgtttgag gacagagaga tgatcgagga acggctgaaa | 2160 |
| acctatgccc acctgttcga cgacaaagtg atgaagcagc tgaagcggcg agatacacc | 2220 |
| ggctggggca ggctgagccg gaagctgatc aacggcatcc gggacaagca gtccggcaag | 2280 |
| acaatcctgg atttcctgaa gtccgacggc ttcgccaaca gaaacttcat gcagctgatc | 2340 |
| cacgacgaca gcctgacctt taaagaggac atccagaaag cccaggtgtc cggccagggc | 2400 |
| gatagcctgc acgagcacat tgccaatctg gccggcagcc ccgccattaa gaagggcatc | 2460 |
| ctgcagacag tgaaggtggt ggacgagctc gtgaaagtga tgggccggca caagcccgag | 2520 |
| aacatcgtga tcgaaatggc cagagagaac cagaccaccc agaagggaca gaagaacagc | 2580 |
| cgcgagagaa tgaagcggat cgaagagggc atcaaagagc tgggcagcca gatcctgaaa | 2640 |
| gaacaccccg tggaaaacac ccagctgcag aacgagaagc tgtacctgta ctacctgcag | 2700 |
| aatgggcggg atatgtacgt ggaccaggaa ctggacatca accggctgtc cgactacgat | 2760 |
| gtggacgcta tcgtgcctca gagctttctg aaggacgact ccatcgacaa caaggtgctg | 2820 |
| accagaagcg acaagaaccg gggcaagagc gacaacgtgc cctccgaaga ggtcgtgaag | 2880 |
| aagatgaaga actactggcg gcagctgctg aacgccaagc tgattaccca gagaaagttc | 2940 |
| gacaatctga ccaaggccga gagaggcggc ctgagcgaac tggataaggc cggcttcatc | 3000 |
| aagagacagc tggtggaaac ccggcagatc acaaagcacg tggcacagat cctggactcc | 3060 |
| cggatgaaca ctaagtacga cgagaatgac aagctgatcc gggaagtgaa agtgatcacc | 3120 |
| ctgaagtcca gctggtgtc cgatttccgg aaggatttcc agttttacaa agtgcgcgag | 3180 |
| atcaacaact accaccacgc ccacgacgcc tacctgaacg ccgtcgtggg aaccgccctg | 3240 |
| atcaaaaagt accctaagct ggaaagcgag ttcgtgtacg gcgactacaa ggtgtacgac | 3300 |
| gtgcggaaga tgatcgccaa gagcgagcag gaaatcggca aggctaccgc caagtacttc | 3360 |
| ttctacagca acatcatgaa cttttttcaag accgagatta ccctggccaa cggcgagatc | 3420 |
| cggaagcggc ctctgatcga gacaaacggc gaaaccgggg agatcgtgtg gataagggc | 3480 |
| cgggattttg ccaccgtgcg gaaagtgctg agcatgcccc aagtgaatat cgtgaaaaag | 3540 |
| accgaggtgc agacaggcgg cttcagcaaa gagtctatcc tgcccaagag aaacagcgat | 3600 |
| aagctgatcg ccagaaagaa ggactgggac cctaagaagt acggcggctt cgacagcccc | 3660 |
| accgtggcct attctgtgct ggtggtggcc aaagtggaaa agggcaagtc caagaaactg | 3720 |
| aagagtgtga aagagctgct ggggatcacc atcatgaaaa gaagcagctt cgagaagaat | 3780 |
| cccatcgact ttctggaagc caagggctac aaagaagtga aaaggacct gatcatcaag | 3840 |
| ctgcctaagt actccctgtt cgagctgaaa acggccgga agagaatgct ggcctctgcc | 3900 |
| ggcgaactgc agaagggaaa cgaactggcc ctgcctcca aatatgtgaa cttcctgtac | 3960 |
| ctggccagcc actatgagaa gctgaagggc tcccccgagg ataatgagca gaaacagctg | 4020 |
| tttgtggaac agcacaagca ctacctggac gagatcatcg agcagatcag cgagttctcc | 4080 |
| aagagagtga tcctggccga cgctaatctg gacaaagtgc tgtccgccta caacaagcac | 4140 |

```
cgggataagc ccatcagaga gcaggccgag aatatcatcc acctgtttac cctgaccaat    4200
ctgggagccc ctgccgcctt caagtacttt gacaccacca tcgaccggaa gaggtacacc    4260
agcaccaaag aggtgctgga cgccaccctg atccaccaga gcatcaccgg cctgtacgag    4320
acacggatcg acctgtctca gctgggaggc gacagcgctg aggaggtgg  aagcggagga    4380 ggaggaagcg gaggaggagg tagcggacct aagaaaaaga ggaaggtggc ggccgct       4437
```

<210> SEQ ID NO 93
<211> LENGTH: 1479
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 93

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Gly
                165                 170                 175

Gly Gly Gly Ser Gly Gly Gly Ser Gly Gly Gly Ser Pro Ser
            180                 185                 190

Gly Gln Ile Ser Asn Gln Ala Leu Ala Leu Ala Pro Ser Ser Ala Pro
        195                 200                 205

Val Leu Ala Gln Thr Met Val Pro Ser Ser Ala Met Val Pro Leu Ala
    210                 215                 220

Gln Pro Pro Ala Pro Ala Pro Val Leu Thr Pro Gly Pro Pro Gln Ser
225                 230                 235                 240

Leu Ser Ala Pro Val Pro Lys Ser Thr Gln Ala Gly Glu Gly Thr Leu
                245                 250                 255

Ser Glu Ala Leu Leu His Leu Gln Phe Asp Ala Asp Glu Asp Leu Gly
            260                 265                 270

Ala Leu Leu Gly Asn Ser Thr Asp Pro Gly Val Phe Thr Asp Leu Ala
        275                 280                 285

Ser Val Asp Asn Ser Glu Phe Gln Gln Leu Leu Asn Gln Gly Val Ser
    290                 295                 300
```

```
Met Ser His Ser Thr Ala Glu Pro Met Leu Met Glu Tyr Pro Glu Ala
305                 310                 315                 320

Ile Thr Arg Leu Val Thr Gly Ser Gln Arg Pro Pro Asp Pro Ala Pro
                325                 330                 335

Thr Pro Leu Gly Thr Ser Gly Leu Pro Asn Gly Leu Ser Gly Asp Glu
            340                 345                 350

Asp Phe Ser Ser Ile Ala Asp Met Asp Phe Ser Ala Leu Leu Ser Gln
                355                 360                 365

Ile Ser Ser Ser Gly Gln Gly Gly Gly Ser Gly Gly Gly Gly Gly Ser
        370                 375                 380

Gly Gly Gly Gly Ser Arg Val Asn Thr Glu Ile Thr Lys Ala Pro Leu
385                 390                 395                 400

Ser Ala Ser Met Ile Lys Arg Tyr Asp Glu His His Gln Asp Leu Thr
                405                 410                 415

Leu Leu Lys Ala Leu Val Arg Gln Gln Leu Pro Glu Lys Tyr Lys Glu
            420                 425                 430

Ile Phe Phe Asp Gln Ser Lys Asn Gly Tyr Ala Gly Tyr Ile Asp Gly
                435                 440                 445

Gly Ala Ser Gln Glu Glu Phe Tyr Lys Phe Ile Lys Pro Ile Leu Glu
        450                 455                 460

Lys Met Asp Gly Thr Glu Glu Leu Leu Val Lys Leu Asn Arg Glu Asp
465                 470                 475                 480

Leu Leu Arg Lys Gln Arg Thr Phe Asp Asn Gly Ser Ile Pro His Gln
                485                 490                 495

Ile His Leu Gly Glu Leu His Ala Ile Leu Arg Arg Gln Glu Asp Phe
            500                 505                 510

Tyr Pro Phe Leu Lys Asp Asn Arg Glu Lys Ile Glu Lys Ile Leu Thr
                515                 520                 525

Phe Arg Ile Pro Tyr Tyr Val Gly Pro Leu Ala Arg Gly Asn Ser Arg
530                 535                 540

Phe Ala Trp Met Thr Arg Lys Ser Glu Glu Thr Ile Thr Pro Trp Asn
545                 550                 555                 560

Phe Glu Glu Val Val Asp Lys Gly Ala Ser Ala Gln Ser Phe Ile Glu
                565                 570                 575

Arg Met Thr Asn Phe Asp Lys Asn Leu Pro Asn Glu Lys Val Leu Pro
                580                 585                 590

Lys His Ser Leu Leu Tyr Glu Tyr Phe Thr Val Tyr Asn Glu Leu Thr
            595                 600                 605

Lys Val Lys Tyr Val Thr Glu Gly Met Arg Lys Pro Ala Phe Leu Ser
            610                 615                 620

Gly Glu Gln Lys Lys Ala Ile Val Asp Leu Leu Phe Lys Thr Asn Arg
625                 630                 635                 640

Lys Val Thr Val Lys Gln Leu Lys Glu Asp Tyr Phe Lys Lys Ile Glu
                645                 650                 655

Cys Phe Asp Ser Val Glu Ile Ser Gly Val Glu Asp Arg Phe Asn Ala
                660                 665                 670

Ser Leu Gly Thr Tyr His Asp Leu Leu Lys Ile Ile Lys Asp Lys Asp
            675                 680                 685

Phe Leu Asp Asn Glu Glu Asn Glu Asp Ile Leu Glu Asp Ile Val Leu
            690                 695                 700

Thr Leu Thr Leu Phe Glu Asp Arg Glu Met Ile Glu Glu Arg Leu Lys
705                 710                 715                 720
```

-continued

Thr Tyr Ala His Leu Phe Asp Asp Lys Val Met Lys Gln Leu Lys Arg
            725                 730                 735

Arg Arg Tyr Thr Gly Trp Gly Arg Leu Ser Arg Lys Leu Ile Asn Gly
            740                 745                 750

Ile Arg Asp Lys Gln Ser Gly Lys Thr Ile Leu Asp Phe Leu Lys Ser
            755                 760                 765

Asp Gly Phe Ala Asn Arg Asn Phe Met Gln Leu Ile His Asp Asp Ser
            770                 775                 780

Leu Thr Phe Lys Glu Asp Ile Gln Lys Ala Gln Val Ser Gly Gln Gly
785                 790                 795                 800

Asp Ser Leu His Glu His Ile Ala Asn Leu Ala Gly Ser Pro Ala Ile
            805                 810                 815

Lys Lys Gly Ile Leu Gln Thr Val Lys Val Val Asp Glu Leu Val Lys
            820                 825                 830

Val Met Gly Arg His Lys Pro Glu Asn Ile Val Ile Glu Met Ala Arg
            835                 840                 845

Glu Asn Gln Thr Thr Gln Lys Gly Gln Lys Asn Ser Arg Glu Arg Met
            850                 855                 860

Lys Arg Ile Glu Glu Gly Ile Lys Glu Leu Gly Ser Gln Ile Leu Lys
865                 870                 875                 880

Glu His Pro Val Glu Asn Thr Gln Leu Gln Asn Glu Lys Leu Tyr Leu
            885                 890                 895

Tyr Tyr Leu Gln Asn Gly Arg Asp Met Tyr Val Asp Gln Glu Leu Asp
            900                 905                 910

Ile Asn Arg Leu Ser Asp Tyr Asp Val Asp Ala Ile Val Pro Gln Ser
            915                 920                 925

Phe Leu Lys Asp Asp Ser Ile Asp Asn Lys Val Leu Thr Arg Ser Asp
            930                 935                 940

Lys Asn Arg Gly Lys Ser Asp Asn Val Pro Ser Glu Glu Val Val Lys
945                 950                 955                 960

Lys Met Lys Asn Tyr Trp Arg Gln Leu Leu Asn Ala Lys Leu Ile Thr
            965                 970                 975

Gln Arg Lys Phe Asp Asn Leu Thr Lys Ala Glu Arg Gly Gly Leu Ser
            980                 985                 990

Glu Leu Asp Lys Ala Gly Phe Ile Lys Arg Gln Leu Val Glu Thr Arg
            995                 1000                1005

Gln Ile Thr Lys His Val Ala Gln Ile Leu Asp Ser Arg Met Asn
            1010                1015                1020

Thr Lys Tyr Asp Glu Asn Asp Lys Leu Ile Arg Glu Val Lys Val
            1025                1030                1035

Ile Thr Leu Lys Ser Lys Leu Val Ser Asp Phe Arg Lys Asp Phe
            1040                1045                1050

Gln Phe Tyr Lys Val Arg Glu Ile Asn Asn Tyr His His Ala His
            1055                1060                1065

Asp Ala Tyr Leu Asn Ala Val Val Gly Thr Ala Leu Ile Lys Lys
            1070                1075                1080

Tyr Pro Lys Leu Glu Ser Glu Phe Val Tyr Gly Asp Tyr Lys Val
            1085                1090                1095

Tyr Asp Val Arg Lys Met Ile Ala Lys Ser Glu Gln Glu Ile Gly
            1100                1105                1110

Lys Ala Thr Ala Lys Tyr Phe Phe Tyr Ser Asn Ile Met Asn Phe
            1115                1120                1125

Phe Lys Thr Glu Ile Thr Leu Ala Asn Gly Glu Ile Arg Lys Arg 1130                1135                1140

Pro Leu Ile Glu Thr Asn Gly Glu Thr Gly Ile Val Trp Asp
    1145                1150                1155

Lys Gly Arg Asp Phe Ala Thr Val Arg Lys Val Leu Ser Met Pro
    1160                1165                1170

Gln Val Asn Ile Val Lys Lys Thr Glu Val Gln Thr Gly Gly Phe
    1175                1180                1185

Ser Lys Glu Ser Ile Leu Pro Lys Arg Asn Ser Asp Lys Leu Ile
    1190                1195                1200

Ala Arg Lys Lys Asp Trp Asp Pro Lys Lys Tyr Gly Gly Phe Asp
    1205                1210                1215

Ser Pro Thr Val Ala Tyr Ser Val Leu Val Val Ala Lys Val Glu
    1220                1225                1230

Lys Gly Lys Ser Lys Lys Leu Lys Ser Val Lys Glu Leu Leu Gly
    1235                1240                1245

Ile Thr Ile Met Glu Arg Ser Ser Phe Glu Lys Asn Pro Ile Asp
    1250                1255                1260

Phe Leu Glu Ala Lys Gly Tyr Lys Glu Val Lys Lys Asp Leu Ile
    1265                1270                1275

Ile Lys Leu Pro Lys Tyr Ser Leu Phe Glu Leu Glu Asn Gly Arg
    1280                1285                1290

Lys Arg Met Leu Ala Ser Ala Gly Glu Leu Gln Lys Gly Asn Glu
    1295                1300                1305

Leu Ala Leu Pro Ser Lys Tyr Val Asn Phe Leu Tyr Leu Ala Ser
    1310                1315                1320

His Tyr Glu Lys Leu Lys Gly Ser Pro Glu Asp Asn Glu Gln Lys
    1325                1330                1335

Gln Leu Phe Val Glu Gln His Lys His Tyr Leu Asp Glu Ile Ile
    1340                1345                1350

Glu Gln Ile Ser Glu Phe Ser Lys Arg Val Ile Leu Ala Asp Ala
    1355                1360                1365

Asn Leu Asp Lys Val Leu Ser Ala Tyr Asn Lys His Arg Asp Lys
    1370                1375                1380

Pro Ile Arg Glu Gln Ala Glu Asn Ile Ile His Leu Phe Thr Leu
    1385                1390                1395

Thr Asn Leu Gly Ala Pro Ala Ala Phe Lys Tyr Phe Asp Thr Thr
    1400                1405                1410

Ile Asp Arg Lys Arg Tyr Thr Ser Thr Lys Glu Val Leu Asp Ala
    1415                1420                1425

Thr Leu Ile His Gln Ser Ile Thr Gly Leu Tyr Glu Thr Arg Ile
    1430                1435                1440

Asp Leu Ser Gln Leu Gly Gly Asp Ser Ala Gly Gly Gly Gly Ser
    1445                1450                1455

Gly Gly Gly Gly Ser Gly Gly Gly Ser Gly Pro Lys Lys Lys
    1460                1465                1470

Arg Lys Val Ala Ala Ala
    1475

<210> SEQ ID NO 94
<211> LENGTH: 4068
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 94

```
atggacaaga agtacagcat cggcctggcc atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca cacggaagaa ccggatctgc     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg acagcaccga caaggccgac ctgcggctga tctatctggc cctggcccac     480
atgatcaagt tccggggcca cttcctgatc gagggcgacc tgaaccccga caacagcgac     540
gtggacaagc tgttcatcca gctggtgcag acctacaacc agctgttcga ggaaaacccc     600
atcaacgcca gcggcgtgga cgccaaggcc atcctgtctg ccagactgag caagagcaga     660
cggctggaaa atctgatcgc ccagctgccc ggcgagaaga gaatggcct gttcggcaac      720
ctgattgccc tgagcctggg cctgaccccc aacttcaaga gcaacttcga cctggccgag     780
gatgccaaac tgcagctgag caaggacacc tacgacgacg acctggacaa cctgctggcc     840
cagatcggcg accagtacgc cgacctgttt ctggccgcca gaaacctgtc cgacgccatc     900
ctgctgagcg acatcctgag agtgaacacc gagatcacca aggccccccct gagcgcctct    960
atgatcaaga gatacgacga gcaccaccag gacctgaccc tgctgaaagc tctcgtgcgg    1020
cagcagctgc ctgagaagta caaagagatt ttcttcgacc agagcaagaa cggctacgcc    1080
ggctacattg acggcggagc cagccaggaa gagttctaca agttcatcaa gcccatcctg    1140
gaaaagatgg acggcaccga ggaactgctc gtgaagctga acagagagga cctgctgcgg    1200
aagcagcgga ccttcgacaa cggcagcatc ccccaccaga tccacctggg agagctgcac    1260
gccattctgc ggcggcagga agattttta ccattcctga aggacaaccg ggaaaagatc      1320
gagaagatcc tgacttcgg catccctac tacgtgggcc ctctggccag ggaaacagc        1380
agattcgcct ggatgaccag aaagagcgag gaaaccatca ccccctggaa cttcgaggaa    1440
gtggtggaca gggcgcttc cgcccagagc ttcatcgagc ggatgaccaa cttcgataag      1500
aacctgccca cgagaaggt gctgcccaag cacagcctgc tgtacgagta cttcaccgtg      1560
tataacgagc tgaccaaagt gaaatacgtg accgagggaa tgagaaagcc cgccttcctg    1620
agcggcgagc agaaaaaggc catcgtggac ctgctgttca agaccaaccg gaaagtgacc    1680
gtgaagcagc tgaaagagga ctacttcaag aaaatcgagt gcttcgactc cgtggaaatc    1740
tccggcgtgg aagatcggtt caacgcctcc ctgggcacat accacgatct gctgaaaatt    1800
atcaaggaca aggacttcct ggacaatgag gaaaacgagg acattctgga agatatcgtg    1860
ctgaccctga cactgtttga ggacagagag atgatcgagg aacggctgaa aacctatgcc    1920
cacctgttcg acgacaaagt gatgaagcag ctgaagcggc ggagatacac cggctggggc    1980
aggctgagcc ggaagctgat caacggcatc cgggacaagc agtccggcaa gacaatcctg    2040
gatttcctga agtccgacgg cttcgccaac agaaacttca tgcagctgat ccacgacgac    2100
agcctgacct ttaaagagga catccagaaa gcccaggtgt ccggccaggg cgatagcctg    2160
cacgagcaca ttgccaatct ggccggcagc cccgccatta gaagggcat cctgcagaca     2220
gtgaaggtgg tggacgagct cgtgaaagtg atgggccggc acaagcccga aacatcgtg     2280
```

-continued

```
atcgaaatgg ccagagagaa ccagaccacc cagaagggac agaagggcgg gggaggctcc   2340
ggtggtgggg gcagcggagg gggggcagc ggacgggctg acgcattgga cgattttgat    2400
ctggatatgc tgggaagtga cgccctcgat gattttgacc ttgacatgct tggttcggat   2460
gcccttgatg actttgacct cgacatgctc ggcagtgacg cccttgatga tttcgacctg   2520
gacatgctga ttaacggcgg gggaggctcc ggtggtgggg gcagcggagg gggggcagc    2580 accaaggccg agagaggcgg cctgagcgaa ctggataagg ccggcttcat caagagacag   2640
ctggtggaaa cccggcagat cacaaagcac gtggcacaga tcctggactc ccggatgaac   2700
actaagtacg acgagaatga caagctgatc cgggaagtga agtgatcac cctgaagtcc    2760 aagctggtgt ccgatttccg gaaggatttc cagttttaca agtgcgcgga tcaacaac    2820 taccaccacg cccacgacgc ctacctgaac gccgtcgtgg aaccgccct gatcaaaaag   2880 taccctaagc tggaaagcga gttcgtgtac ggcgactaca aggtgtacga cgtgcggaag   2940
atgatcgcca agagcgagca ggaaatcggc aaggctaccg ccaagtactt cttctacagc   3000
aacatcatga acttttttcaa gaccgagatt accctggcca acgcgagat ccggaagcgg   3060 cctctgatcg agacaaacgg cgaaaccggg gagatcgtgt gggataaggg ccgggatttt   3120
gccaccgtgc ggaaagtgct gagcatgccc caagtgaata tcgtgaaaaa gaccgaggtg   3180
cagacaggcg gcttcagcaa agagtctatc ctgcccaaga ggaacagcga taagctgatc   3240
gccagaaaga aggactggga ccctaagaag tacgcggct tcgacagccc caccgtggcc    3300
tattctgtgc tggtggtggc caaagtgaaa aagggcaagt ccaagaaact gaagagtgtg   3360
aaagagctgc tggggatcac catcatggaa agaagcagct tcgagaagaa tcccatcgac   3420
tttctggaag ccaagggcta caaagaagtg aaaaaggacc tgatcatcaa gctgcctaag   3480
tactccctgt tcgagctgga aaacggccgg aagagaatgc tggcctctgc cggcgaactg   3540
cagaagggaa acgaactggc cctgccctcc aaatatgtga acttcctgta cctggccagc   3600
cactatgaga agctgaaggg ctcccccgag gataatgagc agaaacagct gtttgtggaa   3660
cagcacaagc actacctgga cgagatcatc gagcagatca gcgagttctc caagagagtg   3720
atcctggccg acgctaatct ggacaaagtg ctgtccgcct acaacaagca ccgggataag   3780
cccatcagag agcaggccga gaatatcatc cacctgttta ccctgaccaa tctgggagcc   3840
cctgccgcct tcaagtactt tgacaccacc atcgaccgga gaggtacac cagcaccaaa   3900 gaggtgctgg acgccaccct gatccaccag agcatcaccg gcctgtacga gacacggatc   3960
gacctgtctc agctggggag cgacagcgct ggaggaggtg gaagcggagg aggaggaagc   4020
ggaggaggag gtagcggacc taagaaaaag aggaaggtgg cggccgct             4068
```

<210> SEQ ID NO 95
<211> LENGTH: 1356
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 95

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

```
Lys Val Leu Gly Asn Thr Asp Arg His Ser Ile Lys Lys Asn Leu Ile
             35                  40                  45

Gly Ala Leu Leu Phe Asp Ser Gly Glu Thr Ala Glu Ala Thr Arg Leu
     50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
```

-continued

```
            450                 455                 460
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Gly Gly Gly Ser Gly Gly Gly Gly
        770                 775                 780

Ser Gly Gly Gly Gly Ser Gly Arg Ala Asp Ala Leu Asp Asp Phe Asp
785                 790                 795                 800

Leu Asp Met Leu Gly Ser Asp Ala Leu Asp Asp Phe Asp Leu Asp Met
                805                 810                 815

Leu Gly Ser Asp Ala Leu Asp Asp Phe Asp Leu Asp Met Leu Gly Ser
            820                 825                 830

Asp Ala Leu Asp Asp Phe Asp Leu Asp Met Leu Ile Asn Gly Gly Gly
        835                 840                 845

Gly Ser Gly Gly Gly Gly Ser Gly Gly Gly Gly Ser Thr Lys Ala Glu
850                 855                 860

Arg Gly Gly Leu Ser Glu Leu Asp Lys Ala Gly Phe Ile Lys Arg Gln
865                 870                 875                 880
```

```
Leu Val Glu Thr Arg Gln Ile Thr Lys His Val Ala Gln Ile Leu Asp
            885                 890                 895

Ser Arg Met Asn Thr Lys Tyr Asp Glu Asn Asp Lys Leu Ile Arg Glu
            900                 905                 910

Val Lys Val Ile Thr Leu Lys Ser Lys Leu Val Ser Asp Phe Arg Lys
            915                 920                 925

Asp Phe Gln Phe Tyr Lys Val Arg Glu Ile Asn Asn Tyr His His Ala
        930                 935                 940

His Asp Ala Tyr Leu Asn Ala Val Val Gly Thr Ala Leu Ile Lys Lys
945                 950                 955                 960

Tyr Pro Lys Leu Glu Ser Glu Phe Val Tyr Gly Asp Tyr Lys Val Tyr
                965                 970                 975

Asp Val Arg Lys Met Ile Ala Lys Ser Glu Gln Glu Ile Gly Lys Ala
            980                 985                 990

Thr Ala Lys Tyr Phe Phe Tyr Ser Asn Ile Met Asn Phe Phe Lys Thr
            995                 1000                1005

Glu Ile Thr Leu Ala Asn Gly Glu Ile Arg Lys Arg Pro Leu Ile
        1010                1015                1020

Glu Thr Asn Gly Glu Thr Gly Glu Ile Val Trp Asp Lys Gly Arg
    1025                1030                1035

Asp Phe Ala Thr Val Arg Lys Val Leu Ser Met Pro Gln Val Asn
    1040                1045                1050

Ile Val Lys Lys Thr Glu Val Gln Thr Gly Gly Phe Ser Lys Glu
    1055                1060                1065

Ser Ile Leu Pro Lys Arg Asn Ser Asp Lys Leu Ile Ala Arg Lys
    1070                1075                1080

Lys Asp Trp Asp Pro Lys Lys Tyr Gly Gly Phe Asp Ser Pro Thr
    1085                1090                1095

Val Ala Tyr Ser Val Leu Val Val Ala Lys Val Glu Lys Gly Lys
    1100                1105                1110

Ser Lys Lys Leu Lys Ser Val Lys Glu Leu Leu Gly Ile Thr Ile
    1115                1120                1125

Met Glu Arg Ser Ser Phe Glu Lys Asn Pro Ile Asp Phe Leu Glu
    1130                1135                1140

Ala Lys Gly Tyr Lys Glu Val Lys Lys Asp Leu Ile Ile Lys Leu
    1145                1150                1155

Pro Lys Tyr Ser Leu Phe Glu Leu Glu Asn Gly Arg Lys Arg Met
    1160                1165                1170

Leu Ala Ser Ala Gly Glu Leu Gln Lys Gly Asn Glu Leu Ala Leu
    1175                1180                1185

Pro Ser Lys Tyr Val Asn Phe Leu Tyr Leu Ala Ser His Tyr Glu
    1190                1195                1200

Lys Leu Lys Gly Ser Pro Glu Asp Asn Glu Gln Lys Gln Leu Phe
    1205                1210                1215

Val Glu Gln His Lys His Tyr Leu Asp Glu Ile Ile Glu Gln Ile
    1220                1225                1230

Ser Glu Phe Ser Lys Arg Val Ile Leu Ala Asp Ala Asn Leu Asp
    1235                1240                1245

Lys Val Leu Ser Ala Tyr Asn Lys His Arg Asp Lys Pro Ile Arg
    1250                1255                1260

Glu Gln Ala Glu Asn Ile Ile His Leu Phe Thr Leu Thr Asn Leu
    1265                1270                1275
```

| Gly | Ala | Pro | Ala | Ala | Phe | Lys | Tyr | Phe | Asp | Thr | Thr | Ile | Asp | Arg |
|---|---|---|---|---|---|---|---|---|---|---|---|---|---|---|
| | 1280 | | | | | 1285 | | | | | 1290 | | | |

| Lys | Arg | Tyr | Thr | Ser | Thr | Lys | Glu | Val | Leu | Asp | Ala | Thr | Leu | Ile |
|---|---|---|---|---|---|---|---|---|---|---|---|---|---|---|
| 1295 | | | | | 1300 | | | | | 1305 | | | | |

| His | Gln | Ser | Ile | Thr | Gly | Leu | Tyr | Glu | Thr | Arg | Ile | Asp | Leu | Ser |
|---|---|---|---|---|---|---|---|---|---|---|---|---|---|---|
| 1310 | | | | | 1315 | | | | | 1320 | | | | |

| Gln | Leu | Gly | Gly | Asp | Ser | Ala | Gly | Gly | Gly | Ser | Gly | Gly | Gly |
|---|---|---|---|---|---|---|---|---|---|---|---|---|---|
| 1325 | | | | | 1330 | | | | | 1335 | | | |

| Gly | Ser | Gly | Gly | Gly | Gly | Ser | Gly | Pro | Lys | Lys | Lys | Arg | Lys | Val |
|---|---|---|---|---|---|---|---|---|---|---|---|---|---|---|
| 1340 | | | | | 1345 | | | | | 1350 | | | | |

| Ala | Ala | Ala |
|---|---|---|
| 1355 | | |

<210> SEQ ID NO 96
<211> LENGTH: 4163
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96

```
aagaagtaca gcatcggcct ggccatcggc accaactctg tgggctgggc cgtgatcacc      60
gacgagtaca aggtgcccag caagaaattc aaggtgctgg gcaacaccga ccggcacagc     120
atcaagaaga acctgatcgg agccctgctg ttcgacagcg gcgaaacagc cgaggccacc     180
cggctgaaga gaaccgccag aagaagatac accagacgga gaaccggat ctgctatctg      240
caagagatct tcagcaacga gatggccaag gtggacgaca gcttcttcca cagactggaa     300
gagtccttcc tggtggaaga ggataagaag acgagcggc accccatctt cggcaacatc      360
gtggacgagg tggcctacca cgagaagtac cccaccatct accacctgag aaagaaactg     420
gtggacagca ccgacaaggc cgacctgcgg ctgatctatc tggccctggc ccacatgatc     480
aagttccggg gccacttcct gatcgagggc gacctgaacc ccgacaacag cgacgtggac     540
aagctgttca tccagctggt gcagacctac aaccagctgt tcgaggaaaa ccccatcaac     600
gccagcggcg tggacgccaa ggccatcctg tctgccagac tgagcaagag cagacggctg     660
gaaaatctga tcgcccagct gcccggcgag aagaagaatg gcctgttcgg caacctgatt     720
gccctgagcc tgggcctgac ccccaacttc aagagcaact tcgacctggc cgaggatgcc     780
aaactgcagc tgagcaagga cacctacgac gacgacctgg acaacctgct ggcccagatc     840
ggcgaccagt acgccgacct gtttctggcc gccaagaacc tgtccgacgc catcctgctg     900
agcgacatcc tgagagtgaa caccgagatc accaaggccc ccctgagcgc ctctatgatc     960
aagagatacg acgagcacca ccaggacctg accctgctga aagctctcgt gcggcagcag    1020
ctgcctgaga gtacaaaga gatttttcttc gaccagagca gaacggcta cgccggctac    1080
attgacggcg gagccagcca ggaagagttc tacaagttca tcaagcccat cctgaaaaag    1140
atggacggca ccgaggaact gctcgtgaag ctgaacagag aggacctgct gcggaagcag    1200
cggaccttcg acaacggcag catccccac cagatccacc tggagagct gcacgccatt    1260
ctgcggcggc aggaagattt ttacccattc ctgaaggaca accgggaaaa gatcgagaag    1320
atcctgacct tccgcatccc ctactacgtg ggccctctgg ccaggggaaa cagcagattc    1380
gcctggatga ccgaaaagag cgaggaaacc atcacccct ggaacttcga ggaagtggtg    1440
gacaagggcg cttccgccca gagcttcatc gagcggatga ccaacttcga taagaacctg    1500
```

```
cccaacgaga aggtgctgcc caagcacagc ctgctgtacg agtacttcac cgtgtataac   1560
gagctgacca aagtgaaata cgtgaccgag ggaatgagaa agcccgcctt cctgagcggc   1620
gagcagaaaa aggccatcgt ggacctgctg ttcaagacca accggaaagt gaccgtgaag   1680
cagctgaaag gagactactt caagaaaatc gagtgcttcg actccgtgga aatctccggc   1740
gtggaagatc ggttcaacgc ctccctgggc acataccacg atctgctgaa aattatcaag   1800
gacaaggact tcctggacaa tgaggaaaac gaggacattc tggaagatat cgtgctgacc   1860
ctgacactgt ttgaggacag agagatgatc gaggaacggc tgaaaaccta tgcccacctg   1920
ttcgacgaca aagtgatgaa gcagctgaag cggcggagat acaccggctg ggcaggctg   1980 agccggaagc tgatcaacgg catccgggac aagcagtccg gcaagacaat cctggatttc   2040
ctgaagtccg acggcttcgc caacagaaac ttcatgcagc tgatccacga cgacagcctg   2100
acctttaaag aggacatcca gaaagcccag gtgtccggcc agggcgatag cctgcacgag   2160
cacattgcca atctgccgg cagccccgcc attaagaagg catcctgca gacagtgaag   2220 gtggtggacg agctcgtgaa agtgatgggc cggcacaagc ccgagaacat cgtgatcgaa   2280
atggccagag agaaccagac cacccagaag ggacagaagg gggtggtgg aagtggcggt   2340 ggcggctccg gaggaggagg aagcggcggc ggtggtagtg gcggcggcgg aagcggaggc   2400
ggcggctccg gacgggctga cgcattggac gatttttgatc tggatatgct gggaagtgac   2460
gccctcgatg attttgacct tgacatgctt ggttcggatg cccttgatga ctttgacctc   2520
gacatgctcg gcagtgacgc ccttgatgat ttcgacctgg acatgctgat taacgggggt   2580
ggtggaagtg gcggtggcgg ctccggagga ggaggaagcg gcggcggtgg tagtggcggc   2640
ggcggaagcg gaggcggcgg ctccaccaag gccgagagag cggcctgag cgaactggat   2700 aaggccggct tcatcaagag acagctggtg gaaacccggc agatcacaaa gcacgtggca   2760
cagatcctgg actcccggat gaacactaag tacgacgaga tgacaagct gatccgggaa   2820 gtgaaagtga tcaccctgaa gtccaagctg gtgtccgatt tccggaagga tttccagttt   2880
tacaaagtgc gcgagatcaa caactaccac cacgcccacg acgcctacct gaacgccgtc   2940
gtgggaaccg ccctgatcaa aaagtaccct aagctggaaa gcgagttcgt gtacggcgac   3000
tacaaggtgt acgacgtgcg gaagatgatc gccaagagcg agcaggaaat cggcaaggct   3060
accgccaagt acttcttcta cagcaacatc atgaactttt tcaagaccga gattaccctg   3120
gccaacggcg agatccggaa gcggcctctg atcgagacaa acggcgaaac cggggagatc   3180
gtgtgggata agggccggga ttttgccacc gtgcggaaag tgctgagcat gccccaagtg   3240
aatatcgtga aaaagaccga ggtgcagaca ggcggcttca gcaaagagtc tatcctgccc   3300
aagaggaaca gcgataagct gatcgccaga aagaaggact gggaccctaa gaagtacggc   3360
ggcttcgaca gccccaccgt ggcctattct gtgctggtgg tggccaaagt ggaaaagggc   3420
aagtccaaga aactgaagag tgtgaaagag ctgctgggga tcaccatcat ggaaagaagc   3480
agcttcgaga agaatcccat cgactttctg gaagccaagg gctacaaaga agtgaaaaag   3540
gacctgatca tcaagctgcc taagtactcc ctgttcgagc tggaaaacgg ccggaagaga   3600
atgctggcct ctgccggcga actgcagaag ggaaacgaac tggcccctgc ctccaaatat   3660
gtgaacttcc tgtacctggc cagccactat gagaagctga aaggctcccc cgaggataat   3720
gagcagaaac agctgtttgt ggaacagcac aagcactacc tggacgagat catcgagcag   3780
atcagcgagt tctccaagag agtgatcctg gccgacgcta atctggacaa agtgctgtcc   3840
```

```
gcctacaaca agcaccggga taagcccatc agagagcagg ccgagaatat catccacctg    3900
tttaccctga ccaatctggg agccctgcc gccttcaagt actttgacac caccatcgac    3960
cggaagaggt acaccagcac caaagaggtg ctggacgcca ccctgatcca ccagagcatc    4020
accggcctgt acgagacacg gatcgacctg tctcagctgg aggcgacag cgctggagga    4080 ggtggaagcg gaggaggagg aagcggagga ggaggtagcg gacctaagaa aaagaggaag    4140
gtggcggccg ctgctagcgg cag                                            4163
```

<210> SEQ ID NO 97
<211> LENGTH: 1387
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 97

```
Lys Lys Tyr Ser Ile Gly Leu Ala Ile Gly Thr Asn Ser Val Gly Trp
1               5                   10                  15

Ala Val Ile Thr Asp Glu Tyr Lys Val Pro Ser Lys Lys Phe Lys Val
            20                  25                  30

Leu Gly Asn Thr Asp Arg His Ser Ile Lys Lys Asn Leu Ile Gly Ala
        35                  40                  45

Leu Leu Phe Asp Ser Gly Glu Thr Ala Glu Ala Thr Arg Leu Lys Arg
    50                  55                  60

Thr Ala Arg Arg Arg Tyr Thr Arg Arg Lys Asn Arg Ile Cys Tyr Leu
65                  70                  75                  80

Gln Glu Ile Phe Ser Asn Glu Met Ala Lys Val Asp Asp Ser Phe Phe
                85                  90                  95

His Arg Leu Glu Glu Ser Phe Leu Val Glu Glu Asp Lys Lys His Glu
            100                 105                 110

Arg His Pro Ile Phe Gly Asn Ile Val Asp Glu Val Ala Tyr His Glu
        115                 120                 125

Lys Tyr Pro Thr Ile Tyr His Leu Arg Lys Lys Leu Val Asp Ser Thr
    130                 135                 140

Asp Lys Ala Asp Leu Arg Leu Ile Tyr Leu Ala Leu Ala His Met Ile
145                 150                 155                 160

Lys Phe Arg Gly His Phe Leu Ile Glu Gly Asp Leu Asn Pro Asp Asn
                165                 170                 175

Ser Asp Val Asp Lys Leu Phe Ile Gln Leu Val Gln Thr Tyr Asn Gln
            180                 185                 190

Leu Phe Glu Glu Asn Pro Ile Asn Ala Ser Gly Val Asp Ala Lys Ala
        195                 200                 205

Ile Leu Ser Ala Arg Leu Ser Lys Ser Arg Arg Leu Glu Asn Leu Ile
    210                 215                 220

Ala Gln Leu Pro Gly Glu Lys Lys Asn Gly Leu Phe Gly Asn Leu Ile
225                 230                 235                 240

Ala Leu Ser Leu Gly Leu Thr Pro Asn Phe Lys Ser Asn Phe Asp Leu
                245                 250                 255

Ala Glu Asp Ala Lys Leu Gln Leu Ser Lys Asp Thr Tyr Asp Asp Asp
            260                 265                 270

Leu Asp Asn Leu Leu Ala Gln Ile Gly Asp Gln Tyr Ala Asp Leu Phe
        275                 280                 285

Leu Ala Ala Lys Asn Leu Ser Asp Ala Ile Leu Leu Ser Asp Ile Leu
```

```
            290                 295                 300
Arg Val Asn Thr Glu Ile Thr Lys Ala Pro Leu Ser Ala Ser Met Ile
305                 310                 315                 320

Lys Arg Tyr Asp Glu His His Gln Asp Leu Thr Leu Leu Lys Ala Leu
                325                 330                 335

Val Arg Gln Gln Leu Pro Glu Lys Tyr Lys Glu Ile Phe Phe Asp Gln
                340                 345                 350

Ser Lys Asn Gly Tyr Ala Gly Tyr Ile Asp Gly Gly Ala Ser Gln Glu
                355                 360                 365

Glu Phe Tyr Lys Phe Ile Lys Pro Ile Leu Glu Lys Met Asp Gly Thr
    370                 375                 380

Glu Glu Leu Leu Val Lys Leu Asn Arg Glu Asp Leu Leu Arg Lys Gln
385                 390                 395                 400

Arg Thr Phe Asp Asn Gly Ser Ile Pro His Gln Ile His Leu Gly Glu
                405                 410                 415

Leu His Ala Ile Leu Arg Arg Gln Glu Asp Phe Tyr Pro Phe Leu Lys
                420                 425                 430

Asp Asn Arg Glu Lys Ile Glu Lys Ile Leu Thr Phe Arg Ile Pro Tyr
                435                 440                 445

Tyr Val Gly Pro Leu Ala Arg Gly Asn Ser Arg Phe Ala Trp Met Thr
    450                 455                 460

Arg Lys Ser Glu Glu Thr Ile Thr Pro Trp Asn Phe Glu Glu Val Val
465                 470                 475                 480

Asp Lys Gly Ala Ser Ala Gln Ser Phe Ile Glu Arg Met Thr Asn Phe
                485                 490                 495

Asp Lys Asn Leu Pro Asn Glu Lys Val Leu Pro Lys His Ser Leu Leu
                500                 505                 510

Tyr Glu Tyr Phe Thr Val Tyr Asn Glu Leu Thr Lys Val Lys Tyr Val
                515                 520                 525

Thr Glu Gly Met Arg Lys Pro Ala Phe Leu Ser Gly Glu Gln Lys Lys
    530                 535                 540

Ala Ile Val Asp Leu Leu Phe Lys Thr Asn Arg Lys Val Thr Val Lys
545                 550                 555                 560

Gln Leu Lys Glu Asp Tyr Phe Lys Lys Ile Glu Cys Phe Asp Ser Val
                565                 570                 575

Glu Ile Ser Gly Val Glu Asp Arg Phe Asn Ala Ser Leu Gly Thr Tyr
                580                 585                 590

His Asp Leu Leu Lys Ile Ile Lys Asp Lys Asp Phe Leu Asp Asn Glu
                595                 600                 605

Glu Asn Glu Asp Ile Leu Glu Asp Ile Val Leu Thr Leu Thr Leu Phe
    610                 615                 620

Glu Asp Arg Glu Met Ile Glu Glu Arg Leu Lys Thr Tyr Ala His Leu
625                 630                 635                 640

Phe Asp Asp Lys Val Met Lys Gln Leu Lys Arg Arg Arg Tyr Thr Gly
                645                 650                 655

Trp Gly Arg Leu Ser Arg Lys Leu Ile Asn Gly Ile Arg Asp Lys Gln
                660                 665                 670

Ser Gly Lys Thr Ile Leu Asp Phe Leu Lys Ser Asp Gly Phe Ala Asn
                675                 680                 685

Arg Asn Phe Met Gln Leu Ile His Asp Asp Ser Leu Thr Phe Lys Glu
                690                 695                 700

Asp Ile Gln Lys Ala Gln Val Ser Gly Gln Gly Asp Ser Leu His Glu
705                 710                 715                 720
```

```
His Ile Ala Asn Leu Ala Gly Ser Pro Ala Ile Lys Lys Gly Ile Leu
            725                 730                 735

Gln Thr Val Lys Val Val Asp Glu Leu Val Lys Val Met Gly Arg His
            740                 745                 750

Lys Pro Glu Asn Ile Val Ile Glu Met Ala Arg Glu Asn Gln Thr Thr
            755                 760                 765

Gln Lys Gly Gln Lys Gly Gly Gly Ser Gly Gly Gly Gly Ser Gly
        770                 775                 780

Gly Gly Gly Ser Gly Gly Gly Ser Gly Gly Gly Ser Gly Gly
785                 790                 795                 800

Gly Gly Ser Gly Arg Ala Asp Ala Leu Asp Asp Phe Asp Leu Asp Met
                805                 810                 815

Leu Gly Ser Asp Ala Leu Asp Asp Phe Asp Leu Asp Met Leu Gly Ser
            820                 825                 830

Asp Ala Leu Asp Asp Phe Asp Leu Asp Met Leu Gly Ser Asp Ala Leu
            835                 840                 845

Asp Asp Phe Asp Leu Asp Met Leu Ile Asn Gly Gly Gly Ser Gly
        850                 855                 860

Gly Gly Ser Gly Gly Gly Ser Gly Gly Gly Ser Gly Gly
865                 870                 875                 880

Gly Gly Ser Gly Gly Gly Ser Thr Lys Ala Glu Arg Gly Gly Leu
            885                 890                 895

Ser Glu Leu Asp Lys Ala Gly Phe Ile Lys Arg Gln Leu Val Glu Thr
            900                 905                 910

Arg Gln Ile Thr Lys His Val Ala Gln Ile Leu Asp Ser Arg Met Asn
            915                 920                 925

Thr Lys Tyr Asp Glu Asn Asp Lys Leu Ile Arg Glu Val Lys Val Ile
            930                 935                 940

Thr Leu Lys Ser Lys Leu Val Ser Asp Phe Arg Lys Asp Phe Gln Phe
945                 950                 955                 960

Tyr Lys Val Arg Glu Ile Asn Asn Tyr His His Ala His Asp Ala Tyr
            965                 970                 975

Leu Asn Ala Val Val Gly Thr Ala Leu Ile Lys Lys Tyr Pro Lys Leu
            980                 985                 990

Glu Ser Glu Phe Val Tyr Gly Asp  Tyr Lys Val Tyr Asp Val Arg Lys
            995                 1000                1005

Met Ile Ala Lys Ser Glu Gln  Glu Ile Gly Lys Ala  Thr Ala Lys
        1010                1015                1020

Tyr Phe Phe Tyr Ser Asn Ile  Met Asn Phe Phe Lys  Thr Glu Ile
        1025                1030                1035

Thr Leu Ala Asn Gly Glu Ile  Arg Lys Arg Pro Leu  Ile Glu Thr
        1040                1045                1050

Asn Gly Glu Thr Gly Glu Ile  Val Trp Asp Lys Gly  Arg Asp Phe
        1055                1060                1065

Ala Thr Val Arg Lys Val Leu  Ser Met Pro Gln Val  Asn Ile Val
        1070                1075                1080

Lys Lys Thr Glu Val Gln Thr  Gly Gly Phe Ser Lys  Glu Ser Ile
        1085                1090                1095

Leu Pro Lys Arg Asn Ser Asp  Lys Leu Ile Ala Arg  Lys Lys Asp
        1100                1105                1110

Trp Asp Pro Lys Lys Tyr Gly  Gly Phe Asp Ser Pro  Thr Val Ala
        1115                1120                1125
```

| | | | | | | | | | | |
|---|---|---|---|---|---|---|---|---|---|---|
|Tyr|Ser 1130|Val|Leu|Val|Val 1135|Ala|Lys|Val|Glu 1140|Lys Gly Lys Ser Lys|

Tyr Ser Val Leu Val Val Ala Lys Val Glu Lys Gly Lys Ser Lys
    1130                1135                1140

Lys Leu Lys Ser Val Lys Glu Leu Leu Gly Ile Thr Ile Met Glu
    1145                1150                1155

Arg Ser Ser Phe Glu Lys Asn Pro Ile Asp Phe Leu Glu Ala Lys
    1160                1165                1170

Gly Tyr Lys Glu Val Lys Lys Asp Leu Ile Ile Lys Leu Pro Lys
    1175                1180                1185

Tyr Ser Leu Phe Glu Leu Glu Asn Gly Arg Lys Arg Met Leu Ala
    1190                1195                1200

Ser Ala Gly Glu Leu Gln Lys Gly Asn Glu Leu Ala Leu Pro Ser
    1205                1210                1215

Lys Tyr Val Asn Phe Leu Tyr Leu Ala Ser His Tyr Glu Lys Leu
    1220                1225                1230

Lys Gly Ser Pro Glu Asp Asn Glu Gln Lys Gln Leu Phe Val Glu
    1235                1240                1245

Gln His Lys His Tyr Leu Asp Glu Ile Ile Glu Gln Ile Ser Glu
    1250                1255                1260

Phe Ser Lys Arg Val Ile Leu Ala Asp Ala Asn Leu Asp Lys Val
    1265                1270                1275

Leu Ser Ala Tyr Asn Lys His Arg Asp Lys Pro Ile Arg Glu Gln
    1280                1285                1290

Ala Glu Asn Ile Ile His Leu Phe Thr Leu Thr Asn Leu Gly Ala
    1295                1300                1305

Pro Ala Ala Phe Lys Tyr Phe Asp Thr Thr Ile Asp Arg Lys Arg
    1310                1315                1320

Tyr Thr Ser Thr Lys Glu Val Leu Asp Ala Thr Leu Ile His Gln
    1325                1330                1335

Ser Ile Thr Gly Leu Tyr Glu Thr Arg Ile Asp Leu Ser Gln Leu
    1340                1345                1350

Gly Gly Asp Ser Ala Gly Gly Gly Ser Gly Gly Gly Ser
    1355                1360                1365

Gly Gly Gly Gly Ser Gly Pro Lys Lys Lys Arg Lys Val Ala Ala
    1370                1375                1380

Ala Ala Ser Gly
    1385

<210> SEQ ID NO 98
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga gaacctgat cggagccctg ctgttcgaca cggccgaaac agccgaggcc     180
acccggctga gagaaccgc cagaagaaga tacaccagac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcacccat cttcggcaac     360 atcgtggacg aggtggccta ccacgagaag taccccacca tctaccacct gagaaagaaa     420

```
ctggtggaca gcaccgacaa ggccgacctg cggctgatct atctggccct ggcccacatg    480
atcaagttcc ggggccactt cctgatcgag ggcgacctga accccgacaa cagcgacgtg    540
gacaagctgt tcatccagct ggtgcagacc tacaaccagc tgttcgagga aaacccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggcaacctg    720
attgccctga gcctgggcct gacccccaac ttcaagagca cttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc accagatcc acctgggaga gctgcacgcc    1260
attctgcggc ggcaggaaga ttttttaccca ttcctgaagg acaaccggga aaagatcgag   1320
aagatcctga ccttccgcat ccctactac gtgggccctc tggccagggg aaacagcaga    1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta agaggacat ccagaaagcc caggtgtccg ccagggcga tagcctgcac    2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc    2280
gaaatggcca gagagaacca gaccacccag aagggacaga agggcggggg aggctccggt   2340
ggtgggggca gcgagggggg gggcagccct tcagggcaga tcagcaacca ggccctggct   2400
ctggccccta gctccgctcc agtgctggcc cagactatgg tgccctctag tgctatggtg   2460
cctctggccc agccacctgc tccagcccct gtgctgaccc caggaccacc ccagtcactg   2520
agcgctccag tgcccaagtc tacacaggcc ggcgagggga ctctgagtga agctctgctg   2580
cacctgcagt tcgacgctga tgaggacctg ggagctctgc tggggaacag caccgatccc   2640
ggagtgttca cagatctggc ctccgtgac aactctgagt tcagcagct gctgaatcag   2700
ggcgtgtcca tgtctcatag tacagccgaa ccaatgctga tggagtaccc cgaagccatt   2760
```

-continued

```
accccggctgg tgaccggcag ccagcggccc cccgaccccg ctccaactcc cctgggaacc      2820
agcggcctgc ctaatgggct gtccggagat gaagacttct caagcatcgc tgatatggac      2880
tttagtgccc tgctgtcaca gatttcctct agtgggcagg gcgggggagg ctccggtggt      2940
gggggcagcg gagggggggg cagcaccaag gccgagagag gcggcctgag cgaactggat      3000
aaggccggct tcatcaagag acagctggtg gaaacccggc agatcacaaa gcacgtggca      3060
cagatcctgg actcccggat gaacactaag tacgacgaga tgacaagct  gatccgggaa      3120 gtgaaagtga tcaccctgaa gtccaagctg gtgtccgatt ccggaaggaa tttccagttt      3180
tacaaagtgc gcgagatcaa caactaccac cacgcccacg acgcctacct gaacgccgtc      3240
gtgggaaccg ccctgatcaa aaagtaccct aagctggaaa gcgagttcgt gtacggcgac      3300
tacaaggtgt acgacgtgcg gaagatgatc gccaagagcg agcaggaaat cggcaaggct      3360
accgccaagt acttcttcta cagcaacatc atgaactttt tcaagaccga gattaccctg      3420
gccaacggcg agatccggaa gcggcctctg atcgagacaa acggcgaaac cggggagatc      3480
gtgtgggata agggccggga ttttgccacc gtgcggaaag tgctgagcat gccccaagtg      3540
aatatcgtga aaaagaccga ggtgcagaca ggcggcttca gcaaagagtc tatcctgccc      3600
aagaggaaca gcgataagct gatcgccaga aagaaggact gggaccctaa gaagtacggc      3660
ggcttcgaca gccccaccgt ggcctattct gtgctggtgg tggccaaagt ggaaagggc      3720 aagtccaaga aactgaagag tgtgaaagag ctgctgggga tcaccatcat ggaaagaagc      3780
agcttcgaga agaatcccat cgactttctg gaagccaagg gctacaaaga agtgaaaaag      3840
gacctgatca tcaagctgcc taagtactcc ctgttcgagc tggaaaacgg ccggaagaga      3900
atgctggcct ctgccggcga actgcagaag ggaaacgaac tggccctgcc ctccaaatat      3960
gtgaacttcc tgtacctggc cagccactat gagaagctga agggctcccc cgaggataat      4020
gagcagaaac agctgtttgt ggaacagcac aagcactacc tggacgagat catcgagcag      4080
atcagcgagt tctccaagag agtgatcctg gccgacgcta atctggacaa agtgctgtcc      4140
gcctacaaca gcaccgggga taagcccatc agagagcagg ccgagaatat catccacctg      4200
tttaccctga ccaatctggg agcccctgcc gccttcaagt actttgacac caccatcgac      4260
cggaagaggt acaccagcac caaagaggtg ctggacgcca ccctgatcca ccagagcatc      4320
accggcctgt acgagacacg gatcgacctg tctcagctgg aggcgac                   4368
```

<210> SEQ ID NO 99
<211> LENGTH: 1456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 99

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr

```
             65                  70                  75                  80
Leu Gln Glu Ile Phe Ser Asn Glu Met Ala Lys Val Asp Asp Ser Phe
                    85                  90                  95

Phe His Arg Leu Glu Glu Ser Phe Leu Val Glu Glu Asp Lys Lys His
                100                 105                 110

Glu Arg His Pro Ile Phe Gly Asn Ile Val Asp Glu Val Ala Tyr His
                115                 120                 125

Glu Lys Tyr Pro Thr Ile Tyr His Leu Arg Lys Lys Leu Val Asp Ser
        130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
                180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
                260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495
```

-continued

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
            645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Gly Gly Gly Ser Gly Gly Gly Gly Ser
            770                 775                 780

Gly Gly Gly Gly Ser Pro Ser Gly Gln Ile Ser Asn Gln Ala Leu Ala
785                 790                 795                 800

Leu Ala Pro Ser Ser Ala Pro Val Leu Ala Gln Thr Met Val Pro Ser
            805                 810                 815

Ser Ala Met Val Pro Leu Ala Gln Pro Pro Ala Pro Ala Pro Val Leu
            820                 825                 830

Thr Pro Gly Pro Pro Gln Ser Leu Ser Ala Pro Val Pro Lys Ser Thr
            835                 840                 845

Gln Ala Gly Glu Gly Thr Leu Ser Glu Ala Leu Leu His Leu Gln Phe
            850                 855                 860

Asp Ala Asp Glu Asp Leu Gly Ala Leu Leu Gly Asn Ser Thr Asp Pro
865                 870                 875                 880

Gly Val Phe Thr Asp Leu Ala Ser Val Asp Asn Ser Glu Phe Gln Gln
            885                 890                 895

Leu Leu Asn Gln Gly Val Ser Met Ser His Ser Thr Ala Glu Pro Met
            900                 905                 910

Leu Met Glu Tyr Pro Glu Ala Ile Thr Arg Leu Val Thr Gly Ser Gln
        915                 920                 925

Arg Pro Pro Asp Pro Ala Pro Thr Pro Leu Gly Thr Ser Gly Leu Pro
    930                 935                 940

Asn Gly Leu Ser Gly Asp Glu Asp Phe Ser Ser Ile Ala Asp Met Asp
945                 950                 955                 960

Phe Ser Ala Leu Leu Ser Gln Ile Ser Ser Ser Gly Gln Gly Gly
            965                 970                 975

Gly Ser Gly Gly Gly Ser Gly Gly Gly Ser Thr Lys Ala Glu
                980                 985                 990

Arg Gly Gly Leu Ser Glu Leu Asp Lys Ala Gly Phe Ile Lys Arg Gln
    995                 1000                1005

Leu Val Glu Thr Arg Gln Ile Thr Lys His Val Ala Gln Ile Leu
    1010                1015                1020

Asp Ser Arg Met Asn Thr Lys Tyr Asp Glu Asn Asp Lys Leu Ile
    1025                1030                1035

Arg Glu Val Lys Val Ile Thr Leu Lys Ser Lys Leu Val Ser Asp
    1040                1045                1050

Phe Arg Lys Asp Phe Gln Phe Tyr Lys Val Arg Glu Ile Asn Asn
    1055                1060                1065

Tyr His His Ala His Asp Ala Tyr Leu Asn Ala Val Val Gly Thr
    1070                1075                1080

Ala Leu Ile Lys Lys Tyr Pro Lys Leu Glu Ser Glu Phe Val Tyr
    1085                1090                1095

Gly Asp Tyr Lys Val Tyr Asp Val Arg Lys Met Ile Ala Lys Ser
    1100                1105                1110

Glu Gln Glu Ile Gly Lys Ala Thr Ala Lys Tyr Phe Phe Tyr Ser
    1115                1120                1125

Asn Ile Met Asn Phe Phe Lys Thr Glu Ile Thr Leu Ala Asn Gly
    1130                1135                1140

Glu Ile Arg Lys Arg Pro Leu Ile Glu Thr Asn Gly Glu Thr Gly
    1145                1150                1155

Glu Ile Val Trp Asp Lys Gly Arg Asp Phe Ala Thr Val Arg Lys
    1160                1165                1170

Val Leu Ser Met Pro Gln Val Asn Ile Val Lys Lys Thr Glu Val
    1175                1180                1185

Gln Thr Gly Gly Phe Ser Lys Glu Ser Ile Leu Pro Lys Arg Asn
    1190                1195                1200

Ser Asp Lys Leu Ile Ala Arg Lys Lys Asp Trp Asp Pro Lys Lys
    1205                1210                1215

Tyr Gly Gly Phe Asp Ser Pro Thr Val Ala Tyr Ser Val Leu Val
    1220                1225                1230

Val Ala Lys Val Glu Lys Gly Lys Ser Lys Lys Leu Lys Ser Val
    1235                1240                1245

Lys Glu Leu Leu Gly Ile Thr Ile Met Glu Arg Ser Ser Phe Glu
    1250                1255                1260

Lys Asn Pro Ile Asp Phe Leu Glu Ala Lys Gly Tyr Lys Glu Val
    1265                1270                1275

Lys Lys Asp Leu Ile Ile Lys Leu Pro Lys Tyr Ser Leu Phe Glu
    1280                1285                1290

Leu Glu Asn Gly Arg Lys Arg Met Leu Ala Ser Ala Gly Glu Leu
    1295                1300                1305

Gln Lys Gly Asn Glu Leu Ala Leu Pro Ser Lys Tyr Val Asn Phe

```
                1310                1315                1320
Leu Tyr Leu Ala Ser His Tyr Glu Lys Leu Lys Gly Ser Pro Glu
    1325                1330                1335

Asp Asn Glu Gln Lys Gln Leu Phe Val Glu Gln His Lys His Tyr
    1340                1345                1350

Leu Asp Glu Ile Ile Glu Gln Ile Ser Glu Phe Ser Lys Arg Val
    1355                1360                1365

Ile Leu Ala Asp Ala Asn Leu Asp Lys Val Leu Ser Ala Tyr Asn
    1370                1375                1380

Lys His Arg Asp Lys Pro Ile Arg Glu Gln Ala Glu Asn Ile Ile
    1385                1390                1395

His Leu Phe Thr Leu Thr Asn Leu Gly Ala Pro Ala Ala Phe Lys
    1400                1405                1410

Tyr Phe Asp Thr Thr Ile Asp Arg Lys Arg Tyr Thr Ser Thr Lys
    1415                1420                1425

Glu Val Leu Asp Ala Thr Leu Ile His Gln Ser Ile Thr Gly Leu
    1430                1435                1440

Tyr Glu Thr Arg Ile Asp Leu Ser Gln Leu Gly Gly Asp
    1445                1450                1455

<210> SEQ ID NO 100
<211> LENGTH: 4536
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
ggacaagaag tacagcatcg gcctggccat cggcaccaac tctgtgggct gggccgtgat    60
caccgacgag tacaaggtgc ccagcaagaa attcaaggtg ctgggcaaca ccgaccggca   120
cagcatcaag aagaacctga tcggagccct gctgttcgac agcggcgaaa cagccgaggc   180
cacccggctg aagagaaccg ccagaagaag atacaccaga cggaagaacc ggatctgcta   240
tctgcaagag atcttcagca acgagatggc caaggtggac gacagcttct tccacagact   300
ggaagagtcc ttcctggtgg aagaggataa gaagcacgag cggcacccca tcttcggcaa   360
catcgtggac gaggtggcct accacgagaa gtaccccacc atctaccacc tgagaaagaa   420
actggtggac agcaccgaca aggccgacct gcggctgatc tatctggccc tggcccacat   480
gatcaagttc cggggccact tcctgatcga gggcgacctg aaccccgaca cagcgacgt    540 ggacaagctg ttcatccagc tggtgcagac ctacaaccag ctgttcgagg aaaaccccat   600
caacgccagc ggcgtggacg ccaaggccat cctgtctgcc agactgagca gagcagacg    660 gctggaaaat ctgatcgccc agctgcccgg cgagaagaag aatggcctgt tcggcaacct   720
gattgccctg agcctgggcc tgaccccccaa cttcaagagc aacttcgacc tggccgagga   780
tgccaaactg cagctgagca aggacaccta cgacgacgac ctggacaacc tgctggccca   840
gatcggcgac cagtacgccg acctgttcct ggccgccaag aacctgtccg acgccatcct   900
gctgagcgac atcctgagag tgaacaccga gatcaccaag gccccctga gcgcctctat    960 gatcaagaga tacgacgagc accaccagga cctgaccctg ctgaaagctc tcgtgcggca  1020
gcagctgcct gagaagtaca aagagatttt cttcgaccag agcaagaacg gctacgccgg  1080
ctacattgac ggcggagcca gccaggaaga gttctacaag ttcatcaagc ccatcctgga  1140
```

-continued

```
aaagatggac ggcaccgagg aactgctcgt gaagctgaac agagaggacc tgctgcggaa    1200
gcagcggacc ttcgacaacg gcagcatccc ccaccagatc cacctgggag agctgcacgc    1260
cattctgcgg cggcaggaag attttaccc attcctgaag acaaccggg aaaagatcga     1320
gaagatcctg accttccgca tcccctacta cgtgggccct ctggccaggg aaacagcag    1380
attcgcctgg atgaccagaa agagcgagga aaccatcacc ccctggaact tcgaggaagt    1440
ggtggacaag ggcgcttccg cccagagctt catcgagcgg atgaccaact tcgataagaa    1500
cctgcccaac gagaaggtgc tgcccaagca cagcctgctg tacgagtact tcaccgtgta    1560
taacgagctg accaaagtga aatacgtgac cgagggaatg agaaagcccg ccttcctgag    1620
cggcgagcag aaaaaggcca tcgtggacct gctgttcaag accaaccgga agtgaccgt     1680
gaagcagctg aaagaggact acttcaagaa aatcgagtgc ttcgactccg tggaaatctc    1740
cggcgtggaa gatcggttca acgcctccct gggcacatac cacgatctgc tgaaaattat    1800
caaggacaag gacttcctgg acaatgagga aaacgaggac attctggaag atatcgtgct    1860
gaccctgaca ctgtttgagg acagagagat gatcgaggaa cggctgaaaa cctatgccca    1920
cctgttcgac gacaaagtga tgaagcagct gaagcggcgg agatacaccg gctggggcag    1980
gctgagccgg aagctgatca acggcatccg ggacaagcag tccggcaaga caatcctgga    2040
tttcctgaag tccgacggct tcgccaacag aaacttcatg cagctgatcc acgacgacag    2100
cctgaccttt aaagaggaca tccagaaagc ccaggtgtcc ggccagggcg atagcctgca    2160
cgagcacatt gccaatctgg ccggcagccc cgccattaag aagggcatcc tgcagacagt    2220
gaaggtggtg acgagctcg tgaaagtgat gggccggcac aagcccgaga catcgtgat     2280
cgaaatggcc agagagaacc agaccaccca aagggacag aaggggggtg gtggaagtgg    2340
cggtggcggc tccggaggag gaggaagcgg cggcggtggt agtggcggcg cggaagcgg    2400
aggcggcggc tcccccttcag ggcagatcag caaccaggcc ctggctctgg ccctagctc    2460
cgctccagtg ctggcccaga ctatggtgcc ctctagtgct atggtgcctc tggcccagcc    2520
acctgctcca gcccctgtgc tgaccccagg accacccag tcactgagcg ctccagtgcc    2580
caagtctaca caggccggcg aggggactct gagtgaagct ctgctgcacc tgcagttcga    2640
cgctgatgag gacctgggag ctctgctggg gaacagcacc gatcccggag tgttcacaga    2700
tctggcctcc gtggacaact ctgagtttca gcagctgctg aatcagggcg tgtccatgtc    2760
tcatagtaca gccgaaccaa tgctgatgga gtacccgaa gccattaccc ggctggtgac     2820
cggcagccag cggcccccg accccgctcc aactcccctg gaaccagcg gcctgcctaa    2880
tgggctgtcc ggagatgaag acttctcaag catcgctgat atggactta gtgccctgct    2940
gtcacagatt tcctctagtg ggcaggggg tggtggaagt ggcggtggcg gctccggagg    3000
aggaggaagc ggcggcggtg gtagtggcgg cggcggaagc ggaggcggcg gctccaccaa    3060
ggccgagaga ggcggcctga gcgaactgga taaggccggc ttcatcaaga acagctggt    3120
ggaaacccgg cagatcacaa agcacgtggc acagatcctg gactcccga tgaacactaa    3180
gtacgacgag aatgacaagc tgatccggga agtgaaagtg atcacctga agtccaagct    3240
ggtgtccgat ttccggaagg attccagtt ttacaaagtg cgcagatca acaactacca    3300
ccacgcccac gacgcctacc tgaacgccgt cgtgggaacc gccctgatca aaaagtaccc    3360
taagctggaa agcgagttcg tgtacggcga ctacaaggtg tacgacgtgc ggaagatgat    3420
cgccaagagc gagcaggaaa tcggcaaggc taccgccaag tacttcttct acagcaacat    3480
catgaacttt ttcaagaccg agattaccct ggccaacggc gagatccgga agcggcctct    3540
```

-continued

```
gatcgagaca aacggcgaaa ccggggagat cgtgtgggat aagggccggg attttgccac   3600
cgtgcggaaa gtgctgagca tgccccaagt gaatatcgtg aaaaagaccg aggtgcagac   3660
aggcggcttc agcaaagagt ctatcctgcc caagaggaac agcgataagc tgatcgccag   3720
aaagaaggac tgggacccta agaagtacgg cggcttcgac agccccaccg tggcctattc   3780
tgtgctggtg gtggccaaag tggaaaaggg caagtccaag aaactgaaga gtgtgaaaga   3840
gctgctgggg atcaccatca tggaaagaag cagcttcgag aagaatccca tcgactttct   3900
ggaagccaag ggctacaaag aagtgaaaaa ggacctgatc atcaagctgc taagtactc    3960 cctgttcgag ctgaaaacg gccggaagag aatgctggcc tctgccggcg aactgcagaa    4020
gggaaacgaa ctggccctgc cctccaaata tgtgaacttc ctgtacctgg ccagccacta   4080
tgagaagctg aagggctccc ccgaggataa tgagcagaaa cagctgtttg tggaacagca   4140
caagcactac ctggacgaga tcatcgagca gatcagcgag ttctccaaga gagtgatcct   4200
ggccgacgct aatctggaca aagtgctgtc cgcctacaac aagcaccggg ataagcccat   4260
cagagagcag gccgagaata tcatccacct gtttaccctg accaatctgg agcccctgc    4320 cgccttcaag tactttgaca ccaccatcga ccggaagagg tacaccagca ccaaagaggt   4380
gctggacgcc accctgatcc accagagcat caccggcctg tacgagacac ggatcgacct   4440
gtctcagctg ggaggcgaca cgctggagg aggtggaagc ggaggaggag aagcggagg    4500 aggaggtagc ggacctaaga aaaagaggaa ggtggc                            4536
```

<210> SEQ ID NO 101
<211> LENGTH: 1486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 101

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175
```

```
Asn Ser Asp Val Asp Lys Leu Phe Ile Gln Leu Val Gln Thr Tyr Asn
            180                 185                 190
Gln Leu Phe Glu Glu Asn Pro Ile Asn Ala Ser Gly Val Asp Ala Lys
            195                 200                 205
Ala Ile Leu Ser Ala Arg Leu Ser Lys Ser Arg Arg Leu Glu Asn Leu
            210                 215                 220
Ile Ala Gln Leu Pro Gly Glu Lys Lys Asn Gly Leu Phe Gly Asn Leu
225                 230                 235                 240
Ile Ala Leu Ser Leu Gly Leu Thr Pro Asn Phe Lys Ser Asn Phe Asp
                245                 250                 255
Leu Ala Glu Asp Ala Lys Leu Gln Leu Ser Lys Asp Thr Tyr Asp Asp
                260                 265                 270
Asp Leu Asp Asn Leu Leu Ala Gln Ile Gly Asp Gln Tyr Ala Asp Leu
            275                 280                 285
Phe Leu Ala Ala Lys Asn Leu Ser Asp Ala Ile Leu Leu Ser Asp Ile
            290                 295                 300
Leu Arg Val Asn Thr Glu Ile Thr Lys Ala Pro Leu Ser Ala Ser Met
305                 310                 315                 320
Ile Lys Arg Tyr Asp Glu His His Gln Asp Leu Thr Leu Leu Lys Ala
                325                 330                 335
Leu Val Arg Gln Gln Leu Pro Glu Lys Tyr Lys Glu Ile Phe Phe Asp
            340                 345                 350
Gln Ser Lys Asn Gly Tyr Ala Gly Tyr Ile Asp Gly Gly Ala Ser Gln
            355                 360                 365
Glu Glu Phe Tyr Lys Phe Ile Lys Pro Ile Leu Glu Lys Met Asp Gly
            370                 375                 380
Thr Glu Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
            420                 425                 430
Lys Asp Asn Arg Glu Lys Ile Glu Lys Ile Leu Thr Phe Arg Ile Pro
            435                 440                 445
Tyr Tyr Val Gly Pro Leu Ala Arg Gly Asn Ser Arg Phe Ala Trp Met
450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
            500                 505                 510
Leu Tyr Glu Tyr Phe Thr Val Tyr Asn Glu Leu Thr Lys Val Lys Tyr
            515                 520                 525
Val Thr Glu Gly Met Arg Lys Pro Ala Phe Leu Ser Gly Glu Gln Lys
            530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
                580                 585                 590
```

```
Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Gly Gly Gly Ser Gly Gly Gly Ser
            770                 775                 780

Gly Gly Gly Gly Ser Gly Gly Gly Ser Gly Gly Gly Ser Gly
785                 790                 795                 800

Gly Gly Gly Ser Pro Ser Gly Gln Ile Ser Asn Gln Ala Leu Ala Leu
                805                 810                 815

Ala Pro Ser Ser Ala Pro Val Leu Ala Gln Thr Met Val Pro Ser Ser
            820                 825                 830

Ala Met Val Pro Leu Ala Gln Pro Pro Ala Pro Val Leu Thr
            835                 840                 845

Pro Gly Pro Pro Gln Ser Leu Ser Ala Pro Val Pro Lys Ser Thr Gln
850                 855                 860

Ala Gly Glu Gly Thr Leu Ser Glu Ala Leu Leu His Leu Gln Phe Asp
865                 870                 875                 880

Ala Asp Glu Asp Leu Gly Ala Leu Leu Gly Asn Ser Thr Asp Pro Gly
                885                 890                 895

Val Phe Thr Asp Leu Ala Ser Val Asp Asn Ser Glu Phe Gln Gln Leu
            900                 905                 910

Leu Asn Gln Gly Val Ser Met Ser His Ser Thr Ala Glu Pro Met Leu
            915                 920                 925

Met Glu Tyr Pro Glu Ala Ile Thr Arg Leu Val Thr Gly Ser Gln Arg
            930                 935                 940

Pro Pro Asp Pro Ala Pro Thr Pro Leu Gly Thr Ser Gly Leu Pro Asn
945                 950                 955                 960

Gly Leu Ser Gly Asp Glu Asp Phe Ser Ser Ile Ala Asp Met Asp Phe
            965                 970                 975

Ser Ala Leu Leu Ser Gln Ile Ser Ser Ser Gly Gln Gly Gly Gly Gly
            980                 985                 990

Ser Gly Gly Gly Ser Gly Gly Gly Gly Ser Gly Gly Gly Gly Ser
    995                 1000                1005

Gly Gly  Gly Gly Ser Gly Gly  Gly Gly Ser Thr Lys Ala Glu Arg
```

-continued

```
              1010                1015                1020
Gly Gly Leu Ser Glu Leu Asp Lys Ala Gly Phe Ile Lys Arg Gln
          1025                1030                1035
Leu Val Glu Thr Arg Gln Ile Thr Lys His Val Ala Gln Ile Leu
          1040                1045                1050
Asp Ser Arg Met Asn Thr Lys Tyr Asp Glu Asn Asp Lys Leu Ile
          1055                1060                1065
Arg Glu Val Lys Val Ile Thr Leu Lys Ser Lys Leu Val Ser Asp
          1070                1075                1080
Phe Arg Lys Asp Phe Gln Phe Tyr Lys Val Arg Glu Ile Asn Asn
          1085                1090                1095
Tyr His His Ala His Asp Ala Tyr Leu Asn Ala Val Val Gly Thr
          1100                1105                1110
Ala Leu Ile Lys Lys Tyr Pro Lys Leu Glu Ser Glu Phe Val Tyr
          1115                1120                1125
Gly Asp Tyr Lys Val Tyr Asp Val Arg Lys Met Ile Ala Lys Ser
          1130                1135                1140
Glu Gln Glu Ile Gly Lys Ala Thr Ala Lys Tyr Phe Phe Tyr Ser
          1145                1150                1155
Asn Ile Met Asn Phe Phe Lys Thr Glu Ile Thr Leu Ala Asn Gly
          1160                1165                1170
Glu Ile Arg Lys Arg Pro Leu Ile Glu Thr Asn Gly Glu Thr Gly
          1175                1180                1185
Glu Ile Val Trp Asp Lys Gly Arg Asp Phe Ala Thr Val Arg Lys
          1190                1195                1200
Val Leu Ser Met Pro Gln Val Asn Ile Val Lys Lys Thr Glu Val
          1205                1210                1215
Gln Thr Gly Gly Phe Ser Lys Glu Ser Ile Leu Pro Lys Arg Asn
          1220                1225                1230
Ser Asp Lys Leu Ile Ala Arg Lys Lys Asp Trp Asp Pro Lys Lys
          1235                1240                1245
Tyr Gly Gly Phe Asp Ser Pro Thr Val Ala Tyr Ser Val Leu Val
          1250                1255                1260
Val Ala Lys Val Glu Lys Gly Lys Ser Lys Lys Leu Lys Ser Val
          1265                1270                1275
Lys Glu Leu Leu Gly Ile Thr Ile Met Glu Arg Ser Ser Phe Glu
          1280                1285                1290
Lys Asn Pro Ile Asp Phe Leu Glu Ala Lys Gly Tyr Lys Glu Val
          1295                1300                1305
Lys Lys Asp Leu Ile Ile Lys Leu Pro Lys Tyr Ser Leu Phe Glu
          1310                1315                1320
Leu Glu Asn Gly Arg Lys Arg Met Leu Ala Ser Ala Gly Glu Leu
          1325                1330                1335
Gln Lys Gly Asn Glu Leu Ala Leu Pro Ser Lys Tyr Val Asn Phe
          1340                1345                1350
Leu Tyr Leu Ala Ser His Tyr Glu Lys Leu Lys Gly Ser Pro Glu
          1355                1360                1365
Asp Asn Glu Gln Lys Gln Leu Phe Val Glu Gln His Lys His Tyr
          1370                1375                1380
Leu Asp Glu Ile Ile Glu Gln Ile Ser Glu Phe Ser Lys Arg Val
          1385                1390                1395
Ile Leu Ala Asp Ala Asn Leu Asp Lys Val Leu Ser Ala Tyr Asn
          1400                1405                1410
```

```
Lys His Arg Asp Lys Pro Ile Arg Glu Gln Ala Glu Asn Ile Ile
    1415                1420                1425

His Leu Phe Thr Leu Thr Asn Leu Gly Ala Pro Ala Ala Phe Lys
    1430                1435                1440

Tyr Phe Asp Thr Thr Ile Asp Arg Lys Arg Tyr Thr Ser Thr Lys
    1445                1450                1455

Glu Val Leu Asp Ala Thr Leu Ile His Gln Ser Ile Thr Gly Leu
    1460                1465                1470

Tyr Glu Thr Arg Ile Asp Leu Ser Gln Leu Gly Gly Asp
    1475                1480                1485
```

<210> SEQ ID NO 102
<211> LENGTH: 4380
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102

```
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga gaacctgat cggagccctg ctgttcgaca cggcgaaac agccgaggcc      180 acccggctga agagaaccgc cagaagaaga taccagac ggaagaaccg atctgctat       240 ctgcaagaga tcttcagcaa cgagatggcc aaggtggacg acagcttctt ccacagactg    300
gaagagtcct tcctggtgga agaggataag aagcacgagc ggcaccccat cttcggcaac    360
atcgtggacg aggtggccta ccacgagaag tacccccacc tctaccacct gagaaagaaa    420
ctggtggaca gcaccgacaa ggccgacctg cggctgatct atctggccct ggcccacatg    480
atcaagttcc ggggccactt cctgatcgag ggcgacctga cccccgacaa cagcgacgtg    540
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggcaacctg    720
attgccctga gcctgggcct gaccccaac ttcaagagca cttcgacct ggccgaggat     780 gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg    960 atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagaggacct gctgcggaag    1200
cagcggacct tcgacaacgg cagcatcccc accagatcc acctgggaga gctgcacgcc    1260
attctgcggc ggcaggaaga ttttaccca ttcctgaagg acaaccggga aaagatcgag    1320
aagatcctga ccttccgcat ccctactac gtgggccctc tggccagggg aaacagcaga    1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
```

```
aacgagctga ccaaagtgaa atacgtgacc gagggaggag ggggggggcag cggacgggct    1620
gacgcattgg acgattttga tctggatatg ctgggaagtg acgccctcga tgattttgac    1680
cttgacatgc ttggttcgga tgcccttgat gactttgacc tcgacatgct cggcagtgac    1740
gcccttgatg atttcgacct ggacatgctg attaacggcg gggaggctc catgagaaag    1800
cccgccttcc tgagcggcga gcagaaaaag gccatcgtgg acctgctgtt caagaccaac    1860
cggaaagtga ccgtgaagca gctgaaagag gactacttca agaaaatcga gtgcttcgac    1920
tccgtggaaa tctccggcgt ggaagatcgg ttcaacgcct ccctgggcac ataccacgat    1980
ctgctgaaaa ttatcaagga caaggacttc ctggacaatg aggaaaacga ggacattctg    2040
gaagatatcg tgctgacccct gacactgttt gaggacagag atgatcga ggaacggctg    2100
aaaacctatg cccacctgtt cgacgacaaa gtgatgaagc agctgaagcg gcggagatac    2160
accggctggg gcaggctgag ccggaagctg atcaacggca tccgggacaa gcagtccggc    2220
aagacaatcc tggatttcct gaagtccgac ggcttcgcca acagaaactt catgcagctg    2280
atccacgacg acagcctgac ctttaaagag gacatccaga agcccaggt gtccggccag    2340
ggcgatagcc tgcacgagca cattgccaat ctggccggca gccccgccat taagaagggc    2400
atcctgcaga cagtgaaggt ggtggacgag ctcgtgaaag tgatgggccg gcacaagccc    2460
gagaacatcg tgatcgaaat ggccagagag aaccagacca cccagaaggg acagaagaac    2520
agccgcgaga gaatgaagcg gatcgaagag ggcatcaaag agctgggcag ccagatcctg    2580
aaagaacacc ccgtggaaaa cacccagctg cagaacgaga gctgtacct gtactacctg    2640
cagaatgggc gggatatgta cgtggaccag gaactggaca tcaaccggct gtccgactac    2700
gatgtggacg ctatcgtgcc tcagagcttt ctgaaggacg actccatcga caacaaggtg    2760
ctgaccagaa gcgacaagaa ccggggcaag agcgacaacg tgccctccga agaggtcgtg    2820
aagaagatga gaactactg gcggcagctg ctgaacgcca agctgattac ccagagaaag    2880
ttcgacaatc tgaccaaggc cgagagaggc ggcctgagcg aactggataa ggccggcttc    2940
atcaagagac agctggtgga aacccggcag atcacaaagc acgtggcaca gatcctggac    3000
tcccggatga acactaagta cgacgagaat gacaagctga tccgggaagt gaaagtgatc    3060
accctgaagt ccaagctggt gtccgatttc cggaaggatt tccagtttta caaagtgcgc    3120
gagatcaaca actaccacca cgcccacgac gcctacctga acgccgtcgt gggaaccgcc    3180
ctgatcaaaa agtaccctaa gctggaaagc gagttcgtgt acggcgacta caaggtgtac    3240
gacgtgcgga agatgatcgc caagagcgag caggaaatcg gcaaggctac cgccaagtac    3300
ttcttctaca gcaacatcat gaactttttc aagaccgaga ttaccctggc caacggcgag    3360
atccggaagc ggcctctgat cgagacaaac ggcgaaaccg gggagatcgt gtgggataag    3420
ggccgggatt ttgccaccgt gcggaaagtg ctgagcatgc cccaagtgaa tatcgtgaaa    3480
aagaccgagt gcagacaggg cggcttcagc aaagagtcta tcctgcccaa gaggaacagc    3540
gataagctga tcgccagaaa aaggactgg acccctaaga agtacggcgg cttcgacagc    3600
cccaccgtgg cctattctgt gctggtggtg gccaaagtgg aaaagggcaa gtccaagaaa    3660
ctgaagagtg tgaaagagct gctggggatc accatcatga aagaagcag cttcgagaag    3720
aatcccatcg actttctgga agccaagggc tacaaagaag tgaaaaagga cctgatcatc    3780
aagctgccta agtactccct gttcgagctg gaaaacggcc ggaagagaat gctggcctct    3840
gccggcgaac tgcagaaggg aaacgaactg gccctgccct ccaaatatgt gaacttcctg    3900
```

```
tacctggcca gccactatga gaagctgaag ggctcccccg aggataatga gcagaaacag    3960
ctgtttgtgg aacagcacaa gcactacctg gacgagatca tcgagcagat cagcgagttc    4020
tccaagagag tgatcctggc cgacgctaat ctggacaaag tgctgtccgc ctacaacaag    4080
caccgggata agcccatcag agagcaggcc gagaatatca tccacctgtt taccctgacc    4140
aatctgggag cccctgccgc cttcaagtac tttgacacca ccatcgaccg gaagaggtac    4200
accagcacca agaggtgct  ggacgccacc ctgatccacc agagcatcac cggcctgtac    4260
gagacacgga tcgacctgtc tcagctggga ggcgacagcg ctggaggagg tggaagcgga    4320
ggaggaggaa gcggaggagg aggtagcgga cctaagaaaa agaggaaggt ggcggccgct    4380
```

<210> SEQ ID NO 103
<211> LENGTH: 1460
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270
```

```
Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
            450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Gly Gly Gly Ser Gly Arg Ala Asp Ala Leu Asp
530                 535                 540

Asp Phe Asp Leu Asp Met Leu Gly Ser Asp Ala Leu Asp Asp Phe Asp
545                 550                 555                 560

Leu Asp Met Leu Gly Ser Asp Ala Leu Asp Asp Phe Asp Leu Asp Met
            565                 570                 575

Leu Gly Ser Asp Ala Leu Asp Asp Phe Asp Leu Asp Met Leu Ile Asn
            580                 585                 590

Gly Gly Gly Gly Ser Met Arg Lys Pro Ala Phe Leu Ser Gly Glu Gln
            595                 600                 605

Lys Lys Ala Ile Val Asp Leu Leu Phe Lys Thr Asn Arg Lys Val Thr
610                 615                 620

Val Lys Gln Leu Lys Glu Asp Tyr Phe Lys Lys Ile Glu Cys Phe Asp
625                 630                 635                 640

Ser Val Glu Ile Ser Gly Val Glu Asp Arg Phe Asn Ala Ser Leu Gly
                645                 650                 655

Thr Tyr His Asp Leu Leu Lys Ile Ile Lys Asp Lys Asp Phe Leu Asp
            660                 665                 670

Asn Glu Glu Asn Glu Asp Ile Leu Glu Asp Ile Val Leu Thr Leu Thr
            675                 680                 685

Leu Phe Glu Asp Arg Glu Met Ile Glu Glu Arg Leu Lys Thr Tyr Ala
```

690             695             700
His Leu Phe Asp Asp Lys Val Met Lys Gln Leu Lys Arg Arg Tyr
705                 710             715             720

Thr Gly Trp Gly Arg Leu Ser Arg Lys Leu Ile Asn Gly Ile Arg Asp
                    725             730             735

Lys Gln Ser Gly Lys Thr Ile Leu Asp Phe Leu Lys Ser Asp Gly Phe
                740             745             750

Ala Asn Arg Asn Phe Met Gln Leu Ile His Asp Asp Ser Leu Thr Phe
            755             760             765

Lys Glu Asp Ile Gln Lys Ala Gln Val Ser Gly Gln Gly Asp Ser Leu
        770             775             780

His Glu His Ile Ala Asn Leu Ala Gly Ser Pro Ala Ile Lys Lys Gly
785             790             795             800

Ile Leu Gln Thr Val Lys Val Val Asp Glu Leu Val Lys Val Met Gly
                805             810             815

Arg His Lys Pro Glu Asn Ile Val Ile Glu Met Ala Arg Glu Asn Gln
                    820             825             830

Thr Thr Gln Lys Gly Gln Lys Asn Ser Arg Glu Arg Met Lys Arg Ile
                835             840             845

Glu Glu Gly Ile Lys Glu Leu Gly Ser Gln Ile Leu Lys Glu His Pro
    850             855             860

Val Glu Asn Thr Gln Leu Gln Asn Glu Lys Leu Tyr Leu Tyr Tyr Leu
865             870             875             880

Gln Asn Gly Arg Asp Met Tyr Val Asp Gln Glu Leu Asp Ile Asn Arg
                885             890             895

Leu Ser Asp Tyr Asp Val Asp Ala Ile Val Pro Gln Ser Phe Leu Lys
                900             905             910

Asp Asp Ser Ile Asp Asn Lys Val Leu Thr Arg Ser Asp Lys Asn Arg
            915             920             925

Gly Lys Ser Asp Asn Val Pro Ser Glu Glu Val Val Lys Lys Met Lys
        930             935             940

Asn Tyr Trp Arg Gln Leu Leu Asn Ala Lys Leu Ile Thr Gln Arg Lys
945             950             955             960

Phe Asp Asn Leu Thr Lys Ala Glu Arg Gly Gly Leu Ser Glu Leu Asp
                965             970             975

Lys Ala Gly Phe Ile Lys Arg Gln Leu Val Glu Thr Arg Gln Ile Thr
            980             985             990

Lys His Val Ala Gln Ile Leu Asp Ser Arg Met Asn Thr Lys Tyr Asp
        995             1000            1005

Glu Asn Asp Lys Leu Ile Arg Glu Val Lys Val Ile Thr Leu Lys
1010            1015            1020

Ser Lys Leu Val Ser Asp Phe Arg Lys Asp Phe Gln Phe Tyr Lys
    1025            1030            1035

Val Arg Glu Ile Asn Asn Tyr His His Ala His Asp Ala Tyr Leu
        1040            1045            1050

Asn Ala Val Val Gly Thr Ala Leu Ile Lys Lys Tyr Pro Lys Leu
    1055            1060            1065

Glu Ser Glu Phe Val Tyr Gly Asp Tyr Lys Val Tyr Asp Val Arg
    1070            1075            1080

Lys Met Ile Ala Lys Ser Glu Gln Glu Ile Gly Lys Ala Thr Ala
    1085            1090            1095

Lys Tyr Phe Phe Tyr Ser Asn Ile Met Asn Phe Phe Lys Thr Glu
    1100            1105            1110

Ile Thr Leu Ala Asn Gly Glu Ile Arg Lys Arg Pro Leu Ile Glu
1115                1120                1125

Thr Asn Gly Glu Thr Gly Glu Ile Val Trp Asp Lys Gly Arg Asp
    1130                1135                1140

Phe Ala Thr Val Arg Lys Val Leu Ser Met Pro Gln Val Asn Ile
1145                1150                1155

Val Lys Lys Thr Glu Val Gln Thr Gly Gly Phe Ser Lys Glu Ser
1160                1165                1170

Ile Leu Pro Lys Arg Asn Ser Asp Lys Leu Ile Ala Arg Lys Lys
1175                1180                1185

Asp Trp Asp Pro Lys Lys Tyr Gly Gly Phe Asp Ser Pro Thr Val
1190                1195                1200

Ala Tyr Ser Val Leu Val Val Ala Lys Val Glu Lys Gly Lys Ser
1205                1210                1215

Lys Lys Leu Lys Ser Val Lys Glu Leu Leu Gly Ile Thr Ile Met
1220                1225                1230

Glu Arg Ser Ser Phe Glu Lys Asn Pro Ile Asp Phe Leu Glu Ala
1235                1240                1245

Lys Gly Tyr Lys Glu Val Lys Lys Asp Leu Ile Ile Lys Leu Pro
1250                1255                1260

Lys Tyr Ser Leu Phe Glu Leu Glu Asn Gly Arg Lys Arg Met Leu
1265                1270                1275

Ala Ser Ala Gly Glu Leu Gln Lys Gly Asn Glu Leu Ala Leu Pro
1280                1285                1290

Ser Lys Tyr Val Asn Phe Leu Tyr Leu Ala Ser His Tyr Glu Lys
1295                1300                1305

Leu Lys Gly Ser Pro Glu Asp Asn Glu Gln Lys Gln Leu Phe Val
1310                1315                1320

Glu Gln His Lys His Tyr Leu Asp Glu Ile Ile Glu Gln Ile Ser
1325                1330                1335

Glu Phe Ser Lys Arg Val Ile Leu Ala Asp Ala Asn Leu Asp Lys
1340                1345                1350

Val Leu Ser Ala Tyr Asn Lys His Arg Asp Lys Pro Ile Arg Glu
1355                1360                1365

Gln Ala Glu Asn Ile Ile His Leu Phe Thr Leu Thr Asn Leu Gly
1370                1375                1380

Ala Pro Ala Ala Phe Lys Tyr Phe Asp Thr Thr Ile Asp Arg Lys
1385                1390                1395

Arg Tyr Thr Ser Thr Lys Glu Val Leu Asp Ala Thr Leu Ile His
1400                1405                1410

Gln Ser Ile Thr Gly Leu Tyr Glu Thr Arg Ile Asp Leu Ser Gln
1415                1420                1425

Leu Gly Gly Asp Ser Ala Gly Gly Gly Ser Gly Gly Gly
1430                1435                1440

Ser Gly Gly Gly Gly Ser Gly Pro Lys Lys Lys Arg Lys Val Ala
1445                1450                1455

Ala Ala
1460

<210> SEQ ID NO 104
<211> LENGTH: 4385
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 104

```
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga agaacctgat cggagccctg ctgttcgaca cggcgaaac agccgaggcc      180
acccggctga agagaaccgc cagaagaaga tacaccagac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag tacccaccca tctaccaccct gagaaagaaa   420
ctggtggaca gcaccgacaa ggccgacctg cggctgatct atctggccct ggcccacatg     480
atcaagttcc ggggccactt cctgatcgag ggcgacctga ccccgacaa cagcgacgtg     540
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga tggcctgtt cggcaacctg      720
attgccctga gcctgggcct gacccccaac ttcaagagca acttcgacct ggccgaggat     780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccccctgag cgcctctatg   960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcgcaag   1200
cagcggaccc tcgacaacgg cagcatcccc caccagatcc acctgggaga gctgcacgcc   1260
attctgcggc ggcaggaaga ttttttaccca ttcctgaagg acaaccggga aaagatcgag   1320
aagatcctga ccttccgcat ccctactac gtgggccctc tggccagggg aaacagcaga    1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaggag ggggggcag cggacgggct    1620
gacgcattgg acgattttga tctggatatg ctgggaagtg acgccctcga tgattttgac   1680
cttgacatgc ttggttcgga tgcccttgat gactttgacc tcgacatgct cggcagtgac   1740
gcccttgatg atttcgacct ggacatgctg attaacggcg gggaggctc catgagaaag   1800
cccgccttcc tgagcggcga gcagaaaaag gccatcgtgg acctgctgtt caagaccaac   1860
cggaaagtga ccgtgaagca gctgaaagag gactacttca gaaaatcga gtgcttcgac   1920
tccgtggaaa tctccggcgt ggaagatcgg ttcaacgcct ccctgggcac ataccacgat   1980
ctgctgaaaa ttatcaagga caaggacttc ctggacaatg aggaaaacga ggacattctg   2040
gaagatatcg tgctgaccct gacactgttt gaggacagag atgatcga ggaacggctg     2100
aaaacctatg cccacctgtt cgacgacaaa gtgatgaagc agctgaagcg gcggagatac    2160
accggctggg gcaggctgag ccggaagctg atcaacggca tccgggacaa gcagtccggc    2220
```

-continued

```
aagacaatcc tggatttcct gaagtccgac ggcttcgcca acagaaactt catgcagctg    2280
atccacgacg acagcctgac ctttaaagag gacatccaga aagcccaggt gtccggccag    2340
ggcgatagcc tgcacgagca cattgccaat ctggccggca gccccgccat taagaagggc    2400
atcctgcaga cagtgaaggt ggtggacgag ctcgtgaaag tgatgggccg gcacaagccc    2460
gagaacatcg tgatcgaaat ggccagagag aaccagacca cccagaaggg acagaagaac    2520
agccgcgaga gaatgaagcg gatcgaagag ggcatcaaag agctgggcag ccagatcctg    2580
aaagaacacc ccgtggaaaa cacccagctg cagaacgaga gctgtacct gtactacctg     2640 cagaatgggc gggatatgta cgtggaccag gaactggaca tcaaccggct gtccgactac    2700
gatgtggacg ctatcgtgcc tcagagcttt ctgaaggacg actccatcga caacaaggtg    2760
ctgaccagaa gcgacaagaa ccggggcaag agcgacaacg tgccctccga agaggtcgtg    2820
aagaagatga agaactactg gcggcagctg ctgaacgcca agctgattac ccagagaaag    2880
ttcgacaatc tgaccaaggc cgagagaggc ggcctgagcg aactggataa ggccggcttc    2940
atcaagagac agctggtgga aacccggcag atcacaaagc acgtggcaca gatcctggac    3000
tcccggatga acactaagta cgacgagaat gacaagctga tccgggaagt gaaagtgatc    3060
accctgaagt ccaagctggt gtccgatttc cggaaggatt tccagtttta caaagtgcgc    3120
gagatcaaca actaccacca cgcccacgac gcctacctga acgccgtcgt gggaaccgcc    3180
ctgatcaaaa agtaccctaa gctggaaagc gagttcgtgt acggcgacta caaggtgtac    3240
gacgtgcgga agatgatcgc caagagcgag caggaaatcg gcaaggctac cgccaagtac    3300
ttcttctaca gcaacatcat gaacttttc aagaccgaga ttaccctggc caacggcgag    3360
atccggaagc ggcctctgat cgagacaaac ggcgaaaccg gggagatcgt gtgggataag    3420
ggccgggatt ttgccaccgt gcggaaagtg ctgagcatgc ccaagtgaa tatcgtgaaa     3480 aagaccgagg tgcagacagg cggcttcagc aaagagtcta tcctgcccaa gaggaacagc    3540
gataagctga tcgccagaaa gaaggactgg gaccctaaga agtacggcgg cttcgacagc    3600
cccaccgtgg cctattctgt gctggtggtg gccaaagtgg aaaagggcaa gtccaagaaa    3660
ctgaagagtg tgaaagagct gctggggatc accatcatgg aaagaagcag cttcgagaag    3720
aatcccatcg actttctgga agccaagggc tacaaagaag tgaaaaagga cctgatcatc    3780
aagctgccta gtactccct gttcgagctg aaaacggcc ggaagagaat gctggcctct     3840
gccggcgaac tgcagaaggg aaacgaactg gccctgccct ccaaatatgt gaacttcctg    3900
tacctggcca gccactatga aagctgaag ggctccccccg aggataatga gcagaaacag    3960
ctgtttgtgg aacagcacaa gcactacctg gacgagatca tcgagcagat cagcgagttc    4020
tccaagagag tgatcctggc cgacgctaat ctggacaaaa tgctgtccgc ctacaacaag    4080
caccgggata agcccatcag agagcaggcc gagaatatca tccacctgtt taccctgacc    4140
aatctgggag cccctgccgc cttcaagtac tttgacacca ccatcgaccg gaagaggtac    4200
accagcacca agaggtgct ggacgccacc ctgatccacc agagcatcac cggcctgtac    4260
gagacacgga tcgacctgtc tcagctggga ggcgacagcg ctggaggagg tggaagcgga    4320
ggaggaggaa gcggagaggaggaggaggagg aggtagcgga cctaagaaaa gaggaaggt ggcggccgct 4380 gctag                                                              4385
```

<210> SEQ ID NO 105
<211> LENGTH: 1461
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

```
Thr Glu Glu Leu Leu Val Lys Leu Asn Arg Glu Asp Leu Arg Lys
385                 390                 395                 400

Gln Arg Thr Phe Asp Asn Gly Ser Ile Pro His Gln Ile His Leu Gly
            405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
                515                 520                 525

Val Thr Glu Gly Gly Gly Gly Ser Gly Arg Ala Asp Ala Leu Asp
        530                 535                 540

Asp Phe Asp Leu Asp Met Leu Gly Ser Asp Ala Leu Asp Asp Phe Asp
545                 550                 555                 560

Leu Asp Met Leu Gly Ser Asp Ala Leu Asp Asp Phe Asp Leu Asp Met
                565                 570                 575

Leu Gly Ser Asp Ala Leu Asp Asp Phe Asp Leu Asp Met Leu Ile Asn
                580                 585                 590

Gly Gly Gly Gly Ser Met Arg Lys Pro Ala Phe Leu Ser Gly Glu Gln
                595                 600                 605

Lys Lys Ala Ile Val Asp Leu Leu Phe Lys Thr Asn Arg Lys Val Thr
            610                 615                 620

Val Lys Gln Leu Lys Glu Asp Tyr Phe Lys Lys Ile Glu Cys Phe Asp
625                 630                 635                 640

Ser Val Glu Ile Ser Gly Val Glu Asp Arg Phe Asn Ala Ser Leu Gly
                645                 650                 655

Thr Tyr His Asp Leu Leu Lys Ile Ile Lys Asp Lys Asp Phe Leu Asp
            660                 665                 670

Asn Glu Glu Asn Glu Asp Ile Leu Glu Asp Ile Val Leu Thr Leu Thr
            675                 680                 685

Leu Phe Glu Asp Arg Glu Met Ile Glu Glu Arg Leu Lys Thr Tyr Ala
        690                 695                 700

His Leu Phe Asp Asp Lys Val Met Lys Gln Leu Lys Arg Arg Arg Tyr
705                 710                 715                 720

Thr Gly Trp Gly Arg Leu Ser Arg Lys Leu Ile Asn Gly Ile Arg Asp
            725                 730                 735

Lys Gln Ser Gly Lys Thr Ile Leu Asp Phe Leu Lys Ser Asp Gly Phe
            740                 745                 750

Ala Asn Arg Asn Phe Met Gln Leu Ile His Asp Asp Ser Leu Thr Phe
        755                 760                 765

Lys Glu Asp Ile Gln Lys Ala Gln Val Ser Gly Gln Gly Asp Ser Leu
    770                 775                 780

His Glu His Ile Ala Asn Leu Ala Gly Ser Pro Ala Ile Lys Lys Gly
785                 790                 795                 800
```

```
Ile Leu Gln Thr Val Lys Val Asp Glu Leu Val Lys Val Met Gly
                805             810             815

Arg His Lys Pro Glu Asn Ile Val Ile Glu Met Ala Arg Glu Asn Gln
                820             825             830

Thr Thr Gln Lys Gly Gln Lys Asn Ser Arg Glu Arg Met Lys Arg Ile
            835             840             845

Glu Glu Gly Ile Lys Glu Leu Gly Ser Gln Ile Leu Lys Glu His Pro
850             855             860

Val Glu Asn Thr Gln Leu Gln Asn Glu Lys Leu Tyr Leu Tyr Tyr Leu
865             870             875             880

Gln Asn Gly Arg Asp Met Tyr Val Asp Gln Glu Leu Asp Ile Asn Arg
                885             890             895

Leu Ser Asp Tyr Asp Val Asp Ala Ile Val Pro Gln Ser Phe Leu Lys
                900             905             910

Asp Asp Ser Ile Asp Asn Lys Val Leu Thr Arg Ser Asp Lys Asn Arg
                915             920             925

Gly Lys Ser Asp Asn Val Pro Ser Glu Glu Val Val Lys Met Lys
930             935             940

Asn Tyr Trp Arg Gln Leu Leu Asn Ala Lys Leu Ile Thr Gln Arg Lys
945             950             955             960

Phe Asp Asn Leu Thr Lys Ala Glu Arg Gly Gly Leu Ser Glu Leu Asp
                965             970             975

Lys Ala Gly Phe Ile Lys Arg Gln Leu Val Glu Thr Arg Gln Ile Thr
                980             985             990

Lys His Val Ala Gln Ile Leu Asp Ser Arg Met Asn Thr Lys Tyr Asp
                995             1000            1005

Glu Asn Asp Lys Leu Ile Arg Glu Val Lys Val Ile Thr Leu Lys
        1010            1015            1020

Ser Lys Leu Val Ser Asp Phe Arg Lys Asp Phe Gln Phe Tyr Lys
        1025            1030            1035

Val Arg Glu Ile Asn Asn Tyr His His Ala His Asp Ala Tyr Leu
        1040            1045            1050

Asn Ala Val Val Gly Thr Ala Leu Ile Lys Lys Tyr Pro Lys Leu
        1055            1060            1065

Glu Ser Glu Phe Val Tyr Gly Asp Tyr Lys Val Tyr Asp Val Arg
        1070            1075            1080

Lys Met Ile Ala Lys Ser Glu Gln Glu Ile Gly Lys Ala Thr Ala
        1085            1090            1095

Lys Tyr Phe Phe Tyr Ser Asn Ile Met Asn Phe Phe Lys Thr Glu
        1100            1105            1110

Ile Thr Leu Ala Asn Gly Glu Ile Arg Lys Arg Pro Leu Ile Glu
        1115            1120            1125

Thr Asn Gly Glu Thr Gly Glu Ile Val Trp Asp Lys Gly Arg Asp
        1130            1135            1140

Phe Ala Thr Val Arg Lys Val Leu Ser Met Pro Gln Val Asn Ile
        1145            1150            1155

Val Lys Lys Thr Glu Val Gln Thr Gly Gly Phe Ser Lys Glu Ser
        1160            1165            1170

Ile Leu Pro Lys Arg Asn Ser Asp Lys Leu Ile Ala Arg Lys Lys
        1175            1180            1185

Asp Trp Asp Pro Lys Lys Tyr Gly Gly Phe Asp Ser Pro Thr Val
        1190            1195            1200

Ala Tyr Ser Val Leu Val Val Ala Lys Val Glu Lys Gly Lys Ser
```

Lys Lys Leu Lys Ser Val Lys Glu Leu Leu Gly Ile Thr Ile Met
1220                1225                1230

Glu Arg Ser Ser Phe Glu Lys Asn Pro Ile Asp Phe Leu Glu Ala
     1235                1240                1245

Lys Gly Tyr Lys Glu Val Lys Lys Asp Leu Ile Ile Lys Leu Pro
1250                1255                1260

Lys Tyr Ser Leu Phe Glu Leu Glu Asn Gly Arg Lys Arg Met Leu
     1265                1270                1275

Ala Ser Ala Gly Glu Leu Gln Lys Gly Asn Glu Leu Ala Leu Pro
1280                1285                1290

Ser Lys Tyr Val Asn Phe Leu Tyr Leu Ala Ser His Tyr Glu Lys
     1295                1300                1305

Leu Lys Gly Ser Pro Glu Asp Asn Glu Gln Lys Gln Leu Phe Val
1310                1315                1320

Glu Gln His Lys His Tyr Leu Asp Glu Ile Ile Glu Gln Ile Ser
     1325                1330                1335

Glu Phe Ser Lys Arg Val Ile Leu Ala Asp Ala Asn Leu Asp Lys
1340                1345                1350

Val Leu Ser Ala Tyr Asn Lys His Arg Asp Lys Pro Ile Arg Glu
     1355                1360                1365

Gln Ala Glu Asn Ile Ile His Leu Phe Thr Leu Thr Asn Leu Gly
1370                1375                1380

Ala Pro Ala Ala Phe Lys Tyr Phe Asp Thr Thr Ile Asp Arg Lys
     1385                1390                1395

Arg Tyr Thr Ser Thr Lys Glu Val Leu Asp Ala Thr Leu Ile His
1400                1405                1410

Gln Ser Ile Thr Gly Leu Tyr Glu Thr Arg Ile Asp Leu Ser Gln
     1415                1420                1425

Leu Gly Gly Asp Ser Ala Gly Gly Gly Ser Gly Gly Gly Gly
1430                1435                1440

Ser Gly Gly Gly Gly Ser Gly Pro Lys Lys Lys Arg Lys Val Ala
     1445                1450                1455

Ala Ala Ala
1460

<210> SEQ ID NO 106
<211> LENGTH: 4768
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga gaaacctgat cggagccctg ctgttcgaca gcggcgaaac agccgaggcc     180
acccggctga agagaaccgc cagaagaaga taccaccaga ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag taccccacca tctaccacct gagaaagaaa     420

```
ctggtggaca gcaccgacaa ggccgacctg cggctgatct atctggccct ggcccacatg    480
atcaagttcc ggggccactt cctgatcgag ggcgacctga accccgacaa cagcgacgtg    540
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggcaacctg    720
attgccctga gcctgggcct gacccccaac ttcaagagca acttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccccctgag cgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttttaccca ttcctgaagg acaacaggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaggag ggggaggcag cccttcaggg   1620
cagatcagca accaggccct ggctctggcc cctagtccg ctccagtgct ggcccagact   1680
atggtgccct ctagtgctat ggtgcctctg gcccagccac tgctccagc ccctgtgctg   1740
accccaggac cacccagtc actgagcgct ccagtgccca gtctacaca ggccggcgag   1800
gggactctga gtgaagctct gctgcacctg cagttcgacg ctgatgagga cctgggagct   1860
ctgctgggga acagcaccga tcccggagtg ttcacagatc tggcctccgt ggacaactct   1920
gagtttcagc agctgctgaa tcagggcgtg tccatgtctc atagtacagc cgaaccaatg   1980
ctgatggagt accccgaagc cattacccgg ctggtgaccg cagccagcg gccccccgac   2040
cccgctccaa ctcccctggg aaccagcggc ctgcctaatg ggctgtccgg agatgaagac   2100
ttctcaagca tcgctgatat ggactttagt gccctgctgt cacagatttc ctctagtggg   2160
cagggagggg ggggcagcat gagaaagccc gccttcctga gcggcgagca gaaaaaggcc   2220
atcgtggacc tgctgttcaa gaccaaccgg aaagtgaccg tgaagcagct gaaagaggac   2280
tacttcaaga aaatcgagtg cttcgactcc gtggaaatct ccggcgtgga agatcggttc   2340
aacgcctccc tgggcacata ccacgatctg ctgaaaatta tcaaggacaa ggacttcctg   2400
gacaatgagg aaaacgagga cattctggaa gatatcgtgc tgaccctgac actgtttgag   2460
gacagagaga tgatcgagga acggctgaaa acctatgccc acctgttcga cgacaaagtg   2520
atgaagcagc tgaagcggcg cgagatacac cggctgggca ggctgagccg gaagctgatc   2580
aacggcatcc gggacaagca gtccggcaag acaatcctgg atttcctgaa gtccgacggc   2640
ttcgccaaca gaaacttcat gcagctgatc cacgacgaca gcctgacctt taaagaggac   2700
atccagaaag cccaggtgtc cggccagggc gatagcctgc acgagcacat tgccaatctg   2760
gccggcagcc ccgccattaa gaagggcatc ctgcagacag tgaaggtggt ggacgagctc   2820
```

```
gtgaaagtga tgggccggca caagcccgag aacatcgtga tcgaaatggc cagagagaac    2880
cagaccaccc agaagggaca gaagaacagc cgcgagagaa tgaagcggat cgagagggc    2940 atcaaagagc tgggcagcca gatcctgaaa gaacaccccg tggaaaacac ccagctgcag    3000
aacgagaagc tgtacctgta ctacctgcag aatgggcggg atatgtacgt ggaccaggaa    3060
ctggacatca accggctgtc cgactacgat gtggacgcta tcgtgcctca gagctttctg    3120
aaggacgact ccatcgacaa caaggtgctg accagaagcg acaagaaccg ggcaagagc    3180 gacaacgtgc cctccgaaga ggtcgtgaag aagatgaaga actactggcg gcagctgctg    3240
aacgccaagc tgattaccca gagaaagttc gacaatctga ccaaggccga gagaggcggc    3300
ctgagcgaac tggataaggc cggcttcatc aagagacagc tggtggaaac ccggcagatc    3360
acaaagcacg tggcacagat cctggactcc cggatgaaca ctaagtacga cgagaatgac    3420
aagctgatcc gggaagtgaa agtgatcacc ctgaagtcca gctggtgtc cgatttccgg    3480 aaggatttcc agttttacaa agtgcgcgag atcaacaact accaccacgc ccacgacgcc    3540
tacctgaacg ccgtcgtggg aaccgccctg atcaaaaagt accctaagct ggaaagcgag    3600
ttcgtgtacg gcgactacaa ggtgtacgac gtgcggaaga tgatcgccaa gagcgagcag    3660
gaaatcggca aggctaccgc caagtacttc ttctacagca acatcatgaa cttttttcaag    3720 accgagatta ccctggccaa cggcgagatc cggaagcggc ctctgatcga gacaaacggc    3780
gaaaccgggg agatcgtgtg ggataagggc cgggattttg ccaccgtgcg gaaagtgctg    3840
agcatgcccc aagtgaatat cgtgaaaaag accgaggtgc agacaggcgg cttcagcaaa    3900
gagtctatcc tgcccaagag gaacagcgat aagctgatcg ccagaaagaa ggactgggac    3960
cctaagaagt acggcggctt cgacagcccc accgtggcct attctgtgct ggtggtggcc    4020
aaagtggaaa agggcaagtc caagaaactg aagagtgtga agagctgct ggggatcacc    4080 atcatggaaa gaagcagctt cgagaagaat cccatcgact ttctggaagc caagggctac    4140
aaagaagtga aaaaggacct gatcatcaag ctgcctaagt actccctgtt cgagctggaa    4200
aacggccgga gagaatgct ggcctctgcc ggcgaactgc agaagggaaa cgaactggcc    4260
ctgccctcca aatatgtgaa cttcctgtac ctggccagcc actatgagaa gctgaagggc    4320 tccccccgagg ataatgagca gaaacagctg tttgtggaac agcacaagca ctacctggac    4380
gagatcatcg agcagatcag cgagttctcc aagagagtga tcctggccga cgctaatctg    4440
gacaaagtgc tgtccgccta caacaagcac cgggataagc ccatcagaga gcaggccgag    4500
aatatcatcc acctgtttac cctgaccaat ctgggagccc ctgccgcctt caagtactttt    4560 gacaccacca tcgaccggaa gaggtacacc agcaccaaag aggtgctgga cgccaccctg    4620
atccaccaga gcatcaccgg cctgtacgag acacggatcg acctgtctca gctgggaggc    4680
gacagcgctg aggaggtgg aagcggagga ggaggaagcg gaggaggagg tagcggacct    4740
aagaaaaaga ggaaggtggc ggccgctg                                       4768
```

<210> SEQ ID NO 107
<211> LENGTH: 1589
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 107

```
Asp Lys Lys Tyr Ser Ile Gly Leu Ala Ile Gly Thr Asn Ser Val Gly
 1               5                  10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
                100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
```

```
            420                 425                 430
Lys Asp Asn Arg Glu Lys Ile Glu Lys Ile Leu Thr Phe Arg Ile Pro
                435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Gly Gly Gly Ser Pro Ser Gly Gln Ile Ser Asn
    530                 535                 540

Gln Ala Leu Ala Leu Ala Pro Ser Ser Ala Pro Val Leu Ala Gln Thr
545                 550                 555                 560

Met Val Pro Ser Ser Ala Met Val Pro Leu Ala Gln Pro Pro Ala Pro
                565                 570                 575

Ala Pro Val Leu Thr Pro Gly Pro Pro Gln Ser Leu Ser Ala Pro Val
            580                 585                 590

Pro Lys Ser Thr Gln Ala Gly Glu Gly Thr Leu Ser Glu Ala Leu Leu
        595                 600                 605

His Leu Gln Phe Asp Ala Asp Glu Asp Leu Gly Ala Leu Leu Gly Asn
    610                 615                 620

Ser Thr Asp Pro Gly Val Phe Thr Asp Leu Ala Ser Val Asp Asn Ser
625                 630                 635                 640

Glu Phe Gln Gln Leu Leu Asn Gln Gly Val Ser Met Ser His Ser Thr
                645                 650                 655

Ala Glu Pro Met Leu Met Glu Tyr Pro Glu Ala Ile Thr Arg Leu Val
            660                 665                 670

Thr Gly Ser Gln Arg Pro Pro Asp Pro Ala Pro Thr Pro Leu Gly Thr
        675                 680                 685

Ser Gly Leu Pro Asn Gly Leu Ser Gly Asp Glu Asp Phe Ser Ser Ile
    690                 695                 700

Ala Asp Met Asp Phe Ser Ala Leu Leu Ser Gln Ile Ser Ser Ser Gly
705                 710                 715                 720

Gln Gly Gly Gly Gly Ser Met Arg Lys Pro Ala Phe Leu Ser Gly Glu
                725                 730                 735

Gln Lys Lys Ala Ile Val Asp Leu Leu Phe Lys Thr Asn Arg Lys Val
            740                 745                 750

Thr Val Lys Gln Leu Lys Glu Asp Tyr Phe Lys Ile Glu Cys Phe
        755                 760                 765

Asp Ser Val Glu Ile Ser Gly Val Glu Asp Arg Phe Asn Ala Ser Leu
    770                 775                 780

Gly Thr Tyr His Asp Leu Leu Lys Ile Ile Lys Asp Lys Asp Phe Leu
785                 790                 795                 800

Asp Asn Glu Glu Asn Glu Asp Ile Leu Glu Asp Ile Val Leu Thr Leu
                805                 810                 815

Thr Leu Phe Glu Asp Arg Glu Met Ile Glu Glu Arg Leu Lys Thr Tyr
            820                 825                 830

Ala His Leu Phe Asp Asp Lys Val Met Lys Gln Leu Lys Arg Arg Arg
        835                 840                 845
```

-continued

Tyr Thr Gly Trp Gly Arg Leu Ser Arg Lys Leu Ile Asn Gly Ile Arg
850                 855                 860

Asp Lys Gln Ser Gly Lys Thr Ile Leu Asp Phe Leu Lys Ser Asp Gly
865                 870                 875                 880

Phe Ala Asn Arg Asn Phe Met Gln Leu Ile His Asp Asp Ser Leu Thr
            885                 890                 895

Phe Lys Glu Asp Ile Gln Lys Ala Gln Val Ser Gly Gln Gly Asp Ser
        900                 905                 910

Leu His Glu His Ile Ala Asn Leu Ala Gly Ser Pro Ala Ile Lys Lys
    915                 920                 925

Gly Ile Leu Gln Thr Val Lys Val Val Asp Glu Leu Val Lys Val Met
930                 935                 940

Gly Arg His Lys Pro Glu Asn Ile Val Ile Glu Met Ala Arg Glu Asn
945                 950                 955                 960

Gln Thr Thr Gln Lys Gly Gln Lys Asn Ser Arg Glu Arg Met Lys Arg
            965                 970                 975

Ile Glu Glu Gly Ile Lys Glu Leu Gly Ser Gln Ile Leu Lys Glu His
        980                 985                 990

Pro Val Glu Asn Thr Gln Leu Gln Asn Glu Lys Leu Tyr Leu Tyr Tyr
    995                 1000                1005

Leu Gln Asn Gly Arg Asp Met Tyr Val Asp Gln Glu Leu Asp Ile
    1010                1015                1020

Asn Arg Leu Ser Asp Tyr Asp Val Asp Ala Ile Val Pro Gln Ser
    1025                1030                1035

Phe Leu Lys Asp Asp Ser Ile Asp Asn Lys Val Leu Thr Arg Ser
    1040                1045                1050

Asp Lys Asn Arg Gly Lys Ser Asp Asn Val Pro Ser Glu Glu Val
    1055                1060                1065

Val Lys Lys Met Lys Asn Tyr Trp Arg Gln Leu Leu Asn Ala Lys
    1070                1075                1080

Leu Ile Thr Gln Arg Lys Phe Asp Asn Leu Thr Lys Ala Glu Arg
    1085                1090                1095

Gly Gly Leu Ser Glu Leu Asp Lys Ala Gly Phe Ile Lys Arg Gln
    1100                1105                1110

Leu Val Glu Thr Arg Gln Ile Thr Lys His Val Ala Gln Ile Leu
    1115                1120                1125

Asp Ser Arg Met Asn Thr Lys Tyr Asp Glu Asn Asp Lys Leu Ile
    1130                1135                1140

Arg Glu Val Lys Val Ile Thr Leu Lys Ser Lys Leu Val Ser Asp
    1145                1150                1155

Phe Arg Lys Asp Phe Gln Phe Tyr Lys Val Arg Glu Ile Asn Asn
    1160                1165                1170

Tyr His His Ala His Asp Ala Tyr Leu Asn Ala Val Val Gly Thr
    1175                1180                1185

Ala Leu Ile Lys Lys Tyr Pro Lys Leu Glu Ser Glu Phe Val Tyr
    1190                1195                1200

Gly Asp Tyr Lys Val Tyr Asp Val Arg Lys Met Ile Ala Lys Ser
    1205                1210                1215

Glu Gln Glu Ile Gly Lys Ala Thr Ala Lys Tyr Phe Phe Tyr Ser
    1220                1225                1230

Asn Ile Met Asn Phe Phe Lys Thr Glu Ile Thr Leu Ala Asn Gly
    1235                1240                1245

Glu Ile Arg Lys Arg Pro Leu Ile Glu Thr Asn Gly Glu Thr Gly
1250            1255                1260

Glu Ile Val Trp Asp Lys Gly Arg Asp Phe Ala Thr Val Arg Lys
1265            1270                1275

Val Leu Ser Met Pro Gln Val Asn Ile Val Lys Lys Thr Glu Val
1280            1285                1290

Gln Thr Gly Gly Phe Ser Lys Glu Ser Ile Leu Pro Lys Arg Asn
1295            1300                1305

Ser Asp Lys Leu Ile Ala Arg Lys Lys Asp Trp Asp Pro Lys Lys
1310            1315                1320

Tyr Gly Gly Phe Asp Ser Pro Thr Val Ala Tyr Ser Val Leu Val
1325            1330                1335

Val Ala Lys Val Glu Lys Gly Lys Ser Lys Lys Leu Lys Ser Val
1340            1345                1350

Lys Glu Leu Leu Gly Ile Thr Ile Met Glu Arg Ser Ser Phe Glu
1355            1360                1365

Lys Asn Pro Ile Asp Phe Leu Glu Ala Lys Gly Tyr Lys Glu Val
1370            1375                1380

Lys Lys Asp Leu Ile Ile Lys Leu Pro Lys Tyr Ser Leu Phe Glu
1385            1390                1395

Leu Glu Asn Gly Arg Lys Arg Met Leu Ala Ser Ala Gly Glu Leu
1400            1405                1410

Gln Lys Gly Asn Glu Leu Ala Leu Pro Ser Lys Tyr Val Asn Phe
1415            1420                1425

Leu Tyr Leu Ala Ser His Tyr Glu Lys Leu Lys Gly Ser Pro Glu
1430            1435                1440

Asp Asn Glu Gln Lys Gln Leu Phe Val Glu Gln His Lys His Tyr
1445            1450                1455

Leu Asp Glu Ile Ile Glu Gln Ile Ser Glu Phe Ser Lys Arg Val
1460            1465                1470

Ile Leu Ala Asp Ala Asn Leu Asp Lys Val Leu Ser Ala Tyr Asn
1475            1480                1485

Lys His Arg Asp Lys Pro Ile Arg Glu Gln Ala Glu Asn Ile Ile
1490            1495                1500

His Leu Phe Thr Leu Thr Asn Leu Gly Ala Pro Ala Ala Phe Lys
1505            1510                1515

Tyr Phe Asp Thr Thr Ile Asp Arg Lys Arg Tyr Thr Ser Thr Lys
1520            1525                1530

Glu Val Leu Asp Ala Thr Leu Ile His Gln Ser Ile Thr Gly Leu
1535            1540                1545

Tyr Glu Thr Arg Ile Asp Leu Ser Gln Leu Gly Gly Asp Ser Ala
1550            1555                1560

Gly Gly Gly Gly Ser Gly Gly Gly Gly Ser Gly Gly Gly Gly Ser
1565            1570                1575

Gly Pro Lys Lys Lys Arg Lys Val Ala Ala Ala
1580            1585

<210> SEQ ID NO 108
<211> LENGTH: 4852
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108

```
ggccaccatg gacaagaagt acagcatcgg cctggccatc ggcaccaact ctgtgggctg      60
ggccgtgatc accgacgagt acaaggtgcc cagcaagaaa ttcaaggtgc tgggcaacac     120
cgaccggcac agcatcaaga agaacctgat cggagccctg ctgttcgaca cggcgaaac     180
agccgaggcc acccggctga agagaaccgc cagaagaaga taccagac ggaagaaccg     240
gatctgctat ctgcaagaga tcttcagcaa cgagatggcc aaggtggacg acagcttctt     300
ccacagactg gaagagtcct tcctggtgga agaggataag aagcacgagc ggcaccccat     360
cttcggcaac atcgtggacg aggtggccta ccacgagaag tacccaccca tctaccacct     420
gagaaagaaa ctggtggaca gcaccgacaa ggccgacctg cggctgatct atctggccct     480
ggcccacatg atcaagttcc ggggccactt cctgatcgag ggcgacctga accccgacaa     540
cagcgacgtg gacaagctgt tcatccagct ggtgcagacc tacaaccagc tgttcgagga     600
aaacccatc aacgccagcg cgtggacgc caaggccatc ctgtctgcca gactgagcaa     660
gagcagacgg ctggaaaatc tgatcgccca gctgccggc gagaagaaga atggcctgtt     720
cggcaacctg attgccctga gcctgggcct gaccccaac ttcaagagca cttcgacct     780
ggccgaggat gccaaactgc agctgagcaa ggacacctac gacgacgacc tggacaacct     840
gctggcccag atcggcgacc agtacgccga cctgtttctg gccgccaaga acctgtccga     900
cgccatcctg ctgagcgaca tcctgagagt gaacaccgag atcaccaagg ccccccctgag     960
cgcctctatg atcaagagat acgacgagca ccaccaggac ctgaccctgc tgaaagctct    1020
cgtgcggcag cagctgcctg agaagtacaa agagattttc ttcgaccaga gcaagaacgg    1080
ctacgccggc tacattgacg gcggagccag ccaggaagag ttctacaagt catcaagcc    1140
catcctggaa aagatggacg gcaccgagga actgctcgtg aagctgaaca gagaggacct    1200
gctgcggaag cagcggacct tcgacaacgg cagcatcccc caccagatcc acctgggaga    1260
gctgcacgcc attctgcggc ggcaggaaga tttttaccca ttcctgaagg acaaccggga    1320
aaagatcgag aagatcctga ccttccgcat ccctactac gtgggccctc tggccagggg    1380
aaacagcaga ttcgcctgga tgaccagaaa gagcgaggaa accatcaccc cctggaactt    1440
cgaggaagtg gtggacaagg cgcttccgc ccagagcttc atcgagcgga tgaccaactt    1500
cgataagaac ctgcccaacg agaaggtgct gcccaagcac agcctgctgt acgagtactt    1560
caccgtgtat aacgagctga ccaaagtgaa atacgtgacc gagggaggcg ggggaggctc    1620
cggtggtggg ggcagcggag gggggggcag cccttcaggg cagatcagca accaggccct    1680
ggctctggcc cctagctccg ctccagtgct ggcccagact atggtgccct ctagtgctat    1740
ggtgcctctg gccagccac ctgctccagc cctgtgctg accccaggac cacccagtc    1800
actgagcgct ccagtgccca gtctacaca ggccggcgag gggactctga gtgaagctct    1860
gctgcacctg cagttcgacg ctgatgagga cctgggagct ctgctgggga cagcaccga    1920
tcccggagtg ttcacagatc tggcctccgt ggacaactct gagtttcagc agctgctgaa    1980
tcagggcgtg tccatgtctc atagtacagc cgaaccaatg ctgatggagt accccgaagc    2040
cattacccgg ctggtgaccg gcagccagcg gcccccgac cccgctccaa ctcccctggg    2100
aaccagcggc ctgcctaatg gctgtccgg agatgaagac ttctcaagca tcgctgatat    2160
ggactttagt gccctgctgt cacagatttc ctctagtggg caggggcggg gaggctccgg    2220
tggtgggggc agcggagggg ggcagcat gagaaagccc gccttcctga gcggcgagca    2280
gaaaaaggcc atcgtggacc tgctgttcaa gaccaaccgg aaagtgaccg tgaagcagct    2340
```

```
gaaagaggac tacttcaaga aaatcgagtg cttcgactcc gtggaaatct ccggcgtgga    2400
agatcggttc aacgcctccc tgggcacata ccacgatctg ctgaaaatta tcaaggacaa    2460
ggacttcctg gacaatgagg aaaacgagga cattctggaa gatatcgtgc tgaccctgac    2520
actgtttgag gacagagaga tgatcgagga acggctgaaa acctatgccc acctgttcga    2580
cgacaaagtg atgaagcagc tgaagcggcg gagatacacc ggctggggca ggctgagccg    2640
gaagctgatc aacggcatcc gggacaagca gtccggcaag acaatcctgg atttcctgaa    2700
gtccgacggc ttcgccaaca gaaacttcat gcagctgatc cacgacgaca gcctgacctt    2760
taaagaggac atccagaaag cccaggtgtc cggccagggc gatagcctgc acgagcacat    2820
tgccaatctg gccggcagcc ccgccattaa gaagggcatc ctgcagacag tgaaggtggt    2880
ggacgagctc gtgaaagtga tgggccggca caagcccgag aacatcgtga tcgaaatggc    2940
cagagagaac cagaccaccc agaagggaca gaagaacagc cgcgagagaa tgaagcggat    3000
cgaagagggc atcaaagagc tgggcagcca gatcctgaaa gaacacccccg tggaaaacac    3060 ccagctgcag aacgagaagc tgtacctgta ctacctgcag aatgggcggg atatgtacgt    3120
ggaccaggaa ctggacatca accggctgtc cgactacgat gtggacgcta tcgtgcctca    3180
gagctttctg aaggacgact ccatcgacaa caaggtgctg accagaagcg acaagaaccg    3240
gggcaagagc gacaacgtgc cctccgaaga ggtcgtgaag aagatgaaga actactggcg    3300
gcagctgctg aacgccaagc tgattaccca gagaaagttc gacaatctga ccaaggccga    3360
gagaggcggc ctgagcgaac tggataaggc cggcttcatc aagagacagc tggtggaaac    3420
ccggcagatc acaaagcacg tggcacagat cctggactcc cggatgaaca ctaagtacga    3480
cgagaatgac aagctgatcc gggaagtgaa agtgatcacc ctgaagtcca gctggtgtc    3540 cgatttccgg aaggatttcc agttttacaa agtgcgcgag atcaacaact accaccacgc    3600
ccacgacgcc tacctgaacg ccgtcgtggg aaccgccctg atcaaaaagt accctaagct    3660
ggaaagcgag ttcgtgtacg gcgactacaa ggtgtacgac gtgcggaaga tgatcgccaa    3720
gagcgagcag gaaatcggca aggctaccgc caagtacttc ttctacagca acatcatgaa    3780 cttttttcaag accgagatta ccctggccaa cggcgagatc cggaagcggc ctctgatcga    3840
gacaaacggc gaaaccgggg agatcgtgtg ggataagggc cgggattttg ccaccgtgcg    3900
gaaagtgctg agcatgcccc aagtgaatat cgtgaaaaag accgaggtgc agacaggcgg    3960
cttcagcaaa gagtctatcc tgcccaagag gaacagcgat aagctgatcg ccagaaagaa    4020
ggactgggac cctaagaagt acggcggctt cgacagcccc accgtggcct attctgtgct    4080
ggtggtggcc aaagtggaaa agggcaagtc caagaaactg aagagtgtga aagagctgct    4140
ggggatcacc atcatggaaa gaagcagctt cgagaagaat ccatcgact ttctggaagc    4200 caagggctac aaagaagtga aaaaggacct gatcatcaag ctgcctaagt actccctgtt    4260
cgagctggaa aacggccgga gagaatgct ggcctctgcc ggcgaactgc agaagggaaa    4320
cgaactggcc ctgcccttcca aatatgtgaa cttcctgtac ctggccagcc actatgagaa    4380
gctgaagggc tccccccgagg ataatgagca gaaacagctg tttgtggaac agcacaagca    4440
ctacctggac gagatcatcg agcagatcag cgagttctcc aagagagtga tcctggccga    4500
cgctaatctg gacaaagtgc tgtccgccta caacaagcac cgggataagc ccatcagaga    4560
gcaggccgag aatatcatcc acctgtttac cctgaccaat ctgggagccc ctgccgcctt    4620
caagtacttt gacaccacca tcgaccggaa gaggtacacc agcaccaaag aggtgctgga    4680
```

-continued

```
cgccaccctg atccaccaga gcatcaccgg cctgtacgag acacggatcg acctgtctca   4740
gctgggaggc gacagcgctg gaggaggtgg aagcggagga ggaggaagcg gaggaggagg   4800
tagcggacct aagaaaaaga ggaaggtggc ggccgctgct agcggcagtg ga           4852
```

<210> SEQ ID NO 109
<211> LENGTH: 1613
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
```

```
                        325                 330                 335
Leu Val Arg Gln Gln Leu Pro Glu Lys Tyr Lys Glu Ile Phe Phe Asp
                340                 345                 350
Gln Ser Lys Asn Gly Tyr Ala Gly Tyr Ile Asp Gly Gly Ala Ser Gln
                355                 360                 365
Glu Glu Phe Tyr Lys Phe Ile Lys Pro Ile Leu Glu Lys Met Asp Gly
                370                 375                 380
Thr Glu Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
                420                 425                 430
Lys Asp Asn Arg Glu Lys Ile Glu Lys Ile Leu Thr Phe Arg Ile Pro
                435                 440                 445
Tyr Tyr Val Gly Pro Leu Ala Arg Gly Asn Ser Arg Phe Ala Trp Met
                450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
                500                 505                 510
Leu Tyr Glu Tyr Phe Thr Val Tyr Asn Glu Leu Thr Lys Val Lys Tyr
                515                 520                 525
Val Thr Glu Gly Gly Gly Gly Ser Gly Gly Gly Ser Gly Gly
                530                 535                 540
Gly Gly Ser Pro Ser Gly Gln Ile Ser Asn Gln Ala Leu Ala Leu Ala
545                 550                 555                 560
Pro Ser Ser Ala Pro Val Leu Ala Gln Thr Met Val Pro Ser Ser Ala
                565                 570                 575
Met Val Pro Leu Ala Gln Pro Pro Ala Pro Ala Pro Val Leu Thr Pro
                580                 585                 590
Gly Pro Pro Gln Ser Leu Ser Ala Pro Val Pro Lys Ser Thr Gln Ala
                595                 600                 605
Gly Glu Gly Thr Leu Ser Glu Ala Leu Leu His Leu Gln Phe Asp Ala
                610                 615                 620
Asp Glu Asp Leu Gly Ala Leu Leu Gly Asn Ser Thr Asp Pro Gly Val
625                 630                 635                 640
Phe Thr Asp Leu Ala Ser Val Asp Asn Ser Glu Phe Gln Gln Leu Leu
                645                 650                 655
Asn Gln Gly Val Ser Met Ser His Ser Thr Ala Glu Pro Met Leu Met
                660                 665                 670
Glu Tyr Pro Glu Ala Ile Thr Arg Leu Val Thr Gly Ser Gln Arg Pro
                675                 680                 685
Pro Asp Pro Ala Pro Thr Pro Leu Gly Thr Ser Gly Leu Pro Asn Gly
                690                 695                 700
Leu Ser Gly Asp Glu Asp Phe Ser Ser Ile Ala Asp Met Asp Phe Ser
705                 710                 715                 720
Ala Leu Leu Ser Gln Ile Ser Ser Ser Gly Gln Gly Gly Gly Gly Ser
                725                 730                 735
Gly Gly Gly Gly Ser Gly Gly Gly Gly Ser Met Arg Lys Pro Ala Phe
                740                 745                 750
```

-continued

```
Leu Ser Gly Glu Gln Lys Lys Ala Ile Val Asp Leu Phe Lys Thr
        755                 760                 765
Asn Arg Lys Val Thr Val Lys Gln Leu Lys Glu Asp Tyr Phe Lys
    770                 775                 780
Ile Glu Cys Phe Asp Ser Val Glu Ile Ser Gly Val Glu Asp Arg Phe
785                 790                 795                 800
Asn Ala Ser Leu Gly Thr Tyr His Asp Leu Leu Lys Ile Ile Lys Asp
                805                 810                 815
Lys Asp Phe Leu Asp Asn Glu Glu Asn Glu Asp Ile Leu Glu Asp Ile
                820                 825                 830
Val Leu Thr Leu Thr Leu Phe Glu Asp Arg Glu Met Ile Glu Glu Arg
                835                 840                 845
Leu Lys Thr Tyr Ala His Leu Phe Asp Asp Lys Val Met Lys Gln Leu
    850                 855                 860
Lys Arg Arg Arg Tyr Thr Gly Trp Gly Arg Leu Ser Arg Lys Leu Ile
865                 870                 875                 880
Asn Gly Ile Arg Asp Lys Gln Ser Gly Lys Thr Ile Leu Asp Phe Leu
                885                 890                 895
Lys Ser Asp Gly Phe Ala Asn Arg Asn Phe Met Gln Leu Ile His Asp
                900                 905                 910
Asp Ser Leu Thr Phe Lys Glu Asp Ile Gln Lys Ala Gln Val Ser Gly
                915                 920                 925
Gln Gly Asp Ser Leu His Glu His Ile Ala Asn Leu Ala Gly Ser Pro
    930                 935                 940
Ala Ile Lys Lys Gly Ile Leu Gln Thr Val Lys Val Val Asp Glu Leu
945                 950                 955                 960
Val Lys Val Met Gly Arg His Lys Pro Glu Asn Ile Val Ile Glu Met
                965                 970                 975
Ala Arg Glu Asn Gln Thr Thr Gln Lys Gly Gln Lys Asn Ser Arg Glu
                980                 985                 990
Arg Met Lys Arg Ile Glu Glu Gly Ile Lys Glu Leu Gly Ser Gln Ile
                995                 1000                1005
Leu Lys Glu His Pro Val Glu Asn Thr Gln Leu Gln Asn Glu Lys
    1010                1015                1020
Leu Tyr Leu Tyr Tyr Leu Gln Asn Gly Arg Asp Met Tyr Val Asp
    1025                1030                1035
Gln Glu Leu Asp Ile Asn Arg Leu Ser Asp Tyr Asp Val Asp Ala
    1040                1045                1050
Ile Val Pro Gln Ser Phe Leu Lys Asp Asp Ser Ile Asp Asn Lys
    1055                1060                1065
Val Leu Thr Arg Ser Asp Lys Asn Arg Gly Lys Ser Asp Asn Val
    1070                1075                1080
Pro Ser Glu Glu Val Val Lys Lys Met Lys Asn Tyr Trp Arg Gln
    1085                1090                1095
Leu Leu Asn Ala Lys Leu Ile Thr Gln Arg Lys Phe Asp Asn Leu
    1100                1105                1110
Thr Lys Ala Glu Arg Gly Gly Leu Ser Glu Leu Asp Lys Ala Gly
    1115                1120                1125
Phe Ile Lys Arg Gln Leu Val Glu Thr Arg Gln Ile Thr Lys His
    1130                1135                1140
Val Ala Gln Ile Leu Asp Ser Arg Met Asn Thr Lys Tyr Asp Glu
    1145                1150                1155
```

-continued

Asn Asp Lys Leu Ile Arg Glu Val Lys Val Ile Thr Leu Lys Ser
1160                    1165                1170

Lys Leu Val Ser Asp Phe Arg Lys Asp Phe Gln Phe Tyr Lys Val
1175                    1180                1185

Arg Glu Ile Asn Asn Tyr His His Ala His Asp Ala Tyr Leu Asn
1190                    1195                1200

Ala Val Val Gly Thr Ala Leu Ile Lys Lys Tyr Pro Lys Leu Glu
1205                    1210                1215

Ser Glu Phe Val Tyr Gly Asp Tyr Lys Val Tyr Asp Val Arg Lys
1220                    1225                1230

Met Ile Ala Lys Ser Glu Gln Glu Ile Gly Lys Ala Thr Ala Lys
1235                    1240                1245

Tyr Phe Phe Tyr Ser Asn Ile Met Asn Phe Phe Lys Thr Glu Ile
1250                    1255                1260

Thr Leu Ala Asn Gly Glu Ile Arg Lys Arg Pro Leu Ile Glu Thr
1265                    1270                1275

Asn Gly Glu Thr Gly Glu Ile Val Trp Asp Lys Gly Arg Asp Phe
1280                    1285                1290

Ala Thr Val Arg Lys Val Leu Ser Met Pro Gln Val Asn Ile Val
1295                    1300                1305

Lys Lys Thr Glu Val Gln Thr Gly Gly Phe Ser Lys Glu Ser Ile
1310                    1315                1320

Leu Pro Lys Arg Asn Ser Asp Lys Leu Ile Ala Arg Lys Lys Asp
1325                    1330                1335

Trp Asp Pro Lys Lys Tyr Gly Gly Phe Asp Ser Pro Thr Val Ala
1340                    1345                1350

Tyr Ser Val Leu Val Val Ala Lys Val Glu Lys Gly Lys Ser Lys
1355                    1360                1365

Lys Leu Lys Ser Val Lys Glu Leu Leu Gly Ile Thr Ile Met Glu
1370                    1375                1380

Arg Ser Ser Phe Glu Lys Asn Pro Ile Asp Phe Leu Glu Ala Lys
1385                    1390                1395

Gly Tyr Lys Glu Val Lys Lys Asp Leu Ile Ile Lys Leu Pro Lys
1400                    1405                1410

Tyr Ser Leu Phe Glu Leu Glu Asn Gly Arg Lys Arg Met Leu Ala
1415                    1420                1425

Ser Ala Gly Glu Leu Gln Lys Gly Asn Glu Leu Ala Leu Pro Ser
1430                    1435                1440

Lys Tyr Val Asn Phe Leu Tyr Leu Ala Ser His Tyr Glu Lys Leu
1445                    1450                1455

Lys Gly Ser Pro Glu Asp Asn Glu Gln Lys Gln Leu Phe Val Glu
1460                    1465                1470

Gln His Lys His Tyr Leu Asp Glu Ile Ile Glu Gln Ile Ser Glu
1475                    1480                1485

Phe Ser Lys Arg Val Ile Leu Ala Asp Ala Asn Leu Asp Lys Val
1490                    1495                1500

Leu Ser Ala Tyr Asn Lys His Arg Asp Lys Pro Ile Arg Glu Gln
1505                    1510                1515

Ala Glu Asn Ile Ile His Leu Phe Thr Leu Thr Asn Leu Gly Ala
1520                    1525                1530

Pro Ala Ala Phe Lys Tyr Phe Asp Thr Thr Ile Asp Arg Lys Arg
1535                    1540                1545

Tyr Thr Ser Thr Lys Glu Val Leu Asp Ala Thr Leu Ile His Gln

| | | | |
|---|---|---|---|
| | 1550 | 1555 | 1560 |

Ser Ile Thr Gly Leu Tyr Glu Thr Arg Ile Asp Leu Ser Gln Leu
    1565                     1570                     1575

Gly Gly Asp Ser Ala Gly Gly Gly Ser Gly Gly Gly Ser
    1580                     1585                     1590

Gly Gly Gly Gly Ser Gly Pro Lys Lys Lys Arg Lys Val Ala Ala
    1595                     1600                     1605

Ala Ala Ser Gly Ser
    1610

```
<210> SEQ ID NO 110
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga gaacctgat cggagccctg ctgttcgaca cggcgaaac agccgaggcc      180 acccggctga gagaaccgc cagaagaaga taccaccaga ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga cccccgacaa cagcgacgtg     540
gacaagctgt tcatccagct ggtgcagacc tacaaccagc tgttcgagga aaaccccatc     600
aacgccagcg gcgtggacgc caaggccatc ctgtctgcca gactgagcaa gagcagacgg     660
ctggaaaatc tgatcgccca gctgcccggc gagaagaaga tgggcctgtt cggcaacctg     720
attgccctga gcctgggcct gacccccaac ttcaagagca cttcgacct ggccgaggat     780 gccaaactgc agctgagcaa ggacacctac gacgacgacc tggacaacct gctggcccag     840
atcggcgacc agtacgccga cctgtttctg gccgccaaga cctgtccga cgccatcctg     900 ctgagcgaca tcctgagagt gaacaccgag atcaccaagg cccccctgag cgcctctatg     960
atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagggacct gctgcggaag    1200 cagcggacct tcgacaacgg cagcatcccc caccagatcc acctgggaga gctgcacgcc    1260
attctgcggc ggcaggaaga ttttaccca ttcctgaagg acaaccggga aaagatcgag    1320
aagatcctga ccttccgcat cccctactac gtgggccctc tggccagggg aaacagcaga    1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
aacgagctga ccaaagtgaa atacgtgacc gagggaatga gaaagcccgc cttcctgagc    1620
```

```
ggcgagcaga aaaaggccat cgtggacctg ctgttcaaga ccaaccggaa agtgaccgtg    1680
aagcagctga agaggactac cttcaagaaa atcgagtgct tcggaggggg aggcagcgga    1740
cgggctgacg cattggacga tttttgatctg gatatgctgg gaagtgacgc cctcgatgat    1800
tttgaccttg acatgcttgg ttcggatgcc cttgatgact tgacctcga catgctcggc    1860 agtgacgccc ttgatgattt cgacctggac atgctgatta acggcggggg aggctccgac    1920
tccgtggaaa tctccggcgt ggaagatcgg ttcaacgcct ccctgggcac ataccacgat    1980
ctgctgaaaa ttatcaagga caaggacttc ctggacaatg aggaaaacga ggacattctg    2040
gaagatatcg tgctgaccct gacactgttt gaggacagag agatgatcga ggaacggctg    2100
aaaacctatg cccacctgtt cgacgacaaa gtgatgaagc agctgaagcg gcggagatac    2160
accggctggg gcaggctgag ccggaagctg atcaacggca tccgggacaa gcagtccggc    2220
aagacaatcc tggatttcct gaagtccgac ggcttcgcca cagaaacttc atgcagctg     2280 atccacgacg acagcctgac ctttaaagag gacatccaga aagcccaggt gtccggccag    2340
ggcgatagcc tgcacgagca cattgccaat ctggccggca gccccgccat taagaagggc    2400
atcctgcaga cagtgaaggt ggtggacgag ctcgtgaaag tgatgggccg gcacaagccc    2460
gagaacatcg tgatcgaaat ggccagagag aaccagacca cccagaaggg acagaagaac    2520
agccgcgaga gatgaagcg gatcgaagag ggcatcaaag agctgggcag ccagatcctg    2580
aaagaacacc ccgtggaaaa cacccagctg cagaacgaga gctgtacct gtactacctg    2640 cagaatgggc gggatatgta cgtggaccag gaactggaca tcaaccggct gtccgactac    2700
gatgtggacg ctatcgtgcc tcagagcttt ctgaaggacg actccatcga caacaaggtg    2760
ctgaccagaa gcgacaagaa ccggggcaag agcgacaacg tgccctccga gaggtcgtg     2820 aagaagatga agaactactg gcggcagctg ctgaacgcca agctgattac ccagagaaag    2880
ttcgacaatc tgaccaaggc cgagagaggc ggcctgagcg aactggataa ggccggcttc    2940
atcaagagac agctggtgga aacccggcag atcacaaagc acgtggcaca gatcctggac    3000
tcccggatga acactaagta cgacgagaat gacaagctga tccgggaagt gaaagtgatc    3060
accctgaagt ccaagctggt gtccgatttc cggaaggatt tccagttttta caagtgcgc    3120 gagatcaaca actaccacca cgcccacgac gcctacctga acgccgtcgt gggaaccgcc    3180
ctgatcaaaa agtaccctaa gctggaaagc gagttcgtgt acggcgacta caaggtgtac    3240
gacgtgcgga gatgatcgc caagagcgag caggaaatcg gcaaggctac cgccaagtac    3300
ttcttctaca gcaacatcat gaactttttc aagaccgaga ttaccctggc caacggcgag    3360
atccggaagc ggcctctgat cgagacaaac ggcgaaaccg gggagatcgt gtgggataag    3420
ggccgggatt tgccaccgt gcggaaagtg ctgagcatgc ccaagtgaa tatcgtgaaa    3480 aagaccgagg tgcagacagg cggcttcagc aaagagtcta tcctgcccaa gaggaacagc    3540
gataagctga tcgccagaaa gaaggactgg gaccctaaga agtacggcgg cttcgacagc    3600
cccaccgtgg cctattctgt gctggtggtg gccaaagtgg aaaagggcaa gtccaagaaa    3660
ctgaagagtg tgaaagagct gctgggatc accatcatgg aaagaagcag cttcgagaag    3720
aatcccatcg actttctgga agccaagggc tacaagaag tgaaaagga cctgatcatc    3780 aagctgccta gtactccct gttcgagctg aaaacggcc ggaagagaat gctggcctct    3840
gccggcgaac tgcagaaggg aaacgaactg gccctgccct ccaaatatgt gaacttcctg    3900
tacctggcca gccactatga aagctgaag ggctcccccg aggataatga gcagaaacag    3960
```

```
ctgtttgtgg aacagcacaa gcactacctg gacgagatca tcgagcagat cagcgagttc    4020
tccaagagag tgatcctggc cgacgctaat ctggacaaag tgctgtccgc ctacaacaag    4080
caccgggata agcccatcag agagcaggcc gagaatatca tccacctgtt taccctgacc    4140
aatctgggag cccctgccgc cttcaagtac tttgacacca ccatcgaccg gaagaggtac    4200
accagcacca agaggtgctg gacgccacc ctgatccacc agagcatcac cggcctgtac    4260
gagacacgga tcgacctgtc tcagctggga ggcgacagcg ctggaggagg tggaagcgga    4320
ggaggaggaa gcggaggagg aggtagcgga cctaagaaaa agaggaaggt ggcg           4374
```

<210> SEQ ID NO 111
<211> LENGTH: 1458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285
```

```
Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Gly Gly
                565                 570                 575

Gly Gly Ser Gly Arg Ala Asp Ala Leu Asp Asp Phe Asp Leu Asp Met
            580                 585                 590

Leu Gly Ser Asp Ala Leu Asp Asp Phe Asp Leu Asp Met Leu Gly Ser
        595                 600                 605

Asp Ala Leu Asp Asp Phe Asp Leu Asp Met Leu Gly Ser Asp Ala Leu
    610                 615                 620

Asp Asp Phe Asp Leu Asp Met Leu Ile Asn Gly Gly Gly Ser Asp
625                 630                 635                 640

Ser Val Glu Ile Ser Gly Val Glu Asp Arg Phe Asn Ala Ser Leu Gly
                645                 650                 655

Thr Tyr His Asp Leu Leu Lys Ile Ile Lys Asp Lys Asp Phe Leu Asp
            660                 665                 670

Asn Glu Glu Asn Glu Asp Ile Leu Glu Asp Ile Val Leu Thr Leu Thr
        675                 680                 685

Leu Phe Glu Asp Arg Glu Met Ile Glu Glu Arg Leu Lys Thr Tyr Ala
    690                 695                 700
```

-continued

His Leu Phe Asp Asp Lys Val Met Lys Gln Leu Lys Arg Arg Tyr
705                 710                 715                 720

Thr Gly Trp Gly Arg Leu Ser Arg Lys Leu Ile Asn Gly Ile Arg Asp
            725                 730                 735

Lys Gln Ser Gly Lys Thr Ile Leu Asp Phe Leu Lys Ser Asp Gly Phe
            740                 745                 750

Ala Asn Arg Asn Phe Met Gln Leu Ile His Asp Asp Ser Leu Thr Phe
            755                 760                 765

Lys Glu Asp Ile Gln Lys Ala Gln Val Ser Gly Gln Gly Asp Ser Leu
770                 775                 780

His Glu His Ile Ala Asn Leu Ala Gly Ser Pro Ala Ile Lys Lys Gly
785                 790                 795                 800

Ile Leu Gln Thr Val Lys Val Val Asp Glu Leu Val Lys Val Met Gly
            805                 810                 815

Arg His Lys Pro Glu Asn Ile Val Ile Glu Met Ala Arg Glu Asn Gln
            820                 825                 830

Thr Thr Gln Lys Gly Gln Lys Asn Ser Arg Glu Arg Met Lys Arg Ile
            835                 840                 845

Glu Glu Gly Ile Lys Glu Leu Gly Ser Gln Ile Leu Lys Glu His Pro
850                 855                 860

Val Glu Asn Thr Gln Leu Gln Asn Glu Lys Leu Tyr Leu Tyr Tyr Leu
865                 870                 875                 880

Gln Asn Gly Arg Asp Met Tyr Val Asp Gln Glu Leu Asp Ile Asn Arg
            885                 890                 895

Leu Ser Asp Tyr Asp Val Asp Ala Ile Val Pro Gln Ser Phe Leu Lys
            900                 905                 910

Asp Asp Ser Ile Asp Asn Lys Val Leu Thr Arg Ser Asp Lys Asn Arg
            915                 920                 925

Gly Lys Ser Asp Asn Val Pro Ser Glu Glu Val Val Lys Lys Met Lys
            930                 935                 940

Asn Tyr Trp Arg Gln Leu Leu Asn Ala Lys Leu Ile Thr Gln Arg Lys
945                 950                 955                 960

Phe Asp Asn Leu Thr Lys Ala Glu Arg Gly Gly Leu Ser Glu Leu Asp
            965                 970                 975

Lys Ala Gly Phe Ile Lys Arg Gln Leu Val Glu Thr Arg Gln Ile Thr
            980                 985                 990

Lys His Val Ala Gln Ile Leu Asp Ser Arg Met Asn Thr Lys Tyr Asp
            995                 1000                1005

Glu Asn Asp Lys Leu Ile Arg Glu Val Lys Val Ile Thr Leu Lys
1010                1015                1020

Ser Lys Leu Val Ser Asp Phe Arg Lys Asp Phe Gln Phe Tyr Lys
1025                1030                1035

Val Arg Glu Ile Asn Asn Tyr His His Ala His Asp Ala Tyr Leu
1040                1045                1050

Asn Ala Val Val Gly Thr Ala Leu Ile Lys Lys Tyr Pro Lys Leu
1055                1060                1065

Glu Ser Glu Phe Val Tyr Gly Asp Tyr Lys Val Tyr Asp Val Arg
1070                1075                1080

Lys Met Ile Ala Lys Ser Glu Gln Glu Ile Gly Lys Ala Thr Ala
1085                1090                1095

Lys Tyr Phe Phe Tyr Ser Asn Ile Met Asn Phe Phe Lys Thr Glu
1100                1105                1110

Ile Thr Leu Ala Asn Gly Glu Ile Arg Lys Arg Pro Leu Ile Glu

```
                    1115                1120                1125

Thr Asn Gly Glu Thr Gly Glu Ile Val Trp Asp Lys Gly Arg Asp
            1130                1135                1140

Phe Ala Thr Val Arg Lys Val Leu Ser Met Pro Gln Val Asn Ile
        1145                1150                1155

Val Lys Lys Thr Glu Val Gln Thr Gly Gly Phe Ser Lys Glu Ser
    1160                1165                1170

Ile Leu Pro Lys Arg Asn Ser Asp Lys Leu Ile Ala Arg Lys Lys
1175                1180                1185

Asp Trp Asp Pro Lys Lys Tyr Gly Gly Phe Asp Ser Pro Thr Val
    1190                1195                1200

Ala Tyr Ser Val Leu Val Val Ala Lys Val Glu Lys Gly Lys Ser
        1205                1210                1215

Lys Lys Leu Lys Ser Val Lys Glu Leu Leu Gly Ile Thr Ile Met
            1220                1225                1230

Glu Arg Ser Ser Phe Glu Lys Asn Pro Ile Asp Phe Leu Glu Ala
                1235                1240                1245

Lys Gly Tyr Lys Glu Val Lys Lys Asp Leu Ile Ile Lys Leu Pro
                    1250                1255                1260

Lys Tyr Ser Leu Phe Glu Leu Glu Asn Gly Arg Lys Arg Met Leu
                        1265                1270                1275

Ala Ser Ala Gly Glu Leu Gln Lys Gly Asn Glu Leu Ala Leu Pro
            1280                1285                1290

Ser Lys Tyr Val Asn Phe Leu Tyr Leu Ala Ser His Tyr Glu Lys
        1295                1300                1305

Leu Lys Gly Ser Pro Glu Asp Asn Glu Gln Lys Gln Leu Phe Val
    1310                1315                1320

Glu Gln His Lys His Tyr Leu Asp Glu Ile Ile Glu Gln Ile Ser
1325                1330                1335

Glu Phe Ser Lys Arg Val Ile Leu Ala Asp Ala Asn Leu Asp Lys
    1340                1345                1350

Val Leu Ser Ala Tyr Asn Lys His Arg Asp Lys Pro Ile Arg Glu
        1355                1360                1365

Gln Ala Glu Asn Ile Ile His Leu Phe Thr Leu Thr Asn Leu Gly
            1370                1375                1380

Ala Pro Ala Ala Phe Lys Tyr Phe Asp Thr Thr Ile Asp Arg Lys
                1385                1390                1395

Arg Tyr Thr Ser Thr Lys Glu Val Leu Asp Ala Thr Leu Ile His
                    1400                1405                1410

Gln Ser Ile Thr Gly Leu Tyr Glu Thr Arg Ile Asp Leu Ser Gln
                        1415                1420                1425

Leu Gly Gly Asp Ser Ala Gly Gly Gly Ser Gly Gly Gly
            1430                1435                1440

Ser Gly Gly Gly Ser Gly Pro Lys Lys Lys Arg Lys Val Ala
        1445                1450                1455
```

<210> SEQ ID NO 112
<211> LENGTH: 4435
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112

```
cagcatcggc ctggccatcg gcaccaactc tgtgggctgg gccgtgatca ccgacgagta    60
caaggtgccc agcaagaaat tcaaggtgct gggcaacacc gaccggcaca gcatcaagaa   120
gaacctgatc ggagccctgc tgttcgacag cggcgaaaca gccgaggcca cccggctgaa   180
gagaaccgcc agaagaagat acaccagacg gaagaaccgg atctgctatc tgcaagagat   240
cttcagcaac gagatggcca aggtggacga cagcttcttc cacagactgg aagagtcctt   300
cctggtggaa gaggataaga agcacgagcg gcaccccatc ttcggcaaca tcgtggacga   360
ggtggcctac cacgagaagt accccaccat ctaccacctg agaaagaaac tggtggacag   420
caccgacaag gccgacctgc ggctgatcta tctggccctg gcccacatga tcaagttccg   480
gggccacttc ctgatcgagg gcgacctgaa ccccgacaac agcgacgtgg acaagctgtt   540
catccagctg gtgcagacct acaaccagct gttcgaggaa aacccccatca cgccagcgg   600
cgtggacgcc aaggccatcc tgtctgccag actgagcaag agcagacggc tggaaaatct   660
gatcgcccag ctgcccggcg agaagaagaa tggcctgttc ggcaacctga ttgccctgag   720
cctgggcctg acccccaact tcaagagcaa cttcgacctg gccgaggatg ccaaactgca   780
gctgagcaag gacaccctac gacgacgacct ggacaacctg ctggcccaga tcggcgacca   840
gtacgccgac ctgtttctgg ccgccaagaa cctgtccgac gccatcctgc tgagcgacat   900
cctgagagtg aacaccgaga tcaccaaggc ccccctgagc gcctctatga tcaagagata   960
cgacgagcac caccaggacc tgaccctgct gaaagctctc gtgcggcagc agctgcctga  1020
gaagtacaaa gagattttct tcgaccagag caagaacggc tacgccggct acattgacgg  1080
cggagccagc caggaagagt tctacaagtt catcaagccc atcctggaaa agatggacgg  1140
caccgaggaa ctgctcgtga agctgaacag agaggacctg ctgcggaagc agcggacctt  1200
cgacaacggc agcatccccc accagatcca cctgggagag ctgcacgcca ttctgcggcg  1260
gcaggaagat ttttacccat tcctgaagga caaccgggaa aagatcgaga gatcctgac   1320
cttccgcatc ccctactacg tgggccctct ggccagggga aacagcagat tcgcctggat  1380
gaccagaaag agcgaggaaa ccatcacccc ctggaacttc gaggaagtgg tggacaaggg  1440
cgcttccgcc cagagcttca tcgagcggat gaccaacttc gataagaacc tgcccaacga  1500
gaaggtgctg cccaagcaca gcctgctgta cgagtacttc accgtgtata acgagctgac  1560
caaagtgaaa tacgtgaccg agggaatgag aaagcccgcc ttcctgagcg gcgagcagaa  1620
aaaggccatc gtggacctgc tgttcaagac caaccggaaa gtgaccgtga agcagctgaa  1680
agaggactac ttcaagaaaa tcgagtgctt cggcggggga ggctccggtg tgggggcag   1740
cggaggggggg ggcagcggac gggctgacgc attggacgat tttgatctgg atatgctggg  1800
aagtgacgcc ctcgatgatt ttgaccttga catgcttggt tcggatgccc ttgatgactt  1860
tgacctcgac atgctcggca gtgacgccct tgatgatttc gacctggaca tgctgattaa  1920
cggcggggga ggctccggtg tgggggcag cggaggggggg ggcagcgact ccgtggaaat  1980
ctccggcgtg aagatcggt tcaacgcctc cctgggcaca taccacgatc tgctgaaaat  2040
tatcaaggac aaggacttcc tggacaatga ggaaaacgag gacattctgg aagatatcgt  2100
gctgaccctc acactgtttg aggacagaga gatgatcgag gaacggctga aaacctatgc  2160
ccacctgttc gacgacaaag tgatgaagca gctgaagcgg cggagataca ccggctgggg  2220
caggctgagc cggaagctga tcaacggcat ccgggacaag cagtccggca agacaatcct  2280
ggatttcctg aagtccgacg gcttcgccaa cagaaacttc atgcagctga tccacgacga  2340
```

```
cagcctgacc tttaaagagg acatccagaa agcccaggtg tccggccagg gcgatagcct    2400
gcacgagcac attgccaatc tggccggcag ccccgccatt aagaagggca tcctgcagac    2460
agtgaaggtg gtggacgagc tcgtgaaagt gatgggccgg cacaagcccg agaacatcgt    2520
gatcgaaatg gccagagaga accagaccac ccagaaggga cagaagaaca gccgcgagag    2580
aatgaagcgg atcgaagagg gcatcaaaga gctgggcagc cagatcctga agaacacccc    2640
cgtggaaaac acccagctgc agaacgagaa gctgtacctg tactacctgc agaatgggcg    2700
ggatatgtac gtggaccagg aactggacat caaccggctg tccgactacg atgtggacgc    2760
tatcgtgcct cagagctttc tgaaggacga ctccatcgac aacaaggtgc tgaccagaag    2820
cgacaagaac cggggcaaga gcgacaacgt gcccctccga gaggtcgtga agaagatgaa    2880
gaactactgg cggcagctgc tgaacgccaa gctgattacc agagaaagt tcgacaatct    2940 gaccaaggcc gagagaggcg gcctgagcga actggataag gccggcttca tcaagagaca    3000
gctggtggaa acccggcaga tcacaaagca cgtggcacag atcctggact cccggatgaa    3060
cactaagtac gacgagaatg acaagctgat ccggagtgt aaagtgatca ccctgaagtc    3120
caagctggtg tccgatttcc ggaaggattt ccagttttac aaagtgcgcg agatcaacaa    3180
ctaccaccac gcccacgacg cctacctgaa cgccgtcgtg gaaccgccc tgatcaaaaa    3240 gtaccctaag ctggaaagcg agttcgtgta cggcgactac aaggtgtacg acgtgcggaa    3300
gatgatcgcc aagagcgagc aggaaatcgg caaggctacc gccaagtact cttctacag    3360 caacatcatg aacttttca gaccgagat accctggcc aacggcgaga tccggaagcg    3420
gcctctgatc gagacaaacg cgaaaccgg ggagatcgtg tgggataagg ccgggatt    3480 tgccaccgtg cggaaagtgc tgagcatgcc ccaagtgaat atcgtgaaaa agaccgaggt    3540
gcagacaggc ggcttcagca aagagtctat cctgcccaag aggaacagcg ataagctgat    3600
cgccagaaag aaggactggg accctaagaa gtacggcggc ttcgacagcc caccgtggc    3660 ctattctgtg ctggtggtgg ccaaagtgga aaagggcaag tccaagaaac tgaagagtgt    3720
gaaagagctg ctggggatca ccatcatgga agaagcagc ttcgagaaga tcccatcga    3780 cttctctggaa gccaagggct acaaagaagt gaaaaaggac ctgatcatca agctgcctaa    3840
gtactccctg ttcgagctgg aaaacggccg gaagagaatg ctggcctctg ccggcgaact    3900
gcagaaggga aacgaactgg ccctgccctc caaatatgtg aacttcctgt acctggccag    3960
ccactatgag aagctgaagg gctcccccga ggataatgag cagaaacagc tgtttgtgga    4020
acagcacaag cactacctgg acgagatcat cgagcagatc agcgagttct ccaagagagt    4080
gatcctggcc gacgctaatc tggacaaagt gctgtccgcc tacaacaagc accgggataa    4140
gcccatcaga gagcaggccg agaatatcat ccacctgttt accctgacca atctgggagc    4200
ccctgccgcc ttcaagtact tgacaccac catcgaccgg aagaggtaca ccagcaccaa    4260
agaggtgctg gacgccaccc tgatccacca gagcatcacc ggcctgtacg agacacggat    4320
cgacctgtct cagctgggag cgacagcgc tggaggaggt ggaagcggag aggaggaag    4380 cggaggagga ggtagcggac ctaagaaaaa gaggaaggtg gcggccgctg ctagc          4435
```

<210> SEQ ID NO 113
<211> LENGTH: 1452
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 113

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Thr Arg Leu Lys
    50                  55                  60

Arg Thr Ala Arg Arg Tyr Thr Arg Arg Lys Asn Arg Ile Cys Tyr
65              70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
```

```
                405                 410                 415
Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
        530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Gly Gly
                565                 570                 575

Gly Gly Ser Gly Gly Gly Gly Ser Gly Gly Gly Gly Ser Gly Arg Ala
            580                 585                 590

Asp Ala Leu Asp Asp Phe Asp Leu Asp Met Leu Gly Ser Asp Ala Leu
            595                 600                 605

Asp Asp Phe Asp Leu Asp Met Leu Gly Ser Asp Ala Leu Asp Asp Phe
        610                 615                 620

Asp Leu Asp Met Leu Gly Ser Asp Ala Leu Asp Asp Phe Asp Leu Asp
625                 630                 635                 640

Met Leu Ile Asn Gly Gly Gly Ser Gly Gly Gly Ser Gly Gly
                645                 650                 655

Gly Gly Ser Asp Ser Val Glu Ile Ser Gly Val Glu Asp Arg Phe Asn
            660                 665                 670

Ala Ser Leu Gly Thr Tyr His Asp Leu Leu Lys Ile Ile Lys Asp Lys
            675                 680                 685

Asp Phe Leu Asp Asn Glu Glu Asn Glu Asp Ile Leu Glu Asp Ile Val
            690                 695                 700

Leu Thr Leu Thr Leu Phe Glu Asp Arg Glu Met Ile Glu Glu Arg Leu
705                 710                 715                 720

Lys Thr Tyr Ala His Leu Phe Asp Asp Lys Val Met Lys Gln Leu Lys
                725                 730                 735

Arg Arg Arg Tyr Thr Gly Trp Gly Arg Leu Ser Arg Lys Leu Ile Asn
            740                 745                 750

Gly Ile Arg Asp Lys Gln Ser Gly Lys Thr Ile Leu Asp Phe Leu Lys
            755                 760                 765

Ser Asp Gly Phe Ala Asn Arg Asn Phe Met Gln Leu Ile His Asp Asp
        770                 775                 780

Ser Leu Thr Phe Lys Glu Asp Ile Gln Lys Ala Gln Val Ser Gly Gln
785                 790                 795                 800

Gly Asp Ser Leu His Glu His Ile Ala Asn Leu Ala Gly Ser Pro Ala
                805                 810                 815

Ile Lys Lys Gly Ile Leu Gln Thr Val Lys Val Val Asp Glu Leu Val
            820                 825                 830
```

```
Lys Val Met Gly Arg His Lys Pro Glu Asn Ile Val Ile Glu Met Ala
        835                 840                 845

Arg Glu Asn Gln Thr Thr Gln Lys Gly Gln Lys Asn Ser Arg Glu Arg
850                 855                 860

Met Lys Arg Ile Glu Glu Gly Ile Lys Glu Leu Gly Ser Gln Ile Leu
865                 870                 875                 880

Lys Glu His Pro Val Glu Asn Thr Gln Leu Gln Asn Glu Lys Leu Tyr
                885                 890                 895

Leu Tyr Tyr Leu Gln Asn Gly Arg Asp Met Tyr Val Asp Gln Glu Leu
            900                 905                 910

Asp Ile Asn Arg Leu Ser Asp Tyr Asp Val Asp Ala Ile Val Pro Gln
            915                 920                 925

Ser Phe Leu Lys Asp Asp Ser Ile Asp Asn Lys Val Leu Thr Arg Ser
930                 935                 940

Asp Lys Asn Arg Gly Lys Ser Asp Asn Val Pro Ser Glu Glu Val Val
945                 950                 955                 960

Lys Lys Met Lys Asn Tyr Trp Arg Gln Leu Leu Asn Ala Lys Leu Ile
                965                 970                 975

Thr Gln Arg Lys Phe Asp Asn Leu Thr Lys Ala Glu Arg Gly Gly Leu
            980                 985                 990

Ser Glu Leu Asp Lys Ala Gly Phe Ile Lys Arg Gln Leu Val Glu Thr
            995                 1000                1005

Arg Gln Ile Thr Lys His Val Ala Gln Ile Leu Asp Ser Arg Met
    1010                1015                1020

Asn Thr Lys Tyr Asp Glu Asn Asp Lys Leu Ile Arg Glu Val Lys
    1025                1030                1035

Val Ile Thr Leu Lys Ser Lys Leu Val Ser Asp Phe Arg Lys Asp
    1040                1045                1050

Phe Gln Phe Tyr Lys Val Arg Glu Ile Asn Asn Tyr His His Ala
    1055                1060                1065

His Asp Ala Tyr Leu Asn Ala Val Val Gly Thr Ala Leu Ile Lys
    1070                1075                1080

Lys Tyr Pro Lys Leu Glu Ser Glu Phe Val Tyr Gly Asp Tyr Lys
    1085                1090                1095

Val Tyr Asp Val Arg Lys Met Ile Ala Lys Ser Glu Gln Glu Ile
    1100                1105                1110

Gly Lys Ala Thr Ala Lys Tyr Phe Phe Tyr Ser Asn Ile Met Asn
    1115                1120                1125

Phe Phe Lys Thr Glu Ile Thr Leu Ala Asn Gly Glu Ile Arg Lys
    1130                1135                1140

Arg Pro Leu Ile Glu Thr Asn Gly Glu Thr Gly Glu Ile Val Trp
    1145                1150                1155

Asp Lys Gly Arg Asp Phe Ala Thr Val Arg Lys Val Leu Ser Met
    1160                1165                1170

Pro Gln Val Asn Ile Val Lys Lys Thr Glu Val Gln Thr Gly Gly
    1175                1180                1185

Phe Ser Lys Glu Ser Ile Leu Pro Lys Arg Asn Ser Asp Lys Leu
    1190                1195                1200

Ile Ala Arg Lys Lys Asp Trp Asp Pro Lys Lys Tyr Gly Gly Phe
    1205                1210                1215

Asp Ser Pro Thr Val Ala Tyr Ser Val Leu Val Val Ala Lys Val
    1220                1225                1230
```

```
Glu Lys Gly Lys Ser Lys Lys Leu Lys Ser Val Lys Glu Leu Leu
    1235            1240                1245

Gly Ile Thr Ile Met Glu Arg Ser Ser Phe Glu Lys Asn Pro Ile
1250            1255                1260

Asp Phe Leu Glu Ala Lys Gly Tyr Lys Glu Val Lys Lys Asp Leu
    1265            1270                1275

Ile Ile Lys Leu Pro Lys Tyr Ser Leu Phe Glu Leu Glu Asn Gly
1280            1285                1290

Arg Lys Arg Met Leu Ala Ser Ala Gly Glu Leu Gln Lys Gly Asn
    1295            1300                1305

Glu Leu Ala Leu Pro Ser Lys Tyr Val Asn Phe Leu Tyr Leu Ala
1310            1315                1320

Ser His Tyr Glu Lys Leu Lys Gly Ser Pro Glu Asp Asn Glu Gln
    1325            1330                1335

Lys Gln Leu Phe Val Glu Gln His Lys His Tyr Leu Asp Glu Ile
1340            1345                1350

Ile Glu Gln Ile Ser Glu Phe Ser Lys Arg Val Ile Leu Ala Asp
    1355            1360                1365

Ala Asn Leu Asp Lys Val Leu Ser Ala Tyr Asn Lys His Arg Asp
1370            1375                1380

Lys Pro Ile Arg Glu Gln Ala Glu Asn Ile Ile His Leu Phe Thr
    1385            1390                1395

Leu Thr Asn Leu Gly Ala Pro Ala Ala Phe Lys Tyr Phe Asp Thr
1400            1405                1410

Thr Ile Asp Arg Lys Arg Tyr Thr Ser Thr Lys Glu Val Leu Asp
    1415            1420                1425

Ala Thr Leu Ile His Gln Ser Ile Thr Gly Leu Tyr Glu Thr Arg
1430            1435                1440

Ile Asp Leu Ser Gln Leu Gly Gly Asp
    1445            1450
```

<210> SEQ ID NO 114
<211> LENGTH: 4764
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114

```
gacaagaagt acagcatcgg cctggccatc ggcaccaact ctgtgggctg ggccgtgatc   60
accgacgagt acaaggtgcc cagcaagaaa ttcaaggtgc tgggcaacac cgaccggcac  120
agcatcaaga gaaacctgat cggagccctg ctgttcgaca cggccgaaac agccgaggcc  180
acccggctga gagaaccgc cagaagaaga taccagac ggaagaaccg gatctgctat  240
ctgcaagaga tcttcagcaa cgagatggcc aaggtggacg acagcttctt ccacagactg  300
gaagagtcct tcctggtgga agaggataag aagcacgagc ggcaccccat cttcggcaac  360
atcgtggacg aggtggccta ccacgagaag taccccacca tctaccacct gagaaagaaa  420
ctggtggaca gcaccgacaa ggccgacctg cggctgatct atctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga aaaccccatc  600
aacgccagcg gcgtggacgc caaggccatc ctgtctgcca gactgagcaa gagcagacgg  660
```

```
ctggaaaatc tgatcgccca gctgccggc gagaagaaga atggcctgtt cggcaacctg      720
attgccctga gcctgggcct gaccccaac ttcaagagca acttcgacct ggccgaggat      780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg    960
atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagaggacct gctgcggaag    1200
cagcggacct tcgacaacgg cagcatcccc accagatcc acctgggaga gctgcacgcc    1260
attctgcggc ggcaggaaga ttttttaccca ttcctgaagg acaaccggga aaagatcgag    1320
aagatcctga ccttccgcat ccctactac gtgggccctc tggccagggg aaacagcaga    1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
aacgagctga ccaaagtgaa atacgtgacc gagggaatga gaaagcccgc cttcctgagc    1620
ggcgagcaga aaaaggccat cgtggacctg ctgttcaaga ccaaccggaa agtgaccgtg    1680
aagcagctga aagaggacta cttcaagaaa atcgagtgct tcggaggggg aggcagccct    1740
tcagggcaga tcagcaacca ggccctggct ctggccccta gctccgctcc agtgctggcc    1800
cagactatgg tgccctctag tgctatggtg cctctggccc agccacctgc tccagcccct    1860
gtgctgaccc caggaccacc ccagtcactg agcgctccag tgcccaagtc tacacaggcc    1920
ggcgagggga ctctgagtga agctctgctg cacctgcagt tcgacgctga tgaggacctg    1980
ggagctctgc tggggaacag caccgatccc ggagtgttca cagatctggc ctccgtggac    2040
aactctgagt ttcagcagct gctgaatcag ggcgtgtcca tgtctcatag tacagccgaa    2100
ccaatgctga tggagtaccc cgaagccatt acccggctgg tgaccggcag ccagcggccc    2160
cccgaccccg ctccaactcc cctgggaacc agcggcctgc taatgggct gtccggagat    2220
gaagacttct caagcatcgc tgatatggac tttagtgccc tgctgtcaca gatttcctct    2280
agtgggcagg gagggggggg cagcgactcc gtggaaatct ccggcgtgga agatcggttc    2340
aacgcctccc tggcacacta ccacgatctg ctgaaaatta tcaaggacaa ggacttcctg    2400
gacaatgagg aaaacgagga cattctggaa gatatcgtgc tgaccctgac actgtttgag    2460
gacagagaga tgatcgagga acggctgaaa acctatgccc acctgttcga cgacaaagtg    2520
atgaagcagc tgaagcggcg cgagatacac cggctgggca ggctgagccg gaagctgatc    2580
aacggcatcc gggacaagca gtccggcaag acaatcctgg atttcctgaa gtccgacggc    2640
ttcgccaaca gaaacttcat gcagctgatc cacgacgaca gcctgacctt taaagaggac    2700
atccagaaag cccaggtgtc cggccagggc atagcctgc acgagcacat tgccaatctg    2760
gccggcagcc ccgccattaa gaagggcatc ctgcagacag tgaaggtggt ggacgagctc    2820
gtgaaagtga tgggccggca aagcccgag aacatcgtga tcgaaatggc cagagagaac    2880
cagaccaccc agaagggaca gaagaacagc cgcgagagaa tgaagcggat cgaagagggc    2940
atcaaagagc tgggcagcca gatcctgaaa gaacaccccg tggaaaacac ccagctgcag    3000
aacgagaagc tgtacctgta ctacctgcag aatgggcggg atatgtacgt ggaccaggaa    3060
```

| | |
|---|---|
| ctggacatca accggctgtc cgactacgat gtggacgcta tcgtgcctca gagctttctg | 3120 |
| aaggacgact ccatcgacaa caaggtgctg accagaagcg acaagaaccg ggcaagagc | 3180 |
| gacaacgtgc cctccgaaga ggtcgtgaag aagatgaaga actactggcg gcagctgctg | 3240 |
| aacgccaagc tgattaccca gagaaagttc gacaatctga ccaaggccga gagaggcggc | 3300 |
| ctgagcgaac tggataaggc cggcttcatc aagagacagc tggtggaaac ccggcagatc | 3360 |
| acaaagcacg tggcacagat cctggactcc cggatgaaca ctaagtacga cgagaatgac | 3420 |
| aagctgatcc gggaagtgaa agtgatcacc ctgaagtcca gctggtgtc cgatttccgg | 3480 |
| aaggatttcc agttttacaa agtgcgcgag atcaacaact accaccacgc ccacgacgcc | 3540 |
| tacctgaacg ccgtcgtggg aaccgccctg atcaaaagt accctaagct ggaaagcgag | 3600 |
| ttcgtgtacg gcgactacaa ggtgtacgac gtgcggaaga tgatcgccaa gagcgagcag | 3660 |
| gaaatcggca aggctaccgc caagtacttc ttctacagca acatcatgaa ctttttcaag | 3720 |
| accgagatta ccctggccaa cggcgagatc cggaagcggc ctctgatcga gacaaacggc | 3780 |
| gaaaccgggg agatcgtgtg ggataagggc cgggattttg ccaccgtgcg gaaagtgctg | 3840 |
| agcatgcccc aagtgaatat cgtgaaaaag accgaggtgc agacaggcgg cttcagcaaa | 3900 |
| gagtctatcc tgcccaagag gaacagcgat aagctgatcg ccagaaagaa ggactgggac | 3960 |
| cctaagaagt acggcggctt cgacagcccc accgtggcct attctgtgct ggtggtggcc | 4020 |
| aaagtggaaa agggcaagtc caagaaactg aagagtgtga agagctgct ggggatcacc | 4080 |
| atcatggaaa gagcagctt cgagaagaat cccatcgact ttctggaagc caagggctac | 4140 |
| aaagaagtga aaaaggacct gatcatcaag ctgcctaagt actccctgtt cgagctggaa | 4200 |
| aacggccgga gagaatgct ggcctctgcc ggcgaactgc agaagggaaa cgaactggcc | 4260 |
| ctgcccctcca aatatgtgaa cttcctgtac ctggccagcc actatgagaa gctgaagggc | 4320 |
| tccccccgagg ataatgagca gaaacagctg tttgtggaac agcacaagca ctacctggac | 4380 |
| gagatcatcg agcagatcag cgagttctcc aagagagtga tcctggccga cgctaatctg | 4440 |
| gacaaagtgc tgtccgccta caacaagcac cgggataagc ccatcagaga gcaggccgag | 4500 |
| aatatcatcc acctgtttac cctgaccaat ctgggagccc ctgccgcctt caagtacttt | 4560 |
| gacaccacca tcgaccggaa gaggtacacc agcaccaaag aggtgctgga cgccaccctg | 4620 |
| atccaccaga gcatcaccgg cctgtacgag acacggatcg acctgtctca gctgggaggc | 4680 |
| gacagcgctg aggaggtgg aagcggagga ggaggaagcg gaggaggagg tagcggacct | 4740 |
| aagaaaaaga ggaaggtggc ggcc | 4764 |

<210> SEQ ID NO 115
<211> LENGTH: 1588
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 115

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

```
Ala Leu Leu Phe Asp Ser Gly Glu Thr Ala Glu Ala Thr Arg Leu Lys
    50                  55                  60

Arg Thr Ala Arg Arg Tyr Thr Arg Arg Lys Asn Arg Ile Cys Tyr
 65              70                  75                  80

Leu Gln Glu Ile Phe Ser Asn Glu Met Ala Lys Val Asp Asp Ser Phe
                 85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
            370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
450                 455                 460
```

```
Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Gly Gly
                565                 570                 575

Gly Gly Ser Pro Ser Gly Gln Ile Ser Asn Gln Ala Leu Ala Leu Ala
            580                 585                 590

Pro Ser Ser Ala Pro Val Leu Ala Gln Thr Met Val Pro Ser Ser Ala
        595                 600                 605

Met Val Pro Leu Ala Gln Pro Pro Ala Pro Ala Pro Val Leu Thr Pro
610                 615                 620

Gly Pro Pro Gln Ser Leu Ser Ala Pro Val Pro Lys Ser Thr Gln Ala
625                 630                 635                 640

Gly Glu Gly Thr Leu Ser Glu Ala Leu Leu His Leu Gln Phe Asp Ala
                645                 650                 655

Asp Glu Asp Leu Gly Ala Leu Leu Gly Asn Ser Thr Asp Pro Gly Val
            660                 665                 670

Phe Thr Asp Leu Ala Ser Val Asp Asn Ser Glu Phe Gln Gln Leu Leu
        675                 680                 685

Asn Gln Gly Val Ser Met Ser His Ser Thr Ala Glu Pro Met Leu Met
    690                 695                 700

Glu Tyr Pro Glu Ala Ile Thr Arg Leu Val Thr Gly Ser Gln Arg Pro
705                 710                 715                 720

Pro Asp Pro Ala Pro Thr Pro Leu Gly Thr Ser Gly Leu Pro Asn Gly
                725                 730                 735

Leu Ser Gly Asp Glu Asp Phe Ser Ser Ile Ala Asp Met Asp Phe Ser
            740                 745                 750

Ala Leu Leu Ser Gln Ile Ser Ser Ser Gly Gln Gly Gly Gly Gly Ser
        755                 760                 765

Asp Ser Val Glu Ile Ser Gly Val Glu Asp Arg Phe Asn Ala Ser Leu
    770                 775                 780

Gly Thr Tyr His Asp Leu Leu Lys Ile Ile Lys Asp Lys Asp Phe Leu
785                 790                 795                 800

Asp Asn Glu Glu Asn Glu Asp Ile Leu Glu Asp Ile Val Leu Thr Leu
                805                 810                 815

Thr Leu Phe Glu Asp Arg Glu Met Ile Glu Glu Arg Leu Lys Thr Tyr
            820                 825                 830

Ala His Leu Phe Asp Asp Lys Val Met Lys Gln Leu Lys Arg Arg Arg
        835                 840                 845

Tyr Thr Gly Trp Gly Arg Leu Ser Arg Lys Leu Ile Asn Gly Ile Arg
    850                 855                 860

Asp Lys Gln Ser Gly Lys Thr Ile Leu Asp Phe Leu Lys Ser Asp Gly
865                 870                 875                 880

Phe Ala Asn Arg Asn Phe Met Gln Leu Ile His Asp Asp Ser Leu Thr
```

-continued

Phe Lys Glu Asp Ile Gln Lys Ala Gln Val Ser Gly Gln Gly Asp Ser
       885                 890                 895
                    900                 905                 910

Leu His Glu His Ile Ala Asn Leu Ala Gly Ser Pro Ala Ile Lys Lys
       915                 920                 925

Gly Ile Leu Gln Thr Val Lys Val Val Asp Glu Leu Val Lys Val Met
       930                 935                 940

Gly Arg His Lys Pro Glu Asn Ile Val Ile Glu Met Ala Arg Glu Asn
945                 950                 955                 960

Gln Thr Thr Gln Lys Gly Gln Lys Asn Ser Arg Glu Arg Met Lys Arg
                965                 970                 975

Ile Glu Glu Gly Ile Lys Glu Leu Gly Ser Gln Ile Leu Lys Glu His
                980                 985                 990

Pro Val Glu Asn Thr Gln Leu Gln Asn Glu Lys Leu Tyr Leu Tyr Tyr
                995                 1000                1005

Leu Gln Asn Gly Arg Asp Met Tyr Val Asp Gln Glu Leu Asp Ile
       1010                1015                1020

Asn Arg Leu Ser Asp Tyr Asp Val Asp Ala Ile Val Pro Gln Ser
       1025                1030                1035

Phe Leu Lys Asp Asp Ser Ile Asp Asn Lys Val Leu Thr Arg Ser
       1040                1045                1050

Asp Lys Asn Arg Gly Lys Ser Asp Asn Val Pro Ser Glu Glu Val
       1055                1060                1065

Val Lys Lys Met Lys Asn Tyr Trp Arg Gln Leu Leu Asn Ala Lys
       1070                1075                1080

Leu Ile Thr Gln Arg Lys Phe Asp Asn Leu Thr Lys Ala Glu Arg
       1085                1090                1095

Gly Gly Leu Ser Glu Leu Asp Lys Ala Gly Phe Ile Lys Arg Gln
       1100                1105                1110

Leu Val Glu Thr Arg Gln Ile Thr Lys His Val Ala Gln Ile Leu
       1115                1120                1125

Asp Ser Arg Met Asn Thr Lys Tyr Asp Glu Asn Asp Lys Leu Ile
       1130                1135                1140

Arg Glu Val Lys Val Ile Thr Leu Lys Ser Lys Leu Val Ser Asp
       1145                1150                1155

Phe Arg Lys Asp Phe Gln Phe Tyr Lys Val Arg Glu Ile Asn Asn
       1160                1165                1170

Tyr His His Ala His Asp Ala Tyr Leu Asn Ala Val Val Gly Thr
       1175                1180                1185

Ala Leu Ile Lys Lys Tyr Pro Lys Leu Glu Ser Glu Phe Val Tyr
       1190                1195                1200

Gly Asp Tyr Lys Val Tyr Asp Val Arg Lys Met Ile Ala Lys Ser
       1205                1210                1215

Glu Gln Glu Ile Gly Lys Ala Thr Ala Lys Tyr Phe Phe Tyr Ser
       1220                1225                1230

Asn Ile Met Asn Phe Phe Lys Thr Glu Ile Thr Leu Ala Asn Gly
       1235                1240                1245

Glu Ile Arg Lys Arg Pro Leu Ile Glu Thr Asn Gly Glu Thr Gly
       1250                1255                1260

Glu Ile Val Trp Asp Lys Gly Arg Asp Phe Ala Thr Val Arg Lys
       1265                1270                1275

Val Leu Ser Met Pro Gln Val Asn Ile Val Lys Lys Thr Glu Val
       1280                1285                1290

```
Gln Thr Gly Gly Phe Ser Lys Glu Ser Ile Leu Pro Lys Arg Asn
    1295                1300                1305

Ser Asp Lys Leu Ile Ala Arg Lys Lys Asp Trp Asp Pro Lys Lys
    1310                1315                1320

Tyr Gly Gly Phe Asp Ser Pro Thr Val Ala Tyr Ser Val Leu Val
    1325                1330                1335

Val Ala Lys Val Glu Lys Gly Lys Ser Lys Lys Leu Lys Ser Val
    1340                1345                1350

Lys Glu Leu Leu Gly Ile Thr Ile Met Glu Arg Ser Ser Phe Glu
    1355                1360                1365

Lys Asn Pro Ile Asp Phe Leu Glu Ala Lys Gly Tyr Lys Glu Val
    1370                1375                1380

Lys Lys Asp Leu Ile Ile Lys Leu Pro Lys Tyr Ser Leu Phe Glu
    1385                1390                1395

Leu Glu Asn Gly Arg Lys Arg Met Leu Ala Ser Ala Gly Glu Leu
    1400                1405                1410

Gln Lys Gly Asn Glu Leu Ala Leu Pro Ser Lys Tyr Val Asn Phe
    1415                1420                1425

Leu Tyr Leu Ala Ser His Tyr Glu Lys Leu Lys Gly Ser Pro Glu
    1430                1435                1440

Asp Asn Glu Gln Lys Gln Leu Phe Val Glu Gln His Lys His Tyr
    1445                1450                1455

Leu Asp Glu Ile Ile Glu Gln Ile Ser Glu Phe Ser Lys Arg Val
    1460                1465                1470

Ile Leu Ala Asp Ala Asn Leu Asp Lys Val Leu Ser Ala Tyr Asn
    1475                1480                1485

Lys His Arg Asp Lys Pro Ile Arg Glu Gln Ala Glu Asn Ile Ile
    1490                1495                1500

His Leu Phe Thr Leu Thr Asn Leu Gly Ala Pro Ala Ala Phe Lys
    1505                1510                1515

Tyr Phe Asp Thr Thr Ile Asp Arg Lys Arg Tyr Thr Ser Thr Lys
    1520                1525                1530

Glu Val Leu Asp Ala Thr Leu Ile His Gln Ser Ile Thr Gly Leu
    1535                1540                1545

Tyr Glu Thr Arg Ile Asp Leu Ser Gln Leu Gly Gly Asp Ser Ala
    1550                1555                1560

Gly Gly Gly Gly Ser Gly Gly Gly Ser Gly Gly Gly Ser
    1565                1570                1575

Gly Pro Lys Lys Lys Arg Lys Val Ala Ala
    1580                1585

<210> SEQ ID NO 116
<211> LENGTH: 4833
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116
accatggaca agaagtacag catcggcctg gccatcggca ccaactctgt gggctgggcc      60
gtgatcaccg acgagtacaa ggtgcccagc aagaaattca aggtgctggg caacaccgac     120
cggcacagca tcaagaagaa cctgatcgga gccctgctgt tcgacagcgg cgaaacagcc     180
```

```
gaggccaccc ggctgaagag aaccgccaga agaagataca ccagacggaa gaaccggatc      240
tgctatctgc aagagatctt cagcaacgag atggccaagg tggacgacag cttcttccac      300
agactggaag agtccttcct ggtggaagag gataagaagc acgagcggca ccccatcttc      360
ggcaacatcg tggacgaggt ggcctaccac gagaagtacc ccaccatcta ccacctgaga      420
aagaaactgg tggacagcac cgacaaggcc gacctgcggc tgatctatct ggccctggcc      480
cacatgatca agttccgggg ccacttcctg atcgagggcg acctgaaccc cgacaacagc      540
gacgtggaca agctgttcat ccagctggtg cagacctaca ccagctgtt cgaggaaaac      600 cccatcaacg ccagcggcgt ggacgccaag gccatcctgt ctgccagact gagcaagagc      660
agacggctgg aaaatctgat cgcccagctg cccggcgaga agaagaatgg cctgttcggc      720
aacctgattg ccctgagcct gggcctgacc cccaacttca agagcaactt cgacctggcc      780
gaggatgcca aactgcagct gagcaaggac acctacgacg acgacctgga caacctgctg      840
gcccagatcg gcgaccagta cgccgacctg tttctggccg ccaagaacct gtccgacgcc      900
atcctgctga gcgacatcct gagagtgaac accgagatca ccaaggcccc cctgagcgcc      960
tctatgatca agagatacga cgagcaccac caggacctga cctgctgaa agctctcgtg     1020 cggcagcagc tgcctgagaa gtacaaagag attttcttcg accagagcaa gaacggctac     1080
gccggctaca ttgacggcgg agccagccag gaagagttct acaagttcat caagcccatc     1140
ctggaaaaga tggacggcac cgaggaactg ctcgtgaagc tgaacagaga ggacctgctg     1200
cggaagcagc ggaccttcga caacggcagc atcccccacc agatccacct gggagagctg     1260
cacgccattc tgcggcggca ggaagatttt tacccattcc tgaaggacaa ccgggaaaag     1320
atcgagaaga tcctgacctt ccgcatcccc tactacgtgg gccctctggc caggggaaac     1380
agcagattcg cctggatgac cagaaagagc gaggaaacca tcaccccctg gaacttcgag     1440
gaagtggtgg acaagggcgc ttccgcccag agcttcatcg agcggatgac caacttcgat     1500
aagaacctgc ccaacgagaa ggtgctgccc aagcacagcc tgctgtacga gtacttcacc     1560
gtgtataacg agctgaccaa agtgaaatac gtgaccgagg gaatgagaaa gcccgccttc     1620
ctgagcggcg agcagaaaaa ggccatcgtg gacctgctgt tcaagaccaa ccggaaagtg     1680
accgtgaagc agctgaaaga ggactacttc aagaaaatcg agtgcttcgg cggggaggc     1740 tccggtggtg ggggcagcgg aggggggggc agcccttcag ggcagatcag caaccaggcc     1800
ctggctctgg cccctagctc cgctccagtg ctggcccaga ctatggtgcc ctctagtgct     1860
atggtgcctc tggcccagcc acctgctcca gcccctgtgc tgaccccagg accaccccag     1920
tcactgagcg ctccagtgcc caagtctaca caggccggcg aggggactct gagtgaagct     1980
ctgctgcacc tgcagttcga cgctgatgag gacctgggag ctctgctggg aacagcacc     2040 gatcccggag tgttcacaga tctggcctcc gtggacaact ctgagtttca gcagctgctg     2100
aatcagggcg tgtccatgtc tcatagtaca gccgaaccaa tgctgatgga gtaccccgaa     2160
gccattaccc ggctggtgac cggcagccag cggccccccg accccgctcc aactcccctg     2220
ggaaccagcg gcctgcctaa tgggctgtcc ggagatgaag acttctcaag catcgctgat     2280 atggactta gtgccctgct gtcacagatt tcctctagtg gcagggcgg gggaggctcc     2340 ggtggtgggg gcagcggagg ggggggcagc gactccgtgg aaatctcccgg cgtggaagat     2400 cggttcaacg cctcccctgg gcacataccac gatctgctga aaattatcaa ggacaaggac     2460
ttcctgcaca atgaggaaaa cgaggacatt ctggaagata tcgtgctgac cctgacactg     2520
tttgaggaca gagagatgat cgaggaacgg ctgaaaacct atgcccacct gttcgacgac     2580
```

-continued

```
aaagtgatga agcagctgaa gcggcggaga tacaccggct ggggcaggct gagccggaag    2640
ctgatcaacg gcatccggga caagcagtcc ggcaagacaa tcctggattt cctgaagtcc    2700
gacggcttcg ccaacagaaa cttcatgcag ctgatccacg acgacagcct gacctttaaa    2760
gaggacatcc agaaagccca ggtgtccggc cagggcgata gcctgcacga gcacattgcc    2820
aatctggccg gcagccccgc cattaagaag ggcatcctgc agacagtgaa ggtggtggac    2880
gagctcgtga agtgatggg ccggcacaag cccgagaaca tcgtgatcga aatggccaga    2940
gagaaccaga ccacccagaa gggacagaag aacagccgcg agagaatgaa gcggatcgaa    3000
gagggcatca agagctggg cagccagatc ctgaaagaac ccccgtgga aaacacccag    3060
ctgcagaacg agaagctgta cctgtactac ctgcagaatg gcgggatat gtacgtggac    3120
caggaactgg acatcaaccg gctgtccgac tacgatgtgg acgctatcgt gcctcagagc    3180
tttctgaagg acgactccat cgacaacaag gtgctgacca agcgacaa gaaccggggc    3240
aagagcgaca acgtgccctc cgaagaggtc gtgaagaaga tgaagaacta ctggcggcag    3300
ctgctgaacg ccaagctgat tacccagaga agttcgaca atctgaccaa ggccgagaga    3360
ggcggcctga cgaactgga taaggccggc ttcatcaaga cagctggt ggaaacccgg    3420
cagatcacaa agcacgtggc acagatcctg gactcccgga tgaacactaa gtacgacgag    3480
aatgacaagc tgatccggga agtgaaagtg atcaccctga agtccaagct ggtgtccgat    3540
ttccggaagg atttccagtt ttacaaagtg cgcgagatca acaactacca ccacgcccac    3600
gacgcctacc tgaacgccgt cgtgggaacc gccctgatca aaaagtaccc taagctggaa    3660
agcgagttcg tgtacggcga ctacaaggtg tacgacgtgc ggaagatgat cgccaagagc    3720
gagcaggaaa tcggcaaggc taccgccaag tacttcttct acagcaacat catgaacttt    3780
ttcaagaccg agattaccct ggccaacggc gagatccgga gcggctct gatcgagaca    3840
aacggcgaaa ccgggggagat cgtgtgggat aagggccggg attttgccac cgtgcggaaa    3900
gtgctgagca tgccccaagt gaatatcgtg aaaaagaccg aggtgcagac aggcggcttc    3960
agcaaagagt ctatcctgcc caagaggaac agcgataagc tgatcgccag aaagaaggac    4020
tgggacccta agaagtacgg cggcttcgac agccccaccg tggcctattc tgtgctggtg    4080
gtggccaaag tggaaaaggg caagtccaag aaactgaaga gtgtgaaaga gctgctgggg    4140
atcaccatca tggaaagaag cagcttcgag aagaatccca tcgactttct ggaagccaag    4200
ggctacaaag aagtgaaaaa ggacctgatc atcaagctgc ctaagtactc cctgttcgag    4260
ctggaaaacg gccggaagag aatgctggcc tctgccggcg aactgcagaa gggaaacgaa    4320
ctggccctgc cctccaaata tgtgaacttc ctgtacctgg ccagccacta tgagaagctg    4380
aagggctccc ccgaggataa tgagcagaaa cagctgtttg tggaacagca caagcactac    4440
ctggacgaga tcatcgagca gatcagcgag ttctccaaga gagtgatcct ggccgacgct    4500
aatctggaca aagtgctgtc cgcctacaac aagcaccggg ataagcccat cagagagcag    4560
gccgagaata tcatccacct gtttaccctg accaatctgg agcccctgc cgccttcaag    4620
tactttgaca ccaccatcga ccggaagagg tacaccagca ccaaagaggt gctggacgcc    4680
accctgatcc accagagcat caccggcctg tacgagacac ggatcgacct gtctcagctg    4740
ggaggcgaca gcgctggagg aggtggaagc ggaggaggag gaagcggagg aggaggtagc    4800
ggacctaaga aaaagaggaa ggtggcggcc gct                                4833
```

<210> SEQ ID NO 117

-continued

```
<211> LENGTH: 1611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Thr Met Asp Lys Lys Tyr Ser Ile Gly Leu Ala Ile Gly Thr Asn Ser
1               5                   10                  15

Val Gly Trp Ala Val Ile Thr Asp Glu Tyr Lys Val Pro Ser Lys Lys
            20                  25                  30

Phe Lys Val Leu Gly Asn Thr Asp Arg His Ser Ile Lys Lys Asn Leu
        35                  40                  45

Ile Gly Ala Leu Leu Phe Asp Ser Gly Glu Thr Ala Glu Ala Thr Arg
50                  55                  60

Leu Lys Arg Thr Ala Arg Arg Tyr Thr Arg Arg Lys Asn Arg Ile
65                  70                  75                  80

Cys Tyr Leu Gln Glu Ile Phe Ser Asn Glu Met Ala Lys Val Asp Asp
                85                  90                  95

Ser Phe Phe His Arg Leu Glu Glu Ser Phe Leu Val Glu Glu Asp Lys
            100                 105                 110

Lys His Glu Arg His Pro Ile Phe Gly Asn Ile Val Asp Glu Val Ala
        115                 120                 125

Tyr His Glu Lys Tyr Pro Thr Ile Tyr His Leu Arg Lys Lys Leu Val
130                 135                 140

Asp Ser Thr Asp Lys Ala Asp Leu Arg Leu Ile Tyr Leu Ala Leu Ala
145                 150                 155                 160

His Met Ile Lys Phe Arg Gly His Phe Leu Ile Glu Gly Asp Leu Asn
                165                 170                 175

Pro Asp Asn Ser Asp Val Asp Lys Leu Phe Ile Gln Leu Val Gln Thr
            180                 185                 190

Tyr Asn Gln Leu Phe Glu Glu Asn Pro Ile Asn Ala Ser Gly Val Asp
        195                 200                 205

Ala Lys Ala Ile Leu Ser Ala Arg Leu Ser Lys Ser Arg Arg Leu Glu
210                 215                 220

Asn Leu Ile Ala Gln Leu Pro Gly Glu Lys Lys Asn Gly Leu Phe Gly
225                 230                 235                 240

Asn Leu Ile Ala Leu Ser Leu Gly Leu Thr Pro Asn Phe Lys Ser Asn
                245                 250                 255

Phe Asp Leu Ala Glu Asp Ala Lys Leu Gln Leu Ser Lys Asp Thr Tyr
            260                 265                 270

Asp Asp Asp Leu Asp Asn Leu Leu Ala Gln Ile Gly Asp Gln Tyr Ala
        275                 280                 285

Asp Leu Phe Leu Ala Ala Lys Asn Leu Ser Asp Ala Ile Leu Leu Ser
290                 295                 300

Asp Ile Leu Arg Val Asn Thr Glu Ile Thr Lys Ala Pro Leu Ser Ala
305                 310                 315                 320

Ser Met Ile Lys Arg Tyr Asp Glu His His Gln Asp Leu Thr Leu Leu
                325                 330                 335

Lys Ala Leu Val Arg Gln Gln Leu Pro Glu Lys Tyr Lys Glu Ile Phe
            340                 345                 350

Phe Asp Gln Ser Lys Asn Gly Tyr Ala Gly Tyr Ile Asp Gly Gly Ala
        355                 360                 365
```

```
Ser Gln Glu Glu Phe Tyr Lys Phe Ile Lys Pro Ile Leu Glu Lys Met
370                 375                 380

Asp Gly Thr Glu Leu Leu Val Lys Leu Asn Arg Glu Asp Leu Leu
385                 390                 395                 400

Arg Lys Gln Arg Thr Phe Asp Asn Gly Ser Ile Pro His Gln Ile His
            405                 410                 415

Leu Gly Glu Leu His Ala Ile Leu Arg Arg Gln Glu Asp Phe Tyr Pro
                420                 425                 430

Phe Leu Lys Asp Asn Arg Glu Lys Ile Glu Lys Ile Leu Thr Phe Arg
            435                 440                 445

Ile Pro Tyr Tyr Val Gly Pro Leu Ala Arg Gly Asn Ser Arg Phe Ala
450                 455                 460

Trp Met Thr Arg Lys Ser Glu Glu Thr Ile Thr Pro Trp Asn Phe Glu
465                 470                 475                 480

Glu Val Val Asp Lys Gly Ala Ser Ala Gln Ser Phe Ile Glu Arg Met
                485                 490                 495

Thr Asn Phe Asp Lys Asn Leu Pro Asn Glu Lys Val Leu Pro Lys His
            500                 505                 510

Ser Leu Leu Tyr Glu Tyr Phe Thr Val Tyr Asn Glu Leu Thr Lys Val
            515                 520                 525

Lys Tyr Val Thr Glu Gly Met Arg Lys Pro Ala Phe Leu Ser Gly Glu
530                 535                 540

Gln Lys Lys Ala Ile Val Asp Leu Leu Phe Lys Thr Asn Arg Lys Val
545                 550                 555                 560

Thr Val Lys Gln Leu Lys Glu Asp Tyr Phe Lys Lys Ile Glu Cys Phe
                565                 570                 575

Gly Gly Gly Gly Ser Gly Gly Gly Ser Gly Gly Gly Ser Pro
            580                 585                 590

Ser Gly Gln Ile Ser Asn Gln Ala Leu Ala Leu Ala Pro Ser Ser Ala
            595                 600                 605

Pro Val Leu Ala Gln Thr Met Val Pro Ser Ser Ala Met Val Pro Leu
            610                 615                 620

Ala Gln Pro Pro Ala Pro Ala Pro Val Leu Thr Pro Gly Pro Pro Gln
625                 630                 635                 640

Ser Leu Ser Ala Pro Val Pro Lys Ser Thr Gln Ala Gly Glu Gly Thr
            645                 650                 655

Leu Ser Glu Ala Leu Leu His Leu Gln Phe Asp Ala Asp Glu Asp Leu
                660                 665                 670

Gly Ala Leu Leu Gly Asn Ser Thr Asp Pro Gly Val Phe Thr Asp Leu
            675                 680                 685

Ala Ser Val Asp Asn Ser Glu Phe Gln Gln Leu Leu Asn Gln Gly Val
690                 695                 700

Ser Met Ser His Ser Thr Ala Glu Pro Met Leu Met Glu Tyr Pro Glu
705                 710                 715                 720

Ala Ile Thr Arg Leu Val Thr Gly Ser Gln Arg Pro Pro Asp Pro Ala
                725                 730                 735

Pro Thr Pro Leu Gly Thr Ser Gly Leu Pro Asn Gly Leu Ser Gly Asp
            740                 745                 750

Glu Asp Phe Ser Ser Ile Ala Asp Met Asp Phe Ser Ala Leu Leu Ser
            755                 760                 765

Gln Ile Ser Ser Gly Gln Gly Gly Gly Ser Gly Gly Gly
770                 775                 780

Ser Gly Gly Gly Gly Ser Asp Ser Val Glu Ile Ser Gly Val Glu Asp
```

```
                785                 790                 795                 800
Arg Phe Asn Ala Ser Leu Gly Thr Tyr His Asp Leu Leu Lys Ile Ile
                805                 810                 815

Lys Asp Lys Asp Phe Leu Asp Asn Glu Glu Asn Glu Asp Ile Leu Glu
                820                 825                 830

Asp Ile Val Leu Thr Leu Thr Leu Phe Glu Asp Arg Glu Met Ile Glu
                835                 840                 845

Glu Arg Leu Lys Thr Tyr Ala His Leu Phe Asp Asp Lys Val Met Lys
        850                 855                 860

Gln Leu Lys Arg Arg Arg Tyr Thr Gly Trp Gly Arg Leu Ser Arg Lys
865                 870                 875                 880

Leu Ile Asn Gly Ile Arg Asp Lys Gln Ser Gly Lys Thr Ile Leu Asp
                885                 890                 895

Phe Leu Lys Ser Asp Gly Phe Ala Asn Arg Asn Phe Met Gln Leu Ile
                900                 905                 910

His Asp Asp Ser Leu Thr Phe Lys Glu Asp Ile Gln Lys Ala Gln Val
                915                 920                 925

Ser Gly Gln Gly Asp Ser Leu His Glu His Ile Ala Asn Leu Ala Gly
        930                 935                 940

Ser Pro Ala Ile Lys Lys Gly Ile Leu Gln Thr Val Lys Val Val Asp
945                 950                 955                 960

Glu Leu Val Lys Val Met Gly Arg His Lys Pro Glu Asn Ile Val Ile
                965                 970                 975

Glu Met Ala Arg Glu Asn Gln Thr Thr Gln Lys Gly Gln Lys Asn Ser
        980                 985                 990

Arg Glu Arg Met Lys Arg Ile Glu  Glu Gly Ile Lys Glu  Leu Gly Ser
        995                 1000                1005

Gln Ile  Leu Lys Glu His Pro  Val Glu Asn Thr Gln  Leu Gln Asn
        1010                1015                1020

Glu Lys  Leu Tyr Leu Tyr Tyr  Leu Gln Asn Gly Arg  Asp Met Tyr
        1025                1030                1035

Val Asp  Gln Glu Leu Asp Ile  Asn Arg Leu Ser Asp  Tyr Asp Val
        1040                1045                1050

Asp Ala  Ile Val Pro Gln Ser  Phe Leu Lys Asp Asp  Ser Ile Asp
        1055                1060                1065

Asn Lys  Val Leu Thr Arg Ser  Asp Lys Asn Arg Gly  Lys Ser Asp
        1070                1075                1080

Asn Val  Pro Ser Glu Glu Val  Val Lys Lys Met Lys  Asn Tyr Trp
        1085                1090                1095

Arg Gln  Leu Leu Asn Ala Lys  Leu Ile Thr Gln Arg  Lys Phe Asp
        1100                1105                1110

Asn Leu  Thr Lys Ala Glu Arg  Gly Gly Leu Ser Glu  Leu Asp Lys
        1115                1120                1125

Ala Gly  Phe Ile Lys Arg Gln  Leu Val Glu Thr Arg  Gln Ile Thr
        1130                1135                1140

Lys His  Val Ala Gln Ile Leu  Asp Ser Arg Met Asn  Thr Lys Tyr
        1145                1150                1155

Asp Glu  Asn Asp Lys Leu Ile  Arg Glu Val Lys Val  Ile Thr Leu
        1160                1165                1170

Lys Ser  Lys Leu Val Ser Asp  Phe Arg Lys Asp Phe  Gln Phe Tyr
        1175                1180                1185

Lys Val  Arg Glu Ile Asn Asn  Tyr His His Ala His  Asp Ala Tyr
        1190                1195                1200
```

-continued

```
Leu Asn Ala Val Val Gly Thr Ala Leu Ile Lys Lys Tyr Pro Lys
1205                1210                1215

Leu Glu Ser Glu Phe Val Tyr Gly Asp Tyr Lys Val Tyr Asp Val
1220                1225                1230

Arg Lys Met Ile Ala Lys Ser Glu Gln Glu Ile Gly Lys Ala Thr
1235                1240                1245

Ala Lys Tyr Phe Phe Tyr Ser Asn Ile Met Asn Phe Phe Lys Thr
1250                1255                1260

Glu Ile Thr Leu Ala Asn Gly Glu Ile Arg Lys Arg Pro Leu Ile
1265                1270                1275

Glu Thr Asn Gly Glu Thr Gly Glu Ile Val Trp Asp Lys Gly Arg
1280                1285                1290

Asp Phe Ala Thr Val Arg Lys Val Leu Ser Met Pro Gln Val Asn
1295                1300                1305

Ile Val Lys Lys Thr Glu Val Gln Thr Gly Gly Phe Ser Lys Glu
1310                1315                1320

Ser Ile Leu Pro Lys Arg Asn Ser Asp Lys Leu Ile Ala Arg Lys
1325                1330                1335

Lys Asp Trp Asp Pro Lys Lys Tyr Gly Gly Phe Asp Ser Pro Thr
1340                1345                1350

Val Ala Tyr Ser Val Leu Val Val Ala Lys Val Glu Lys Gly Lys
1355                1360                1365

Ser Lys Lys Leu Lys Ser Val Lys Glu Leu Leu Gly Ile Thr Ile
1370                1375                1380

Met Glu Arg Ser Ser Phe Glu Lys Asn Pro Ile Asp Phe Leu Glu
1385                1390                1395

Ala Lys Gly Tyr Lys Glu Val Lys Lys Asp Leu Ile Ile Lys Leu
1400                1405                1410

Pro Lys Tyr Ser Leu Phe Glu Leu Glu Asn Gly Arg Lys Arg Met
1415                1420                1425

Leu Ala Ser Ala Gly Glu Leu Gln Lys Gly Asn Glu Leu Ala Leu
1430                1435                1440

Pro Ser Lys Tyr Val Asn Phe Leu Tyr Leu Ala Ser His Tyr Glu
1445                1450                1455

Lys Leu Lys Gly Ser Pro Glu Asp Asn Glu Gln Lys Gln Leu Phe
1460                1465                1470

Val Glu Gln His Lys His Tyr Leu Asp Glu Ile Ile Glu Gln Ile
1475                1480                1485

Ser Glu Phe Ser Lys Arg Val Ile Leu Ala Asp Ala Asn Leu Asp
1490                1495                1500

Lys Val Leu Ser Ala Tyr Asn Lys His Arg Asp Lys Pro Ile Arg
1505                1510                1515

Glu Gln Ala Glu Asn Ile Ile His Leu Phe Thr Leu Thr Asn Leu
1520                1525                1530

Gly Ala Pro Ala Ala Phe Lys Tyr Phe Asp Thr Thr Ile Asp Arg
1535                1540                1545

Lys Arg Tyr Thr Ser Thr Lys Glu Val Leu Asp Ala Thr Leu Ile
1550                1555                1560

His Gln Ser Ile Thr Gly Leu Tyr Glu Thr Arg Ile Asp Leu Ser
1565                1570                1575

Gln Leu Gly Gly Asp Ser Ala Gly Gly Gly Gly Ser Gly Gly Gly
1580                1585                1590
```

Gly Ser Gly Gly Gly Gly Ser Gly Pro Lys Lys Lys Arg Lys Val
    1595                1600            1605

Ala Ala Ala
    1610

<210> SEQ ID NO 118
<211> LENGTH: 4380
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

| | | | | | |
|---|---|---|---|---|---|
| gacaagaagt | acagcatcgg | cctggccatc | ggcaccaact | ctgtgggctg | ggccgtgatc | 60 |
| accgacgagt | acaaggtgcc | cagcaagaaa | ttcaaggtgc | tgggcaacac | cgaccggcac | 120 |
| agcatcaaga | agaacctgat | cggagccctg | ctgttcgaca | gcggcgaaac | agccgaggcc | 180 |
| acccggctga | agagaaccgc | cagaagaaga | tacaccagac | ggaagaaccg | gatctgctat | 240 |
| ctgcaagaga | tcttcagcaa | cgagatggcc | aaggtggacg | acagcttctt | ccacagactg | 300 |
| gaagagtcct | tcctggtgga | agaggataag | aagcacgagc | ggcaccccat | cttcggcaac | 360 |
| atcgtggacg | aggtggccta | ccacgagaag | tacccaccca | tctaccacct | gagaaagaaa | 420 |
| ctggtgcaga | caccgacaa | ggccgacctg | cggctgatct | atctggccct | ggcccacatg | 480 |
| atcaagttcc | ggggccactt | cctgatcgag | ggcgacctga | accccgacaa | cagcgacgtg | 540 |
| gacaagctgt | tcatccagct | ggtgcagacc | tacaaccagc | tgttcgagga | aaacccatc | 600 |
| aacgccagcg | gcgtggacgc | caaggccatc | ctgtctgcca | gactgagcaa | gagcagacgg | 660 |
| ctggaaaatc | tgatcgccca | gctgcccggc | gagaagaaga | atggcctgtt | cggcaacctg | 720 |
| attgccctga | gcctgggcct | gacccccaac | ttcaagagca | acttcgacct | ggccgaggat | 780 |
| gccaaactgc | agctgagcaa | ggacacctac | gacgacgacc | tggacaacct | gctggcccag | 840 |
| atcggcgacc | agtacgccga | cctgtttctg | gccgccaaga | acctgtccga | cgccatcctg | 900 |
| ctgagcgaca | tcctgagagt | gaacaccgag | atcaccaagg | ccccctgag | cgcctctatg | 960 |
| atcaagagat | acgacgagca | ccaccaggac | ctgaccctgc | tgaaagctct | cgtgcggcag | 1020 |
| cagctgcctg | agaagtacaa | agagattttc | ttcgaccaga | gcaagaacgg | ctacgccggc | 1080 |
| tacattgacg | gcggagccag | ccaggaagag | ttctacaagt | tcatcaagcc | catcctggaa | 1140 |
| aagatggacg | gcaccgagga | actgctcgtg | aagctgaaca | gagaggacct | gctgcggaag | 1200 |
| cagcggacct | tcgacaacgg | cagcatcccc | caccagatcc | acctgggaga | gctgcacgcc | 1260 |
| attctgcggc | ggcaggaaga | tttttaccca | ttcctgaagg | acaaccggga | aaagatcgag | 1320 |
| aagatcctga | ccttccgcat | ccctactac | gtgggccctc | tggccagggg | aaacagcaga | 1380 |
| ttcgcctgga | tgaccagaaa | gagcgaggaa | accatcaccc | cctggaactt | cgaggaagtg | 1440 |
| gtggacaagg | gcgcttccgc | ccagagcttc | atcgagcgga | tgaccaactt | cgataagaac | 1500 |
| ctgcccaacg | agaaggtgct | gcccaagcac | agcctgctgt | acgagtactt | caccgtgtat | 1560 |
| aacgagctga | ccaaagtgaa | atacgtgacc | gagggaatga | gaaagcccgc | cttcctgagc | 1620 |
| ggcgagcaga | aaaaggccat | cgtggacctg | ctgttcaaga | ccaaccggaa | agtgaccgtg | 1680 |
| aagcagctga | agaggactac | cttcaagaaa | atcgagtgct | tcgactccgt | ggaaatctcc | 1740 |
| ggcgtggaag | atcggttcaa | cgcctccctg | ggcacatacc | acgatctgct | gaaaattatc | 1800 |
| aaggacaagg | acttcctgga | caatgaggaa | aacgaggaca | ttctggaaga | tatcgtgctg | 1860 |

```
accctgacac tgtttgagga cagagagatg atcgaggaac ggctgaaaac ctatgcccac   1920
ctgttcgacg acaaagtgat gaagcagctg aagcggcgga gataccacgg ctggggcagg   1980
ctgagccgga agctgatcaa cggcatccgg acaagcagt ccggcaagac aatcctggat    2040
ttcctgaagt ccgacggctt cgccaacaga aacttcatgc agctgatcca cgacgacagc   2100 ctgacccttta agaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc    2280 gaaatggcca gagagaacca gaccacccag aagggacaga gaacagccg cgagagaatg    2340 aagcggatcg aagagggcat caaagagctg ggcagccaga tcctgaaaga cacccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgctatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcacccct gaagtccaag   2880 ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact ttttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga cagcgataa gctgatcgcc   3360 agaaagaagg actgggaccc taagaagtac ggcggcttcg acagccccac cgtggcctat   3420
tctgtgctgg tggtggccaa agtggaaaag ggcaaggag gggaggcag cggacgggct    3480 gacgcattgg acgattttga tctggatatg ctgggaagtg acgccctcga tgattttgac   3540
cttgacatgc ttggttcgga tgcccttgat gactttgacc tcgacatgct cggcagtgac   3600
gcccttgatg atttcgacct ggacatgctg attaacggcg ggggaggctc ctccaagaaa   3660
ctgaagagtg tgaaagagct gctggggatc accatcatgg aaagaagcag cttcgagaag   3720
aatcccatcg actttctgga agccaagggc tacaagaag tgaaaaagga cctgatcatc    3780
aagctgccta agtactccct gttcgagctg gaaaacggcc ggaagagaat gctggcctct   3840
gccggcgaac tgcagaaggg aaacgaactg gccctgccct ccaaatatgt gaacttcctg   3900
tacctggcca gccactatga gaagctgaag ggctcccccg aggataatga gcagaaacag   3960
ctgtttgtgg aacagcacaa gcactacctg gacgagatca tcgagcagat cagcgagttc   4020
tccaagagag tgatcctggc cgacgctaat ctggacaaag tgctgtccgc ctacaacaag   4080
caccgggata gcccatcag agagcaggcc gagaatatca tccacctgtt taccctgacc   4140
aatctgggag cccctgccgc cttcaagtac tttgacacca ccatcgaccg gaagaggtac   4200
```

-continued

```
accagcacca aagaggtgct ggacgccacc ctgatccacc agagcatcac cggcctgtac    4260
gagacacgga tcgacctgtc tcagctggga ggcgacagcg ctggaggagg tggaagcgga    4320
ggaggaggaa gcggaggagg aggtagcgga cctaagaaaa agaggaaggt ggcggccgct    4380
```

<210> SEQ ID NO 119
<211> LENGTH: 1460
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
```

-continued

```
                325                 330                 335
Leu Val Arg Gln Gln Leu Pro Glu Lys Tyr Lys Glu Ile Phe Phe Asp
                340                 345                 350
Gln Ser Lys Asn Gly Tyr Ala Gly Tyr Ile Asp Gly Gly Ala Ser Gln
                355                 360                 365
Glu Glu Phe Tyr Lys Phe Ile Lys Pro Ile Leu Glu Lys Met Asp Gly
                370                 375                 380
Thr Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
                420                 425                 430
Lys Asp Asn Arg Glu Lys Ile Glu Lys Ile Leu Thr Phe Arg Ile Pro
                435                 440                 445
Tyr Tyr Val Gly Pro Leu Ala Arg Gly Asn Ser Arg Phe Ala Trp Met
                450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
                500                 505                 510
Leu Tyr Glu Tyr Phe Thr Val Tyr Asn Glu Leu Thr Lys Val Lys Tyr
                515                 520                 525
Val Thr Glu Gly Met Arg Lys Pro Ala Phe Leu Ser Gly Glu Gln Lys
                530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
                580                 585                 590
Tyr His Asp Leu Leu Lys Ile Ile Lys Asp Lys Asp Phe Leu Asp Asn
                595                 600                 605
Glu Glu Asn Glu Asp Ile Leu Glu Asp Ile Val Leu Thr Leu Thr Leu
                610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
                645                 650                 655
Gly Trp Gly Arg Leu Ser Arg Lys Leu Ile Asn Gly Ile Arg Asp Lys
                660                 665                 670
Gln Ser Gly Lys Thr Ile Leu Asp Phe Leu Lys Ser Asp Gly Phe Ala
                675                 680                 685
Asn Arg Asn Phe Met Gln Leu Ile His Asp Asp Ser Leu Thr Phe Lys
                690                 695                 700
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
                740                 745                 750
```

-continued

```
His Lys Pro Glu Asn Ile Val Ile Glu Met Ala Arg Glu Asn Gln Thr
        755                 760                 765
Thr Gln Lys Gly Gln Lys Asn Ser Arg Glu Arg Met Lys Arg Ile Glu
        770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu
                820                 825                 830
Ser Asp Tyr Asp Val Asp Ala Ile Val Pro Gln Ser Phe Leu Lys Asp
                835                 840                 845
Asp Ser Ile Asp Asn Lys Val Leu Thr Arg Ser Asp Lys Asn Arg Gly
        850                 855                 860
Lys Ser Asp Asn Val Pro Ser Glu Glu Val Val Lys Lys Met Lys Asn
865                 870                 875                 880
Tyr Trp Arg Gln Leu Leu Asn Ala Lys Leu Ile Thr Gln Arg Lys Phe
                885                 890                 895
Asp Asn Leu Thr Lys Ala Glu Arg Gly Gly Leu Ser Glu Leu Asp Lys
                900                 905                 910
Ala Gly Phe Ile Lys Arg Gln Leu Val Glu Thr Arg Gln Ile Thr Lys
                915                 920                 925
His Val Ala Gln Ile Leu Asp Ser Arg Met Asn Thr Lys Tyr Asp Glu
        930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                965                 970                 975
Ile Asn Asn Tyr His His Ala His Asp Ala Tyr Leu Asn Ala Val Val
                980                 985                 990
Gly Thr Ala Leu Ile Lys Lys Tyr Pro Lys Leu Glu Ser Glu Phe Val
        995                 1000                1005
Tyr Gly Asp Tyr Lys Val Tyr Asp Val Arg Lys Met Ile Ala Lys
        1010                1015                1020
Ser Glu Gln Glu Ile Gly Lys Ala Thr Ala Lys Tyr Phe Phe Tyr
        1025                1030                1035
Ser Asn Ile Met Asn Phe Phe Lys Thr Glu Ile Thr Leu Ala Asn
        1040                1045                1050
Gly Glu Ile Arg Lys Arg Pro Leu Ile Glu Thr Asn Gly Glu Thr
        1055                1060                1065
Gly Glu Ile Val Trp Asp Lys Gly Arg Asp Phe Ala Thr Val Arg
        1070                1075                1080
Lys Val Leu Ser Met Pro Gln Val Asn Ile Val Lys Lys Thr Glu
        1085                1090                1095
Val Gln Thr Gly Gly Phe Ser Lys Glu Ser Ile Leu Pro Lys Arg
        1100                1105                1110
Asn Ser Asp Lys Leu Ile Ala Arg Lys Lys Asp Trp Asp Pro Lys
        1115                1120                1125
Lys Tyr Gly Gly Phe Asp Ser Pro Thr Val Ala Tyr Ser Val Leu
        1130                1135                1140
Val Val Ala Lys Val Glu Lys Gly Lys Gly Gly Gly Ser Gly
        1145                1150                1155
```

```
Arg Ala Asp Ala Leu Asp Asp Phe Asp Leu Asp Met Leu Gly Ser
    1160            1165                1170

Asp Ala Leu Asp Asp Phe Asp Leu Asp Met Leu Gly Ser Asp Ala
    1175            1180                1185

Leu Asp Asp Phe Asp Leu Asp Met Leu Gly Ser Asp Ala Leu Asp
    1190            1195                1200

Asp Phe Asp Leu Asp Met Leu Ile Asn Gly Gly Gly Gly Ser Ser
    1205            1210                1215

Lys Lys Leu Lys Ser Val Lys Glu Leu Leu Gly Ile Thr Ile Met
    1220            1225                1230

Glu Arg Ser Ser Phe Glu Lys Asn Pro Ile Asp Phe Leu Glu Ala
    1235            1240                1245

Lys Gly Tyr Lys Glu Val Lys Lys Asp Leu Ile Ile Lys Leu Pro
    1250            1255                1260

Lys Tyr Ser Leu Phe Glu Leu Glu Asn Gly Arg Lys Arg Met Leu
    1265            1270                1275

Ala Ser Ala Gly Glu Leu Gln Lys Gly Asn Glu Leu Ala Leu Pro
    1280            1285                1290

Ser Lys Tyr Val Asn Phe Leu Tyr Leu Ala Ser His Tyr Glu Lys
    1295            1300                1305

Leu Lys Gly Ser Pro Glu Asp Asn Glu Gln Lys Gln Leu Phe Val
    1310            1315                1320

Glu Gln His Lys His Tyr Leu Asp Glu Ile Ile Glu Gln Ile Ser
    1325            1330                1335

Glu Phe Ser Lys Arg Val Ile Leu Ala Asp Ala Asn Leu Asp Lys
    1340            1345                1350

Val Leu Ser Ala Tyr Asn Lys His Arg Asp Lys Pro Ile Arg Glu
    1355            1360                1365

Gln Ala Glu Asn Ile Ile His Leu Phe Thr Leu Thr Asn Leu Gly
    1370            1375                1380

Ala Pro Ala Ala Phe Lys Tyr Phe Asp Thr Thr Ile Asp Arg Lys
    1385            1390                1395

Arg Tyr Thr Ser Thr Lys Glu Val Leu Asp Ala Thr Leu Ile His
    1400            1405                1410

Gln Ser Ile Thr Gly Leu Tyr Glu Thr Arg Ile Asp Leu Ser Gln
    1415            1420                1425

Leu Gly Gly Asp Ser Ala Gly Gly Gly Ser Gly Gly Gly Gly
    1430            1435                1440

Ser Gly Gly Gly Gly Ser Gly Pro Lys Lys Lys Arg Lys Val Ala
    1445            1450                1455

Ala Ala
    1460

<210> SEQ ID NO 120
<211> LENGTH: 4445
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
gacaagaagt acagcatcgg cctggccatc ggcaccaact ctgtgggctg ggccgtgatc    60
accgacgagt acaaggtgcc cagcaagaaa ttcaaggtgc tgggcaacac cgaccggcac   120
```

```
agcatcaaga agaacctgat cggagccctg ctgttcgaca gcggcgaaac agccgaggcc    180
acccggctga agagaaccgc cagaagaaga tacaccagac ggaagaaccg gatctgctat    240
ctgcaagaga tcttcagcaa cgagatggcc aaggtggacg acagcttctt ccacagactg    300
gaagagtcct tcctggtgga agaggataag aagcacgagc ggcacccat cttcggcaac     360 atcgtggacg aggtggccta ccacgagaag taccccacca tctaccacct gagaaagaaa    420
ctggtgacca gcaccgacaa ggccgacctg cggctgatct atctggccct ggcccacatg    480
atcaagttcc ggggccactt cctgatcgag ggcgacctga accccgacaa cagcgacgtg    540
gacaagctgt tcatccagct ggtgcagacc tacaaccagc tgttcgagga aaacccatc     600 aacgccagcg gcgtggacgc caaggccatc ctgtctgcca gactgagcaa gagcagacgg    660
ctggaaaatc tgatcgccca gctgcccggc gagaagaaga tggcctgtt cggcaacctg     720 attgccctga gcctgggcct gaccccaac ttcaagagca cttcgacct ggccgaggat      780 gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg cccccctgag cgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt catcaagcc atcctggaa     1140 aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga aaagcccgc cttcctgagc    1620 ggcgagcaga aaaaggccat cgtggacctg ctgttcaaga ccaaccggaa agtgaccgtg   1680
aagcagctga agaggactac cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga atacaccgg ctggggcagg   1980 ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctttta aagaggacat ccagaaagcc caggtgtccg gcagggcga tagcctgcac   2160 gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280 gaaatggcca gagagaacca gaccacccag aagggacaga gaacagccg cgagagaatg   2340 aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgctatc   2520
```

-continued

```
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca gtacttctt ctacagcaac    3120 atcatgaact ttttcaagac cgagattacc ctggccaacg gcgagatccg gaagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagccccac cgtggcctat    3420
tctgtgctgg tggtggccaa agtggaaaag gcaagggcg ggggaggctc cggtggtggg    3480
ggcagcggag ggggggcag cggacgggct gacgcattgg acgattttga tctggatatg    3540
ctgggaagtg acgccctcga tgattttgac cttgacatgc ttggttcgga tgcccttgat    3600
gactttgacc tcgacatgct cggcagtgac gcccttgatg atttcgacct ggacatgctg    3660
attaacggcg gggaggctc cggtggtggg ggcagcggag ggggggcag ctccaagaaa    3720 ctgaagagtg tgaaagagct gctggggatc accatcatg aaagaagcag cttcgagaag    3780
aatcccatcg actttctgga agccaagggc tacaaagaag tgaaaaagga cctgatcatc    3840
aagctgccta agtactccct gttcgagctg gaaaacggcc ggaagagaat gctggcctct    3900
gccggcgaac tgcagaaggg aaacgaactg gccctgccct ccaaatatgt gaacttcctg    3960
tacctggcca gccactatga aagctgaag ggctcccccg aggataatga gcagaaacag    4020
ctgtttgtgg aacagcacaa gcactacctg gacgagatca tcgagcagat cagcgagttc    4080
tccaagagag tgatcctggc cgacgctaat ctggacaaag tgctgtccgc ctacaacaag    4140
caccgggata agcccatcag agagcaggcc gagaatatca tccacctgtt taccctgacc    4200
aatctgggag cccctgccgc cttcaagtac tttgacacca ccatcgaccg gaagaggtac    4260
accagcacca agaggtgct ggacgccacc ctgatccacc agagcatcac cggcctgtac    4320
gagacacgga tcgacctgtc tcagctggga ggcgacagcg gggaggagg tggaagcgga    4380 ggaggaggaa gcggaggagg aggtagcgga cctaagaaaa agaggaaggt ggcggccgct    4440
gctag                                                              4445
```

<210> SEQ ID NO 121
<211> LENGTH: 1481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
                100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
        130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
                180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
        210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
                260                 265                 270

Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
        290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
        370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
```

-continued

```
                420             425             430
Lys Asp Asn Arg Glu Lys Ile Glu Lys Ile Leu Thr Phe Arg Ile Pro
            435             440             445
Tyr Tyr Val Gly Pro Leu Ala Arg Gly Asn Ser Arg Phe Ala Trp Met
450             455             460
Thr Arg Lys Ser Glu Glu Thr Ile Thr Pro Trp Asn Phe Glu Glu Val
465             470             475             480
Val Asp Lys Gly Ala Ser Ala Gln Ser Phe Ile Glu Arg Met Thr Asn
            485             490             495
Phe Asp Lys Asn Leu Pro Asn Glu Lys Val Leu Pro Lys His Ser Leu
        500             505             510
Leu Tyr Glu Tyr Phe Thr Val Tyr Asn Glu Leu Thr Lys Val Lys Tyr
        515             520             525
Val Thr Glu Gly Met Arg Lys Pro Ala Phe Leu Ser Gly Glu Gln Lys
        530             535             540
Lys Ala Ile Val Asp Leu Leu Phe Lys Thr Asn Arg Lys Val Thr Val
545             550             555             560
Lys Gln Leu Lys Glu Asp Tyr Phe Lys Lys Ile Glu Cys Phe Asp Ser
            565             570             575
Val Glu Ile Ser Gly Val Glu Asp Arg Phe Asn Ala Ser Leu Gly Thr
            580             585             590
Tyr His Asp Leu Leu Lys Ile Ile Lys Asp Lys Asp Phe Leu Asp Asn
        595             600             605
Glu Glu Asn Glu Asp Ile Leu Glu Asp Ile Val Leu Thr Leu Thr Leu
        610             615             620
Phe Glu Asp Arg Glu Met Ile Glu Glu Arg Leu Lys Thr Tyr Ala His
625             630             635             640
Leu Phe Asp Asp Lys Val Met Lys Gln Leu Lys Arg Arg Arg Tyr Thr
            645             650             655
Gly Trp Gly Arg Leu Ser Arg Lys Leu Ile Asn Gly Ile Arg Asp Lys
            660             665             670
Gln Ser Gly Lys Thr Ile Leu Asp Phe Leu Lys Ser Asp Gly Phe Ala
        675             680             685
Asn Arg Asn Phe Met Gln Leu Ile His Asp Asp Ser Leu Thr Phe Lys
        690             695             700
Glu Asp Ile Gln Lys Ala Gln Val Ser Gly Gln Gly Asp Ser Leu His
705             710             715             720
Glu His Ile Ala Asn Leu Ala Gly Ser Pro Ala Ile Lys Lys Gly Ile
            725             730             735
Leu Gln Thr Val Lys Val Val Asp Glu Leu Val Lys Val Met Gly Arg
            740             745             750
His Lys Pro Glu Asn Ile Val Ile Glu Met Ala Arg Glu Asn Gln Thr
        755             760             765
Thr Gln Lys Gly Gln Lys Asn Ser Arg Glu Arg Met Lys Arg Ile Glu
        770             775             780
Glu Gly Ile Lys Glu Leu Gly Ser Gln Ile Leu Lys Glu His Pro Val
785             790             795             800
Glu Asn Thr Gln Leu Gln Asn Glu Lys Leu Tyr Leu Tyr Tyr Leu Gln
            805             810             815
Asn Gly Arg Asp Met Tyr Val Asp Gln Glu Leu Asp Ile Asn Arg Leu
            820             825             830
Ser Asp Tyr Asp Val Asp Ala Ile Val Pro Gln Ser Phe Leu Lys Asp
        835             840             845
```

Asp Ser Ile Asp Asn Lys Val Leu Thr Arg Ser Asp Lys Asn Arg Gly
        850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Gly Gly Gly Ser Gly
    1145                1150                1155

Gly Gly Gly Ser Gly Gly Gly Ser Gly Arg Ala Asp Ala Leu
    1160                1165                1170

Asp Asp Phe Asp Leu Asp Met Leu Gly Ser Asp Ala Leu Asp Asp
    1175                1180                1185

Phe Asp Leu Asp Met Leu Gly Ser Asp Ala Leu Asp Asp Phe Asp
    1190                1195                1200

Leu Asp Met Leu Gly Ser Asp Ala Leu Asp Asp Phe Asp Leu Asp
    1205                1210                1215

Met Leu Ile Asn Gly Gly Gly Ser Gly Gly Gly Ser Gly
    1220                1225                1230

Gly Gly Gly Ser Ser Lys Lys Leu Lys Ser Val Lys Glu Leu Leu
    1235                1240                1245

| | | | | | | | | | | |
|---|---|---|---|---|---|---|---|---|---|---|
| Gly | Ile | Thr | Ile | Met | Glu | Arg | Ser | Ser | Phe | Glu | Lys | Asn | Pro | Ile |
| 1250 | | | | | 1255 | | | | | 1260 | | | | |

Gly Ile Thr Ile Met Glu Arg Ser Ser Phe Glu Lys Asn Pro Ile
  1250                1255                1260

Asp Phe Leu Glu Ala Lys Gly Tyr Lys Glu Val Lys Lys Asp Leu
  1265                1270                1275

Ile Ile Lys Leu Pro Lys Tyr Ser Leu Phe Glu Leu Glu Asn Gly
  1280                1285                1290

Arg Lys Arg Met Leu Ala Ser Ala Gly Glu Leu Gln Lys Gly Asn
  1295                1300                1305

Glu Leu Ala Leu Pro Ser Lys Tyr Val Asn Phe Leu Tyr Leu Ala
  1310                1315                1320

Ser His Tyr Glu Lys Leu Lys Gly Ser Pro Glu Asp Asn Glu Gln
  1325                1330                1335

Lys Gln Leu Phe Val Glu Gln His Lys His Tyr Leu Asp Glu Ile
  1340                1345                1350

Ile Glu Gln Ile Ser Glu Phe Ser Lys Arg Val Ile Leu Ala Asp
  1355                1360                1365

Ala Asn Leu Asp Lys Val Leu Ser Ala Tyr Asn Lys His Arg Asp
  1370                1375                1380

Lys Pro Ile Arg Glu Gln Ala Glu Asn Ile Ile His Leu Phe Thr
  1385                1390                1395

Leu Thr Asn Leu Gly Ala Pro Ala Ala Phe Lys Tyr Phe Asp Thr
  1400                1405                1410

Thr Ile Asp Arg Lys Arg Tyr Thr Ser Thr Lys Glu Val Leu Asp
  1415                1420                1425

Ala Thr Leu Ile His Gln Ser Ile Thr Gly Leu Tyr Glu Thr Arg
  1430                1435                1440

Ile Asp Leu Ser Gln Leu Gly Gly Asp Ser Ala Gly Gly Gly Gly
  1445                1450                1455

Ser Gly Gly Gly Gly Ser Gly Gly Gly Ser Gly Pro Lys Lys
  1460                1465                1470

Lys Arg Lys Val Ala Ala Ala Ala
  1475                1480

<210> SEQ ID NO 122
<211> LENGTH: 4767
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga agaacctgat cggagccctg ctgttcgaca cggccgaaac agccgaggcc     180
acccggctga agagaaccgc cagaagaaga taccaccgac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag tacccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaaccccatc     600

```
aacgccagcg gcgtggacgc caaggccatc ctgtctgcca gactgagcaa gagcagacgg     660
ctggaaaatc tgatcgccca gctgcccggc gagaagaaga atggcctgtt cggcaacctg     720
attgccctga gcctgggcct gacccccaac ttcaagagca acttcgacct ggccgaggat     780
gccaaactgc agctgagcaa ggacacctac gacgacgacc tggacaacct gctggcccag     840
atcggcgacc agtacgccga cctgtttctg gccgccaaga acctgtccga cgccatcctg     900
ctgagcgaca tcctgagagt gaacaccgag atcaccaagg ccccctgag cgcctctatg     960 atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagaggacct gctgcggaag    1200
cagcggacct tcgacaacgg cagcatcccc caccagatcc acctgggaga gctgcacgcc    1260
attctgcggc ggcaggaaga ttttacccca ttcctgaagg acaaccggga aaagatcgag    1320
aagatcctga ccttccgcat cccctactac gtgggccctc tggccagggg aaacagcaga    1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
aacgagctga ccaaagtgaa atacgtgacc gagggaatga gaaagccgc cttcctgagc    1620 ggcgagcaga aaaaggccat cgtggacctg ctgttcaaga ccaaccggaa agtgaccgtg    1680
aagcagctga agaggactac cttcaagaaa atcgagtgct cgactccgt ggaaatctcc    1740 ggcgtggaag atcggttcaa cgcctccctg ggcacatacc acgatctgct gaaaattatc    1800
aaggacaagg acttcctgga caatgaggaa aacgaggaca ttctggaaga tatcgtgctg    1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100 ctgacctta aagaggacat ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc    2280 gaaatggcca gagagaacca gaccacccag aagggacaga gaacagccg cgagagaatg    2340 aagcggatcg aagagggcat caaagagctg ggcagccaga tcctgaaaga cacccgtg    2400 gaaaacaccc agctgcagaa cgagaagctg tacctgtact acctgcagaa tgggcgggat    2460
atgtacgtgg accaggaact ggacatcaac cggctgtccg actacgatgt ggacgctatc    2520
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
```

```
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga atcggcaag gctaccgcca agtacttctt ctacagcaac    3120
atcatgaact ttttcaagac cgagattacc ctggccaacg cgagatccg gaagcggcct    3180 ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagcccac cgtggcctat    3420 tctgtgctgg tggtggccaa agtggaaaag ggcaaggag ggggaggcag cccttcaggg    3480
cagatcagca accaggccct ggctctggcc cctagctccg ctccagtgct ggcccagact    3540
atggtgccct ctagtgctat ggtgcctctg gcccagccac ctgctccagc ccctgtgctg    3600
accccaggac cacccagtc actgagcgct ccagtgccca gtctacaca ggccggcgag    3660 gggactctga gtgaagctct gctgcacctg cagttcgacg ctgatgagga cctgggagct    3720
ctgctgggga acagcaccga tcccggagtg ttcacagatc tggcctccgt ggacaactct    3780
gagtttcagc agctgctgaa tcagggcgtg tccatgtctc atagtacagc cgaaccaatg    3840
ctgatggagt accccgaagc cattacccgg ctggtgaccg cagccagcg gccccccgac    3900 cccgctccaa ctcccctggg aaccagcggc ctgcctaatg ggctgtccgg agatgaagac    3960
ttctcaagca tcgctgatat ggactttagt gccctgctgt cacagatttc ctctagtggg    4020
cagggagggg ggggcagctc caagaaactg aagagtgtga agagctgct ggggatcacc    4080 atcatggaaa gaagcagctt cgagaagaat cccatcgact ttctggaagc caagggctac    4140
aaagaagtga aaaggacct gatcatcaag ctgcctaagt actccctgtt cgagctggaa    4200
aacggccgga gagaatgct ggcctctgcc ggcgaactgc agaagggaaa cgaactggcc    4260
ctgccctcca aatatgtgaa cttcctgtac ctggccagcc actatgagaa gctgaagggc    4320
tcccccgagg ataatgagca gaaacagctg tttgtggaac agcacaagca ctacctggac    4380
gagatcatcg agcagatcag cgagttctcc aagagagtga tcctggccga cgctaatctg    4440
gacaaagtgc tgtccgccta caacaagcac cgggataagc ccatcagaga gcaggccgag    4500
aatatcatcc acctgtttac cctgaccaat ctggagccc ctgccgcctt caagtacttt    4560
gacaccacca tcgaccggaa gaggtacacc agcaccaaag aggtgctgga cgccaccctg    4620
atccaccaga gcatcaccgg cctgtacgag acacggatcg acctgtctca gctgggaggc    4680
gacagcgctg aggaggtgg aagcggagga ggaggaagcg gaggaggagg tagcggacct    4740
aagaaaaaga ggaaggtggc ggccgct                                       4767
```

<210> SEQ ID NO 123
<211> LENGTH: 1589
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30
```

```
Val Leu Gly Asn Thr Asp Arg His Ser Ile Lys Lys Asn Leu Ile Gly
         35                  40                  45

Ala Leu Leu Phe Asp Ser Gly Glu Thr Ala Glu Ala Thr Arg Leu Lys
 50                  55                  60

Arg Thr Ala Arg Arg Tyr Thr Arg Arg Lys Asn Arg Ile Cys Tyr
 65                  70                  75                  80

Leu Gln Glu Ile Phe Ser Asn Glu Met Ala Lys Val Asp Asp Ser Phe
                     85                  90                  95

Phe His Arg Leu Glu Glu Ser Phe Leu Val Glu Glu Asp Lys Lys His
                 100                 105                 110

Glu Arg His Pro Ile Phe Gly Asn Ile Val Asp Glu Val Ala Tyr His
                 115                 120                 125

Glu Lys Tyr Pro Thr Ile Tyr His Leu Arg Lys Lys Leu Val Asp Ser
 130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                 165                 170                 175

Asn Ser Asp Val Asp Lys Leu Phe Ile Gln Leu Val Gln Thr Tyr Asn
             180                 185                 190

Gln Leu Phe Glu Glu Asn Pro Ile Asn Ala Ser Gly Val Asp Ala Lys
         195                 200                 205

Ala Ile Leu Ser Ala Arg Leu Ser Lys Ser Arg Arg Leu Glu Asn Leu
 210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                 245                 250                 255

Leu Ala Glu Asp Ala Lys Leu Gln Leu Ser Lys Asp Thr Tyr Asp Asp
             260                 265                 270

Asp Leu Asp Asn Leu Leu Ala Gln Ile Gly Asp Gln Tyr Ala Asp Leu
         275                 280                 285

Phe Leu Ala Ala Lys Asn Leu Ser Asp Ala Ile Leu Leu Ser Asp Ile
 290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                 325                 330                 335

Leu Val Arg Gln Gln Leu Pro Glu Lys Tyr Lys Glu Ile Phe Phe Asp
             340                 345                 350

Gln Ser Lys Asn Gly Tyr Ala Gly Tyr Ile Asp Gly Gly Ala Ser Gln
         355                 360                 365

Glu Glu Phe Tyr Lys Phe Ile Lys Pro Ile Leu Glu Lys Met Asp Gly
 370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                 405                 410                 415

Glu Leu His Ala Ile Leu Arg Arg Gln Glu Asp Phe Tyr Pro Phe Leu
             420                 425                 430

Lys Asp Asn Arg Glu Lys Ile Glu Lys Ile Leu Thr Phe Arg Ile Pro
 435                 440                 445
```

-continued

```
Tyr Tyr Val Gly Pro Leu Ala Arg Gly Asn Ser Arg Phe Ala Trp Met
    450                 455                 460
Thr Arg Lys Ser Glu Glu Thr Ile Thr Pro Trp Asn Phe Glu Val
465                 470                  475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
            500                 505                 510
Leu Tyr Glu Tyr Phe Thr Val Tyr Asn Glu Leu Thr Lys Val Lys Tyr
        515                 520                 525
Val Thr Glu Gly Met Arg Lys Pro Ala Phe Leu Ser Gly Glu Gln Lys
    530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
            580                 585                 590
Tyr His Asp Leu Leu Lys Ile Ile Lys Asp Lys Asp Phe Leu Asp Asn
        595                 600                 605
Glu Glu Asn Glu Asp Ile Leu Glu Asp Ile Val Leu Thr Leu Thr Leu
    610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
                645                 650                 655
Gly Trp Gly Arg Leu Ser Arg Lys Leu Ile Asn Gly Ile Arg Asp Lys
            660                 665                 670
Gln Ser Gly Lys Thr Ile Leu Asp Phe Leu Lys Ser Asp Gly Phe Ala
        675                 680                 685
Asn Arg Asn Phe Met Gln Leu Ile His Asp Asp Ser Leu Thr Phe Lys
    690                 695                 700
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
            740                 745                 750
His Lys Pro Glu Asn Ile Val Ile Glu Met Ala Arg Glu Asn Gln Thr
        755                 760                 765
Thr Gln Lys Gly Gln Lys Asn Ser Arg Glu Arg Met Lys Arg Ile Glu
    770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu
            820                 825                 830
Ser Asp Tyr Asp Val Asp Ala Ile Val Pro Gln Ser Phe Leu Lys Asp
        835                 840                 845
Asp Ser Ile Asp Asn Lys Val Leu Thr Arg Ser Asp Lys Asn Arg Gly
    850                 855                 860
Lys Ser Asp Asn Val Pro Ser Glu Glu Val Val Lys Lys Met Lys Asn
```

```
              865                 870                 875                 880
Tyr Trp Arg Gln Leu Leu Asn Ala Lys Leu Ile Thr Gln Arg Lys Phe
                    885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
        930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Gly Gly Gly Ser Pro
    1145                1150                1155

Ser Gly Gln Ile Ser Asn Gln Ala Leu Ala Leu Ala Pro Ser Ser
    1160                1165                1170

Ala Pro Val Leu Ala Gln Thr Met Val Pro Ser Ser Ala Met Val
    1175                1180                1185

Pro Leu Ala Gln Pro Pro Ala Pro Ala Pro Val Leu Thr Pro Gly
    1190                1195                1200

Pro Pro Gln Ser Leu Ser Ala Pro Val Pro Lys Ser Thr Gln Ala
    1205                1210                1215

Gly Glu Gly Thr Leu Ser Glu Ala Leu Leu His Leu Gln Phe Asp
    1220                1225                1230

Ala Asp Glu Asp Leu Gly Ala Leu Leu Gly Asn Ser Thr Asp Pro
    1235                1240                1245

Gly Val Phe Thr Asp Leu Ala Ser Val Asp Asn Ser Glu Phe Gln
    1250                1255                1260

Gln Leu Leu Asn Gln Gly Val Ser Met Ser His Ser Thr Ala Glu
    1265                1270                1275
```

Pro Met Leu Met Glu Tyr Pro Glu Ala Ile Thr Arg Leu Val Thr
    1280            1285            1290

Gly Ser Gln Arg Pro Pro Asp Pro Ala Pro Thr Pro Leu Gly Thr
    1295            1300            1305

Ser Gly Leu Pro Asn Gly Leu Ser Gly Asp Glu Asp Phe Ser Ser
    1310            1315            1320

Ile Ala Asp Met Asp Phe Ser Ala Leu Leu Ser Gln Ile Ser Ser
    1325            1330            1335

Ser Gly Gln Gly Gly Gly Gly Ser Ser Lys Lys Leu Lys Ser Val
    1340            1345            1350

Lys Glu Leu Leu Gly Ile Thr Ile Met Glu Arg Ser Ser Phe Glu
    1355            1360            1365

Lys Asn Pro Ile Asp Phe Leu Glu Ala Lys Gly Tyr Lys Glu Val
    1370            1375            1380

Lys Lys Asp Leu Ile Ile Lys Leu Pro Lys Tyr Ser Leu Phe Glu
    1385            1390            1395

Leu Glu Asn Gly Arg Lys Arg Met Leu Ala Ser Ala Gly Glu Leu
    1400            1405            1410

Gln Lys Gly Asn Glu Leu Ala Leu Pro Ser Lys Tyr Val Asn Phe
    1415            1420            1425

Leu Tyr Leu Ala Ser His Tyr Glu Lys Leu Lys Gly Ser Pro Glu
    1430            1435            1440

Asp Asn Glu Gln Lys Gln Leu Phe Val Glu Gln His Lys His Tyr
    1445            1450            1455

Leu Asp Glu Ile Ile Glu Gln Ile Ser Glu Phe Ser Lys Arg Val
    1460            1465            1470

Ile Leu Ala Asp Ala Asn Leu Asp Lys Val Leu Ser Ala Tyr Asn
    1475            1480            1485

Lys His Arg Asp Lys Pro Ile Arg Glu Gln Ala Glu Asn Ile Ile
    1490            1495            1500

His Leu Phe Thr Leu Thr Asn Leu Gly Ala Pro Ala Ala Phe Lys
    1505            1510            1515

Tyr Phe Asp Thr Thr Ile Asp Arg Lys Arg Tyr Thr Ser Thr Lys
    1520            1525            1530

Glu Val Leu Asp Ala Thr Leu Ile His Gln Ser Ile Thr Gly Leu
    1535            1540            1545

Tyr Glu Thr Arg Ile Asp Leu Ser Gln Leu Gly Gly Asp Ser Ala
    1550            1555            1560

Gly Gly Gly Gly Ser Gly Gly Gly Gly Ser Gly Gly Gly Gly Ser
    1565            1570            1575

Gly Pro Lys Lys Lys Arg Lys Val Ala Ala Ala
    1580            1585

<210> SEQ ID NO 124
<211> LENGTH: 4830
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124
atggacaaga agtacagcat cggcctggcc atcggcacca actctgtggg ctgggccgtg     60
atcaccgacg agtacaaggt gcccagcaag aaattcaagg tgctgggcaa caccgaccgg    120

-continued

```
cacagcatca agaagaacct gatcggagcc ctgctgttcg acagcggcga aacagccgag    180
gccacccggc tgaagagaac cgccagaaga agatacacca gacggaagaa ccggatctgc    240
tatctgcaag agatcttcag caacgagatg gccaaggtgg acgacagctt cttccacaga    300
ctggaagagt ccttcctggt ggaagaggat aagaagcacg agcggcaccc catcttcggc    360
aacatcgtgg acgaggtggc ctaccacgag aagtacccca ccatctacca cctgagaaag    420
aaactggtga cagcaccgga caaggccgac ctgcggctga tctatctggc cctgcccac    480
atgatcaagt tccggggcca cttcctgatc gagggcgacc tgaaccccga acagcgac    540
gtggacaagc tgttcatcca gctggtgcag acctacaacc agctgttcga ggaaaacccc    600
atcaacgcca gcggcgtgga cgccaaggcc atcctgtctg ccagactgag caagagcaga    660
cggctggaaa atctgatcgc ccagctgccc ggcgagaaga gaatggcct gttcggcaac    720
ctgattgccc tgagcctggg cctgaccccc aacttcaaga gcaacttcga cctggccgag    780
gatgccaaac tgcagctgag caaggacacc tacgacgacg acctggacaa cctgctggcc    840
cagatcggcg accagtacgc cgacctgttt ctggccgcca gaacctgtc cgacgccatc    900
ctgctgagcg acatcctgag agtgaacacc gagatcacca aggcccccct gagcgcctct    960
atgatcaaga gatacgacga gcaccaccag gacctgaccc tgctgaaagc tctcgtgcgg    1020
cagcagctgc ctgagaagta caaagagatt ttcttcgacc agagcaagaa cggctacgcc    1080
ggctacattg acggcggagc cagccaggaa gagttctaca gttcatcaa gcccatcctg    1140
gaaaagatgg acggcaccga ggaactgctc gtgaagctga acagagagga cctgctgcgg    1200
aagcagcgga ccttcgacaa cggcagcatc ccccaccaga tccacctggg agagctgcac    1260
gccattctgc ggcggcagga agatttttac ccattcctga aggacaaccg ggaaaagatc    1320
gagaagatcc tgacctttcg catcccctac tacgtgggcc ctctggccag ggaaaacagc    1380
agattcgcct ggatgaccag aaagagcgag gaaaccatca ccccctgaa cttcgaggaa    1440
gtggtggaca agggcgcttc cgcccagagc ttcatcgagc ggatgaccaa cttcgataag    1500
aacctgccca cgagaaggt gctgcccaag cacagcctgc tgtacgagta cttcaccgtg    1560
tataacgagc tgaccaaagt gaaatacgtg accgaggaa tgagaaagcc cgccttcctg    1620
agcggcgagc agaaaaaggc catcgtggac ctgctgttca gaccaaccg gaaagtgacc    1680
gtgaagcagc tgaaagagga ctacttcaag aaaatcgagt gcttcgactc cgtggaaatc    1740
tccggcgtgg aagatcggtt caacgcctcc ctgggcacat accacgatct gctgaaaatt    1800
atcaaggaca aggacttcct ggacaatgag gaaaacgagg acattctgga agatatcgtg    1860
ctgaccctga cactgtttga ggacagagag atgatcgagg aacggctgaa aacctatgcc    1920
cacctgttcg acgacaaagt gatgaagcag ctgaagcggc ggagatacac cggctggggc    1980
aggctgagcc ggaagctgat caacggcatc cgggacaagc agtccggcaa gacaatcctg    2040
gatttcctga gtccgacgg cttcgccaac agaaacttca tgcagctgat ccacgacgac    2100
agcctgacct ttaaagagga catccagaaa gcccaggtgt ccggccaggg cgatagcctg    2160
cacgagcaca ttgccaatct ggccggcagc cccgccatta agaagggcat cctgcagaca    2220
gtgaaggtgg tggacgagct cgtgaaagtg atgggccggc acaagcccga acatcgtg    2280
atcgaaatgg ccagagagaa ccagaccacc cagaagggac agaagaacag ccgcgagaga    2340
atgaagcgga tcgaagaggg catcaaagag ctggcagcc agatcctgaa agaacacccc    2400
gtggaaaaca cccagctgca gaacgagaag ctgtacctgt actacctgca gaatgggcgg    2460
```

-continued

```
gatatgtacg tggaccagga actggacatc aaccggctgt ccgactacga tgtggacgct   2520
atcgtgcctc agagctttct gaaggacgac tccatcgaca acaaggtgct gaccagaagc   2580
gacaagaacc ggggcaagag cgacaacgtg ccctccgaag aggtcgtgaa aagagatgaag   2640 aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaatga caagctgatc cgggaagtga aagtgatcac cctgaagtcc   2880
aagctggtgt ccgatttccg gaaggatttc cagttttaca agtgcgcga tcaacaac      2940 taccaccacg cccacgacgc ctacctgaac gccgtcgtgg aaccgccct gatcaaaaag    3000 taccctaagc tggaaagcga gttcgtgtac ggcgactaca aggtgtacga cgtgcggaag   3060
atgatcgcca agagcgagca ggaaatcggc aaggctaccg ccaagtactt cttctacagc   3120
aacatcatga cttttttcaa gaccgagatt accctggcca acggcgagat ccggaagcgg   3180
cctctgatcg agacaaacgg cgaaaccggg agatcgtgt gggataaggg ccgggatttt   3240
gccaccgtgc ggaaagtgct gagcatgccc caagtgaata tcgtgaaaaa gaccgaggtg   3300
cagacaggcg gcttcagcaa agagtctatc ctgcccaaga ggaacagcga taagctgatc   3360
gccagaaaga aggactggga ccctaagaag tacggcggct cgacagccc caccgtggcc   3420 tattctgtgc tggtggtggc caaagtggaa aagggcaagg gcggggagg ctccggtggt   3480 gggggcagcg agggggggg cagcccttca gggcagatca gcaaccaggc cctggctctg   3540
gcccctagct ccgctccagt gctggcccag actatggtgc cctctagtgc tatggtgcct   3600
ctggcccagc cacctgctcc agccctgtg ctgaccccag gaccacccca gtcactgagc   3660
gctccagtgc ccaagtctac acaggccggc gaggggactc tgagtgaagc tctgctgcac   3720
ctgcagttcg acgctgatga ggacctggga gctctgctgg ggaacagcac cgatccgga   3780 gtgttcacag atctggcctc cgtggacaac tctgagttc agcagctgct gaatcagggc   3840
gtgtccatgt ctcatagtac agccgaacca atgctgatgg agtaccccga agccattacc   3900
cggctggtga ccggcagcca gcggccccc gaccccgctc caactcccct gggaaccagc   3960
ggcctgccta atgggctgtc cggagatgaa gacttctcaa gcatcgctga tatggactt   4020 agtgccctgc tgtcacagat ttcctctagt gggcagggcg ggggaggctc cggtggtggg   4080
ggcagcggag ggggggcag ctccaagaaa ctgaagagtg tgaaagagct gctggggatc   4140
accatcatgg aaagaagcag cttcgagaag aatcccatcg actttctgga agccaagggc   4200
tacaaagaag tgaaaaagga cctgatcatc aagctgccta agtactccct gttcgagctg   4260
gaaaacggcc ggaagagaat gctggcctct gccggcgaac tgcagaaggg aaacgaactg   4320
gccctgccct ccaaatatgt gaacttcctg tacctggcca ccactatga aagctgaag    4380 ggctccccg aggataatga gcagaaacag ctgttttgg aacagcacaa gcactacctg    4440
gacgagatca tcgagcagat cagcgagttc tccaagagag tgatcctggc cgacgctaat   4500
ctggacaaag tgctgtccgc ctacaacaag caccggata agcccatcag agagcaggcc    4560
gagaatatca tccacctgtt taccctgacc aatctgggag ccctgccgc cttcaagtac   4620 tttgacacca ccatcgaccg gaagaggtac accagcacca aagaggtgct ggacgccacc   4680
ctgatccacc agagcatcac cggcctgtac gagacacgga tcgacctgtc tcagctggga   4740
ggcgacagcg ctggagaggg tggaagcgga ggaggaggaa gcggaggaag aggtagcgga   4800
cctaagaaaa agaggaaggt ggcggccgct                                   4830
```

<210> SEQ ID NO 125
<211> LENGTH: 1610
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile

```
            770                 775                 780
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
       1010                1015                1020

Lys Ser Glu Gln Glu Ile Gly Lys Ala Thr Ala Lys Tyr Phe Phe
       1025                1030                1035

Tyr Ser Asn Ile Met Asn Phe Phe Lys Thr Glu Ile Thr Leu Ala
       1040                1045                1050

Asn Gly Glu Ile Arg Lys Arg Pro Leu Ile Glu Thr Asn Gly Glu
       1055                1060                1065

Thr Gly Glu Ile Val Trp Asp Lys Gly Arg Asp Phe Ala Thr Val
       1070                1075                1080

Arg Lys Val Leu Ser Met Pro Gln Val Asn Ile Val Lys Lys Thr
       1085                1090                1095

Glu Val Gln Thr Gly Gly Phe Ser Lys Glu Ser Ile Leu Pro Lys
       1100                1105                1110

Arg Asn Ser Asp Lys Leu Ile Ala Arg Lys Lys Asp Trp Asp Pro
       1115                1120                1125

Lys Lys Tyr Gly Gly Phe Asp Ser Pro Thr Val Ala Tyr Ser Val
       1130                1135                1140

Leu Val Val Ala Lys Val Glu Lys Gly Lys Gly Gly Gly Ser
       1145                1150                1155

Gly Gly Gly Gly Ser Gly Gly Gly Ser Pro Ser Gly Gln Ile
       1160                1165                1170

Ser Asn Gln Ala Leu Ala Leu Ala Pro Ser Ser Ala Pro Val Leu
       1175                1180                1185
```

```
Ala Gln Thr Met Val Pro Ser   Ser Ala Met Val Pro   Leu Ala Gln
    1190            1195                  1200

Pro Pro Ala Pro Ala Pro Val   Leu Thr Pro Gly Pro   Pro Gln Ser
    1205            1210                  1215

Leu Ser Ala Pro Val Pro Lys   Ser Thr Gln Ala Gly   Glu Gly Thr
    1220            1225                  1230

Leu Ser Glu Ala Leu Leu His   Leu Gln Phe Asp Ala   Asp Glu Asp
    1235            1240                  1245

Leu Gly Ala Leu Leu Gly Asn   Ser Thr Asp Pro Gly   Val Phe Thr
    1250            1255                  1260

Asp Leu Ala Ser Val Asp Asn   Ser Glu Phe Gln Gln   Leu Leu Asn
    1265            1270                  1275

Gln Gly Val Ser Met Ser His   Ser Thr Ala Glu Pro   Met Leu Met
    1280            1285                  1290

Glu Tyr Pro Glu Ala Ile Thr   Arg Leu Val Thr Gly   Ser Gln Arg
    1295            1300                  1305

Pro Pro Asp Pro Ala Pro Thr   Pro Leu Gly Thr Ser   Gly Leu Pro
    1310            1315                  1320

Asn Gly Leu Ser Gly Asp Glu   Asp Phe Ser Ser Ile   Ala Asp Met
    1325            1330                  1335

Asp Phe Ser Ala Leu Leu Ser   Gln Ile Ser Ser Ser   Gly Gln Gly
    1340            1345                  1350

Gly Gly Gly Ser Gly Gly Gly   Gly Ser Gly Gly Gly   Gly Ser Ser
    1355            1360                  1365

Lys Lys Leu Lys Ser Val Lys   Glu Leu Leu Gly Ile   Thr Ile Met
    1370            1375                  1380

Glu Arg Ser Ser Phe Glu Lys   Asn Pro Ile Asp Phe   Leu Glu Ala
    1385            1390                  1395

Lys Gly Tyr Lys Glu Val Lys   Lys Asp Leu Ile Ile   Lys Leu Pro
    1400            1405                  1410

Lys Tyr Ser Leu Phe Glu Leu   Glu Asn Gly Arg Lys   Arg Met Leu
    1415            1420                  1425

Ala Ser Ala Gly Glu Leu Gln   Lys Gly Asn Glu Leu   Ala Leu Pro
    1430            1435                  1440

Ser Lys Tyr Val Asn Phe Leu   Tyr Leu Ala Ser His   Tyr Glu Lys
    1445            1450                  1455

Leu Lys Gly Ser Pro Glu Asp   Asn Glu Gln Lys Gln   Leu Phe Val
    1460            1465                  1470

Glu Gln His Lys His Tyr Leu   Asp Glu Ile Ile Glu   Gln Ile Ser
    1475            1480                  1485

Glu Phe Ser Lys Arg Val Ile   Leu Ala Asp Ala Asn   Leu Asp Lys
    1490            1495                  1500

Val Leu Ser Ala Tyr Asn Lys   His Arg Asp Lys Pro   Ile Arg Glu
    1505            1510                  1515

Gln Ala Glu Asn Ile Ile His   Leu Phe Thr Leu Thr   Asn Leu Gly
    1520            1525                  1530

Ala Pro Ala Ala Phe Lys Tyr   Phe Asp Thr Thr Ile   Asp Arg Lys
    1535            1540                  1545

Arg Tyr Thr Ser Thr Lys Glu   Val Leu Asp Ala Thr   Leu Ile His
    1550            1555                  1560

Gln Ser Ile Thr Gly Leu Tyr   Glu Thr Arg Ile Asp   Leu Ser Gln
    1565            1570                  1575
```

Leu Gly Gly Asp Ser Ala Gly Gly Gly Ser Gly Gly Gly
    1580            1585                1590

Ser Gly Gly Gly Gly Ser Gly Pro Lys Lys Lys Arg Lys Val Ala
    1595            1600            1605

Ala Ala
    1610

<210> SEQ ID NO 126
<211> LENGTH: 4359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126

| | |
|---|---|
| atggacaaga agtacagcat cggcctggcc atcggcacca actctgtggg ctgggccgtg | 60 |
| atcaccgacg agtacaaggt gcccagcaag aaattcaagg tgctgggcaa caccgaccgg | 120 |
| cacagcatca agaagaacct gatcggagcc ctgctgttcg acagcggcga aacagccgag | 180 |
| gccacccggc tgaagagaac cgccagaaga agatacacca cacggaagaa ccggatctgc | 240 |
| tatctgcaag agatcttcag caacgagatg gccaaggtgg acgacagctt cttccacaga | 300 |
| ctggaagagt ccttcctggt ggaagaggat aagaagcacg agcggcaccc catcttcggc | 360 |
| aacatcgtgg acgaggtggc ctaccacgag aagtacccca ccatctacca cctgagaaag | 420 |
| aaactggtgg acagcaccga caaggccgac ctgcggctga tctatctggc cctggcccac | 480 |
| atgatcaagt tccggggcca cttcctgatc gagggcgacc tgaaccccga caacagcgac | 540 |
| gtggacaagc tgttcatcca gctggtgcag acctacaacc agctgttcga ggaaaacccc | 600 |
| atcaacgcca gcggcgtgga cgccaaggcc atcctgtctg ccagactgag caagagcaga | 660 |
| cggctggaaa atctgatcgc ccagctgccc ggcgagaaga gaatggcct gttcggcaac | 720 |
| ctgattgccc tgagcctggg cctgacccc aacttcaaga gcaacttcga cctggccgag | 780 |
| gatgccaaac tgcagctgag caaggacacc tacgacgacg acctggacaa cctgctggcc | 840 |
| cagatcggcg accagtacgc cgacctgttt ctggccgcca gaaacctgtc cgacgccatc | 900 |
| ctgctgagcg acatcctgag agtgaacacc gagatcacca aggccccct gagcgcctct | 960 |
| atgatcaaga gatacgacga gcaccaccag gacctgaccc tgctgaaagc tctcgtgcgg | 1020 |
| cagcagctgc ctgagaagta caaagagatt ttcttcgacc agagcaagaa cggctacgcc | 1080 |
| ggctacattg acggcggagc cagccaggaa gagttctaca agttcatcaa gcccatcctg | 1140 |
| gaaaagatgg acggcaccga ggaactgctc gtgaagctga acagagagga cctgctgcgg | 1200 |
| aagcagcgga ccttcgacaa cggcagcatc ccccaccaga tccacctggg agagctgcac | 1260 |
| gccattctgc ggcggcagga agattttac ccattcctga aggacaaccg ggaaaagatc | 1320 |
| gagaagatcc tgaccttccg catccctac tacgtgggcc ctctggccag ggaaacagc | 1380 |
| agattcgcct ggatgaccag aaagagcgag gaaaccatca cccctggaa cttcgaggaa | 1440 |
| gtggtggaca gggcgcttc cgcccagagc ttcatcgagc ggatgaccaa cttcgataag | 1500 |
| aacctgccca acgagaaggt gctgcccaag cacagcctgc tgtacgagta cttcaccgtg | 1560 |
| tataacgagc tgaccaaagt gaaatacgtg accgagggaa tgagaaagcc cgccttcctg | 1620 |
| agcggcgagc agaaaaaggc catcgtggac ctgctgttca gaccaaccg gaaagtgacc | 1680 |
| gtgaagcagc tgaaagagga ctacttcaag aaaatcgagt gcttcgactc cgtggaaatc | 1740 |

-continued

```
tccggcgtgg aagatcggtt caacgcctcc ctgggcacat accacgatct gctgaaaatt     1800
atcaaggaca aggacttcct ggacaatgag gaaaacgagg acattctgga agatatcgtg     1860
ctgaccctga cactgtttga ggacagagag atgatcgagg aacggctgaa aacctatgcc     1920
cacctgttcg acgacaaagt gatgaagcag ctgaagcggc ggagatacac cggctggggc     1980
aggctgagcc ggaagctgat caacggcatc cgggacaagc agtccggcaa gacaatcctg     2040
gatttcctga gtccgacgg cttcgccaac agaaacttca tgcagctgat ccacgacgac     2100
agcctgacct ttaaagagga catccagaaa gcccaggtgt ccggccaggg cgatagcctg     2160
cacgagcaca ttgccaatct ggccggcagc ccgccatta agaagggcat cctgcagaca     2220
gtgaaggtgg tggacgagct cgtgaaagtg atgggccggc acaagcccga aacatcgtg      2280 atcgaaatgg ccagagagaa ccagaccacc cagaagggac agaagaacag ccgcgagaga     2340
atgaagcgga tcgaagaggg catcaaagag ctgggcagcc agatcctgaa agaacacccc     2400
gtggaaaaca cccagctgca gaacgagaag ctgtacctgt actacctgca gaatgggcgg     2460
gatatgtacg tggaccagga actggacatc aaccggctgt ccgactacga tgtggaccac     2520
atcgtgcctc agagctttct gaaggacgac tccatcgaca caaggtgct gaccagaagc      2580 gacaaggccc ggggcaagag cgacaacgtg ccctccgaag aggtcgtgaa gaagatgaag     2640
aactactggc ggcagctgct gaacgccaag ctgattaccc agagaaagtt cgacaatctg     2700
accaaggccg agagaggcgg cctgagcgaa ctggataagg ccggcttcat caagagacag     2760
ctggtggaaa cccggcagat cacaaagcac gtggcacaga tcctggactc ccggatgaac     2820
actaagtacg acgagaatga caagctgatc cgggaagtga agtgatcac cctgaagtcc      2880 aagctggtgt ccgatttccg gaaggatttc cagtttaca aagtgcgcga tcaacaac       2940 taccaccacg cccacgacgc ctacctgaac gccgtcgtgg aaccgccct gatcaaaaag      3000 taccctaagc tggaaagcga gttcgtgtac ggcgactaca aggtgtacga cgtgcggaag     3060
atgatcgcca gagcgagca ggaaatcggc aaggctaccg ccaagtactt cttctacagc      3120
aacatcatga actttttcaa gaccgagatt accctggcca acggcgagat ccggaagcgg     3180
cctctgatcg agacaaacgg cgaaaccggg gagatcgtgt gggataaggg ccgggatttt     3240
gccaccgtgc ggaaagtgct gagcatgccc caagtgaata tcgtgaaaaa gaccgaggtg     3300
cagacaggcg gcttcagcaa agagtctatc ctgcccaaga ggaacagcga taagctgatc     3360
gccagaaaga aggactggga ccctaagaag tacggcggct cgacagccc caccgtggcc      3420 tattctgtgc tggtggtggc caaagtgaa aagggcaagt ccaagaaact gaagagtgtg      3480
aaagagctgc tggggatcac catcatggaa agaagcagct cgagaagaa tcccatcgac      3540 tttctggaag ccaagggcta caaagaagtg aaaaaggacc tgatcatcaa gctgcctaag     3600
tactccctgt tcgagctgga aaacggccgg aagagaatgc tggcctctgc cggcgaactg     3660
cagaagggaa cgaactggc cctgccctcc aaatatgtga acttcctgta cctggccagc      3720
cactatgaga agctgaaggg ctccccccgag gataatgagc agaaacagct gtttgtggaa    3780
cagcacaagc actacctgga cgagatcatc gagcagatca gcgagttctc caagagagtg     3840
atcctggccg acgctaatct ggacaaagtg ctgtccgcct acaacaagca ccgggataag     3900
cccatcagag agcaggccga gaatatcatc cacctgttta cctgaccaa tctgggagcc     3960 cctgccgcct tcaagtactt tgacaccacc atcgaccgga agaggtacac cagcaccaaa    4020
gaggtgctga cgccaccct gatccaccag agcatcaccg gcctgtacga gacacggatc      4080
gacctgtctc agctgggagg cgacagcgct ggaggaggtg gaagcggagg aggaggaagc     4140
```

```
ggaggaggag gtagcggacc taagaaaaag aggaaggtgg cggccgctgg atccggacgg   4200
gctgacgcat tggacgattt tgatctggat atgctgggaa gtgacgccct cgatgatttt   4260
gaccttgaca tgcttggttc ggatgccctt gatgactttg acctcgacat gctcggcagt   4320
gacgcccttg atgatttcga cctggacatg ctgattaac                          4359
```

<210> SEQ ID NO 127
<211> LENGTH: 1453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
```

-continued

```
            305                 310                 315                 320
        Met Ile Lys Arg Tyr Asp Glu His His Gln Asp Leu Thr Leu Leu Lys
                            325                 330                 335

Ala Leu Val Arg Gln Gln Leu Pro Glu Lys Tyr Lys Glu Ile Phe Phe
                            340                 345                 350

Asp Gln Ser Lys Asn Gly Tyr Ala Gly Tyr Ile Asp Gly Gly Ala Ser
                            355                 360                 365

Gln Glu Glu Phe Tyr Lys Phe Ile Lys Pro Ile Leu Glu Lys Met Asp
                            370                 375                 380

Gly Thr Glu Glu Leu Leu Val Lys Leu Asn Arg Glu Asp Leu Leu Arg
        385                 390                 395                 400

Lys Gln Arg Thr Phe Asp Asn Gly Ser Ile Pro His Gln Ile His Leu
                            405                 410                 415

Gly Glu Leu His Ala Ile Leu Arg Arg Gln Glu Asp Phe Tyr Pro Phe
                            420                 425                 430

Leu Lys Asp Asn Arg Glu Lys Ile Glu Lys Ile Leu Thr Phe Arg Ile
                            435                 440                 445

Pro Tyr Tyr Val Gly Pro Leu Ala Arg Gly Asn Ser Arg Phe Ala Trp
                            450                 455                 460

Met Thr Arg Lys Ser Glu Glu Thr Ile Thr Pro Trp Asn Phe Glu Glu
        465                 470                 475                 480

Val Val Asp Lys Gly Ala Ser Ala Gln Ser Phe Ile Glu Arg Met Thr
                            485                 490                 495

Asn Phe Asp Lys Asn Leu Pro Asn Glu Lys Val Leu Pro Lys His Ser
                            500                 505                 510

Leu Leu Tyr Glu Tyr Phe Thr Val Tyr Asn Glu Leu Thr Lys Val Lys
                            515                 520                 525

Tyr Val Thr Glu Gly Met Arg Lys Pro Ala Phe Leu Ser Gly Glu Gln
                            530                 535                 540

Lys Lys Ala Ile Val Asp Leu Leu Phe Lys Thr Asn Arg Lys Val Thr
        545                 550                 555                 560

Val Lys Gln Leu Lys Glu Asp Tyr Phe Lys Lys Ile Glu Cys Phe Asp
                            565                 570                 575

Ser Val Glu Ile Ser Gly Val Glu Asp Arg Phe Asn Ala Ser Leu Gly
                            580                 585                 590

Thr Tyr His Asp Leu Leu Lys Ile Ile Lys Asp Lys Asp Phe Leu Asp
                            595                 600                 605

Asn Glu Glu Asn Glu Asp Ile Leu Glu Asp Ile Val Leu Thr Leu Thr
                            610                 615                 620

Leu Phe Glu Asp Arg Glu Met Ile Glu Glu Arg Leu Lys Thr Tyr Ala
        625                 630                 635                 640

His Leu Phe Asp Asp Lys Val Met Lys Gln Leu Lys Arg Arg Arg Tyr
                            645                 650                 655

Thr Gly Trp Gly Arg Leu Ser Arg Lys Leu Ile Asn Gly Ile Arg Asp
                            660                 665                 670

Lys Gln Ser Gly Lys Thr Ile Leu Asp Phe Leu Lys Ser Asp Gly Phe
                            675                 680                 685

Ala Asn Arg Asn Phe Met Gln Leu Ile His Asp Asp Ser Leu Thr Phe
                            690                 695                 700

Lys Glu Asp Ile Gln Lys Ala Gln Val Ser Gly Gln Gly Asp Ser Leu
        705                 710                 715                 720

His Glu His Ile Ala Asn Leu Ala Gly Ser Pro Ala Ile Lys Lys Gly
                            725                 730                 735
```

```
Ile Leu Gln Thr Val Lys Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770             775                 780

Glu Gly Ile Lys Glu Leu Gly Ser Gln Ile Leu Lys Glu His Pro
785             790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Ala Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140
```

-continued

```
Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Ala Gly Gly Gly Gly Ser Gly Gly Gly Gly Ser Gly Gly Gly
    1370                1375                1380

Gly Ser Gly Pro Lys Lys Lys Arg Lys Val Ala Ala Ala Gly Ser
    1385                1390                1395

Gly Arg Ala Asp Ala Leu Asp Asp Phe Asp Leu Asp Met Leu Gly
    1400                1405                1410

Ser Asp Ala Leu Asp Asp Phe Asp Leu Asp Met Leu Gly Ser Asp
    1415                1420                1425

Ala Leu Asp Asp Phe Asp Leu Asp Met Leu Gly Ser Asp Ala Leu
    1430                1435                1440

Asp Asp Phe Asp Leu Asp Met Leu Ile Asn
    1445                1450
```

<210> SEQ ID NO 128
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (59)..(79)
<223> OTHER INFORMATION: a, c, t, g, unknown or other
<220> FEATURE:
<221> NAME/KEY: variation
<222> LOCATION: (68)..(76)

-continued

```
<223> OTHER INFORMATION: /replace=" "
<220> FEATURE:
<221> NAME/KEY: misc_feature
<222> LOCATION: (68)..(76)
<223> OTHER INFORMATION: /note="Variant nucleotides given in the
      sequence have no preference with respect to those in the
      annotations for variant positions"

<400> SEQUENCE: 128
aatgatacgg cgaccaccga gatctacact ctttccctac acgacgctct tccgatctnn    60
nnnnnnnnnn nnnnnngctt tatatatctt gtggaaagga cgaaacacc              109

<210> SEQ ID NO 129
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (25)..(32)
<223> OTHER INFORMATION: a, c, t, g, unknown or other

<400> SEQUENCE: 129
caagcagaag acggcatacg agatnnnnnn nngtgactgg agttcagacg tgtgctcttc    60
cgatctgcca agttgataac ggactagcct t                                  91

<210> SEQ ID NO 130
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
gttttagagc tagaggcagg agaatggcgt gaacccggga ggtggccgag atcgctccag    60
cctgggtgac agagcgagac tctgtctcta gcaagttaaa ataaggctag tccgttatca   120
acttggagca gacgatatgg cgtcgctcca agtggcaccg agtcggtgct tttttt       176

<210> SEQ ID NO 131
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
gttttagagc taggagcaga cgatatggcg tcgctcctag caagttaaaa taaggctagt    60
ccgttatcaa cttgaggcag gagaatggcg tgaacccggg aggtggccga gatcgctcca   120
gcctgggtga cagagcgaga ctctgtctca gtggcaccg agtcggtgct tttttt        176

<210> SEQ ID NO 132
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 132

```
gttttagagc tagaggcagg agaatggcgt gaacccggga ggtggccgag atcgctccag      60
cctgggtgac agagcgagac tctgtctcta gcaagttaaa ataaggctag tccgttatca     120
acttgaggca ggagaatggc gtgaacccgg gaggtggccg agatcgctcc agcctgggtg     180
acagagcgag actctgtctc aagtggcacc gagtcggtgc tttttttt                 227
```

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133

```
tactggagca ctcaggccct                                                  20
```

<210> SEQ ID NO 134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134

```
aggtagcaaa gtgacgccga                                                  20
```

<210> SEQ ID NO 135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135

```
tgccagagcg gcgctcggcg                                                  20
```

<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136

```
gcggcgcggc gggcccggag                                                  20
```

<210> SEQ ID NO 137
<211> LENGTH: 240
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 137

```
gttttagagc taggccggag cagacgatat ggcgtcgctc cggcctagca agttaaaata      60
aggctagtcc gttatcaact tggccggagc agacgatatg gcgtcgctcc ggccaagtgg     120
caccgagtcg gtgcgaggca ggagaatggc gtgaacccgg gaggtggagc ttgcagcgag     180
ccgagatcgc gccactgcac tccagcctgg gtgacagagc gagactctgt ctcttttttt     240
```

<210> SEQ ID NO 138
<211> LENGTH: 237
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 138

```
gttttagagc taggccggag cagacgatat ggcgtcgctc cggcctagca agttaaaata      60
aggctagtcc gttatcaact tggccggagc agacgatatg gcgtcgctcc ggccaagtgg     120
caccgagtcg gtgctactaa aaatacaaaa aattgaggca ggagaatggc gtgaacccgg     180
gaggtggccg agatcgctcc agcctgggtg acagagcgag actctgtctc tttttt        237
```

<210> SEQ ID NO 139
<211> LENGTH: 260
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 139

```
gttttagagc taggccggag cagacgatat ggcgtcgctc cggcctagca agttaaaata      60
aggctagtcc gttatcaact tggccggagc agacgatatg gcgtcgctcc ggccaagtgg     120
caccgagtcg gtgctactaa aaatacaaaa aattgaggca ggagaatggc gtgaacccgg     180
gaggtggagc ttgcagcgag ccgagatcgc gccactgcac tccagcctgg gtgacagagc     240
gagactctgt ctcttttttt                                                260
```

<210> SEQ ID NO 140
<211> LENGTH: 217
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140

```
gttttagagc taggccggag cagacgatat ggcgtcgctc cggcctagca agttaaaata      60
aggctagtcc gttatcaact tggccggagc agacgatatg gcgtcgctcc ggccaagtgg     120
caccgagtcg gtgcgaggca ggagaatggc gtgaacccgg gaggtggccg agatcgctcc     180
agcctgggtg acagagcgag actctgtctc tttttt                              217
```

<210> SEQ ID NO 141
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 141
gcuagaaaua gca                                                          13

<210> SEQ ID NO 142
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
caccgagucg gug                                                          13

<210> SEQ ID NO 143
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 143
nnnnnnnnnn nnnnnnnnnn guuuuagagc uaggccaaca tgaggatcac ccatgtctgc       60
agggccuagc aaguuaaaau aaggcua                                           87

<210> SEQ ID NO 144
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
guuuuagagc uaggcc                                                       16

<210> SEQ ID NO 145
<211> LENGTH: 44
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ggccuagcaa guuaaaauaa ggcuaguccg uuaucaacuu ggcc                        44

<210> SEQ ID NO 146
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 146
ggccaagugg caccgagucg gugcuuuu          28

<210> SEQ ID NO 147
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
uagcaaguua aaauaaggcu aguccguuau caacuu          36

<210> SEQ ID NO 148
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
aaguggcacc gagucggugc uuuu          24

<210> SEQ ID NO 149
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
guuuaagagc uaugcug          17

<210> SEQ ID NO 150
<211> LENGTH: 41
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
cagcauagca aguuuaaaua aggcuagucc guuaucaacu u          41

<210> SEQ ID NO 151
<211> LENGTH: 40
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
ggccuagcaa guuaaaauaa ggcuaguccg uuaucaacuu          40

<210> SEQ ID NO 152
<211> LENGTH: 16

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
guuuaagagc uaggcc                                                  16

<210> SEQ ID NO 153
<211> LENGTH: 44
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
ggccuagcaa guuuaaauaa ggcuaguccg uuaucaacuu ggcc                    44

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
guuuaagagc uaugcugggc c                                            21

<210> SEQ ID NO 155
<211> LENGTH: 49
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
ggcccagcau agcaaguuua aauaaggcua guccguuauc aacuuggcc              49

<210> SEQ ID NO 156
<211> LENGTH: 40
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
uagcaaguua aauaaggcu aguccguuau caacuuggcc                         40

<210> SEQ ID NO 157
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
```

```
guuuuagag                                                              9

<210> SEQ ID NO 158
<211> LENGTH: 37
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
caaguuaaaa uaaggcuagu ccguuaucaa cuuggcc                              37

<210> SEQ ID NO 159
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
ggccuagcaa guuaaaauaa ggcuaguccg uuauca                               36

<210> SEQ ID NO 160
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
ggcaccgagu cggugcuuuu                                                 20

<210> SEQ ID NO 161
<211> LENGTH: 390
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161
atggcttcaa actttactca gttcgtgctc gtggacaatg gtgggacagg ggatgtgaca      60
gtggctcctt ctaatttcgc taatggggtg gcagagtgga tcagctccaa ctcacggagc    120
caggcctaca aggtgacatg cagcgtcagg cagtctagtg cccagaagag aaagtatacc    180
atcaaggtgg aggtccccaa agtggctacc cagacagtgg gcggagtcga actgcctgtc    240
gccgcttgga ggtcctacct gaacatggag ctcactatcc aattttcgc taccaattct     300 gactgtgaac tcatcgtgaa ggcaatgcag gggctcctca agacggtaa tcctatccct     360 tccgccatcg ccgctaactc aggtatctac                                    390

<210> SEQ ID NO 162
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 162
ggacctaaga aaagaggaa ggtggcggcc gct                                              33

<210> SEQ ID NO 163
<211> LENGTH: 165
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
ggacgggctg acgcattgga cgattttgat ctggatatgc tgggaagtga cgccctcgat       60
gattttgacc ttgacatgct tggttcggat gcccttgatg actttgacct cgacatgctc     120
ggcagtgacg cccttgatga tttcgacctg gacatgctga ttaac                      165

<210> SEQ ID NO 164
<211> LENGTH: 552
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
ccttcagggc agatcagcaa ccaggccctg gctctggccc ctagctccgc tccagtgctg       60
gcccagacta tggtgccctc tagtgctatg gtgcctctgg cccagccacc tgctccagcc     120
cctgtgctga ccccaggacc accccagtca ctgagcgctc cagtgcccaa gtctacacag     180
gccggcgagg ggactctgag tgaagctctg ctgcacctgc agttcgacgc tgatgaggac     240 ctggagctc tgctggggaa cagcaccgat cccggagtgt tcacagatct ggcctccgtg      300
gacaactctg agtttcagca gctgctgaat cagggcgtgt ccatgtctca gtacagcc       360 gaaccaatgc tgatggagta ccccgaagcc attacccggc tggtgaccgg cagccagcgg     420 cccccccgacc ccgctccaac tccctggga accagcggc tgcctaatgg gctgtccgga     480
gatgaagact tctcaagcat cgctgatatg gactttagtg ccctgctgtc acagatttcc     540
tctagtgggc ag                                                          552

<210> SEQ ID NO 165
<211> LENGTH: 1419
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 165
atggcttcaa actttactca gttcgtgctc gtggacaatg gtgggacagg ggatgtgaca       60
gtggctcctt ctaatttcgc taatggggtg gcagagtgga tcagctccaa ctcacggagc     120
caggcctaca aggtgacatg cagcgtcagg cagtctagtg cccagaagag aaagtatacc     180
atcaaggtgg aggtccccaa agtggctacc agacagtgg gcggagtcga actgcctgtc      240
gccgcttgga ggtcctacct gaacatggag ctcactatcc aattttcgc taccaattct      300 gactgtgaac tcatcgtgaa ggcaatgcag gggctcctca aagacggtaa tcctatccct     360

| tccgccatcg | ccgctaactc | aggtatctac | agcgctggag | gaggtggaag | cggaggagga | 420 |
| ggaagcggag | gaggaggtag | cggacctaag | aaaaagagga | aggtggcggc | cgctggatcc | 480 |
| ccttcagggc | agatcagcaa | ccaggccctg | gctctggccc | ctagctccgc | tccagtgctg | 540 |
| gcccagacta | tggtgccctc | tagtgctatg | gtgcctctgg | cccagccacc | tgctccagcc | 600 |
| cctgtgctga | ccccaggacc | accccagtca | ctgagcgctc | cagtgcccaa | gtctacacag | 660 |
| gccggcgagg | ggactctgag | tgaagctctg | ctgcacctgc | agttcgacgc | tgatgaggac | 720 |
| ctgggagctc | tgctggggaa | cagcaccgat | cccggagtgt | tcacagatct | ggcctccgtg | 780 |
| gacaactctg | agtttcagca | gctgctgaat | cagggcgtgt | ccatgtctca | tagtacagcc | 840 |
| gaaccaatgc | tgatggagta | ccccgaagcc | attacccggc | tggtgaccgg | cagccagcgg | 900 |
| ccccccgacc | ccgctccaac | tcccctggga | accagcggcc | tgcctaatgg | gctgtccgga | 960 |
| gatgaagact | tctcaagcat | cgctgatatg | gactttagtg | ccctgctgtc | acagatttcc | 1020 |
| tctagtgggc | agggaggagg | tggaagcggc | ttcagcgtgg | acaccagtgc | cctgctggac | 1080 |
| ctgttcagcc | cctcggtgac | cgtgcccgac | atgagcctgc | ctgaccttga | cagcagcctg | 1140 |
| gccagtatcc | aagagctcct | gtctccccag | gagcccccca | ggcctcccga | ggcagagaac | 1200 |
| agcagcccgg | attcagggaa | gcagctggtg | cactacacag | cgcagccgct | gttcctgctg | 1260 |
| gaccccggct | ccgtggacac | cgggagcaac | gacctgccgg | tgctgtttga | gctgggagag | 1320 |
| ggctcctact | tctccgaagg | ggacggcttc | gccgaggacc | ccaccatctc | cctgctgaca | 1380 |
| ggctcggagc | ctcccaaagc | caaggacccc | actgtctcc | | | 1419 |

<210> SEQ ID NO 166
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 166

| ggcttcagcg | tggacaccag | tgccctgctg | gacctgttca | gcccctcggt | gaccgtgccc | 60 |
| gacatgagcc | tgcctgacct | tgacagcagc | ctggccagta | tccaagagct | cctgtctccc | 120 |
| caggagcccc | ccaggcctcc | cgaggcagag | aacagcagcc | cggattcagg | gaagcagctg | 180 |
| gtgcactaca | cagcgcagcc | gctgttcctg | ctggaccccg | gctccgtgga | caccgggagc | 240 |
| aacgacctgc | cggtgctgtt | tgagctggga | gagggctcct | acttctccga | aggggacggc | 300 |
| ttcgccgagg | accccaccat | ctccctgctg | acaggctcgg | agcctcccaa | agccaaggac | 360 |
| cccactgtct | cc | | | | | 372 |

<210> SEQ ID NO 167
<211> LENGTH: 1236
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 167

| atggcttcaa | actttactca | gttcgtgctc | gtggacaatg | gtgggacagg | ggatgtgaca | 60 |
| gtggctcctt | ctaatttcgc | taatgggtg | gcagagtgga | tcagtccaa | ctcacggagc | 120 |
| caggcctaca | aggtgacatg | cagcgtcagg | cagtctagtg | cccagaagag | aaagtatacc | 180 |

```
atcaaggtgg aggtccccaa agtggctacc cagacagtgg gcggagtcga actgcctgtc    240
gccgcttgga ggtcctacct gaacatggag ctcactatcc aattttcgc taccaattct    300 gactgtgaac tcatcgtgaa ggcaatgcag gggctcctca agacggtaa tcctatccct    360 tccgccatcg ccgctaactc aggtatctac agcgctggag gaggtggaag cggaggagga    420
ggaagcggag gaggaggtag cggacctaag aaaaagagga aggtggcggc cgctggatcc    480
ccttcagggc agatcagcaa ccaggccctg gctctggccc ctagctccgc tccagtgctg    540
gcccagacta tggtgccctc tagtgctatg gtgcctctgg cccagccacc tgctccagcc    600
cctgtgctga ccccaggacc accccagtca ctgagcgctc cagtgcccaa gtctacacag    660
gccggcgagg ggactctgag tgaagctctg ctgcacctgc agttcgacgc tgatgaggac    720
ctgggagctc tgctggggaa cagcaccgat cccggagtgt tcacagatct ggcctccgtg    780
gacaactctg agtttcagca gctgctgaat cagggcgtgt ccatgtctca tagtacagcc    840
gaaccaatgc tgatggagta ccccgaagcc attacccggc tggtgaccgg cagccagcgg    900
ccccccgacc ccgctccaac tcccctggga accagcggcc tgcctaatgg gctgtccgga    960
gatgaagact tctcaagcat cgctgatatg gactttagtg ccctgctgtc acagatttcc    1020
tctagtgggc agggaggagg tggaagcatg gagcttcttt ctcctcctct gcgggatgtt    1080
gacctgactg cgcccgacgg ctctctttgc tccttcgcca caaccgacga cttctacgat    1140
gatccatgtt ttgacagccc cgatctcagg ttctttgagg atctcgatcc tagactgatg    1200
cacgtgggcg cactgctcaa acctgaggaa catagc                              1236
```

<210> SEQ ID NO 168
<211> LENGTH: 189
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 168

```
atggagcttc tttctcctcc tctgcgggat gttgacctga ctgcgcccga cggctctctt    60
tgctccttcg ccacaaccga cgacttctac gatgatccat gttttgacag ccccgatctc    120
aggttctttg aggatctcga tcctagactg atgcacgtgg gcgcactgct caaacctgag    180
gaacatagc                                                             189
```

<210> SEQ ID NO 169
<211> LENGTH: 4356
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 169

```
gacaagaagt acagcatcgg cctggccatc ggcaccaact ctgtgggctg ggccgtgatc    60
accgacgagt acaaggtgcc cagcaagaaa ttcaaggtgc tgggcaacac cgaccggcac    120
agcatcaaga gaacctgat cggagccctg ctgttcgaca gcggcgaaac agccgaggcc    180
acccggctga agagaaccgc cagaagaaga taccaccagac ggaagaaccg gatctgctat    240
ctgcaagaga tcttcagcaa cgagatggcc aaggtggacg acagcttctt ccacagactg    300
```

-continued

```
gaagagtcct tcctggtgga agaggataag aagcacgagc ggcaccccat cttcggcaac    360
atcgtggacg aggtggccta ccacgagaag taccccacca tctaccacct gagaaagaaa    420
ctggtggaca gcaccgacaa ggccgacctg cggctgatct atctggccct ggcccacatg    480
atcaagttcc ggggccactt cctgatcgag ggcgacctga accccgacaa cagcgacgtg    540
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggcaacctg    720
attgccctga cctgggcct gaccccaac ttcaagagca cttcgacct ggccgaggat    780 gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg    960 atcaagagat acgacgagca ccaccaggac ctgaccctgc tgaaagctct cgtgcggcag   1020
cagctgcctg agaagtacaa agagatttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280 gaaatggcca gagagaacca gaccacccag aagggacaga gaacagccg cgagagaatg   2340 aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgctatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
```

```
aaggccgaga gaggcggcct gagcgaactg gataaggccg gcttcatcaa gagacagctg      2760
gtggaaaccc ggcagatcac aaagcacgtg gcacagatcc tggactcccg gatgaacact      2820
aagtacgacg agaatgacaa gctgatccgg gaagtgaaag tgatcaccct gaagtccaag      2880
ctggtgtccg atttccggaa ggatttccag ttttacaaag tgcgcgagat caacaactac      2940
caccacgccc acgacgccta cctgaacgcc gtcgtgggaa ccgccctgat caaaaagtac      3000
cctaagctgg aaagcgagtt cgtgtacggc gactacaagg tgtacgacgt gcggaagatg      3060
atcgccaaga gcgagcagga aatcggcaag gctaccgcca agtacttctt ctacagcaac      3120
atcatgaact ttttcaagac cgagattacc ctggccaacg gcgagatccg gaagcggcct      3180
ctgatcgaga caaacggcga aaccggggag atcgtgtggg ataagggccg ggattttgcc      3240
accgtgcgga aagtgctgag catgccccaa gtgaatatcg tgaaaaagac cgaggtgcag      3300
acaggcggct tcagcaaaga gtctatcctg cccaagagga cagcgataa gctgatcgcc       3360 agaaagaagg actgggaccc taagaagtac ggcggcttcg acagccccac cgtggcctat      3420
tctgtgctgg tggtggccaa agtggaaaag ggcaagtcca gaaaactgaa gagtgtgaaa      3480
gagctgctgg ggatcaccat catggaaaga agcagcttcg agaagaatcc catcgacttt      3540
ctggaagcca agggctacaa agaagtgaaa aaggacctga tcatcaagct gcctaagtac      3600
tccctgttcg agctggaaaa cggccggaag agaatgctgg cctctgccgg cgaactgcag      3660
aagggaaacg aactggccct gccctccaaa tatgtgaact tcctgtacct ggccagccac      3720
tatgagaagc tgaagggctc ccccgaggat aatgagcaga acagctgtt tgtggaacag      3780 cacaagcact acctggacga gatcatcgag cagatcagcg agttctccaa gagagtgatc      3840
ctggccgacg ctaatctgga caaagtgctg tccgcctaca acaagcaccg ggataagccc      3900
atcagagagc aggccgagaa tatcatccac ctgtttaccc tgaccaatct gggagcccct      3960
gccgccttca gtactttgga caccaccatc gaccggaaga ggtacaccag caccaaagag      4020
gtgctggacg ccacccctga tccaccagagc atcaccggcc tgtacgagac acggatcgac      4080
ctgtctcagc tggaggcga cagcgctgga ggaggtggaa gcggaggagg aggaagcgga      4140
ggaggaggta gcggacctaa gaaaaagagg aaggtggcgg ccgctggatc cggacgggct      4200
gacgcattgg acgatttga tctggatatg ctgggaagtg acgccctcga tgattttgac      4260
cttgacatgc ttggttcgga tgcccttgat gactttgacc tcgacatgct cggcagtgac      4320
gcccttgatg atttcgacct ggacatgctg attaac                                4356

<210> SEQ ID NO 170
<211> LENGTH: 4101
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 170
gacaagaagt acagcatcgg cctggccatc ggcaccaact ctgtgggctg ggccgtgatc        60
accgacgagt acaaggtgcc cagcaagaaa ttcaaggtgc tgggcaacac cgaccggcac       120
agcatcaaga gaacctgat cggagccctg ctgttcgaca gcggcgaaac agccgaggcc        180
acccggctga agagaaccgc cagaagaaga taccaccagac ggaagaaccg gatctgctat      240
ctgcaagaga tcttcagcaa cgagatggcc aaggtggacg acagcttctt ccacagactg      300
```

-continued

```
gaagagtcct tcctggtgga agaggataag aagcacgagc ggcaccccat cttcggcaac     360
atcgtggacg aggtggccta ccacgagaag tacccacca tctaccacct gagaaagaaa      420
ctggtggaca gcaccgacaa ggccgacctg cggctgatct atctgccct ggcccacatg       480 atcaagttcc ggggccactt cctgatcgag ggcgacctga cccccgacaa cagcgacgtg      540
gacaagctgt tcatccagct ggtgcagacc tacaaccagc tgttcgagga aaaccccatc     600
aacgccagcg gcgtggacgc caaggccatc ctgtctgcca gactgagcaa gagcagacgg     660
ctggaaaatc tgatcgccca gctgcccggc gagaagaaga atggcctgtt cggcaacctg     720
attgccctga gcctgggcct gacccccaac ttcaagagca acttcgacct ggccgaggat     780
gccaaactgc agctgagcaa ggacacctac gacgacgacc tggacaacct gctggcccag     840
atcggcgacc agtacgccga cctgtttctg gccgccaaga acctgtccga cgccatcctg     900
ctgagcgaca tcctgagagt gaacaccgag atcaccaagg ccccctgag cgcctctatg      960 atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagaggacct gctgcggaag    1200
cagcggacct tcgacaacgg cagcatcccc caccagatcc acctgggaga gctgcacgcc    1260
attctgcggc ggcaggaaga tttttaccca ttcctgaagg acaaccggga aaagatcgag    1320
aagatcctga ccttccgcat ccctactac gtgggccctc tggccagggg aaacagcaga    1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
aacgagctga ccaaagtgaa atacgtgacc gagggaatga gaaagcccgc cttcctgagc    1620
ggcgagcaga aaaaggccat cgtggacctg ctgttcaaga ccaaccggaa agtgaccgtg    1680
aagcagctga aagaggacta cttcaagaaa atcgagtgct tcgactccgt ggaaatctcc    1740
ggcgtggaag atcggttcaa cgcctccctg ggcacatacc acgatctgct gaaaattatc    1800
aaggacaagg acttcctgga caatgaggaa aacgaggaca ttctggaaga tatcgtgctg    1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100 ctgacctta aagaggacat ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc    2280 gaaatggcca gagagaacca gaccacccag aagggacaga agaacagccg cgagagaatg    2340
aagcggatcg aagagggcat caaagagctg ggcagccaga tcctgaaaga acaccccgtg    2400
gaaaacaccc agctgcagaa cgagaagctg tacctgtact acctgcagaa tgggcgggat    2460
atgtacgtgg accaggaact ggacatcaac cggctgtccg actacgatgt ggacgctatc    2520
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
```

```
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact ttttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga cagcgataa gctgatcgcc   3360 agaaagaagg actgggaccc taagaagtac ggcggcttcg acagccccac cgtggcctat   3420
tctgtgctgg tggtggccaa agtggaaaag ggcaagtcca agaaactgaa gagtgtgaaa   3480
gagctgctgg ggatcaccat catggaaaga agcagcttcg agaagaatcc catcgacttt   3540
ctggaagcca agggctacaa agaagtgaaa aaggacctga tcatcaagct gcctaagtac   3600
tccctgttcg agctggaaaa cggccggaag agaatgctgg cctctgccgg cgaactgcag   3660
aagggaaacg aactggccct gccctccaaa tatgtgaact tcctgtacct ggccagccac   3720
tatgagaagc tgaagggctc ccccgaggat aatgagcaga acagctgtt tgtggaacag   3780 cacaagcact acctggacga gatcatcgag cagatcagcg agttctccaa gagagtgatc   3840
ctggccgacg ctaatctgga caaagtgctg tccgcctaca acaagcaccg ggataagccc   3900
atcagagagc aggccgagaa tatcatccac ctgtttaccc tgaccaatct gggagcccct   3960
gccgccttca gtactttga caccaccatc gaccggaaga ggtacaccag caccaaagag   4020
gtgctggacg ccaccctgat ccaccagagc atcaccggcc tgtacgagac acggatcgac   4080
ctgtctcagc tgggaggcga c                                           4101
```

<210> SEQ ID NO 171
<211> LENGTH: 4743
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 171

```
gacaagaagt acagcatcgg cctggccatc ggcaccaact ctgtgggctg ggccgtgatc    60
accgacgagt acaaggtgcc cagcaagaaa ttcaaggtgc tgggcaacac cgaccggcac   120
agcatcaaga gaacctgat cggagccctg ctgttcgaca cggcgaaac agccgaggcc   180 acccggctga agagaaccgc cagaagaaga taccagac ggaagaaccg gatctgctat   240
ctgcaagaga tcttcagcaa cgagatggcc aaggtggacg acagcttctt ccacagactg   300
gaagagtcct tcctggtgga agaggataag aagcacgagc ggcaccccat cttcggcaac   360
atcgtggacg aggtggccta ccacgagaag taccccacca tctaccacct gagaaagaaa   420
ctggtggaca gcaccgacaa ggccgacctg cggctgatct atctggccct ggcccacatg   480
atcaagttcc ggggccactt cctgatcgag ggcgacctga accccgacaa cagcgacgtg   540
```

```
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggcaacctg    720
attgccctga gcctgggcct gaccccccaac ttcaagagca acttcgacct ggccgaggat   780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg     960 atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttttaccca ttcctgaagg acaaccggga aaagatcgag   1320
aagatcctga ccttccgcat ccctactac gtgggccctc tggccagggg aaacagcaga    1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga aaagcccgc cttcctgagc    1620 ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc    2280 gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgctatc   2520
gtgcctcaga gctttctgaa ggacgactcc atcgacaaca aggtgctgac cagagcgac    2580 aagaaccggg gcaagagcga caacgtgccc tccgaagagg tcgtgaagaa gatgaagaac   2640
tactggcggc agctgctgaa cgccaagctg attacccaga aaagttcga caatctgacc   2700 aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
```

```
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag ctaccgcca agtacttctt ctacagcaac     3120
atcatgaact ttttcaagac cgagattacc ctggccaacg gcgagatccg gaagcggcct    3180
ctgatcgaga caaacggcga accggggag atcgtgtggg ataagggccg ggattttgcc     3240
accgtgcgga aagtgctgag catgccccaa gtgaatatcg tgaaaaagac cgaggtgcag    3300
acaggcggct tcagcaaaga gtctatcctg cccaagagga acagcgataa gctgatcgcc    3360
agaaagaagg actgggaccc taagaagtac ggcggcttcg acagcccac cgtggcctat     3420 tctgtgctgg tggtggccaa agtggaaaag gcaagtcca agaaactgaa gagtgtgaaa     3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtgaacag     3780 cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga gtacaccag caccaaagag      4020 gtgctggacg ccaccctgat ccaccagagc atcaccggcc tgtacgagac acggatcgac    4080
ctgtctcagc tggaggcga cagcgctgga ggaggtggaa gcggaggagg aggaagcgga    4140
ggaggaggta gcggacctaa gaaaaagagg aaggtggcgg ccgctggatc cccttcaggg    4200
cagatcagca accaggccct ggctctggcc cctagctccg ctccagtgct ggcccagact    4260
atggtgccct ctagtgctat ggtgcctctg gcccagccac ctgctccagc ccctgtgctg    4320
accccaggac caccaagtc actgagcgct ccagtgccca agtctacaca ggccggcgag    4380
gggactctga gtgaagctct gctgcacctg cagttcgacg ctgatgagga cctgggagct    4440
ctgctgggga acagcaccga tcccggagtg ttcacagatc tggcctccgt ggacaactct    4500
gagtttcagc agctgctgaa tcaggcgtg tccatgtctc atagtacagc cgaaccaatg    4560
ctgatggagt accccgaagc cattacccgg ctggtgaccg cagccagcg gccccccgac    4620 cccgctccaa ctcccctggg aaccagcggc ctgcctaatg gctgtccgg agatgaagac    4680 ttctcaagca tcgctgatat ggactttagt gccctgctgt cacagatttc ctctagtggg    4740
cag                                                                   4743
```

<210> SEQ ID NO 172
<211> LENGTH: 6131
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 172

```
tgcaaagatg gataaagttt taaacagaga ggaatctttg cagctaatgg accttctagg    60
tcttgaaagg agtgggaatt ggctccggtg cccgtcagtg gcagagcgc acatcgccca    120
```

-continued

| | | | | |
|---|---|---|---|---|
| cagtccccga | gaagttgggg | ggaggggtcg | gcaattgaac | cggtgcctag agaaggtggc | 180 |
| gcggggtaaa | ctgggaaagt | gatgtcgtgt | actggctccg | ccttttttccc gagggtgggg | 240 |
| gagaaccgta | tataagtgca | gtagtcgccg | tgaacgttct | ttttcgcaac gggtttgccg | 300 |
| ccagaacaca | ggtaagtgcc | gtgtgtggtt | cccgcgggcc | tggcctcttt acgggttatg | 360 |
| gcccttgcgt | gccttgaatt | acttccactg | gctgcagtac | gtgattcttg atcccgagct | 420 |
| tcgggttgga | agtgggtggg | agagttcgag | gccttgcgct | taaggagccc cttcgcctcg | 480 |
| tgcttgagtt | gaggcctggc | ctgggcgctg | gggccgccgc | gtgcgaatct ggtggcacct | 540 |
| tcgcgcctgt | ctcgctgctt | tcgataagtc | tctagccatt | taaaattttt gatgacctgc | 600 |
| tgcgacgctt | tttttctggc | aagatagtct | tgtaaatgcg | ggccaagatc tgcacactgg | 660 |
| tatttcggtt | tttggggccg | cgggcggcga | cggggcccgt | gcgtcccagc gcacatgttc | 720 |
| ggcgaggcgg | ggcctgcgag | cgcggccacc | gagaatcgga | cgggggtagt ctcaagctgg | 780 |
| ccggcctgct | ctggtgcctg | gcctcgcgcc | gccgtgtatc | gccccgccct gggcggcaag | 840 |
| gctggcccgg | tcggcaccag | ttgcgtgagc | ggaaagatgg | ccgcttcccg gccctgctgc | 900 |
| agggagctca | aaatggagga | cgcggcgctc | gggagagcgg | gcgggtgagt cacccacaca | 960 |
| aaggaaaagg | gcctttccgt | cctcagccgt | cgcttcatgt | gactccacgg agtaccgggc | 1020 |
| gccgtccagg | cacctcgatt | agttctcgag | cttttggagt | acgtcgtctt taggttgggg | 1080 |
| ggaggggttt | tatgcgatgg | agtttccccca | cactgagtgg | gtggagactg aagttaggcc | 1140 |
| agcttggcac | ttgatgtaat | tctccttgga | atttgcccctt | tttgagtttg atcttggtt | 1200 |
| cattctcaag | cctcagacag | tggttcaaag | tttttttctt | ccatttcagg tgtcgtgacg | 1260 |
| tacggccacc | catgagcccc | aagaagaaga | gaaaggtgga | ggccagcgac aagaagtaca | 1320 |
| gcatcggcct | ggccatcggc | accaactctg | tgggctgggc | cgtgatcacc gacgagtaca | 1380 |
| aggtgcccag | caagaaattc | aaggtgctgg | gcaacaccga | ccggcacagc atcaagaaga | 1440 |
| acctgatcgg | agccctgctg | ttcgacagcg | gcgaaacagc | cgaggccacc cggctgaaga | 1500 |
| gaaccgccag | aagaagatac | accagacgga | agaaccggat ctgctatctg caagagatct | 1560 |
| tcagcaacga | gatggccaag | gtggacgaca | gcttcttcca | cagactggaa gagtccttcc | 1620 |
| tggtggaaga | ggataagaag | cacgagcggc | accccatctt | cggcaacatc gtggacgagg | 1680 |
| tggcctacca | cgagaagtac | cccaccatct | accacctgag | aaagaaactg gtggacagca | 1740 |
| ccgacaaggc | cgacctgcgg | ctgatctatc | tggccctggc | ccacatgatc aagttccggg | 1800 |
| gccacttcct | gatcgagggc | gacctgaacc | ccgacaacag | cgacgtggac aagctgttca | 1860 |
| tccagctggt | gcagacctac | aaccagctgt | tcgaggaaaa | ccccatcaac gccagcggcg | 1920 |
| tggacgccaa | ggccatcctg | tctgccagac | tgagcaagag | cagacggctg gaaaatctga | 1980 |
| tcgcccagct | gcccggcgag | aagaagaatg | gcctgttcgg | caacctgatt gccctgagcc | 2040 |
| tgggcctgac | ccccaacttc | aagagcaact | tcgacctggc | cgaggatgcc aaactgcagc | 2100 |
| tgagcaagga | cacctacgac | gacgacctgg | acaacctgct | ggcccagatc ggcgaccagt | 2160 |
| acgccgacct | gtttctggcc | gccaagaacc | tgtccgacgc | catcctgctg agcgacatcc | 2220 |
| tgagagtgaa | caccgagatc | accaaggccc | cctgagcgc | ctctatgatc aagagatacg | 2280 |
| acgagcacca | ccaggacctg | accctgctga | agctctcgt gcggcagcag | ctgcctgaga | 2340 |
| agtacaaaga | gattttcttc | gaccagagca | agaacggcta cgccggctac attgacggcg | 2400 |
| gagccagcca | ggaagagttc | tacaagttca | tcaagcccat | cctggaaaag atggacggca | 2460 |
| ccgaggaact | gctcgtgaag | ctgaacagag | aggacctgct | gcggaagcag cggaccttcg | 2520 |

```
acaacggcag catcccccac cagatccacc tgggagagct gcacgccatt ctgcggcggc    2580
aggaagattt ttacccattc ctgaaggaca accgggaaaa gatcgagaag atcctgacct    2640
tccgcatccc ctactacgtg ggccctctgg ccagggaaaa cagcagattc gcctggatga    2700
ccagaaagag cgaggaaacc atcacccccct ggaacttcga ggaagtggtg gacaagggcg   2760
cttccgccca gagcttcatc gagcggatga ccaacttcga taagaacctg cccaacgaga    2820
aggtgctgcc caagcacagc ctgctgtacg agtacttcac cgtgtataac gagctgacca    2880
aagtgaaata cgtgaccgag ggaatgagaa agcccgcctt cctgagcggc gagcagaaaa    2940
aggccatcgt ggacctgctg ttcaagacca accggaaagt gaccgtgaag cagctgaaag    3000
aggactactt caagaaaatc gagtgcttcg actccgtgga aatctccggc gtggaagatc    3060
ggttcaacgc ctccctgggc acataccacg atctgctgaa aattatcaag gacaaggact    3120
tcctggacaa tgaggaaaac gaggacattc tggaagatat cgtgctgacc ctgacactgt    3180
ttgaggacag agagatgatc gaggaacggc tgaaaaccta tgcccacctg ttcgacgaca    3240
aagtgatgaa gcagctgaag cggcggagat acaccggctg gggcaggctg agccggaagc    3300
tgatcaacgg catccgggac aagcagtccg gcaagacaat cctggatttc ctgaagtccg    3360
acggcttcgc caacagaaac ttcatgcagc tgatccacga cgacagcctg acctttaaag    3420
aggacatcca gaaagcccag gtgtccggcc agggcgatag cctgcacgag cacattgcca    3480
atctggccgg cagccccgcc attaagaagg gcatcctgca gacagtgaag gtggtggacg    3540
agctcgtgaa agtgatgggc cggcacaagc ccgagaacat cgtgatcgaa atggccagag    3600
agaaccagac cacccagaag ggacagaaga acagccgcga gagaatgaag cggatcgaag    3660
agggcatcaa agagctgggc agccagatcc tgaaagaaca ccccgtggaa aacacccagc    3720
tgcagaacga gaagctgtac ctgtactacc tgcagaatgg gcgggatatg tacgtggacc    3780
aggaactgga catcaaccgg ctgtccgact acgatgtgga ccacatcgtg cctcagagct    3840
ttctgaagga cgactccatc gacaacaagg tgctgaccag aagcgacaag gcccggggca    3900
agagcgacaa cgtgccctcc gaagaggtcg tgaagaagat gaagaactac tggcggcagc    3960
tgctgaacgc caagctgatt acccagagaa agttcgacaa tctgaccaag gccgagagag    4020
gcggcctgag cgaactggat aaggccggct tcatcaagag acagctggtg gaaacccggc    4080
agatcacaaa gcacgtggca cagatcctgg actcccggat gaacactaag tacgacgaga    4140
atgacaagct gatccgggaa gtgaaagtga tcacccctga agtccaagctg tgtccgatt    4200 tccggaagga tttccagttt tacaaagtgc gcgagatcaa caactaccac cacgcccacg    4260
acgcctacct gaacgccgtc gtgggaaccg ccctgatcaa aaagtaccct aagctggaaa    4320
gcgagttcgt gtacgcgac tacaaggtgt acgacgtgcg gaagatgatc gccaagagcg    4380
agcaggaaat cggcaaggct accgccaagt acttcttcta cagcaacatc atgaactttt    4440
tcaagaccga gattaccctg gccaacgcg agatccggaa cgcctctg atcgagacaa    4500 acggcgaaac cggggagatc gtgtgggata agggcccggga ttttgccacc gtgcggaaag    4560
tgctgagcat gccccaagtg aatatcgtga aaaagaccga ggtgcagaca ggcggcttca    4620
gcaaagagtc tatcctgccc aagaggaaca gcgataagct gatcgccaga aagaaggact    4680 gggacccta agagtacggc ggcttcgaca gccccaccgt ggcctattct gtgctggtgg    4740
tggccaaagt ggaaaagggc aagtccaaga aactgaagag tgtgaagag ctgctgggga    4800 tcaccatcat ggaaagaagc agcttcgaga agaatcccat cgactttctg gaagccaagg    4860
```

```
gctacaaaga agtgaaaaag gacctgatca tcaagctgcc taagtactcc ctgttcgagc    4920
tggaaaacgg ccggaagaga atgctggcct ctgccggcga actgcagaag ggaaacgaac    4980
tggccctgcc ctccaaatat gtgaacttcc tgtacctggc cagccactat gagaagctga    5040
agggctcccc cgaggataat gagcagaaac agctgtttgt ggaacagcac aagcactacc    5100
tggacgagat catcgagcag atcagcgagt tctccaagag agtgatcctg gccgacgcta    5160
atctggacaa agtgctgtcc gcctacaaca gcaccggga taagcccatc agagagcagg    5220
ccgagaatat catccacctg tttaccctga ccaatctggg agcccctgcc gccttcaagt    5280
actttgacac caccatcgac cggaagaggt acaccagcac caagagggtg ctggacgcca    5340
ccctgatcca ccagagcatc accggcctgt acgagacacg gatcgacctg tctcagctgg    5400
gaggcgacag cgctggagga ggtggaagcg gaggaggagg aagcggagga ggaggtagcg    5460
gacctaagaa aaagaggaag gtggcggccg ctggatccgg acgggctgac gcattggacg    5520
attttgatct ggatatgctg ggaagtgacg ccctcgatga ttttgacctt gacatgcttg    5580
gttcggatgc ccttgatgac tttgacctcg acatgctcgg cagtgacgcc cttgatgatt    5640
tcgacctgga catgctgatt aactgtacag gcagtggaga gggcagagga agtctgctaa    5700
catgcggtga cgtcgaggag aatcctggcc caatggccaa gcctttgtct caagaagaat    5760
ccaccctcat tgaaagagca acggctacaa tcaacagcat ccccatctct gaagactaca    5820
gcgtcgccag cgcagctctc tctagcgacg ccgcatcttc cactggtgtc aatgtatatc    5880
attttactgg gggaccttgt gcagaactcg tggtgctggg cactgctgct gctgcggcag    5940 ctggcaaccct gacttgtatc gtcgcgatcg gaaatgagaa caggggcatc ttgagcccct    6000
gcggacggtg ccgacaggtg cttctcgatc tgcatcctgg gatcaaagcc atagtgaagg    6060
acagtgatgg acagccgacg gcagttggga ttcgtgaatt gctgccctct ggttatgtgt    6120
gggagggcta a                                                        6131
```

<210> SEQ ID NO 173
<211> LENGTH: 1258
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 173

```
tgcaaagatg gataaagttt taaacagaga ggaatctttg cagctaatgg accttctagg      60
tcttgaaagg agtgggaatt ggctccggtg cccgtcagtg ggcagagcgc acatcgccca     120
cagtccccga gaagttgggg ggaggggtcg gcaattgaac cggtgcctag agaaggtggc     180
gcggggtaaa ctgggaaagt gatgtcgtgt actggctccg ccttttttccc gagggtgggg     240 gagaaccgta tataagtgca gtagtcgccg tgaacgttct ttttcgcaac gggtttgccg     300
ccagaacaca ggtaagtgcc gtgtgtggtt cccgcgggcc tggcctcttt acgggttatg     360
gcccttgcgt gccttgaatt acttccactg gctgcagtac gtgattcttg atcccgagct     420
tcgggttgga agtgggtggg agagttcgag gccttgcgct taaggagccc cttcgcctcg     480
tgcttgagtt gaggcctggc ctgggcgctg gggccgccgc gtgcgaatct ggtggcacct     540
tcgcgcctgt ctcgctgctt tcgataagtc tctagccatt taaaattttt gatgacctgc     600
tgcgacgctt tttttctggc aagatagtct tgtaaatgcg ggccaagatc tgcacactgg     660
tatttcggtt tttggggccg cgggcggcga cggggcccgt gcgtcccagc gcacatgttc     720
```

```
ggcgaggcgg ggcctgcgag cgcggccacc gagaatcgga cgggggtagt ctcaagctgg      780
ccggcctgct ctggtgcctg gcctcgcgcc gccgtgtatc gccccgccct gggcggcaag      840
gctggcccgg tcggcaccag ttgcgtgagc ggaaagatgg ccgcttcccg gccctgctgc      900
agggagctca aaatggagga cgcggcgctc gggagagcgg gcgggtgagt cacccacaca      960
aaggaaaagg gcctttccgt cctcagccgt cgcttcatgt gactccacgg agtaccgggc     1020
gccgtccagg cacctcgatt agttctcgag cttttggagt acgtcgtctt taggttgggg     1080
ggagggtttt tatgcgatgg agtttcccca cactgagtgg gtggagactg aagttaggcc     1140
agcttggcac ttgatgtaat tctccttgga atttgcccct tttgagtttg gatcttggtt     1200
cattctcaag cctcagacag tggttcaaag ttttttttctt ccatttcagg tgtcgtga     1258
```

<210> SEQ ID NO 174  
<211> LENGTH: 36  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic oligonucleotide"

<400> SEQUENCE: 174

```
atgagcccca agaagaagag aaaggtggag gccagc                                 36
```

<210> SEQ ID NO 175  
<211> LENGTH: 4101  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 175

```
gacaagaagt acagcatcgg cctggccatc ggcaccaact ctgtgggctg ggccgtgatc       60
accgacgagt acaaggtgcc cagcaagaaa ttcaaggtgc tgggcaacac cgaccggcac      120
agcatcaaga gaacctgat cggagccctg ctgttcgaca cggcgaaac agccgaggcc       180 acccggctga agaaccgc cagaagaaga tacaccagac ggaagaaccg gatctgctat       240
ctgcaagaga tcttcagcaa cgagatggcc aaggtggacg acagcttctt ccacagactg      300
gaagagtcct tcctggtgga agaggataag aagcacgagc ggcacccat cttcggcaac      360 atcgtggacg aggtggccta ccacgagaag taccccacca tctaccacct gagaaagaaa      420
ctggtggaca gcaccgacaa ggccgacctg cggctgatct atctggccct ggcccacatg      480
atcaagttcc ggggccactt cctgatcgag ggcgacctga accccgacaa cagcgacgtg      540
gacaagctgt tcatccagct ggtgcagacc tacaaccagc tgttcgagga aaaccccatc      600
aacgccagcg gcgtggacgc caaggccatc ctgtctgcca gactgagcaa gagcagacgg      660
ctggaaaatc tgatcgccca gctgcccggc gagaagaaga atggcctgtt cggcaacctg      720
attgccctga gcctgggcct gacccccaac ttcaagagca acttcgacct ggccgaggat      780
gccaaactgc agctgagcaa ggacacctac gacgacgacc tggacaacct gctggcccag      840
atcggcgacc agtacgccga cctgtttctg gccgccaaga acctgtccga cgccatcctg      900
ctgagcgaca tcctgagagt gaacaccgag atcaccaagg cccccctgag cgcctctatg      960
atcaagagat acgacgagca ccaccaggac ctgaccctgc tgaaagctct cgtgcggcag     1020
```

```
cagctgcctg agaagtacaa agagattttc ttcgaccaga gcaagaacgg ctacgccggc     1080
tacattgacg gcggagccag ccaggaagag ttctacaagt tcatcaagcc catcctggaa     1140
aagatggacg gcaccgagga actgctcgtg aagctgaaca gagaggacct gctgcggaag     1200
cagcggacct tcgacaacgg cagcatcccc accagatcc acctgggaga gctgcacgcc      1260
attctgcggc ggcaggaaga ttttttaccca ttcctgaagg acaaccggga aaagatcgag    1320
aagatcctga ccttccgcat cccctactac gtgggccctc tggccagggg aaacagcaga    1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat   1560
aacgagctga ccaaagtgaa atacgtgacc gagggaatga aaagcccgc cttcctgagc     1620 ggcgagcaga aaaaggccat cgtggacctg ctgttcaaga ccaaccggaa agtgaccgtg    1680
aagcagctga agaggacta cttcaagaaa atcgagtgct tcgactccgt ggaaatctcc    1740
ggcgtggaag atcggttcaa cgcctccctg ggcacatacc acgatctgct gaaaattatc    1800
aaggacaagg acttcctgga caatgaggaa aacgaggaca ttctggaaga tatcgtgctg    1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100 ctgacccttta aagaggacat ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc     2280 gaaatggcca gagagaacca gaccacccag aagggacaga gaacagccg cgagagaatg    2340 aagcggatcg aagagggcat caaagagctg ggcagccaga tcctgaaaga acaccccgtg    2400
gaaaacaccc agctgcagaa cgagaagctg tacctgtact acctgcagaa tgggcgggat    2460
atgtacgtgg accaggaact ggacatcaac cggctgtccg actacgatgt ggaccacatc    2520
gtgcctcaga gctttctgaa ggacgactcc atcgacaaca aggtgctgac cagaagcgac    2580
aaggcccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact tttcaagac cgagattacc ctggccaacg gcgagatccg gaagcggcct    3180
ctgatcgaga caaacggcga aaccggggag atcgtgtggg ataagggccg ggattttgcc    3240
accgtgcgga agtgctgag catgcccaa gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagccccac cgtggcctat    3420
```

```
tctgtgctgg tggtggccaa agtggaaaag gcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca caagcaccg ggataagccc    3900 atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga c                                             4101
```

<210> SEQ ID NO 176
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176

```
ggcagtggag agggcagagg aagtctgcta acatgcggtg acgtcgagga gaatcctggc    60
cca                                                                 63
```

<210> SEQ ID NO 177
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 177

```
atggccaagc ctttgtctca agaagaatcc accctcattg aaagagcaac ggctacaatc    60
aacagcatcc ccatctctga agactacagc gtcgccagcg cagctctctc tagcgacggc   120
cgcatcttca ctggtgtcaa tgtatatcat tttactgggg gaccttgtgc agaactcgtg   180
gtgctgggca ctgctgctgc tgcggcagct ggcaacctga cttgtatcgt cgcgatcgga   240
aatgagaaca gggcatctt gagccctgc ggacggtgcc gacaggtgct tctcgatctg   300
catcctggga tcaaagccat agtgaaggac agtgatggac agccgacggc agttgggatt   360
cgtgaattgc tgccctctgg ttatgtgtgg gagggctaa                          399
```

<210> SEQ ID NO 178
<211> LENGTH: 3797
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 178

-continued

```
tgcaaagatg gataaagttt taaacagaga ggaatctttg cagctaatgg accttctagg      60
tcttgaaagg agtgggaatt ggctccggtg cccgtcagtg ggcagagcgc acatcgccca     120
cagtccccga gaagttgggg ggaggggtcg gcaattgaac cggtgcctag agaaggtggc     180
gcggggtaaa ctgggaaagt gatgtcgtgt actggctccg ccttttttccc gagggtgggg    240
gagaaccgta tataagtgca gtagtcgccg tgaacgttct ttttcgcaac gggtttgccg     300
ccagaacaca ggtaagtgcc gtgtgtggtt cccgcgggcc tggcctcttt acgggttatg     360
gcccttgcgt gccttgaatt acttccacct ggctgcagta cgtgattctt gatcccgagc     420
ttcgggttgg aagtgggtgg gagagttcga ggccttgcgc ttaaggagcc ccttcgcctc     480
gtgcttgagt tgaggcctgg cctgggcgct ggggccgccg cgtgcgaatc tggtggcacc     540
ttcgcgcctg tctcgctgct ttcgataagt ctctagccat ttaaaatttt tgatgacctg     600
ctgcgacgct ttttttctgg caagatagtc ttgtaaatgc gggccaagat ctgcacactg     660
gtatttcggt ttttgggggcc gcgggcggcg acggggcccg tgcgtcccag cgcacatgtt    720
cggcgaggcg gggcctgcga gcgcggccac cgagaatcgg acggggtag tctcaagctg      780
gccggcctgc tctggtgcct ggcctcgcgc cgccgtgtat cgccccgccc tgggcggcaa     840
ggctggcccg gtcggcacca gttgcgtgag cggaaagatg gccgcttccc ggccctgctg     900
cagggagctc aaaatggagg acgcggcgct cgggagagcg ggcgggtgag tcacccacac     960
aaaggaaaag ggccttttccg tcctcagccg tcgcttcatg tgactccacg gagtaccggg   1020
cgccgtccag gcacctcgat tagttctcga gcttttggag tacgtcgtct ttaggttggg    1080
gggaggggtt ttatgcgatg gagtttcccc acactgagtg ggtggagact gaagttaggc    1140
cagcttggca cttgatgtaa ttctccttgg aatttgccct ttttgagttt ggatcttggt    1200
tcattctcaa gcctcagaca gtggttcaaa gttttttttct tccatttcag gtgtcgtgac   1260
gtacggccac catggcttca aactttactc agttcgtgct cgtggacaat ggtgggacag    1320
gggatgtgac agtggctcct tctaatttcg ctaatgggt ggcagagtgg atcagctcca     1380
actcacggag ccaggcctac aaggtgacat gcagcgtcag gcagtctagt gcccagaaga    1440
gaaagtatac catcaaggtg gaggtcccca aagtggctac ccagacagtg ggcggagtcg    1500
aactgcctgt cgccgcttgg aggtcctacc tgaacatgga gctcactatc ccaattttcg    1560
ctaccaattc tgactgtgaa ctcatcgtga aggcaatgca ggggctcctc aaagacggta    1620
atcctatccc ttccgccatc gccgctaact caggtatcta cagcgctgga ggaggtggaa    1680
gcggaggagg aggaagcgga ggaggaggta gcggacctaa gaaaaagagg aaggtggcgg    1740
ccgctggatc cccttcaggg cagatcagca accaggccct ggctctggcc cctagctccg    1800
ctccagtgct ggcccagact atggtgccct ctagtgctat ggtgcctctg gcccagccac    1860
ctgctccagc ccctgtgctg accccaggac cacccagtc actgagcgct ccagtgccca    1920
agtctacaca ggccggcgag gggactctga gtgaagctct gctgcacctg cagttcgacg    1980
ctgatgagga cctgggagct ctgctgggga acagcaccga tcccggagtg ttcacagatc    2040
tggcctccgt ggacaactct gagtttcagc agctgctgaa tcagggcgtg tccatgtctc    2100
atagtacagc cgaaccaatg ctgatggagt accccgaagc cattacccgg ctggtgaccg    2160
gcagccagcg gccccccgac cccgctccaa ctcccctggg aaccagcggc ctgcctaatg    2220
ggctgtccgg agatgaagac ttctcaagca tcgctgatat ggactttagt gccctgctgt    2280
cacagatttc ctctagtggg cagggaggag gtggaagcgg cttcagcgtg gacaccagtg    2340
ccctgctgga cctgttcagc ccctcggtga ccgtgcccga catgagcctg cctgaccttg    2400
```

```
acagcagcct ggccagtatc caagagctcc tgtctcccca ggagccccc  aggcctcccg   2460 aggcagagaa cagcagcccg gattcaggga agcagctggt gcactacaca gcgcagccgc   2520
tgttcctgct ggaccccggc tccgtggaca ccgggagcaa cgacctgccg gtgctgtttg   2580
agctgggaga gggctcctac ttctccgaag ggacggctt cgccgaggac cccaccatct    2640
ccctgctgac aggctcggag cctcccaaag ccaaggaccc cactgtctcc tgtacaggca   2700
gtggagaggg cagaggaagt ctgctaacat gcggtgacgt cgaggagaat cctgcccaa    2760 ccatgaaaaa gcctgaactc accgctacct ctgtcgagaa gtttctgatc gaaaagttcg   2820
acagcgtctc cgacctgatg cagctctccg agggcgaaga atctcgggct ttcagcttcg   2880
atgtgggagg gcgtggatat gtcctgcggg tgaatagctg cgccgatggt ttctacaaag   2940
atcgctatgt ttatcggcac tttgcatccg ccgctctccc tattcccgaa gtgcttgaca   3000
ttggggagtt cagcgagagc ctgacctatt gcatctcccg ccgtgcacag ggtgtcacct   3060
tgcaagacct gcctgaaacc gaactgcccg ctgttctcca gcccgtcgcc gaggccatgg   3120
atgccatcgc tgccgccgat cttagccaga ccagcgggtt cggcccattc ggacctcaag   3180
gaatcggtca atacactaca tggcgcgatt tcatctgcgc tattgctgat ccccatgtgt   3240
atcactggca aactgtgatg gacgacaccg tcagtgcctc cgtcgcccag gctctcgatg   3300
agctgatgct ttgggccgag gactgccccg aagtccggca cctcgtgcac gccgatttcg   3360
gctccaacaa tgtcctgacc gacaatggcc gcataacagc cgtcattgac tggagcgagg   3420
ccatgttcgg ggattcccaa tacgaggtcg ccaacatctt cttctggagg ccctggttgg   3480
cttgtatgga gcagcagacc cgctacttcg agcggaggca tcccgagctt gcaggatctc   3540
ctcggctccg ggcttatatg ctccgcattg gtcttgacca actctatcag agcttggttg   3600
acggcaattt cgatgatgca gcttgggctc agggtcgctg cgacgcaatc gtccggtccg   3660
gagccgggac tgtcgggcgt acacaaatcg cccgcagaag cgctgccgtc tggaccgatg   3720
gctgtgtgga agtgctcgcc gatagtggaa acagacgccc cagcactcgt cctagggcaa   3780
aggatctgca gtaatga                                                  3797
```

<210> SEQ ID NO 179
<211> LENGTH: 1259
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 179

```
tgcaaagatg gataaagttt taaacagaga ggaatctttg cagctaatgg accttctagg     60
tcttgaaagg agtgggaatt ggctccggtg cccgtcagtg ggcagagcgc acatcgccca   120
cagtccccga gaagttgggg ggaggggtcg gcaattgaac cggtgcctag agaaggtggc   180
gcggggtaaa ctgggaaagt gatgtcgtgt actggctccg ccttttttccc gagggtgggg   240 gagaaccgta tataagtgca gtagtcgccg tgaacgttct ttttcgcaac gggtttgccg    300
ccagaacaca ggtaagtgcc gtgtgtggtt cccgcgggcc tggcctcttt acgggttatg    360
gcccttgcgt gccttgaatt acttccaccct ggctgcagta cgtgattctt gatcccgagc    420
ttcgggttgg aagtgggtgg gagagttcga ggccttgcgc ttaaggagcc cttcgcctc     480 gtgcttgagt tgaggcctgg cctgggcgct ggggccgccg cgtgcgaatc tggtggcacc    540
```

```
ttcgcgcctg tctcgctgct ttcgataagt ctctagccat ttaaaatttt tgatgacctg    600
ctgcgacgct ttttttctgg caagatagtc ttgtaaatgc gggccaagat ctgcacactg    660
gtatttcggt ttttggggcc gcgggcggcg acggggcccg tgcgtcccag cgcacatgtt    720
cggcgaggcg gggcctgcga gcgcggccac cgagaatcgg acgggggtag tctcaagctg    780
gccggcctgc tctggtgcct ggcctcgcgc cgccgtgtat cgccccgccc tgggcggcaa    840
ggctggcccg tcggcacca gttgcgtgag cggaaagatg gccgcttccc ggccctgctg      900
cagggagctc aaaatggagg acgcggcgct cgggagagcg ggcgggtgag tcacccacac    960
aaaggaaaag ggcctttccg tcctcagccg tcgcttcatg tgactccacg gagtaccggg   1020
cgccgtccag gcacctcgat tagttctcga gcttttggag tacgtcgtct ttaggttggg   1080
gggaggggtt ttatgcgatg gagtttcccc acactgagtg ggtggagact gaagttaggc   1140
cagcttggca cttgatgtaa ttctccttgg aatttgccct ttttgagttt ggatcttggt   1200
tcattctcaa gcctcagaca gtggttcaaa gttttttct tccatttcag gtgtcgtga    1259
```

<210> SEQ ID NO 180
<211> LENGTH: 1038
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 180

```
accatgaaaa agcctgaact caccgctacc tctgtcgaga agtttctgat cgaaaagttc     60
gacagcgtct ccgacctgat gcagctctcc gagggcgaag aatctcgggc tttcagcttc    120
gatgtgggag gcgtggata tgtcctgcgg gtgaatagct cgccgatgg tttctacaaa      180 gatcgctatg tttatcggca ctttgcatcc gccgctctcc ctattcccga agtgcttgac    240
attggggagt tcagcgagag cctgacctat tgcatctccc gccgtgcaca gggtgtcacc    300
ttgcaagacc tgcctgaaac cgaactgccc gctgttctcc agcccgtcgc cgaggccatg    360
gatgccatcg ctgccgccga tcttagccag accagcgggt tcggcccatt cggacctcaa    420
ggaatcggtc aatacactac atggcgcgat ttcatctgcg ctattgctga tccccatgtg    480
tatcactggc aaactgtgat ggacgacacc gtcagtgcct ccgtcgccca ggctctcgat    540
gagctgatgc tttgggccga ggactgcccc gaagtccggc acctcgtgca cgccgatttc    600
ggctccaaca atgtcctgac cgacaatggc cgcataacag ccgtcattga ctggagcgag    660
gccatgttcg gggattccca atacgaggtc gccaacatct tcttctggag gccctggttg    720
gcttgtatgg agcagcagac ccgctacttc gagcggaggc atcccgagct tgcaggatct    780
cctcggctcc gggcttatat gctccgcatt ggtcttgacc aactctatca gagcttggtt    840
gacggcaatt tcgatgatgc agcttgggct caggtcgct gcgacgcaat cgtccggtcc     900
ggagccggga ctgtcgggcg tacacaaatc gcccgcagaa gcgctgccgt ctggaccgat    960
ggctgtgtgg aagtgctcgc cgatagtgga aacagacgcc ccagcactcg tcctagggca   1020
aaggatctgc agtaatga                                                  1038
```

<210> SEQ ID NO 181
<211> LENGTH: 2057
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 181

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccg gagacgggat accgtctctg ttttagagct aggccaacat gaggatcacc   300
catgtctgca gggcctagca agttaaaata aggctagtcc gttatcaact tggccaacat   360
gaggatcacc catgtctgca gggccaagtg caccgagtc ggtgcttttt ttggatcctg    420
caaagatgga taaagtttta aacagagagg aatctttgca gctaatggac cttctaggtc   480
ttgaaaggag tgggaattgg ctccggtgcc cgtcagtggg cagagcgcac atcgcccaca   540
gtccccgaga agttgggggg aggggtcggc aattgatccg gtgcctagag aaggtggcgc   600
ggggtaaact gggaaagtga tgtcgtgtac tggctccgcc tttttcccga gggtggggga   660
gaaccgtata taagtgcagt agtcgccgtg aacgttcttt ttcgcaacgg gtttgccgcc   720
agaacacagg taagtgccgt gtgtggttcc cgcgggcctg gcctctttac gggttatggc   780
ccttgcgtgc cttgaattac ttccactggc tgcagtacgt gattcttgat cccgagcttc   840
gggttggaag tgggtgggag agttcgaggc cttgcgctta aggagcccct tcgcctcgtg   900
cttgagttga ggcctggcct gggcgctggg gccgccgcgt gcgaatctgg tggcaccttc   960
gcgcctgtct cgctgctttc gataagtctc tagccattta aaattttga tgacctgctg   1020
cgacgctttt tttctggcaa gatagtcttg taaatgcggg ccaagatctg cacactggta  1080
tttcggtttt tggggccgcg gcggcgacg gggcccgtgc gtcccagcgc acatgttcgg   1140
cgaggcgggg cctgcgagcg cggccaccga gaatcggacg ggggtagtct caagctggcc  1200
ggcctgctct ggtgcctggc ctcgcgccgc cgtgtatcgc cccgccctgg gcggcaaggc  1260
tggcccggtc ggcaccagtt gcgtgagcgg aaagatggcc gcttccggc cctgctgcag   1320
ggagctcaaa atggaggacg cggcgctcgg gagagcgggc gggtgagtca cccacacaaa  1380
ggaaaagggc cttcccgtcc tcagccgtcg cttcatgtga ctccacggag taccgggcgc  1440
cgtccaggca cctcgattag ttctcgagct tttggagtac gtcgtcttta ggttgggggg  1500
aggggtttta tgcgatggag tttccccaca ctgagtgggt ggagactgaa gttaggccag  1560
cttggcactt gatgtaattc tccttggaat ttgccctttt tgagtttgga tcttggttca  1620
ttctcaagcc tcagacagtg gttcaaagtt ttttcttcc atttcaggtg tcgtgatgta   1680
caatggccaa gttgaccagt gccgttccgg tgctcaccgc gcgcgacgtc gccggagcgg   1740
tcgagttctg gaccgaccgg ctcgggttct cccgggactt cgtggaggac gacttcgccg  1800
gtgtggtccg ggacgacgtg accctgttca tcagcgcgt ccaggaccag gtggtgccgg   1860
acaacaccct ggcctgggtg tgggtgcgcg gcctggacga gctgtacgcc gagtggtcgg  1920
aggtcgtgtc cacgaacttc cgggacgcct ccggccggc catgaccgag atcggcgagc   1980
agccgtgggg gcgggagttc gccctgcgcg acccggccgg caactgcgtg cacttcgtgg  2040
ccgaggagca ggactga                                                 2057
```

<210> SEQ ID NO 182
<211> LENGTH: 249
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacacc                                                          249

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
aagatgaaag gaaaggcgtt                                               20

<210> SEQ ID NO 184
<211> LENGTH: 136
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
gttttagagc taggccaaca tgaggatcac ccatgtctgc agggcctagc aagttaaaat    60
aaggctagtc cgttatcaac ttggccaaca tgaggatcac ccatgtctgc agggccaagt   120
ggcaccgagt cggtgc                                                  136

<210> SEQ ID NO 185
<211> LENGTH: 1258
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 185
tgcaaagatg gataaagttt taaacagaga ggaatctttg cagctaatgg accttctagg    60
tcttgaaagg agtgggaatt ggctccggtg cccgtcagtg ggcagagcgc acatcgccca   120
cagtccccga gaagttgggg ggaggggtcg gcaattgatc cggtgcctag agaaggtggc   180
gcggggtaaa ctgggaaagt gatgtcgtgt actggctccg ccttttttccc gagggtgggg   240 gagaaccgta tataagtgca gtagtcgccg tgaacgttct ttttcgcaac gggtttgccg   300
ccagaacaca ggtaagtgcc gtgtgtggtt cccgcgggcc tggcctcttt acgggttatg   360
gcccttgcgt gccttgaatt acttccactg gctgcagtac gtgattcttg atcccgagct   420
tcgggttgga agtgggtggg agagttcgag gccttgcgct taaggagccc cttcgcctcg   480
tgcttgagtt gaggcctggc ctgggcgctg gggccgccgc gtgcgaatct ggtggcacct   540

```
tcgcgcctgt ctcgctgctt tcgataagtc tctagccatt taaaattttt gatgacctgc        600
tgcgacgctt tttttctggc aagatagtct tgtaaatgcg ggccaagatc tgcacactgg        660
tatttcggtt tttggggccg cgggcggcga cggggcccgt gcgtcccagc gcacatgttc        720
ggcgaggcgg ggcctgcgag cgcggccacc gagaatcgga cggggtagt  ctcaagctgg        780 ccggcctgct ctggtgcctg gcctcgcgcc gccgtgtatc gccccgccct gggcggcaag        840
gctggcccgg tcgcaccag  ttgcgtgagc ggaaagatgg ccgcttcccg gccctgctgc        900
agggagctca aaatggagga cgcggcgctc gggagagcgg gcgggtgagt cacccacaca        960
aaggaaaagg gcctttccgt cctcagccgt cgcttcatgt gactccacgg agtaccgggc       1020
gccgtccagg cacctcgatt agttctcgag cttttggagt acgtcgtctt taggttgggg       1080
ggaggggttt tatgcgatgg agtttcccca cactgagtgg gtggagactg aagttaggcc       1140
agcttggcac ttgatgtaat tctccttgga atttgccctt tttgagtttg atcttggtt        1200 cattctcaag cctcagacag tggttcaaag ttttttttctt ccatttcagg tgtcgtga       1258
```

<210> SEQ ID NO 186
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 186

```
atggccaagt tgaccagtgc cgttccggtg ctcaccgcgc gcgacgtcgc cggagcggtc         60
gagttctgga ccgaccggct cgggttctcc cgggacttcg tggaggacga cttcgccggt        120
gtggtccggg acgacgtgac cctgttcatc agcgcggtcc aggaccaggt ggtgccggac        180
aacaccctgg cctgggtgtg ggtgcgcggc ctggacgagc tgtacgccga gtggtcggag        240
gtcgtgtcca cgaacttccg ggacgcctcc gggccggcca tgaccgagat cggcgagcag        300
ccgtgggggc gggagttcgc cctgcgcgac ccggccggca actgcgtgca cttcgtggcc        360
gaggagcagg actga                                                        375
```

<210> SEQ ID NO 187
<211> LENGTH: 2282
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 187

```
gagggcctat ttcccatgat tccttcatat ttgcatatac gatacaaggc tgttagagag         60
ataattggaa ttaatttgac tgtaaacaca aagatattag tacaaaatac gtgacgtaga        120
aagtaataat ttcttgggta gtttgcagtt ttaaaattat gttttaaaat ggactatcat        180
atgcttaccg taacttgaaa gtatttcgat ttcttggctt tatatatctt gtggaaagga        240
cgaaacaccg agacgggat accgtctctg ttttagagct aggccaacat gaggatcacc        300
catgtctgca gggcctagca agttaaaata aggctagtcc gttatcaact tggccaacat        360
gaggatcacc catgtctgca gggccaagtg caccgagtc ggtgcttttt ttggatcctg        420
caaagatgga taaagtttta aacagagagg aatctttgca gctaatggac cttctaggtc        480
```

```
ttgaaaggag tgggaattgg ctccggtgcc cgtcagtggg cagagcgcac atcgcccaca    540
gtccccgaga agttgggggg aggggtcggc aattgatccg gtgcctagag aaggtggcgc    600
ggggtaaact gggaaagtga tgtcgtgtac tggctccgcc tttttcccga gggtgggggga   660
gaaccgtata taagtgcagt agtcgccgtg aacgttcttt ttcgcaacgg gtttgccgcc    720
agaacacagg taagtgccgt gtgtggttcc cgcgggcctg gcctctttac gggttatggc    780
ccttgcgtgc cttgaattac ttccaccggc tgcagtacgt gattcttgat cccgagcttc    840
gggttggaag tgggtgggag agttcgaggc cttgcgctta aggagcccct tcgcctcgtg    900
cttgagttga ggcctggcct gggcgctggg ccgccgcgt gcgaatctgg tggcaccttc     960
gcgcctgtct cgctgctttc gataagtctc tagccattta aaattttga tgacctgctg    1020
cgacgctttt tttctggcaa gatagtcttg taaatgcggg ccaagatctg cacactggta   1080
tttcggtttt tggggccgcg ggcggcgacg gggcccgtgc gtcccagcgc acatgttcgg   1140
cgaggcgggg cctgcgagcg cggccaccga gaatcggacg ggggtagtct caagctggcc   1200
ggcctgctct ggtgcctggc ctcgcgccgc cgtgtatcgc cccgcccctgg gcggcaaggc  1260
tggccccggtc ggcaccagtt gcgtgagcgg aaagatggcc gcttcccggc cctgctgcag  1320
ggagctcaaa atggaggacg cggcgctcgg gagagcgggc gggtgagtca cccacacaaa   1380
ggaaaagggc ctttccgtcc tcagccgtcg cttcatgtga ctccacggag taccgggcgc   1440
cgtccaggca cctcgattag ttctcgagct tttggagtac gtcgtcttta ggttgggggg   1500
aggggttttta tgcgatggag tttccccaca ctgagtgggt ggagactgaa gttaggccag  1560
cttggcactt gatgtaattc tccttggaat ttgccctttt tgagtttgga tcttggttca   1620
ttctcaagcc tcagacagtg gttcaaagtt tttttcttcc atttcaggtg tcgtgatgta   1680
caatgaccga gtacaagccc acggtgcgcc tcgccacccg cgacgacgtc cccagggccg   1740
tacgcaccct cgccgccgcg ttcgccgact accccgccac gcgccacacc gtcgatccgg   1800
accgccacat cgagcgggtc accgagctgc aagaactctt cctcacgcgc gtcgggctcg   1860
acatcggcaa ggtgtgggtc gcggacgacg gcgccgccgt ggcggtctgg accacgccgg   1920
agagcgtcga agcgggggcg tgttcgccg agatcggccc gcgcatggcc gagttgagcg    1980
gttcccggct ggccgcgcag caacagatgg aaggcctcct ggcgccgcac cggcccaagg   2040
agcccgcgtg gttcctggcc accgtcggag tctcgcccga ccaccagggc aagggtctgg   2100
gcagcgccgt cgtgctcccc ggagtggagg cggccgagcg cgccggggtg cccgccttcc   2160
tggagacctc cgcgccccgc aacctcccct tctacgagcg gctcggcttc accgtcaccg   2220
ccgacgtcga ggtgcccgaa ggaccgcgca cctggtgcat gacccgcaag cccggtgcct   2280
ga                                                                  2282
```

<210> SEQ ID NO 188
<211> LENGTH: 1258
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 188

```
tgcaaagatg gataaagttt taaacagaga ggaatctttg cagctaatgg accttctagg     60
tcttgaaagg agtgggaatt ggctccggtg cccgtcagtg ggcagagcgc acatcgccca   120
cagtccccga gaagttgggg ggaggggtcg gcaattgatc cggtgcctag agaaggtggc   180
```

-continued

```
gcggggtaaa ctgggaaagt gatgtcgtgt actggctccg cctttttccc gagggtgggg        240
gagaaccgta tataagtgca gtagtcgccg tgaacgttct ttttcgcaac gggtttgccg        300
ccagaacaca ggtaagtgcc gtgtgtggtt cccgcgggcc tggcctcttt acgggttatg        360
gcccttgcgt gccttgaatt acttccaccg gctgcagtac gtgattcttg atcccgagct        420
tcgggttgga agtgggtggg agagttcgag gccttgcgct taaggagccc cttcgcctcg        480
tgcttgagtt gaggcctggc ctgggcgctg ggccgccgc gtgcgaatct ggtggcacct         540
tcgcgcctgt ctcgctgctt tcgataagtc tctagccatt taaaatttt gatgacctgc         600 tgcgacgctt tttttctggc aagatagtct tgtaaatgcg ggccaagatc tgcacactgg        660
tatttcggtt tttggggccg cgggcggcga cggggcccgt gcgtcccagc gcacatgttc        720
ggcgaggcgg ggcctgcgag cgcggccacc gagaatcgga cggggtagt ctcaagctgg         780 ccggcctgct ctggtgcctg gcctcgcgcc gccgtgtatc gccccgccct gggcggcaag        840
gctggcccgg tcggcaccag ttgcgtgagc ggaaagatgg ccgcttcccg gccctgctgc        900
agggagctca aaatggagga cgcggcgctc gggagagcgg gcgggtgagt cacccacaca        960
aaggaaaagg gcctttccgt cctcagccgt cgcttcatgt gactccacgg agtaccgggc       1020
gccgtccagg cacctcgatt agttctcgag cttttggagt acgtcgtctt taggttgggg       1080 ggagggtt tatgcgatgg agtttcccca cactgagtgg gtggagactg aagttaggcc         1140
agcttggcac ttgatgtaat tctccttgga atttgcctt tttgagtttg gatcttggtt        1200
cattctcaag cctcagacag tggttcaaag tttttttctt ccatttcagg tgtcgtga        1258
```

<210> SEQ ID NO 189
<211> LENGTH: 600
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 189

```
atgaccgagt acaagcccac ggtgcgcctc gccacccgcg acgacgtccc cagggccgta         60
cgcaccctcg ccgccgcgtt cgccgactac cccgccacgc gccacaccgt cgatccggac        120
cgccacatcg agcgggtcac cgagctgcaa gaactcttcc tcacgcgcgt cgggctcgac        180
atcggcaagg tgtgggtcgc ggacgacggc gccgccgtgg cggtctggac cacgccggag        240
agcgtcgaag cggggcggt gttcgccgag atcggcccgc gcatggccga gttgagcggt         300
tcccggctgg ccgcgcagca acagatggaa ggcctcctgg cgccgcaccg gcccaaggag        360
cccgcgtggt tcctggccac cgtcggagtc tcgcccgacc accagggcaa gggtctgggc        420
agcgccgtcg tgctccccgg agtggaggcg gccgagcgcg ccggggtgcc cgccttcctg        480
gagacctccg cgccccgcaa cctccccttc tacgagcggc tcggcttcac cgtcaccgcc        540
gacgtcgagg tgcccgaagg accgcgcacc tggtgcatga cccgcaagcc cggtgcctga        600
```

<210> SEQ ID NO 190
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 190
tggttcagtg gctgcgtgtc					20

<210> SEQ ID NO 191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
gccggccgcg cgggggaggc					20

<210> SEQ ID NO 192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
ccatgtgacg ggggctgtca					20

<210> SEQ ID NO 193
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
ggcaggcgag gaggggggagg					20

<210> SEQ ID NO 194
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gctgccgggt tttgcatgaa					20

<210> SEQ ID NO 195
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gtatcccctc tcgcagcaac					20

<210> SEQ ID NO 196
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 196
aggagccgcc gcgcgctgat                                                    20

<210> SEQ ID NO 197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
tttacccact tccttcgaaa                                                    20

<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
gcagggtact taaatgagga                                                    20

<210> SEQ ID NO 199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
cgccaggagg ggtgggtcta                                                    20

<210> SEQ ID NO 200
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
gattaactga gaattcacaa                                                    20

<210> SEQ ID NO 201
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
tctagttccc cacctagtct                                                    20
```

<210> SEQ ID NO 202
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
gccttggtga gactggtaga                                        20

<210> SEQ ID NO 203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
tgtcttcagg ttctgttgct                                        20

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
tgatttaaaa gttggaaacg                                        20

<210> SEQ ID NO 205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
catattcctg atttaaaagt                                        20

<210> SEQ ID NO 206
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
tcccaattta ctgggattac                                        20

<210> SEQ ID NO 207
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 207
gcgcgctcca cacaactcac                                                 20

<210> SEQ ID NO 208
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
aaggaacgcg cgccggcggc                                                 20

<210> SEQ ID NO 209
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
atgggagaag gcggaggaaa                                                 20

<210> SEQ ID NO 210
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gcaacgatgg aagggagcct                                                 20

<210> SEQ ID NO 211
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gcgcacgtgg gggcggggga                                                 20

<210> SEQ ID NO 212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gcctggctgg cgtcacggcc                                                 20

<210> SEQ ID NO 213
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
gccgccgaca ccactgccgc                                              20

<210> SEQ ID NO 214
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
cggttcctcg cgccccgcgc                                              20

<210> SEQ ID NO 215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gacacaactg gcgcccctcc                                              20

<210> SEQ ID NO 216
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216 gggggggagaa actgaggcga                                             20

<210> SEQ ID NO 217
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
tctgtggggg acctgcactg                                              20

<210> SEQ ID NO 218
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
ggcacagtgc cagaggtctg                                              20
```

<210> SEQ ID NO 219
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
ggtgaaatga gggcttgcga                                              20

<210> SEQ ID NO 220
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
tcaaggctag tgggtgggac                                              20

<210> SEQ ID NO 221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
ggtggtggca atggtgtctg                                              20

<210> SEQ ID NO 222
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
acaggaattc aagaccagcc                                              20

<210> SEQ ID NO 223
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
gcaaagaggg aacggctctc                                              20

<210> SEQ ID NO 224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 224
acagagtttc cggggggcgga                                              20

<210> SEQ ID NO 225
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
cccttcattg cggcgggctg                                               20

<210> SEQ ID NO 226
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
ggcccgagcc gcgtgtggaa                                               20

<210> SEQ ID NO 227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gcgggccggg ggcggggtcc                                               20

<210> SEQ ID NO 228
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
tttaaaagtc ggctggtagc                                               20

<210> SEQ ID NO 229
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
tccctgaact tttcaaaaat                                               20

<210> SEQ ID NO 230
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
cactggagct agagacaaga                                                20

<210> SEQ ID NO 231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
gtatcctcta tgatgggaga                                                20

<210> SEQ ID NO 232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
aaaaactgga atgactgaat                                                20

<210> SEQ ID NO 233
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
aaaattagca gtatcctctt                                                20

<210> SEQ ID NO 234
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
atgcaaatat ctgtctgaaa                                                20

<210> SEQ ID NO 235
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
```
cttgaccaat agccttgaca                                              20

<210> SEQ ID NO 236
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
ggctagggat gaagaataaa                                              20

<210> SEQ ID NO 237
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
gccgcacgca cctgttccca                                              20

<210> SEQ ID NO 238
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
ctgcaccctg ggagcgcgag                                              20

<210> SEQ ID NO 239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gcccggagca gctgcgctgt                                              20

<210> SEQ ID NO 240
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
ccaggaccgc gcttcccacg                                              20

<210> SEQ ID NO 241
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 241
gagctggaag gtgaaggggc                                                 20

<210> SEQ ID NO 242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
cccgacccct cccgggtccc                                                 20

<210> SEQ ID NO 243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ggaaaggaag gggaggggct                                                 20

<210> SEQ ID NO 244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gcggccccgc cctctcctcg                                                 20

<210> SEQ ID NO 245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ttagtatatg tgggacaaag                                                 20

<210> SEQ ID NO 246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gaaaatccag tattttaatg                                                 20

<210> SEQ ID NO 247
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
gaaaacaatg catatttgca                                                 20

<210> SEQ ID NO 248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
ctctggttca tggaagggca                                                 20

<210> SEQ ID NO 249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
agtattggtg gaagcttctt                                                 20

<210> SEQ ID NO 250
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
tttaacttga ttgtgaaatc                                                 20

<210> SEQ ID NO 251
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
tggctttcaa aagcagaagt                                                 20

<210> SEQ ID NO 252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
```
aaaaacagcg agggagaaac                                            20

<210> SEQ ID NO 253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
aaactccaca atctagaata                                            20

<210> SEQ ID NO 254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
ttaacagtta aaaatcatac                                            20

<210> SEQ ID NO 255
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
tggaaaacca actcttccac                                            20

<210> SEQ ID NO 256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
agcatctttt tctctttaat                                            20

<210> SEQ ID NO 257
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
atcactttaa aaccacctct                                            20

<210> SEQ ID NO 258
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 258
aaacttatgc ggcgtttcct                                               20

<210> SEQ ID NO 259
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
gagtacatga tcacccagat                                               20

<210> SEQ ID NO 260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gacccagcac tgcagcctgg                                               20

<210> SEQ ID NO 261
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
tagcaataca gtcacattaa                                               20

<210> SEQ ID NO 262
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
gccgggcgtc tgggctctgg                                               20

<210> SEQ ID NO 263
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
tgcccggcgg ccgggctgag                                               20
```

```
<210> SEQ ID NO 264
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
gcctgggggc cccgggctga                                               20

<210> SEQ ID NO 265
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
ccgggcagag agtgaacgcg                                               20

<210> SEQ ID NO 266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
gcggcgcccc agggcggggc                                               20

<210> SEQ ID NO 267
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
accctggcgg agctgatggg                                               20

<210> SEQ ID NO 268
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gggtcttggg aggggcgca                                                20

<210> SEQ ID NO 269
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 269
ggccccacgg aagcctgagc                                               20

<210> SEQ ID NO 270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
cagtgcgttc tcggtgtgga                                               20

<210> SEQ ID NO 271
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
tttgtcaaac agtactgcta                                               20

<210> SEQ ID NO 272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
gcgcgcgtag ttaattcatg                                               20

<210> SEQ ID NO 273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
agctagagtg ctcggctgcc                                               20

<210> SEQ ID NO 274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
ggttcccaaa gcagagggcg                                               20

<210> SEQ ID NO 275
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 275
tctcgctaat ctccgcccac                                                   20

<210> SEQ ID NO 276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
ccctttataa tgcgagggtc                                                   20

<210> SEQ ID NO 277
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
agaagcaggc cgcgcattcc                                                   20

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
gcgggtcagc tccaagcagc                                                   20

<210> SEQ ID NO 279
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
tctgattggc cagcgccgcc                                                   20

<210> SEQ ID NO 280
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
cccatctcca gttgtgcgtg                                                   20
```

```
<210> SEQ ID NO 281
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
tctgagaagg gacaccccag                                                20

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
cggagggaaa gggagggaa                                                 20

<210> SEQ ID NO 283
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
ggggctgccc gcggggggtt                                                20

<210> SEQ ID NO 284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
gggagccttt gaaaagccgt                                                20

<210> SEQ ID NO 285
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
tgggcaggcc cggcccggcg                                                20

<210> SEQ ID NO 286
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 286
gcgcactctg gggccagcag                                              20

<210> SEQ ID NO 287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ggctgggatg acctcgctga                                              20

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288 tgatctttt aaggacaggc                                               20

<210> SEQ ID NO 289
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
tctcaagtag ctgggactac                                              20

<210> SEQ ID NO 290
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
caggtgcggt ggctcatgcc                                              20

<210> SEQ ID NO 291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
ctcactgcaa cctctgtctg                                              20

<210> SEQ ID NO 292
<211> LENGTH: 20
<212> TYPE: DNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
ggtggggcag ggaaggaagg                                               20

<210> SEQ ID NO 293
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
gcaccattca cccgggggag                                               20

<210> SEQ ID NO 294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
tgcacccgtc gtccccgccg                                               20

<210> SEQ ID NO 295
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
gtgggcggag cggggggggcc                                              20

<210> SEQ ID NO 296
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
gcgcgctctt cacttcttgg                                               20

<210> SEQ ID NO 297
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
tcgtagagaa acatgacggt                                               20
```

<210> SEQ ID NO 298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
cgcggctgcg gcggcggccg                                              20

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
ttggcggcct ctgcgcccgc                                              20

<210> SEQ ID NO 300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
tcggagccac tccctcctct                                              20

<210> SEQ ID NO 301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
aatttgtcat agtcttgagt                                              20

<210> SEQ ID NO 302
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
tctttttaca ttgactgata                                              20

<210> SEQ ID NO 303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 303
tgcttttgaa tgaacaccca                                               20

<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
ttggggtcta ctcacaattt                                               20

<210> SEQ ID NO 305
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
gttctgtgaa gtccagtccc                                               20

<210> SEQ ID NO 306
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
agcaagtact caatatattt                                               20

<210> SEQ ID NO 307
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
agtagagagg ccaggcacag                                               20

<210> SEQ ID NO 308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
taaaatagag cggagatatc                                               20

<210> SEQ ID NO 309
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
ccttcttgaa ggtgcactca                                            20

<210> SEQ ID NO 310
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
caggctgtgg ttgtgacctg                                            20

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
tttctctcct gcgtcctggg                                            20

<210> SEQ ID NO 312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
cacgcttcca gccacccgct                                            20

<210> SEQ ID NO 313
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
cgatgcgctt gctgggtcgc                                            20

<210> SEQ ID NO 314
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
```

```
ggctcccagc cccagccccc                                                 20

<210> SEQ ID NO 315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
accagctgcc ttcttccccc                                                 20

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
cagcccctcc ttctaccctt                                                 20

<210> SEQ ID NO 317
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gggcaggagg tggagtgtca                                                 20

<210> SEQ ID NO 318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gggggccgga gggggagagg                                                 20

<210> SEQ ID NO 319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
gcaggctgag aagggtgggc                                                 20

<210> SEQ ID NO 320
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 320
tctcatcaag tgtccactca                                              20

<210> SEQ ID NO 321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
gtctcccatc tctcctgccc                                              20

<210> SEQ ID NO 322
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
gggtgtggaa agcctggtct                                              20

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
tgactctagg cagagtggga                                              20

<210> SEQ ID NO 324
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
tcgcggctgg aggacgctgc                                              20

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
cgccccagcc ccgggggacg                                              20

<210> SEQ ID NO 326
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
cagggacacg atggtccaaa                                              20

<210> SEQ ID NO 327
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
gtcaggagtt tccagcccga                                              20

<210> SEQ ID NO 328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
cccaggagga ggctgggccc                                              20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
gagtgagttg gattaaactg                                              20

<210> SEQ ID NO 330
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
ctgctatacg cgaagttgcc                                              20

<210> SEQ ID NO 331
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
```

```
acgttctaga ttcacatgtc                                              20

<210> SEQ ID NO 332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
ctgaaaaagg aaggagttga                                              20
```